US010111874B2

(12) United States Patent
Janes et al.

(10) Patent No.: US 10,111,874 B2
(45) Date of Patent: *Oct. 30, 2018

(54) COMBINATION THERAPIES FOR TREATMENT OF CANCER

(71) Applicant: Araxes Pharma LLC, La Jolla, CA (US)

(72) Inventors: Matthew Robert Janes, Encinitas, CA (US); Matthew Peter Patricelli, San Diego, CA (US); Liansheng Li, San Diego, CA (US); Pingda Ren, San Diego, CA (US); Yi Liu, San Diego, CA (US)

(73) Assignee: Araxes Pharma LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/858,766

(22) Filed: Sep. 18, 2015

(65) Prior Publication Data

US 2016/0166571 A1 Jun. 16, 2016

Related U.S. Application Data

(60) Provisional application No. 62/195,633, filed on Jul. 22, 2015, provisional application No. 62/052,332, filed on Sep. 18, 2014.

(51) Int. Cl.
*A61K 31/517* (2006.01)
*A61K 31/00* (2006.01)
*A61K 31/337* (2006.01)
*A61K 31/4745* (2006.01)
*A61K 31/496* (2006.01)
*A61K 45/06* (2006.01)

(52) U.S. Cl.
CPC ............ *A61K 31/517* (2013.01); *A61K 31/00* (2013.01); *A61K 31/337* (2013.01); *A61K 31/4745* (2013.01); *A61K 31/496* (2013.01); *A61K 45/06* (2013.01)

(58) Field of Classification Search
CPC .... A61K 31/517; A61K 31/00; A61K 31/337; A61K 31/4745; A61K 31/496; A61K 45/06
See application file for complete search history.

(56) References Cited

U.S. PATENT DOCUMENTS

| 3,702,849 A | 11/1972 | Cronin et al. |
| 3,752,660 A | 8/1973 | Little |
| 4,439,606 A | 3/1984 | Du et al. |
| 4,649,219 A | 3/1987 | Itoh et al. |
| 4,861,760 A | 8/1989 | Mazuel et al. |
| 4,911,920 A | 3/1990 | Jani et al. |
| 5,010,175 A | 4/1991 | Rutter et al. |
| 5,033,252 A | 7/1991 | Carter |
| 5,052,558 A | 10/1991 | Carter |
| 5,212,162 A | 5/1993 | Missel et al. |
| 5,288,514 A | 2/1994 | Ellman |
| 5,323,907 A | 6/1994 | Kalvelage |
| 5,403,841 A | 4/1995 | Lang et al. |
| 5,538,848 A | 7/1996 | Livak et al. |
| 5,539,083 A | 7/1996 | Cook et al. |
| 5,593,853 A | 1/1997 | Chen et al. |
| 5,605,798 A | 2/1997 | Köster |
| 5,731,352 A | 3/1998 | Lesieur et al. |
| 5,777,324 A | 7/1998 | Hillenkamp |
| 5,858,659 A | 1/1999 | Sapolsky et al. |
| 5,861,510 A | 1/1999 | Piscopio et al. |
| 5,863,949 A | 1/1999 | Robinson et al. |
| 5,919,626 A | 7/1999 | Shi et al. |
| 5,925,525 A | 7/1999 | Fodor et al. |
| 5,952,174 A | 9/1999 | Nikiforov et al. |
| 6,017,696 A | 1/2000 | Heller |
| 6,043,031 A | 3/2000 | Köster et al. |
| 6,045,996 A | 4/2000 | Cronin et al. |
| 6,051,380 A | 4/2000 | Sosnowski et al. |
| 6,068,818 A | 5/2000 | Ackley et al. |
| 6,214,872 B1 | 4/2001 | Robinson |
| 6,251,639 B1 | 6/2001 | Kurn |
| 6,903,118 B1 | 6/2005 | Biedermann et al. |
| 7,595,397 B2 | 9/2009 | Zindell et al. |
| 7,879,863 B2 | 2/2011 | Tokumasu et al. |
| 8,399,454 B2 | 3/2013 | Bian et al. |
| 8,426,401 B2 | 4/2013 | Bian et al. |
| 8,604,017 B2 | 12/2013 | Bian et al. |
| 8,697,684 B2 | 4/2014 | Bian et al. |
| 8,741,887 B2 | 6/2014 | Bian et al. |
| 8,759,333 B2 | 6/2014 | Connolly et al. |

(Continued)

FOREIGN PATENT DOCUMENTS

| CN | 1267291 A | 9/2000 |
| CN | 104 418 860 B | 9/2016 |
| EP | 0 094 498 A2 | 11/1983 |
| EP | 0 606 046 A1 | 7/1994 |
| EP | 0 780 386 A1 | 6/1997 |
| EP | 0 818 442 A2 | 1/1998 |
| EP | 0 931 788 A2 | 7/1999 |
| EP | 1 004 578 A1 | 5/2000 |
| EP | 1 736 465 A1 | 12/2006 |
| EP | 2 270 002 A1 | 1/2011 |
| EP | 2 889 291 A1 | 7/2015 |
| GB | 939516 A | 10/1963 |

(Continued)

OTHER PUBLICATIONS

Arkin et al., "Binding of small molecules to an adaptive protein—protein interface," *PNAS* 100(4):1603-1608, Feb. 2003.

(Continued)

*Primary Examiner* — Sahar Javanmard
(74) *Attorney, Agent, or Firm* — Seed IP Law Group LLP

(57) ABSTRACT

Combination therapies for treatment of cancers associated with mutations in the KRAS gene are provided. Compositions comprising therapeutic agents for treatment of cancers associated with mutations in the KRAS gene are also provided.

20 Claims, 16 Drawing Sheets

(56) References Cited

U.S. PATENT DOCUMENTS

| | | | |
|---|---|---|---|
| 9,227,978 | B2 | 1/2016 | Ren et al. |
| 9,376,559 | B2 | 6/2016 | Holtcamp et al. |
| 9,745,319 | B2 | 8/2017 | Ren et al. |
| 9,810,690 | B2 | 11/2017 | Patricelli et al. |
| 9,840,516 | B2 | 12/2017 | Li et al. |
| 9,862,701 | B2 | 1/2018 | Li et al. |
| 9,926,267 | B2 | 3/2018 | Ren et al. |
| 2002/0169300 | A1* | 11/2002 | Waterman .......... C07K 14/4705 536/23.1 |
| 2003/0022344 | A1 | 1/2003 | Williams et al. |
| 2003/0166620 | A1 | 9/2003 | Lee et al. |
| 2005/0012070 | A1 | 1/2005 | Inoue et al. |
| 2005/0227997 | A1 | 10/2005 | Noe et al. |
| 2008/0004285 | A1 | 1/2008 | De Jonghe et al. |
| 2008/0004348 | A1 | 1/2008 | Yous et al. |
| 2008/0039450 | A1 | 2/2008 | Jensen et al. |
| 2009/0036430 | A1 | 2/2009 | De Jonghe et al. |
| 2009/0054402 | A1 | 2/2009 | Wang et al. |
| 2009/0124636 | A1 | 5/2009 | Barber et al. |
| 2009/0298075 | A1 | 12/2009 | Travers et al. |
| 2010/0331300 | A1 | 12/2010 | Bian et al. |
| 2011/0046370 | A1 | 2/2011 | Sim et al. |
| 2011/0230476 | A1 | 9/2011 | Niu et al. |
| 2011/0269244 | A1 | 11/2011 | Petter et al. |
| 2011/0311447 | A1 | 12/2011 | Tu et al. |
| 2011/0319290 | A1 | 12/2011 | Raymond et al. |
| 2013/0012489 | A1 | 1/2013 | Mederski et al. |
| 2013/0029964 | A1 | 1/2013 | Aoki et al. |
| 2013/0274252 | A1 | 10/2013 | Pandey et al. |
| 2013/0302407 | A1 | 11/2013 | Rao et al. |
| 2014/0315886 | A1 | 10/2014 | Suzuki et al. |
| 2015/0087628 | A1 | 3/2015 | Ostrem et al. |
| 2015/0239900 | A1 | 8/2015 | Li et al. |
| 2016/0031898 | A1 | 2/2016 | Ren et al. |
| 2016/0297774 | A1 | 10/2016 | Li et al. |
| 2016/0368930 | A1 | 12/2016 | Ostrem et al. |
| 2017/0022184 | A1 | 1/2017 | Li et al. |
| 2017/0131278 | A1 | 5/2017 | Patricelli et al. |
| 2017/0190672 | A1 | 7/2017 | Mani et al. |
| 2017/0197945 | A1 | 7/2017 | Li et al. |
| 2017/0247376 | A1 | 8/2017 | Li et al. |
| 2018/0015087 | A1 | 1/2018 | Liu et al. |
| 2018/0086753 | A1 | 3/2018 | Li et al. |
| 2018/0127396 | A1 | 5/2018 | Li et al. |
| 2018/0141927 | A1 | 5/2018 | Li et al. |
| 2018/0155348 | A1 | 6/2018 | Li et al. |

FOREIGN PATENT DOCUMENTS

| | | |
|---|---|---|
| JP | 58-203966 A | 11/1983 |
| JP | 59-163372 A | 9/1984 |
| JP | 2005-502623 A | 1/2005 |
| JP | 2005-179557 A | 7/2005 |
| JP | 2007-016011 A | 1/2007 |
| JP | 2008-524154 A | 7/2008 |
| JP | 4775259 B2 | 9/2011 |
| JP | 2013-504325 A | 2/2013 |
| WO | 86/01207 A1 | 2/1986 |
| WO | 90/05719 A1 | 5/1990 |
| WO | 91/19735 A1 | 12/1991 |
| WO | 92/00091 A1 | 1/1992 |
| WO | 93/20242 A1 | 10/1993 |
| WO | 96/05309 A2 | 2/1996 |
| WO | 96/13262 A1 | 5/1996 |
| WO | 96/27583 A1 | 9/1996 |
| WO | 96/33172 A1 | 10/1996 |
| WO | 97/00271 A1 | 1/1997 |
| WO | 98/57948 A1 | 1/1997 |
| WO | 98/03516 A1 | 1/1998 |
| WO | 98/07697 A1 | 2/1998 |
| WO | 98/30566 A1 | 7/1998 |
| WO | 98/33496 A1 | 8/1998 |
| WO | 98/33768 A1 | 8/1998 |
| WO | 98/34915 A1 | 8/1998 |
| WO | 98/34918 A1 | 8/1998 |
| WO | 98/57948 A1 | 12/1998 |
| WO | 99/29667 A1 | 6/1999 |
| WO | 99/52889 A1 | 10/1999 |
| WO | 99/52910 A1 | 10/1999 |
| WO | 99/67641 A1 | 12/1999 |
| WO | 00/39587 A1 | 7/2000 |
| WO | 03/004480 A2 | 1/2003 |
| WO | 2004/074283 A1 | 9/2004 |
| WO | 2014/152588 A1 | 9/2004 |
| WO | 2005/070891 A2 | 8/2005 |
| WO | 2005/082892 A2 | 9/2005 |
| WO | 2006/066948 A1 | 6/2006 |
| WO | 2006/135993 A1 | 12/2006 |
| WO | 2017/015562 A1 | 1/2007 |
| WO | 2007/095588 A1 | 8/2007 |
| WO | 2007/113226 A1 | 10/2007 |
| WO | 2007/144394 A2 | 12/2007 |
| WO | 2008/009078 A2 | 1/2008 |
| WO | 2008/112440 A1 | 9/2008 |
| WO | 2010/027746 A2 | 3/2010 |
| WO | 2010/087399 A1 | 8/2010 |
| WO | 2010/121918 A1 | 10/2010 |
| WO | 2011/148922 A1 | 10/2010 |
| WO | 2011/031896 A2 | 3/2011 |
| WO | 2011/093524 A1 | 8/2011 |
| WO | 2011/153553 A2 | 12/2011 |
| WO | 2012/016082 A1 | 2/2012 |
| WO | 2012/041872 A1 | 4/2012 |
| WO | 2012/054716 A1 | 4/2012 |
| WO | 2012/174489 A2 | 12/2012 |
| WO | 2013/064068 A1 | 5/2013 |
| WO | 2013/140148 A1 | 9/2013 |
| WO | 2013/155223 A1 | 10/2013 |
| WO | 2013/184757 A1 | 12/2013 |
| WO | 2014/011900 A2 | 1/2014 |
| WO | 2014/143659 A1 | 9/2014 |
| WO | 2014/152588 A1 | 9/2014 |
| WO | 2014/159837 A1 | 10/2014 |
| WO | 2014/201435 A1 | 12/2014 |
| WO | 2015/003166 A1 | 1/2015 |
| WO | 2015/017501 a1 | 2/2015 |
| WO | 2015/054572 A1 | 4/2015 |
| WO | 2015/108992 A1 | 7/2015 |
| WO | 2015/132799 A2 | 9/2015 |
| WO | 2015/143148 A1 | 9/2015 |
| WO | 2015/144001 A1 | 10/2015 |
| WO | 2015/184349 A2 | 12/2015 |
| WO | 2016/044772 A1 | 3/2016 |
| WO | 2016/049524 A1 | 3/2016 |
| WO | 2016/049565 A1 | 3/2016 |
| WO | 2016/049568 A1 | 3/2016 |
| WO | 2016/118951 A2 | 7/2016 |
| WO | 2016/164675 A1 | 10/2016 |
| WO | 2016/168540 A1 | 10/2016 |
| WO | 2017/058902 A1 | 4/2017 |
| WO | 2017/058915 A1 | 4/2017 |
| WO | 2017/070256 A2 | 4/2017 |
| WO | 2017/087528 A1 | 5/2017 |
| WO | 2017/100546 A1 | 6/2017 |
| WO | 2017/172979 A1 | 10/2017 |

OTHER PUBLICATIONS

Choong et al., "Identification of Potent and Selective Small-Molecule Inhibitors of Caspase-3 through the Use of Extended Tethering and Structure-Based Drug Design," *J. Med. Chem.* 45:5005-5022, 2002.

Erlanson et al., "Site-directed ligand discovery," *Proc. Natl Acad. Sci. U.S.A.* 97(17):9367-9372, Aug. 2000.

Forbes et al., "COSMIC 2005," *British Journal of Cancer* 94:318-322, 2006.

Gorfe et al., "Mapping the Nucleotide and Isoform-Dependent Structural and Dynamical Features of Ras Proteins," *Structure* 16:885-896, Jun. 2008.

Hall et al., "The Effect of $Mg^{2+}$ on Guanine Nucleotide Exchange Rate of $p21^{N-ras}$," *The Journal of Biological Chemistry* 261(24):10963-10965, 1986.

(56) References Cited

OTHER PUBLICATIONS

Hall et al., "The structural basis for the transition from Ras-GTP to Ras-GDP," *PNAS* 99(19):12138-12142, Sep. 2002.
Hardy et al., "Discovery of an allosteric in the caspases," *PNAS* 101(34):12461-12466, Aug. 2004.
Hattori et al., "Neutralizing monoclonal antibody against ras oncogene product p21 which impairs guanine nucleotide exchange," *Mol. Cell. Biol.* 7(5):1999-2002, May 1987.
Ito et al., "Regional Polysterism in the GTP-Bound Form of the Human c-Ha-Ras Protein," *Biochemistry* 36(30):9109-1919, Jul. 1997.
Kraulis et al., "Solution Structure and Dynamics of Ras p21-GDP Determined by Heteronuclear Three- and Four-Dimensional NMR Spectroscopy," *Biochemistry* 33:3515-3531, 1994.
Lee et al., "The mutation spectrum revealed by paired genome sequences from a lung cancer patient," *Nature* 465:473-477, May 2010.
Lenzen et al., "[10] Analysis of Intrinsic and CDC25-Stimulated Guanine Nucleotide Exchange of p21$^{ras}$—Nucleotide Complexes by Fluorescence Measurements," *Methods in Enzymology* 255:95-109, 1995.
Li et al., "Substituted Quinazoline Compounds and Methods of Use Thereof," U.S. Appl. No. 15/093,951, filed Apr. 8, 2016, 349 pages.
Malani et al., "Synthesis, characterization and in vitro screening on bacterial, fungal and malarial strain of piprazinyl cyano biphenyl based compounds," *Bioorganic Chemistry* 51:16-23, 2013.
Margarit et al., "Structural Evidence for Feedback Activation by Ras•GTP of the Ras-Specific Nucleotide Exchange Factor SOS," *Cell* 112:685-695, Mar. 2008.
Milburn et al., "Molecular switch for signal transduction: structural differences between active and inactive forms of protooncogenic ras proteins," *Science* 247(4945):939-945, Feb. 1990.
Pacold et al., "Crystal structure and functional analysis of Ras binding to its effector phosphoinositide 3-kinase gamma," *Cell* 103(6):931-943, Dec. 2000.
Palmioli et al., "First experimental identification of Ras-inhibitor binding interface using a water-soluble Ras ligand," *Bioorganic and Medicinal Chemistry* 19:4217-4222, 2009.
PubChem Compound, "AKOS024742141," retrieved from http://pubchem.ncbi.nim.nih.gov/compound/49702158#x304 on Nov. 27, 2010, CID 49702158, 12 pages.
Rensland et al., "Substrate and Product Structural Requirements for Binding of Nucleotides to H-ras p21: The Mechanism of Discrimination between Guanosine and Adenosine Nucleotides," *Biochemistry* 34(2):593-599, 1995.
Sydor et al., "Transient Kinetic Studies on the Interaction of Ras and the Ras-Binding Domain of c-Raf-1 Reveal Rapid Equilibration of the Complex," *Biochemistry* 37:14292-14299, 1998.
Taveras et al., "Ras Oncoprotein Inhibitors: The Discovery of Potent, Ras Nucleotide Exchange Inhibitors and the Structural Determination of a Drug-Protein Complex," *Bioorganic and Medicinal Chemistry* 5(1):125-133, 1997.
Vetter et al., "The Guanine Nucleotide-Binding Switch in Three Dimensions," *Science* 294(5545):1299-1304, Nov. 2001.
Yang et al., "Fragment-Based Discovery of Nonpeptidic BACE-1 Inhibitors Using Tethering," *Biochemistry* 48:4488-4496, 2009.
Banker et al. (eds.), *Modern Pharmaceutics*, New York, Marcel Dekker, Inc., 1996, pp. 451 and 596. (3 pages).
Duncan et al., "N-Dialkylaminoalkybiphenylamines as Antimalarial and Atischistosomal Agents," *Journal of Medicinal Chemistry* 12:25-29, Jan. 1969.
Kumar et al., "Synthesis of 3-Sulfonylamino Quinolines form 1-(2-Aminophenyl) Propargyl Alcohols through a Ag(I)-Catalyzed Hydroamination, (2+3) Cycloaddition, and an Unusual Strain-Driven Ring Expansion," *Organic Letters* 17(9):2226-2229, Apr. 2015.
Ohnmacht, Jr. et al., "Antimalarials. 5. α-Dibutylaminomethyl- and α-(2-Piperidyl)-3-quinolinemethanols," *Journal of Medicinal Chemistry* 14(1):17-24, 197.
Singh et al., "A Gene Expression Signature Associated with "K-Ras Addiction" Reveals Regulators of EMT and Tumor Cell Survival," *Cancer Cell* 15:489-500, Jun. 2009.
Sunaga et al., "Knockdown of Oncogenic KRAS in Non-Small Cell Lung Cancers Suppresses Tumor Growth and Sensitizes Tumor Cells to Targeted Therapy," *Molecular Cancer Therapeutics* 10(2):336-346, Feb. 2011.
Young et al., "Oncogenic and Wild-type Ras Play Divergent Roles in the Regulation of Mitogen-Activated Protein Kinase Signaling," *Cancer Discovery* 3(1):112-123, Jan. 2013.
Appel et al., "Supramolecular Cross-Linked Networks via Host-Guest Complexation with Cucurbit [8]uril," *J. Am. Chem. Soc.* 132(40):14251-14260, Jul. 2010.
Barbe et al., "Highly Chemoselective Metal-Free Reduction of Tertiary Amides," *J. Am. Chem. Soc.* 130:18-19, 2008.
Bégué et al., "Ions α-Cetocarbenium. Influence De La Structure Sur L'Evolution Des Ions α-Cetocyclohexylcarbenium," *Tetrahedron* 31(20):2205-2511, 1975. (English Abstract Only).
Johnson et al., "The Chemistry of γ-Bromopropionyl Isocyanate. I. Synthesis of 1-Aryldihydrouracils," *The Journal of Organic Chemistry* 24(9):1391-1392, Sep. 1959.
Jordan, "Tamoxifen: A most unlikely pioneering medicine," *Nature Reviews* 2:205-213, Mar. 2003.
Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," *Bioorganic & Medicinial Chemistry* 6:673-686, 1998.
Le Picard et al., "Design and Synthesis of Naphthalenic Derivatives as Potential Inhibitors of Hydroxyindole-O-methyltransferase,"*Pharm. Pharmacol. Commun.* 5:183-188, 1999.
Liansheng Li et al., "Inhibitors of Kras G12C Mutant Proteins," U.S. Appl. No. 14/866,147, filed Sep. 25, 2015, 110 pages.
Liu et al., "*Polygonatum cyrtonema* lectin induces murine fibrosarcoma L929 cell apoptosis and autophagy via blocking Ras-Raf and PI3K-Akt signaling pathways," *Biochimie* 92:1934-1938, 2010.
Loboda et al., "A gene expression signature of RAS pathway dependence predicts response to PI3K and RAS pathway inhibitors and expands the population of RAS pathway activated tumors," *BMC Medical Genomics* 3(26): 1-11, 2010.
Ostrem et al., "K-Ras(G12C) inhibitors allosterically control GTP affinity and effector interactions," *Nature* 000, 2013, 14 pages.
Palmioli et al., "Selective cytotoxicity of a bicyclic Ras inhibitor in cancer cells expressing K-Ras$^{G13D}$," *Biochemical and Biophysical Research Communications* 386(4):593-597, Sep. 2009.
Pédeboscq et al., "Synthesis and evaluation of apoptosis induction of thienopyrimidine compounds on KRAS and BRAF mutated colorectal cancer cell lines," *Bioorganic & Medicinal Chemistry* 20:6724-6731, 2012.
Peri et al., "Arabinose-derived bicyclic amino acids: synthesis, conformational analysis and construction of an $α_v β_3$-selective RGD peptide," *J. Am. Chem. Soc., Perkins Trans* 1(5):638-644, Feb. 2002.
Peri et al., "Sugar-Derived Ras Inhibitors: Group Epitope Mapping by NMR Spectroscopy and Biological Evaluation," *Eur. J. Org. Chem.* 2006(16):3707-3720, Aug. 2006.
Peri et al., "Synthesis of bicyclic sugar azido acids and their incorporation in cyclic peptides," *Chem. Commun.* 23:2303-2304, Jan. 2000.
Pingda Ren et al., "Covalent Inhibitors of KRAS G12C," U.S. Appl. No. 14/933,734, filed Nov. 5, 2015, 355 pages.
PubChem Compound, "(2S,6R)-hexahydrofuro[3,2-b]furan-2,6-diyl dicarbonochloridate:Compound Summary CID 53396983," Oct. 30, 2011, retrieved from http://pubchem.ncbi.nlm.nih.gov/compound/53396983, 6 pages.
PubChem Compound, "(4-hydroxypiperidin-1-y1)-pyridin-4-ylmethanone: AC1L5BNJ," retrieved on Feb. 17, 2014, from http://pubchem.ncbi.nlm.nih.gov/summary/summary.cgi?CID=76837, Jul. 8, 2005, 5 pages.
PubChem Compound, "AKOS024742141," Nov. 27, 2010, retrieved from http://pubchem.ncbi.nim.nih.gov/compound/49702158#x304, CID 49702158, 12 pages.

(56) References Cited

OTHER PUBLICATIONS

PubChem Compound, "Compound Summary for CID 21765509: Molecular Formula $C_{18}H_{21}N_5O_8$," Dec. 5, 2007, retriieved from http://pubchem.ncbi.nlm.nih.gov/compound/21765509, 4 pages.
PubChem Compound, "Compound Summary for CID 21765511: Molecular Formula $C_{18}H_{21}N_5O_8$," Dec. 5, 2007, retrieved from http://pubchem.ncbi.nlm.nih.gov/compound/21765511, 4 pages.
PubChem Compound, "Compound Summary for CID 60018735: Molecular Formula $C_{30}H_{30}O_{13}$," Aug. 20, 2012, retrieved from http://pubchem.ncbi.nlm.nih.gov/compound/60018735#section=Top, 1 page.
PubChem Compound, "Compound Summary for CID 72623693: AGN-PC-0D83J7," Jan. 9, 2014, retrieved from http://pubchem.ncbi.nlm.nih.gov/compound/72623693, 6 pages.
PubChem Compound, "Compound Summary for CID 9897840: Molecular Formula $C_{50}H_{46}O_{20}$," Oct. 25, 2006, retrieved from http://pubchem.ncbi.nlm.nih.gov/compound/9897840, 6 pages.
PubChem Compound, "SCHEMBL6674271," Dec. 1, 2012, retrieved from http://pubchem.ncbi.nim.nih.gov/compound/69861127#x304, CID 69861127, 12 pages.
PubChem Compound, "SCHEMBL6797439," Dec. 1, 2012, retrieved from http://pubchem.ncbi.nim.nih.gov/compound/69898605#x304, CID 69898605, 12 pages.
Sasaki et al., "Selective Formation of Stable Triplexes Including a TA or a CG Interrupting Site with New Bicyclic Nucleoside Analogues (WNA)," *J. Am. Chem. Soc.* 126(2):516-528, Jan. 2004.
Spiegel et al., "Small-molecule modulation of Ras signaling," *Nature Chemical Biology* 10:613-622, Aug. 2014.
Streuff et al., "First asymmetric aminohydroxylation of acrylamides," *Tetrahedron: Asymmetry* 16(21):3492-3496, Oct. 2005.
Tsubaki et al., "Reduction of metastasis, cell invasion, and adhesion in mouse osteosarcoma by YM529/ONO-5920-induced blockade of the RAS/MEK/ERK and Ras/PI3K/Akt pathway," *Toxicology and Applied Pharmacology* 259(3):402-410, Jan. 2012.
Tulshian et al., "Synthesis and Phosphodiesterase Activity of Carboxylic Acid Mimetics of Cyclic Guanosine 3',5'-Monophosphate," *J. Med. Chem.* 36(9):1210-1220, Jan. 1993.
Wolff, (ed.), *Burger's Medicinal Chemistry and Drug Discovery, Fifth Edition, vol. 1: Principles and Practice*, San Diego, California, John Wiley & Sons, 1994, pp. 975-977.
Wu et al., "Stereoselective synthesis of dioxabicycles from 1-C-allyl-2-O-benzyl-glycosides—An intramolecular cyclization between 2-O-benzyl oxygen and the allyl double bond," *Can. J. Chem.* 84(1):597-602, Jan. 2006.
Zenkl et al., "Sugar-Responsive Fluorescent Nanospheres,"*Macromol. Biosci.* 8:146-152, 2008.
Adibekian et al., "Optimization and characterization of a triazole urea dual inhibitor for lysophosphlipase 1 (LYPLA1) and lysophospholipase 2 (LYPLA2)," *Probe Reports from the NIH Molecular Libraries Program*, 2011, 42 pages.
Al-Muhammed et al., "In-vivo studies on dexamethasone sodium phosphate liposomes," *J. Microencapsulation* 13(3):293-306, 1996.
Berge et al., "Pharmaceutical Salts," *Journal of Pharmaceutical Sciences* 66(1):1-19, 1977.
Chemcats Chemical Abstract, Accession No. 1301347730, Sep. 9, 2015, 2 pages.
Chemocare, "Taxol," retrieved from http://www.chemocare.com/chemotherapy/drug-info/Taxol.aspx on Feb. 22, 2017, 3 pages.
Cho et al., "An Unnatural Biopolymer," *Science* 261:1303-1305, Sep. 3, 1993.
Chonn et al., "Recent advances in liposomal drug-delivery systems," *Current Opinion in Biotechnology* 6:698-708, 1995.
DeWitt et al., ""Diversomers": An approach to nonpeptide, nonoligomeric chemical diversity," *Proc. Natl. Acad. Sci.* 90:6909-6913, Aug. 1993.
Furka et al., "General method for rapid synthesis of multicomponent peptide mixtures," *Int. J. Peptide Protein Res.* 37:487-493, 1991.
Hagihara et al., "Vinylogous Polypeptides: An Alternative Peptide Backbone," *J. Am. Chem. Soc.* 114:6568-6570, 1992.
Jones et al., "Increased frequency of the k-ras G12C mutation in MYH polyposis colorectal adenomas," *British Journal of Cancer* 90:1591-1593, 2004.
Knochel et al., "Functionalization of heterocyclic compounds using polyfunctional magnesium and zinc reagents," *Beilstein Journal of Organic Chemistry* 7:1261-1277, 2011.
Li et al., "Methods and Compositions for Inhibition of RAS," U.S. Appl. No. 15/508,387, filed Mar. 2, 2017, 145 pages.
Liang et al., "Parallel Synthesis and Screening of a Solid Phase Carbohydrate Library," *Science* 274:1520-1522, Nov. 1996.
Lone et al., "A substrate-free activity-based protein profiling screen for the discovery of selective PREPL inhibitors," *J. Am Chem Soc.* 133(30):11665-11674, Aug. 2011, 20 pages.
Long, "Taxol: An important compound with an impressive structure," Organic and General Chemistry at Flathead Valley Community College, Sep. 10, 2011, retrieved from https://longscience.com/2011/09/10/taxol-an-organic-compound-you-should-know-about/ on Feb. 22, 2017, 4 pages.
Maurer et al., "Small-molecule ligands bind to a distinct pocket in Ras and inhibit SOS-mediated nucleotide exchange activity," *PNAS* 109(14):5299-5304, Apr. 3, 2012.
McMahon, "VEGF Receptor Signaling in Tumor Angiogenesis," *The Oncologist* 5(suppl. 1):3-10, 2000.
Minto et al., "Pharmacokinetics and Pharmacodynamics of Nandrolone Esters in Oil Vehicle: Effects of Ester, Injection Site and Injection Volume," *The Journal of Pharmacology and Experimental Therapeutics* 281(1):93-102, 1997.
Pathan et al., "Lead identification for the K-Ras protein: virtual screening and combinatorial fragment-based approaches," *OncoTargets and Therapy* 9:2575-2584, 2016.
Patricelli et al., "Selective Inhibition of Oncogenic KRAS Output with Small Molecules Targeting the Inactive State," *Cancer Discovery* 6(3)316-329, 2016.
Pautsch et al., "Crystal structure of the C3bot-RaIA complex reveals a novel type of action of a bacterial exoenzyme," *The EMBO Journal* 24:3670-3680, 2005.
Pinedo et al., "Aggressive combination therapy to cure patients with metastatic cancer," *The Lancet Oncology* 1:72-73, Oct. 2000.
Pinedo et al., "Translational Research: The Role of VEGF in Tumor Angiogenesis," *The Oncologist* 5(suppl. 1):1-2, 2000.
PubChem Substance Record for SID 22405303, Mar. 5, 2007, CID 2579941 (MLS000416491), retreived from https://pubchem.ncbi.nlm.nih.gov/substance/22405303, on May 15, 2017, 7 pages.
PubChem Substance Record for SID 44253980, Dec. 5, 2007, CID 966800 (1-BENZOYLPYRROLIDINE), retrieved from https://pubchem.ncbi.nlm.nih.gov/substance/44253980#section=Top on May 11, 2017, 5 pages.
Schubbert et al., "Biochemical and Functional Characterization of Germ Line KRAS Mutations," *Molecular and Cellular Biology* 27(22):7765-7770, Nov. 2007.
Vippagunta et al., "Crystalline solids," *Advanced Drug Delivery Reviews* 48:3-26, 2001.
Yan et al., "Discovery and characterization of small molecules that target the GRPase Ral," *Nature* 515:443-447, Nov. 2014, 15 pages.
Bachovchin et al., "Identification of selective inhibitors of uncharacterized enzymes by high-throughput screening with fluorescent activity-based probes," *Nature Biotechnology* 27(4):387-394, 2009. (11 pages).
CAS Registry No. 5530-21-2, "1-Propanone, 1[4-[2-(2-methoxy-4-propylphenoxy)acety1]-1-piperazinyl]-," entered into STN Nov. 16, 1984, last updated Dec. 15, 2008, 6 pages.
Cox et al., "Drugging the undruggable RAS: Mission Possible?," *Nature Reviews Drug Discovery* 13:828-851, 2014.
Pardin et al., "Synthesis and evaluation of peptidic irreversible inhibitors of tissue transglutaminase," *Bioorganic & Medicinal Chemistry* 14:8379-8385, 2006.
Pubchem, "1-methoxy-3-tert-butyl-1H-isoindole," Compound Summary for CID 10375614, creation date Oct. 25, 2006, retrieved from https://pubchem.ncbi.nlm.nih.gov/compound/10375614, 9 pages.
Shima et al., "Discovery of Small-Molecule Ras Inhibitors that Display Antitumor Activity by Interfering with RAS•GTP-Effector Interaction," *The Enzymes* 34:1-23, 2013.

(56) References Cited

OTHER PUBLICATIONS

Stefanachi et al., "1-, 3-, and 8-substituted-9-deazaxanthines as potent and selective antagonists at the human $A_{2B}$ adenosine receptor," *Bioorg Med Chem* 16(6):2852-2869, 2008.

Sun et al., "Discovery of Small Molecules that Bind to K-Ras and Inhibit Sos-Mediated Activation," *Angew. Chem. Int. Ed.* 51:6140-6143, 2012.

Xu et al., "Design, Synthesis, and Biological Evaluation of 2-Oxo-3,4-dihydropyrimido[4,5-d]pyrimidinyl Derivatives as New Irreversible Epidermal Growth Factor Receptor Inhibitors with Improved Pharmacokinetic Properties," *Journal of Medicinal Chemistry* 56:8803-8813, 2013.

Haggam et al., "Facile synthesis of some condensed 1,3-thiazines and thiazoles under conventional conditions: antitumor activity," *Res. Chem. Intermed.* 43:6299-6315, 2017.

Janes et al., "Targeting KRAS Mutant Cancers with a Covalent G12C-Specific Inhibitor," *Cell* 172:578-589, 2018.

Kuroyanagi et al., "Structure-Activity Relationships of 1,3-Benzoxazole-4-carbonitriles as Novel Antifungal Agents with Potent in Vivo Efficacy," *Chem. Pharm. Bull.* 59(3):341-352, 2011.

\* cited by examiner

COMBINATION THERAPIES FOR TREATMENT OF CANCER

BACKGROUND

Technical Field

Embodiments of the present invention are generally directed to combination therapies for treatment of cancers associated with mutations in the KRAS gene.

Description of the Related Art

Ras represents a group of closely related monomeric globular proteins of 189 amino acids (21 kDa molecular mass) which are associated with the plasma membrane and which bind either GDP or GTP. Ras acts as a molecular switch. When Ras contains bound GDP, it is in the resting or off position and is "inactive." In response to exposure of the cell to certain growth promoting stimuli, Ras is induced to exchange its bound GDP for a GTP. With GTP bound, Ras is "switched on" and is able to interact with and activate other proteins (its "downstream targets"). The Ras protein itself has a very low intrinsic ability to hydrolyze GTP back to GDP, thus turning itself into the off state. Switching Ras off requires extrinsic proteins termed GTPase-activating proteins (GAPs) that interact with Ras and greatly accelerate the conversion of GTP to GDP. Any mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive Ras signaling may ultimately lead to cancer.

Structurally, Ras proteins contain a G domain which is responsible for the enzymatic activity of Ras—the guanine nucleotide binding and the hydrolysis (GTPase reaction). It also contains a C-terminal extension, known as the CAAX box, which may be post-translationally modified and is responsible for targeting the protein to the membrane. The G domain is approximately 21-25 kDa in size and it contains a phosphate binding loop (P-loop). The P-loop represents the pocket where the nucleotides are bound in the protein, and this is the rigid part of the domain with conserved amino acid residues which are essential for nucleotide binding and hydrolysis (Glycine 12, Threonine 26 and Lysine 16). The G domain also contains the so called Switch I (residues 30-40) and Switch II (residues 60-76) regions, both of which are the dynamic parts of the protein which are often represented as the "spring-loaded" mechanism because of their ability to switch between the resting and loaded state. The key interaction is the hydrogen bonds formed by Threonine-35 and glycine-60 with the γ-phosphate of GTP which maintain Switch 1 and Switch 2 regions respectively in their active conformation. After hydrolysis of GTP and release of phosphate, these two relax into the inactive GDP conformation.

The most notable members of the Ras subfamily are HRAS, KRAS and NRAS, mainly for being implicated in many types of cancer. However, there are many other members including DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS and RRAS2.

Mutations in any one of the three main isoforms of RAS (HRAS, NRAS, or KRAS) genes are among the most common events in human tumorigenesis. KRAS mutations occur in more than 20% of all human cancers with the highest levels in pancreatic (~90%), colorectal (~40%), and lung (~35%), with G12C being a common mutation (glycine-12 to cysteine). This translates into more than 150,000 newly diagnosed cases of KRAS driven cancer yearly in the US alone. These patients have no effective treatment options and their chances for long term survival are extremely low.

After many years of failed efforts, the direct targeting of KRAS was long considered to be impossible. More recently an approach targeting a specific KRAS mutation, G12C, which accounts for nearly 50% of KRAS mutant lung cancers, has been reported (Ostrem et al., Nature 2013, 503:548). We have refined this strategy to yield quite potent inhibitors of KRAS G12C function in cells and in vivo. These compounds hold great promise for the treatment of cancers harboring the KRAS G12C mutation.

While KRAS is a critical driver mutation in many types of cancer, its precise role in established tumors is the subject of some debate. KRAS mutated cancer cells show varied degrees of growth inhibition when mutant KRAS is depleted, with some lines showing only modest effects (Singh et al., Cancer Cell 2009, 15:489). Further, even in lines with clear growth dependence on mutant KRAS, depletion of KRAS does not lead to robust induction of cell death or apoptosis (Sunaga et al., Mol Cancer Ther 2011, 10:336; Young et al., Cancer Discov 2013, 3:112). Thus, despite the central role for mutant KRAS in tumorigenesis, it is possible that inhibition of KRAS alone may not be sufficient for a desirable clinical outcome.

Accordingly, while progress has been made in this field, there remains a need in the art for improved methods for treatment of KRAS mutant cancers, for example combination therapies. The present invention fulfills this need and provides further related advantages.

BRIEF SUMMARY

In brief, the present invention provides methods for treatment of cancer, for example cancers associated with mutations in the KRAS gene. In one embodiment, the disclosure provides a method for treating a KRAS, HRAS or NRAS G12C mutant cancer, the method comprising administering an effective amount of a KRAS, HRAS or NRAS G12C mutant modulating compound and an additional therapeutic agent to a subject in need thereof. Exemplary cancers that can be treated by the disclosed method include, but are not limited to, hematological cancers, pancreatic cancer, MYH associated polyposis, colorectal cancer and/or lung cancer.

In a different embodiment, the disclosure provides a method for inducing apoptosis in a cell population comprising a KRAS, HRAS or NRAS G12C mutant protein, the method comprising administering an effective amount of a KRAS, HRAS or NRAS G12C mutant modulating compound and an additional therapeutic agent.

In still other embodiments, the disclosure is directed to a method for inhibiting tumor metastasis in a subject having a KRAS, HRAS or NRAS G12C mutant cancer, the method comprising administering an effective amount of a KRAS, HRAS or NRAS G12C mutant modulating compound and an additional therapeutic agent.

Pharmaceutical compositions and kits for combination therapy of different cancers are also provided.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
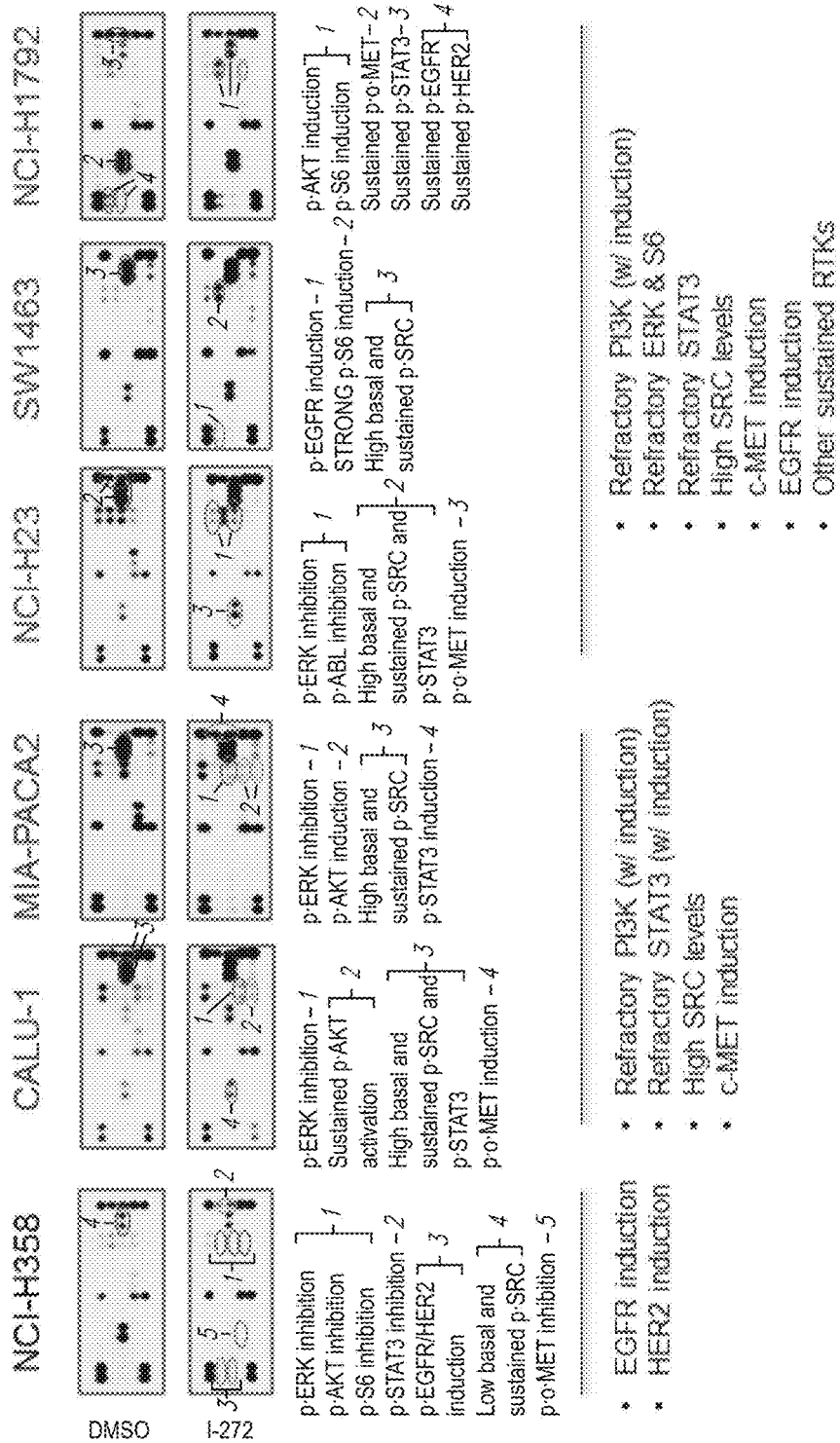
FIG. 1 provides western blots for identifying synergistic pathways for targeting in combination with KRAS G12C inhibition. Shown are dot blot arrays for detection of phosphorylated receptor tyrosine kinases (p-RTK) and phosphorylated signaling kinases (ie. p-ERK, or p-AKT) for indicated cell lines treated with indicated K-Ras G12C inhibitor. Notable signaling targets and their respective pathways that are induced or maintained following treatment are summarized for various cell lines.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a," "an," and "the" include plural references unless the context clearly dictates otherwise.

"Amidinyl" refers to a radical of the form —(C=NR$_a$)NR$_b$R$_c$, wherein R$_a$, R$_b$ and R$_c$ are each independently H or C$_1$-C$_6$ alkyl.

"Amino" refers to the —NH$_2$ radical.

"Aminylsulfone" refers to the —S(O)$_2$NH$_2$ radical.

"Carboxy" or "carboxyl" refers to the —CO$_2$H radical.

"Cyano" refers to the —CN radical.

"Guanidinyl" refers to a radical of the form —NR$_d$(C=NR$_a$)NR$_b$R$_c$, wherein R$_a$, R$_b$, R$_c$, and R$_d$ are each independently H or C$_1$-C$_6$ alkyl.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms (C$_1$-C$_{12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds such as ethynyl and the like). "Amidinylalkyl" refers to an alkyl group comprising at least one amidinyl substituent. "Guanidinylalkyl" refers to an alkyl group comprising at least one guanidinyl substituent. Unless stated otherwise specifically in the specification, an alkyl, amidinylalkyl and/or guanidinylalkyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Alkylcycloalkyl" refers to a radical of the formula —R$_b$R$_d$ where R$_b$ is cycloalkyl chain as defined herein and R$_d$ is an alkyl radical as defined above. Unless stated otherwise specifically in the specification, an alkylcycloalkyl group is optionally substituted.

"Alkoxy" refers to a radical of the formula —OR$_a$ where R$_a$ is an alkyl radical as defined above containing one to twelve carbon atoms. "Amidinylalkyloxy" refers to an alkoxy group comprising at least one amidinyl substituent on the alkyl group. "Guanidinylalkyloxy" refers to an alkoxy group comprising at least one guanidinyl substituent on the alkyl group. "Alkylcarbonylaminylalkyloxy" refers to an alkoxy group comprising at least one alkylcarbonylaminyl substituent on the alkyl group. "Heterocyclylalkyloxy" refers to an alkoxy group comprising at least one heterocyclyl substituent on the alkyl group. "Heteroarylalkyloxy" refers to an alkoxy group comprising at least one heteroaryl substituent on the alkyl group. "Aminylalkyloxy" refers to an alkoxy group comprising at least one substituent of the form —NR$_a$R$_b$, where R$_a$ and R$_b$ are each independently H or C$_1$-C$_6$ alkyl, on the alkyl group. Unless stated otherwise specifically in the specification, an alkoxy, amidinylalkyloxy, guanidinylalkyloxy, alkylcarbonylaminyl, heterocyclylalkyloxy, heteroarylalkyloxy and/or aminylalkyloxy group is optionally substituted.

"Alkoxyalkyl" refers to a radical of the formula —R$_b$OR$_a$ where R$_a$ is an alkyl radical as defined above containing one to twelve carbon atoms and R$_b$ is an alkylene radical as defined above containing one to twelve carbon atoms. Unless stated otherwise specifically in the specification, an alkoxyalkyl group is optionally substituted.

"Alkoxycarbonyl" refers to a radical of the formula —C(=O)OR$_a$ where R$_a$ is an alkyl radical as defined above containing one to twelve carbon atoms. Unless stated otherwise specifically in the specification, an alkoxycarbonyl group is optionally substituted.

"Aryloxy" refers to a radical of the formula —OR$_a$ where R$_a$ is an aryl radical as defined herein. Unless stated otherwise specifically in the specification, an aryloxy group is optionally substituted.

"Alkylaminyl" refers to a radical of the formula —NHR$_a$ or —NR$_a$R$_a$ where each R$_a$ is, independently, an alkyl radical as defined above containing one to twelve carbon atoms. A "haloalkylaminyl" group is an alkylaminyl group comprising at least one halo substituent on the alkyl group. A "hydroxylalkylaminyl" group is an alkylaminyl group comprising at least one hydroxyl substituent on the alkyl group. An "amidinylalkylaminyl" group is an alkylaminyl group comprising at least one amidinyl substituent on the alkyl group. A "guanidinylalkylaminyl" group is an alkylaminyl group comprising at least one guanidinyl substituent on the alkyl group. Unless stated otherwise specifically in the specification, an alkylaminyl, haloalkylaminyl, hydroxylalkylaminyl, amidinylalkylaminyl and/or guanidinylalkylaminyl group is optionally substituted.

"Aminylalkyl" refers to an alkyl group comprising at least one aminyl substituent (—NR$_a$R$_b$ wherein R$_a$ and R$_b$ are each independently H or C$_1$-C$_6$ alkyl). The aminyl substituent can be on a tertiary, secondary or primary carbon. Unless stated otherwise specifically in the specification, an aminylalkyl group is optionally substituted.

"Aminylalkylaminyl" refers to a radical of the formula —NR$_a$R$_b$ wherein R$_a$ is H or C$_1$-C$_6$ alkyl and R$_b$ is aminylalkyl. Unless stated otherwise specifically in the specification, an aminylalkylaminyl group is optionally substituted.

"Alkylcarbonylaminyl" refers to a radical of the formula —NH(C=O)R$_a$ where R$_a$ is an alkyl radical as defined above containing one to twelve carbon atoms. Unless stated otherwise specifically in the specification, an alkylcarbonylaminyl group is optionally substituted. An alkenylcarbonylaminyl is an alkylcarbonylaminyl containing at least one carbon-carbon double bond. An alkenylcarbonylaminyl group is optionally substituted.

"Alkylaminylalkyl" refers to an alkyl group comprising at least one alkylaminyl substituent. The alkylaminyl substituent can be on a tertiary, secondary or primary carbon. Unless stated otherwise specifically in the specification, an alkylaminylalkyl group is optionally substituted.

"Aminylcarbonyl" refers to a radical of the formula —C(=O)NH$_2$. Unless stated otherwise specifically in the specification, an aminylcarbonyl group is optionally substituted.

"Alkylaminylcarbonyl" refers to a radical of the formula —C(=O)NR$_a$R$_b$, where R$_a$ and R$_b$ are each independently H or alkyl, provided at least one of R$_a$ or R$_b$ is alkyl. Unless stated otherwise specifically in the specification, an alkylaminylcarbonyl group is optionally substituted.

"Aminylcarbonylalkyl" refers to a radical of the formula —R$_c$C(=O)NR$_a$R$_b$, where R$_a$ and R$_b$ are each independently H or alkyl and R$_c$ is alkylene. Unless stated otherwise specifically in the specification, an aminylcarbonylalkyl group is optionally substituted.

"Aminylcarbonycycloalkylalkyl" refers to a radical of the formula —R$_c$C(=O)NR$_a$R$_b$, where R$_a$ and R$_b$ are each independently H or alkyl and R$_c$ is cycloalkyl. Unless stated otherwise specifically in the specification, an aminylcarbonylcycloalkyl group is optionally substituted.

"Aryl" refers to a hydrocarbon ring system radical comprising hydrogen, 6 to 18 carbon atoms and at least one aromatic ring. For purposes of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group is optionally substituted.

"Carboxyalkyl" refers to a radical of the formula —R$_b$—R$_c$ where R$_b$ is an alkylene chain as defined above and R$_c$ is a carboxy group as defined above. Unless stated otherwise specifically in the specification, carboxyalkyl group is optionally substituted.

"Cyanoalkyl" refers to a radical of the formula —R$_b$—R$_c$ where R$_b$ is an alkylene chain as defined above and R$_c$ is a cyano group as defined above. Unless stated otherwise specifically in the specification, a cyanoalkyl group is optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbomyl, decalinyl, 7,7-dimethyl-bicyclo[2.2.1]heptanyl, and the like. A "cycloalkenyl" is a cycloalkyl comprising one or more carbon-carbon double bonds within the ring. Unless otherwise stated specifically in the specification, a cycloalkyl (or cycloalkenyl) group is optionally substituted.

"Cyanocycloalkyl" refers to a radical of the formula —R$_b$—R$_c$ where R$_b$ is cycloalkylene chain and R$_c$ is a cyano group as defined above. Unless stated otherwise specifically in the specification, a cyanocycloalkyl group is optionally substituted.

"Cycloalkylaminylcarbonyl" refers to a radical of the formula —C(=O)NR$_a$R$_b$, where R$_a$ and R$_b$ are each independently H or cycloalkyl, provided at least one of R$_a$ or R$_b$ is cycloalkyl. Unless stated otherwise specifically in the specification, n cycloalkylaminylcarbonyl group is optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group is optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Halolkoxy" refers to a radical of the formula —OR$_a$ where R$_a$ is a haloalkyl radical as defined herein containing one to twelve carbon atoms. Unless stated otherwise specifically in the specification, a haloalkoxy group is optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification. "Heterocyclyloxy" refers to a heterocyclyl group bound to the remainder of the molecule via an oxygen bond (—O—). "Heterocyclylaminyl" refers to a heterocyclyl group bound to the remainder of the molecule via a nitrogen bond (—NR$_a$—, where R$_a$ is H or C$_1$-C$_6$ alkyl). Unless stated otherwise specifically in the specification, a heterocyclyl, heterocyclyloxy and/or hetercyclylaminyl group is optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group is optionally substituted.

"Heterocyclylalkyl" refers to a radical of the formula —$R_b R_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). "Heteroaryloxy" refers to a heteroaryl group bound to the remainder of the molecule via an oxygen bond (—O—). "Heteroarylaminyl" refers to a heteroaryl group bound to the remainder of the molecule via a nitrogen bond (—$NR_a$—, where $R_a$ is H or $C_1$-$C_6$ alkyl). Unless stated otherwise specifically in the specification, a heteroaryl, heteroaryloxy and/or heteroarylaminyl group is optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group is optionally substituted.

"Heteroarylalkyl" refers to a radical of the formula —$R_b R_f$ where $R_b$ is an alkylene chain as defined above and $R_f$ is a heteroaryl radical as defined above. Unless stated otherwise specifically in the specification, a heteroarylalkyl group is optionally substituted.

"Hydroxylalkyl" refers to an alkyl group comprising at least one hydroxyl substituent. The —OH substituent may be on a primary, secondary or tertiary carbon. Unless stated otherwise specifically in the specification, a hydroxylalkyl group is optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group is optionally substituted.

The term "substituted" used herein means any of the above groups (e.g., alkyl, alkylene, alkylcycloalkyl, alkoxy, alkoxyalkyl, alkoxycarbonyl, aryloxy, alkylaminyl, alkylcarbonylaminyl, alkylaminylalkyl, aminylcarbonyl, alkylaminylcarbonyl, aminylcarbonylalkyl, aminylcarbonycycloalkylalkyl, thioalkyl, aryl, aralkyl, carboxyalkyl, cyanoalkyl, cycloalkyl, cyanocycloalkyl, cycloalkylaminylcarbonyl, cycloalkylalkyl, haloalkyl, haloalkoxy, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_g R_h$, —$NR_g C(=O)R_h$, —$NR_g C(=O)NR_g R_h$, —$NR_g C(=O)OR_h$, —$NR_g SO_2 R_h$, —$OC(=O)NR_g R_h$, —$OR_g$, —$SR_g$, —$SOR_g$, —$SO_2 R_g$, —$OSO_2 R_g$, —$SO_2 OR_g$, =$NSO_2 R_g$, and —$SO_2 NR_g R_h$. "Substituted also means any of the above groups in which one or more hydrogen atoms are replaced with —$C(=O)R_g$, —$C(=O)OR_g$, —$C(=O)NR_g R_h$, —$CH_2 SO_2 R_g$, —$CH_2 SO_2 NR_g R_h$. In the foregoing, $R_g$ and $R_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Electrophile" or "electrophilic moiety" is any moiety capable of reacting with a nucleophile (e.g., a moiety having a lone pair of electrons, a negative charge, a partial negative charge and/or an excess of electrons, for example a —SH group). Electrophiles typically are electron poor or comprise atoms which are electron poor. In certain embodiments an electrophile contains a positive charge or partial positive charge, has a resonance structure which contains a positive charge or partial positive charge or is a moiety in which delocalization or polarization of electrons results in one or more atom which contains a positive charge or partial positive charge. In some embodiments, the electrophiles comprise conjugated double bonds, for example an α,β-unsaturated carbonyl or α,β-unsaturated thiocarbonyl compound.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The terms "antagonist" and "inhibitor" are used interchangeably, and they refer to a compound having the ability to inhibit a biological function of a target protein, whether by inhibiting the activity or expression of the protein, such as KRAS, HRAS or NRAS G12C. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent is water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the invention, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The present invention includes all manner of rotamers and conformationally restricted states of a compound of the invention.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

A. Treatment Methods

The present disclosure is generally directed to methods for treatment of various cancers. The present inventors have discovered that a combination of mutant specific KRAS, NRAS or HRAS G12C inhibitory molecules with clinically relevant molecular targeted drugs and/or chemotherapy agents is a surprisingly effective method for treatment of certain cancers, for example cancers associated with KRAS, NRAS or HRAS G12C mutant proteins (a "KRAS, HRAS or NRAS G12C mutant cancer"). In various embodiments, inhibition of mutant KRAS dramatically sensitizes cancer cells to the described combination therapies, leading to robust cell death. Such combination methods have the possibility to greatly improve the outcomes for patients with tumors harboring the KRAS, NRAS or HRAS G12C mutation.

Example 1 describes a strategy for identifying and assessing potential targets that would benefit from a combination treatment including a KRAS G12C inhibitor and a second agent that would inhibit any cell signaling pathway that was hyperactivated or maintained following KRAS G12C inhibition. Exemplary targets identified include RTK, PI3K, mTOR, SRC, and JAK/STAT.

Examples 2-10 describe additional data obtained in support of certain embodiments of the present invention. In Example 2, a combination of an exemplary KRAS G12C inhibitor was used with one of an RTK, a PI3K, an mTOR, an SRC, or a JAK inhibitor. The synergistic effect of the combination was assessed by monitoring both cell proliferation and apoptosis in the presence of each agent alone and in the presence of the combination. This example was carried out on a variety of mutant cell lines (H358, H1792, Calu-1, SW1463, SW1573, MiaPaca2, NCI-H23) or control cell line (A549). The proliferation data was combined with apoptosis data to assess the synergistic effect of the compounds used in combination.

In Example 3, multiple KRAS G12C cell lines were evaluated for evidence of apoptosis induction in the presence of KRAS G12C inhibitors alone, or in combination with targeted agents (EGFR, PI3K, IGF1R, and MEK inhibitors) or chemotherapeutic agents (Taxol, Docetaxel, SN38 (active ingredient in Irinotecan)). In similar fashion, Examples 4-10 each show an evaluation of a KRAS G12C inhibitor used in combination with one of many different types of inhibitors (e.g., EGFR, PI3K, MEK, SRC, JAK) for synergistic pathway inhibition or induction of apoptosis in relevant cancer cell lines.

Synergistic apoptosis induction was observed with treatment of KRAS G12C mutated cell lines with combinations of a KRAS G12C inhibitor and selected targeted and chemotherapeutic agents. In many cases, the levels of apoptosis induced by these combinations rivaled what is seen with high dose staurosporine or Taxol. As with the single agent treatments, the effects varied by cell-type and by the precise combination. The greatest synergy was observed when a KRAS G12C inhibitor was combined with an EGFR inhibitor (e.g., erlotinib and afatinib), a PI3K inhibitor (e.g., GDC0941, BYL-719), or the chemotherapeutic agent SN38 (active ingredient in Irinotecan). Some positive results were also seen with MEK inhibitors, IGF1R inhibitors, JAK inhibitors, SRC inhibitors, and the chemotherapeutic agents Taxol, Docetaxel, and Paclitaxel.

Overall the data support that inhibition of mutant KRAS activity can dramatically alter the sensitivity of KRAS mutant cell lines to both targeted cancer therapies and, more broadly, active chemotherapies. The levels of apoptosis observed with optimal combinations are equal to potent apoptosis inducers and suggest that nearly 100% cell killing is possible. In a clinical setting this type of behavior should allow for optimal therapeutic combinations to lead to dramatic tumor regression.

Figure 9:
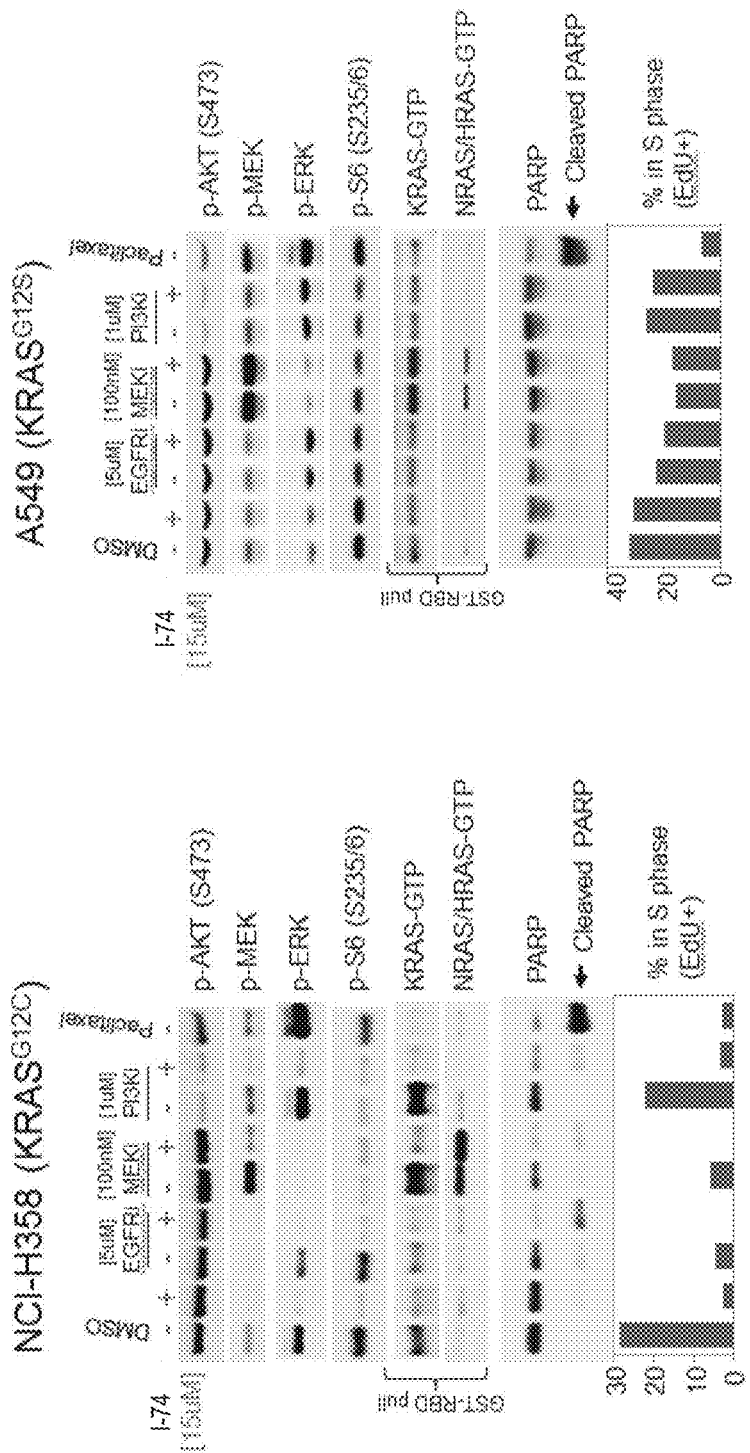
FIG. 9 is western blot data for combinations of an exemplary KRAS G12C inhibitor with an EGFR, MEK or PI3K inhibitor.

The effectiveness of different combinations varied with the different cell lines despite sharing the KRAS G12C mutation. While not wishing to be bound by theory, this is may be related to differences in the genetic background and varied oncogene addictions in each of these lines. FIG. 9 provides data for an effective combination strategy for Calu-1 cells. Calu-1 cells were generally resistant to single agent KRAS G12C treatment as well as combinations with targeted kinase inhibitors. Comparison of tyrosine kinase phosphorylation levels between H358 and Calu-1 cells revealed that Calu-1 cells have high levels of c-SRC phosphorylation (FIG. 9A). Combination treatment of Calu-1 cells with a KRAS G12C inhibitor and a SRC inhibitor (Dasatinib) revealed a strong synergistic induction of apoptosis (FIG. 9B).

Given that KRAS is a centrally important oncogene that universally leads to treatment-resistant cancer, we anticipate that eliminating the oncogenic KRAS signaling will uncover enhanced sensitivities to a broad range of cancer therapeutics beyond what has been examined here.

Accordingly, in one embodiment a method for treating a KRAS, HRAS or NRAS G12C mutant cancer is provided, the method comprising administering an effective amount of a KRAS, HRAS or NRAS G12C mutant modulating compound and an additional therapeutic agent to a subject in need thereof. In certain embodiments, the cancer is a KRAS G12C mutant cancer. The KRAS, HRAS or NRAS G12C mutant modulating compound is not particularly limited provided the compound modulates (e.g., inhibits) the activity of the KRAS, HRAS or NRAS G12C mutant. Exemplary compounds for this purpose are described herein in the section entitled "Compounds."

In various embodiments of the method, the additional therapeutic agent is an epidermal growth factor receptor (EGFR) inhibitor, phosphatidylinositol kinase (PI3K) inhibitor, insulin-like growth factor receptor (IGF1R) inhibitor, Janus kinase (JAK) inhibitor, a Met (MET) kinase inhibitor, a SRC family kinase (SFK) inhibitor, a mitogen-activated protein kinase (MEK) inhibitor, an extracellular-signal-regulated kinase (ERK) inhibitor, mechanistic target of rapamycin (mTOR) inhibitor, a topoisomerase inhibitor (such as irinotecan, or such as etoposide, or such as doxorubicin), taxanes (such as anti-microtubule agents including paclitaxel and docetaxel), anti-metabolite agents (such as 5-FU or such as gemcitabine), alkylating agents (such as cisplatin or such as cyclophosphamide), or a taxane.

In some other embodiments of the method, the additional therapeutic agent is an epidermal growth factor receptor (EGFR) inhibitor, phosphatidylinositol kinase (PI3K) inhibitor, insulin-like growth factor receptor (IGF1R) inhibitor, Janus kinase (JAK) inhibitor, a Met (MET) kinase inhibitor, a SRC family kinase (SFK) inhibitor, a mitogen-activated protein kinase (MEK) inhibitor, an extracellular-signal-regulated kinase (ERK) inhibitor, a topoisomerase inhibitor (such as irinotecan, or such as etoposide, or such as doxorubicin), taxanes (such as anti-microtubule agents including paclitaxel and docetaxel), anti-metabolite agents (such as 5-FU or such as gemcitabine), alkylating agents (such as cisplatin or such as cyclophosphamide), or a taxane.

In some embodiments, the additional therapeutic agent is an epidermal growth factor receptor (EGFR) inhibitor, such as erlotinib or such as afatinib. In some embodiments the additional therapeutic agent is Iressa. In some embodiments the additional therapeutic agent is a monoclonal antibody such as cetuximab (Erbitux) or panitumumab (Vectibix). In some embodiments the GFR inhibitor is a dual or pan-HER inhibitor. In other embodiments, the additional therapeutic agent is a phosphatidylinositol-3kinase (PI3K) inhibitor, such as GDC0941, MLN1117, BYL719 (Alpelisib) or BKM120 (Buparlisib). GDC0941 refers to 2-(1H-indazol-4-yl)-6-(4-methanesulfonyl-piperazin-1-ylmethyl)-4-morpholin-4-yl-thieno[3,2-d]pyrimidine or a salt thereof (e.g., bismesylate salt).

In still different embodiments, the additional therapeutic agent is an insulin-like growth factor receptor (IGF1R) inhibitor. For example, in some embodiments the insulin-like growth factor receptor (IGF1R) inhibitor is NVP-AEW541. In other embodiments, the additional therapeutic agent is IGOSI-906 (Linsitinib), BMS-754807, or in other embodiments the additional therapeutic agent is a neutralizing monoclonal antibodies specific to IGF1R such as AMG-479 (ganitumab), CP-751,871 (figitumumab), IMC-A12 (cixutumumab), MK-0646 (dalotuzumab), and R-1507 (robatumumab).

In some other embodiments, the additional therapeutic agent is a Janus kinase (JAK) inhibitor. In some embodiments, the additional therapeutic agent is CYT387, GLPG0634, Baricitinib, Lestaurtinib, momelotinib, Pacritinib, Ruxolitinib or TG101348

In some other embodiments the additional therapeutic agent is an MET kinase inhibitor, such as Crizotinib, tivantinib, AMG337, cabozantinib, foretinib. In other embodiments the additional therapeutic agent is a neutralizing monoclonal antibody to MET such as onartuzumab.

In more embodiments, the additional therapeutic agent is a SRC family non-receptor tyrosine kinase inhibitor. For example in some embodiments the additional therapeutic agent is an inhibitor of the subfamily of SRC family non-receptor tyrosine kinases. Exemplary inhibitors in this respect include Dasatinib. Other examples in this regard include Ponatinib, sarcatinib, and bosutinib In yet different embodiments, the additional therapeutic agent is a mitogen-activated protein kinase (MEK) inhibitor. In some of these embodiments, the mitogen-activated protein kinase (MEK) inhibitor is trametinib, selumetinib, cobimetinib, PD0325901, or RO5126766. In other embodiments the MEK inhibitor is GSK-1120212, also known as trametinib.

In yet different embodiments, the additional therapeutic agent is an extracellular-signal-regulated kinase (ERK) inhibitor. In some of these embodiments, the extracellular-signal-regulated kinase (ERK) inhibitor is SCH722984 or GDC-0994.

In other embodiments, the additional therapeutic agent is a protein kinase inhibitor, such as Staurosporine or Midostaurin. In other embodiments the protein kinase inhibitor is Afatinib, Axitinib, Bevacizumab, Bostutinib, Cetuximab, Crizotinib, Dasatinib, Erlotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, or Vemurafenib. In still more embodiments, the additional therapeutic agent is a topoisomerase inhibitor. In some of these embodiments, the topoisomerase inhibitor is Irinotecan. In some more embodiments, the additional therapeutic agent is a taxane. Exemplary taxanes include Taxol and Docetaxel.

In still different embodiments, wherein the additional therapeutic agent is an mTOR inhibitor, such as Rapamycin or MLN0128.

The exact method for administering the compound and the additional therapeutic agent will be apparent to one of ordinary skill in the art. In some exemplary embodiments the compound and the additional therapeutic agent are co-administered. In other embodiments, the compound and the additional therapeutic agent are separately administered.

In some embodiments, the compound and the additional therapeutic agent are administered with the second agent simultaneously or separately. This administration in combination can include simultaneous administration of the two agents in the same dosage form, simultaneous administration in separate dosage forms, and separate administration. That is, the compound and any of the additional therapeutic agents described herein can be formulated together in the same dosage form and administered simultaneously. Alternatively, the compound and any of the additional therapeutic agents described herein can be simultaneously administered, wherein both the agents are present in separate formulations. In another alternative, the compound can be administered just followed by and any of the additional therapeutic agents described herein, or vice versa. In some embodiments of the separate administration protocol, the compound and any of the additional therapeutic agents described herein are administered a few minutes apart, or a few hours apart, or a few days apart.

While not wishing to be bound by theory, it is believed that the effectiveness of the presently described combination therapies is related, at least in part, to the synergistic ability of the individual components to induce apoptosis in cells comprising KRAS, HRAS or NRAS G12C mutant protein. Accordingly, in certain embodiments a method for inducing apoptosis in a cell population comprising a KRAS, HRAS or NRAS G12C mutant protein is provided, the method comprising administering an effective amount of a KRAS, HRAS or NRAS G12C mutant modulating compound and an additional therapeutic agent. Compounds and additional therapeutic agents useful in such methods include any of these described herein.

The described methods also find utility for inhibiting tumor metastasis, and in some embodiments, a method for inhibiting tumor metastasis in a subject having a KRAS, HRAS or NRAS G12C mutant cancer is provided, the method comprising administering an effective amount of a KRAS, HRAS or NRAS G12C mutant modulating compound and an additional therapeutic agent. Compounds and additional therapeutic agents useful for inhibiting tumor metastasis include any of these described herein.

The described methods are generally applicable to any type of cancer. In certain embodiments the cancer is associated with a KRAS, HRAS or NRAS G12C mutant protein. In some more specific embodiments, the cancer is associated with a KRAS, HRAS or NRAS G12C mutant protein. While many cancers are can be treated according to the disclosed methods, some embodiments are directed to treatment of hematological cancer, pancreatic cancer, MYH associated polyposis, colorectal cancer or lung cancer.

KRAS, HRAS or NRAS G12C mutations have also been identified in hematological malignancies (e.g., cancers that affect blood, bone marrow and/or lymph nodes). Accordingly, certain embodiments of the methods are directed to treatment of a hematological malignancy. Such malignancies include, but are not limited to leukemias and lymphomas. For example, the presently disclosed combination therapy can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the methods are useful for treatment of lymphomas such as all subtypes of Hodgkin's lymphoma or non-Hodgkin's lymphoma.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g., Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes, specific for the KRAS, HRAS or NRAS G12C mutation, are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

In some embodiments, the disclosed methods are for treating a hyperproliferative disorder in a subject that comprises administering to said subject a therapeutically effective amount of a KRAS, HRAS or NRAS G12C mutant modulating compound and an additional therapeutic agent to a subject in need thereof. The compounds and additional therapeutic reagents useful in this regard include any of those described herein. In some embodiments, said method relates to the treatment of cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In certain particular embodiments, the invention relates to methods for treatment of lung cancers, the methods comprise administering an effective amount of a KRAS, HRAS or NRAS G12C mutant modulating compound and an additional therapeutic agent to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with the methods of this invention include, for example, subjects that have been diagnosed as having acute myeloid leukemia, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing's sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/ plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments subjects that are treated according to the methods of the invention include subjects that have been diagnosed as having a non-cancerous hyperproliferative disorder such as benign hyperplasia of the skin (e. g., psoriasis), restenosis, or prostate (e. g., benign prostatic hypertrophy (BPH)).

The invention further provides methods of modulating a G12C Mutant KRAS, HRAS or NRAS protein activity by contacting the protein with an effective amount of a KRAS, HRAS or NRAS G12C mutant modulating compound and an additional therapeutic agent. Modulation can be inhibiting or activating protein activity. In some embodiments, the invention provides methods of inhibiting protein activity by contacting the G12C Mutant KRAS, HRAS or NRAS protein with an effective amount of a KRAS, HRAS or NRAS G12C mutant modulating compound and an additional therapeutic agent in solution. In some embodiments, the invention provides methods of inhibiting the G12C Mutant KRAS, HRAS or NRAS protein activity by contacting a cell, tissue, organ that express the protein of interest with a KRAS, HRAS or NRAS G12C mutant modulating compound and an additional therapeutic agent. In some embodiments, the invention provides methods of inhibiting protein activity in subject including but not limited to rodents and mammal (e.g., human) by administering into the subject an effective amount of a KRAS, HRAS or NRAS G12C mutant modulating compound and an additional therapeutic agent. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the invention provides methods of inhibiting KRAS, HRAS or NRAS G12C activity in a cell by contacting said cell with an amount of a KRAS, HRAS or NRAS G12C mutant modulating compound and an additional therapeutic agent sufficient to inhibit the activity of KRAS, HRAS or NRAS G12C in said cell. In some embodiments, the invention provides methods of inhibiting KRAS, HRAS or NRAS G12C activity in a tissue by contacting said tissue with an amount of a KRAS, HRAS or NRAS G12C mutant modulating compound and an additional therapeutic agent sufficient to inhibit the activity of KRAS, HRAS or NRAS G12C in said tissue. In some embodiments, the invention provides methods of inhibiting KRAS, HRAS or NRAS G12C activity in an organism by contacting said organism with an amount of a KRAS, HRAS or NRAS G12C mutant modulating compound and an additional therapeutic agent sufficient to inhibit the activity of KRAS, HRAS or NRAS G12C in said organism. In some embodiments, the invention provides methods of inhibiting KRAS, HRAS or NRAS G12C activity in an animal by contacting said animal with an amount of a KRAS, HRAS or NRAS G12C mutant modulating compound and an additional therapeutic agent sufficient to inhibit the activity of KRAS, HRAS or NRAS G12C in said animal. In some embodiments, the invention provides methods of inhibiting KRAS, HRAS or NRAS G12C activity in a subject by contacting said subject with an amount of a KRAS, HRAS or NRAS G12C mutant modulating compound and an additional therapeutic agent sufficient to inhibit the activity of KRAS, HRAS or NRAS G12C in said subject. In some embodiments, the invention provides methods of inhibiting KRAS, HRAS or NRAS G12C activity in a human by contacting said human with an amount of a KRAS, HRAS or NRAS G12C mutant modulating compound and an additional therapeutic agent sufficient to inhibit the activity of KRAS, HRAS or NRAS G12C in said human. The present invention provides methods of treating a disease mediated by KRAS, HRAS or NRAS G12C activity in a subject in need of such treatment.

The additional therapeutic agent can be selected from any number of therapeutic agents useful for treating cancer. Such therapeutic agents can be approved for use in humans or experimental. In some embodiments, the additional therapeutic agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In addition to the above examples, other non-limiting examples of additional therapeutic agents useful in the described methods are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This invention further relates to a method for using a KRAS, HRAS or NRAS G12C mutant modulating compound and an additional therapeutic agent, in combination with radiation therapy for inhibiting abnormal cell growth or treating the hyperproliferative disorder in the subject. Techniques for administering radiation therapy are known in the art, and these techniques can be used in the combination therapy described herein. The administration of the a KRAS, HRAS or NRAS G12C mutant modulating compound and an additional therapeutic agent in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the methods of the present invention can render abnormal cells more sensitive to treatment with radiation for purposes of killing and/or inhibiting the growth of such cells. Accordingly, this invention further relates to a method for sensitizing abnormal cells in a subject to treatment with radiation which comprises administering to the subject an amount of a KRAS, HRAS or NRAS G12C mutant modulating compound and an additional therapeutic agent, which amount is effective is sensitizing abnormal cells to treatment with radiation. The amount of the KRAS, HRAS or NRAS G12C mutant modulating compound and an additional therapeutic agent in this method can be determined according to the means for ascertaining effective amounts known in the art.

In other embodiments, the additional therapeutic agent is selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used as the additional therapeutic agent in the methods described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

B. Compounds

As noted above, embodiments of the present methods include administration of a KRAS, HRAS or NRAS G12C mutant modulating compound ("compound"). The compounds have activity as modulators of KRAS, HRAS or NRAS G12C mutant protein activity. In some embodiments, the compound is a KRAS, HRAS or NRAS G12C mutant modulating compound. In an aspect, the compounds are capable of selectively binding to and/or modulating a G12C mutant KRAS, HRAS or NRAS protein. The compounds may modulate the G12C mutant KRAS, HRAS or NRAS protein by reaction with an amino acid. While not wishing to be bound by theory, the present applicants believe that, in some embodiments, the compounds selectively react with the G12C mutant KRAS, HRAS or NRAS proteins by forming a covalent bond with the cysteine at the 12 position of a G12C mutant KRAS, HRAS or NRAS protein. By binding to the Cystine 12, the compounds may lock the switch II of the G12C mutant KRAS, HRAS or NRAS into an inactive stage. This inactive stage may be distinct from those observed for GTP and GDP bound KRAS, HRAS or NRAS. Some of the compounds may also be able to perturb the switch I conformation. Some of the compounds may favor the binding of the bound KRAS, HRAS or NRAS to GDP rather than GTP and therefore sequester the KRAS, HRAS or NRAS into an inactive KRAS, HRAS or NRAS GDP state. Because effector binding to KRAS, HRAS or NRAS is highly sensitive to the conformation of switch I and II, the irreversible binding of these compounds may disrupt KRAS, HRAS or NRAS downstream signaling.

The present methods are not limited by the exact structure of the KRAS, HRAS or NRAS G12C mutant modulating compound, provided it has the above noted functionality (e.g., modulating KRAS, HRAS or NRAS G12C mutant protein activity). Examples of compounds useful in certain embodiments of the methods are provided in PCT Pub. Nos. WO 2013/155223 and 2015/054572, the compounds and methods of which are incorporated herein by reference in their entirety. Other compounds useful in different embodiments of the method are provided herein below.

1. Compounds of Structure (I)

As noted above, in one embodiment of the present invention, compounds having activity as modulators of a G12C mutant KRAS, HRAS or NRAS protein are provided, the compounds have the following structure (I):

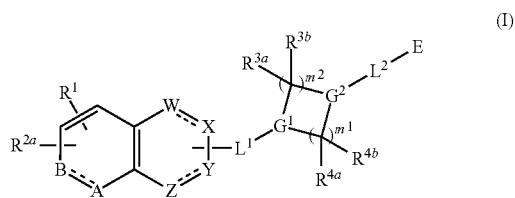

(I)

or a pharmaceutically acceptable salt, tautomer, prodrug or stereoisomer thereof, wherein:

A is $CR^1$, $CR^{2b}$, $NR^5$ or S;

B is a bond, $CR^1$ or $CR^{2c}$ $G^1$ and $G^2$ are each independently N or CH;

W, X and Y are each independently N, $NR^5$ or $CR^6$;

Z is a bond, N or $CR^6$;

$L^1$ is a bond or $NR^7$;

$L^2$ is a bond or alkylene;

$R^1$ is H, cyano, halo, $C_1$-$C_6$alkyl, $C_1$-$C_6$alkylaminyl, $C_3$-$C_8$ cycloalkyl, $C_1$-$C_6$alkenyl or $C_3$-$C_8$cycloalkenyl, heterocyclyl, heteroaryl, aryloxy or aryl;

$R^{2a}$, $R^{2b}$ and $R^{2c}$ are each independently H, halo, hydroxyl, $C_1$-$C_6$ alkyl, $C_1$-$C_6$ haloalkyl, $C_1$-$C_6$ alkoxy, $C_3$-$C_8$ cycloalkyl or aryl;

$R^{3a}$ and $R^{3b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{3a}$ and $R^{3b}$ join to form a carbocyclic or heterocyclic ring; or $R^{3a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{4a}$ and $R^{4b}$ join to form a carbocyclic or heterocyclic ring; or $R^{4a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ is, at each occurrence, independently H, $C_1$-$C_6$ alkyl or a bond to $L^1$;

$R^6$ is, at each occurrence, independently H, oxo, cyano, cyanoalkyl, amino, aminylalkyl, aminylalkylaminyl, aminylcarbonyl, alkylaminyl, haloalkylaminyl, hydroxylalkyaminyl, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylaminyl, heterocyclylalkylaminyl, heteroaryl, heteroaryloxy, heteroarylalkyloxy, heteroarylaminyl, heteroarylalkylaminyl, aryl, aryloxy, arylamino, arylalkylamino, arylalkyloxy or a bond to $L^1$;

$R^7$ is H or $C_1$-$C_6$ alkyl;

$m^1$ and $m^2$ are each independently 1, 2 or 3;

----- indicates a single or double bond such that all valences are satisfied; and E is an electrophilic moiety capable of forming a covalent bond with the cysteine residue at position 12 of a KRAS, HRAS or NRAS G12C mutant protein, wherein at least one of W, X, Y or Z is $CR^6$ where $R^6$ is a bond to $L^1$.

In some embodiments when $R^1$, $R^{2a}$, $R^{2b}$ and $R^{2c}$ are all independently selected from H and halo, then X and Z are both N and at least one of $R^{3a}$, $R^{3b}$, $R^{4a}$ or $R^{4b}$ is not H, and provided that at least one of $R^{2a}$, $R^{2b}$ or $R^{2c}$ is not H when $R^1$ is pyridyl.

In other embodiments, the compound has the following structure (I):

(I)

or a pharmaceutically acceptable salt, tautomer, prodrug or stereoisomer thereof, wherein:

A is $CR^1$, $CR^{2b}$, $NR^7$ or S;

B is a bond, $CR^1$ or $CR^{2c}$ $G^1$ and $G^2$ are each independently N or CH;

W, X and Y are each independently N, $NR^5$ or $CR^6$;

Z is a bond, N or $CR^{6a}$ or Z is NH when Y is C=O;

$L^1$ is a bond or $NR^7$;

$L^2$ is a bond or alkylene;

$R^1$ is H, cyano, halo, heterocyclyl, heteroaryl, aryloxy or aryl;

$R^{2a}$, $R^{2b}$ and $R^{2C}$ are each independently H, halo, hydroxyl, $C_1$-$C_6$ alkyl, $C_1$-$C_6$ haloalkyl, $C_1$-$C_6$ alkoxy, $C_3$-$C_8$ cycloalkyl or aryl;

$R^{3a}$ and $R^{3b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminocarbonylalkyl or aminocarbonyl; or $R^{3a}$ and $R^{3b}$ join to form a carbocyclic or heterocyclic ring; or $R^{3a}$ is H, —OH, —NH$_2$, —CO$_2$H, halo, cyano, $C_1$-$C_6$ alkyl, $C_1$-$C_6$ alkynyl, hydroxylalkly, aminoalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminocarbonylalkyl or aminocarbonyl; or $R^{4a}$ and $R^{4b}$ join to form a carbocyclic or heterocyclic ring; or $R^{4a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminoalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ is, at each occurrence, independently H, $C_1$-$C_6$ alkyl or a bond to $L^1$;

$R^6$ is, at each occurrence, independently H, oxo, cyano, cyanoalkyl, amino, aminylalkyl, aminylalkylaminyl, aminocarbonyl, alkylaminyl, haloalkylamino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino, arylalkyloxy or a bond to $L^1$;

$R^{6a}$ is H, alkyl or a bond to $L^1$;

$R^7$ is H or $C_1$-$C_6$ alkyl $m^1$ and $m^2$ are each independently 1, 2 or 3;

----- indicates a single or double bond such that all valences are satisfied; and E is an electrophilic moiety capable of forming a covalent bond with the cysteine residue at position 12 of a KRAS, HRAS or NRAS G12C mutant protein, wherein at least one of W, X, Y or Z is $CR^6$ where $R^6$ is a bond to $L^1$ or at least one of W, X or Y is $NR^5$, wherein $R^5$ is a bond to $L^1$.

In some embodiments of the compound of structure (I), the bond between W and X is a double bond. In other embodiments, the bond between Y and Z is a double bond. In more embodiments, the bond between A and B is a double bond. In still more embodiments, the bonds between W and X, Y and Z and A and B are each double bonds.

In some more embodiments of the foregoing compound of structure (I):

A is $CR^1$, $CR^{2b}$, $NR^7$ or S;

B is a bond, $CR^1$ or $CR^{2c}$ $G^1$ and $G^2$ are each independently N or CH;

W, X and Y are each independently N, $NR^5$ or $CR^6$;

Z is a bond, N or $CR^6$;

$L^1$ is a bond or $NR^7$;

$L^2$ is a bond or alkylene;

$R^1$ is H, cyano, halo, heterocyclyl, heteroaryl, aryloxy or aryl;

$R^{2a}$, $R^{2b}$ and $R^{2C}$ are each independently H, halo, hydroxyl, $C_1$-$C_6$ alkyl, $C_1$-$C_6$ haloalkyl $C_3$-$C_8$ cycloalkyl or aryl;

$R^{3a}$ and $R^{3b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{3a}$ and $R^{3b}$ join to form a carbocyclic or heterocyclic ring; or $R^{3a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl; or $R^{4a}$ and $R^{4b}$ join to form a carbocyclic or heterocyclic ring; or $R^{4a}$ is H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminylcarbonylalkyl or aminylcarbonyl, and $R^{4b}$ joins with $R^{3b}$ to form a carbocyclic or heterocyclic ring;

$R^5$ and $R^7$ are each independently H or $C_1$-$C_6$ alkyl;

$R^6$ is, at each occurrence, independently H, oxo, cyano, cyanoalkyl, amino, aminylcarbonyl, alkylaminyl, $C_1$-$C_6$ alkoxy, $C_1$-$C_6$ alkyl or a bond to $L^1$;

$m^1$ and $m^2$ are each independently 1, 2 or 3;

----- indicates a single or double bond such that all valences are satisfied; and E is an electrophilic moiety capable of forming a covalent bond with the cysteine residue at position 12 of a KRAS, HRAS or NRAS G12C mutant protein, wherein at least one of W, X, Y or Z is $CR^6$ where $R^6$ is a bond to $L^1$, and provided that when $R^1$, $R^{2a}$, $R^{2b}$ and $R^{2c}$ are all independently selected from H and halo, then X and Z are both N and at least one of $R^{3a}$, $R^{3b}$, $R^{4a}$ or $R^{4b}$ is not H, and provided that at least one of $R^{2a}$, $R^{2b}$ or $R^{2c}$ is not H when $R^1$ is pyridyl.

In some other embodiments of the foregoing compound of structure (I):

A is $CR^{2b}$, $NR^7$ or S;
B is a bond or $CR^{2c}$
$G^1$ and $G^2$ are each independently N or CH;
W, X and Y are each independently N, $NR^5$ or $CR^6$;
Z is a bond, N or $CR^6$;
$L^1$ is a bond or $NR^7$;
$L^2$ is a bond or alkylene;
$R^1$ is cyano, $C_1$-$C_6$alkyl, $C_1$-$C_6$alkylaminyl, $C_3$-$C_8$ cycloalkyl, $C_1$-$C_6$alkenyl or $C_3$-$C_8$ cycloalkenyl, heterocyclyl or aryl;
$R^{2a}$, $R^{2b}$ and $R^{2C}$ are each independently H, halo, $C_1$-$C_6$ alkyl or $C_3$—C cycloalkyl;
$R^{3a}$ and $R^{3b}$ are, at each occurrence, independently H, —OH, —$NH_2$, —$CO_2H$, halo, cyano, hydroxylalkly, aminylalkyl, cyanoalkyl, carboxyalkyl or aminylcarbonyl; or $R^{3a}$ and $R^{3b}$ join to form a carbocyclic or heterocyclic ring; or $R^{3a}$ is H, —OH, —$NH_2$, —$CO_2H$, halo, cyano, hydroxylalkly, aminylalkyl, cyanoalkyl, carboxyalkyl or aminylcarbonyl, and $R^{3b}$ joins with $R^{4b}$ to form a carbocyclic or heterocyclic ring;
$R^{4a}$ and $R^{4b}$ are, at each occurrence, independently H, —OH, —$NH_2$, —$CO_2H$, halo, cyano, hydroxylalkly, aminylalkyl, cyanoalkyl, carboxyalkyl or aminylcarbonyl; or $R^{4a}$ and $R^{4b}$ join to form a carbocyclic or heterocyclic ring; or $R^{4a}$ is H, —OH, —$NH_2$, —$CO_2H$, halo, cyano, hydroxylalkly, aminylalkyl, cyanoalkyl, carboxyalkyl or aminylcarbonyl, and $R^{4b}$ joins with $R^{3b}$ to form a carbocyclic or heterocyclic ring;
$R^5$ and $R^7$ are each independently H or $C_1$-$C_6$alkyl;
$R^6$ is, at each occurrence, independently H, cyano, amino, alkylaminyl, $C_1$-$C_6$alkoxy, $C_1$-$C_6$alkyl or a bond to $L^1$;
$m^1$ and $m^2$ are each independently 1, 2 or 3;
----- indicates a single or double bond such that all valences are satisfied; and E is an electrophilic moiety capable of forming a covalent bond with the cysteine residue at position 12 of a KRAS, HRAS or NRAS G12C mutant protein, wherein at least one of W, X or Y is $CR^6$ where $R^6$ is a bond to $L^1$.

In still other embodiments of the foregoing compound of structure (I), $R^1$ is H, cyano, halo, heterocyclyl, heteroaryl, aryloxy or aryl.

The structure of E is not particularly limited provided it is capable of forming a covalent bond with a nucleophile, such as the cysteine residue at position 12 of a KRAS, HRAS or NRAS G12C mutant protein. Accordingly, moieties which are capable of reaction with (e.g., by covalent bond formation) a nucleophile are preferred. In certain embodiments, E is capable of reacting in a conjugate addition manner (e.g., 1,4-conjugate addition) with an appropriately reactive nucleophile. In some embodiments, E comprises conjugated pi bonds such that delocalization of electrons results in at least one atom (e.g., a carbon atom) having a positive charge, partial positive charge or a polarized bond. In other embodiments, E comprises one or more bonds wherein the electronegativity of the two atoms forming the bonds is sufficiently different such that a partial positive charge (e.g., by polarization of the bond) resides on one of the atoms, for example on a carbon atom. E moieties comprising carbon-halogen bonds, carbon-oxygen bonds or carbon bonds to various leaving groups known in the art are examples of such E moieties.

In certain embodiments of the foregoing, E has the following structure:

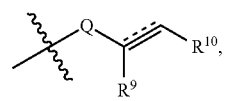

wherein:

$\equiv$ represents a double or triple bond;
Q is —C(=O)—, —C(=$NR^{8'}$)—, —$NR^8C$(=O)—, —S(=O)$_2$— or —$NR^8S$(=O)$_2$—;
$R^8$ is H, $C_1$-$C_6$alkyl or hydroxylalkyl;
$R^{8'}$ is H, —OH, —CN or $C_1$-$C_6$alkyl; and when $\equiv$ is a double bond then $R^9$ and $R^{10}$ are each independently H, cyano, carboxyl, $C_1$-$C_6$alkyl, alkoxycarbonyl, aminylalkyl, alkylaminylalkyl, or hydroxylalkyl or $R^9$ and $R^{10}$ join to form a carbocyclic or heterocyclic ring;

when $\equiv$ is a triple bond; then $R^9$ is absent and $R^{10}$ is H, $C_1$-$C_6$alkyl, aminylalkyl, alkylaminylalkyl or hydroxylalkyl.

In certain embodiments when $\equiv$ is a double bond then $R^9$ and $R^{10}$ are each independently H, cyano, $C_1$-$C_6$alkyl, aminylalkyl, alkylaminylalkyl, or hydroxylalkyl or $R^9$ and $R^{10}$ join to form a carbocyclic or heterocyclic ring.

In some of the foregoing embodiments, Q is —C(=O)—, —$NR^8C$(=O)—, —S(=O)$_2$— or —$NR^8S$(=O)$_2$—.

In some other of the foregoing embodiments, Q is —C(=$NR^{8'}$)—, wherein $R^{8'}$ is H, —OH, —CN or $C_1$-$C_6$alkyl. For example, in some embodiments $R^{8'}$ is H. In other embodiments, $R^{8'}$ is —CN. In other embodiments, $R^{8'}$ is —OH.

In some embodiments, the compound has the following structure (I'):

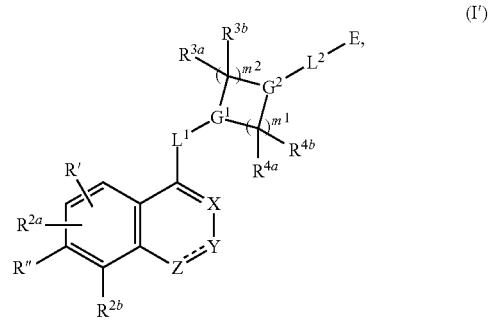

wherein R' is $R^1$ and R" is $R^{2c}$ or R' is H and R" is $R^1$.

In other embodiments, the compound has the following structure (I'a):

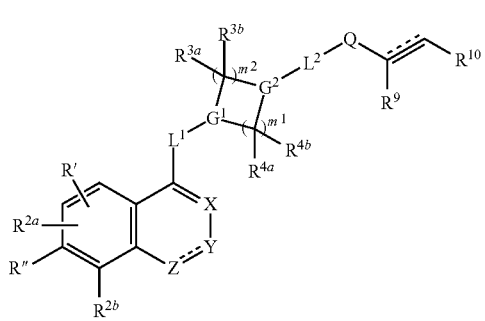

(I'a)

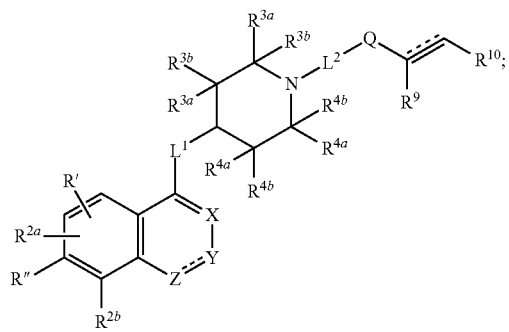

(I'c)

wherein:

≡ represents a double or triple bond;

Q is —C(=O)—, —C(=NR⁸')—, —NR⁸C(=O)—, —S(=O)₂— or —NR⁸S(=O)₂—;

$R^8$ is H, $C_1$-$C_6$alkyl or hydroxylalkyl;

$R^{8'}$ is H, —OH, —CN or $C_1$-$C_6$alkyl;

when ≡ is a double bond then $R^9$ and $R^{10}$ are each independently H, cyano, carboxyl, $C_1$-$C_6$alkyl, alkoxycarbonyl, aminylalkyl, alkylaminylalkyl, heteroaryl or hydroxylalkyl or $R^9$ and $R^{10}$ join to form a carbocyclic or heterocyclic ring;

when ≡ is a triple bond then $R^9$ is absent and $R^{10}$ is H, $C_1$-$C_6$alkyl, aminylalkyl, alkylaminylalkyl or hydroxylalkyl; and R' is $R^1$ and R" is $R^{2c}$ or R' is H and R" is $R^1$.

In some of the foregoing embodiments of compound (I'a), Q is Q is —C(=O)—, —NR⁸C(=O)—, —S(=O)₂— or —NR⁸S(=O)₂—.

In some other of the foregoing embodiments of compound (I'a), Q is —C(=NR⁸')—, wherein $R^{8'}$ is H, —OH, —CN or $C_1$-$C_6$alkyl. For example, in some embodiments $R^{8'}$ is H. In other embodiments, $R^{8'}$ is —CN. In other embodiments, $R^{8'}$ is —OH.

In still more embodiments of the foregoing compounds, the compound has one of the following structures (I'b), (I'c), (I'd) or (I'e):

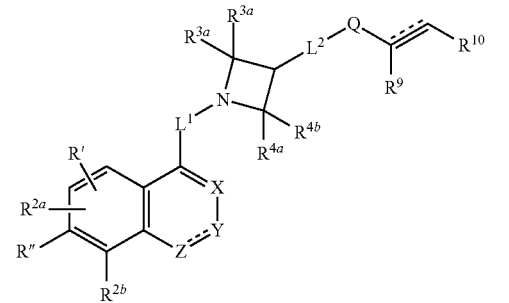

(I'd)

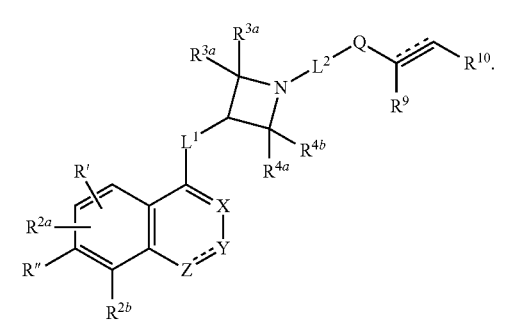

(I'e)

In still more embodiments, the compound has one of the following structures (I'f), (I'g), (I'h) or (I'i):

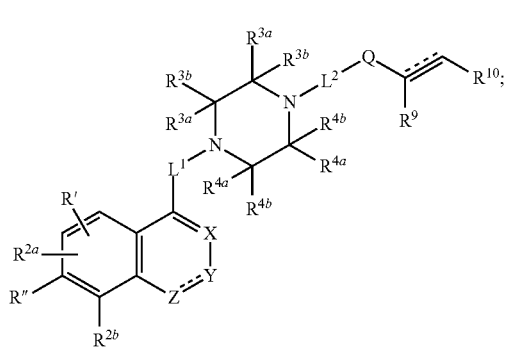

(I'b)

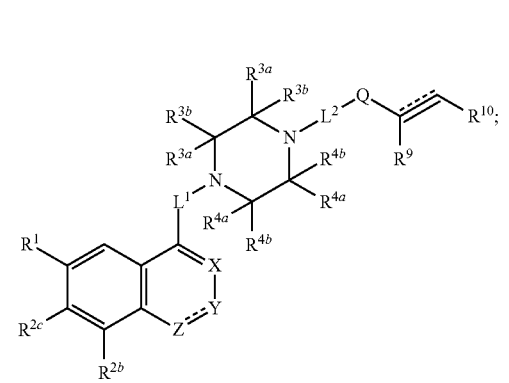

(I'f)

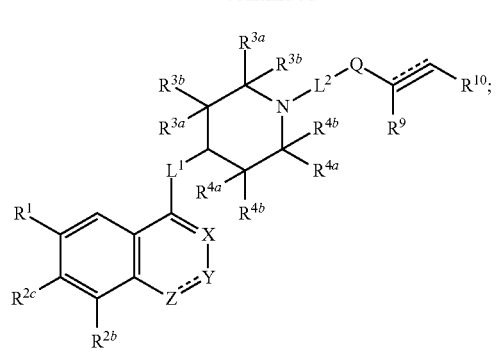

(I'g)

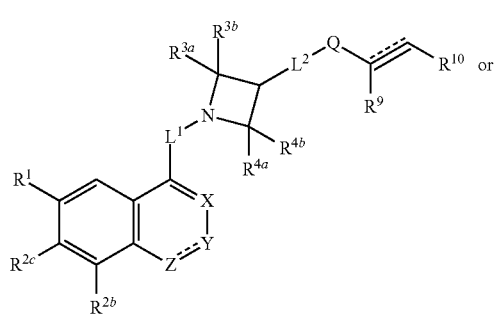

(I'h)

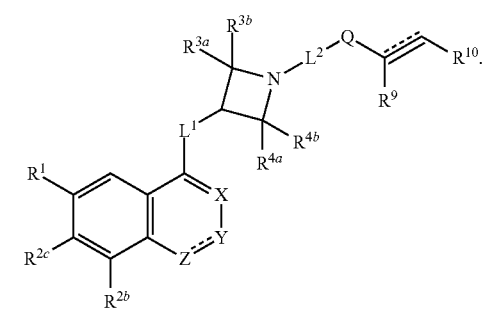

(I'i)

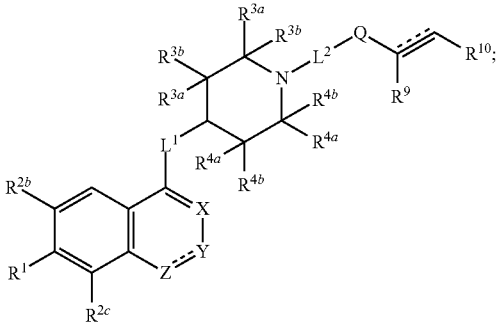

(I'k)

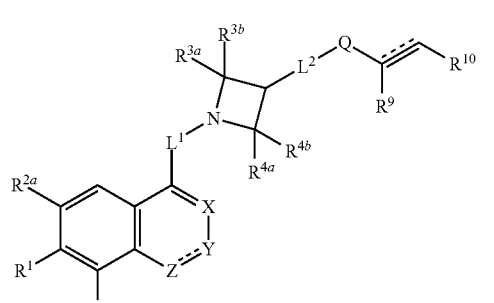

(I'l) or

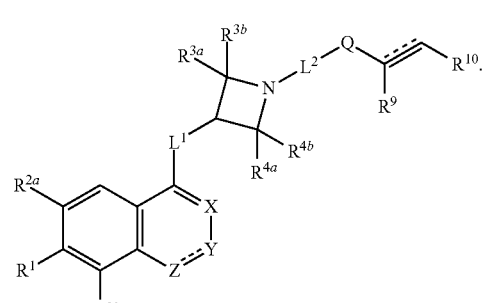

(I'm)

In some embodiments of the compounds of structures (I'f), (I'g), (I'h) or (I'i), $R^1$ is aryl and $R^{2c}$ and $R^{2b}$ are independently selected from H and halo, for example in some further embodiments $R^1$ is aryl and $R^{2c}$ and $R^{2b}$ are independently selected from halo.

In different embodiments, the compound has one of the following structures (I'j), (I'k), (I'l) or (I'm):

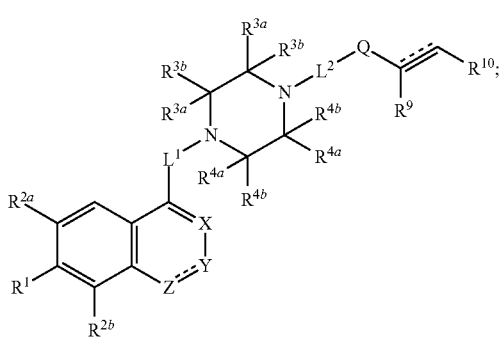

(I'j)

In some embodiments of the compounds of structures (I'j), (I'k), (I'l) or (I'm), $R^1$ is aryl and $R^{2a}$ and $R^{2b}$ are independently selected from H and halo, for example in some further embodiments $R^1$ is aryl and $R^{2a}$ and $R^{2b}$ are independently selected from halo.

In other embodiments, the compound has the following structure (I''):

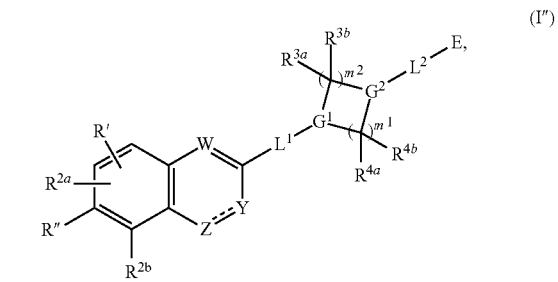

(I'')

wherein R' is $R^1$ and R'' is $R^{2c}$ or R' is H and R'' is $R^1$. For example, in some embodiments the compound has the following structure (I''a):

(I″a)

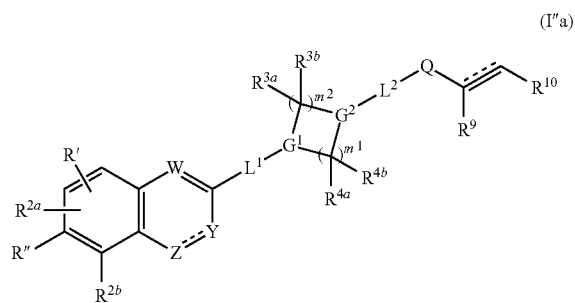

wherein:

≡ represents a double or triple bond;
Q is —C(=O)—, —C(=NR⁸')—, —NR⁸C(=O)—, —S(=O)₂— or —NR⁸S(=O)₂—;
$R^8$ is H, $C_1$-$C_6$alkyl or hydroxylalkyl;
$R^{8'}$ is H, —OH, —CN or $C_1$-$C_6$alkyl;
when ≡ is a double bond then $R^9$ and $R^{10}$ are each independently H, cyano, carboxyl, $C_1$-$C_6$alkyl, alkoxycarbonyl, aminylalkyl, alkylaminylalkyl, heteroaryl or hydroxylalkyl or $R^9$ and $R^{10}$ join to form a carbocyclic or heterocyclic ring;
when ≡ is a triple bond then $R^9$ is absent and $R^{10}$ is H, $C_1$-$C_6$alkyl, aminylalkyl, alkylaminylalkyl or hydroxylalkyl; and
R' is $R^1$ and R" is $R^{2c}$ or R' is H and R" is $R^1$.

In some of the foregoing embodiments of compound (I″a), Q is Q is —C(=O)—, —NR⁸C(=O)—, —S(=O)₂— or —NR⁸S(=O)₂—.

In some other of the foregoing embodiments of compound (I″a), Q is —C(=NR⁸')—, wherein $R^{8'}$ is H, —OH, —CN or $C_1$-$C_6$alkyl. For example, in some embodiments $R^{8'}$ is H. In other embodiments, $R^{8'}$ is —CN. In other embodiments, $R^{8'}$ is —OH.

In other embodiments, the compound has one of the following structures (I″b), (I″c), (I″d) or (I″e):

(I″b)

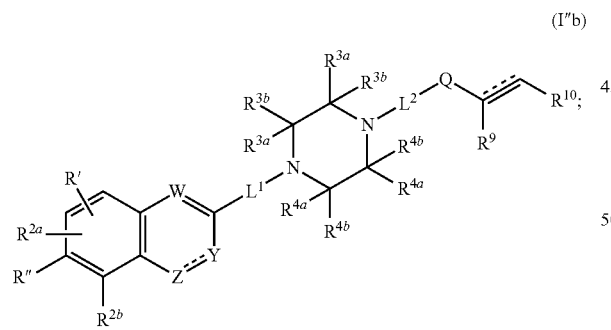

(I″c)

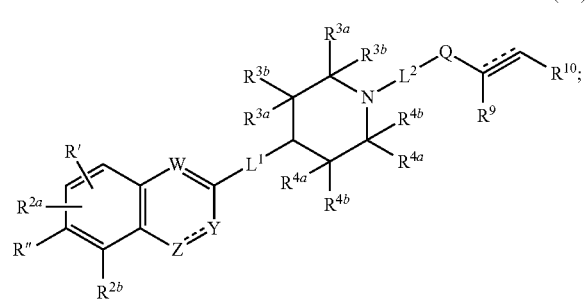

(I″d)

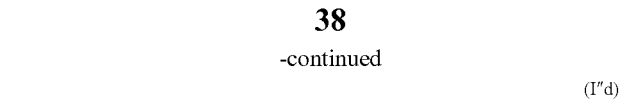

(I″e)

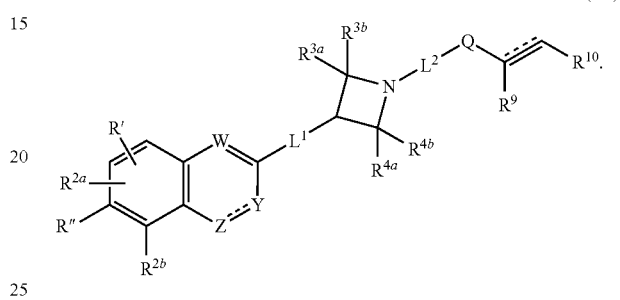

In other embodiments, the compound has one of the following structures (I″f), (I″g), (I″h) or (I″i):

(I″f)

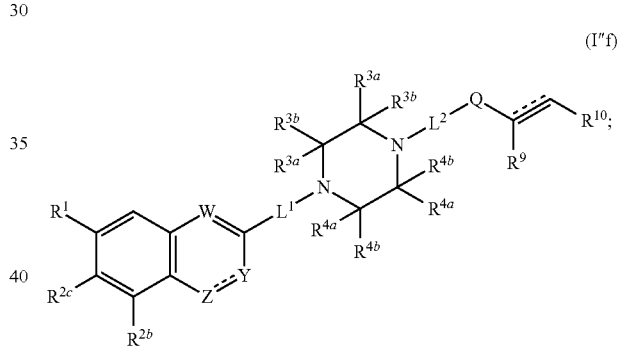

(I″g)

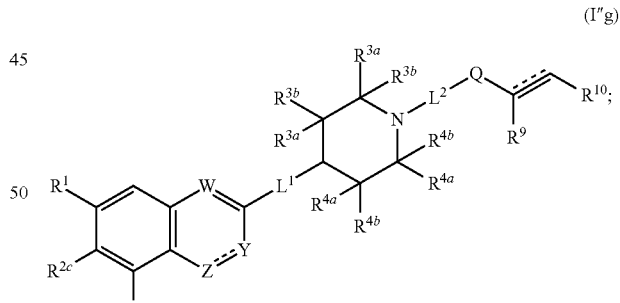

(I″h)

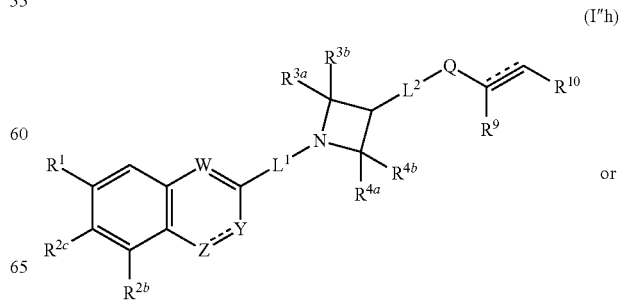

or

-continued

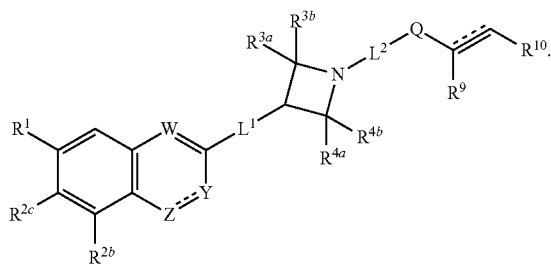
(I″i)

In some different embodiments, the compound has one of the following structures (I″j), (I″k), (I″l) or (I″m):

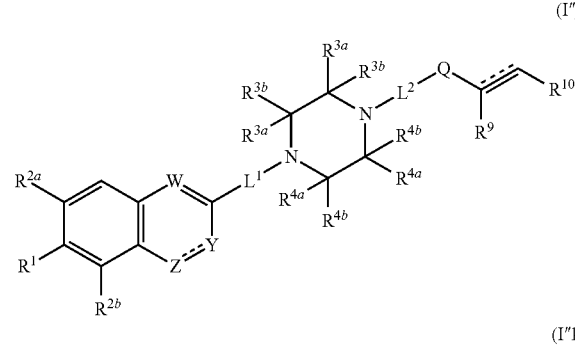
(I″j)

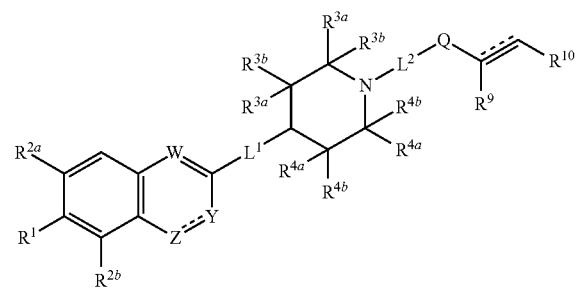
(I″k)

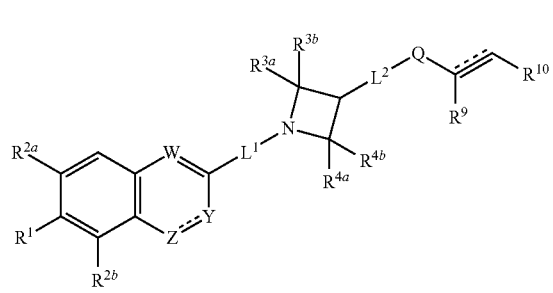
(I″l)

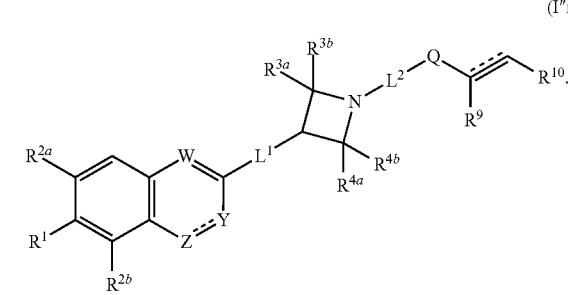
(I″m)

In other various embodiments, the compound has the following structure (I‴):

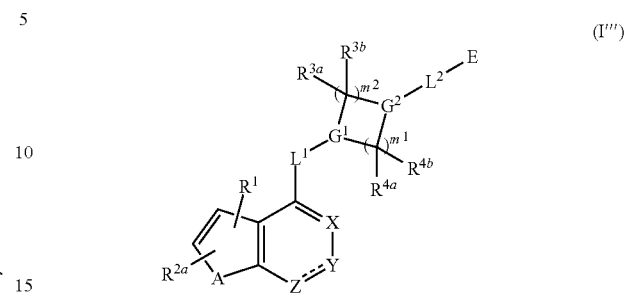
(I‴)

wherein A is NH or S.

For example, in some embodiments, the compound has the following structure (I‴a):

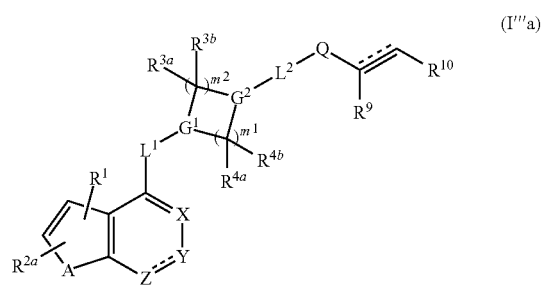
(I‴a)

wherein:

≡ represents a double or triple bond;

Q is —C(=O)—, —C(=NR$^{8'}$)—, —NR$^8$C(=O)—, —S(=O)$_2$— or —NR$^8$S(=O)$_2$—;

R$^8$ is H, C$_1$-C$_6$alkyl or hydroxylalkyl;

R$^{8'}$ is H, —OH, —CN or C$_1$-C$_6$alkyl; and when ≡ is a double bond then R$^9$ and R$^{10}$ are each independently H, cyano, carboxyl, C$_1$-C$_6$alkyl, alkoxycarbonyl, aminylalkyl, alkylaminylalkyl, heteroaryl or hydroxylalkyl or R$^9$ and R$^{10}$ join to form a carbocyclic or heterocyclic ring;

when ≡ is a triple bond then R$^9$ is absent and R$^{10}$ is H, C$_1$-C$_6$alkyl, aminylalkyl, alkylaminylalkyl or hydroxylalkyl; and A is NH or S.

In some of the foregoing embodiments of compound (I‴a), Q is Q is —C(=O)—, —NR$^8$C(=O)—, —S(=O)$_2$— or —NR$^8$S(=O)$_2$—.

In some other of the foregoing embodiments of compound (I‴a), Q is —C(=NR$^{8'}$)—, wherein R$^8$ is H, —OH, —CN or C$_1$-C$_6$alkyl. For example, in some embodiments R$^{8'}$ is H. In other embodiments, R$^{8'}$ is —CN. In other embodiments, R$^{8'}$ is —OH.

In other embodiments, the compound has one of the following structures (I‴b), (I‴c), (I‴d) or (I‴e):

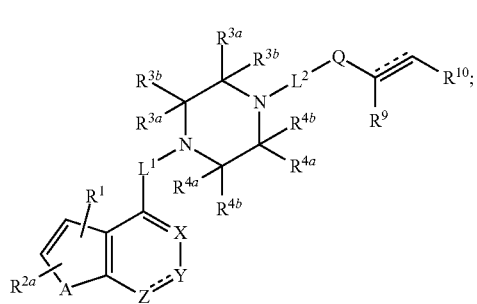
(I'''b)

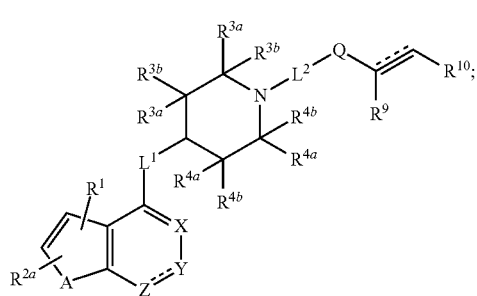
(I'''c)

(I'''d)

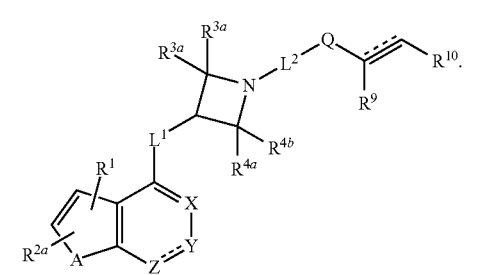
(I'''e)

In still more embodiments, the compound has one of the following structures (I'''f), (I'''g), (I'''h) or (I'''i):

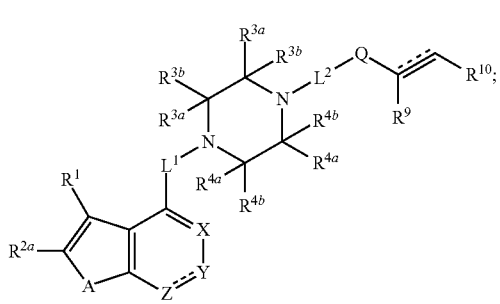
(I'''f)

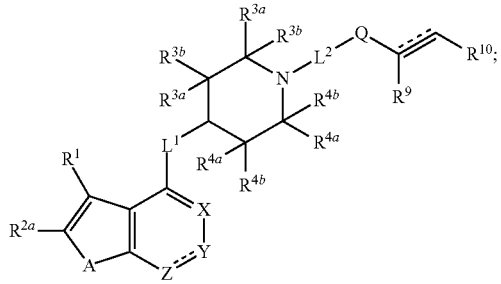
(I'''g)

(I'''h)

or (I'''i)

In certain embodiments of any of the foregoing, at least one of $G^1$ or $G^2$ is N. In other embodiments, at least one of W, X or Y is N or $NR^5$. In other embodiments, at least one of W, X or Y is N and at least one of W, X or Y is $CR^6$. For example, in some embodiments two of W, X and Y are N and one of W, X and Y is $CR^6$.

In some embodiments, at least one of W, X or Y is N or $NR^5$, wherein $R^5$ is a bond to $L^1$. In some other embodiments, at least one of W, X or Y is N or $CR^6$, wherein $R^6$ is a bond to $L^1$.

For example, in some different embodiments, the compound has one of the following structures:

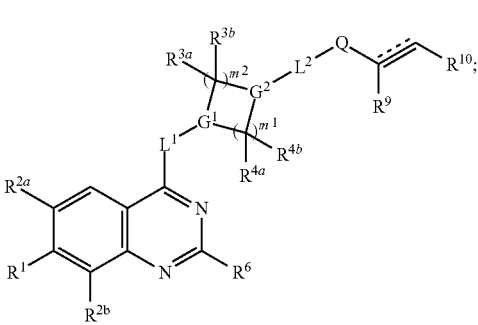
(I'n)

-continued

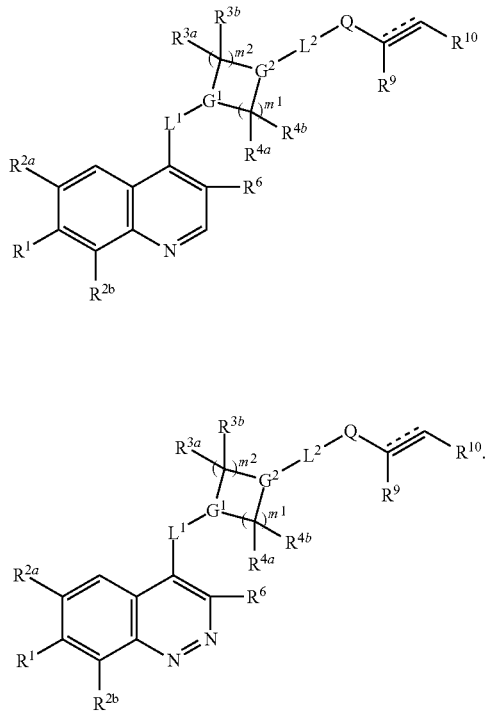

wherein:
═ represents a double or triple bond;
Q is —C(═O)—, —C(═NR⁸')—, —NR⁸C(═O)—, —S(═O)₂— or —NR⁸S(═O)₂—;
R⁸ is H, $C_1$-$C_6$alkyl or hydroxylalkyl;
R⁸' is H, —OH, —CN or $C_1$-$C_6$alkyl;
when ═ is a double bond then R⁹ and R¹⁰ are each independently H, cyano, carboxyl, $C_1$-$C_6$alkyl, alkoxycarbonyl, aminylalkyl, alkylaminylalkyl, heteroaryl or hydroxylalkyl or R⁹ and R¹⁰ join to form a carbocyclic or heterocyclic ring; and
when ═ is a triple bond then R⁹ is absent and R¹⁰ is H, $C_1$-$C_6$alkyl, aminylalkyl, alkylaminylalkyl or hydroxylalkyl.

In some embodiments of the compounds of structures (I'n), (I'o) or (I'p), R¹ is aryl or heteroaryl and $R^{2a}$ and $R^{2b}$ are independently selected from H and halo, for example in some further embodiments R¹ is aryl or heteroaryl and $R^{2a}$ and $R^{2b}$ are independently selected from halo, such as chloro and fluoro. In some embodiments, R¹ is aryl or heteroaryl, $R^{2a}$ is chloro and $R^{2b}$ is fluoro. In other embodiments R¹ is aryl or heteroaryl, one of $R^{2a}$ or $R^{2b}$ is halo, such as chloro or fluoro, and the other one of $R^{2a}$ or $R^{2b}$ is H. In other embodiments of the foregoing, R⁶ is H, cyano, cyanoalkyl, amino, or $C_1$-$C_6$ alkyl.

In other different embodiments, the bond between W and X Y and Z are both single bonds. For example, in some embodiments the compound has one of the following structures (I''''a) or (I''''b):

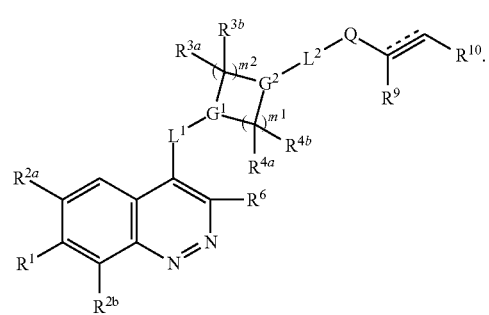

wherein:
═ represents a double or triple bond;
Q is —C(═O)—, —C(═NR⁸')—, —NR⁸C(═O)—, —S(═O)₂— or —NR⁸S(═O)₂—;
R⁸ is H, $C_1$-$C_6$alkyl or hydroxylalkyl;
R⁸' is H, —OH, —CN or $C_1$-$C_6$alkyl;
when ═ is a double bond then R⁹ and R¹⁰ are each independently H, cyano, carboxyl, $C_1$-$C_6$alkyl, alkoxycarbonyl, aminylalkyl, alkylaminylalkyl, heteroaryl or hydroxylalkyl or R⁹ and R¹⁰ join to form a carbocyclic or heterocyclic ring; and
when ═ a triple bond then R⁹ is absent and R¹⁰ is H, $C_1$-$C_6$alkyl, aminylalkyl, alkylaminylalkyl or hydroxylalkyl.

In some embodiments of the compounds of structures (I''''a) or (I''''b), R¹ is aryl or heteroaryl and $R^{2a}$ and $R^{2b}$ are independently selected from H and halo, for example in some further embodiments R¹ is aryl or heteroaryl and $R^{2a}$ and $R^{2b}$ are independently selected from halo, such as chloro and fluoro. In some embodiments, R¹ is aryl or heteroaryl, $R^{2a}$ is chloro and $R^{2b}$ is fluoro. In other embodiments R¹ is aryl or heteroaryl, one of $R^{2a}$ or $R^{2b}$ is halo, such as chloro or fluoro, and the other one of $R^{2a}$ or $R^{2b}$ is H. In other embodiments of the foregoing, R⁶ is H, cyano, cyanoalkyl, amino, or $C_1$-$C_6$ alkyl.

In yet more of any of the foregoing embodiments, E has the following structure:

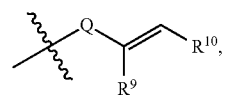

wherein:
Q is —C(═O)—, —C(═NR⁸')—, —NR⁸C(═O)—, —S(═O)₂— or —NR⁸S(═O)₂—;
R⁸ is H, $C_1$-$C_6$alkyl or hydroxylalkyl;
R⁸' is H, —OH, —CN or $C_1$-$C_6$alkyl; and $R^9$ and $R^{10}$ are each independently H, cyano, $C_1$-$C_6$alkyl, aminylalkyl, alkylaminylalkyl, or hydroxylalkyl or $R^9$ and $R^{10}$ join to form a carbocyclic or heterocyclic ring.

In some of the foregoing embodiments, Q is —C(═O)—, —NR$^8$C(═O)—, —S(═O)$_2$— or —NR$^8$S(═O)$_2$—.

In some other of the foregoing embodiments, Q is —C(═NR$^{8'}$)—, wherein R$^{8'}$ is H, —OH, —CN or $C_1$-$C_6$ alkyl. For example, in some embodiments R$^{8'}$ is H. In other embodiments, R$^{8'}$ is —CN. In other embodiments, R$^{8'}$ is —OH.

In still other of any of the foregoing embodiments, E has the following structure:

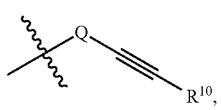

wherein:

Q is —C(═O)—, —NR$^8$C(═O)—, —S(═O)$_2$— or —NR$^8$S(═O)$_2$—;

R$^8$ is H, $C_1$-$C_6$alkyl or hydroxylalkyl; and

R$^{10}$ is H, $C_1$-$C_6$alkyl, aminylalkyl, alkylaminylalkyl or hydroxylalkyl.

In some embodiments $m^1$ is 1. In other embodiments $m^1$ is 2. In still more embodiments, $m^1$ is 3. In different embodiments, $m^2$ is 1. In some other embodiments, $m^2$ is 2. In yet still more embodiments, $m^2$ is 3.

In some other particular embodiments of any of the foregoing compounds, $m^1$ is 1, and $m^2$ is 1. In other embodiments, $m^1$ is 1 and, $m^2$ is 2. In still other embodiments $m^1$ is 2, and $m^2$ is 2. In more embodiments, $m^1$ is 1, and $m^2$ is 3.

In any of the foregoing embodiments, $G^1$ and $G^2$ are each independently selected from N and CH. In some embodiments, at least one of $G^1$ or $G^2$ is N. In some embodiments, each of $G^1$ and $G^2$ are N. In some embodiments, each of $G^1$ and $G^2$ are N and $m^1$ and $m^2$ are each 2. In some other embodiments, at least one of $G^1$ or $G^2$ is CH. In other embodiments, each of $G^1$ and $G^2$ are CH.

Without wishing to be bound by theory, Applicants believe correct selection of the $R^1$ substituent may play a part in the compounds' inhibitory activity (e.g., against KRAS, HRAS or NRAS G12C). In some embodiments, $R^1$ is aryl or heterocyclyl (e.g., heteroaryl or aliphatic heterocyclyl), each of which is optionally substituted with one or more substituents. In some embodiments, $R^1$ is capable of reversible interaction with KRAS, HRAS or NRAS G12C mutant protein. In some embodiments $R^1$ has high affinity towards KRAS, HRAS or NRAS and is highly specific towards G12C KRAS, HRAS or NRAS. In some embodiments $R^1$ is capable of hydrophobic interaction with KRAS, HRAS or NRAS G12C. In some embodiments $R^1$ is able to form hydrogen bonds with various residues of G12C KRAS, HRAS or NRAS protein.

In other of the foregoing embodiments, $R^1$ is heterocyclyl, heteroaryl or aryl.

In certain embodiments of any of the foregoing, $R^1$ is aryl. For example, in some embodiments $R^1$ is phenyl. In other embodiments, $R^1$ is naphthyl. In some of these embodiments, $R^1$ is unsubstituted aryl, such as unsubstituted phenyl or unsubstituted naphthyl. In other embodiments, $R^1$ is substituted with one or more substituents. In some of these embodiments, the substituents are selected from halo, cyano, hydroxyl, $C_1$-$C_6$alkyl, $C_1$-$C_6$alkoxy and $C_3$-$C_8$cycloalkyl. In other more specific embodiments, the substituents are selected from fluoro, chloro, bromo, hydroxyl, methoxy and cyclopropyl.

In other embodiments, the $R^1$ substituents are selected from halo, cyano, cyano$C_1$-$C_6$alkyl, cyano$C_3$-$C_8$cycloalkyl, hydroxyl, $C_1$-$C_6$alkyl, $C_1$-$C_6$alkylcycloalky, $C_2$-$C_6$alkynyl, $C_1$-$C_6$alkoxy, $C_1$-$C_6$haloalkoxy, $C_1$-$C_6$alkylaminyl, $C_1$-$C_6$alkylcarbonylaminyl, $C_1$-$C_6$hydroxylalkyl, $C_1$-$C_6$haloalkyl, $C_1$-$C_6$alkoxyalkyl, aminylsulfone, aminylcarbonyl, aminylcarbonyl$C_1$-$C_6$alkyl, aminylcarbonyl$C_3$-$C_8$cycloalkyl, $C_1$-$C_6$alkylaminylcarbonyl, $C_3$-$C_8$cycloalkylaminylcarbonyl, $C_3$-$C_8$cycloalkylalkyl and $C_3$-$C_8$cycloalkyl, $C_3$-$C_8$fusedcycloalkyl and heteroaryl.

In still other embodiments, the $R^1$ substituents are selected from fluoro, chloro, bromo, cyano, hydroxyl, hydroxylmethyl, methoxy, methoxymethyl, ethyl, isopropyl, trifluoromethyl, aminylcarbonyl and cyclopropyl.

In still more embodiments, the $R^1$ substituents are selected from fluoro, chloro, bromo, cyano, hydroxyl, hydroxylmethyl, methoxy, methoxymethyl, methyl, ethyl, isopropyl, difluoromethyl, trifluoromethyl, aminylcarbonyl and cyclopropyl.

In certain embodiments, $R^1$ has one of the following structures:

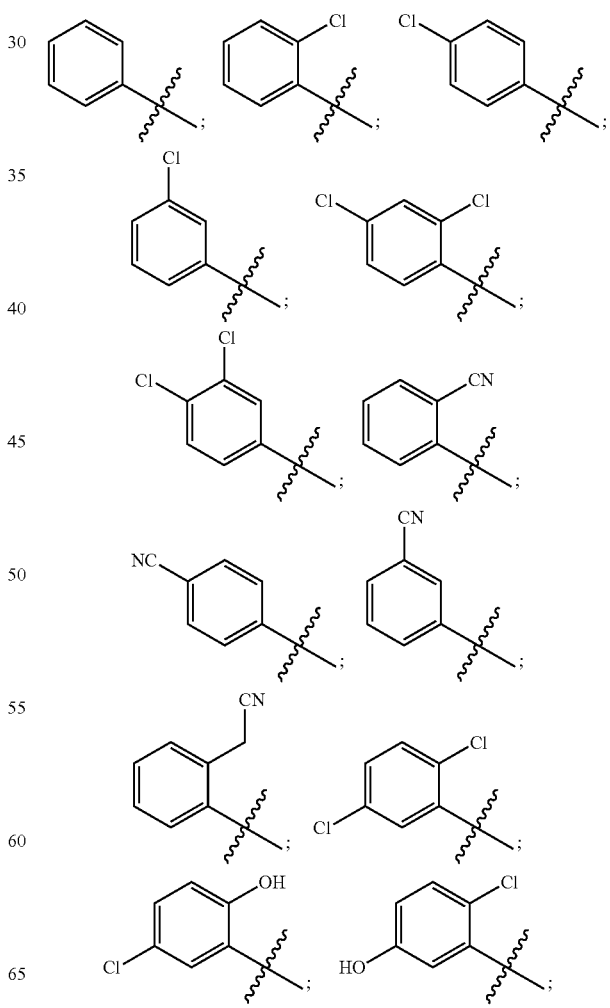

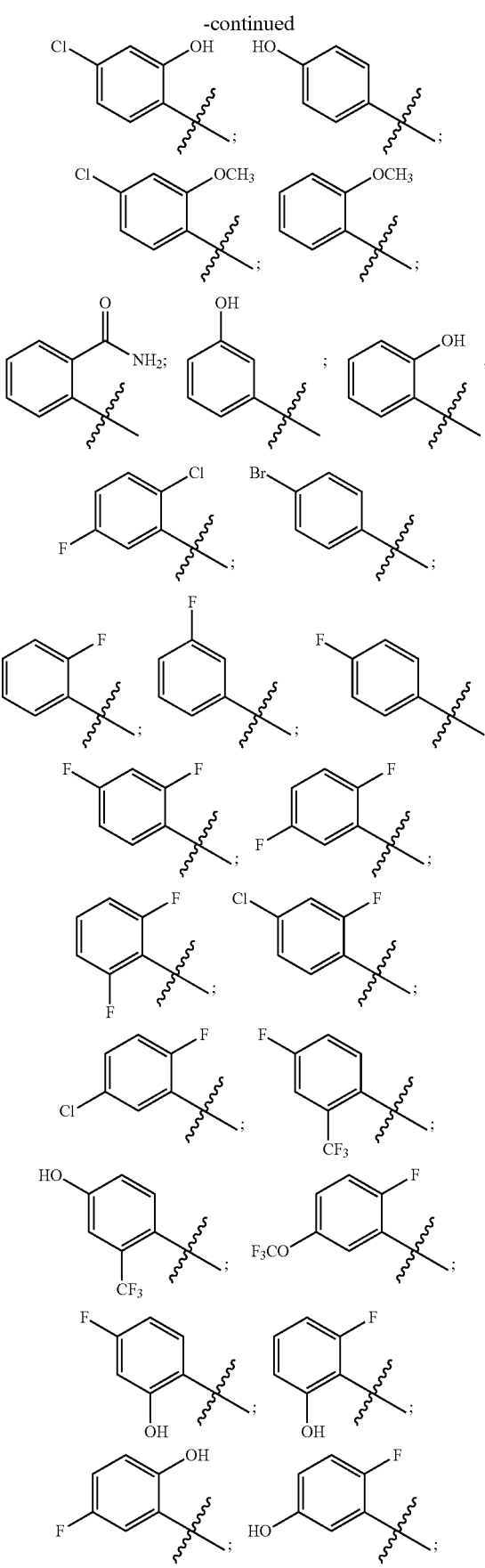
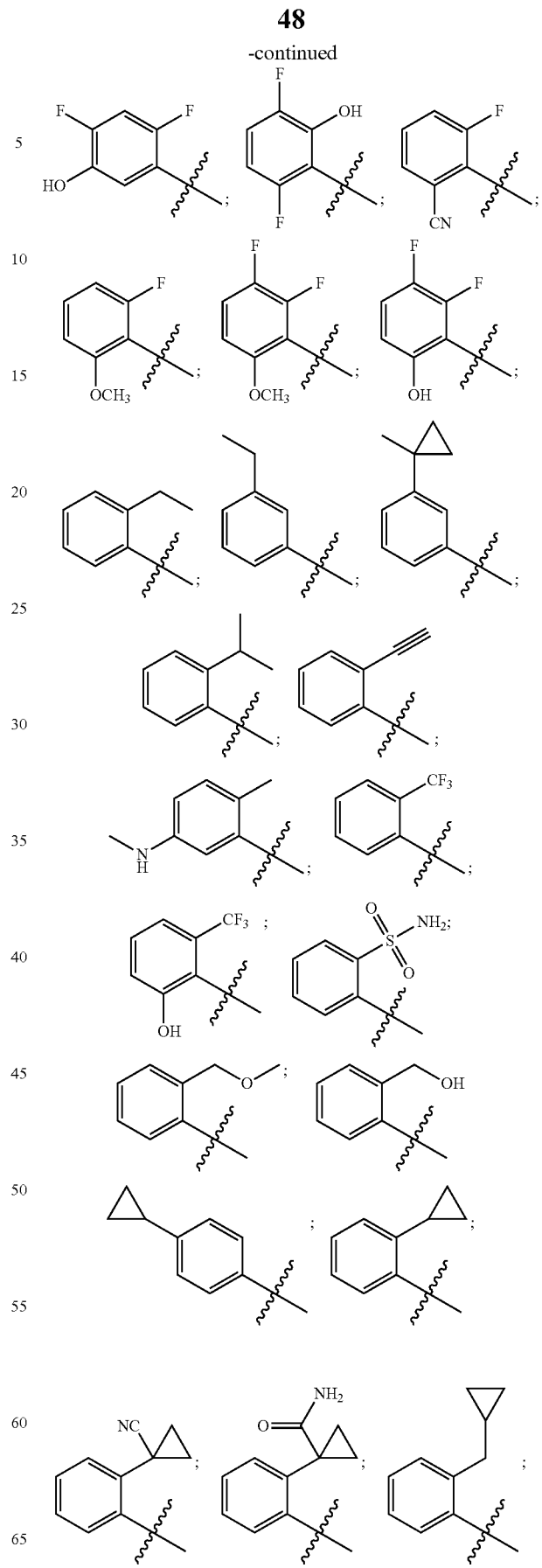

-continued
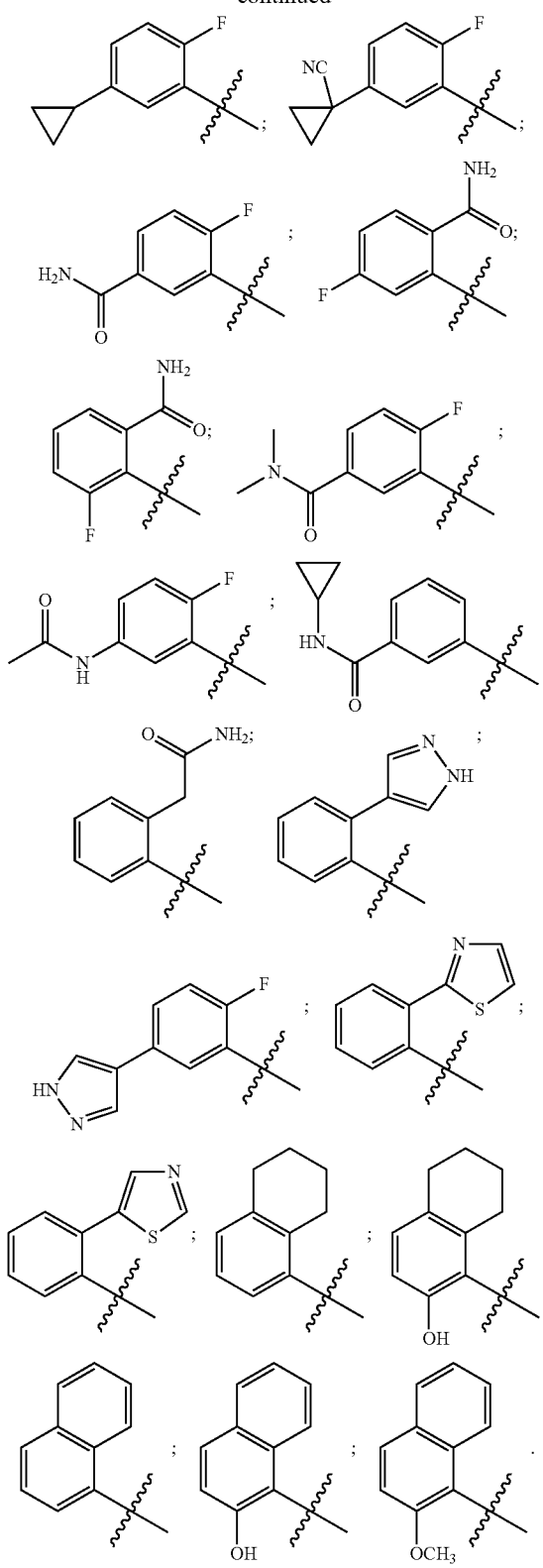
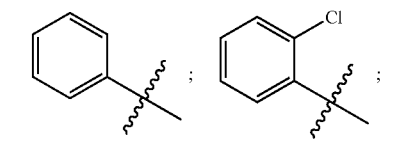
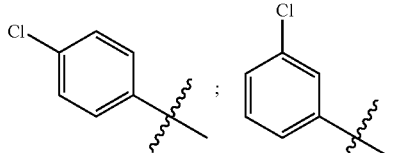
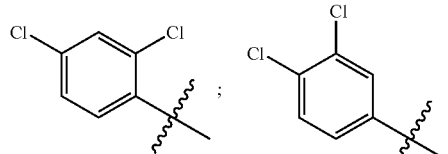
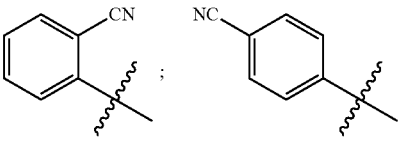
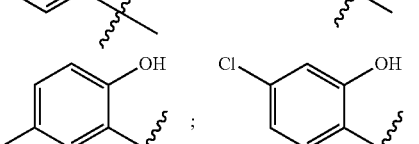
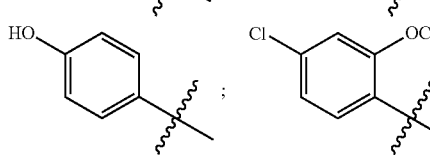
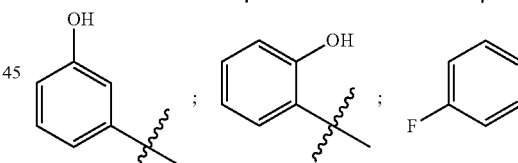
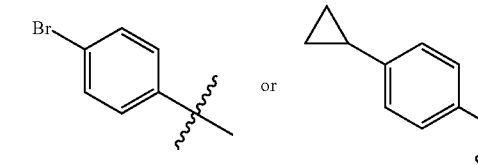
In other of the foregoing embodiments, R¹ has one of the following structures:
In still other embodiments, R¹ has one of the following structures:
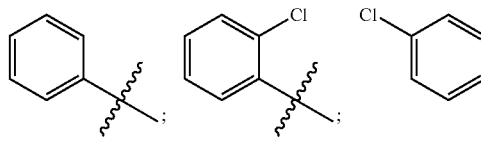

-continued
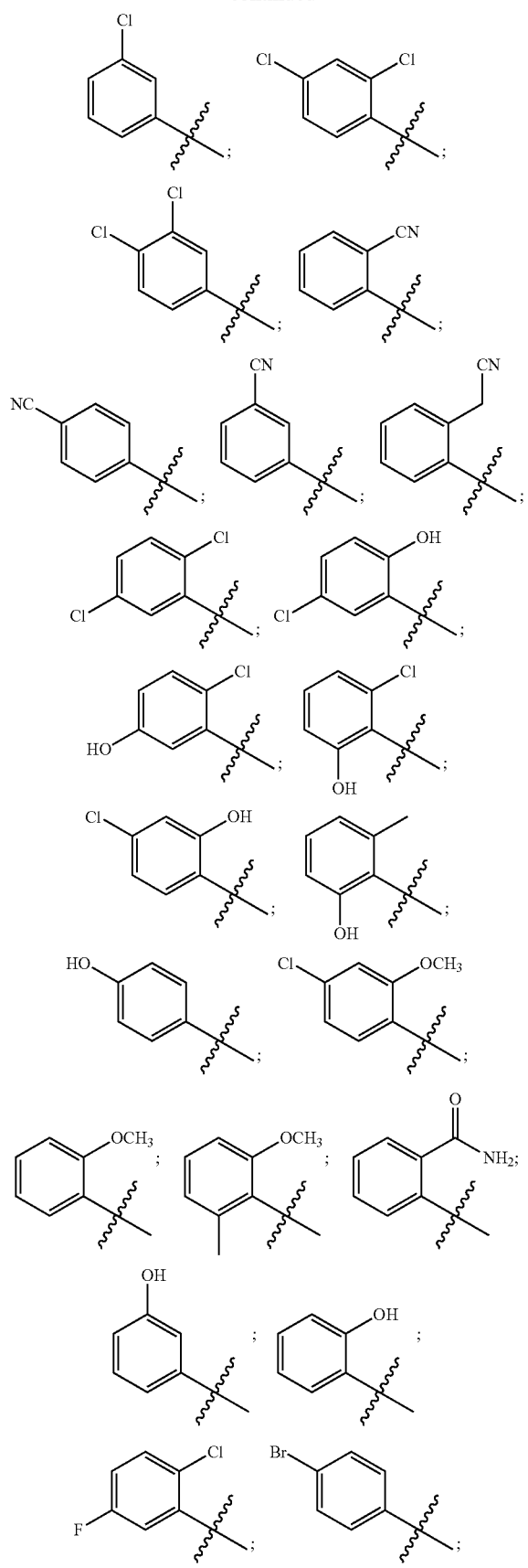
-continued
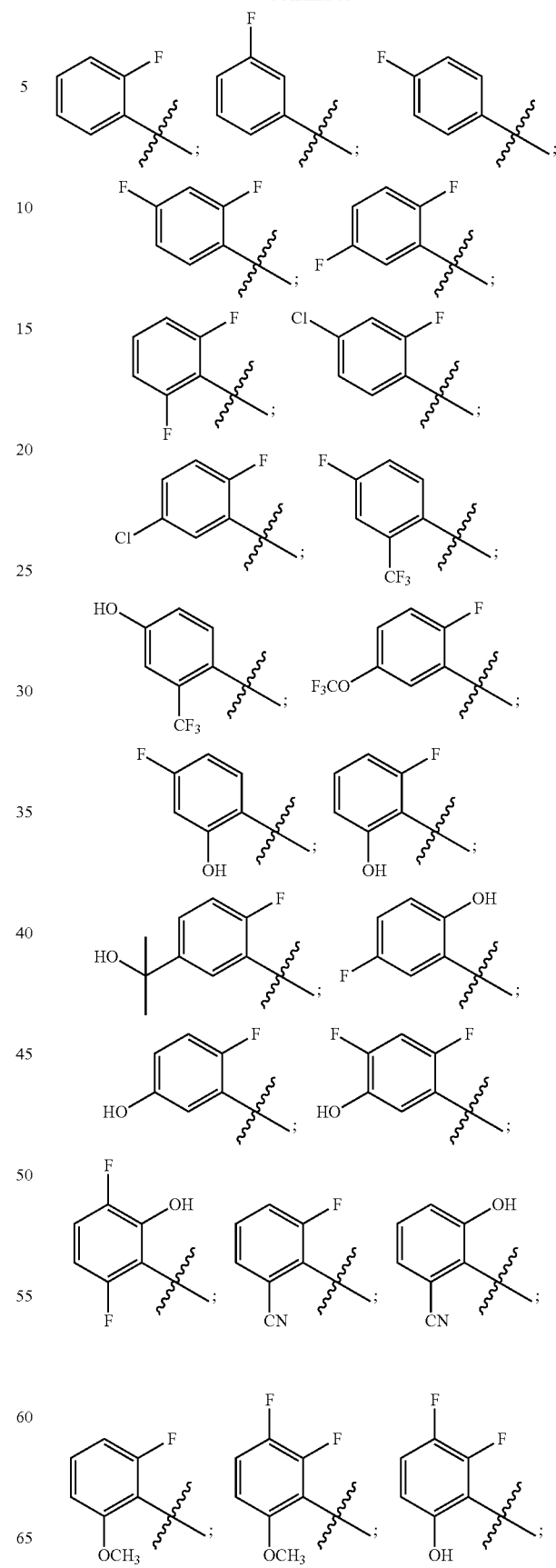

-continued
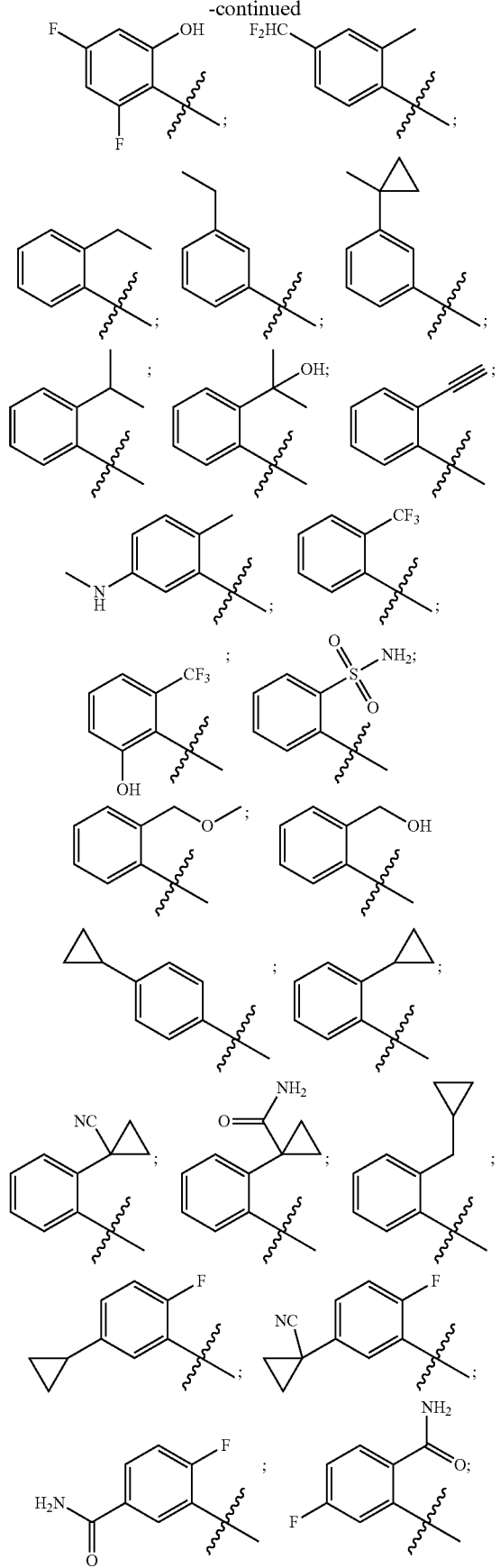
-continued
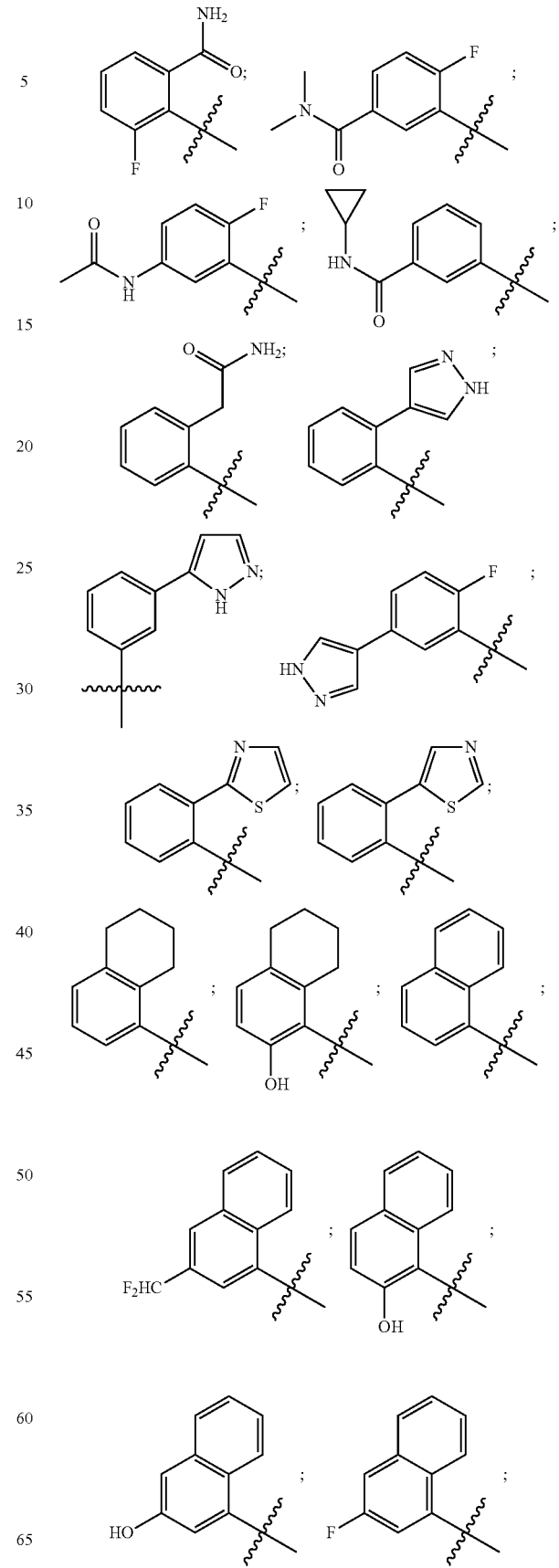

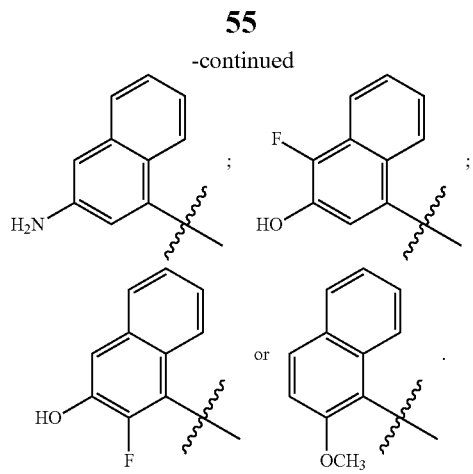

In some different embodiments of any of the foregoing, $R^1$ is heteroaryl. In certain embodiments, $R^1$ comprises oxygen, sulfur, nitrogen or combinations thereof. In some of these embodiments, $R^1$ comprises sulfur or nitrogen. In certain embodiments, $R^1$ is thiophenyl, pyridinyl, pyridinonyl, pyrimidinyl, benzooxazolyl, benzoisoxazolyl, benzodioxazolyl, benzoimidazolyl, quinolinyl, quinolinonyl, dihydroquinolinonyl, tetrahydroquinolinyl, quinazolinyl, indazolyl, indolinonyl, benzothiophenyl or dihydrobenzodioxinyl.

In some embodiments, $R^1$ is substituted or unsubstituted indazolyl. In some of these embodiments the indazolyl is substituted with one or more $C_1$-$C_6$ alkyl, $C_1$-$C_6$ alkoxy and/or halo groups. For example, in some embodiments, the indazolyl is substituted with one or more methyl, methoxy, chloro and/or fluoro groups.

For example, in some embodiments $R^1$ is pyridinyl. In some embodiments $R^1$ is unsubstituted pyridinyl, for example unsubstituted pyridin-4-yl or unsubstituted pyridin-3-yl. In other embodiments $R^1$ is thiophenyl. In some embodiments $R^1$ is unsubstituted thiophenyl, for example unsubstituted thiophen-2-yl.

In other embodiments, $R^1$ is substituted with one or more substituents. For example, in some embodiments, the substituents are selected from halo, $C_1$-$C_6$alkyl, $C_1$-$C_6$alkoxy, or $C_2$-$C_6$alkenylcarbonylaminyl. In some of these embodiments, the substituents are selected from halo and $C_1$-$C_6$alkyl. In other embodiments, the substituents are selected from fluoro, chloro, amino and methyl. For example, in more specific embodiments, the substituents are selected from chloro and methyl. In other embodiments at least one R1 substituent is fluoro.

In some embodiments, $R^1$ has one of the following structures:

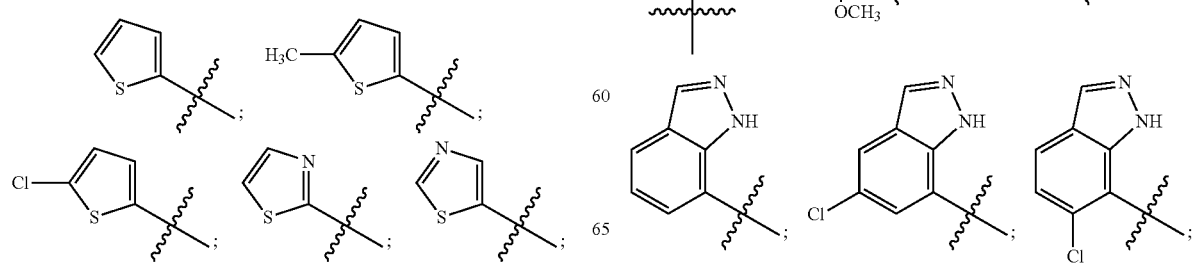

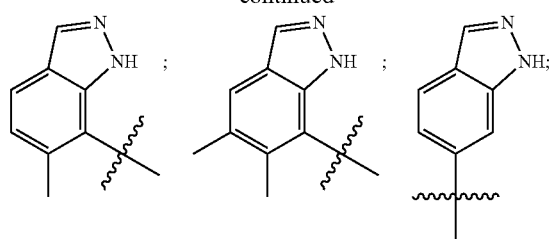
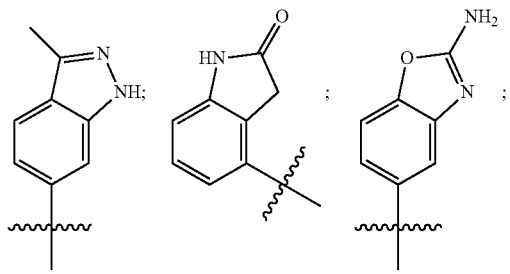
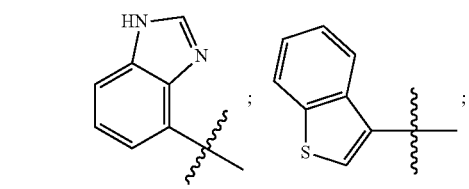
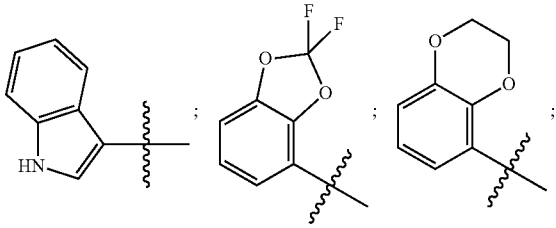
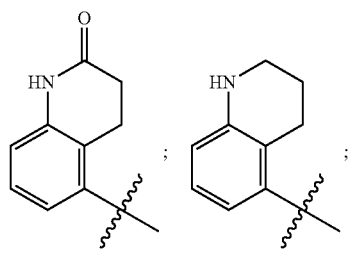
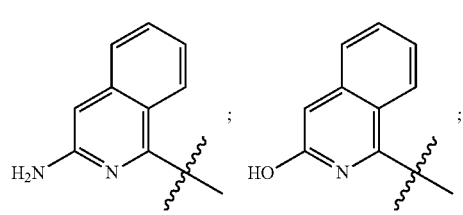
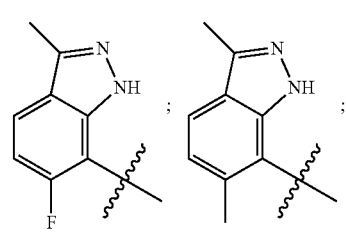
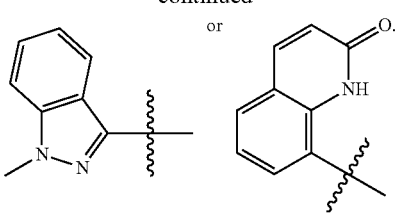
In certain embodiments, $R^1$ has one of the following structures:
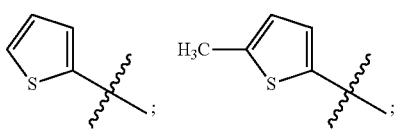
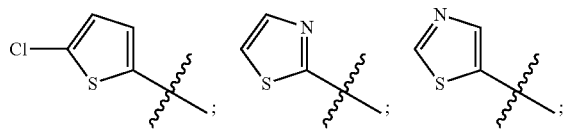
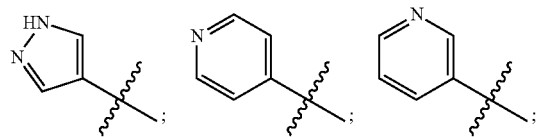
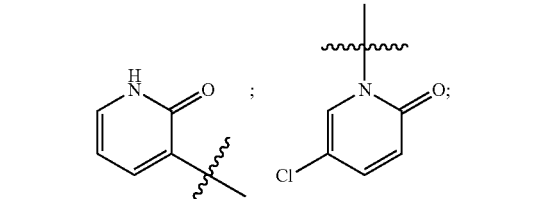
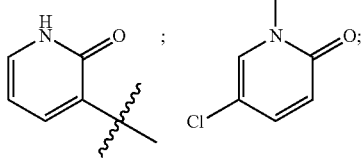
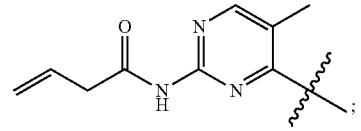
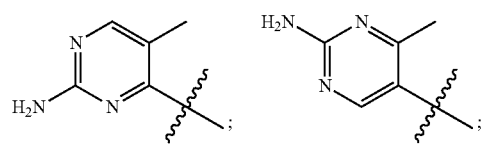
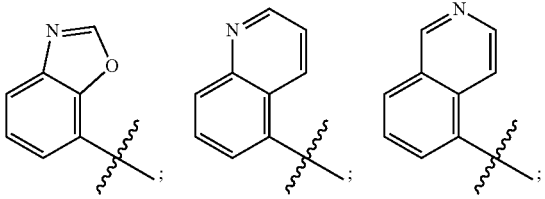
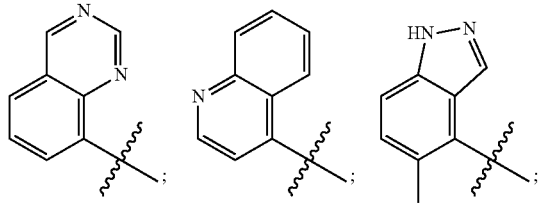

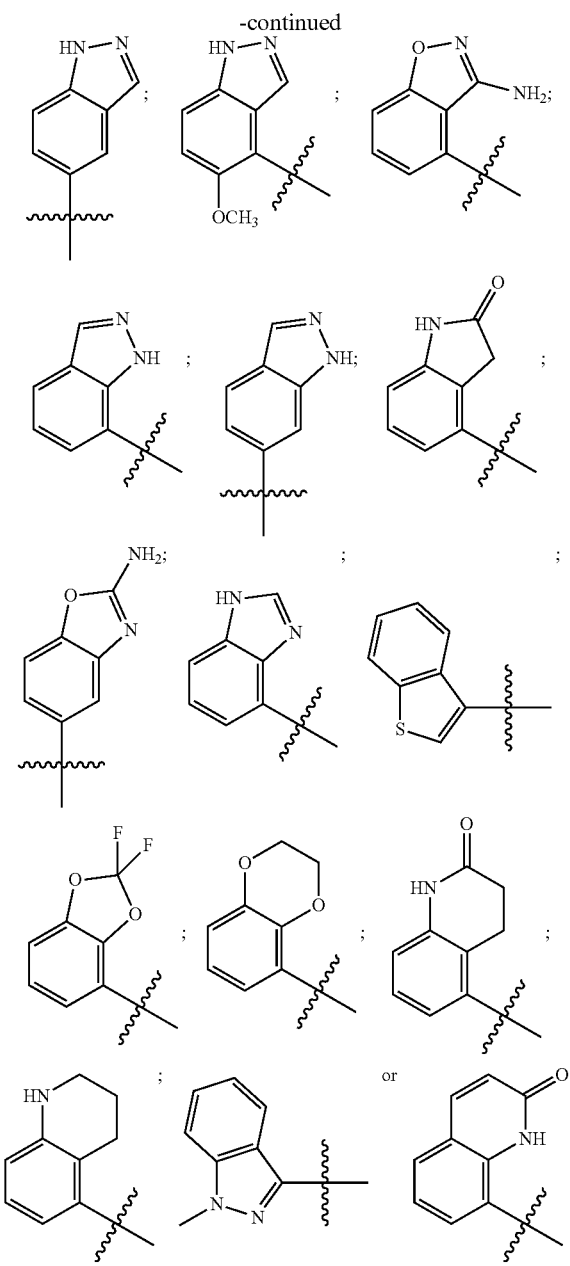

In some of the foregoing embodiments, $R^1$ has one of the following structures:

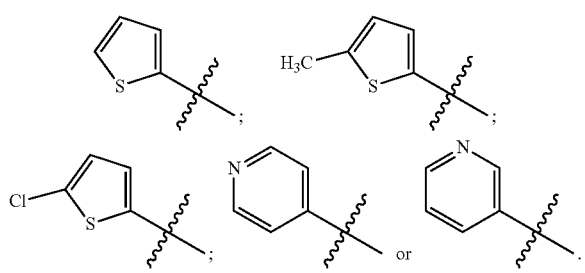

In still other embodiments, $R^1$ is aliphatic heterocyclyl. In some embodiments the aliphatic heterocyclyl comprises oxygen and/or nitrogen. In some further embodiments, $R^1$ is morpholinyl. For example, in some embodiments $R^1$ has the following structure:

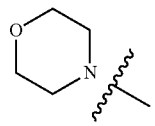

In various embodiments of the foregoing, $R^1$ is unsubstituted.

In some of the foregoing embodiments, $R^{2a}$ is H. In other embodiments, $R^{2a}$ is halo, for example in some embodiments $R^{2a}$ is chloro or fluoro. In still other embodiments of the foregoing, $R^{2a}$ is $C_1$-$C_6$alkyl. For example, in some embodiments $R^{2a}$ is $C_3$-$C_8$ cycloalkyl, such as cyclopropyl.

In other embodiments of the foregoing compounds, $R^{2b}$ and $R^{2c}$, when present, are H. In different embodiments, $R^{2b}$ and $R^{2c}$, when present, are each independently halo. In yet other embodiments, $R^{2b}$, when present, is halo. In more embodiments, $R^{2c}$, when present, is halo. In certain of the foregoing embodiments, halo is chloro or fluoro.

The Q moiety is typically selected to optimize the reactivity (i.e., electrophilicity) of E. In certain of the foregoing embodiments, Q is —C(=O)—. In other embodiments, Q is —S(=O)$_2$—. In still more embodiments, Q is —NR$^8$C(=O)—. In still more different embodiments, Q is —NR$^8$S(=O)$_2$—.

In some of the immediately foregoing embodiments, $R^8$ is H. In other of these embodiments, $R^8$ is hydroxylalkyl, for example in some embodiments the hydroxylalkyl is 2-hydroxylalkyl.

In some embodiments, Q is —C(=NR$^{8'}$)—, wherein $R^{8'}$ is H, —OH, —CN or $C_1$-$C_6$alkyl. For example, in some embodiments $R^{8'}$ is H. In other embodiments, $R^{8'}$ is —CN.

In other embodiments, $R^8$ is —OH.

In some of any one of the foregoing embodiments, at least one of $R^9$ or $R^{10}$ is H. For example, in some embodiments each of $R^9$ and $R^{10}$ are H.

In other of the foregoing embodiments, $R^{10}$ is alkylaminylalkyl. In some of these embodiments, $R^{10}$ has the following structure:

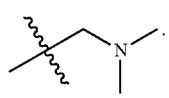

In other embodiments, $R^{10}$ is hydroxylalkyl, such as 2-hydroxylalkyl.

In some other different embodiments of the foregoing embodiments, $R^9$ and $R^{10}$ join to form a carbocyclic ring. For example, in some of these embodiments the carbocyclic ring is a cyclopentene, cyclohexene or phenyl ring. In other embodiments, the carbocyclic ring is a cyclopentene or cyclohexene ring. In other embodiments, the carbocyclic ring is a phenyl ring, for example a phenyl ring having the following structure:

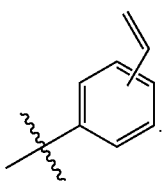

In some of any of the foregoing embodiments E is an electrophile capable of bonding with a KRAS, HRAS or NRAS protein comprising G12C mutation. In some embodiments, the electrophile E is capable of forming an irreversible covalent bond with a G12C mutant KRAS, HRAS or NRAS protein. In some cases, the electrophile E may bind with the cysteine residue at the position 12 of a G12C mutant KRAS, HRAS or NRAS protein. In various embodiments of any of the foregoing, E has one of the following structures:

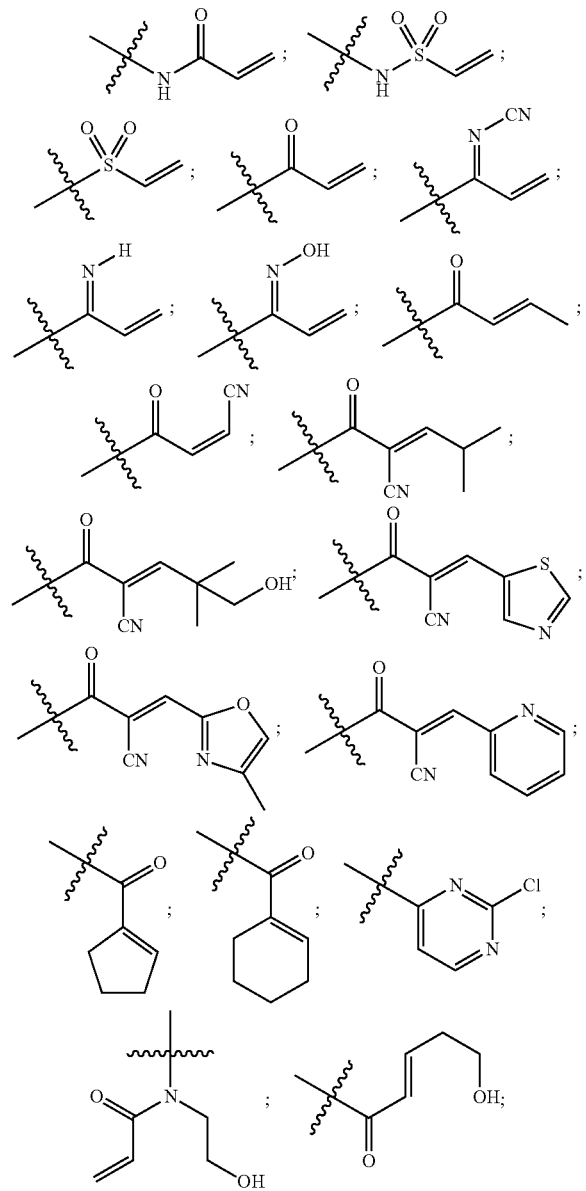

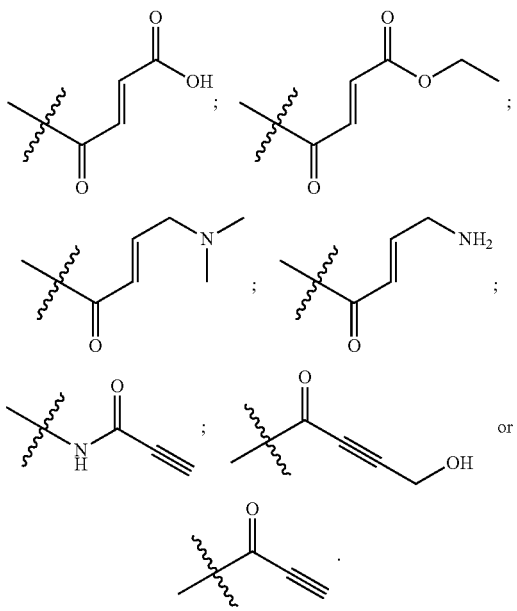

In other embodiments of any of the foregoing, E has one of the following structures:

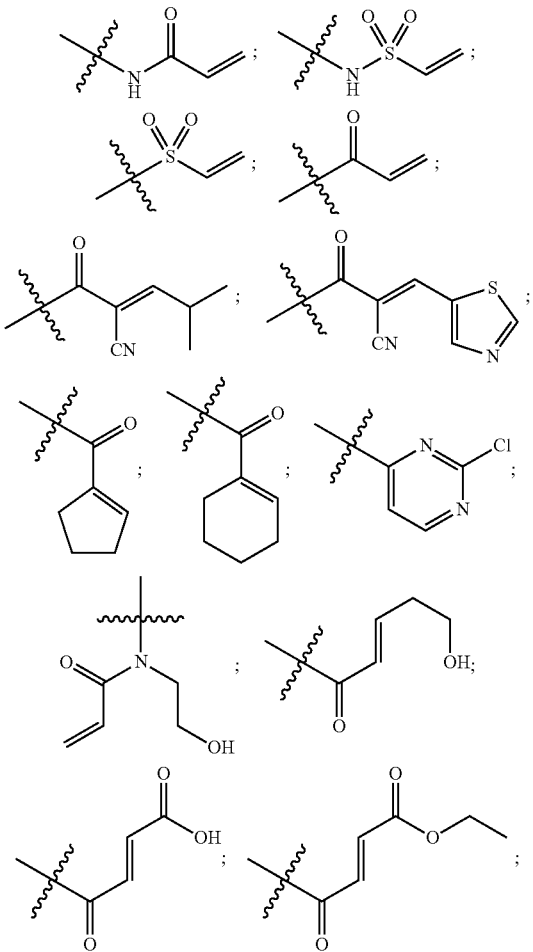

-continued

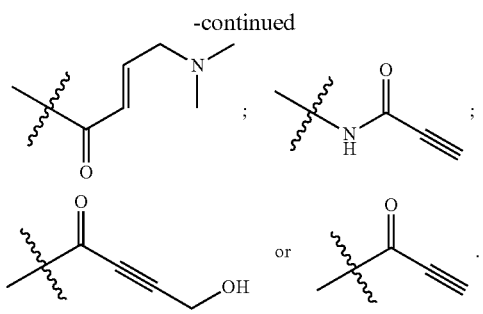

In different embodiments, E has one of the following structures:

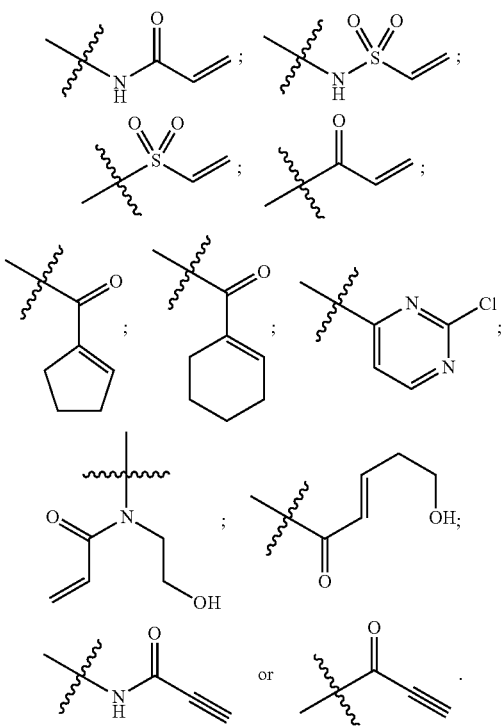

In some cases E has one of the following structures:

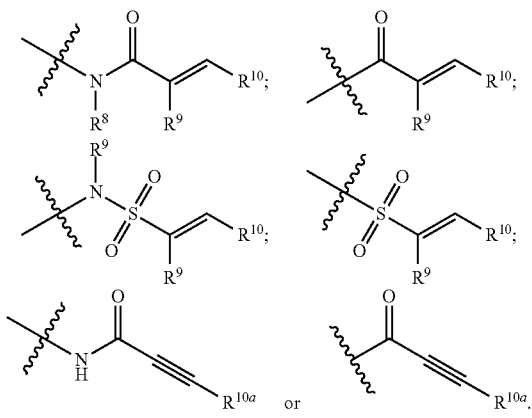

wherein:
R$^8$ is H or C$_1$-C$_6$alkyl;
R$^9$ is H, cyano or C$_1$-C$_6$alkyl, or R$^9$ joins with R$^{10}$ to form a carbocycle;
R$^{10}$ is H or C$_1$-C$_6$alkyl or R$^{10}$ joins with R$^9$ to form a carbocycle and
R$^{10a}$ is H or C$_1$-C$_6$alkyl.

In some embodiments E is

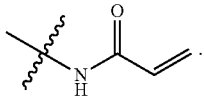

In some embodiments E is

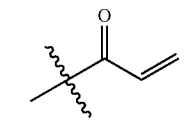 [SMILES: *C(=O)C=C]

In some embodiments E is

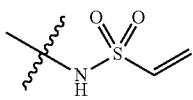

In some of any of the foregoing embodiments, L$^1$ is a bond. In other embodiments, L$^1$ is NR$^7$. For example, in some of these embodiments, R$^7$ is C$_1$-C$_6$alkyl. In other embodiments, L$^1$ is NH.

L$^2$ can be selected to provide proper spacing and/or orientation for the E group to form a bond with the KRAS, HRAS or NRAS protein. In some of the foregoing embodiments, L$^2$ is a bond. In other of the foregoing embodiments, L$^2$ is alkylene. In some embodiments, the alkylene is substituted. In other embodiments the alkylene is unsubstituted. For example, in some embodiments L$^2$ is CH$_2$ or CH$_2$CH$_2$.

In certain embodiments, R$^{3a}$ and R$^{3b}$ are, at each occurrence, independently H, —OH, —NH$_2$, —CO$_2$H, halo, cyano, hydroxylalkly, aminylalkyl, cyanoalkyl, carboxyalkyl or aminylcarbonyl, and R$^{4a}$ and R$^{4b}$ are, at each occurrence, independently H, —OH, —NH$_2$, —CO$_2$H, halo, cyano, hydroxylalkly, aminylalkyl, cyanoalkyl, carboxyalkyl or aminylcarbonyl.

In other of the foregoing embodiments, R$^{3a}$ and R$^{4a}$ are, at each occurrence, independently H, —OH, hydroxylalkly, cyano, or aminylcarbonyl and R$^{3b}$ and R$^{4b}$ are H.

In certain other embodiments, R$^{3a}$ and R$^{4a}$ are H and R$^{3b}$ and R$^{4b}$ are, at each occurrence, independently H, —OH, —NH$_2$, —CO$_2$H, halo, cyano, hydroxylalkly, aminylalkyl, cyanoalkyl, carboxyalkyl or aminylcarbonyl.

In any of the foregoing embodiments, at least one of R$^{3a}$, R$^{3b}$, R$^{4a}$ or R$^{4b}$ is H. In some embodiments, each of R$^{3a}$, R$^{3b}$, R$^{4a}$ and R$^{4b}$ are H.

In some embodiments, R$^{3a}$ is —OH, —NH$_2$, —CO$_2$H, halo, cyano, hydroxylalkly, aminylalkyl, cyanoalkyl, carboxyalkyl or aminylcarbonyl, and R$^{3b}$, R$^{4a}$ and R$^{4b}$ are H.

In other embodiments, R$^{4a}$ is —OH, —NH$_2$, —CO$_2$H, halo, cyano, hydroxylalkly, aminylalkyl, cyanoalkyl, carboxyalkyl or aminylcarbonyl, and R$^{3a}$, R$^{3b}$ and R$^{4b}$ are H.

In other embodiments, R$^{3a}$ is H, —OH, —NH$_2$, —CO$_2$H, halo, cyano, hydroxylalkly, aminylalkyl, cyanoalkyl, carboxyalkyl or aminylcarbonyl, and $R^{3b}$ joins with $R^{4b}$ to form a carbocyclic or heterocyclic ring;

In still more embodiments, $R^{4a}$ is H, —OH, —NH$_2$, —CO$_2$H, halo, cyano, hydroxylalkly, aminylalkyl, cyanoalkyl, carboxyalkyl or aminylcarbonyl, and $R^{4b}$ joins with $R^{3b}$ to form a carbocyclic or heterocyclic ring.

In other embodiments, $R^{3a}$ and $R^{3b}$ join to form a carbocyclic or heterocyclic ring. In other embodiments, $R^{4a}$ and $R^{4b}$ join to form a carbocyclic or heterocyclic ring.

In still other embodiments, $R^{3a}$ or $R^{4a}$ is aminylcarbonyl. For example, in certain embodiments, the aminylcarbonyl is

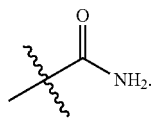

In other embodiments, $R^{3a}$ or $R^{4a}$ is cyano. In other embodiments, $R^{3a}$ or $R^{4a}$ is —OH. In other embodiments, $R^{3a}$ or $R^{4a}$ is hydroxylalkyl, for example hydroxylmethyl.

In some embodiments, $R^6$ is, at each occurrence, independently H, oxo, cyano, cyanoalkyl, aminyl, aminylalkyl, aminylalkylaminyl, aminylcarbonyl, alkylaminyl, haloalkylaminyl, hydroxylalkyaminyl, amindinylalkyl, amidinylalkoxy, amindinylalkylaminyl, guanidinylalkyl, guanidinylalkoxy, guanidinylalkylaminyl, C$_1$-C$_6$ alkoxy, aminylalkoxy, alkylcarbonylaminylalkoxy, C$_1$-C$_6$ alkyl, heterocyclyl, heterocyclyloxy, heterocyclylalkyloxy, heterocyclylaminyl, heterocyclylalkylaminyl, heteroaryl, heteroaryloxy, heteroarylalkyloxy, heteroarylaminyl, heteroarylalkylaminyl, aryl, aryloxy, arylamino, arylalkylamino, arylalkyloxy or a bond to L.

Each of the foregoing $R^6$ moieties may be substituted with one or more substituents. For example, in some embodiments the one or more substituents are aminyl (e.g., substituted or substituted), alkylcarbonyl aminyl, hydroxyl, haloalkyl or heterocycyclyl (e.g., substituted or substituted aliphatic heterocycle or substituted or substituted heteroaryl). For example, in some embodiments, the $R^6$ moiety is C$_1$-C$_6$ alkyl, C$_1$-C$_6$ alkoxy or alkylaminyl, which is further substituted with alkylcarbonylaminyl, hydroxyl, —CN or haloalkyl. For example, in some embodiments, $R^6$ has one of the following structures:

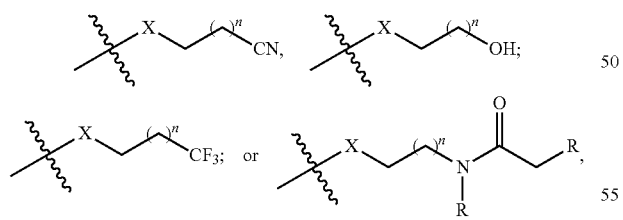

wherein X is a bond, —O— or —NR—; each R is independently H or C$_1$-C$_6$alkyl and n is an integer from 0 to 6.

Various different $R^6$ moieties are included in the scope of the compounds.

For example, in various embodiments, $R^6$ is H. In other embodiments, $R^6$ is —CN. In more embodiments, $R^6$ is methoxy.

In various other embodiments, $R^6$ is aminylalkyl, aminylalkyloxy or aminylalkyaminyl. For example, in some embodiments $R^6$ has the following structures:

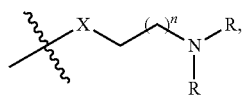

wherein X is a bond, —O— or —NR—; each R is independently H or C$_1$-C$_6$alkyl and n is an integer from 0 to 6.

In other embodiments, $R^6$ is amindinylalkyl, amidinylalkoxy, amindinylalkylaminyl, guanidinylalkyl, guanidinylalkoxy or guanidinylalkylaminyl. For example, in some embodiments $R^6$ has one of the following structures:

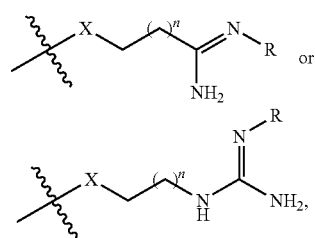

wherein X is a bond, —O— or —NR—; each R is independently H or C$_1$-C$_6$alkyl and n is an integer from 0 to 6.

In other embodiments, $R^6$ is heterocyclyl, heterocyclyloxy, heterocyclylalkyloxy, heterocyclylaminyl, heterocyclylalkylaminyl, heteroaryl, heteroaryloxy, heteroarylalkyloxy, heteroarylaminyl or heteroarylalkylaminyl. For example, in some embodiments $R^6$ has one of the following structures:

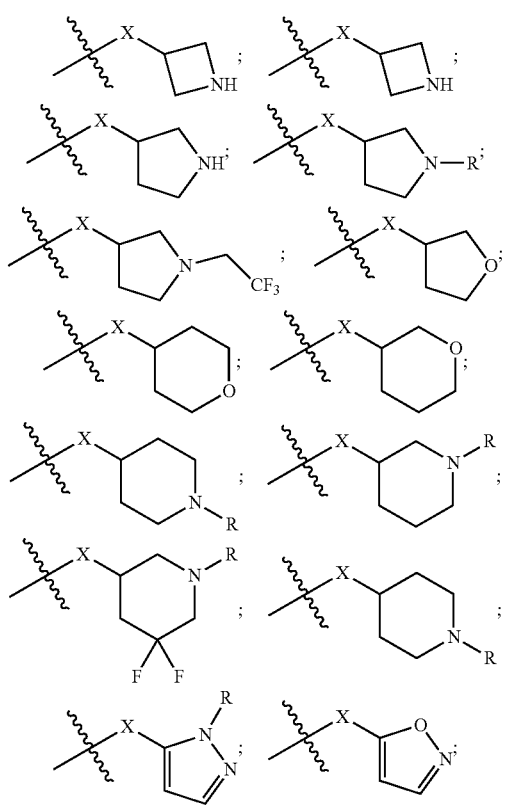

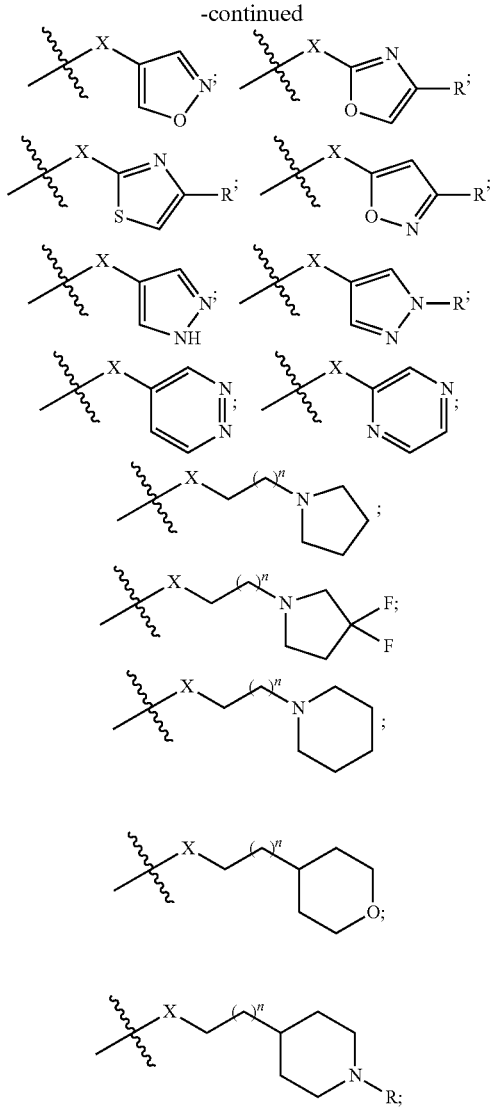

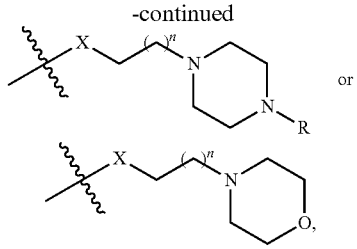

wherein X is a bond, —O— or —NR—; each R is independently H or $C_1$-$C_6$alkyl and n is an integer from 0 to 6.

In some of the foregoing embodiments, X is N. in other of the foregoing embodiments, X is N. In other of the foregoing embodiments, Z is N. In still more embodiments, X is N and Z is N.

In some embodiments, Z is N and Y is N. In other embodiments, X is N, Z is N, Y is $CR^6$, wherein $R^6$ is H and W is $CR^6$, wherein $R^6$ is a bond to $L^1$. In different embodiments, Z is N and Y is $CR^6$, wherein $R^6$ is H, W is $CR^6$, wherein $R^6$ is a bond to $L^1$ and X is $CR^6$, wherein $R^6$ is cyano, methoxy or amino.

In other embodiments, Z is N, X is $CR^6$ and $R^6$ is cyano, Y is $CR^6$, wherein $R^6$ is H and W is $CR^6$, wherein $R^6$ is a bond to $L^1$.

In other embodiments, Y is N, Z is N, W is $CR^6$, wherein $R^6$ is a bond to $L^1$ and X is $CR^6$, wherein $R^6$ is H.

In other of the foregoing embodiments, Z is a bond.

In certain embodiments, Y is $NR^5$. In some of these embodiments, $R^5$ is $C_1$-$C_6$alkyl. In other embodiments, $R^5$ is H.

In still other embodiments, X or Y is $CR^6$. In some of these embodiments, $R^6$ is, at each occurrence, independently H, cyano, amino, $C_1$-$C_6$alkoxy or a bond to $L^1$. In some other of these embodiments, $R^6$ is H. In other embodiments, $R^6$ is $C_1$-$C_6$alkoxy. In other embodiments, $R^6$ is cyano. In more embodiments, $R^6$ is methoxy. In other embodiments, $R^6$ is amino.

In various different embodiments, the compound has one of the structures set forth in Table 1 below:

TABLE 1

| | Exemplary Compounds of Structure (I) | | | |
|---|---|---|---|---|
| No. | Structure | Name | Method | $[M + H]^+$ |
| I-1 | (structure shown) | 1-(4-(7-chloro-6-(2-chlorophenyl)quinazolin-4-yl)piperazin-1-yl)prop-2-en-1-one | A | 413.20 |

TABLE 1-continued

Exemplary Compounds of Structure (I)

| No. | Structure | Name | Method | [M + H]⁺ |
|---|---|---|---|---|
| I-2 | 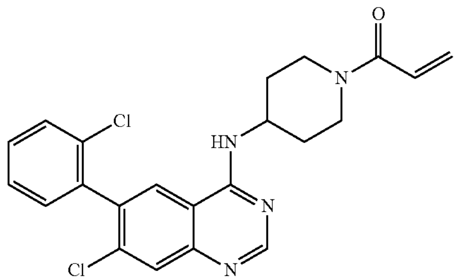 [SMILES: C=CC(=O)N1CCC(Nc2ncnc3cc(Cl)c(-c4ccccc4Cl)cc23)CC1] | 1-(4-(7-chloro-6-(2-chlorophenyl)quinazolin-4-ylamino)piperidin-1-yl)prop-2-en-1-one | A | 427.25 |
| I-3 | 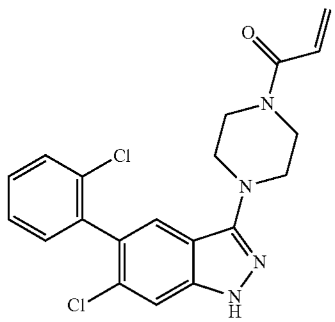 [SMILES: C=CC(=O)N1CCN(c2n[nH]c3cc(Cl)c(-c4ccccc4Cl)cc23)CC1] | 1-(4-(6-chloro-5-(2-chlorophenyl)-1H-indazol-3-yl)piperazin-1-yl)prop-2-en-1-one | C | 401.20 |
| I-4 | 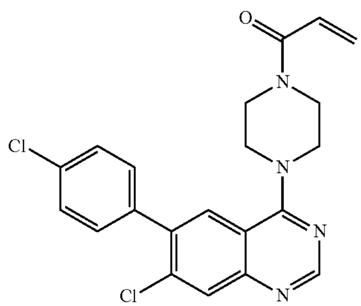 [SMILES: C=CC(=O)N1CCN(c2ncnc3cc(Cl)c(-c4ccc(Cl)cc4)cc23)CC1] | 1-(4-(7-chloro-6-(4-chlorophenyl)quinazolin-4-yl)piperazin-1-yl)prop-2-en-1-one | B | 413.25 |
| I-5 | 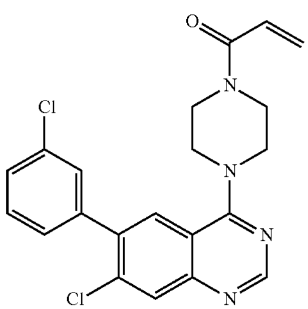 [SMILES: C=CC(=O)N1CCN(c2ncnc3cc(Cl)c(-c4cccc(Cl)c4)cc23)CC1] | 1-(4-(7-chloro-6-(3-chlorophenyl)quinazolin-4-yl)piperazin-1-yl)prop-2-en-1-one | B | 413.20 |
| I-6 | 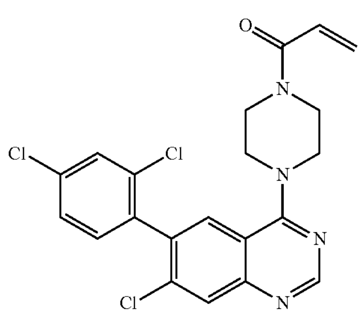 [SMILES: C=CC(=O)N1CCN(c2ncnc3cc(Cl)c(-c4ccc(Cl)cc4Cl)cc23)CC1] | 1-(4-(7-chloro-6-(2,4-dichlorophenyl)quinazolin-4-yl)piperazin-1-yl)prop-2-en-1-one | B | 447.20[#] |

TABLE 1-continued

Exemplary Compounds of Structure (I)

| No. | Structure | Name | Method | [M + H]+ |
|---|---|---|---|---|
| I-7 | 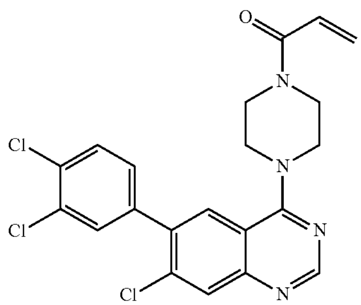 [SMILES: C=CC(=O)N1CCN(c2ncnc3cc(Cl)c(-c4ccc(Cl)c(Cl)c4)cc23)CC1] | 1-(4-(7-chloro-6-(3,4-dichlorophenyl)quinazolin-4-yl)piperazin-1-yl)prop-2-en-1-one | B | 449.15 |
| I-8 | 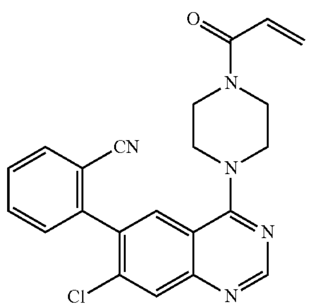 [SMILES: C=CC(=O)N1CCN(c2ncnc3cc(Cl)c(-c4ccccc4C#N)cc23)CC1] | 2-(4-(4-acryloylpiperazin-1-yl)-7-chloroquinoazlin-6-yl)benzonitrile | B | 404.1 |
| I-9 | 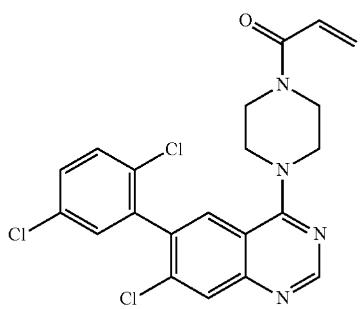 [SMILES: C=CC(=O)N1CCN(c2ncnc3cc(Cl)c(-c4cc(Cl)ccc4Cl)cc23)CC1] | 1-(4-(7-chloro-6-(2,5-dichlorophenyl)quinazolin-4-yl)piperazain-1-yl)prop-2-en-1-one | B | 448.45 |
| I-10 | 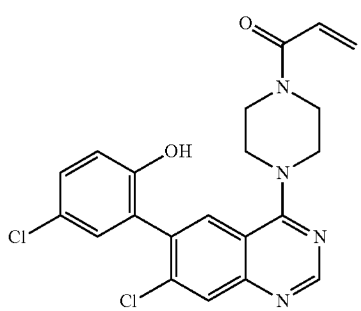 [SMILES: C=CC(=O)N1CCN(c2ncnc3cc(Cl)c(-c4cc(Cl)ccc4O)cc23)CC1] | 1-(4-(7-chloro-6-(5-chloro-2-hydroxyphenyl)quinazolin-4-yl)piperazin-1-yl)prop-2-en-1-one | B | 429.25 |
| I-11 | 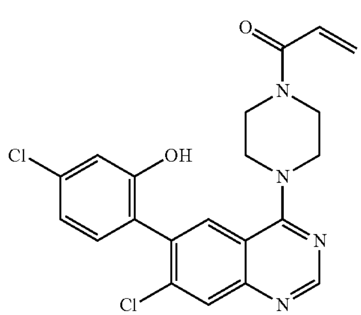 [SMILES: C=CC(=O)N1CCN(c2ncnc3cc(Cl)c(-c4ccc(Cl)cc4O)cc23)CC1] | 1-(4-(7-chloro-6-(4-chloro-2-hydroxyphenyl)quinoazlin-4-yl)piperazin-1-yl)prop-2-en-1-one | B | 429.25 |

TABLE 1-continued

Exemplary Compounds of Structure (I)

| No. | Structure | Name | Method | [M + H]+ |
|---|---|---|---|---|
| I-12 | 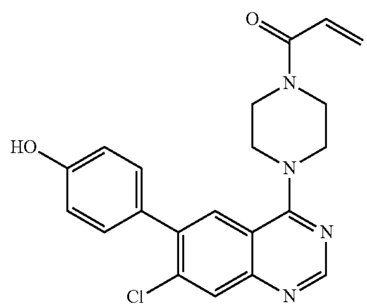 | 1-(4-(7-chloro-6-(4-hydroxyphenyl)quinazolin-4-yl)piperazin-1-yl)prop-2-en-1-one | B | 395.25 |
| I-13 | 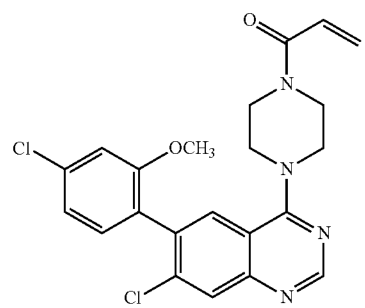 [SMILES: C=CC(=O)N1CCN(c2ncnc3cc(Cl)c(-c4ccc(Cl)cc4OC)cc23)CC1] | 1-(4-(7-chloro-6-(4-chloro-2-methoxyphenyl)quinoazlin-4-yl)piperazin-1-yl)prop-2-en-1-one | B | 443.30 |
| I-14 | 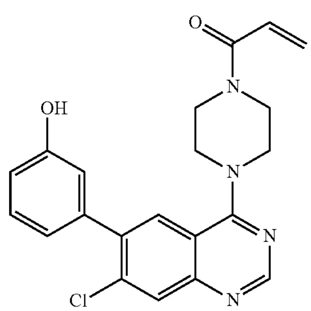 [SMILES: C=CC(=O)N1CCN(c2ncnc3cc(Cl)c(-c4cccc(O)c4)cc23)CC1] | 1-(4-(7-chloro-6-(3-hydroxyphenyl)quinazolin-4-yl)piperazin-1-yl)prop-2-en-1-one | B | 395.25 |
| I-15 | 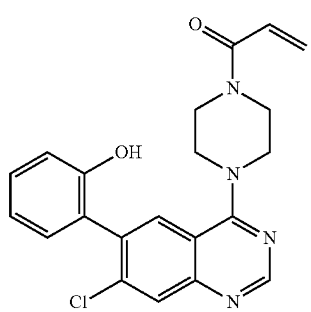 [SMILES: C=CC(=O)N1CCN(c2ncnc3cc(Cl)c(-c4ccccc4O)cc23)CC1] | 1-(4-(7-chloro-6-(2-hydroxyphenyl)quinoazlin-4-yl)piperazin-1-yl)prop-2-en-1-one | B | 395.25 |
| I-16 | 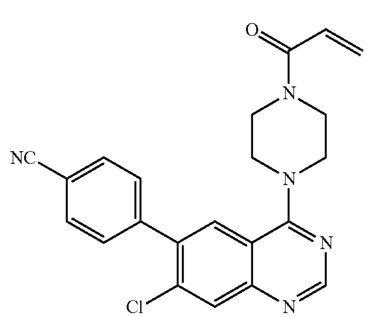 [SMILES: C=CC(=O)N1CCN(c2ncnc3cc(Cl)c(-c4ccc(C#N)cc4)cc23)CC1] | 4-(4-(4-acryloylpiperazin-1-yl)-7-chloroquinazolin-6-yl)benzonitrile | B | 404.3 |

TABLE 1-continued

Exemplary Compounds of Structure (I)

| No. | Structure | Name | Method | [M + H]+ |
|---|---|---|---|---|
| I-17 | 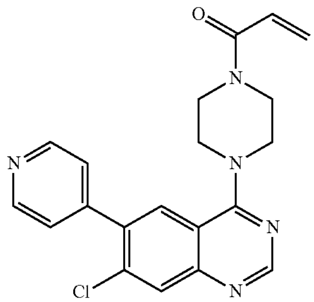 [SMILES: C=CC(=O)N1CCN(c2ncnc3cc(Cl)c(-c4ccncc4)cc23)CC1] | 1-(4-(7-chloto-6-(pyridin-4-yl)quinazolin-4-yl)piperazin-1-yl)prop-2-en-1-one | B | 380.25 |
| I-18 | 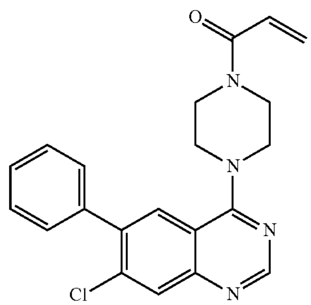 [SMILES: C=CC(=O)N1CCN(c2ncnc3cc(Cl)c(-c4ccccc4)cc23)CC1] | 1-(4-(7-chloro-6-phenylquinazolin-4-yl)piperazin-1-yl)prop-2-en-1-one | B | 379.25 |
| I-19 | 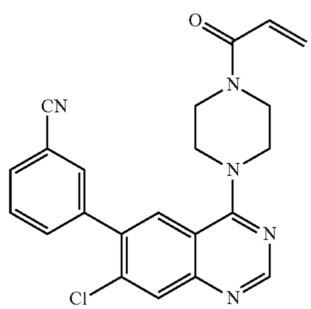 [SMILES: C=CC(=O)N1CCN(c2ncnc3cc(Cl)c(-c4cccc(C#N)c4)cc23)CC1] | 3-(4-(4-acryloylpiperazin-1-yl)-7-chloroquinazolin-6-yl)benzonitrile | B | 404.25 |
| I-20 | 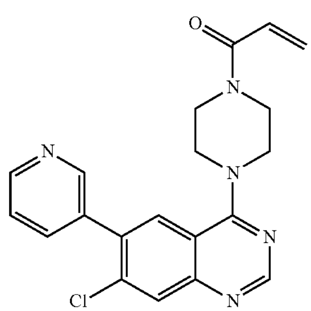 [SMILES: C=CC(=O)N1CCN(c2ncnc3cc(Cl)c(-c4cccnc4)cc23)CC1] | 1-(4-(7-chloro-6-(pyridin-3-yl)quinazolin-4-yl)piperazin-1-yl)prop-2-en-1-one | B | 380.25 |
| I-21 | 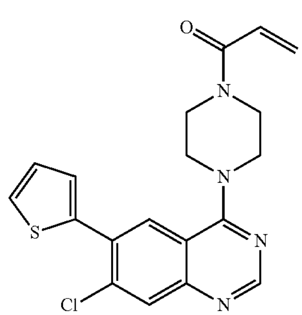 [SMILES: C=CC(=O)N1CCN(c2ncnc3cc(Cl)c(-c4cccs4)cc23)CC1] | 1-(4-(7-chloro-6-(thiophen-2-yl)quinazolin-4-yl)piperazin-1-yl)prop-2-en-1-one | B | 385.25 |

TABLE 1-continued

Exemplary Compounds of Structure (I)

| No. | Structure | Name | Method | [M + H]+ |
|---|---|---|---|---|
| I-22 | 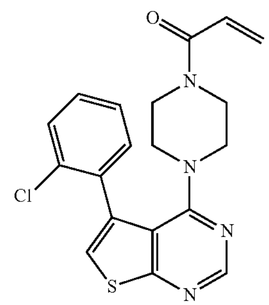 [SMILES: C=CC(=O)N1CCN(c2ncnc3scc(-c4ccccc4Cl)c23)CC1] | 1-(4-(5-(2-chlorophenyl)-4a,7a-dihydrothieno[2,3-d]pyrimidin-4-yl)piperazin-1-yl)prop-2-en-1-one | B | 385.20 |
| I-23 | 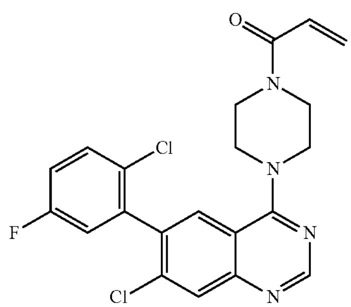 [SMILES: C=CC(=O)N1CCN(c2ncnc3cc(Cl)c(-c4cc(F)ccc4Cl)cc23)CC1] | 1-(4-(7-chloro-6-(2-chloro-5-fluorophenyl)quinazolin-4-yl)piperazin-1-yl)prop-2-en-1-one | B | 431.20 |
| I-24 | 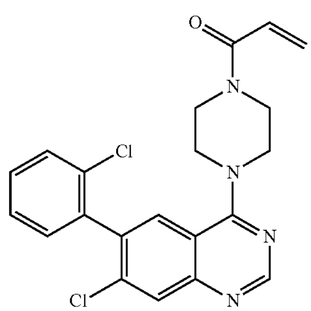 [SMILES: C=CC(=O)N1CCN(c2ncnc3cc(Cl)c(-c4ccccc4Cl)cc23)CC1] | 1-(4-(6-chloro-7-(2-chlorophenyl)isoquinolin-1-yl)piperazin-1-yl)prop-2-en-1-one | D | 412.20 |
| I-25 | 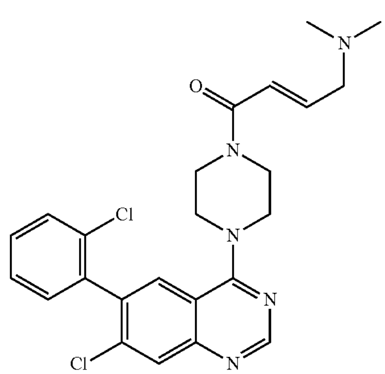 [SMILES: CN(C)C/C=C/C(=O)N1CCN(c2ncnc3cc(Cl)c(-c4ccccc4Cl)cc23)CC1] | (E)-1-(4-(7-chloro-6-(2-chlorophenyl)quinazolin-4-yl)piperazin-1-yl)-4-(dimethylamino)but-2-en-1-one | A | 470.35 |

TABLE 1-continued

Exemplary Compounds of Structure (I)

| No. | Structure | Name | Method | [M + H]+ |
|---|---|---|---|---|
| I-26 | 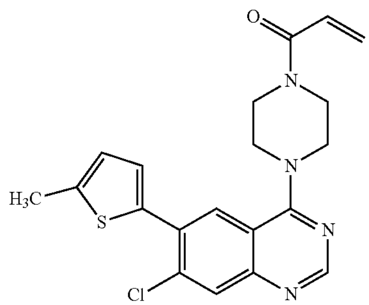 [SMILES: C=CC(=O)N1CCN(c2ncnc3cc(Cl)c(-c4ccc(C)s4)cc23)CC1] | 1-(4-(7-chloro-6-(5-methylthiophen-2-yl)quinazolin-4-yl)piperazin-1-yl)prop-2-en-1-one | B | 399.20 |
| I-27 | 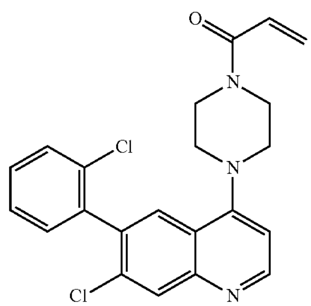 [SMILES: C=CC(=O)N1CCN(c2ccnc3cc(Cl)c(-c4ccccc4Cl)cc23)CC1] | 1-(4-(7-chloro-6-(2-chlorophenyl)quinolin-4-yl)piperazin-1-yl)prop-2-en-1-one | E | 412.20 |
| I-28 | 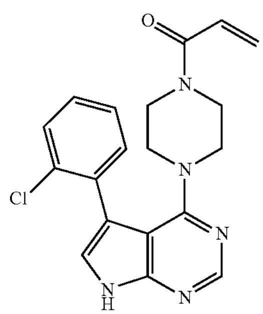 [SMILES: C=CC(=O)N1CCN(c2ncnc3[nH]cc(-c4ccccc4Cl)c23)CC1] | 1-(4-(5-(2-chlorophenyl)-7,7a-dihydro-4aH-pyrrolo[2,3-d]pyrimidin-4-yl)piperazin-1-yl)prop-2-en-1-one | J | 368.25 |
| I-29 | 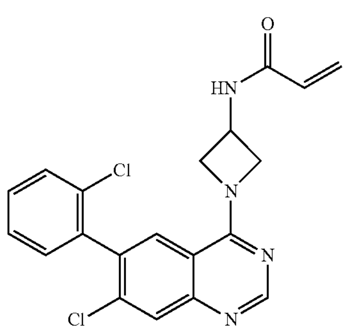 [SMILES: C=CC(=O)NC1CN(c2ncnc3cc(Cl)c(-c4ccccc4Cl)cc23)C1] | N-(1-(7-chloro-6-(2-chlorophenyl)quinazolin-4-yl)azetidin-3-yl)acrylamide | B | 399.20 |
| I-30 | 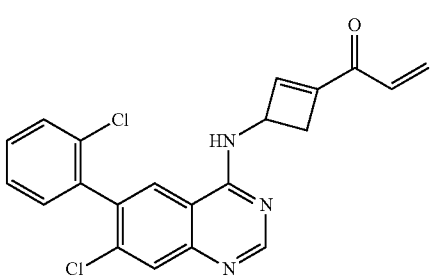 [SMILES: C=CC(=O)C1=CC(Nc2ncnc3cc(Cl)c(-c4ccccc4Cl)cc23)C1] | 1-(3-(7-chloro-6-(2-chlorophenyl)quinazolin-4-ylamino)azetidin-1-yl)prop-2-en-1-one | B | 399.20 |

TABLE 1-continued

Exemplary Compounds of Structure (I)

| No. | Structure | Name | Method | [M + H]⁺ |
|---|---|---|---|---|
| I-31 | 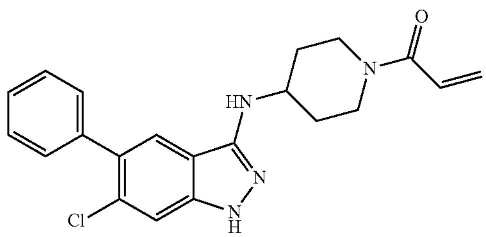 [SMILES: C=CC(=O)N1CCC(Nc2n[nH]c3cc(Cl)c(-c4ccccc4)cc23)CC1] | 1-(4-(6-chloro-5-(2-chlorophenyl)-1H-indazol-3-ylamino)piperidin-1-yl)prop-2-en-1-one | C | 413.40⁺ |
| I-32 | 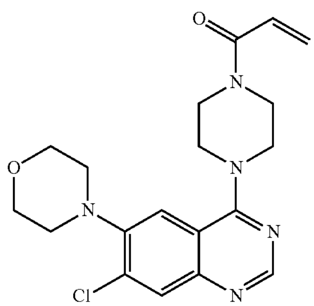 [SMILES: C=CC(=O)N1CCN(c2ncnc3cc(Cl)c(N4CCOCC4)cc23)CC1] | 1-(4-(7-chloro-6-morpholinoquinazolin-4-yl)piperazin-1-yl)prop-2-en-1-one | L | 388.25 |
| I-33 | 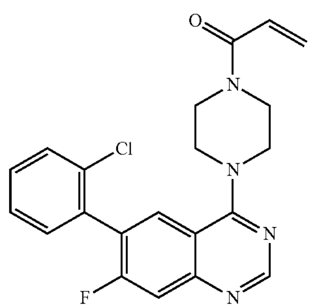 [SMILES: C=CC(=O)N1CCN(c2ncnc3cc(F)c(-c4ccccc4Cl)cc23)CC1] | 1-(4-(6-(2-chlorophenyl)-7-fluoroquinazolin-4-yl)piperazin-1-yl)prop-2-en-1-one | B | 397.20 |
| I-34 | 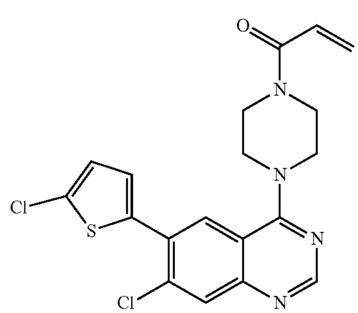 [SMILES: C=CC(=O)N1CCN(c2ncnc3cc(Cl)c(-c4ccc(Cl)s4)cc23)CC1] | 1-(4-(7-chloro-6-(5-chlorothiophen-2-yl)quinazolin-4-yl)piperazin-1-yl)prop-2-en-1-one | B | 419.15 |
| I-35 | 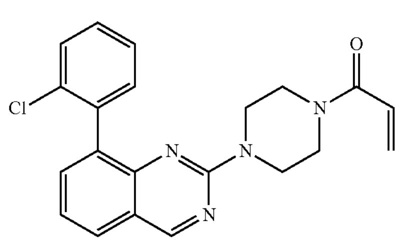 [SMILES: C=CC(=O)N1CCN(c2ncc3cccc(-c4ccccc4Cl)c3n2)CC1] | 1-(4-(8-(2-chlorophenyl)quinazolin-2-yl)piperazin-1-yl)prop-2-en-1-one | I | 379.1 |

TABLE 1-continued

Exemplary Compounds of Structure (I)

| No. | Structure | Name | Method | [M + H]⁺ |
|-----|-----------|------|--------|----------|
| I-36 | 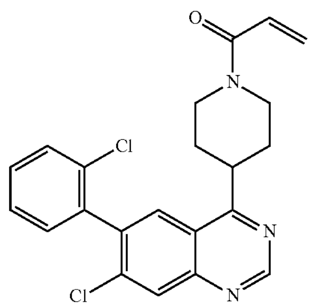 [SMILES: C=CC(=O)N1CCC(c2ncnc3cc(Cl)c(-c4ccccc4Cl)cc23)CC1] | 1-(4-(7-chloro-6-(2-chlorophenyl)quinazolin-4-yl)piperidin-1-yl)prop-2-en-1-one | K | 410.35⁺ |
| I-37 | 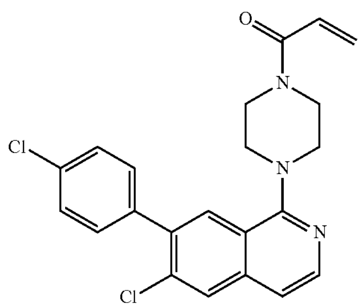 [SMILES: C=CC(=O)N1CCN(c2nccc3cc(Cl)c(-c4ccc(Cl)cc4)cc23)CC1] | 1-(4-(6-chloro-7-(4-chlorophenyl)isoquinolin-1-yl)piperazin-1-yl)prop-2-en-1-one | D | 412.20 |
| I-38 | 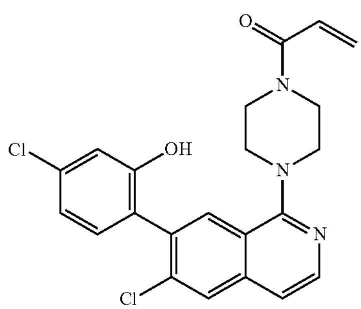 [SMILES: C=CC(=O)N1CCN(c2nccc3cc(Cl)c(-c4ccc(Cl)cc4O)cc23)CC1] | 1-(4-(6-chloro-7-(4-chloro-23-hydroxyphenyl)isoquinolin-1-yl)piperazin-1-yl)prop-2-en-1-one | D | 428.25 |
| I-39 | 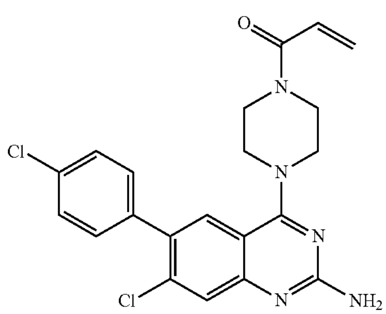 [SMILES: C=CC(=O)N1CCN(c2nc(N)nc3cc(Cl)c(-c4ccc(Cl)cc4)cc23)CC1] | 1-(4-(2-amino-7-chloro-6-(4-chlorophenyl)quinazolin-4-yl)piperazin-1-yl)prop-2-en-1-one | F | 428.3 |
| I-40 | 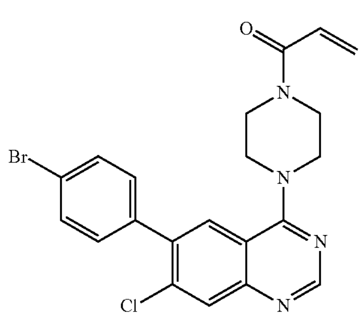 | 1-(4-(6-(4-bromophenyl)-7-chloroquinazolin-4-yl)piperazin-1-yl)prop-2-en-1-one | B | 459.25 |

TABLE 1-continued

Exemplary Compounds of Structure (I)

| No. | Structure | Name | Method | [M + H]+ |
|---|---|---|---|---|
| I-41 | 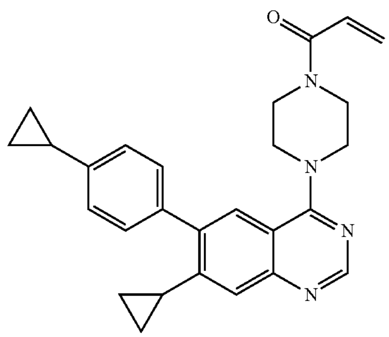 [SMILES: C=CC(=O)N1CCN(c2ncnc3cc(C4CC4)c(-c4ccc(C5CC5)cc4)cc23)CC1] | 1-(4-(7-cyclopropyl-6-(4-cyclopropylphenyl)quinazolin-4-yl)piperazin-1-yl)prop-2-en-1-one | B | 425.25 |
| I-42 | 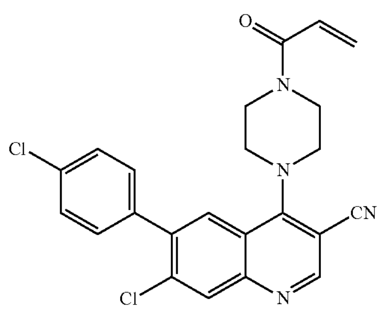 [SMILES: C=CC(=O)N1CCN(c2c(C#N)cnc3cc(Cl)c(-c4ccc(Cl)cc4)cc23)CC1] | 4-(4-acryloylpiperazin-1-yl)-7-chloro-6-(4-chlorophenyl)quinoline-3-carbonitrile | G | 437.25 |
| I-43 | 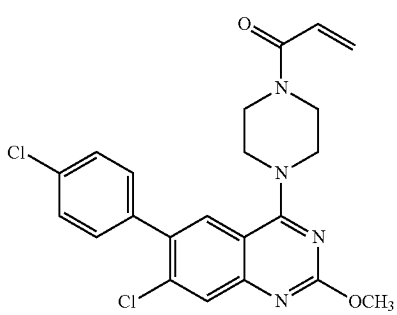 [SMILES: C=CC(=O)N1CCN(c2nc(OC)nc3cc(Cl)c(-c4ccc(Cl)cc4)cc23)CC1] | 1-(4-(7-chloro-6-(4-chlorophenyl)-2-methoxyquinazolin--4-yl)piperazin-1-yl)prop-2-en-1-one | F | 465.30* |
| I-44 | 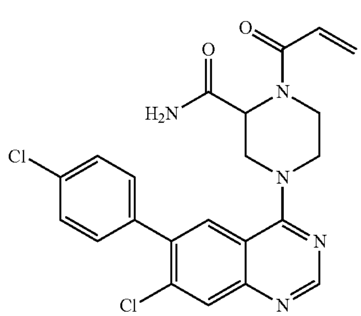 [SMILES: C=CC(=O)N1CCN(c2ncnc3cc(Cl)c(-c4ccc(Cl)cc4)cc23)CC1C(N)=O] | 1-acryloyl-4-(7-chloro-6-(4-chlorophenyl)quinazolin-4-yl)piperazin-2-carboxamide | A | 454.35+ |

TABLE 1-continued

Exemplary Compounds of Structure (I)

| No. | Structure | Name | Method | [M + H]+ |
|---|---|---|---|---|
| I-45 | 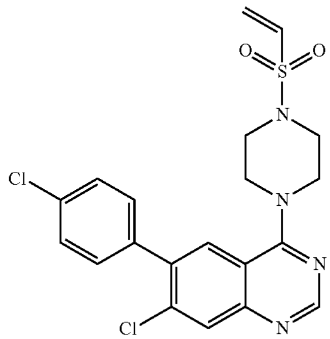 [SMILES: C=CS(=O)(=O)N1CCN(c2ncnc3cc(Cl)c(-c4ccc(Cl)cc4)cc23)CC1] | 7-chloro-6-(4-chlorophenyl)-4-(4-(vinylsulfonyl)piperazin-1-yl)quinazoline | A | 449.25 |
| I-46 | 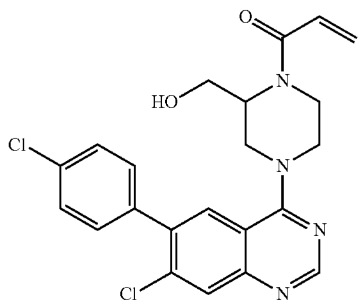 [SMILES: C=CC(=O)N1CCN(c2ncnc3cc(Cl)c(-c4ccc(Cl)cc4)cc23)CC1CO] | 1-(4-(7-chloro-6-(4-chlorophenyl)quinazolin-4-yl)-2-(hydroxymethyl)piperazin-1-yl)prop-2-en-1-one | A | 443.30 |
| I-47 | 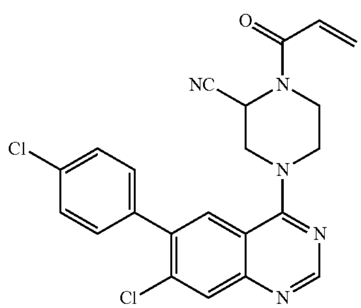 | 1-acryloyl-4-(7-chloro-6-(4-chlorophenyl)quinazolin-4-yl)piperazine-2-carbonitrile | A | 438.25 |
| I-48 | 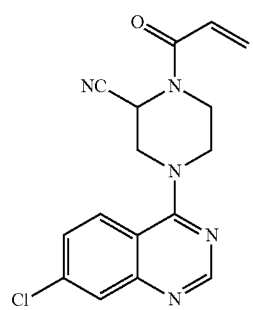 [SMILES: C=CC(=O)N1CCN(c2ncnc3cc(Cl)ccc23)CC1C#N] | 1-acryloyl-4-(7-chloroquinazolin-4-yl)piperazine-2-carbonitrile | A | 328.2 |
| I-49 | 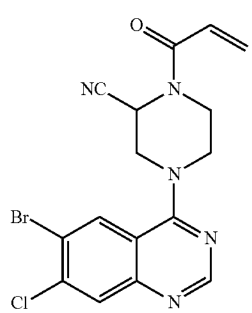 | 1-acryloyl-4-(6-bromo-7-chloroquinazolin-4-yl)piperazine-2-carbonitrile | A | 408.20 |

TABLE 1-continued

Exemplary Compounds of Structure (I)

| No. | Structure | Name | Method | [M + H]⁺ |
|---|---|---|---|---|
| I-50 | 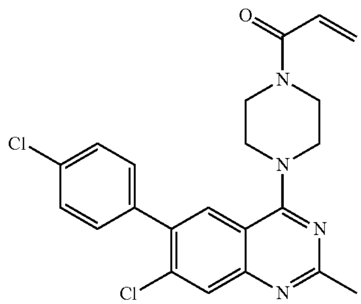 [SMILES: C=CC(=O)N1CCN(c2nc(C)nc3cc(Cl)c(-c4ccc(Cl)cc4)cc23)CC1] | 1-(4-(7-chloro-6-(4-chlorophenyl)-2-methylquinazolin-4-yl)piperazin-1-yl)prop-2-en-1-one | M | 427.35 |
| I-51 | 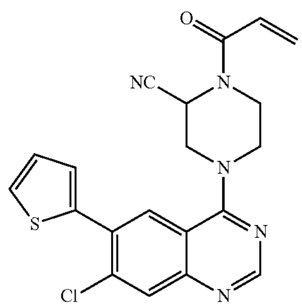 [SMILES: C=CC(=O)N1CCN(c2ncnc3cc(Cl)c(-c4cccs4)cc23)CC1C#N] | 1-acryoyl-4-(7-chloro-6-(thiophen-2-yl)quinazaolin-4-yl)piperazine-2-carbonitrile | A | 410.30 |
| I-52 | 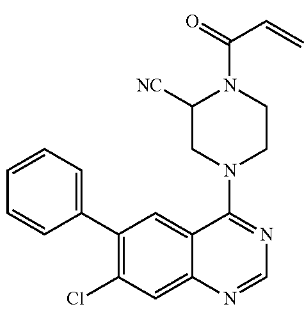 [SMILES: C=CC(=O)N1CCN(c2ncnc3cc(Cl)c(-c4ccccc4)cc23)CC1C#N] | 1-acryloyl-4-(7-chloro-6-phenylquinazolin-4-yl)piperazine-2-carbonitrile | A | 404.35 |
| I-53 | 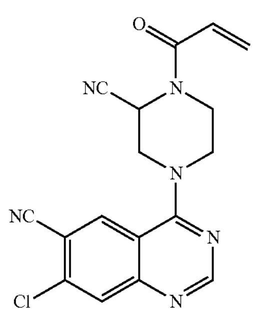 [SMILES: C=CC(=O)N1CCN(c2ncnc3cc(Cl)c(C#N)cc23)CC1C#N] | 4-(4-acryloyl-3-cyanopiperazin-1-yl)-7-chloroquinazoline-6-carbonitrile | B | 353.20 |
| I-54 | 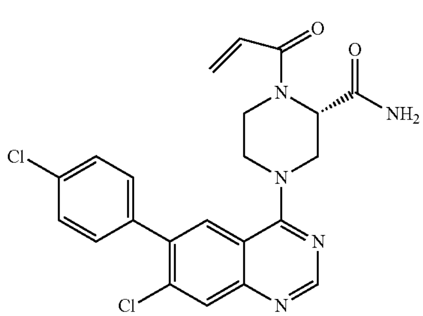 [SMILES: C=CC(=O)N1CCN(c2ncnc3cc(Cl)c(-c4ccc(Cl)cc4)cc23)C[C@H]1C(N)=O] | (S)-1-acryloyl-4-(7-chloro-6-(4-chlorophenyl)quinazolin-4-yl)piperazine-2-carboxamide | A | 456.30 |

TABLE 1-continued

Exemplary Compounds of Structure (I)

| No. | Structure | Name | Method | [M + H]+ |
|---|---|---|---|---|
| I-55 | 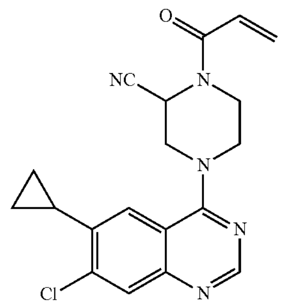 [SMILES: C=CC(=O)N1CCN(c2ncnc3cc(Cl)c(C4CC4)cc23)CC1C#N] | 1-acryoyl-4-(7-chloro-6-cyclopropylquinazolin-4-yl)piperazin-2-carbonitrile | B | 368.25 |
| I-56 | 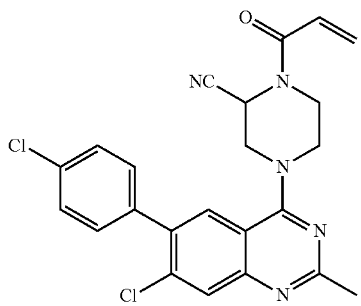 [SMILES: C=CC(=O)N1CCN(c2nc(C)nc3cc(Cl)c(-c4ccc(Cl)cc4)cc23)CC1C#N] | 1-acryloyl-4-(7-chloro-6-(4-chlorophenyl)-2-methylquinazolin-4-yl)piperazine-2-carbonitrile | M | 452.30 |
| I-57 | 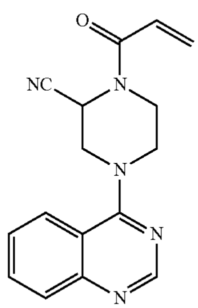 [SMILES: C=CC(=O)N1CCN(c2ncnc3ccccc23)CC1C#N] | 1-acryloyl-4-(quinazolin-4-yl)piperazine-2-carbontrile | A | 294.20 |
| I-58 | 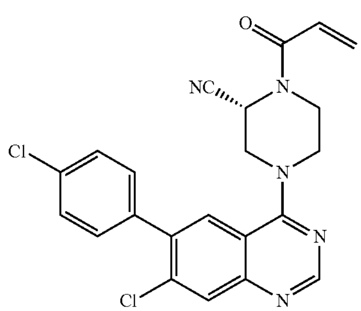 [SMILES: C=CC(=O)N1CCN(c2ncnc3cc(Cl)c(-c4ccc(Cl)cc4)cc23)C[C@@H]1C#N] | (R)-1-acryloyl-4-(7-chloro-6-(4-chlorophenyl)quinazolin-4-yl)piperazine-2-carbonitrile | A | 438.20 |
| I-59 | 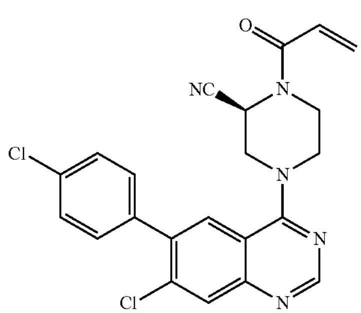 [SMILES: C=CC(=O)N1CCN(c2ncnc3cc(Cl)c(-c4ccc(Cl)cc4)cc23)C[C@H]1C#N] | (S)-1-acryloyl-4-(7-chloro-6-(4-chlorophenyl)quinazolin-4-yl)piperazine-2-carbonitrile | A | 438.25 |

TABLE 1-continued

Exemplary Compounds of Structure (I)

| No. | Name | Method | [M + H]+ |
|---|---|---|---|
| I-60 | 1-(4-(7-chloro-6-(4-chlorophenyl)quinazolin-4-yl)-2-((dimethylamino)methyl)piperazin-1-yl)prop-2-en-1-one | A | 470.35 |
| I-61 | 1-acryloyl-4-(6-chloroisoquinolin-1-yl)piperazine-2-carbonitrile | D | 327.20 |
| I-62 | 1-(4-(7-chloro-6-(4-chlorophenyl)quinazolin-4-yl)-2-(2-hydroxyethyl)piperazin-1-yl)prop-2-en-1-one | A | 457.35 |
| I-63 | (S)-1-(4-(7-chloro-6-(4-chlorophenyl)quinazolin-4-yl)-2-(hydroxymethyl)piperazin-1-yl)prop-2-en-1-one | A | 443.30 |
| I-64 | (R)-1-acryloyl-4-(7-chloro-6-(4-chlorophenyl)quinazolin-4-yl)piperazine-2-carboxamide | A | 456.30 |

TABLE 1-continued

Exemplary Compounds of Structure (I)

| No. | Structure | Name | Method | [M + H]+ |
|---|---|---|---|---|
| I-65 | 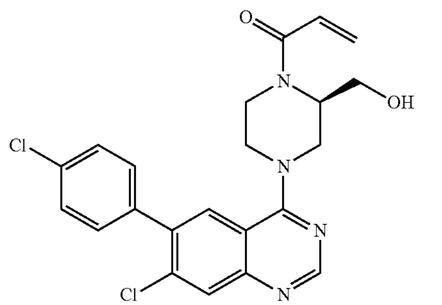 [SMILES: C=CC(=O)N1CCN(c2ncnc3cc(Cl)c(-c4ccc(Cl)cc4)cc23)C[C@@H]1CO] | (R)-1-(4-(7-chloro-6-(4-chlorophenyl)quinazolin-4-yl)-2-(hydroxymethyl)piperazin-1-yl)prop-2-en-1-one | A | 443.35 |
| I-66 | 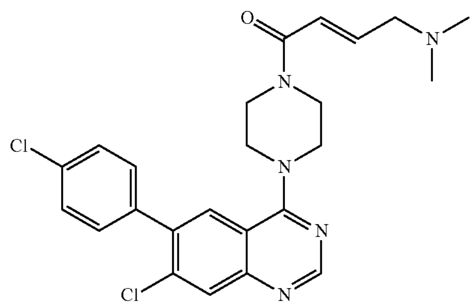 [SMILES: CN(C)C/C=C/C(=O)N1CCN(c2ncnc3cc(Cl)c(-c4ccc(Cl)cc4)cc23)CC1] | (E)-4-(7-chloro-6-(4-chlorophenyl)quinazolin-4-yl)-1-(4-(dimethylamino)but-2-enoyl)piperazine-2-carbonitrile | A | 495.40 |
| I-67 | 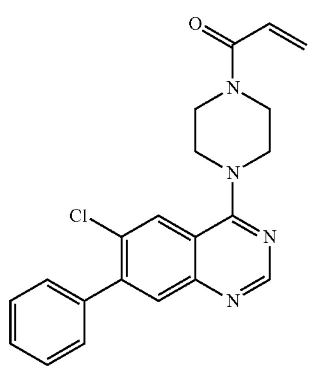 [SMILES: C=CC(=O)N1CCN(c2ncnc3cc(-c4ccccc4)c(Cl)cc23)CC1] | 1-(4-(6-chloro-7-phenylquinazolin-4-yl)piperazin-1-yl)prop-2-en-1-one | B | 379.30 |
| I-68 | 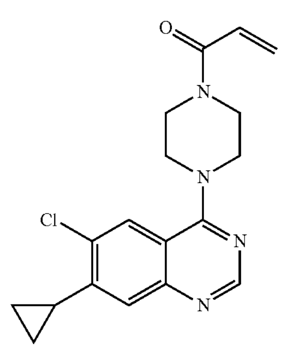 [SMILES: C=CC(=O)N1CCN(c2ncnc3cc(C4CC4)c(Cl)cc23)CC1] | 1-(4-(6-chloro-7-cyclopropylquinazolin-4-yl)piperazin-1-yl)prop-2-en-1-one | A | 343.25 |

TABLE 1-continued

Exemplary Compounds of Structure (I)

| No. | Structure | Name | Method | [M + H]+ |
|---|---|---|---|---|
| I-69 | 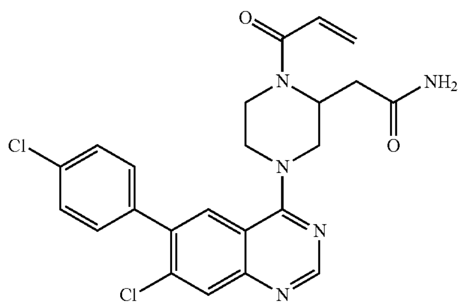 [SMILES: C=CC(=O)N1CCN(c2ncnc3cc(Cl)c(-c4ccc(Cl)cc4)cc23)CC1CC(N)=O] | 2-(1-acryloyl-4-(7-chloro-6-(4-chlorophenyl)quinazolin-4-yl)piperazin-2-yl)acetamide | A | 470.35 |
| I-70 | 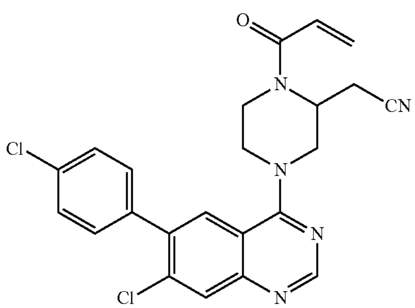 [SMILES: C=CC(=O)N1CCN(c2ncnc3cc(Cl)c(-c4ccc(Cl)cc4)cc23)CC1CC#N] | 2-(1-acryloyl-4-(7-chloro-6-(4-chlorophenyl)quinazolin-4-yl)piperazin-2-yl)acetonitrile | A | 452.35 |
| I-71 | 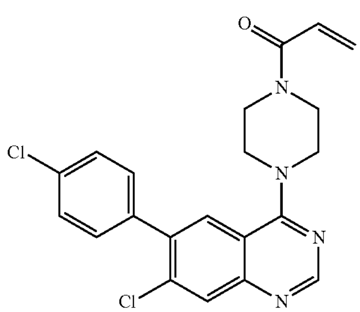 [SMILES: C=CC(=O)N1CCN(c2ncnc3cc(Cl)c(-c4ccc(Cl)cc4)cc23)CC1] | 1-(4-(6-(4-chlorophenyl)quinazolin-4-yl)piperazin-1-yl)prop-2-en-1-one | A | 379.30 |
| I-72 | 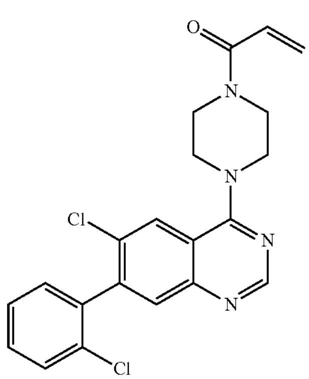 [SMILES: C=CC(=O)N1CCN(c2ncnc3cc(-c4ccccc4Cl)c(Cl)cc23)CC1] | 1-(4-(6-chloro-7-(2-chlorophenyl)quinazolin-4-yl)piperazin-1-yl)prop-2-en-1-one | A | 413.25 |

TABLE 1-continued
Exemplary Compounds of Structure (I)
| No. | Structure | Name | Method | [M + H]+ |
|---|---|---|---|---|
| I-73 | 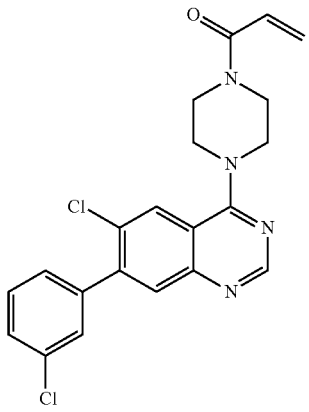 [SMILES: C=CC(=O)N1CCN(c2ncnc3cc(-c4cccc(Cl)c4)c(Cl)cc23)CC1] | 1-(4-(6-chloro-7-(3-chlorophenyl)quinazolin-4-yl)piperazin-1-yl)prop-2-en-1-one | A | 413.3 |
| I-74 | 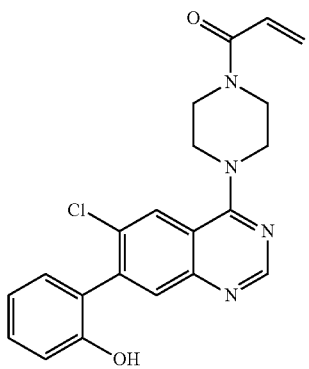 | 1-(4-(6-chloro-7-(2-hydroxyphenyl)quinazolin-4-yl)piperazin-1-yl)prop-2-en-1-one | A | 395.25 |
| I-75 | 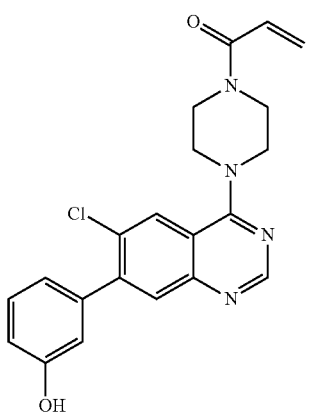 | 1-(4-(6-chloro-7-(3-hydroxyphenyl)quinazolin-4-yl)piperazin-1-yl)prop-2-en-1-one | A | 395.25 |
| I-76 | 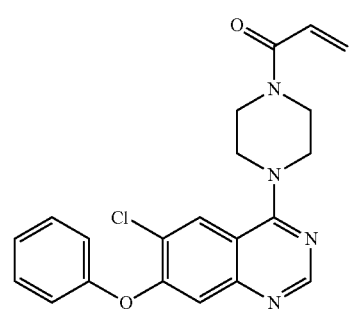 [SMILES: C=CC(=O)N1CCN(c2ncnc3cc(Oc4ccccc4)c(Cl)cc23)CC1] | 1-(4-(6-chloro-7-phenoxyquinazolin-4-yl)piperazin-1-yl)prop-2-en-1-one | L | 395.25 |

TABLE 1-continued

Exemplary Compounds of Structure (I)

| No. | Structure | Name | Method | [M + H]+ |
|---|---|---|---|---|
| I-77 | 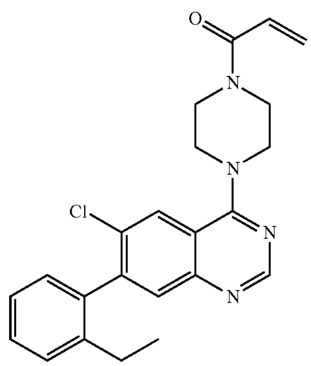 [SMILES: C=CC(=O)N1CCN(c2ncnc3cc(-c4ccccc4CC)c(Cl)cc23)CC1] | 1-(4-(6-chloro-7-(2-ethylphenyl)quinazolin-4-yl)piperazin-1-yl)prop-2-en-1-one | A | 407.75 |
| I-78 | 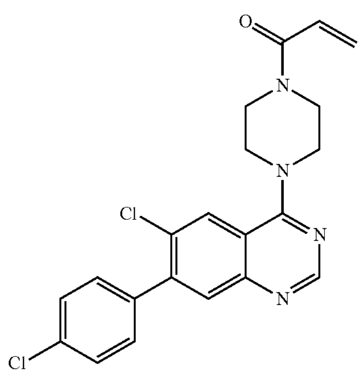 [SMILES: C=CC(=O)N1CCN(c2ncnc3cc(-c4ccc(Cl)cc4)c(Cl)cc23)CC1] | 1-(4-(6-chloro-7-(4-chlorophenyl)quinazolin-4-yl)piperazin-1-yl)prop-2-en-1-one | A | 413.25 |
| I-79 | 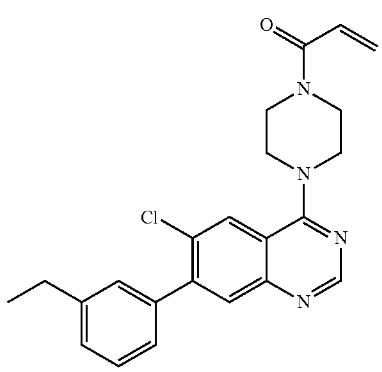 [SMILES: C=CC(=O)N1CCN(c2ncnc3cc(-c4cccc(CC)c4)c(Cl)cc23)CC1] | 1-(4-(6-chloro-7-(3-ethylphenyl)quinazolin-4-yl)piperazin-1-yl)prop-2-en-1-one | A | 407.30 |
| I-80 | 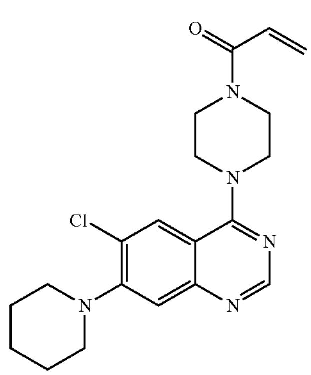 [SMILES: C=CC(=O)N1CCN(c2ncnc3cc(N4CCCCC4)c(Cl)cc23)CC1] | 1-(4-(6-chloro-7-(piperazin-1-yl)quinazolin-4-yl)piperazin-1-yl)prop-2-en-1-one | L | 387.25 |

TABLE 1-continued
Exemplary Compounds of Structure (I)
| No. | Structure | Name | Method | [M + H]+ |
|---|---|---|---|---|
| I-81 | 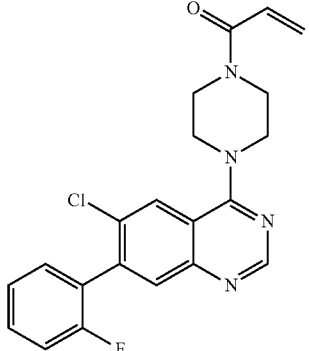 | 1-(4-(6-chloro-7-(2-fluorophenyl)quinazolin-4-yl)piperazin-1-yl)prop-2-en-1-one | A | 397.25 |
| I-82 | 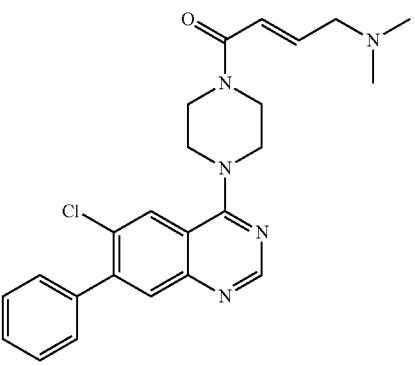 [SMILES: CN(C)C/C=C/C(=O)N1CCN(c2ncnc3cc(-c4ccccc4)c(Cl)cc23)CC1] | (E)-1-(4-(6-chloro-7-phenylquinazolin-4-yl)piperazin-1-yl)-4-(dimethylamino)but-2-en-1-one | A | 436.40 |
| I-83 | 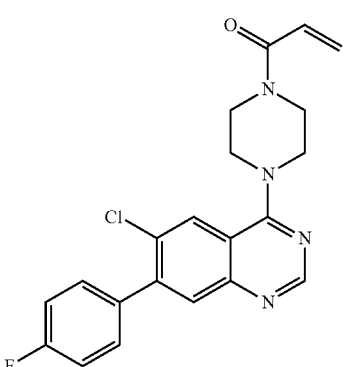 | 1-(4-(6-chloro-7-(4-fluorophenyl)quinazolin-4-yl)piperazin-1-yl)prop-2-en-1-one | A | 397.25 |
| I-84 | 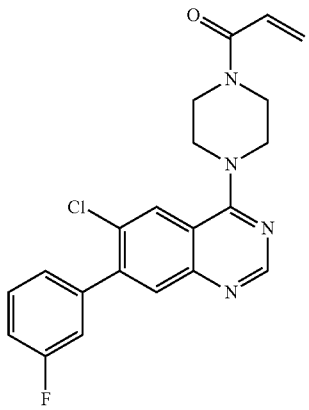 [SMILES: C=CC(=O)N1CCN(c2ncnc3cc(-c4cccc(F)c4)c(Cl)cc23)CC1] | 1-(4-(6-chloro-7-(3-fluorophenyl)quinazolin-4-yl)piperazin-1-yl)prop-2-en-1-one | A | 397.25 |

TABLE 1-continued

Exemplary Compounds of Structure (I)

| No. | Structure | Name | Method | [M + H]+ |
|---|---|---|---|---|
| I-85 | 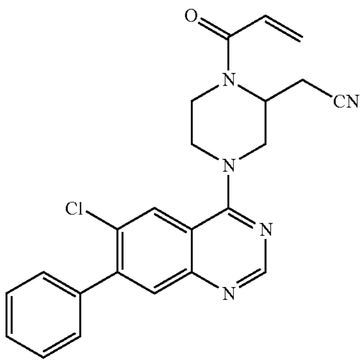 [SMILES: C=CC(=O)N1CCN(c2ncnc3cc(-c4ccccc4)c(Cl)cc23)CC1CC#N] | 2-(1-acryloyl-4-(6-chloro-7-phenylquinazolin-4-yl)piperazin-2-yl)acetonitrile | A | 418.30 |
| I-86 | 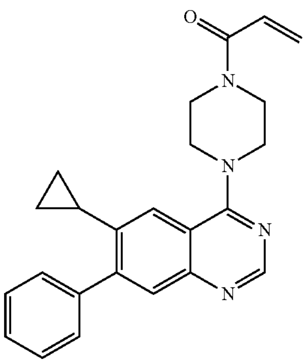 [SMILES: C=CC(=O)N1CCN(c2ncnc3cc(-c4ccccc4)c(C4CC4)cc23)CC1] | 1-(4-(6-cyclopropyl-7-phenylquinazolin-4-yl)piperazin-1-yl)prop-2-en-1-one | B | 385.75 |
| I-87 | 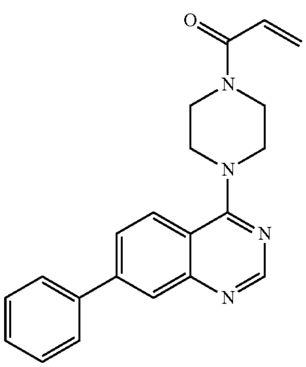 [SMILES: C=CC(=O)N1CCN(c2ncnc3cc(-c4ccccc4)ccc23)CC1] | 1-(4-97-phenylquinazolin-4-yl)piperazin-1-yl)prop-2-en-1-one | B | 345.20 |
| I-88 | 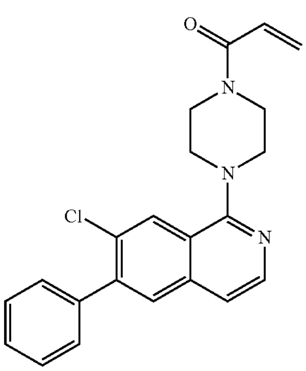 [SMILES: C=CC(=O)N1CCN(c2nccc3cc(-c4ccccc4)c(Cl)cc23)CC1] | 1-(4-(7-chloro-6-phenylisoquinolin-1-yl)piperazin-1-yl)prop-2-en-1-one | D | 378.20 |

TABLE 1-continued

Exemplary Compounds of Structure (I)

| No. | Structure | Name | Method | [M + H]+ |
|---|---|---|---|---|
| I-89 | 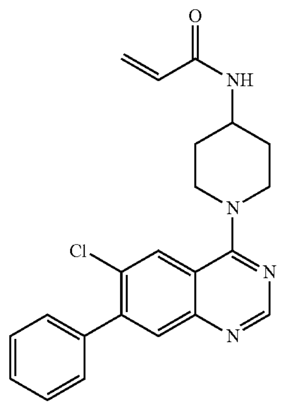 [SMILES: C=CC(=O)NC1CCN(c2ncnc3cc(-c4ccccc4)c(Cl)cc23)CC1] | N-(1-(6-chloro-7-phenylquinazolin-4-yl)piperidin-4-yl)acrylamide | B | 393.25 |
| I-90 | 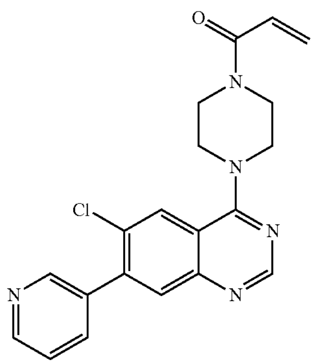 [SMILES: C=CC(=O)N1CCN(c2ncnc3cc(-c4cccnc4)c(Cl)cc23)CC1] | 1-(4-(6-chloro-7-(pyridin-3-yl)quinazolin-4-yl)piperazain-1-yl)prop-2-en-1-one | B | 380.25 |
| I-91 | 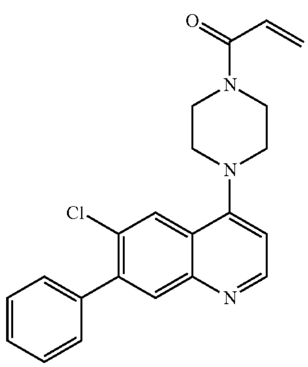 [SMILES: C=CC(=O)N1CCN(c2ccnc3cc(-c4ccccc4)c(Cl)cc23)CC1] | 1-(4-(6-chloro-7-phenylquinolin-4-yl)piperazin-1-yl)prop-2-en-1-one | E | 378.20 |
| I-92 | 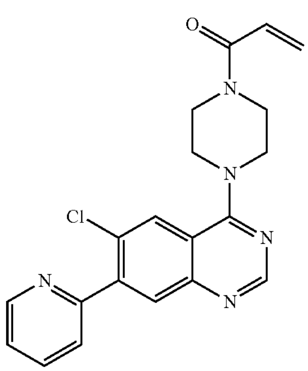 [SMILES: C=CC(=O)N1CCN(c2ncnc3cc(-c4ccccn4)c(Cl)cc23)CC1] | 1-(4-(6-chloro-7-(pyridin-2-yl)quinazolin-4-yl)piperazin-1-yl)prop-2-en-1-one | B | 380.25 |

TABLE 1-continued

Exemplary Compounds of Structure (I)

| No. | Structure | Name | Method | [M + H]⁺ |
|---|---|---|---|---|
| I-93 | 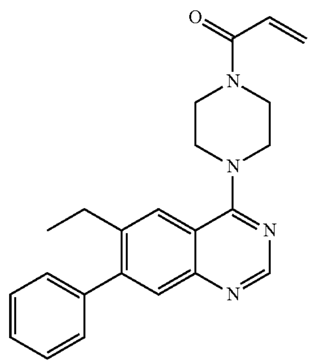 [SMILES: C=CC(=O)N1CCN(c2ncnc3cc(-c4ccccc4)c(CC)cc23)CC1] | 1-(4-(6-ethyl-7-phenylquinazolin-4-yl)piperazin-1-yl)prop-2-en-1-one | B | 373.75 |
| I-94 | 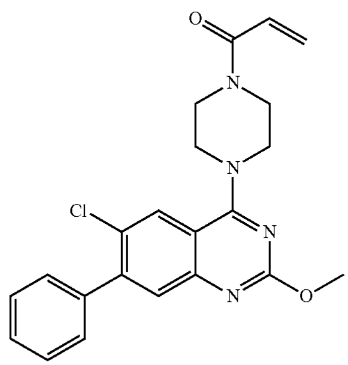 [SMILES: C=CC(=O)N1CCN(c2nc(OC)nc3cc(-c4ccccc4)c(Cl)cc23)CC1] | 1-(4-(6-chloro-2-methoxy-7-phenylquinazolin-4-yl)piperazin-1-yl)prop-2-en-1-one | F | 409.30 |
| I-95 | 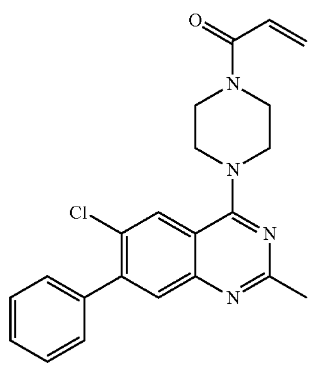 [SMILES: C=CC(=O)N1CCN(c2nc(C)nc3cc(-c4ccccc4)c(Cl)cc23)CC1] | 1-(4-(6-chloro-2-methyl-7-phenylquinazolin-4-yl)piperazin-1-yl)prop-2-en-1-one | M | 393.70 |
| I-(6 | 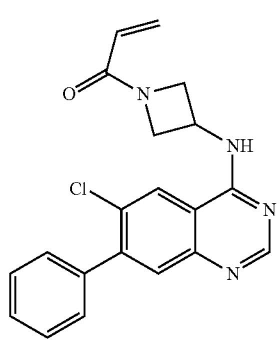 [SMILES: C=CC(=O)N1CC(Nc2ncnc3cc(-c4ccccc4)c(Cl)cc23)C1] | 1-(3-(6-chloro-7-phenylquinazolin-4-ylamino)azetidin-1-yl)prop-2-en-1-one | A | 365.20 |

TABLE 1-continued

Exemplary Compounds of Structure (I)

| No. | Structure | Name | Method | [M + H]+ |
|---|---|---|---|---|
| I-97 | 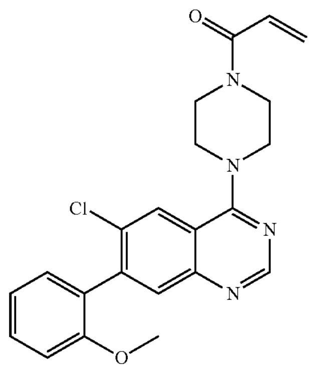 [SMILES: C=CC(=O)N1CCN(c2ncnc3cc(-c4ccccc4OC)c(Cl)cc23)CC1] | 1-(4-(6-chloro-7-(2-methoxyphenyl)quinazolin-4-yl)piperazin-1-yl)prop-2-en-1-one | B | 409.7 |
| I-98 | 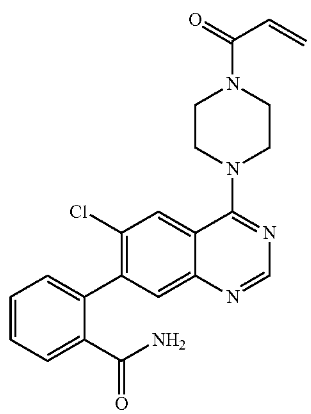 [SMILES: C=CC(=O)N1CCN(c2ncnc3cc(-c4ccccc4C(N)=O)c(Cl)cc23)CC1] | 2-(4-(4-acryloylpiperazin-1-yl)-6-chloroquinazolin-7-yl)benzamide | B | 422.30 |
| I-99 | 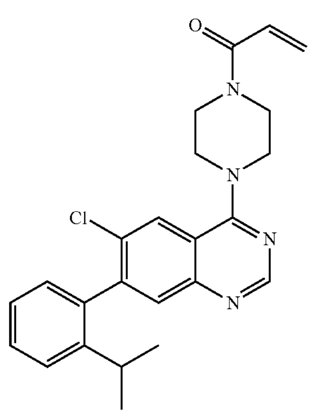 [SMILES: C=CC(=O)N1CCN(c2ncnc3cc(-c4ccccc4C(C)C)c(Cl)cc23)CC1] | 1-(4-(6-chloro-7-(2-isopeopylphenyl)quinazolin-4-yl)piperazin-1-yl)prop-2-en-1-one | B | 421.35 |
| I-100 | 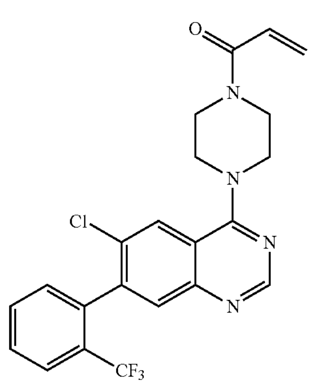 [SMILES: C=CC(=O)N1CCN(c2ncnc3cc(-c4ccccc4C(F)(F)F)c(Cl)cc23)CC1] | 1-(4-(6-chloro-7-(2-(trifluoromethyl)phenyl)quinazolin-4-yl)piperazin-1-yl)prop-2-en-1-one | B | 447.80 |

TABLE 1-continued

Exemplary Compounds of Structure (I)

| No. | Structure | Name | Method | [M + H]+ |
|---|---|---|---|---|
| I-101 | 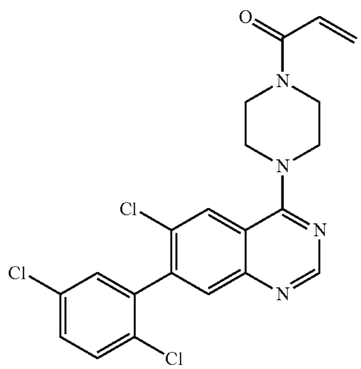 [SMILES: C=CC(=O)N1CCN(c2ncnc3cc(-c4cc(Cl)ccc4Cl)c(Cl)cc23)CC1] | 1-(4-(6-chloro-7-(2,5-dichlorophenyl)quinazolin-4-yl)piperazin-1-yl)prop-2-en-1-one | B | 447.25 |
| I-102 | 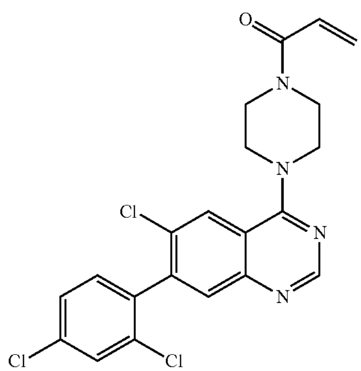 [SMILES: C=CC(=O)N1CCN(c2ncnc3cc(-c4ccc(Cl)cc4Cl)c(Cl)cc23)CC1] | 1-(4-(6-chloro-7-(2,4-dichlorophenyl)quinazolin-4-yl)piperazin-1-yl)prop-2-en-1-one | B | 447.30 |
| I-103 | 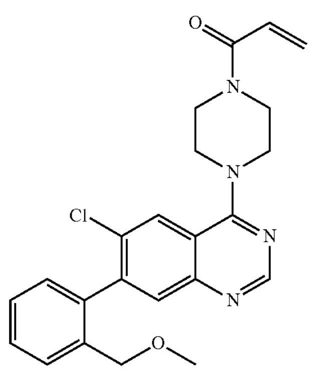 [SMILES: C=CC(=O)N1CCN(c2ncnc3cc(-c4ccccc4COC)c(Cl)cc23)CC1] | 1-(4-(6-chloro-7-(2-(methoxymethyl)phenyl)quinazolin-4-yl)piperazin-1-yl)prop-2-en-1-one | B | 423.35 |
| I-104 | 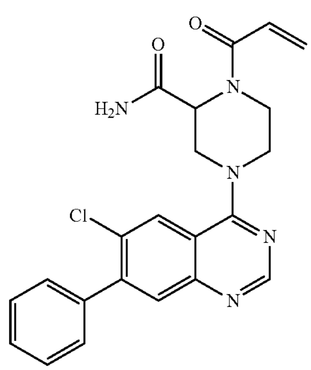 [SMILES: C=CC(=O)N1CCN(c2ncnc3cc(-c4ccccc4)c(Cl)cc23)CC1C(N)=O] | 1-acryloyl-4-(6-chloro-7-phenylquinazolin-4-yl)piperazine-2-carboxamide | B | 422.35 |

TABLE 1-continued

Exemplary Compounds of Structure (I)

| No. | Structure | Name | Method | [M + H]+ |
|---|---|---|---|---|
| I-105 | 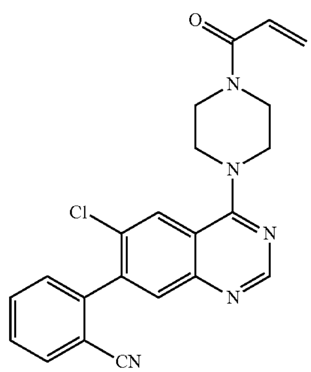 [SMILES: C=CC(=O)N1CCN(c2ncnc3cc(-c4ccccc4C#N)c(Cl)cc23)CC1] | 2-(4-(4-acryloylpiperazin-1-yl)-6-chloroquinazolin-7-yl)benzonitrile | B | 405.20 |
| I-106 | 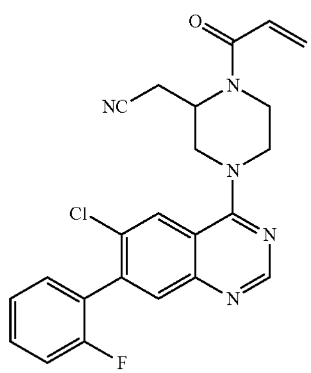 [SMILES: C=CC(=O)N1CCN(c2ncnc3cc(-c4ccccc4F)c(Cl)cc23)CC1CC#N] | 2-(1-acryloyl-4-(6-chloro-7-(2-fluorophenyl)quinazolin-4-yl)piperazin-1-yl)acetonitrile | B | 437.30 |
| I-107 | 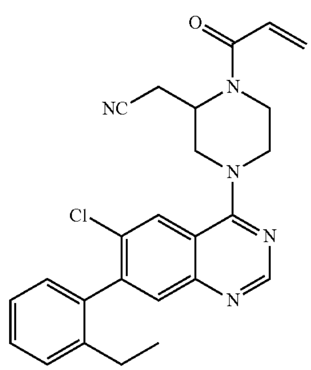 [SMILES: C=CC(=O)N1CCN(c2ncnc3cc(-c4ccccc4CC)c(Cl)cc23)CC1CC#N] | 2-(1-acryloyl-4-(6-chloro-7-(2-ethylphenyl)quinazolin-4-yl)piperazin-2-yl)acetonitrile | B | 446.35 |
| I-108 | 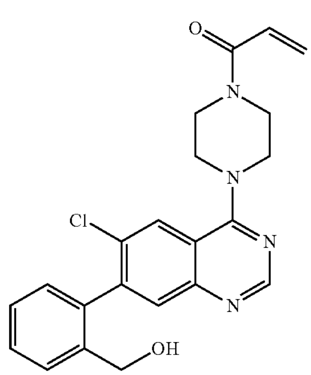 | 1-(4-(6-chloro-7-(2-(hydroxymethyl)phenyl)quinazolin-4-yl)piperazin-1-yl)prop-2-en-1-one | B | 409.30 |

TABLE 1-continued

Exemplary Compounds of Structure (I)

| No. | Structure | Name | Method | [M + H]+ |
|---|---|---|---|---|
| I-109 | 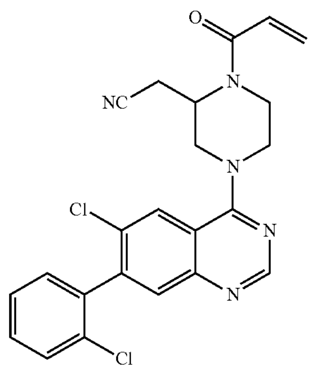 [SMILES: C=CC(=O)N1CCN(c2ncnc3cc(-c4ccccc4Cl)c(Cl)cc23)CC1CC#N] | 2-(1-acryloyl-4-(6-chloro-7-(2-chlorophenyl)quinazolin-4-yl)piperazin-2-yl)acetonitrile | B | 452.30 |
| I-110 | 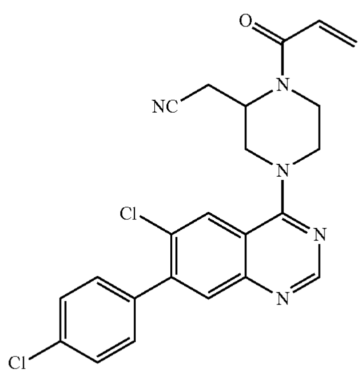 [SMILES: C=CC(=O)N1CCN(c2ncnc3cc(-c4ccc(Cl)cc4)c(Cl)cc23)CC1CC#N] | 2-(1-acryloyl-4-(6-chloro-7-(4-chlorophenyl)quinazolin-4-yl)piperazin-2-yl)acetonitrile | B | 452.25 |
| I-111 | 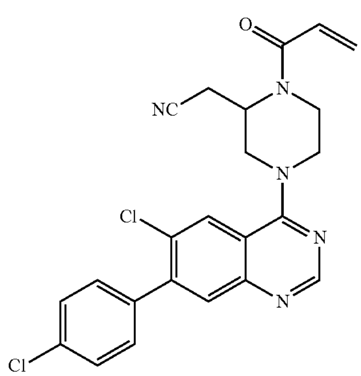 [SMILES: C=CC(=O)N1CCN(c2ncnc3cc(-c4ccc(Cl)cc4)c(Cl)cc23)CC1CC#N] | 2-(1-acryloyl-4-(6-chloro-7-(4-chlorophenyl)quinazolin-4-yl)piperazin-2-yl)acetonitrile | B | 452.25 |
| I-112 | 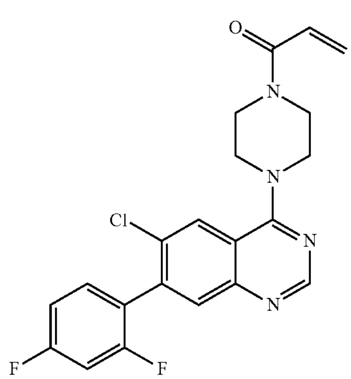 [SMILES: C=CC(=O)N1CCN(c2ncnc3cc(-c4ccc(F)cc4F)c(Cl)cc23)CC1] | 1-(4-(6-chloro-7-(2,4-difluorophenyl)quinazolin-4-yl)piperazin-1-yl)prop-2-en-1-one | B | 415.0 |

TABLE 1-continued

Exemplary Compounds of Structure (I)

| No. | Structure | Name | Method | [M + H]+ |
|---|---|---|---|---|
| I-113 | 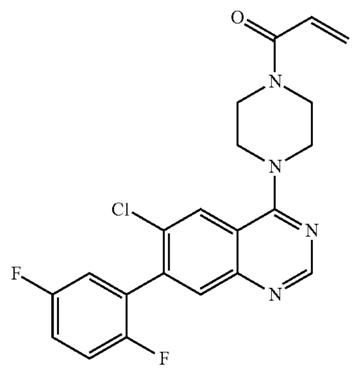 [SMILES: C=CC(=O)N1CCN(c2ncnc3cc(-c4cc(F)ccc4F)c(Cl)cc23)CC1] | 1-(4-(6-chloro-7-(2,5-difluorophenyl)quinazolin-4-yl)piperazin-1-yl)prop-2-en-1-one | B | 415.10 |
| I-114 | 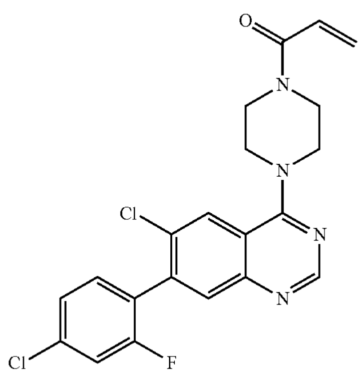 [SMILES: C=CC(=O)N1CCN(c2ncnc3cc(-c4ccc(Cl)cc4F)c(Cl)cc23)CC1] | 1-(4-(6-chloro-7-(4-chloro-2-fluorophenyl)quinazolin-4-yl)piperazin-1-yl)prop-2-en-1-one | B | 431.05 |
| I-115 | 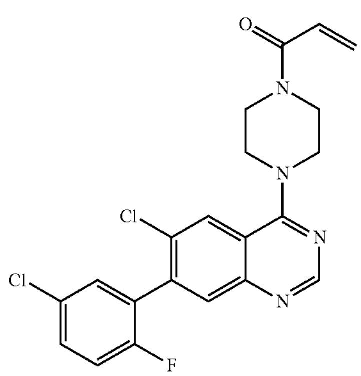 [SMILES: C=CC(=O)N1CCN(c2ncnc3cc(-c4cc(Cl)ccc4F)c(Cl)cc23)CC1] | 1-(4-(6-chloro-7-(5-chloro-2-fluorophenyl)quinazolin-4-yl)piperazin-1-yl)prop-2-en-1-one | B | 431.05 |
| I-116 | 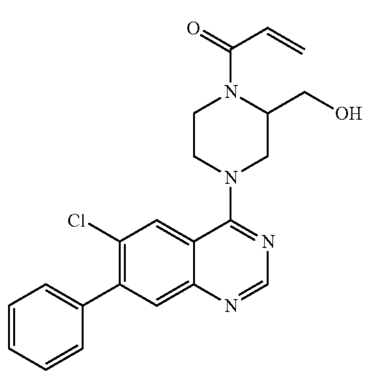 [SMILES: C=CC(=O)N1CCN(c2ncnc3cc(-c4ccccc4)c(Cl)cc23)CC1CO] | 1-(4-(6-chloro-7-phenylquinazolin-4-yl)-2-(hydroxymethyl)piperazin-1-yl)prop-2-en-1-one | B | 409.25 |

TABLE 1-continued

Exemplary Compounds of Structure (I)

| No. | Structure | Name | Method | [M + H]+ |
|---|---|---|---|---|
| I-117 | 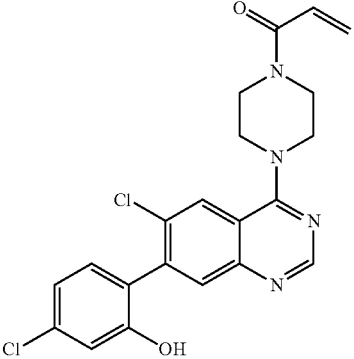 [SMILES: C=CC(=O)N1CCN(c2ncnc3cc(-c4ccc(Cl)cc4O)c(Cl)cc23)CC1] | 1-(4-(6-chloro-7-(4-chloro-2-hydroxyphenyl)quinazolin-4-yl)piperazin-1-yl)prop-2-en-1-one | B | 429.35 |
| I-118 | 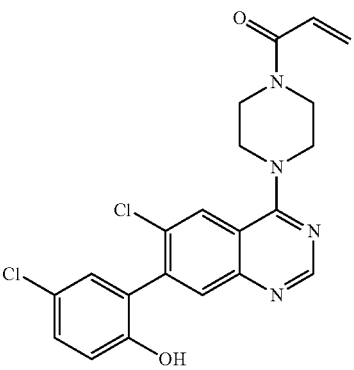 [SMILES: C=CC(=O)N1CCN(c2ncnc3cc(-c4cc(Cl)ccc4O)c(Cl)cc23)CC1] | 1-(4-(6-chloro-7-(5-chloro-2-hydroxyphenyl)quinazolin-4-yl)piperazin-1-yl)prop-2-en-1-one | B | 429.30 |
| I-119 | 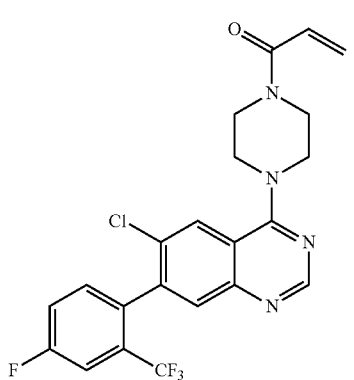 [SMILES: C=CC(=O)N1CCN(c2ncnc3cc(-c4ccc(F)cc4C(F)(F)F)c(Cl)cc23)CC1] | 1-(4-(6-chloro-7-(4-fluoro-2-(trifluoromethyl)phenyl)quinazolin-4-yl)piperazin-1-yl)prop-2-en-1-one | B | 465.35 |
| I-120 | 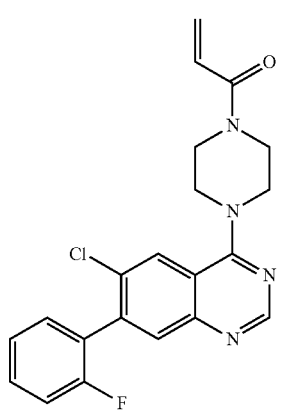 [SMILES: C=CC(=O)N1CCN(c2ncnc3cc(-c4ccccc4F)c(Cl)cc23)CC1] | 1-acryloyl-4-(6-chloro-7-(2-fluorophenyl)quinazolin-4-yl)piperazine-2-carboxamide | B | 440.30 |

TABLE 1-continued

Exemplary Compounds of Structure (I)

| No. | Structure | Name | Method | [M + H]⁺ |
|---|---|---|---|---|
| I-121 | 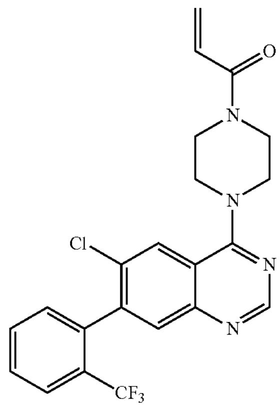 [SMILES: C=CC(=O)N1CCN(c2ncnc3cc(-c4ccccc4C(F)(F)F)c(Cl)cc23)CC1] | 1-acryloyl-4-(6-chloro-7-(2-(trifluoromethyl)phenyl)quinazolin-4-yl)piperazine-2-carboxamide | B | 490.40 |
| I-122 | 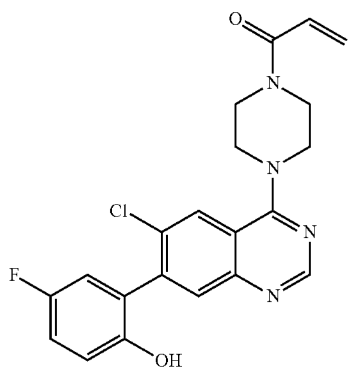 [SMILES: C=CC(=O)N1CCN(c2ncnc3cc(-c4cc(F)ccc4O)c(Cl)cc23)CC1] | 1-(4-(6-chloro-7-(5-fluoro-2-hydroxyphenyl)quinazolin-4-yl)piperazin-1-yl)prop-2-en-1-one | B | 413.30 |
| I-123 | 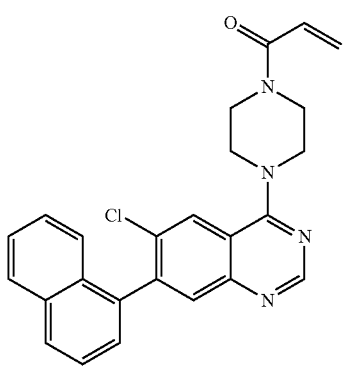 [SMILES: C=CC(=O)N1CCN(c2ncnc3cc(-c4cccc5ccccc45)c(Cl)cc23)CC1] | 1-(4-(6-chloro-7-(naphthalen-1-yl)quinazolin-4-yl)piperazin-1-yl)prop-2-en-1-one | B | 429.35 |
| I-124 | 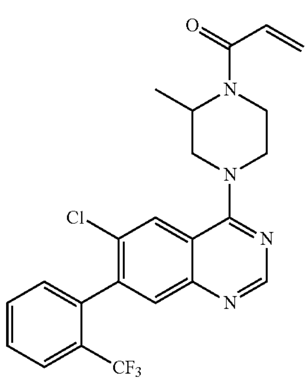 [SMILES: C=CC(=O)N1CCN(c2ncnc3cc(-c4ccccc4C(F)(F)F)c(Cl)cc23)CC1C] | 1-(4-(6-chloro-7-(2-(trifluoromethyl)phenyl)quinazolin-4-yl)-2-methylpiperazin-1-yl)prop-2-en-1-one | B | 461.35 |

TABLE 1-continued

Exemplary Compounds of Structure (I)

| No. | Structure | Name | Method | [M + H]+ |
|---|---|---|---|---|
| I-125 | 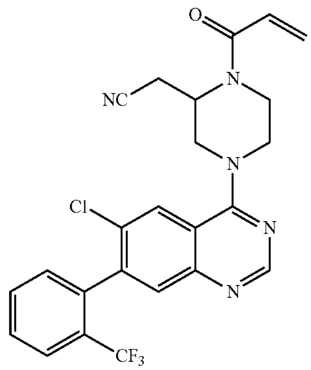 [SMILES: C=CC(=O)N1CCN(c2ncnc3cc(-c4ccccc4C(F)(F)F)c(Cl)cc23)CC1CC#N] | 2-(1-acryloyl-4-(6-chloro-7-(2-(trifluoromethyl)phenyl)quinazolin-4-yl)piperazin-2-yl)acetonitrile | B | 486.40 |
| I-126 | 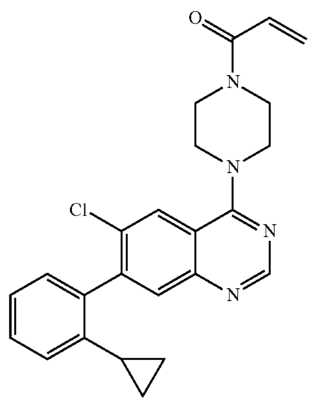 [SMILES: C=CC(=O)N1CCN(c2ncnc3cc(-c4ccccc4C4CC4)c(Cl)cc23)CC1] | 1-(4-(6-chloro-7-(2-cyclopropylphenyl)quinazolin-4-yl)piperazin-1-yl)prop-2-en-1-one | B | 419.20 |
| I-127 | 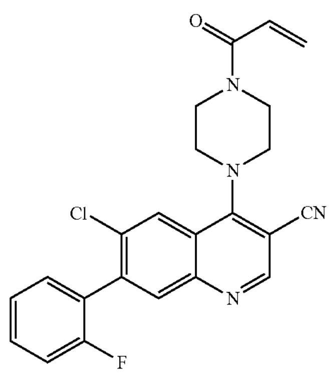 [SMILES: C=CC(=O)N1CCN(c2c(C#N)cnc3cc(-c4ccccc4F)c(Cl)cc23)CC1] | 4-(4-acryloylpiperazin-1-yl)-6-chloro-7-(2-fluorophenyl)quinazolin-3-carbonitrile | G | 421.30 |
| I-128 | 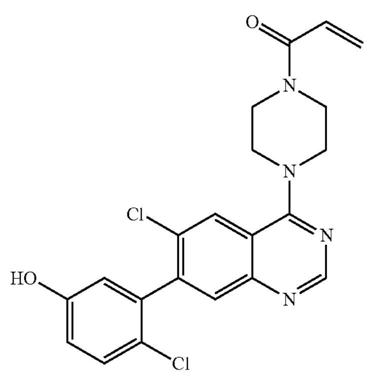 [SMILES: C=CC(=O)N1CCN(c2ncnc3cc(-c4cc(O)ccc4Cl)c(Cl)cc23)CC1] | 1-(4-(6-chloro-7-(2-chloro-5-hydroxyphenyl)quinazolin-4-yl)piperazin-1-yl)prop-2-en-1-one | B | 430.10 |

TABLE 1-continued
Exemplary Compounds of Structure (I)
| No. | Structure | Name | Method | [M + H]+ |
|---|---|---|---|---|
| I-129 | 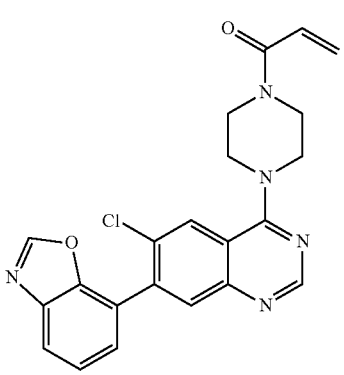 [SMILES: C=CC(=O)N1CCN(c2ncnc3cc(-c4cccc5ncoc45)c(Cl)cc23)CC1] | 1-(4-(7-(benzo[d]oxazol-7-yl)-6-chloroquinazolin-4-yl)piperazin-1-yl)prop-2-en-1-one | B | 420.10 |
| I-130 | 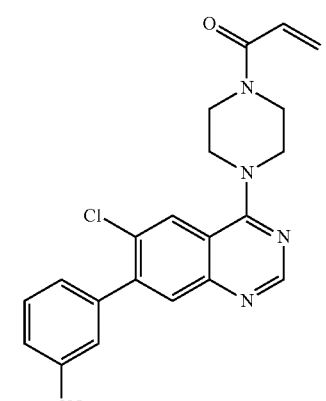 | 3-(4-(4-acryloylpiperazin-1-yl)-6-chloroquinazolin-7-yl)benzonitrile | B | 404.10 |
| I-131 | 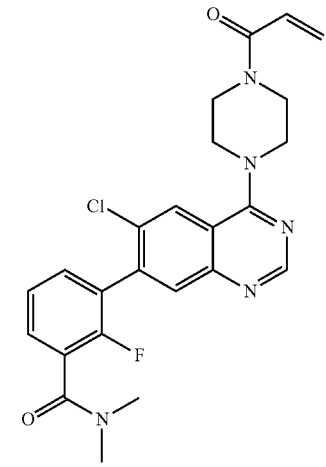 [SMILES: C=CC(=O)N1CCN(c2ncnc3cc(-c4cccc(C(=O)N(C)C)c4F)c(Cl)cc23)CC1] | 3-(4-(4-acryloylpiperazin-1-yl)-6-chloroquinazolin-7-yl)-2-fluoro-N,N-dimethylbenzamide | B | 468.10 |

TABLE 1-continued

Exemplary Compounds of Structure (I)

| No. | Structure | Name | Method | [M + H]+ |
|---|---|---|---|---|
| I-132 | 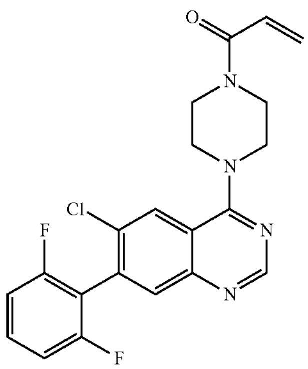 [SMILES: C=CC(=O)N1CCN(c2ncnc3cc(-c4c(F)cccc4F)c(Cl)cc23)CC1] | 1-(4-(6-chloro-7-(2,6-difluorophenyl)quinazolin-4-yl)piperazin-1-yl)prop-2-en-1-one | B | 415.3 |
| I-133 | 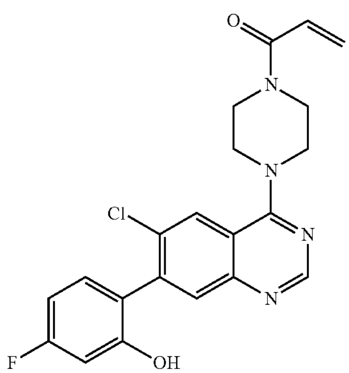 [SMILES: C=CC(=O)N1CCN(c2ncnc3cc(-c4ccc(F)cc4O)c(Cl)cc23)CC1] | 1-0(4-(6-chloro-7-(4-fluoro-2-hydroxyphenyl)quinazolin-4-yl)piperazin-1-yl)prop-2-en-1-one | B | 413.30 |
| I-134 | 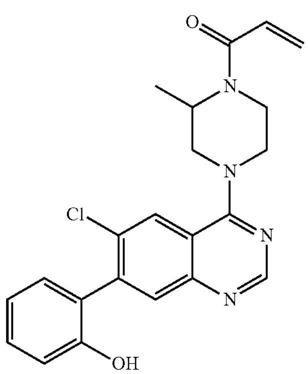 [SMILES: C=CC(=O)N1CCN(c2ncnc3cc(-c4ccccc4O)c(Cl)cc23)CC1C] | 1-(4-(6-chloro-7-(2-hydroxyphenyl)quinazolin-4-yl)-2-methylpiperazin-1-yl)prop-2-en-1-one | B | 409.30 |
| I-135 | 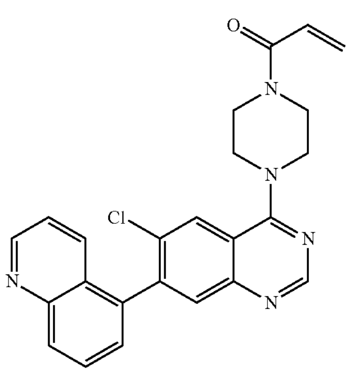 [SMILES: C=CC(=O)N1CCN(c2ncnc3cc(-c4cccc5ncccc45)c(Cl)cc23)CC1] | 1-(4-(6-chloro-7-(quinolin-5-yl)quinazolin-4-yl)piperazin-1-yl)prop-2-en-1-one | B | 430.30 |

TABLE 1-continued

Exemplary Compounds of Structure (I)

| No. | Structure | Name | Method | [M + H]+ |
|---|---|---|---|---|
| I-136 | 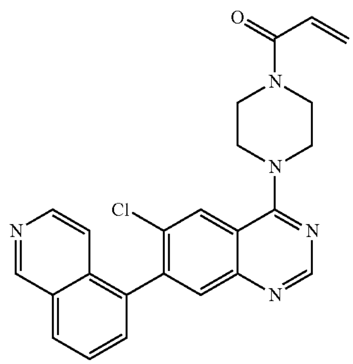 [SMILES: C=CC(=O)N1CCN(c2ncnc3cc(-c4cccc5cnccc45)c(Cl)cc23)CC1] | 1-(4-(6-chloro-7-(isoquinolin-5-yl)quinazolin-4-yl)piperazin-1-yl)prop-2-en-1-one | B | 430.35 |
| I-137 | 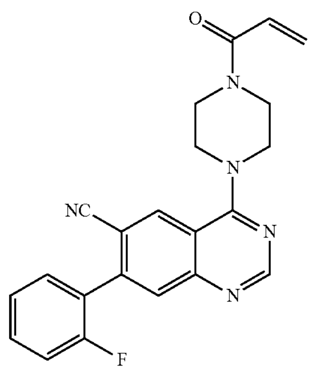 [SMILES: C=CC(=O)N1CCN(c2ncnc3cc(-c4ccccc4F)c(C#N)cc23)CC1] | 4-(4-acryloylpiperazin-1-yl)-7-(2-fluorophenyl)quinazoline-6-carbonitrile | B | 388.30 |
| I-138 | 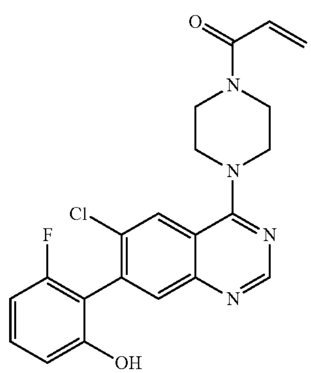 [SMILES: C=CC(=O)N1CCN(c2ncnc3cc(-c4c(O)cccc4F)c(Cl)cc23)CC1] | 1-(4-(6-chloro-7-(2-fluoro-6-hydroxyphenyl)quinazolin-4-yl)piperazin-1-yl)prop-2-en-1-one | B | 413.25 |
| I-139 | 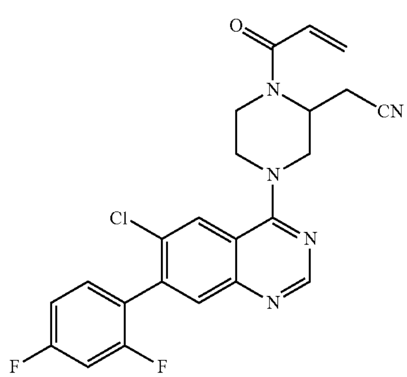 [SMILES: C=CC(=O)N1CCN(c2ncnc3cc(-c4ccc(F)cc4F)c(Cl)cc23)CC1CC#N] | 2-(1-acryloyl-4-(6-chloro-7-(2,4-difluorophenyl)quinazolin-4-yl)piperazin-2-yl)acetonitrile | B | 454.30 |

TABLE 1-continued

Exemplary Compounds of Structure (I)

| No. | Structure | Name | Method | [M + H]+ |
|---|---|---|---|---|
| I-140 | 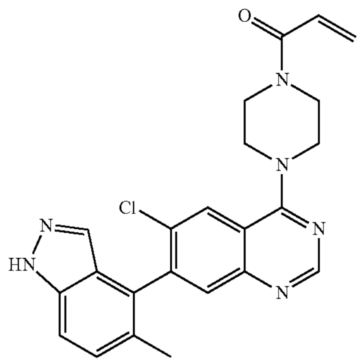 [SMILES: C=CC(=O)N1CCN(c2ncnc3cc(-c4c(C)ccc5[nH]ncc45)c(Cl)cc23)CC1] | 1-(4-(6-chloro-7-(5-methyl-1H-indazol-4-yl)quinazolin-4-yl)piperazin-1-yl)prop-2-en-1-one | Q | 433.15 |
| I-141 | 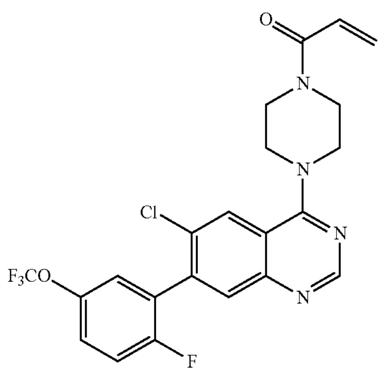 [SMILES: C=CC(=O)N1CCN(c2ncnc3cc(-c4cc(OC(F)(F)F)ccc4F)c(Cl)cc23)CC1] | 1-(4-(6-chloro-7-(2-fluoro-5-(trifluoromethoxy)phenyl)quinazolin-4-yl)piperazin-1-yl)prop-2-en-1-one | B | 481.10 |
| I-142 | 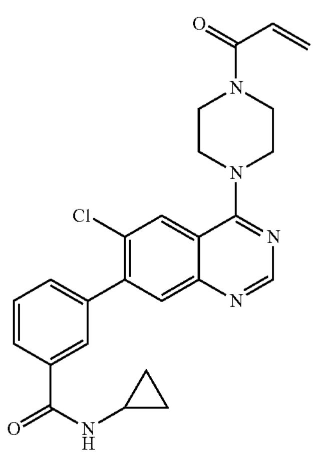 [SMILES: C=CC(=O)N1CCN(c2ncnc3cc(-c4cccc(C(=O)NC5CC5)c4)c(Cl)cc23)CC1] | 3-(4-(4-acryloylpiperazin-1-yl)-6-chloroquinazolin-7-yl)-N-cyclopropylbenzamide | B | 462.20 |
| I-143 | 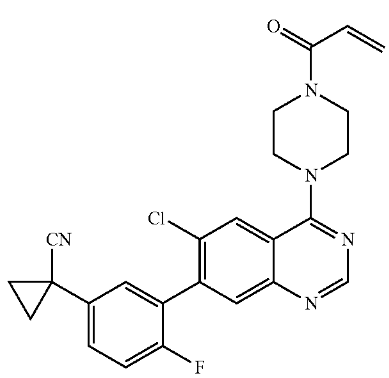 [SMILES: C=CC(=O)N1CCN(c2ncnc3cc(-c4cc(C5(C#N)CC5)ccc4F)c(Cl)cc23)CC1] | 1-(3-(4-(4-acryloylpiperazin-1-yl)-6-chloroquinazolin-7-yl)-4-fluorophenyl)cyclopropanecarbonitrile | B | 462.10 |

TABLE 1-continued

Exemplary Compounds of Structure (I)

| No. | Structure | Name | Method | [M + H]⁺ |
| --- | --- | --- | --- | --- |
| I-144 | 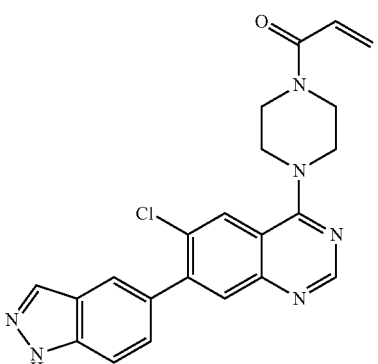 | 1-(4-(6-chloro-7-(1H-indazol-5-yl)quinazolin-4-yl)piperazin-1-yl)prop-2-en-1-one | B | 419.25 |
| I-145 | 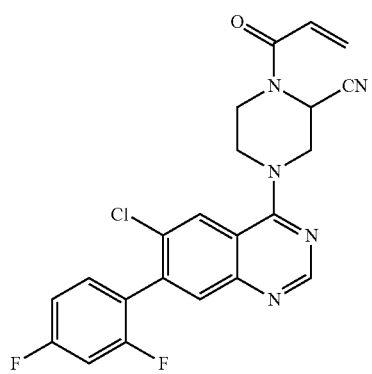 [SMILES: C=CC(=O)N1CCN(c2ncnc3cc(-c4ccc(F)cc4F)c(Cl)cc23)CC1C#N] | 1-acryloyl-4-(6-chloro-7-(2,4-difluorophenyl)quinazolin-4-yl)piperazine-2-carbonitrile | B | 440.30 |
| I-146 | 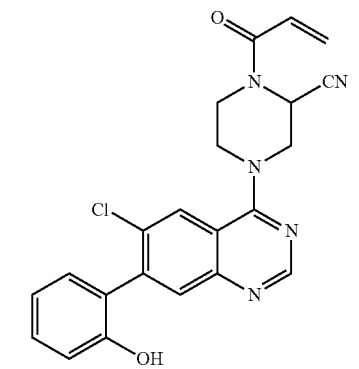 [SMILES: C=CC(=O)N1CCN(c2ncnc3cc(-c4ccccc4O)c(Cl)cc23)CC1C#N] | 1-acryloyl-4-(6-chloro-7-(2-hydroxyphenyl)quinazolin-4-yl)piperazine-2-carbonitrile | B | 420.25 |
| I-147 | 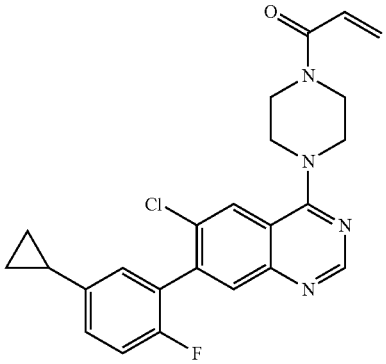 [SMILES: C=CC(=O)N1CCN(c2ncnc3cc(-c4cc(C5CC5)ccc4F)c(Cl)cc23)CC1] | 1-(4-(6-chloro-7-(5-cyclopropyl-2-fluorophenyl)quinazolin-4-yl)piperazin-1-yl)prop-2-en-1-one | B | 437.10 |

TABLE 1-continued

Exemplary Compounds of Structure (I)

| No. | Structure | Name | Method | [M + H]+ |
|---|---|---|---|---|
| I-148 | 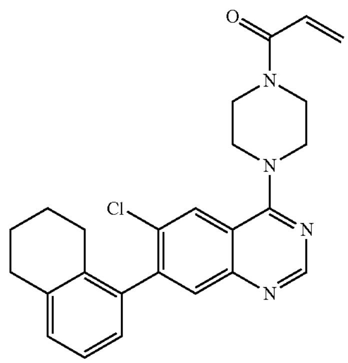 [SMILES: C=CC(=O)N1CCN(c2ncnc3cc(-c4cccc5c4CCCC5)c(Cl)cc23)CC1] | 1-(4-(6-chloro-7-(5,6,7,8-tetrahydronaphthalen-1-yl)quinazolin-4-yl)piperazin-1-yl)prop-2-en-1-one | B | 433.20 |
| I-149 | 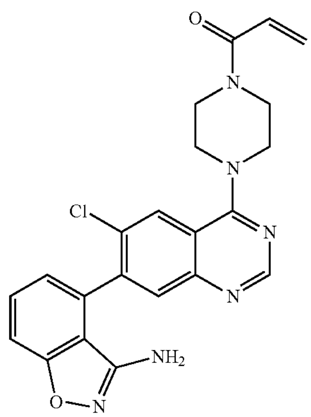 [SMILES: C=CC(=O)N1CCN(c2ncnc3cc(-c4cccc5onc(N)c45)c(Cl)cc23)CC1] | 1-(4-(7-(3-aminobenzo[d]isoxazol-4-yl)-6-chloroquinazolin-4-yl)piperazin-1-yl)prop-2-en-1-one | B | 435.30 |
| I-150 | 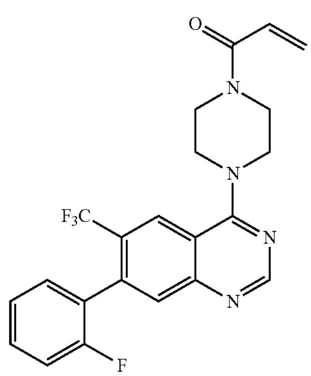 [SMILES: C=CC(=O)N1CCN(c2ncnc3cc(-c4ccccc4F)c(C(F)(F)F)cc23)CC1] | 1-(4-(7-(2-fluorophenyl)-6-(trifluoromethyl)quinazolin-4-yl)piperazin-1-yl)prop-2-en-1-one | R | 431.30 |
| I-151 | 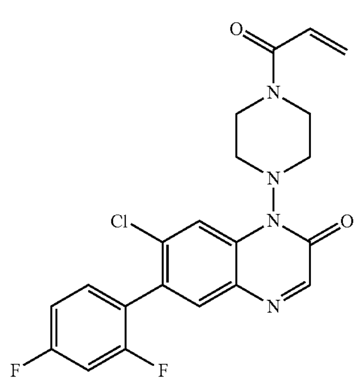 [SMILES: C=CC(=O)N1CCN(n2c(=O)cnc3cc(-c4ccc(F)cc4F)c(Cl)cc32)CC1] | 1-(4-acryloylpiperazin-1-yl)-7-chloro-6-(2,4-difluorophenyl)quinazolin-2(1H)-one | S | 430.30 |

TABLE 1-continued

Exemplary Compounds of Structure (I)

| No. | Structure | Name | Method | [M + H]+ |
|---|---|---|---|---|
| I-152 | 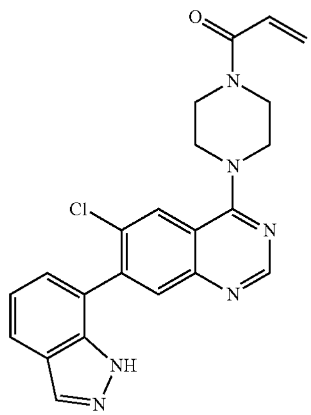 [SMILES: C=CC(=O)N1CCN(c2ncnc3cc(-c4cccc5cn[nH]c45)c(Cl)cc23)CC1] | 1-(4-(6-chloro-7-(1H-indazol-7-yl)quinazolin-4-yl)piperazin-1-yl)prop-2-en-1-one | B | 419.30 |
| I-153 | 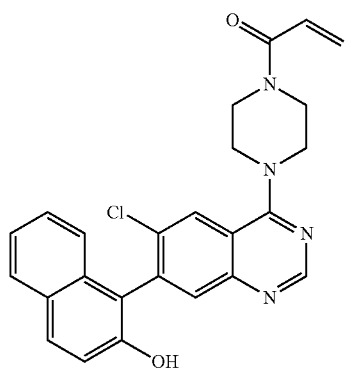 [SMILES: C=CC(=O)N1CCN(c2ncnc3cc(-c4c(O)ccc5ccccc45)c(Cl)cc23)CC1] | 1-(4-(6-chloro-7-(2-hydroxynaphthalen-1-yl)quinazolin-4-yl)piperazin-1-yl)prop-2-en-1-one | Q | 445.10 |
| I-154 | 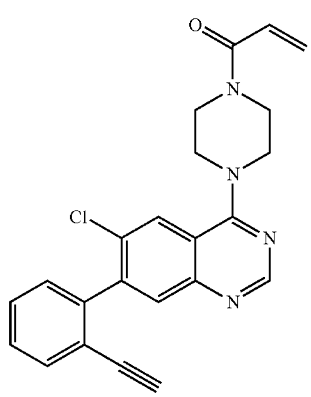 [SMILES: C#Cc1ccccc1-c1cc2ncnc(N3CCN(C(=O)C=C)CC3)c2cc1Cl] | 1-(4-(6-chloro-7-(2-ethynylphenyl)quinazolin-4-yl)piperazin-1-yl)prop-2-en-1-one | B | 403.25 |
| I-155 | 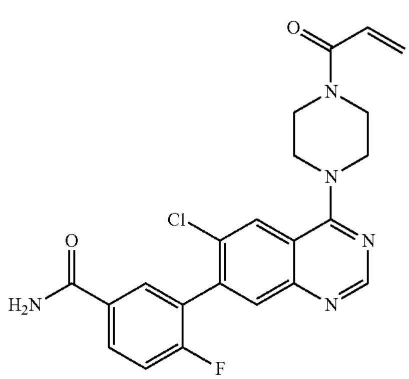 [SMILES: C=CC(=O)N1CCN(c2ncnc3cc(-c4cc(C(N)=O)ccc4F)c(Cl)cc23)CC1] | 3-(4-(4-acryloylpiperazin-1-yl)-6-chloroquinazolin-7-yl)-4-fluorobenzamide | B | 440.25 |

TABLE 1-continued

Exemplary Compounds of Structure (I)

| No. | Structure | Name | Method | [M + H]+ |
|---|---|---|---|---|
| I-156 | 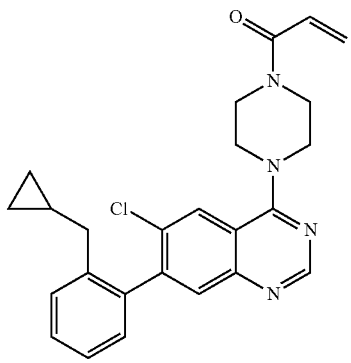 [SMILES: C=CC(=O)N1CCN(c2ncnc3cc(-c4ccccc4CC4CC4)c(Cl)cc23)CC1] | 1-(4-(6-chloro-7-(2-(cyclopropylmethyl)phenyl)quinazolin-4-yl)piperazin-1-yl)prop-2-en-1-one | B | 433.35 |
| I-157 | 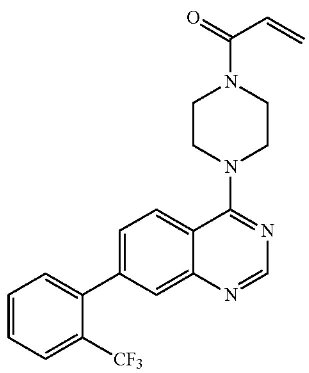 [SMILES: C=CC(=O)N1CCN(c2ncnc3cc(-c4ccccc4C(F)(F)F)ccc23)CC1] | 1-(4-(7-(2-(trifluoromethyl)phenyl)quinazolin-4-yl)piperazin-1-yl)prop-2-en-1-one | B | 413.10 |
| I-158 | 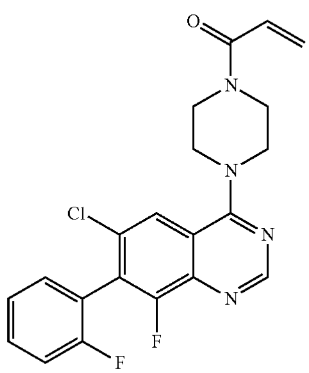 [SMILES: C=CC(=O)N1CCN(c2ncnc3c(F)c(-c4ccccc4F)c(Cl)cc23)CC1] | 1-(4-(6-chloro-8-fluoro-7-(2-fluorophenyl)quinazolin-4-yl)piperazin-1-yl)prop-2-en-1-one | O | 415.25 |
| I-159 | 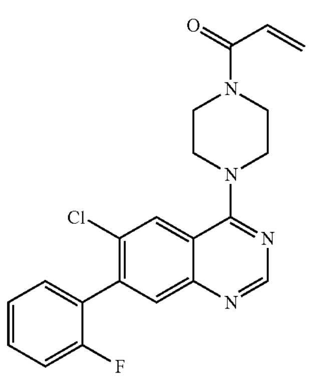 [SMILES: C=CC(=O)N1CCN(c2ncnc3cc(-c4ccccc4F)c(Cl)cc23)CC1] | 1-(4-(6-chloro-7-(2-fluorophenyl)cinnolin-4-yl)piperazin-1-yl)prop-2-en-1-one | N | 397.25 |

TABLE 1-continued

Exemplary Compounds of Structure (I)

| No. | Structure | Name | Method | [M + H]+ |
|---|---|---|---|---|
| I-160 | 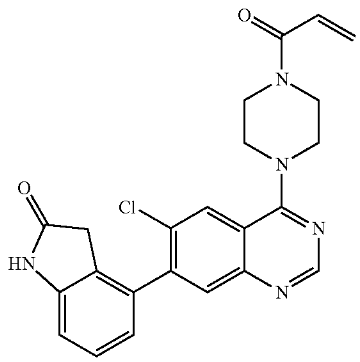 [SMILES: C=CC(=O)N1CCN(c2ncnc3cc(-c4cccc5c4CC(=O)N5)c(Cl)cc23)CC1] | 4-(4-(4-acryloylpiperazin-1-yl)-6-chloroquinazolin-7-yl)indolin-2-one | B | 434.25 |
| I-161 | 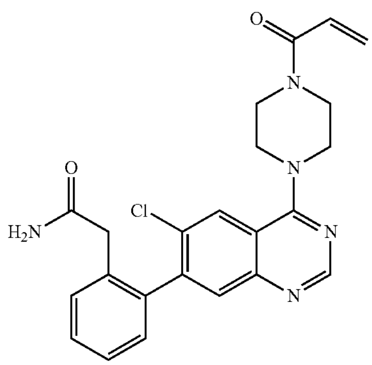 [SMILES: C=CC(=O)N1CCN(c2ncnc3cc(-c4ccccc4CC(N)=O)c(Cl)cc23)CC1] | 2-(2-(4-(4-acryloylpiperazin-1-yl)-6-chloroquinazolin-7-yl)phenyl)acetamide | B | 436.1 |
| I-162 | 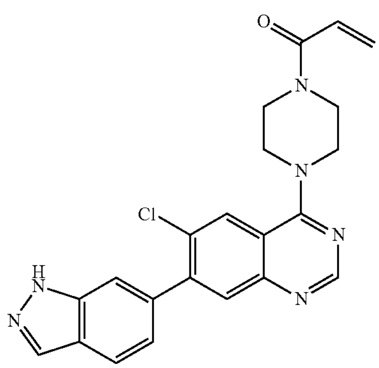 [SMILES: C=CC(=O)N1CCN(c2ncnc3cc(-c4ccc5cn[nH]c5c4)c(Cl)cc23)CC1] | 1-(4-(6-chloro-7-(1H-indazol-6-yl)quinazolin-4-yl)piperazin-1-yl)prop-2-en-1-one | B | 419.3 |
| I-163 | 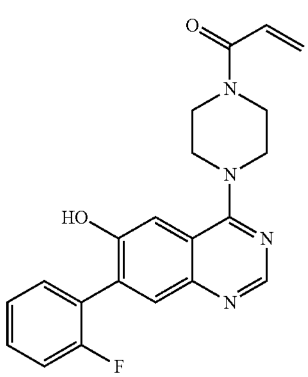 | 1-(4-(7-(2-fluorophenyl)-6-hydroxyquinazolin-4-yl)piperazin-1-yl)prop-2-en-1-one | A | 379.25 |

TABLE 1-continued

Exemplary Compounds of Structure (I)

| No. | Structure | Name | Method | [M + H]+ |
|-----|-----------|------|--------|----------|
| I-164 | 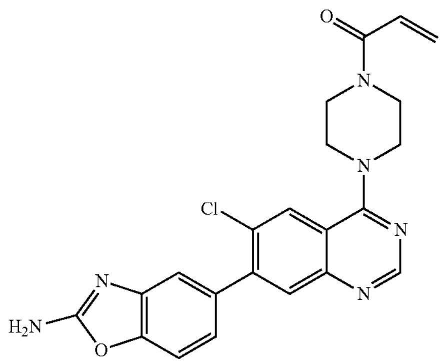 [SMILES: C=CC(=O)N1CCN(c2ncnc3cc(-c4ccc5oc(N)nc5c4)c(Cl)cc23)CC1] | 1-(4-(7-(2-aminobenzo[d]oxazol-5-yl)-6-chloroquinazolin-4-yl)piperazin-1-yl)prop-2-en-1-one | B | 435.25 |
| I-165 | 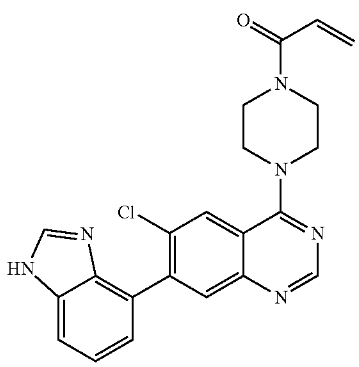 [SMILES: C=CC(=O)N1CCN(c2ncnc3cc(-c4cccc5[nH]cnc45)c(Cl)cc23)CC1] | 1-(4-(7-(1H-benzo[d]imidazol-4-yl)-6-chloroquinazolin-4-yl)piperazin-1-yl)prop-2-en-1-one | B | 419.30 |
| I-166 | 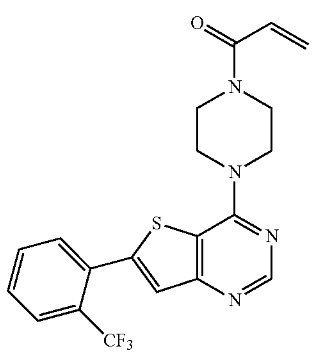 [SMILES: C=CC(=O)N1CCN(c2ncnc3cc(-c4ccccc4C(F)(F)F)sc23)CC1] | 1-(4-(6-(2-(trifluoromethyl)phenyl)thieno[3,2-d]pyrimidin-4-yl)piperazin-1-yl)prop-2-en-1-one | H | 419.10 |
| I-167 | 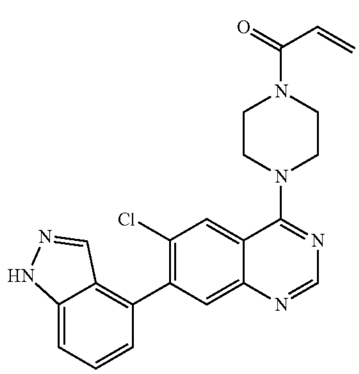 [SMILES: C=CC(=O)N1CCN(c2ncnc3cc(-c4cccc5[nH]ncc45)c(Cl)cc23)CC1] | 1-(4-(6-chloro-7-(1H-indazol-4-yl)quinazolin-4-yl)piperazin-1-yl)prop-2-en-1-one | B | 419.30 |

TABLE 1-continued

Exemplary Compounds of Structure (I)

| No. | Structure | Name | Method | [M + H]+ |
|---|---|---|---|---|
| I-168 | 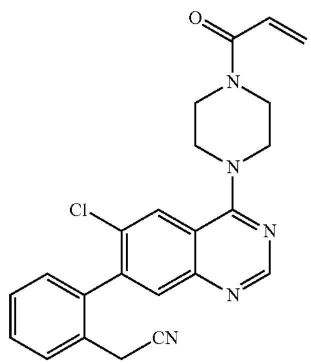 [SMILES: C=CC(=O)N1CCN(c2ncnc3cc(-c4ccccc4CC#N)c(Cl)cc23)CC1] | 2-(2-(4-(4-acryloylpiperazin-1-yl)-6-chloroquinazolin-7-yl)phenyl)acetonitrile | B | 418.1 |
| I-169 | 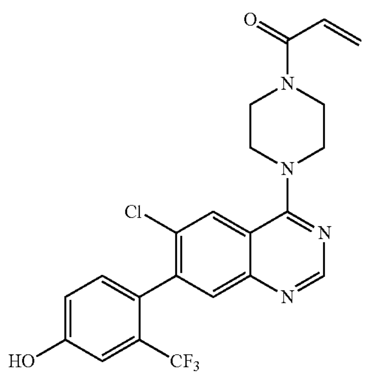 [SMILES: C=CC(=O)N1CCN(c2ncnc3cc(-c4ccc(O)cc4C(F)(F)F)c(Cl)cc23)CC1] | 1-(4-(6-chloro-7-(4-hydroxy-2-(trifluoromethyl)phenyl)quinazolin-4-yl)piperazin-1-yl)prop-2-en-1-one | B | 463.30 |
| I-170 | 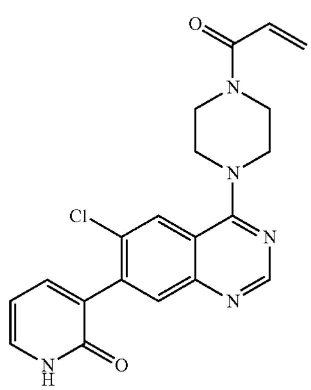 [SMILES: C=CC(=O)N1CCN(c2ncnc3cc(-c4ccc[nH]c4=O)c(Cl)cc23)CC1] | 3-(4-(4-acryloylpiperazin-1-yl)-6-chloroquinazolin-7-yl)pyridin-2(1H)-one | B | 396.25 |
| I-171 | 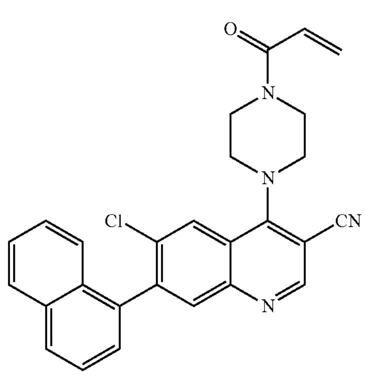 [SMILES: C=CC(=O)N1CCN(c2c(C#N)cnc3cc(-c4cccc5ccccc45)c(Cl)cc23)CC1] | 4-(4-acryloylpiperazin-1-yl)-6-chloro-7-(naphthalen-1-yl)quinolin-3-carbonitrile | P | 453.30 |

TABLE 1-continued

Exemplary Compounds of Structure (I)

| No. | Structure | Name | Method | [M + H]+ |
|---|---|---|---|---|
| I-172 | 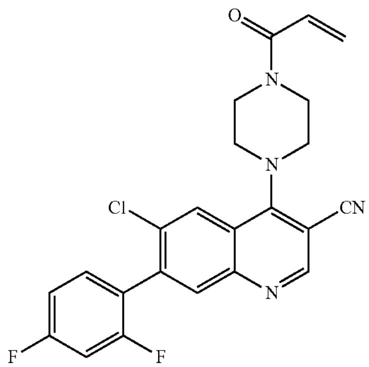 [SMILES: C=CC(=O)N1CCN(c2c(C#N)cnc3cc(-c4ccc(F)cc4F)c(Cl)cc23)CC1] | 4-(4-acryloylpiperazin-1-yl)-6-chloro-7-(2,4-difluorophenyl)quinolin-3-carbonitrile | P | 439.25 |
| I-173 | 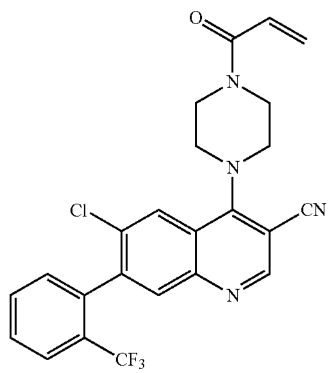 [SMILES: C=CC(=O)N1CCN(c2c(C#N)cnc3cc(-c4ccccc4C(F)(F)F)c(Cl)cc23)CC1] | 4-(4-acryloylpiperazin-1-yl)-6-chloro-7-(2-(trifluoromethyl)phenyl)quinoline-3-carbonitrile | P | 471.35 |
| I-174 | 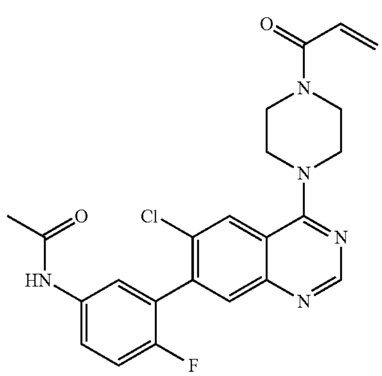 [SMILES: C=CC(=O)N1CCN(c2ncnc3cc(-c4cc(NC(C)=O)ccc4F)c(Cl)cc23)CC1] | N-(3-(4-(4-acryloylpiperazin-1-yl)-6-chloroquinazolin-7-yl)-4-fluorophenyl)acetamide | B | 454.10 |
| I-175 | 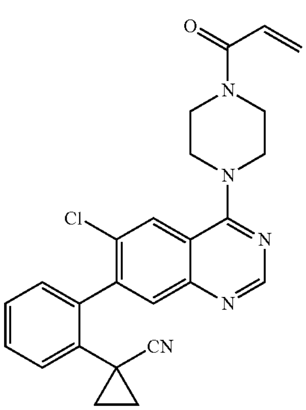 [SMILES: C=CC(=O)N1CCN(c2ncnc3cc(-c4ccccc4C4(C#N)CC4)c(Cl)cc23)CC1] | 1-(2-(4-(4-acryloylpiperazin-1-yl)-6-chloroquinazolin-7-yl)phenyl)cyclopropanecarbonitrile | B | 444.1 |

TABLE 1-continued

Exemplary Compounds of Structure (I)

| No. | Name | Method | [M + H]+ |
|---|---|---|---|
| I-176 | 1-(2-(4-(4-acryloylpiperazin-1-yl)-6-chloroquinazolin-7-yl)phenyl)cyclopropanecarboxamide | B | 462.2 |
| I-177 | 1-(4-(4-acryloylpiperazin-1-yl)-6-chloroquinazolin-7-yl)-5-chloropyridin-2(1H)-one | T | 430.20 |
| I-178 | N-(4-(4-(4-acryloylpiperazin-1-yl)-6-chloroquinazolin-7-yl)-5-methylpyrimidin-2-yl)acrylamide | B | 464.10 |
| I-179 | 1-(4-(7-(2-amino-5-methylpyrimidin-4-yl)-6-chloroquinazolin-4-yl)piperazin-1-yl)prop-2-en-1-one | B | 410.10 |

TABLE 1-continued

Exemplary Compounds of Structure (I)

| No. | Structure | Name | Method | [M + H]+ |
|---|---|---|---|---|
| I-180 | 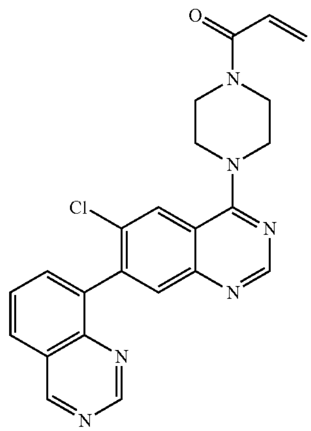 [SMILES: C=CC(=O)N1CCN(c2ncnc3cc(-c4cccc5cncnc45)c(Cl)cc23)CC1] | 1-(4-(6-chloro-7,8'-biquinazolin-4-yl)piperazin-1-yl)prop-2-en-1-one | B | 431.10 |
| I-181 | 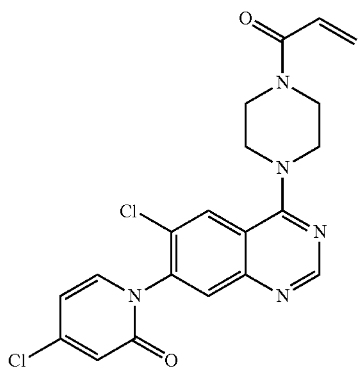 [SMILES: C=CC(=O)N1CCN(c2ncnc3cc(-n4ccc(Cl)cc4=O)c(Cl)cc23)CC1] | 1-(4-(4-acryloylpiperazin-1-yl)-6-chloroquinazolin-7-yl)-4-chloropyridin-2(1H)-one | T | 430.10 |
| I-182 | 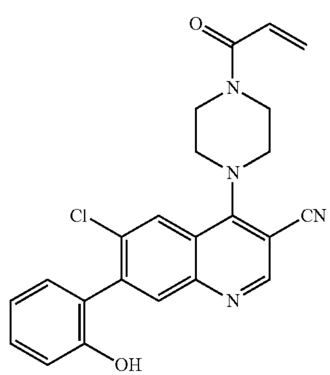 [SMILES: C=CC(=O)N1CCN(c2c(C#N)cnc3cc(-c4ccccc4O)c(Cl)cc23)CC1] | 4-(4-acryloylpiperazin-1-yl)-6-chloro-7-(2-hydroxyphenyl)quinoline-3-carbonitrile | P | 419.15 |
| I-183 | 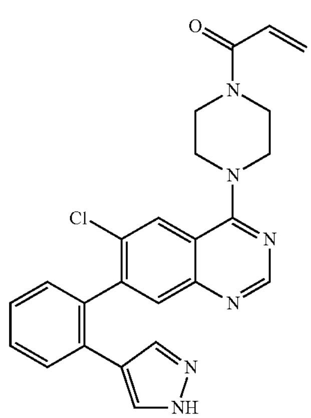 [SMILES: C=CC(=O)N1CCN(c2ncnc3cc(-c4ccccc4-c4cn[nH]c4)c(Cl)cc23)CC1] | 1-(4-(7-(2-(1H-pyrazol-4-yl)phenyl)-6-chloroquinazolin-4-yl)piperazin-1-yl)prop-2-en-1-one | B | 445.20 |

TABLE 1-continued

Exemplary Compounds of Structure (I)

| No. | Structure | Name | Method | [M + H]⁺ |
|---|---|---|---|---|
| I-184 | 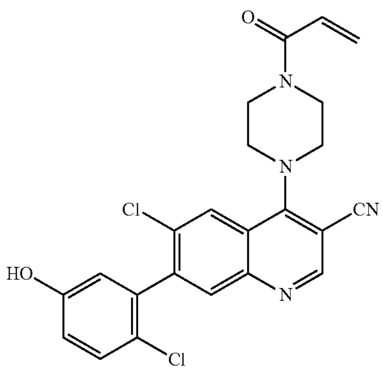 [SMILES: C=CC(=O)N1CCN(c2c(C#N)cnc3cc(-c4cc(O)ccc4Cl)c(Cl)cc23)CC1] | 4-(4-acryloylpiperazin-1-yl)-6-chloro-7-(2-chloro-5-hydroxyphenyl)quinoline-3-carbonitrile | P | 453.15 |
| I-185 | 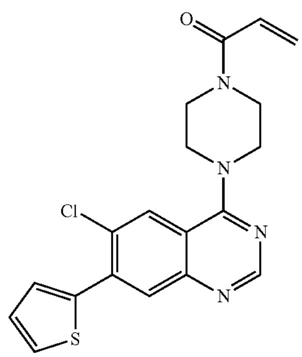 [SMILES: C=CC(=O)N1CCN(c2ncnc3cc(-c4cccs4)c(Cl)cc23)CC1] | 1-(4-(6-chloro-7-(thiophen-2-yl)quinazolin-4-yl)piperazin-1-yl)prop-2-en-1-one | B | 385.10 |
| I-186 | 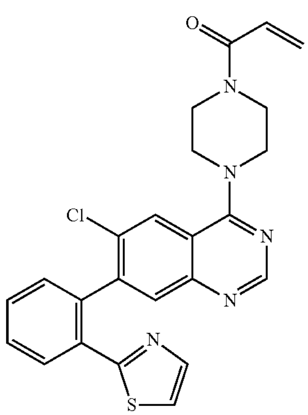 [SMILES: C=CC(=O)N1CCN(c2ncnc3cc(-c4ccccc4-c4nccs4)c(Cl)cc23)CC1] | 1-(4-(6-chloro-7-(2-(thiazol-2-yl)phenyl)quinazolin-4-yl)piperazin-1-yl)prop-2-en-1-one | U | 462.25 |
| I-187 | 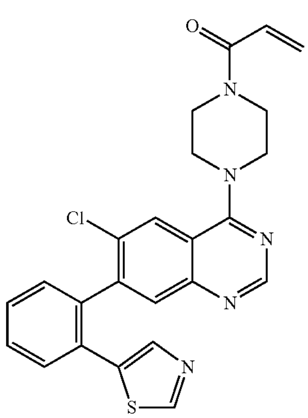 [SMILES: C=CC(=O)N1CCN(c2ncnc3cc(-c4ccccc4-c4cncs4)c(Cl)cc23)CC1] | 1-(4-(6-chloro-7-(2-(thiazol-5-yl)phenyl)quinazolin-4-yl)piperazin-1-yl)prop-2-en-1-one | U | 462.25 |

TABLE 1-continued

Exemplary Compounds of Structure (I)

| No. | Structure | Name | Method | [M + H]+ |
|---|---|---|---|---|
| I-188 | 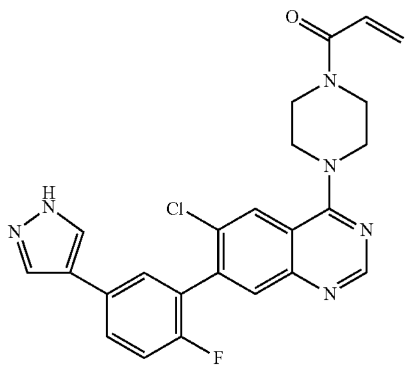 [SMILES: C=CC(=O)N1CCN(c2ncnc3cc(-c4cc(-c5cn[nH]c5)ccc4F)c(Cl)cc23)CC1] | 1-(4-(6-chloro-7-(2-fluoro-5-(1H-pyrazol-4-yl)phenyl)quinazolin-4-yl)piperazin-1-yl)prop-2-en-1-one | B | 463.20 |
| I-189 | 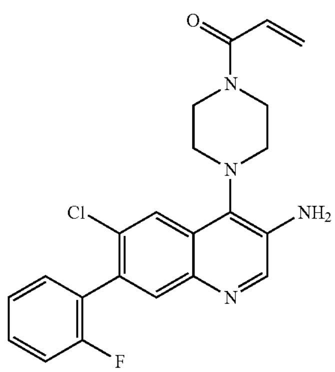 [SMILES: C=CC(=O)N1CCN(c2c(N)cnc3cc(-c4ccccc4F)c(Cl)cc23)CC1] | 4-(4-acryloylpiperazin-1-yl)-6-chloro-7-(2-fluorophenyl)quinazolin-3-carboxamide | P | 439.60 |
| I-190 | 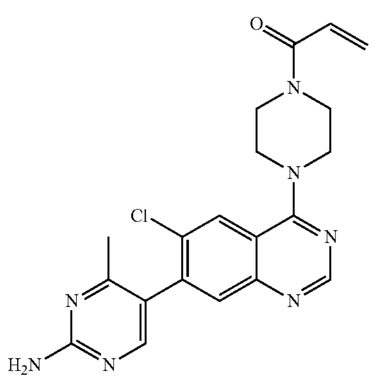 [SMILES: C=CC(=O)N1CCN(c2ncnc3cc(-c4cnc(N)nc4C)c(Cl)cc23)CC1] | 1-(4-(7-(2-amino-4-methylpyrimidin-5-yl)-6-chloroquinazolin-4-yl)piperazin-1-yl)prop-2-en-1-one | B | 410.10 |
| I-191 | 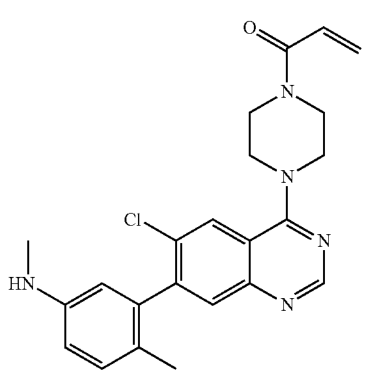 [SMILES: C=CC(=O)N1CCN(c2ncnc3cc(-c4cc(NC)ccc4C)c(Cl)cc23)CC1] | 1-(4-(6-chloro-7-(2-methyl-5-(methylamino)phenyl)quinazolin-4-yl)piperazin-1-yl)prop-2-en-1-one | B | 422.20 |

TABLE 1-continued

Exemplary Compounds of Structure (I)

| No. | Structure | Name | Method | [M + H]+ |
|---|---|---|---|---|
| I-192 | 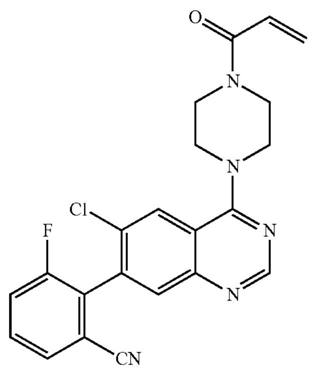 [SMILES: C=CC(=O)N1CCN(c2ncnc3cc(-c4c(F)cccc4C#N)c(Cl)cc23)CC1] | 2-(4-(4-acryloylpiperazin-1-yl)-6-chloroquinazolin-7-yl)-3-fluorobenzonitrile | B | 422.10 |
| I-193 | 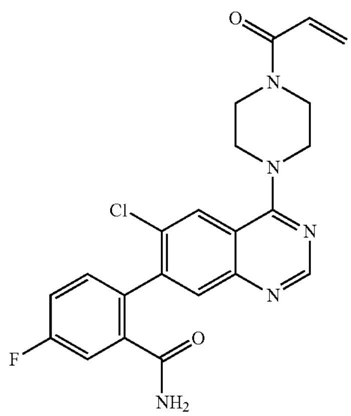 [SMILES: C=CC(=O)N1CCN(c2ncnc3cc(-c4ccc(F)cc4C(N)=O)c(Cl)cc23)CC1] | 2-(4-(4-acryloylpiperazin-1-yl)-6-chloroquinazolin-7-yl)-5-fluorobenzamide | B | 440.20 |
| I-194 | 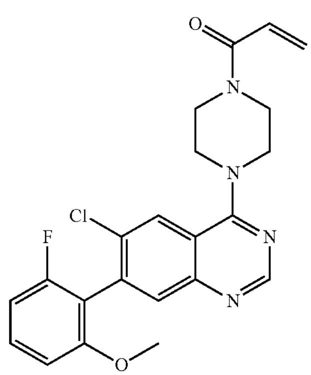 [SMILES: C=CC(=O)N1CCN(c2ncnc3cc(-c4c(F)cccc4OC)c(Cl)cc23)CC1] | 1-(4-(6-chloro-7-(2-fluoro-6-methoxyphenyl)quinazolin-4-yl)piperazin-1-yl)prop-2-en-1-one | B | 427.15 |
| I-195 | 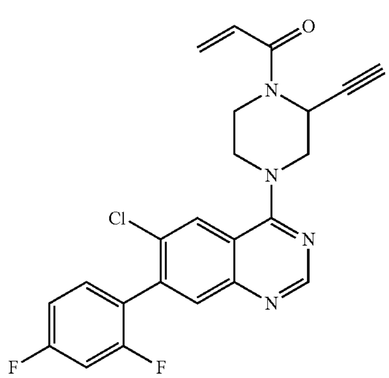 [SMILES: C#CC1CN(c2ncnc3cc(-c4ccc(F)cc4F)c(Cl)cc23)CCN1C(=O)C=C] | 1-(4-(6-chloro-7-(2,4-difluorophenyl)quinazolin-4-yl)-2-ethynylpiperazin-1-yl)prop-2-en-1-one | B | 439.15 |

TABLE 1-continued

Exemplary Compounds of Structure (I)

| No. | Structure | Name | Method | [M + H]+ |
|---|---|---|---|---|
| I-196 | 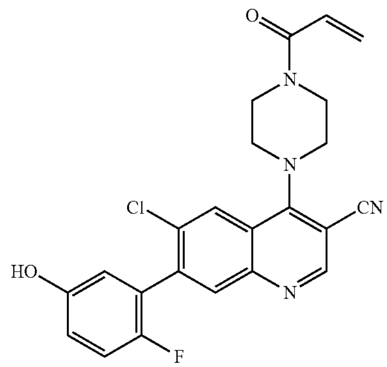 [SMILES: C=CC(=O)N1CCN(c2c(C#N)cnc3cc(-c4cc(O)ccc4F)c(Cl)cc23)CC1] | 4-(4-acryloylpiperazin-1-yl)-6-chloro-7-(2-fluoro-5-hydroxyphenyl)quinoline-3-carbonitrile | P | 437.15 |
| I-197 | 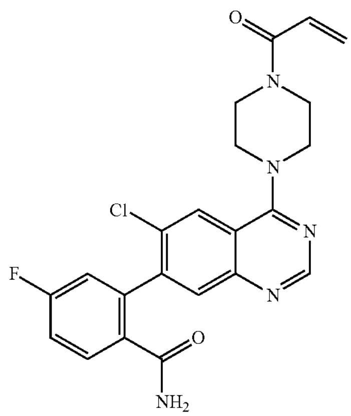 [SMILES: C=CC(=O)N1CCN(c2ncnc3cc(-c4cc(F)ccc4C(N)=O)c(Cl)cc23)CC1] | 2-(4-(4-acryloylpiperazin-1-yl)-6-chloroquinazolin-7-yl)-4-fluorobenzamide | B | 440.20 |
| I-198 | 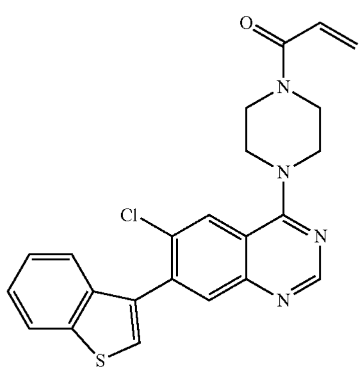 [SMILES: C=CC(=O)N1CCN(c2ncnc3cc(-c4csc5ccccc45)c(Cl)cc23)CC1] | 1-(4-(7-(benzo[d]thiophen-3-yl)-6-chloroquinazolin-4-yl)piperazin-1-yl)prop-2-en-1-one | B | 435.15 |
| I-199 | 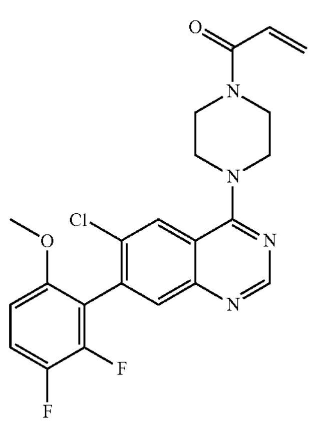 [SMILES: C=CC(=O)N1CCN(c2ncnc3cc(-c4c(OC)ccc(F)c4F)c(Cl)cc23)CC1] | 1-(4-(6-chloro-7-(2,3-difluoro-6-methoxyphenyl)quinazolin-4-yl)piperazin-1-yl)prop-2-en-1-one | B | 445.1 |

TABLE 1-continued

Exemplary Compounds of Structure (I)

| No. | Structure | Name | Method | [M + H]+ |
|-----|-----------|------|--------|----------|
| I-200 | 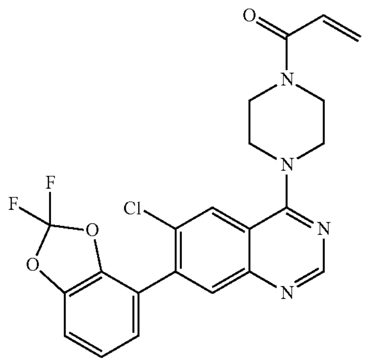 [SMILES: C=CC(=O)N1CCN(c2ncnc3cc(-c4cccc5c4OC(F)(F)O5)c(Cl)cc23)CC1] | 1-(4-(6-chloro-7-(2,2-difluorobenzo[d][1,3]dioxol-4-yl)quinazolin-4-yl)piperazin-1-yl)prop-2-en-1-one | B | 459.10 |
| I-201 | 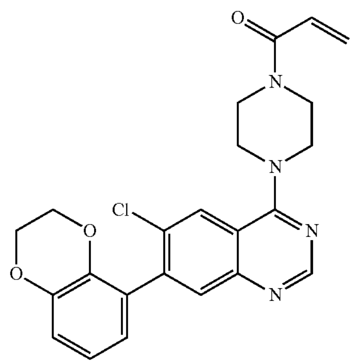 [SMILES: C=CC(=O)N1CCN(c2ncnc3cc(-c4cccc5c4OCCO5)c(Cl)cc23)CC1] | 1-(4-(6-chloro-7-(2,3-dihydrobenzo[d][1,4]dioxol-5-yl)quinazolin-4-yl)piperazin-1-yl)prop-2-en-1-one | B | 437.1 |
| I-202 | 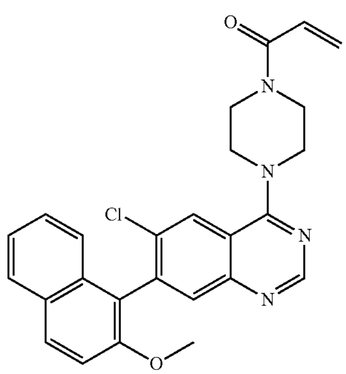 [SMILES: C=CC(=O)N1CCN(c2ncnc3cc(-c4c(OC)ccc5ccccc45)c(Cl)cc23)CC1] | 1-(4-(6-chloro-7-(2-methoxynaphthalen-1-yl)quinazolin-4-yl)piperazin-1-yl)prop-2-en-1-one | O | 459.15 |
| I-203 | 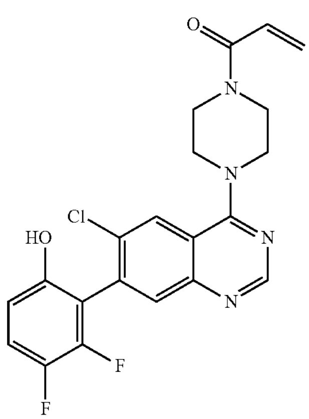 [SMILES: C=CC(=O)N1CCN(c2ncnc3cc(-c4c(O)ccc(F)c4F)c(Cl)cc23)CC1] | 1-(4-(6-chloro-7-(2,3-difluoro-6-hydroxyphenyl)quinazolin-4-yl)piperazin-1-yl)prop-2-en-1-one | B | 431.10 |

TABLE 1-continued

Exemplary Compounds of Structure (I)

| No. | Structure | Name | Method | [M + H]+ |
|---|---|---|---|---|
| I-204 | 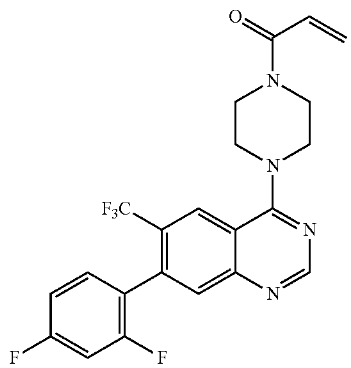 [SMILES: C=CC(=O)N1CCN(c2ncnc3cc(-c4ccc(F)cc4F)c(C(F)(F)F)cc23)CC1] | 1-(4-(7-(2,4-difluorophenyl)-6-(trifluoromethyl)quinazolin-4-yl)piperazin-1-yl)prop-2-en-1-one | B | 449.15 |
| I-205 | 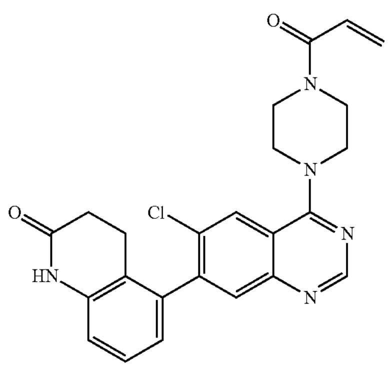 [SMILES: C=CC(=O)N1CCN(c2ncnc3cc(-c4cccc5c4CCC(=O)N5)c(Cl)cc23)CC1] | 5-(4-(4-acryloylpiperazin-1-yl)-6-chloroquinazolin-7-yl)-3,4-dihydroquinolin-2(1H)-one | B | 448.15 |
| I-206 | 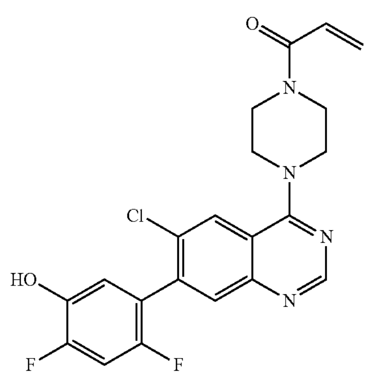 [SMILES: C=CC(=O)N1CCN(c2ncnc3cc(-c4cc(O)c(F)cc4F)c(Cl)cc23)CC1] | 1-(4-(6-chloro-7-(2,4-difluoro-5-hydroxyphenyl)quinazolin-4-yl)piperazin-1-yl)prop-2-en-1-one | U | 431.10 |
| I-207 | 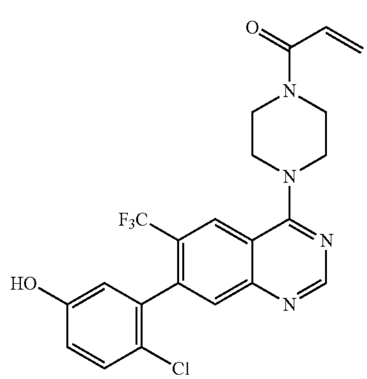 [SMILES: C=CC(=O)N1CCN(c2ncnc3cc(-c4cc(O)ccc4Cl)c(C(F)(F)F)cc23)CC1] | 1-(4-(7-(2-chloro-5-hydroxyphenyl)-6-(trifluoromethyl)quinazolin-4-yl)piperazin-1-yl)prop-2-en-1-one | R | 463.15 |

TABLE 1-continued

Exemplary Compounds of Structure (I)

| No. | Structure | Name | Method | [M + H]+ |
|---|---|---|---|---|
| I-208 | 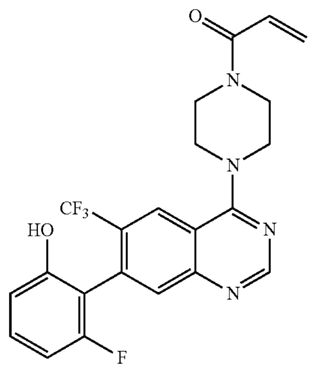 [SMILES: C=CC(=O)N1CCN(c2ncnc3cc(-c4c(O)cccc4F)c(C(F)(F)F)cc23)CC1] | 1-(4-(7-(2-fluoro-6-hydroxyphenyl)-6-(trifluoromethyl)quinazolin-4-yl)piperazin-1-yl)prop-2-en-1-one | R | 447.20 |
| I-209 | 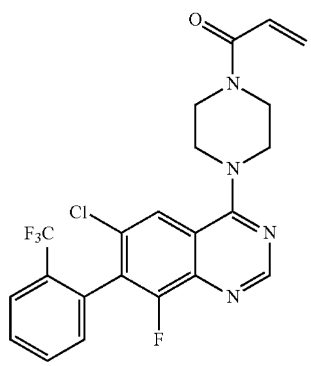 [SMILES: C=CC(=O)N1CCN(c2ncnc3c(F)c(-c4ccccc4C(F)(F)F)c(Cl)cc23)CC1] | 1-(4-(6-chloro-8-fluoro-7-(2-(trifluoromethyl)phenyl)quinazolin-4-yl)piperazin-1-yl)prop-2-en-1-one | O | 465.15 |
| I-210 | 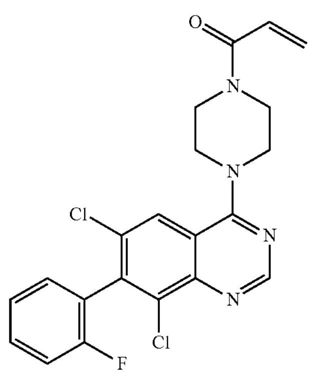 [SMILES: C=CC(=O)N1CCN(c2ncnc3c(Cl)c(-c4ccccc4F)c(Cl)cc23)CC1] | 1-(4-(6,8-dichloro-7-(2-fluorophenyl)quinazolin-4-yl)piperazin-1-yl)prop-2-en-1-one | V | 431.10 |
| I-211 | 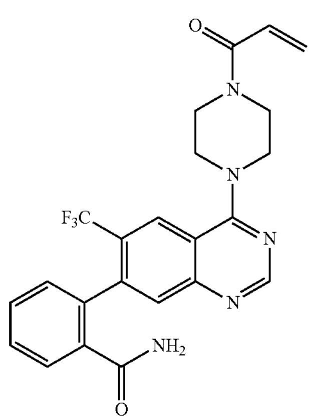 [SMILES: C=CC(=O)N1CCN(c2ncnc3cc(-c4ccccc4C(N)=O)c(C(F)(F)F)cc23)CC1] | 2-(4-(4-acryloylpiperazin-1-yl)-6-(trifluoromethyl)quinazolin-7-yl)benzamide | R | 456.15 |

TABLE 1-continued

Exemplary Compounds of Structure (I)

| No. | Structure | Name | Method | [M + H]+ |
|-----|-----------|------|--------|----------|
| I-212 | 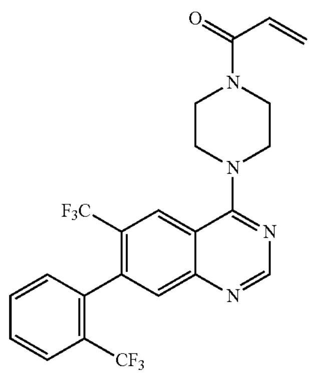 [SMILES: C=CC(=O)N1CCN(c2ncnc3cc(-c4ccccc4C(F)(F)F)c(C(F)(F)F)cc23)CC1] | 1-(4-(6-(trifluoromethyl)-7-(2-(trifluoromethyl)phenyl)quinazolin-4-yl)piperazin-1-yl)prop-2-en-1-one | R | 481.20 |
| I-213 | 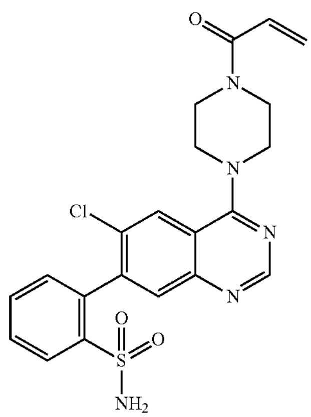 [SMILES: C=CC(=O)N1CCN(c2ncnc3cc(-c4ccccc4S(N)(=O)=O)c(Cl)cc23)CC1] | 2-(4-(4-acryloylpiperaqzin-1-yl)-6-chloroquinazolin-7-yl)benzenesulfonamide | B | 458.10 |
| I-214 | 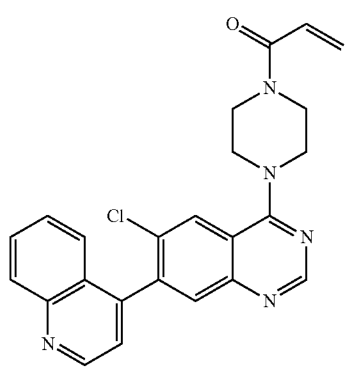 [SMILES: C=CC(=O)N1CCN(c2ncnc3cc(-c4ccnc5ccccc45)c(Cl)cc23)CC1] | 1-(4-(6-chloro-7-(quinolin-4-yl)quinazolin-4-yl)piperazin-1-yl)prop-2-en-1-one | Q | 430.10 |
| I-215 | 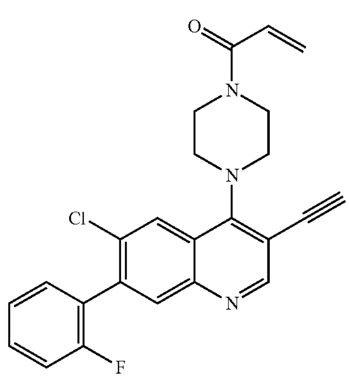 [SMILES: C#Cc1cnc2cc(-c3ccccc3F)c(Cl)cc2c1N1CCN(C(=O)C=C)CC1] | 1-(4-(6-chloro-3-ethynyl-7-(2-fluorophenyl)quinazolin-4-yl)piperazin-1-yl)prop-2-en-1-one | G | 430.10 |

TABLE 1-continued

Exemplary Compounds of Structure (I)

| No. | Structure | Name | Method | [M + H]+ |
|---|---|---|---|---|
| I-216 | 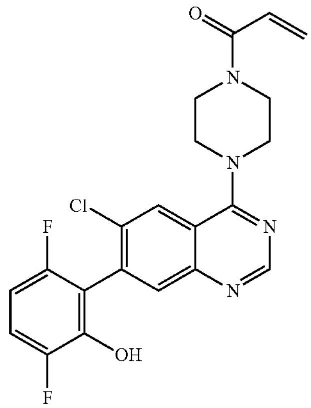 [SMILES: C=CC(=O)N1CCN(c2ncnc3cc(-c4c(F)ccc(F)c4O)c(Cl)cc23)CC1] | 1-(4-(6-chloro-7-(3,6-difluoro-2-hydroxyphenyl)quinazolin-4-yl)piperazin-1-yl)prop-2-en-1-one | U | 431.15 |
| I-217 | 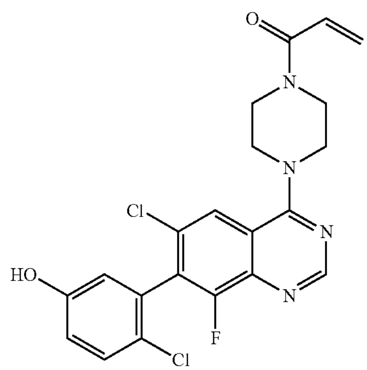 [SMILES: C=CC(=O)N1CCN(c2ncnc3c(F)c(-c4cc(O)ccc4Cl)c(Cl)cc23)CC1] | 1-(4-(6-chloro-7-(2-chloro-5-hydroxyphenyl)-8-fluoroquinazolin-4-yl)piperazin-1-yl)prop-2-en-1-one | O | 447.05 |
| I-218 | 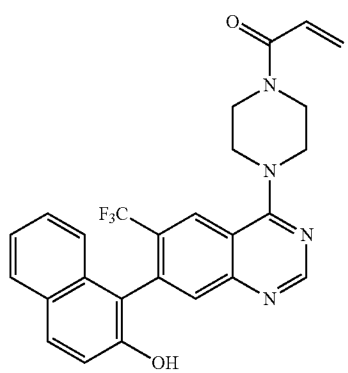 [SMILES: C=CC(=O)N1CCN(c2ncnc3cc(-c4c(O)ccc5ccccc45)c(C(F)(F)F)cc23)CC1] | 1-(4-(7-(2-hydroxynaphthalen-1-yl)-6-(trifluoromethyl)quinazolin-4-yl)piperazin-1-yl)prop-2-en-1-one | R | 479.20 |
| I-219 | 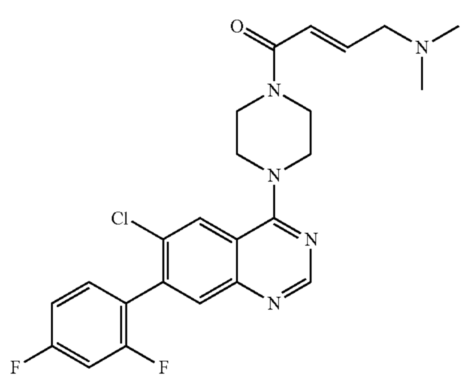 [SMILES: CN(C)C/C=C/C(=O)N1CCN(c2ncnc3cc(-c4ccc(F)cc4F)c(Cl)cc23)CC1] | (E)-1-(4-(6-chloro-7-(2,4-difluorophenyl)quinazolin-4-yl)piperazin-1-yl)-4-(dimethylamino)but-2-en-1-one | O | 472.10 |

TABLE 1-continued

Exemplary Compounds of Structure (I)

| No. | Structure | Name | Method | [M + H]+ |
|---|---|---|---|---|
| I-220 | 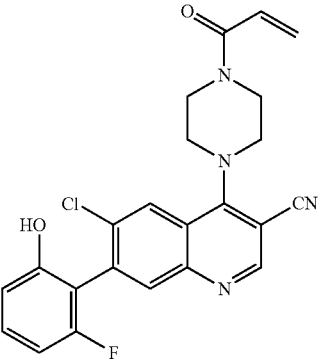 [SMILES: C=CC(=O)N1CCN(c2c(C#N)cnc3cc(-c4c(O)cccc4F)c(Cl)cc23)CC1] | 4-(4-acryloylpiperazin-- yl)-6-chloro-7-(2-fluoro- 6- hydroxyphenyl)quinoline- 3-carbonitrile | P | 437.15 |
| I-221 | 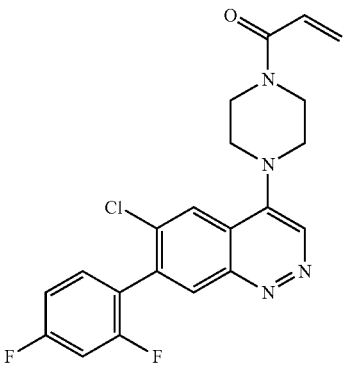 [SMILES: C=CC(=O)N1CCN(c2cnnc3cc(-c4ccc(F)cc4F)c(Cl)cc23)CC1] | 1-(4-(6-chloro-7-(2,4- difluorophenyl)cinnolin- 4-yl)piperazin-1-yl)prop- 2-en-1-one | N | 415.10 |
| I-222 | 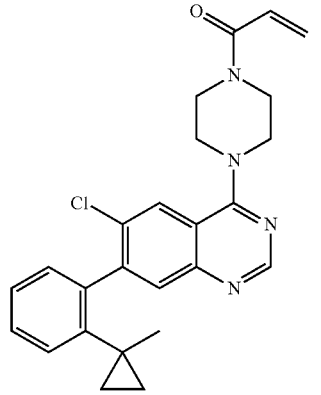 [SMILES: C=CC(=O)N1CCN(c2ncnc3cc(-c4ccccc4C4(C)CC4)c(Cl)cc23)CC1] | 1-(4-(6-chloro-7-(2-(1- methylcyclopropyl)phenyl) quinazolin-4- yl)piperazin-1-yl)prop-2- en-1-one | B | 433.20 |
| I-223 | 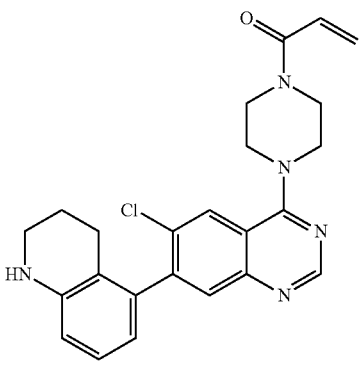 [SMILES: C=CC(=O)N1CCN(c2ncnc3cc(-c4cccc5c4CCCN5)c(Cl)cc23)CC1] | 1-(4-(6-chloro-7-(1,2,3,4- tetrahydroquinolin-5- yl)quinazolin-4- yl)piperazin-1-yl)prop-2- en-1-one | B | 434.15 |

TABLE 1-continued

Exemplary Compounds of Structure (I)

| No. | Structure | Name | Method | [M + H]+ |
|---|---|---|---|---|
| I-224 | 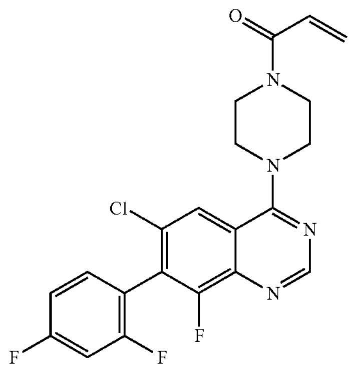 [SMILES: C=CC(=O)N1CCN(c2ncnc3c(F)c(-c4ccc(F)cc4F)c(Cl)cc23)CC1] | 1-(4-(6-chloro-7-(2,4-difluorophenyl)-8-fluoroquinazolin-4-yl)piperazin-1-yl)prop-2-en-1-one | O | 433.10 |
| I-225 | 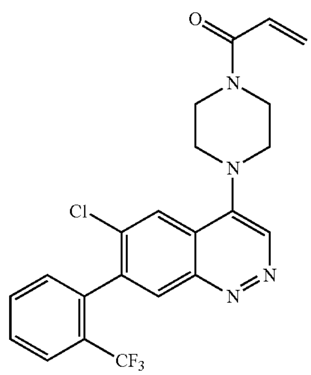 [SMILES: C=CC(=O)N1CCN(c2cnnc3cc(-c4ccccc4C(F)(F)F)c(Cl)cc23)CC1] | 1-(4-(6-chloro-7-(2-(trifluoromethyl)phenyl)cinnolin-4-yl)piperazin-1-yl)prop-2-en-1-one | N | 447.05 |
| I-226 | 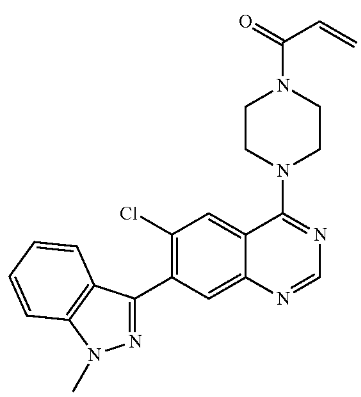 [SMILES: C=CC(=O)N1CCN(c2ncnc3cc(-c4nn(C)c5ccccc45)c(Cl)cc23)CC1] | 1-(4-(6-chloro-7-(1-methyl-1H-indazol-3-yl)quinazolin-4-yl)piperazin-1-yl)prop-2-en-1-one | B | 433.05 |
| I-227 | 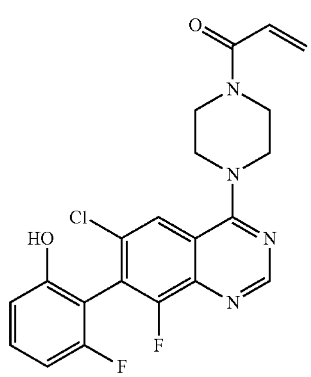 [SMILES: C=CC(=O)N1CCN(c2ncnc3c(F)c(-c4c(O)cccc4F)c(Cl)cc23)CC1] | 1-(4-(6-chloro-8-fluoro-7-(2-fluoro-6-hydroxyphenyl)quinazolin-4-yl)piperazin-1-yl)prop-2-en-1-one | O | 431.05 |

TABLE 1-continued

Exemplary Compounds of Structure (I)

| No. | Structure | Name | Method | [M + H]+ |
|---|---|---|---|---|
| I-228 | 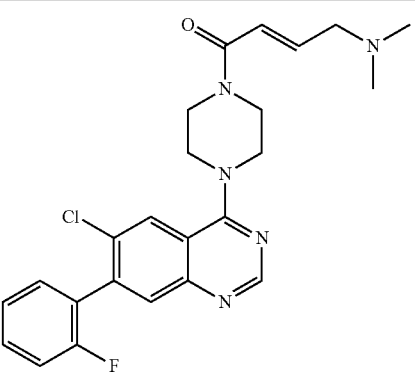 [SMILES: CN(C)C/C=C/C(=O)N1CCN(c2ncnc3cc(-c4ccccc4F)c(Cl)cc23)CC1] | (E)0-1-(4-(6-chloro-7-(2-fluorophenyl)quinazolin-4-yl)piperazin-1-yl)-4-(dimethylamino)but-2-en-1-one | B | 454.15 |
| I-229 | 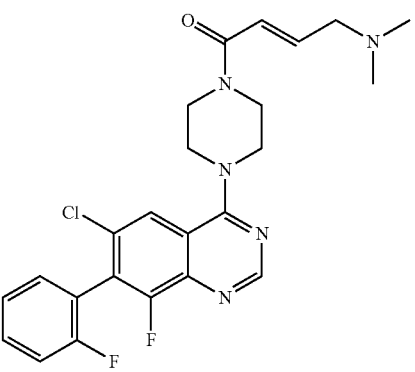 [SMILES: CN(C)C/C=C/C(=O)N1CCN(c2ncnc3c(F)c(-c4ccccc4F)c(Cl)cc23)CC1] | (E)-1-(4-(6-chloro-8-fluoro-7-(2-fluorophenyl)quinazolin-4-yl)piperazin-1-yl)-4-(dimethylamino)but-2-en-1-one | O | 472.15 |
| I-230 | 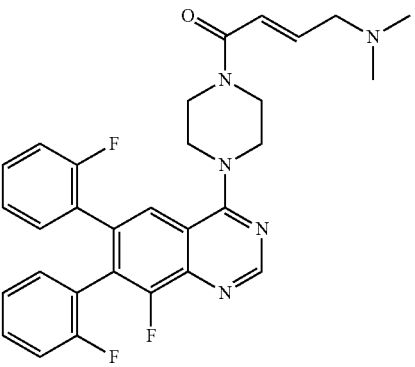 [SMILES: CN(C)C/C=C/C(=O)N1CCN(c2ncnc3c(F)c(-c4ccccc4F)c(-c4ccccc4F)cc23)CC1] | (E)-4-(dimethylamino)-1-(4-(8-fluoro-6,7-bis(2-fluorophenyl)quinazolin-4-yl)piperazin-1-yl)but-2-en-1-one | O | 532.25 |
| I-231 | 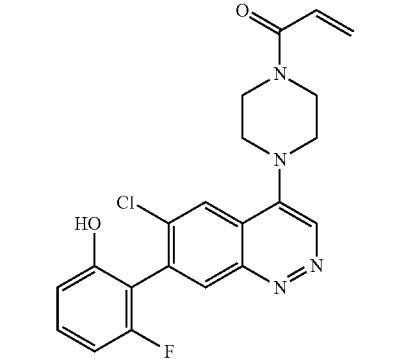 [SMILES: C=CC(=O)N1CCN(c2cnnc3cc(-c4c(O)cccc4F)c(Cl)cc23)CC1] | 1-(4-(6-chloro-7-(2-fluoro-6-hydroxyphenyl)cinnolin-4-yl)piperazin-1-yl)prop-2-en-1-one | N | 413.10 |

TABLE 1-continued

Exemplary Compounds of Structure (I)

| No. | Structure | Name | Method | [M + H]+ |
|---|---|---|---|---|
| I-232 | 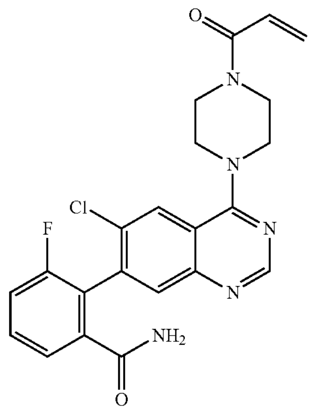 [SMILES: C=CC(=O)N1CCN(c2ncnc3cc(-c4c(F)cccc4C(N)=O)c(Cl)cc23)CC1] | 2-(4-(4-acryloylpiperazin-1-yl)-6-chloroquinazolin-7-yl)-3-fluorobenzamide | Q | 440.10 |
| I-233 | 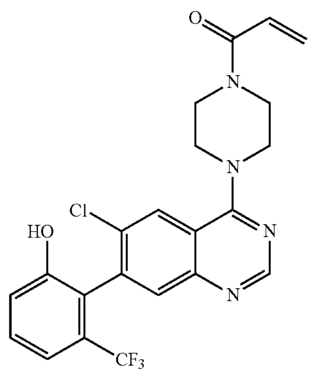 [SMILES: C=CC(=O)N1CCN(c2ncnc3cc(-c4c(O)cccc4C(F)(F)F)c(Cl)cc23)CC1] | 1-(4-(6-chloro-7-(2-hydroxy-6-(trifluoromethyl)phenyl)quinazolin-4-yl)piperazin-1-yl)prop-2-en-1-one | B | 463.10 |
| I-234 | 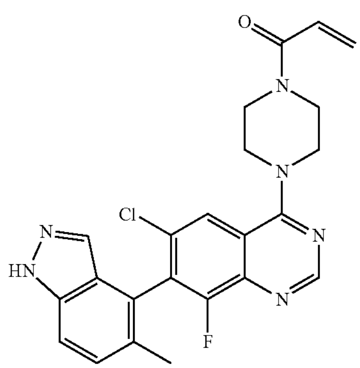 [SMILES: C=CC(=O)N1CCN(c2ncnc3c(F)c(-c4c(C)ccc5[nH]ncc45)c(Cl)cc23)CC1] | 1-(4-(6-chloro-8-fluoro-7-(5-methyl-1H-indazol-4-yl)quinazolin-4-yl)piperazin-1-yl)prop-2-en-1-one | O | 451.1 |
| I-235 | 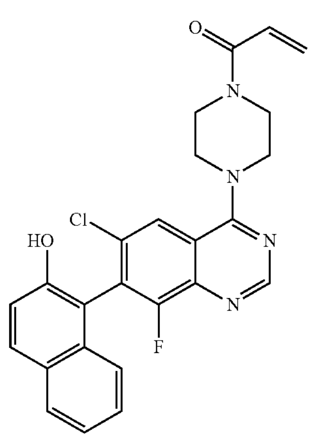 [SMILES: C=CC(=O)N1CCN(c2ncnc3c(F)c(-c4c(O)ccc5ccccc45)c(Cl)cc23)CC1] | 1-(4-(6-chloro-8-fluoro-7-(2-hydroxynaphthalen-1-yl)quinazolin-4-yl)piperazin-1-yl)prop-2-en-1-one | O | 463.10 |

TABLE 1-continued

Exemplary Compounds of Structure (I)

| No. | Structure | Name | Method | [M + H]+ |
|---|---|---|---|---|
| I-236 | 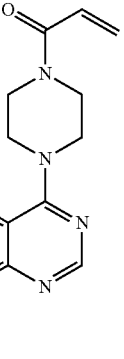 | 2-(4-(4-acryloylpiperazin-1-yl)-6-chloro-8-fluoroquinazolin-7-yl)benzamide | O | 440.10 |
| I-237 | 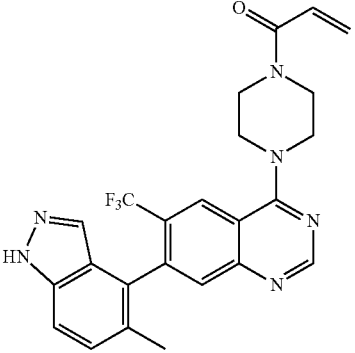 [SMILES: C=CC(=O)N1CCN(c2ncnc3cc(-c4c(C)ccc5[nH]ncc45)c(C(F)(F)F)cc23)CC1] | 1-(4-(7-(5-methyl-1H-indazol-4-yl)-6-(trifluoromethyl)quinazolin-4-yl)piperazin-1-yl)prop-2-en-1-one | R | 467.20 |
| I-238 | 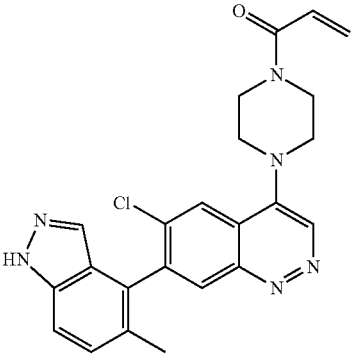 [SMILES: C=CC(=O)N1CCN(c2cnnc3cc(-c4c(C)ccc5[nH]ncc45)c(Cl)cc23)CC1] | 1-(4-(6-chloro-7-(5-methyl-1H-indazol-4-yl)cinnolin-4-yl)piperazin-1-yl)prop-2-en-1-one | N | 433.10 |
| I-239 | 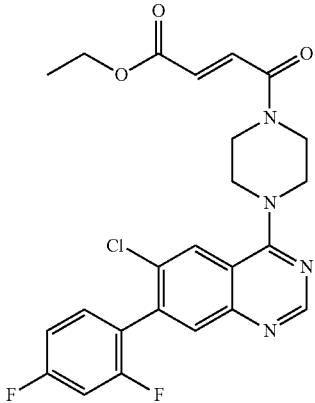 [SMILES: CCOC(=O)/C=C/C(=O)N1CCN(c2ncnc3cc(-c4ccc(F)cc4F)c(Cl)cc23)CC1] | (E)-ethyl 4-(4-(6-chloro-7-(2,4-difluorophenyl)quinazolin-4-yl)piperazin-1-yl)-4-oxobut-2-enoate | O | 487.10 |

TABLE 1-continued

Exemplary Compounds of Structure (I)

| No. | Structure | Name | Method | [M + H]+ |
|---|---|---|---|---|
| I-240 | 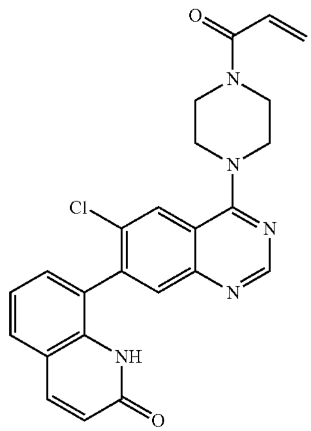 [SMILES: C=CC(=O)N1CCN(c2ncnc3cc(-c4cccc5ccc(=O)[nH]c45)c(Cl)cc23)CC1] | 8-(4-(4-acryloylpiperazin-1-yl)-6-chloroquinazolin-7-yl)quinolin-2(1H)-one | U | 446.10 |
| I-241 | 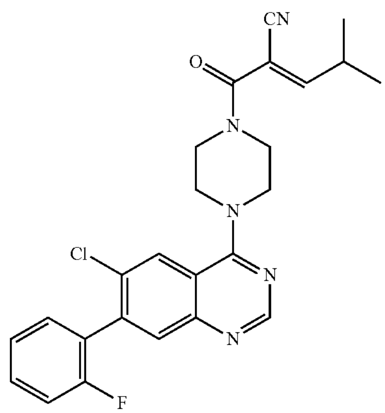 [SMILES: CC(C)/C=C(\C#N)C(=O)N1CCN(c2ncnc3cc(-c4ccccc4F)c(Cl)cc23)CC1] | (E)-2-(4-(6-chloro-7-(2-fluorophenyl)quinazolin-4-yl)piperazine-1-carbonyl)-4-methylpent-2-enenitrile | B | 464.10 |
| I-242 | 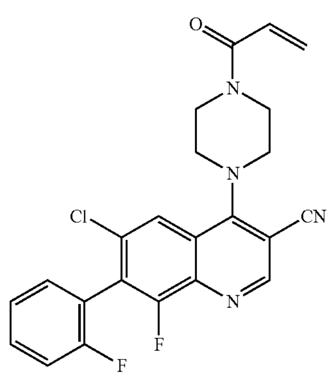 [SMILES: C=CC(=O)N1CCN(c2c(C#N)cnc3c(F)c(-c4ccccc4F)c(Cl)cc23)CC1] | 4-(4-acryloylpiperazin-1-yl)-6-chloro-8-fluoro-7-(2-fluorophenyl)quinoline-3-carbonitrile | P | 439.10 |
| I-243 | 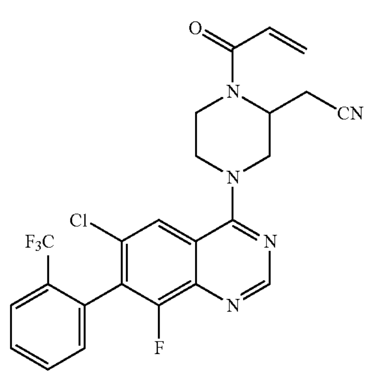 [SMILES: C=CC(=O)N1CCN(c2ncnc3c(F)c(-c4ccccc4C(F)(F)F)c(Cl)cc23)CC1CC#N] | 2-(1-acryloyl-4-(6-chloro-8-fluoro-7-(2-(trifluoromethyl)phenyl)quinazolin-4-yl)piperazin-2-yl)acetonitrile | O | 504.10 |

TABLE 1-continued

Exemplary Compounds of Structure (I)

| No. | Structure | Name | Method | [M + H]+ |
|---|---|---|---|---|
| I-244 | 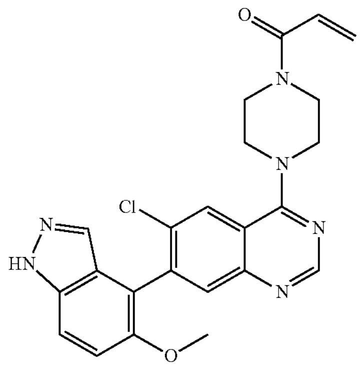 [SMILES: C=CC(=O)N1CCN(c2ncnc3cc(-c4c(OC)ccc5[nH]ncc45)c(Cl)cc23)CC1] | 1-(4-(6-chloro-7-(5-methoxy-1H-indazol-4-yl)quinazolin-4-yl)piperazin-1-yl)prop-2-en-1-one | B | 449.10 |
| I-245 | 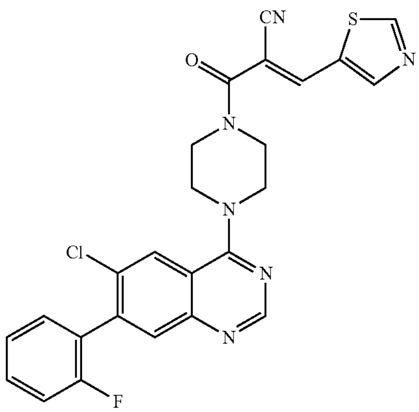 [SMILES: N#C/C(=C\c1cncs1)C(=O)N1CCN(c2ncnc3cc(-c4ccccc4F)c(Cl)cc23)CC1] | (E)-2-(4-(6-chloro-7-(2-fluorophenyl)quinazolin-4-yl)piperazine-1-carbonyl)-3-(thiazol-5-yl)acrylonitrile | B | 505.10 |
| I-246 | 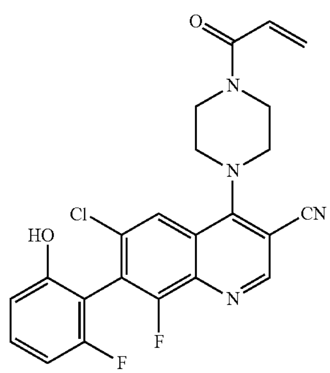 [SMILES: C=CC(=O)N1CCN(c2c(C#N)cnc3c(F)c(-c4c(O)cccc4F)c(Cl)cc23)CC1] | 4-(4-acryloylpiperazin-1-yl)-6-chloro-8-fluoro-7-(2-fluoro-6-hydroxyphenyl)quinoline-3-carbonitrile | P | 455.15 |
| I-247 | 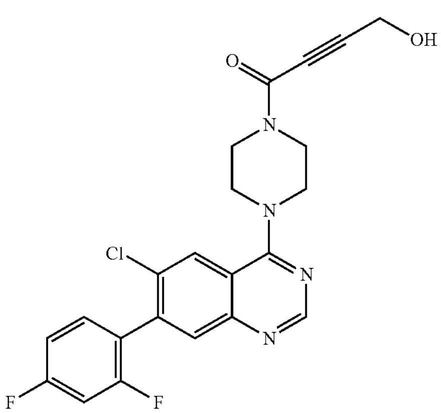 [SMILES: O=C(C#CCO)N1CCN(c2ncnc3cc(-c4ccc(F)cc4F)c(Cl)cc23)CC1] | 1-(4-(6-chloro-7-(2,4-difluorophenyl)quinazolin-4-yl)piperazain-1-yl)-4-hydoxybut-2-yn-1-one | O | 443.1 |

TABLE 1-continued
Exemplary Compounds of Structure (I)
| No. | Structure | Name | Method | [M + H]+ |
|---|---|---|---|---|
| I-248 | 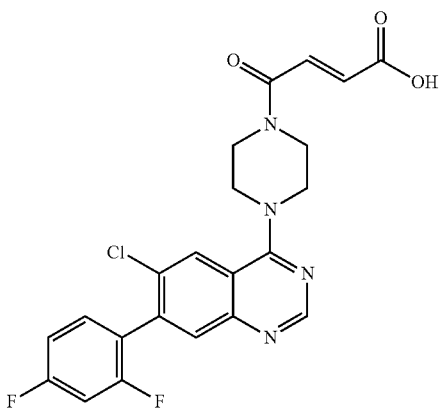 [SMILES: O=C(O)/C=C/C(=O)N1CCN(c2ncnc3cc(-c4ccc(F)cc4F)c(Cl)cc23)CC1] | (E)-4-(4-(6-chloro-7-(2,4-difluorophenyl)quinazolin-4-yl)piperazin-1-yl)-4-oxxobut-2-enoic acid | O | 459.05 |
| I-249 | 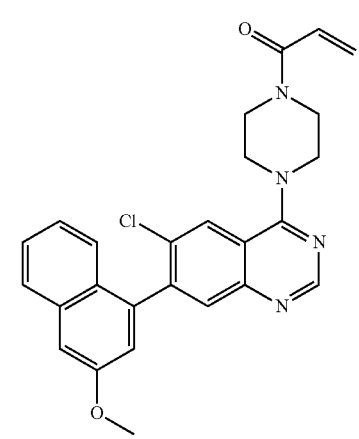 [SMILES: C=CC(=O)N1CCN(c2ncnc3cc(-c4cc(OC)cc5ccccc45)c(Cl)cc23)CC1] | 1-(4-(6-chloro-7-(3-methoxynaphthalen-1-yl)quinazolin-4-yl)piperazin-1-yl)prop-2-en-1-one | Q | 459.1 |
| I-250 | 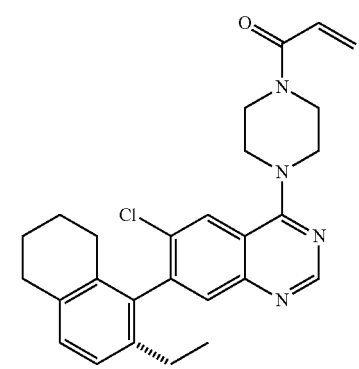 | 1-(4-(6-chloro-7-(2-hydroxy-5,6,7,8-tetrahydronaphthalen-1-yl)quinazolin-4-yl)piperazin-1-yl)prop-2-en-1-one | O | 449.10 |

TABLE 1-continued
Exemplary Compounds of Structure (I)
| No. | Structure | Name | Method | [M + H]⁺ |
|---|---|---|---|---|
| I-251 | 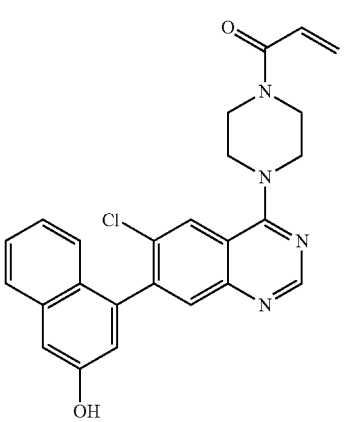 [SMILES: C=CC(=O)N1CCN(c2ncnc3cc(-c4cc(O)cc5ccccc45)c(Cl)cc23)CC1] | 1-(4-(6-chloro-7-(3-hydroxynaphthalen-1-yl)quinazolin-4-yl)piperazin-1-yl)prop-2-en-1-one | Q | 445.10 |
| I-252 | 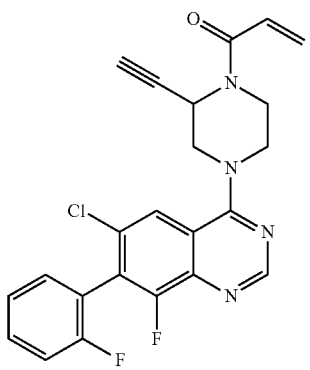 [SMILES: C#CC1CN(c2ncnc3c(F)c(-c4ccccc4F)c(Cl)cc23)CCN1C(=O)C=C] | 1-(4-(6-chloro-8-fluoro-7-(2-fluorophenyl)quinazolin-4-yl)-2-ethynylpiperazin-1-yl)prop-2-en-1-one | O | 439.10 |
| I-253 | 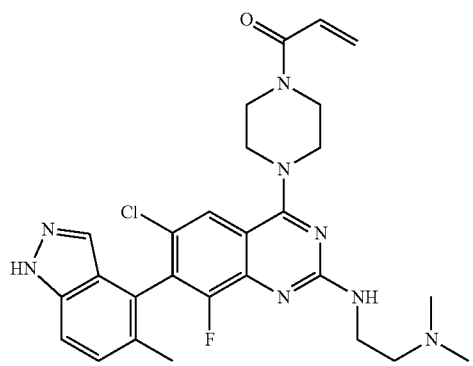 [SMILES: C=CC(=O)N1CCN(c2nc(NCCN(C)C)nc3c(F)c(-c4c(C)ccc5[nH]ncc45)c(Cl)cc23)CC1] | 1-(4-(6-chloro-2-(2-(dimethylamino)ethylamino)-8-fluoro-7-(5-methyl-1H-indazol-4-yl)piperazin-1-yl)prop-2-en-1-one | € | 537.4 |

TABLE 1-continued
Exemplary Compounds of Structure (I)
| No. | Structure | Name | Method | [M + H]+ |
|---|---|---|---|---|
| I-254 | 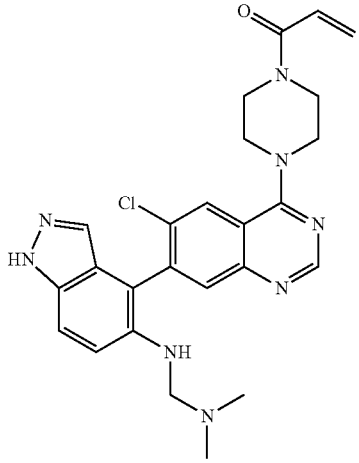 [SMILES: C=CC(=O)N1CCN(c2ncnc3cc(-c4c(NCN(C)C)ccc5[nH]ncc45)c(Cl)cc23)CC1] | 1-(4-(6-chloro-2-((dimethylamino)methylamino)-8-fluoro-7-(5-methyl-1H-indazol-4-yl)quinazolin-4-yl)piperazin-1-yl)prop-2-en-1-one | € | 508.3 |
| I-255 | 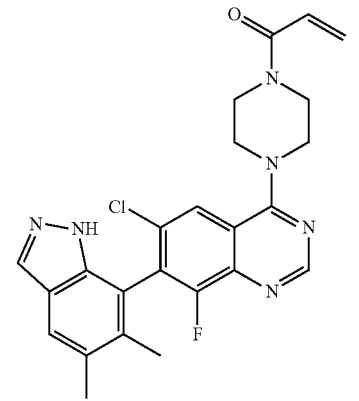 [SMILES: C=CC(=O)N1CCN(c2ncnc3c(F)c(-c4c(C)c(C)cc5cn[nH]c45)c(Cl)cc23)CC1] | 1-(4-(6-chloro-7-(5,6-dimethyl-1H-indazol-7-yl)-8-fluoroquinaolin-4-yl)piperazin-1-yl)prop-2-en-1-one | € | 465.1 |
| I-256 | 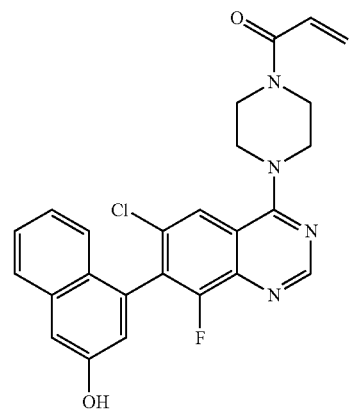 [SMILES: C=CC(=O)N1CCN(c2ncnc3c(F)c(-c4cc(O)cc5ccccc45)c(Cl)cc23)CC1] | 1-(4-(6-chloro-8-fluoro-7-(3-hydroxynaphthalen-1-yl)quinazolin-4-yl)piperazin-1-yl)prop-2-en-1-one | € | 493.3 |

TABLE 1-continued

Exemplary Compounds of Structure (I)

| No. | Structure | Name | Method | [M + H]+ |
|---|---|---|---|---|
| I-257 | 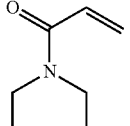 | 1-(4-(6-chloro-8-fluoro-7-(5-methyl-1H-indazol-4-yl)-2-(methylamino)quinazolin-4-yl)piperazin-1-yl)prop-2-en-1-one | € | 480.2 |
| I-258 | 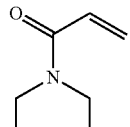 | 1-(4-(6-chloro-7-(2-hydroxynaphthalen-1-yl)cinnolin-4-yl)piperazin-1-yl)prop-2-en-1-one | € | 445.1 |
| I-259 | 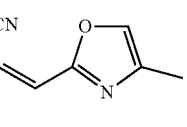 | (E)-2-(4-(6-chloro-7-(2-fluorophenyl)quinazolin-4-yl)piperazine-1-carbonyl)-3-(4-methyloxazol-2-yl)acrylonitrile | € | 503.2 |
| I-260 | 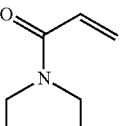 | 4-(4-acryloylpiperazin-1-yl)-6-chloro-7-(2-hydroxynaphthalen-1-yl)quinoline-3-carbonitrile | € | 469.1 |

TABLE 1-continued
Exemplary Compounds of Structure (I)
| No. | Structure | Name | Method | [M + H]⁺ |
|---|---|---|---|---|
| I-261 | 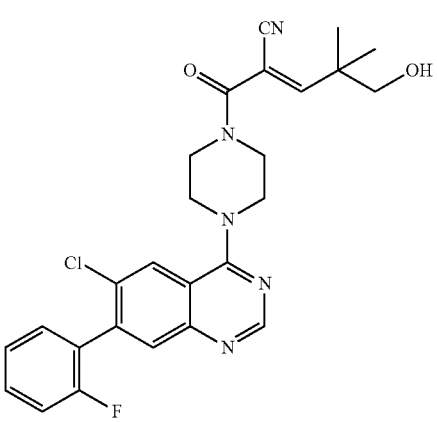 [SMILES: CC(C)(/C=C(\C#N)C(=O)N1CCN(c2ncnc3cc(-c4ccccc4F)c(Cl)cc23)CC1)CO] | (E)-2-(4-(6-chloro-7-(2-fluorophenyl)quinazolin-4-yl)piperazine-1-carbonyl)-5-hydroxy-4,4-dimethylpent-2-enenitrile | € | 494.4 |
| I-262 | 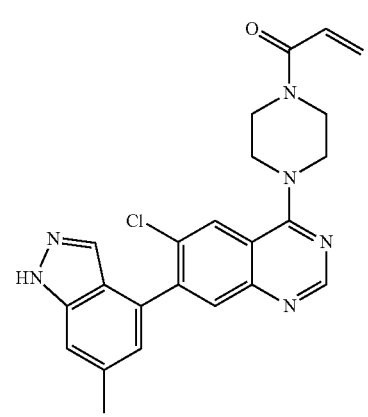 [SMILES: C=CC(=O)N1CCN(c2ncnc3cc(-c4cc(C)cc5[nH]ncc45)c(Cl)cc23)CC1] | 1-(4-(6-chloro-7-(6-methyl-1H-indazol-4-yl)quinolin-4-yl)piperazin-1-yl)prop-2-en-1-one | € | 494.3 |
| I-263 | 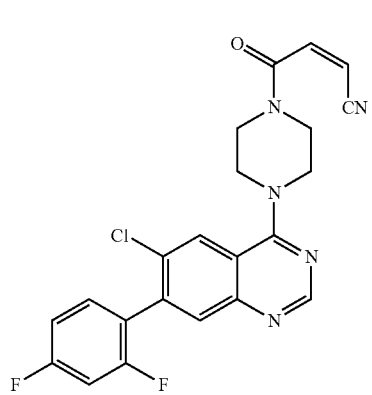 [SMILES: N#C/C=C\C(=O)N1CCN(c2ncnc3cc(-c4ccc(F)cc4F)c(Cl)cc23)CC1] | (Z)-4-(4-(6-chloro-7-(2,4-difluorophenyl)quinaozlin-4-yl)piperazin-1-yl)-4-oxobut-2-enenitrile | € | 440.1 |

TABLE 1-continued

Exemplary Compounds of Structure (I)

| No. | Structure | Name | Method | [M + H]+ |
|---|---|---|---|---|
| I-264 | 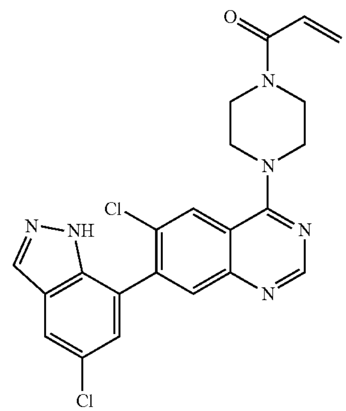 [SMILES: C=CC(=O)N1CCN(c2ncnc3cc(-c4cc(Cl)cc5cn[nH]c45)c(Cl)cc23)CC1] | 1-(4-(6-chloro-7-(5-chloro-1H-indazol-7-yl)quinazolin-4-yl)piperazin-1-yl)prop-2-en-1-one | є | 454.1 |
| I-265 | 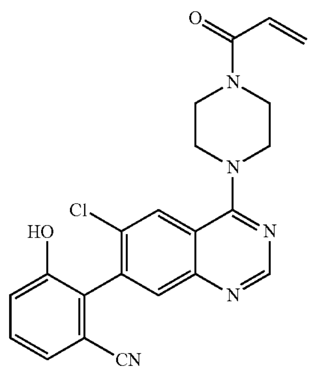 [SMILES: C=CC(=O)N1CCN(c2ncnc3cc(-c4c(O)cccc4C#N)c(Cl)cc23)CC1] | 2-(4-(4-acryloylpiperazin-1-yl)-6-chloroquinazolin-7-yl)-3-hydroxybenzonitrile | є | 420.1 |
| I-266 | 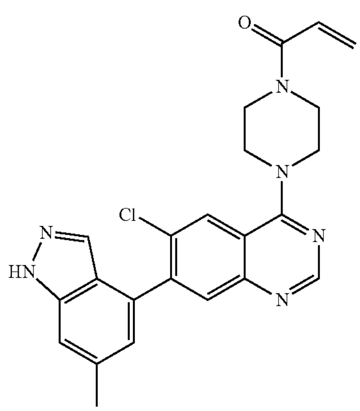 [SMILES: C=CC(=O)N1CCN(c2ncnc3cc(-c4cc(C)cc5[nH]ncc45)c(Cl)cc23)CC1] | 1-(4-(6-chloro-7-(5-chloro-1H-indazol-4-yl)quinazolin-4-yl)piperazin-1-yl)prop-2-en-1-one | є | 453.1 |
| I-267 | 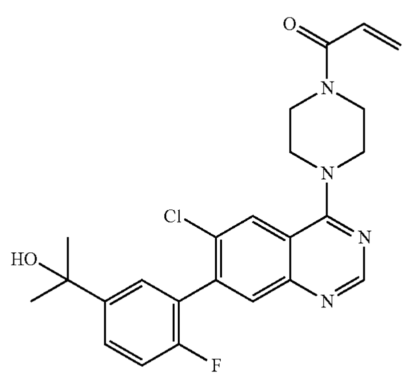 [SMILES: C=CC(=O)N1CCN(c2ncnc3cc(-c4cc(C(C)(C)O)ccc4F)c(Cl)cc23)CC1] | 1-(4-(6-chloro-7-(2-fluoro-5-(2-hydroxypropan-2-yl)phenyl)quinazolin-4-yl)piperazin-1-yl)prop-2-en-1-one | є | 455.1 |

TABLE 1-continued

Exemplary Compounds of Structure (I)

| No. | Structure | Name | Method | [M + H]⁺ |
|---|---|---|---|---|
| I-268 | 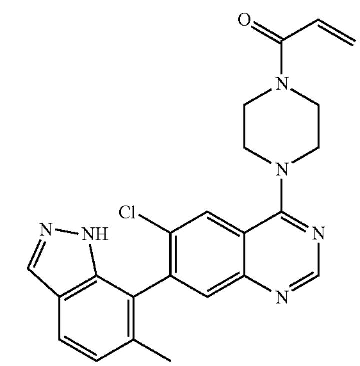 [SMILES: C=CC(=O)N1CCN(c2ncnc3cc(-c4c(C)ccc5cn[nH]c45)c(Cl)cc23)CC1] | 1-(4-(6-chloro-7-(6-methyl-1H-indazol-7-yl)quinazolin-4-yl)piperazin-1-yl)prop-2-en-1-one | € | 433.2 |
| I-269 | 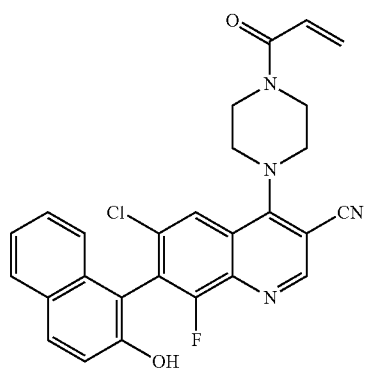 [SMILES: C=CC(=O)N1CCN(c2c(C#N)cnc3c(F)c(-c4c(O)ccc5ccccc45)c(Cl)cc23)CC1] | 4-(4-acryloylpiperazin-1-yl)-6-chloro-8-fluoro-7-(2-hydroxynaphthalen-1-yl)quinoline-3-carbonitrile | € | 487.1 |
| I-270 | 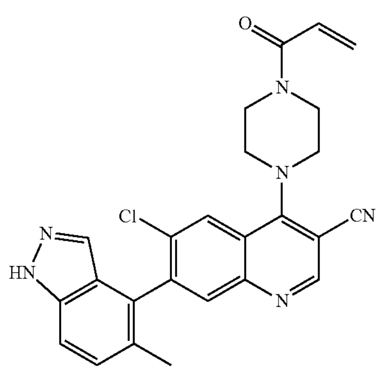 [SMILES: C=CC(=O)N1CCN(c2c(C#N)cnc3cc(-c4c(C)ccc5[nH]ncc45)c(Cl)cc23)CC1] | 4-(4-acryloylpiperazin-1-yl)-6-chloro-7-(5-methyl-1H-indazol-4-yl)quinoline-3-carbonitrile | € | 457.1 |
| I-271 | 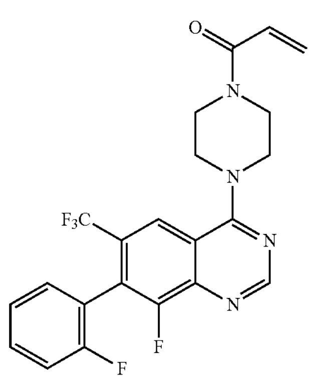 [SMILES: C=CC(=O)N1CCN(c2ncnc3c(F)c(-c4ccccc4F)c(C(F)(F)F)cc23)CC1] | 1-(4-(8-fluoro-7-(2-fluorophenyl)-6-(trifluorophenyl)quinazolin-4-yl)piperazin-1-yl)prop-2-en-1-one | € | 449.2 |

TABLE 1-continued

Exemplary Compounds of Structure (I)

| No. | Structure | Name | Method | [M + H]+ |
|---|---|---|---|---|
| I-272 | 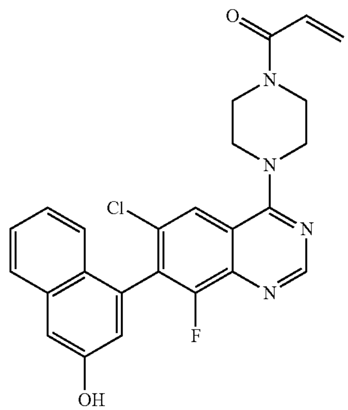 [SMILES: C=CC(=O)N1CCN(c2ncnc3c(F)c(-c4cc(O)cc5ccccc45)c(Cl)cc23)CC1] | 1-(4-(6-chloro-8-fluoro-7-(3-hydroxynaphthalen-1-yl)quinazolin-4-yl)piperazin-1-yl)prop-2-en-1-one | € | 463.2 |
| I-273 | 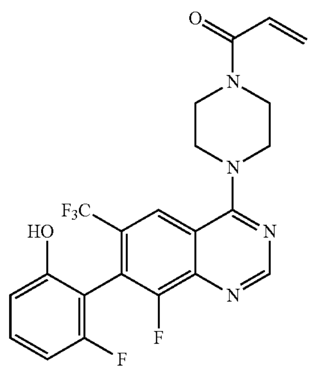 [SMILES: C=CC(=O)N1CCN(c2ncnc3c(F)c(-c4c(O)cccc4F)c(C(F)(F)F)cc23)CC1] | 1-(4-(8-fluoro-7-(2-dluoro-6-hydroxyphenyl)-6-(trifluoromethyl)quinaozlin-4-yl)piperazin-1-yl)prop-2-en-1-one | € | 465.2 |
| I-274 | 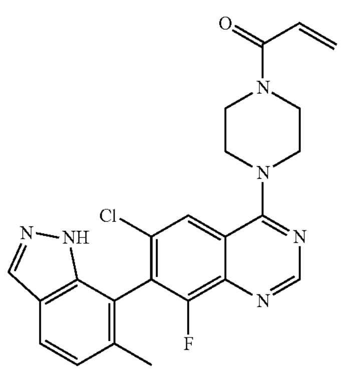 [SMILES: C=CC(=O)N1CCN(c2ncnc3c(F)c(-c4c(C)ccc5cn[nH]c45)c(Cl)cc23)CC1] | 1-(4-(6-chloro-8-fluoro-7-(6-methyl-1H-indazol-7-yl)quinazolin-4-yl)piperazin-1-yl)prop-2-en-1-one | € | 451.2 |
| I-275 | 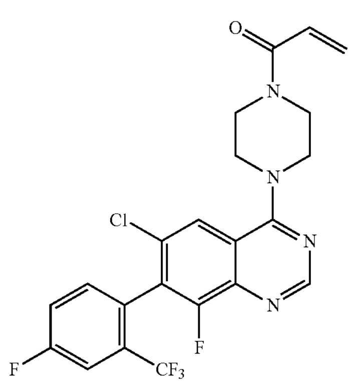 [SMILES: C=CC(=O)N1CCN(c2ncnc3c(F)c(-c4ccc(F)cc4C(F)(F)F)c(Cl)cc23)CC1] | 1-(4-(6-chloro-8-fluoro-7-(4-fluoro-2-(trifluoromethyl)phenyl)quinazolin-4-yl)piperazin-1-yl)prop-2-en-1-one | € | 483.2 |

TABLE 1-continued

Exemplary Compounds of Structure (I)

| No. | Structure | Name | Method | [M + H]+ |
|---|---|---|---|---|
| I-276 | 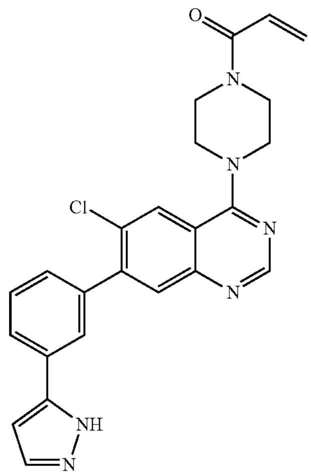 [SMILES: C=CC(=O)N1CCN(c2ncnc3cc(-c4cccc(-c5ccn[nH]5)c4)c(Cl)cc23)CC1] | 1-(4-(7-(3-(1H-pyrazol-5-yl)phenyl)-6-chloroquinazolin-4-yl)piperazin-1-yl)prop-2-en-1-one | € | 445.2 |
| I-277 | 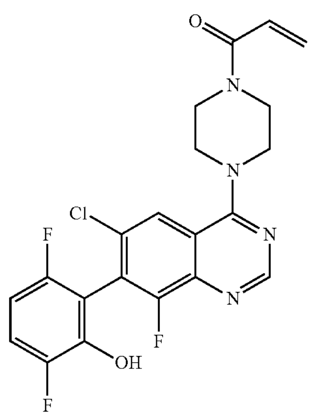 [SMILES: C=CC(=O)N1CCN(c2ncnc3c(F)c(-c4c(F)ccc(F)c4O)c(Cl)cc23)CC1] | 1-(4-(6-chloro-7-(3,6-ddifluoro-2-hydroxyphenyl)-8-fluoroquinazolin-4-yl)piperazin-1-yl)prop-2-en-1-one | € | 449.1 |
| I-278 | 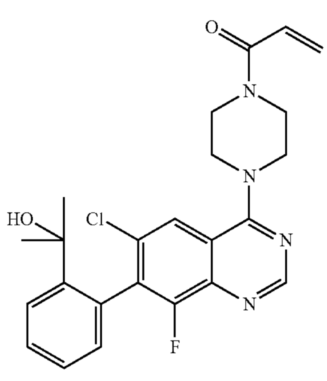 [SMILES: C=CC(=O)N1CCN(c2ncnc3c(F)c(-c4ccccc4C(C)(C)O)c(Cl)cc23)CC1] | 1-(4-(6-chloro-8-fluoro-7-(2-(2-hydroxypropan-2-yl)phenyl)quinazolin-4-yl)piperazin-1-yl)prop-2-en-1-one | € | 455.2 |

TABLE 1-continued

Exemplary Compounds of Structure (I)

| No. | Structure | Name | Method | [M + H]+ |
|---|---|---|---|---|
| I-279 | 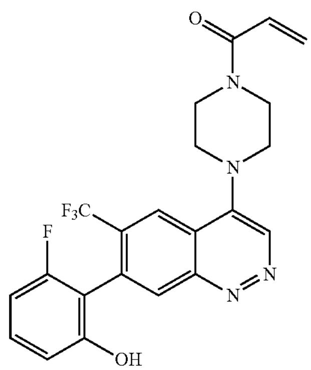 [SMILES: C=CC(=O)N1CCN(c2cnnc3cc(-c4c(O)cccc4F)c(C(F)(F)F)cc23)CC1] | 1-(4-(7-(2-fluoro-6-hydroxyphenyl)-6-(trifluoromethyl)cinnolin-4-yl)piperazin-1-yl)prop-2-en-1-one | e | 447.2 |
| I-280 | 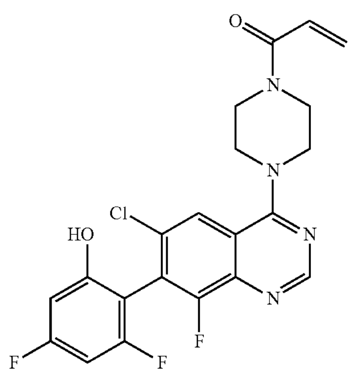 [SMILES: C=CC(=O)N1CCN(c2ncnc3c(F)c(-c4c(O)cc(F)cc4F)c(Cl)cc23)CC1] | 1-(4-(6-chloro-7-(2,4-difluoro-6-hydroxyphenyl)-8-fluoroquinazolin-4-yl)piperazin-1-yl)prop-2-en-1-one | e | 449.1 |
| I-281 | 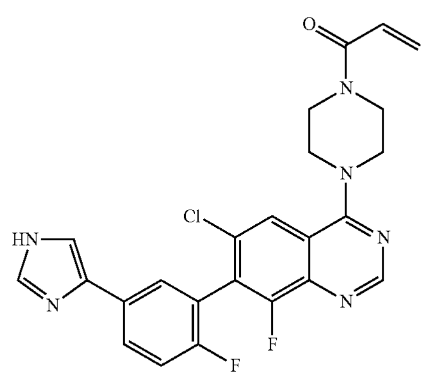 [SMILES: C=CC(=O)N1CCN(c2ncnc3c(F)c(-c4cc(-c5c[nH]cn5)ccc4F)c(Cl)cc23)CC1] | 1-(4-(6-chloro-8-fluoro-7-(2-fluoro-5-(1H-imidazol-4-yl)phenyl)quinazolin-4-yl)piperazin-1-yl)prop-2-en-1-one | e | 481.2 |
| I-282 | 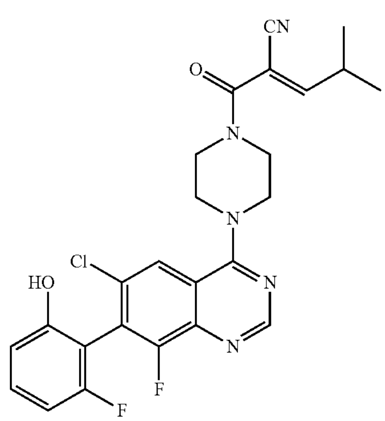 [SMILES: CC(C)/C=C(\C#N)C(=O)N1CCN(c2ncnc3c(F)c(-c4c(O)cccc4F)c(Cl)cc23)CC1] | (E)-2-(4-(6-chloro-8-fluoro-7-(2-fluoro-6-hydroxyphenyl)quinazolin-4-yl)piperazine-1-carbonyl)-4-methylpent-2-enenitrile | e | 498.2 |

TABLE 1-continued

Exemplary Compounds of Structure (I)

| No. | Structure | Name | Method | [M + H]+ |
|---|---|---|---|---|
| I-283 | 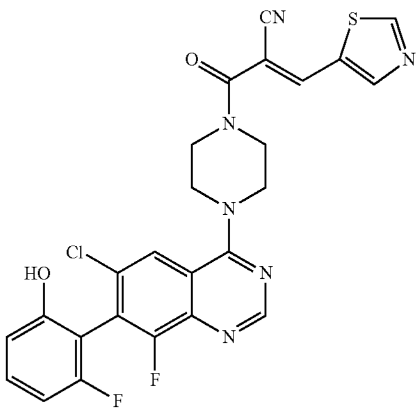 [SMILES: N#C/C(=C\c1cncs1)C(=O)N1CCN(c2ncnc3c(F)c(-c4c(O)cccc4F)c(Cl)cc23)CC1] | (E)-2-(4-(6-chloro-8-fluoro-7-(2-fluoro-6-hydroxyphenyl)quinazolin-4-yl)piperazine-1-carbonyl)-3-(thiazol-5-yl)acrylonitrile | € | 539.2 |
| I-284 | 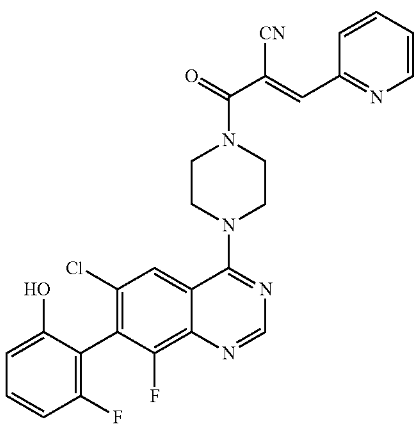 [SMILES: N#C/C(=C\c1ccccn1)C(=O)N1CCN(c2ncnc3c(F)c(-c4c(O)cccc4F)c(Cl)cc23)CC1] | (E)-2-(4-(6-chloro-8-fluoro-7-(2-fluoro-6-hydroxyphenyl)quinazolin-4-yl)piperazine-1-carbonyl)-3-(pyridin-2-yl)acrylonitrile | € | 533.2 |
| I-285 | 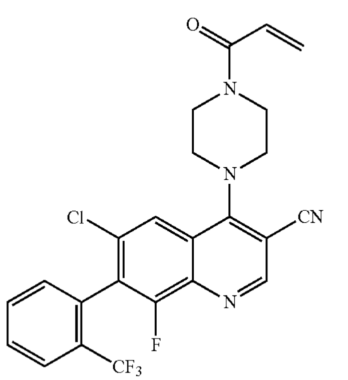 [SMILES: C=CC(=O)N1CCN(c2c(C#N)cnc3c(F)c(-c4ccccc4C(F)(F)F)c(Cl)cc23)CC1] | 4-(4-acryloylpiperazin-1-yl)-6-chloro-8-fluoro-7-(2-(trifluoromethyl)phenyl)quinoline-3-carbonitrile | € | 489.2 |

TABLE 1-continued

Exemplary Compounds of Structure (I)

| No. | Name | Method | [M + H]+ |
|---|---|---|---|
| I-286 | 1-(4-(6,8-dichloro-7-(2-methoxynaphthalen-1-yl)quinazolin-4-yl)piperazin-1-yl)prop-2-en-1-one | € | 494.1 |
| I-287 | 1-(4-(6-chloro-8-fluoro-7-(2-methoxy-6-methylphenyl)quinazolin-4-yl)piperazin-1-yl)prop-2-en-1-one | € | 441.2 |
| I-288 | 1-(4-(6-chloro-8-fluoro-7-(1H-indol-3-yl)quinazolin-4-yl)piperazin-1-yl)prop-2-en-1-one | € | 436.1 |
| I-289 | 1-(4-(6-chloro-7-(2-chloro-6-hydroxyphenyl)-8-fluoroquinazolin-4-yl)piperazin-1-yl)prop-2-en-1-one | € | 448.0 |

TABLE 1-continued

Exemplary Compounds of Structure (I)

| No. | Structure | Name | Method | [M + H]+ |
|---|---|---|---|---|
| I-290 | 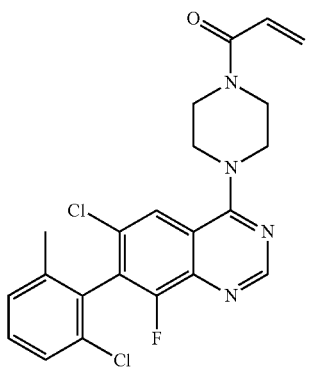 [SMILES: C=CC(=O)N1CCN(c2ncnc3c(F)c(-c4c(C)cccc4Cl)c(Cl)cc23)CC1] | 1-(4-(6-chloro-7-(2-chloro-6-methylphenyl)-8-fluoroquinazolin-4-yl)piperazin-1-yl)prop-2-en-1-one | ϵ | 427.1 |
| I-291 | 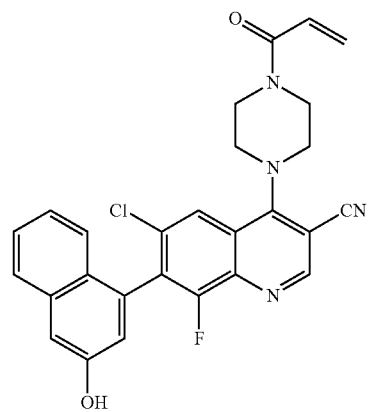 [SMILES: C=CC(=O)N1CCN(c2c(C#N)cnc3c(F)c(-c4cc(O)cc5ccccc45)c(Cl)cc23)CC1] | 4-(4-acryloylpiperazin-1-yl)-6-chloro-8-fluoro-7-(3-hydroxynaphthalen-1-yl)quinoline-3-carbonitrile | ϵ | 487.1 |
| I-292 | 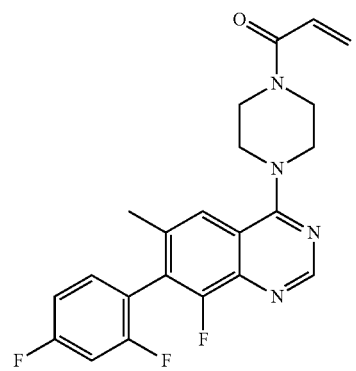 [SMILES: C=CC(=O)N1CCN(c2ncnc3c(F)c(-c4ccc(F)cc4F)c(C)cc23)CC1] | 1-(4-(7-(2,4-difluorophenyl)-8-fluoro-6-methylquinazolin-4-yl)piperazin-1-yl)prop-2-en-1-one | ϵ | 413.2 |
| I-293 | 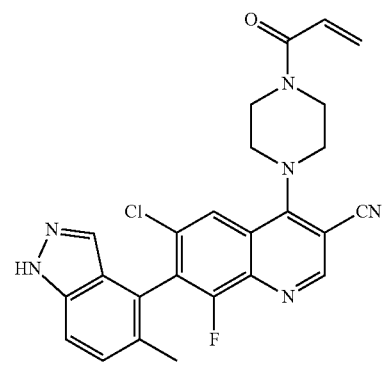 [SMILES: C=CC(=O)N1CCN(c2c(C#N)cnc3c(F)c(-c4c(C)ccc5[nH]ncc45)c(Cl)cc23)CC1] | 4-(4-acryloylpiperazin-1-yl)-6-chloro-8-fluoro-7-(5-methyl-1H-indazol-4-yl)quinoline-3-carbonitrile | ϵ | 475.2 |

TABLE 1-continued

Exemplary Compounds of Structure (I)

| No. | Structure | Name | Method | [M + H]+ |
|---|---|---|---|---|
| I-294 | 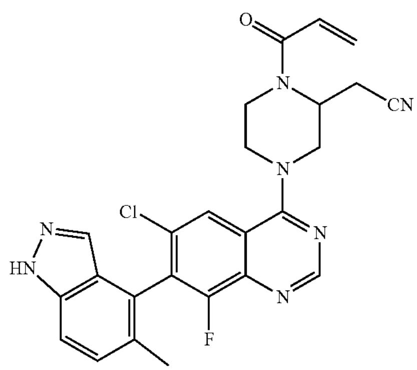 [SMILES: C=CC(=O)N1CCN(c2ncnc3c(F)c(-c4c(C)ccc5[nH]ncc45)c(Cl)cc23)CC1CC#N] | 2-(1-acryloyl-4-(6-chloro-8-fluoro-7-(5-methyl-1H-indazol-4-yl)quinazolin-4-yl)piperazin-2-acetonitrile | € | 490.2 |
| I-295 | 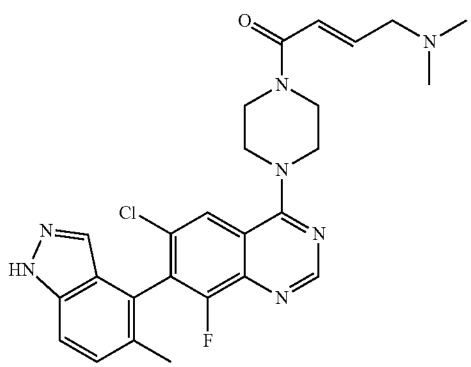 [SMILES: Cc1ccc2[nH]ncc2c1-c1c(Cl)cc2c(N3CCN(C(=O)/C=C/CN(C)C)CC3)ncnc2c1F] | (E)-1-(4-(6-chloro-8-fluoro-7-(5-methyl-1H-indazol-4-yl)quinazolin-4-yl)piperazin-1-yl)-4-(dimethylamino)but-2-en-1-one | € | 508.2 |
| I-296 | 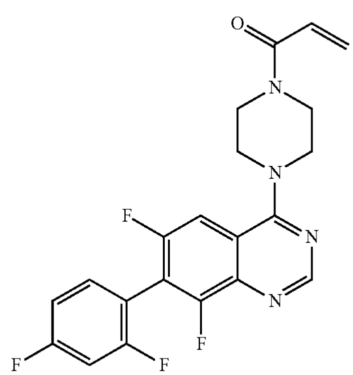 [SMILES: C=CC(=O)N1CCN(c2ncnc3c(F)c(-c4ccc(F)cc4F)c(F)cc23)CC1] | 1-(4-(7-(2,4-difluorophenyl)-6,8-difluoroquinolin-4-yl)piperazin-1-yl)prop-2-en-1-one | € | 417.22 |
| I-297 | 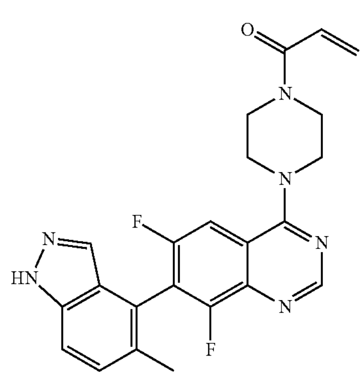 [SMILES: C=CC(=O)N1CCN(c2ncnc3c(F)c(-c4c(C)ccc5[nH]ncc45)c(F)cc23)CC1] | 1-(4-(6,8-difluoro-7-(5-methyl-1H-indazol-4-yl)quinazolin-4-yl)piperazin-1-yl)prop-2-en-1-one | € | 435.3 |

TABLE 1-continued

Exemplary Compounds of Structure (I)

| No. | Structure | Name | Method | [M + H]+ |
|---|---|---|---|---|
| I-298 | 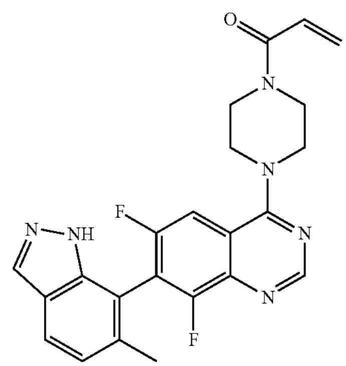 [SMILES: C=CC(=O)N1CCN(c2ncnc3c(F)c(-c4c(C)ccc5cn[nH]c45)c(F)cc23)CC1] | 1-(4-(6,8-difluoro-7-(6-methyl-1H-indazol-7-yl)-quinazolin-4-yl)piperazin-1-yl)prop-2-en-1-one | € | 435.3 |
| I-299 | 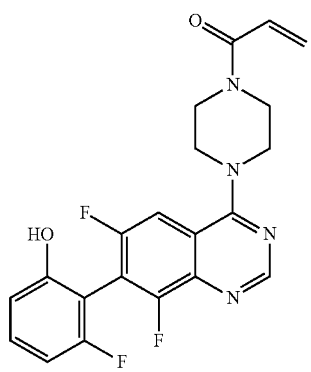 [SMILES: C=CC(=O)N1CCN(c2ncnc3c(F)c(-c4c(O)cccc4F)c(F)cc23)CC1] | 1-(4-(6,8-difluoro-7-(2-fluoro-6-hydroxyphenyl)quinazolin-4-yl)piperazin-1-yl)prop-2-en-1-one | € | 415.3 |
| I-300 | 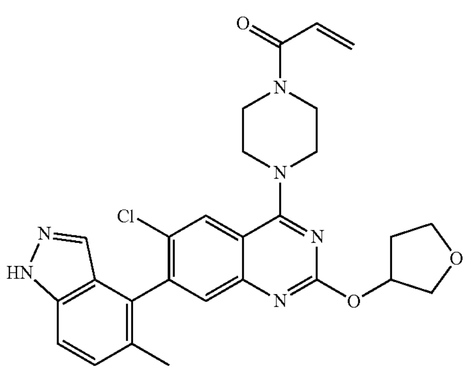 [SMILES: C=CC(=O)N1CCN(c2nc(OC3CCOC3)nc3cc(-c4c(C)ccc5[nH]ncc45)c(Cl)cc23)CC1] | 1-(4-(6-chloro-7-(5-methyl-1H-indazol-4-yl)-2-(tetrahydrofuran-3-yloxy)quinazolin-4-yl)piperazin-1-yl)prop-2-en-1-one | € | 519.3 |
| I-301 | 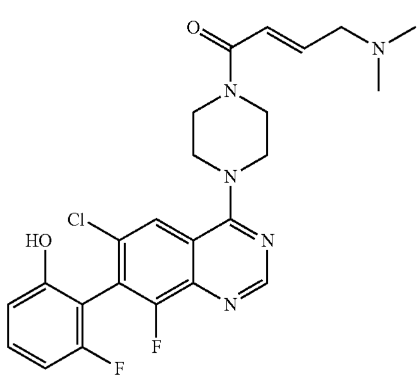 [SMILES: CN(C)C/C=C/C(=O)N1CCN(c2ncnc3c(F)c(-c4c(O)cccc4F)c(Cl)cc23)CC1] | (E)-1-(4-(6-chloro-8-fluoro-7-(2-fluoro-6-hydroxyphenyl)quinazolin-4-yl)piperazin-1-yl)-4-(dimethylamino)but-2-en-1-one | € | 488.2 |

TABLE 1-continued

Exemplary Compounds of Structure (I)

| No. | Structure | Name | Method | [M + H]⁺ |
|---|---|---|---|---|
| I-302 | 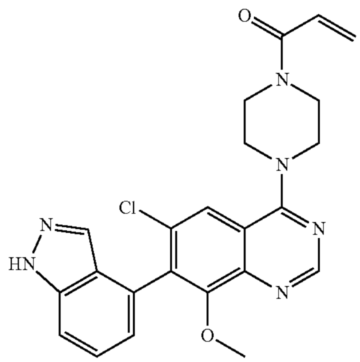 [SMILES: C=CC(=O)N1CCN(c2ncnc3c(OC)c(-c4cccc5[nH]ncc45)c(Cl)cc23)CC1] | 1-(4-(6-chloro-8-methoxy-7-(5-methyl-1H-indazol-4-yl)quinazolin-4-yl)piperazin-1-yl)prop-2-en-1-one | € | 463.3 |
| I-303 | 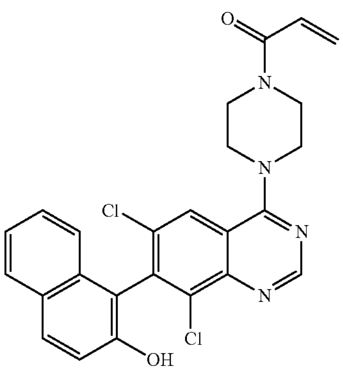 [SMILES: C=CC(=O)N1CCN(c2ncnc3c(Cl)c(-c4c(O)ccc5ccccc45)c(Cl)cc23)CC1] | 1-(4-(6,8-dichloro-7-(2-hydroxynaphthalen-1-yl)quinazolin-4-yl)piperazin-1-yl)prop-2-en-1-one | € | 479.1 |
| I-304 | 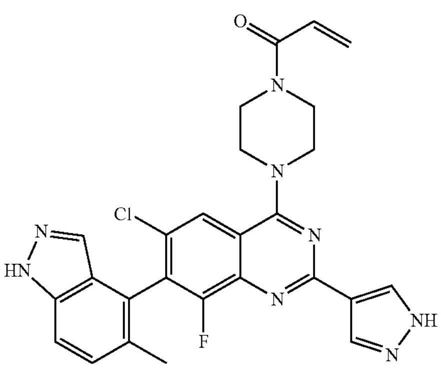 [SMILES: C=CC(=O)N1CCN(c2nc(-c3cn[nH]c3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1H-pyrazol-4-yl)quinazolin-4-yl)piperazin-1-yl)prop-2-en-1-one | € | 517.0 |
| I-305 | 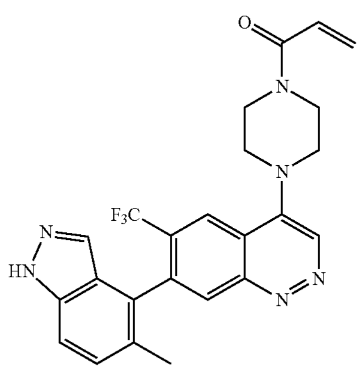 [SMILES: C=CC(=O)N1CCN(c2cnnc3cc(-c4c(C)ccc5[nH]ncc45)c(C(F)(F)F)cc23)CC1] | 1-(4-(7-(5-methyl-1H-indazol-4-yl)-6-(trifluoromethyl)cinnolin-4-yl)piperazin-1-yl)prop-2-en-1-one | € | 467.2 |

TABLE 1-continued

Exemplary Compounds of Structure (I)

| No. | Structure | Name | Method | [M + H]+ |
|---|---|---|---|---|
| I-306 | 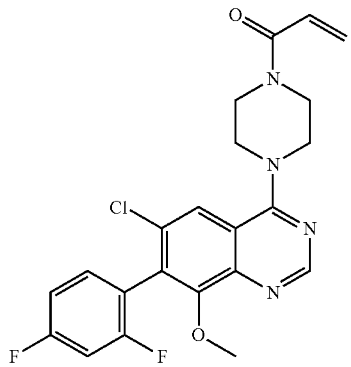 [SMILES: C=CC(=O)N1CCN(c2ncnc3c(OC)c(-c4ccc(F)cc4F)c(Cl)cc23)CC1] | 1-(4-(6-chloro-7-(2,4-difluorophenyl)-8-methoxyquinazolin-4-yl)piperazin-1-yl)prop-2-en-1-one | e | 445.2 |
| I-307 | 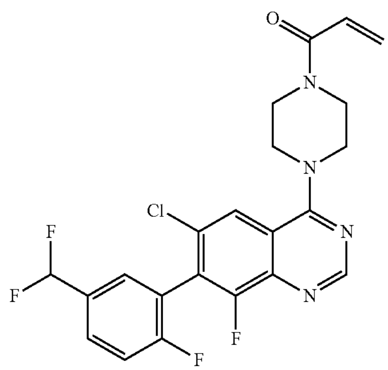 [SMILES: C=CC(=O)N1CCN(c2ncnc3c(F)c(-c4cc(C(F)F)ccc4F)c(Cl)cc23)CC1] | 1-(4-(6-chloro-7-(5-(difluoromethyl)-2-fluorophenyl)-8-fluoroquinazolin-4-yl)piperazin-1-yl)prop-2-en-1-one | e | 461.2 |
| I-308 | 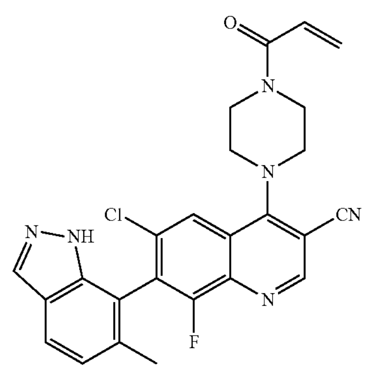 [SMILES: C=CC(=O)N1CCN(c2c(C#N)cnc3c(F)c(-c4c(C)ccc5cn[nH]c45)c(Cl)cc23)CC1] | 4-(4-acryloylpiperazin-1-yl)-6-chloro-8-fluoro-7-(6-methyl-1H-indazol-7-yl)quinoline-3-carbonitrile | e | 475.1 |
| I-309 | 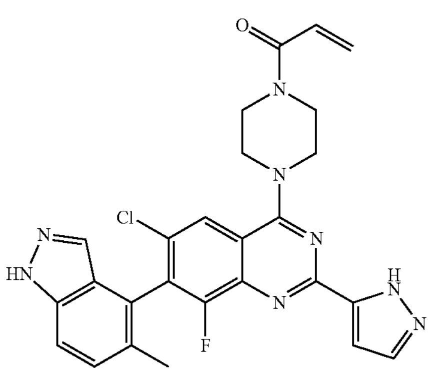 [SMILES: C=CC(=O)N1CCN(c2nc(-c3ccn[nH]3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1H-pyrazol-5-yl)quinazolin-4-yl)piperazin-1-yl)prop-2-en-1-one | e | 517.1 |

TABLE 1-continued

Exemplary Compounds of Structure (I)

| No. | Structure | Name | Method | [M + H]+ |
|---|---|---|---|---|
| I-310 | 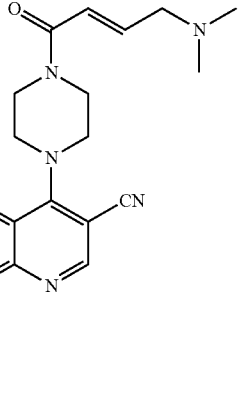 | (E)-6-chloro-4-(4-(4-(dimethylamino)but-2-enoyl)piperazin-1-yl)-8-fluoro-7-(3-hydroxynaphthalen-1-yl)quinoline-3-carbonitrile | ϵ | 544.2 |
| I-311 | 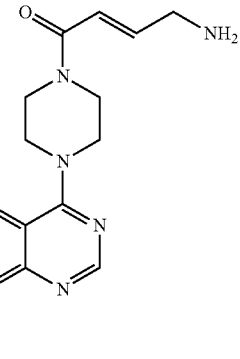 | (E)-4-amino-1-(4-(6-chloro-8-fluoro-7-(5-methyl-1H-indazol-4-yl)quinazolin-4-yl)piperazin-1-yl)but-2-en-1-one | ϵ | 480.2 |
| I-312 | 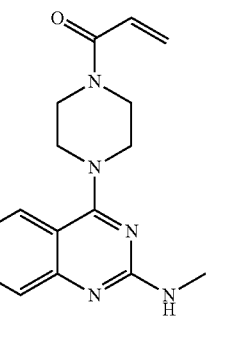 | 1-(4-(6-chloro-7-(5-methyl-1H-indazol-4-yl)-2-(methylamino)quinazolin-4-yl)piperazin-1-yl)prop-2-en-1-one | ϵ | 462.3 |
| I-313 | 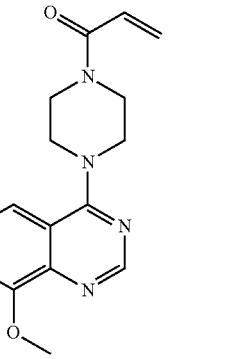 | 1-(4-(6-chloro-7-(2-fluoro-6-hydroxyphenyl)-8-methoxyquinazolin-4-yl)piperazin-1-yl)prop-2-en-1-one | ϵ | 443.2 |

TABLE 1-continued

Exemplary Compounds of Structure (I)

| No. | Structure | Name | Method | [M + H]⁺ |
|---|---|---|---|---|
| I-314 | 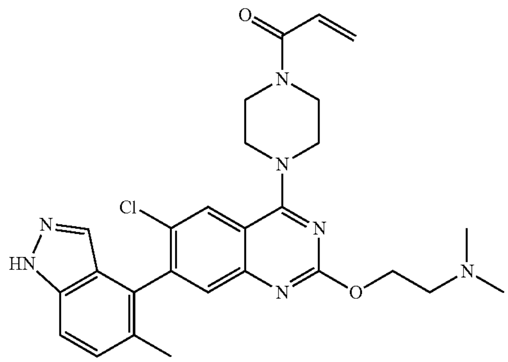 [SMILES: C=CC(=O)N1CCN(c2nc(OCCN(C)C)nc3cc(-c4c(C)ccc5[nH]ncc45)c(Cl)cc23)CC1] | 1-(4-(6-chloro-2-(2-(dimethylamino)ethoxy)-7-(5-methyl-1H-indazol-4-yl)quinazolin-4-yl)piperazin-1-yl)prop-2-en-1-one | € | 520.4 |
| I-315 | 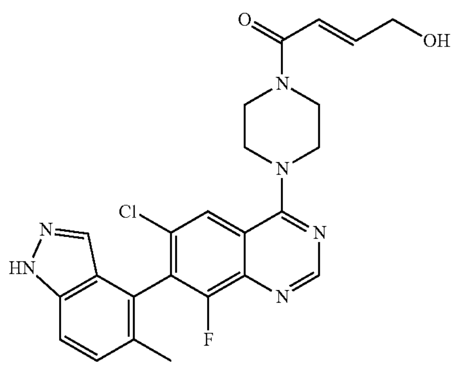 [SMILES: Cc1ccc2[nH]ncc2c1-c1c(Cl)cc2c(N3CCN(C(=O)/C=C/CO)CC3)ncnc2c1F] | (E)-1-(4-(6-chloro-8-fluoro-7-(5-methyl-1H-indazol-4-yl)quinazolin-4-yl)piperazin-1-yl)-4-hydroxybut-2-en-1-one | € | 481.3 |
| I-316 | 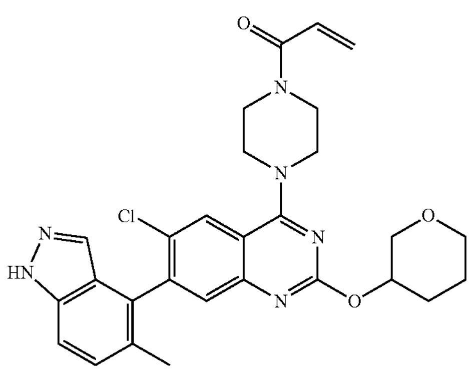 [SMILES: C=CC(=O)N1CCN(c2nc(OC3CCCOC3)nc3cc(-c4c(C)ccc5[nH]ncc45)c(Cl)cc23)CC1] | 1-(4-(6-chloro-7-(5-methyl-1H-indazol-4-yl)-2-(tetrahydro-2H-pyran-3-yloxy)quinazolin-4-yl)piperazin-1-yl)prop-2-en-1-one | € | 533.3 |
| I-317 | 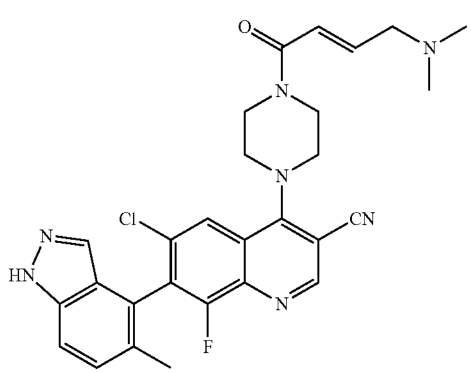 [SMILES: Cc1ccc2[nH]ncc2c1-c1c(Cl)cc2c(N3CCN(C(=O)/C=C/CN(C)C)CC3)c(C#N)cnc2c1F] | (E)-6-chloro-4-(4-(4-(dimethylamino)but-2-enoyl)piperazin-1-yl)-8-fluoro-7-(5-methyl-1H-indazol-4-yl)quinoline-3-carbonitrile | € | 532.3 |

TABLE 1-continued

Exemplary Compounds of Structure (I)

| No. | Structure | Name | Method | [M + H]⁺ |
|---|---|---|---|---|
| I-318 | 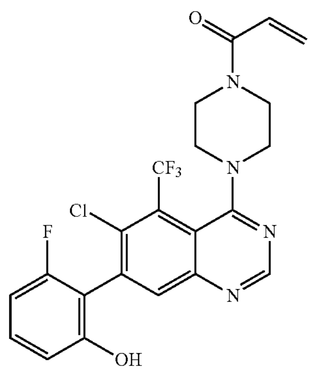 [SMILES: C=CC(=O)N1CCN(c2ncnc3cc(-c4c(O)cccc4F)c(Cl)c(C(F)(F)F)c23)CC1] | 1-(4-(6-chloro-7-(2-fluoro-6-hydroxyphenyl)-5-(trifluoromethyl)quinazolin-4-yl)piperazin-1-yl)prop-2-en-1-one | € | 481.1 |
| I-319 | 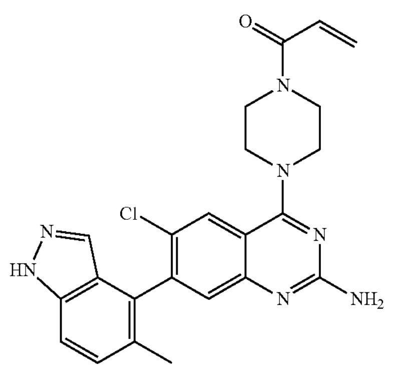 [SMILES: C=CC(=O)N1CCN(c2nc(N)nc3cc(-c4c(C)ccc5[nH]ncc45)c(Cl)cc23)CC1] | 1-(4-(2-amino-6-chloro-7-(5-methyl-1H-indazol-4-yl)quinazolin-4-yl)piperazin-1-yl)prop-2-en-1-one | € | 448.2 |
| I-320 | 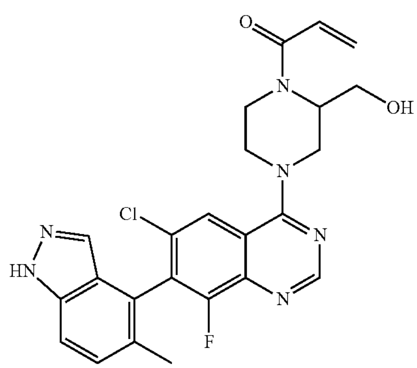 [SMILES: C=CC(=O)N1CCN(c2ncnc3c(F)c(-c4c(C)ccc5[nH]ncc45)c(Cl)cc23)CC1CO] | 1-(4-(6-chloro-8-fluoro-7-(5-methyl-1H-indazol-4-yl)quinazolin-4-yl)-2-(hydroxymethyl)piperazin-1-yl)prop-2-en-1-one | € | 481.2 |
| I-321 | 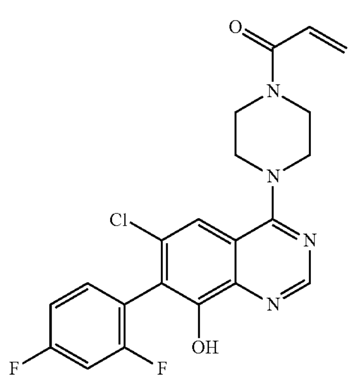 | 1-(4-(6-chloro-7-(2,4-difluorophenyl)-8-hydroxyquinazolin-4-yl)piperazin-1-yl)prop-2-en-1-one | € | 431.1 |

TABLE 1-continued

Exemplary Compounds of Structure (I)

| No. | Structure | Name | Method | [M + H]+ |
|---|---|---|---|---|
| I-322 | 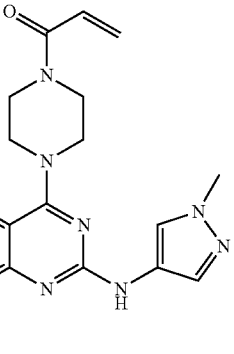 | 1-(4-(6-chloro-8-fluoro-7-(5-methyl-1H-indazol-4-yl)-2-(1-methyl-1H-pyrazol-4-ylamino)quinazolin-4-yl)piperazin-1-yl)prop-2-en-1-one | € | 546.2 |
| I-323 | 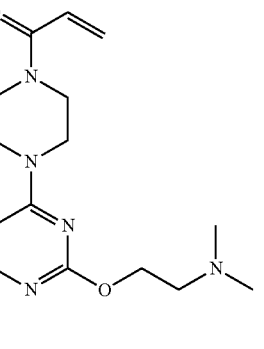 | 1-(4-(6-chloro-2-(2-(dimethylamino)ethoxy)-8-fluoro-7-(5-methyl-1H-indazol-4-yl)quinazolin-4-yl)piperazin-1-yl)prop-2-en-1-one | € | 538.2 |
| I-324 | 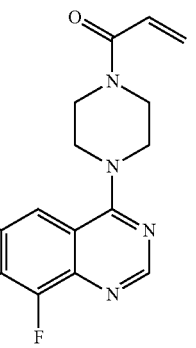 | 1-(4-(6-chloro-8-fluoro-7-(3-methyl-1H-indazol-7-yl)quinazolin-4-yl)piperazin-1-yl)prop-2-en-1-one | € | 451.1 |
| I-325 | 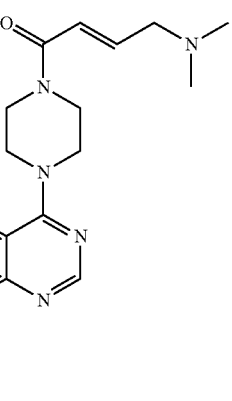 | (E)-1-(4-(6-chloro-8-fluoro-7-(3-hydroxynaphthalen-1-yl)quinazolin-4-yl)piperazin-1-yl)-4-(dimethylamino)but-2-en-1-one | € | 520.3 |

TABLE 1-continued

Exemplary Compounds of Structure (I)

| No. | Structure | Name | Method | [M + H]+ |
|---|---|---|---|---|
| I-326 | 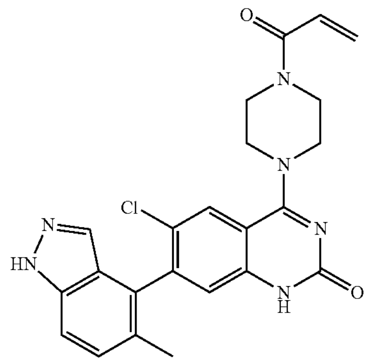 [SMILES: C=CC(=O)N1CCN(c2nc(=O)[nH]c3cc(-c4c(C)ccc5[nH]ncc45)c(Cl)cc23)CC1] | 4-(4-acryloylpiperazin-1-yl)-6-chloro-7-(5-methyl-1H-indazol-4-yl)quinazolin-2(1H)-one | € | 448.2 |
| I-327 | 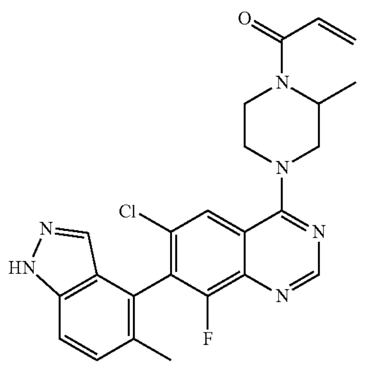 [SMILES: C=CC(=O)N1CCN(c2ncnc3c(F)c(-c4c(C)ccc5[nH]ncc45)c(Cl)cc23)CC1C] | 1-(4-(6-chloro-8-fluoro-7-(5-methyl-1H-indazol-4-yl)quinazolin-4-yl)-2-methylpiperazin-1-yl)prop-2-en-1-one | € | 465.2 |
| I-328 | 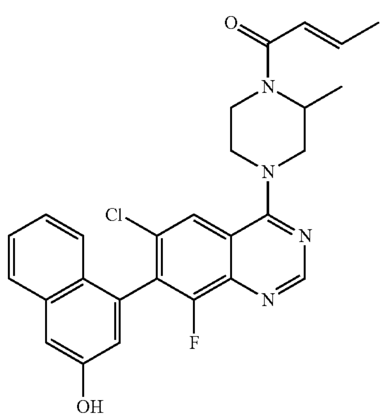 [SMILES: C/C=C/C(=O)N1CCN(c2ncnc3c(F)c(-c4cc(O)cc5ccccc45)c(Cl)cc23)CC1C] | (E)-1-(4-(6-chloro-8-fluoro-7-(3-hydroxynaphthalen-1-yl)quinazolin-4-yl)-2-methylpiperazin-1-yl)but-2-en-1-one | € | 477.2 |
| I-329 | 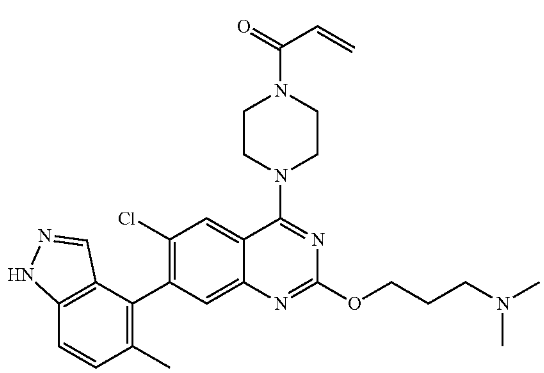 [SMILES: C=CC(=O)N1CCN(c2nc(OCCCN(C)C)nc3cc(-c4c(C)ccc5[nH]ncc45)c(Cl)cc23)CC1] | 1-(4-(6-chloro-2-(3-(dimethylamino)propoxy)-7-(5-methyl-1H-indazol-4-yl)quinazolin-4-yl)piperazin-1-yl)prop-2-en-1-one | € | 534.3 |

TABLE 1-continued

Exemplary Compounds of Structure (I)

| No. | Structure | Name | Method | [M + H]+ |
|---|---|---|---|---|
| I-330 | 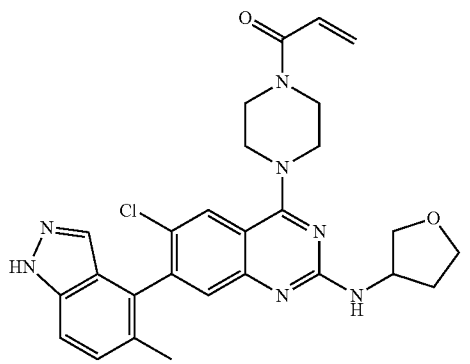 [SMILES: C=CC(=O)N1CCN(c2nc(NC3CCOC3)nc3cc(-c4c(C)ccc5[nH]ncc45)c(Cl)cc23)CC1] | 1-(4-(6-chloro-7-(5-methyl-1H-indazol-4-yl)-2-(tetrahydrofuran-3-ylamino)quinazolin-4-yl)piperazin-1-yl)prop-2-en-1-one | € | 518.3 |
| I-331 | 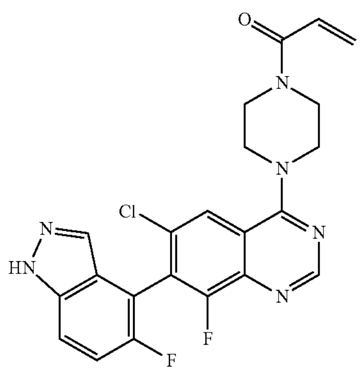 [SMILES: C=CC(=O)N1CCN(c2ncnc3c(F)c(-c4c(F)ccc5[nH]ncc45)c(Cl)cc23)CC1] | 1-(4-(6-chloro-8-fluoro-7-(5-fluoro-1H-indazol-4-yl)quinazolin-4-yl)piperazin-1-yl)prop-2-en-1-one | € | 455.1 |
| I-332 | 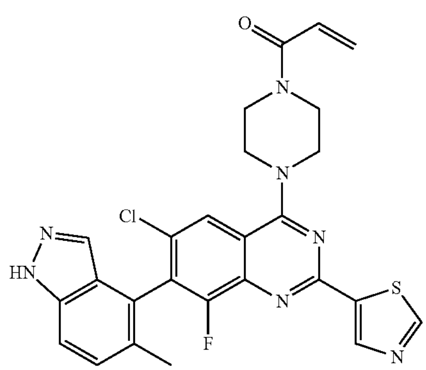 [SMILES: C=CC(=O)N1CCN(c2nc(-c3cncs3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(thiazol-5-yl)quinazolin-4-yl)piperazin-1-yl)prop-2-en-1-one | € | 534.1 |
| I-333 | 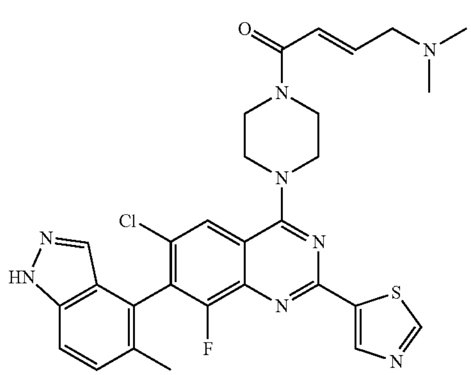 [SMILES: Cc1ccc2[nH]ncc2c1-c1c(Cl)cc2c(N3CCN(C(=O)/C=C/CN(C)C)CC3)nc(-c3cncs3)nc2c1F] | (E)-1-(4-(6-chloro-8-fluoro-7-(5-methyl-1H-indazol-4-yl)-2-(thiazol-5-yl)quinazolin-4-yl)piperazin-1-yl)-4-(dimethylamino)but-2-en-1-one | € | 591.1 |

TABLE 1-continued

Exemplary Compounds of Structure (I)

| No. | Structure | Name | Method | [M + H]+ |
|---|---|---|---|---|
| I-334 | 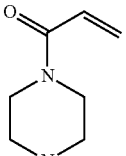 | 1-(4-(6-chloro-8-fluoro-7-(5-methyl-1H-indazol-4-yl)quinazolin-4-yl)piperazin-1-yl)prop-2-en-1-one | є | 451.2 |
| I-335 | 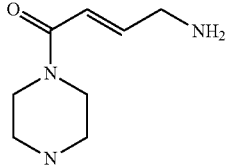 | (E)-4-amino-1-(4-(6-chloro-8-fluoro-7-(3-hydroxynaphthalen-1-yl)quinazolin-4-yl)piperazin-1-yl)but-2-en-1-one | є | 492.2 |
| I-336 | 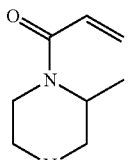 | 4-(4-acryloyl-3-methylpiperazin-1-yl)-6-chloro-8-fluoro-7-(5-methyl-1H-indazol-4-yl)quinoline-3-carbonitrile | є | 489.2 |
| I-337 | 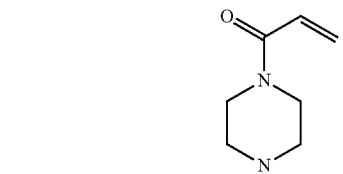 | 1-(4-(6-chloro-7-93-(difluoromethyl)naphthalen-1-yl)-8-fluoroquinazolin-4-yl)piperazin-1-yl)prop-2-en-1-one | є | 497.2 |

TABLE 1-continued

Exemplary Compounds of Structure (I)

| No. | Structure | Name | Method | [M + H]⁺ |
|---|---|---|---|---|
| I-338 | 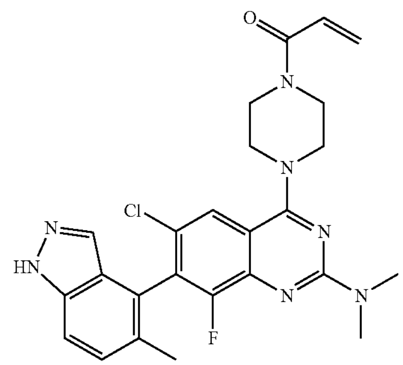 [SMILES: C=CC(=O)N1CCN(c2nc(N(C)C)nc3c(F)c(-c4c(C)ccc5[nH]ncc45)c(Cl)cc23)CC1] | 1-(4-(6-chloro-2-(dimethylamino)-8-fluoro-7-(5-methyl-1H-indazol-4-yl)quinazolin-4-yl)piperazin-1-yl)prop-2-en-1-one | € | 494.4 |
| I-339 | 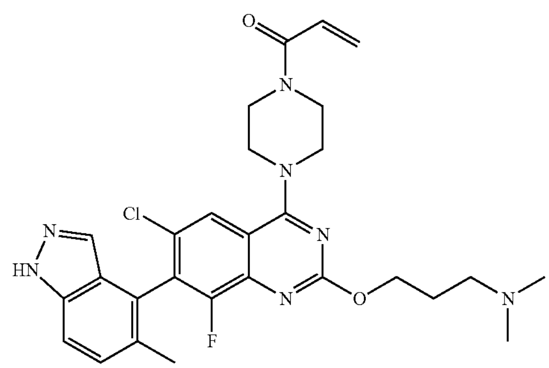 [SMILES: C=CC(=O)N1CCN(c2nc(OCCCN(C)C)nc3c(F)c(-c4c(C)ccc5[nH]ncc45)c(Cl)cc23)CC1] | 1-(4-(6-chloro-2-(3-(dimethylamino)propoxy)-8-fluoro-7-(5-methyl-1H-indazol-4-yl)quinazolin-4-yl)piperazin-1-yl)prop-2-en-1-one | € | 552.2 |
| I-340 | 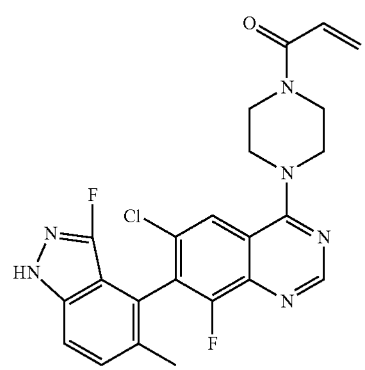 [SMILES: C=CC(=O)N1CCN(c2ncnc3c(F)c(-c4c(C)ccc5[nH]nc(F)c45)c(Cl)cc23)CC1] | 1-(4-(6-chloro-8-fluoro-7-(3-fluoro-5-methyl-1H-indazol-4-yl)quinazolin-4-yl)piperazin-1-yl)prop-2-en-1-one | € | 469.1 |
| I-341 | 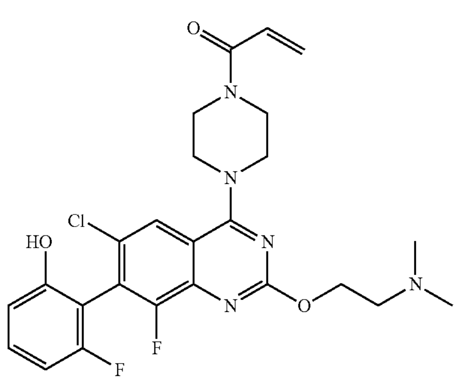 [SMILES: C=CC(=O)N1CCN(c2nc(OCCN(C)C)nc3c(F)c(-c4c(O)cccc4F)c(Cl)cc23)CC1] | 1-(4-(6-chloro-2-(2-(dimethylamino)ethoxy)-8-fluoro-7-(2-fluoro-6-hydroxyphenyl)quinazolin-4-yl)piperazin-1-yl)prop-2-en-1-one | € | 518.2 |

TABLE 1-continued

Exemplary Compounds of Structure (I)

| No. | Structure | Name | Method | [M + H]+ |
|---|---|---|---|---|
| I-342 | 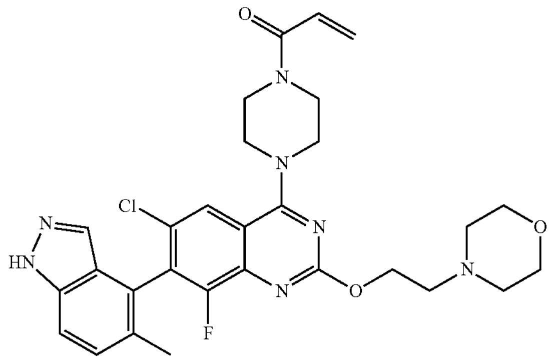 [SMILES: C=CC(=O)N1CCN(c2nc(OCCN3CCOCC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(2-morpholinoethoxy)quinazolin-4-yl)piperazin-1-yl)prop-2-en-1-one | € | 580.2 |
| I-343 | 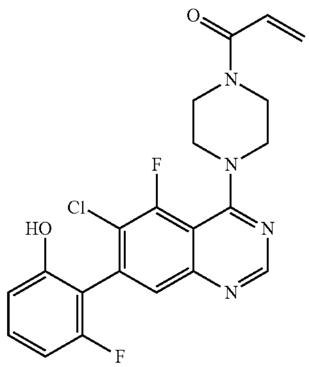 [SMILES: C=CC(=O)N1CCN(c2ncnc3cc(-c4c(O)cccc4F)c(Cl)c(F)c23)CC1] | 1-(4-(6-chloro-5-fluoro-7-(2-fluoro-6-hydroxyphenyl)quinazolin-4-yl)piperazin-1-yl)prop-2-en-1-one | € | 431.2 |
| I-344 | 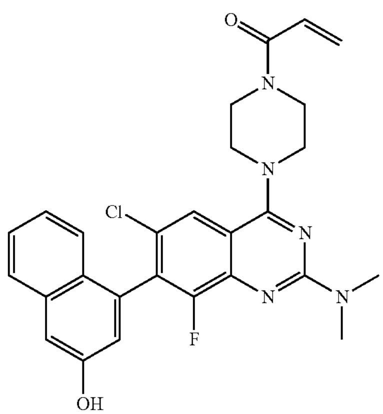 [SMILES: C=CC(=O)N1CCN(c2nc(N(C)C)nc3c(F)c(-c4cc(O)cc5ccccc45)c(Cl)cc23)CC1] | 1-(4-(6-chloro-2-(dimethylamino)-8-fluoro-7-(3-hydroxynaphthalen-1-yl)quinazolin-4-yl)piperazin-1-yl)prop-2-en-1-one | € | 506.3 |
| I-345 | 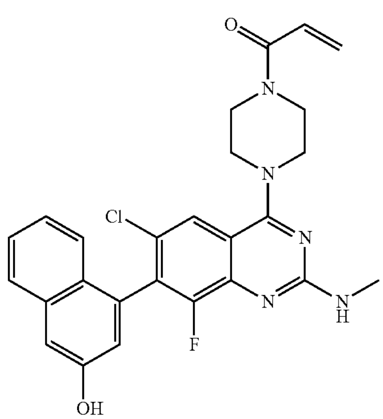 [SMILES: C=CC(=O)N1CCN(c2nc(NC)nc3c(F)c(-c4cc(O)cc5ccccc45)c(Cl)cc23)CC1] | 1-(4-(6-chloro-8-fluoro-7-(3-hydroxynaphthalen-1-yl)-2-(methylamino)quinazolin-4-yl)piperazin-1-yl)porp-2-en-1-one | € | 492.2 |

TABLE 1-continued

Exemplary Compounds of Structure (I)

| No. | Structure | Name | Method | [M + H]⁺ |
|---|---|---|---|---|
| I-346 | 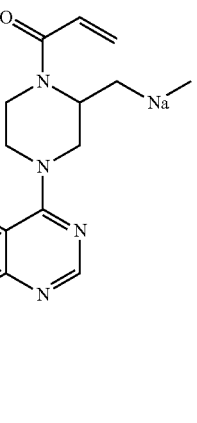 | 1-(4-(6-chloro-8-fluoro-7-(3-hydroxynaphthalen-1-yl)quinazolin-4-yl)-2-((dimethylamino)methyl)piperazin-1-yl)prop-2-en-1-one | є | 520.2 |
| I-347 | 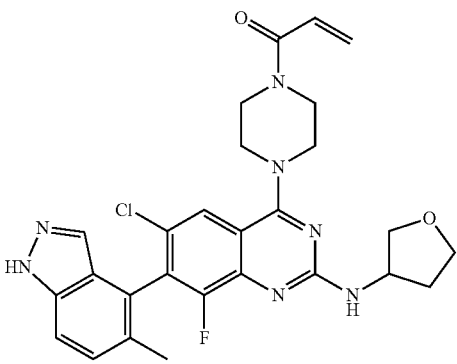 [SMILES: C=CC(=O)N1CCN(c2nc(NC3CCOC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(tetrahydrofuran-3-ylamino)quinazolin-4-yl)piperazin-1-yl)prop-2-en-1-one | є | 536.3 |
| I-348 | 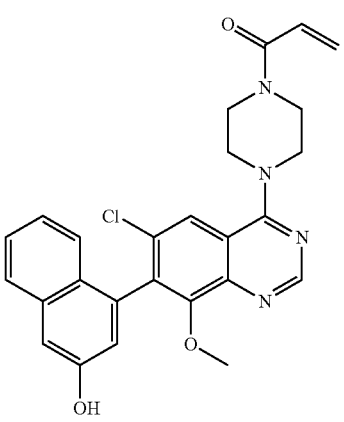 [SMILES: C=CC(=O)N1CCN(c2ncnc3c(OC)c(-c4cc(O)cc5ccccc45)c(Cl)cc23)CC1] | 1-(4-(6-chloro-7-(3-hydroxynaphthalen-1-yl)-8-methoxyquinazolin-4-yl)piperazin-1-yl)prop-2-en-1-one | є | 475.3 |

TABLE 1-continued

Exemplary Compounds of Structure (I)

| No. | Name | Method | [M + H]+ |
|---|---|---|---|
| I-349 | 1-(4-(6-chloro-8-fluoro-7-(3-hydroxynaphthalen-1-yl)-2-(1-(2,2,2-trifluoroethyl)pyrrolidin-3-ylamino)quinazolin-4-yl)piperazin-1-yl)prop-2-en-1-one | € | 629.3 |
| I-350 | 1-(4-(7-(5-methyl-1H-indazol-4-yl)-6-(trifluoromethyl)cinnolin-4-yl)piperazin-1-yl)prop-2-en-1-one | € | 467.3 |
| I-351 | 1-(4-(7-(3-hydroxynaphthalen-1-yl)-6-(trifluoromethyl)cinnolin-4-yl)piperazin-1-yl)prop-2-en-1-one | € | 479.2 |
| 352 | 1-(4-(6-chloro-8-fluoro-2-(2-(1-methyl-1H-imidazol-2-yl)ethylamino)-7-(5-methyl-1H-indazol-4-yl)quinazolin-4-yl)piperazin-1-yl)prop-2-en-1-one | F | 575.2 |

TABLE 1-continued

Exemplary Compounds of Structure (I)

| No. | Structure | Name | Method | [M + H]+ |
|---|---|---|---|---|
| 353 | 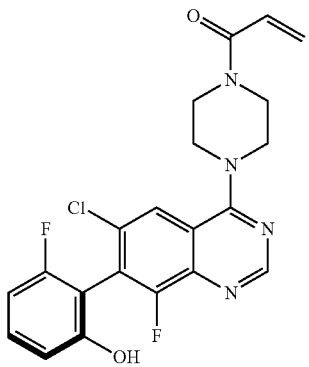 | (S)-1-(4-(6-chloro-8-fluoro-7-(2-fluoro-6-hydroxyphenyl)quinazolin-4-yl)piperaszin-1-yl)prop-2-en-1-one | O | 431.2 |
| 354 | 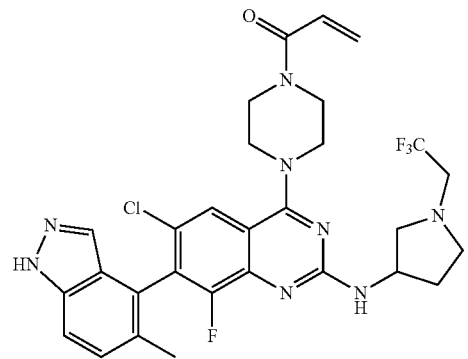 [SMILES: C=CC(=O)N1CCN(c2nc(NC3CCN(CC(F)(F)F)C3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1-(2,2,2-trifluoroethyl)pyrrolidin-3-ylamino)quinazolin-4-yl)piperazin-1-yl)prop-2-en-1-one | AC | 617.3 |
| 355 | 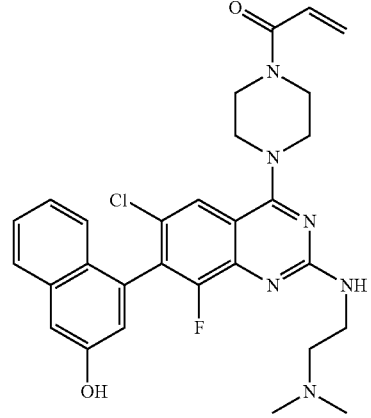 [SMILES: C=CC(=O)N1CCN(c2nc(NCCN(C)C)nc3c(F)c(-c4cc(O)cc5ccccc45)c(Cl)cc23)CC1] | 1-(4-(6-chloro-2-(2-(dimethylamino)ethylamino)-8-fluoro-7-(3-hydroxynaphthalen-1-yl)quinazolin-4-yl)piperazin-1-yl)prop-2-en-1-one | AC | 549.3 |
| 356 | 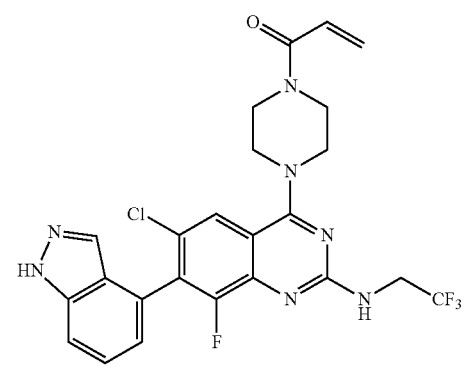 [SMILES: C=CC(=O)N1CCN(c2nc(NCC(F)(F)F)nc3c(F)c(-c4cccc5[nH]ncc45)c(Cl)cc23)CC1] | 1-(4-(6-chloro-8-fluoro-7-(5-methyl-1H-indazol-4-yl)-2-(2,2,2-trifluoroethylamino)quinazolin-4-yl)piperazin-1-yl)prop-2-en-1-one | AC | 548.3 |

TABLE 1-continued

Exemplary Compounds of Structure (I)

| No. | Structure | Name | Method | [M + H]+ |
|---|---|---|---|---|
| 357 | 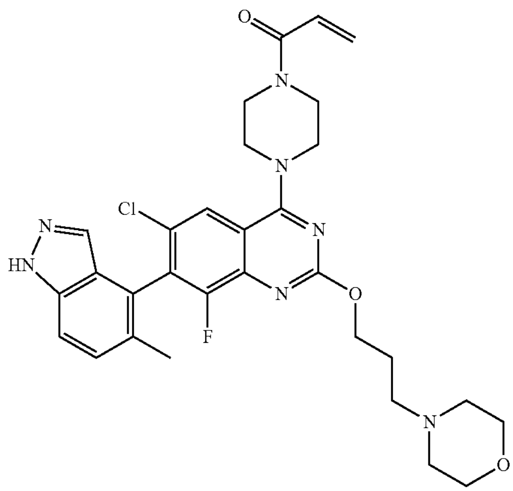 [SMILES: C=CC(=O)N1CCN(c2nc(OCCCN3CCOCC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(3-morpholinopropoxy)quinazolin-4-yl)piperazin-1-yl)prop-2-en-1-one | F | 594.2 |
| 358 | 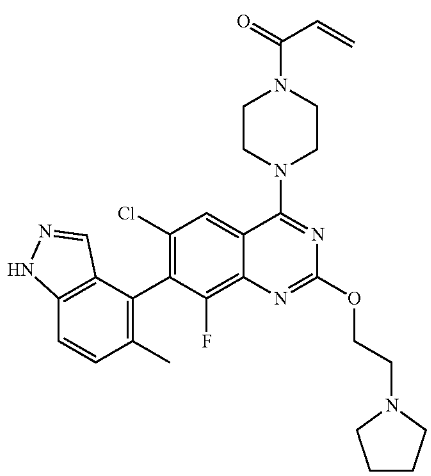 [SMILES: C=CC(=O)N1CCN(c2nc(OCCN3CCCC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(2-(pyrrolidin-1-yl)ethoxy)quinazolin-4-yl)piperazin-1-yl)prop-2-en-1-one | F | 564.2 |
| 359 | 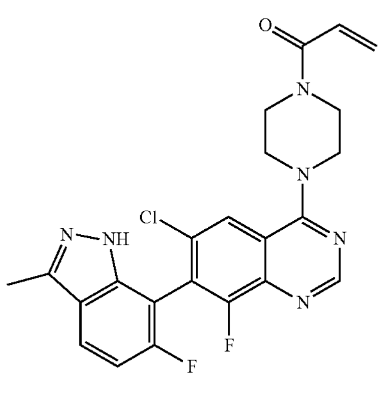 [SMILES: C=CC(=O)N1CCN(c2ncnc3c(F)c(-c4c(F)ccc5c(C)n[nH]c45)c(Cl)cc23)CC1] | 1-(4-(6-chloro-8-fluoro-7-(6-fluoro-3-methyl-1H-indazol-7-yl)quinazolin-4-yl)piperazin-1-yl)prop-2-en-1-one | B | 469.1 |

TABLE 1-continued

Exemplary Compounds of Structure (I)

| No. | Structure | Name | Method | [M + H]+ |
|---|---|---|---|---|
| 360 | 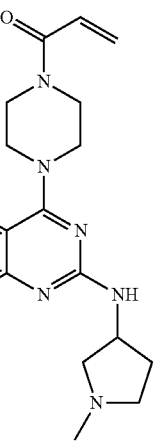 | 1-(4-(6-chloro-8-fluoro-7-(3-hydroxynaphthalen-1-yl)-2-(1-methylpyrrolidin-3-ylamino)quinazolin-4-yl)piperazin-1-yl)prop-2-en-1-one | AC | 561.4 |
| 361 | 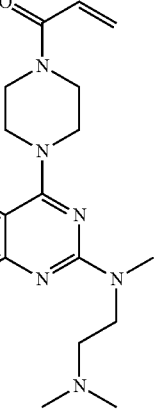 | 1-(4-(6-chloro-2-((2-(dimethylamino)ethyl)(methyl)amino)-8-fluoro-7-(3-hydroxynaphthalen-1-yl)quinazolin-4-yl)piperazin-1-yl)prop-2-en-1-one | AC | 563.4 |
| 362 | 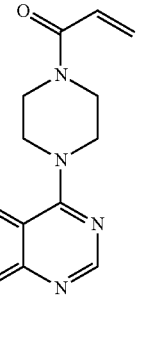 | 1-(4-(6-chloro-7-(2-((dimethylamino)methyl)-6-fluorophenyl)-8-fluoroquinazolin-4-yl)piperazin-1-yl)prop-2-en-1-one | O | 472.3 |

TABLE 1-continued

Exemplary Compounds of Structure (I)

| No. | Structure | Name | Method | [M + H]+ |
|---|---|---|---|---|
| 363 | 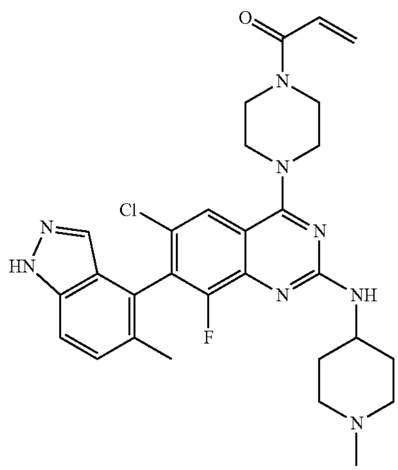 [SMILES: C=CC(=O)N1CCN(c2nc(NC3CCN(C)CC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1-methylpiperidin-4-ylamino)quinazolin-4-yl)piperazin-1-yl)prop-2-en-1-one | AC | 563.4 |
| 364 | 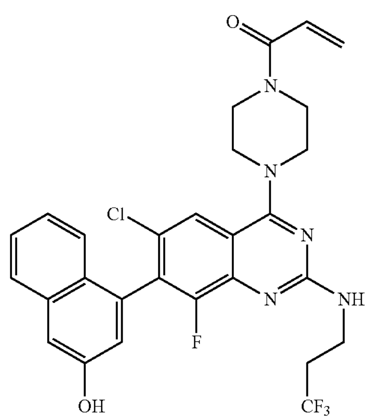 [SMILES: C=CC(=O)N1CCN(c2nc(NCCC(F)(F)F)nc3c(F)c(-c4cc(O)cc5ccccc45)c(Cl)cc23)CC1] | 1-(4-(6-chloro-8-fluoro-7-(3-hydroxynaphthalen-1-yl)-2-(3,3,3-trifluoropropylamino)quinazolin-4-yl)piperazin-1-yl)prop-2-en-1-one | AC | 560.30 |
| 365 | 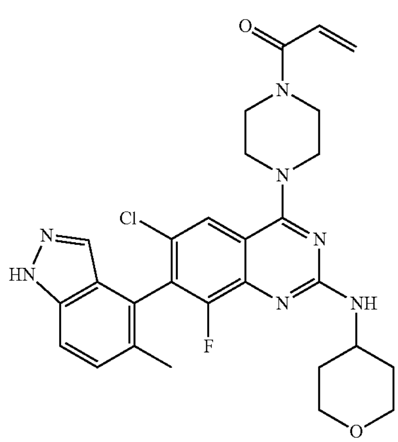 [SMILES: C=CC(=O)N1CCN(c2nc(NC3CCOCC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(tetrahydro-2H-pyran-4-ylamino)quinazolin-4-yl)piperazin-1-yl)prop-2-en-1-one | AC | 550.30 |

TABLE 1-continued

Exemplary Compounds of Structure (I)

| No. | Structure | Name | Method | [M + H]+ |
|---|---|---|---|---|
| 366 | 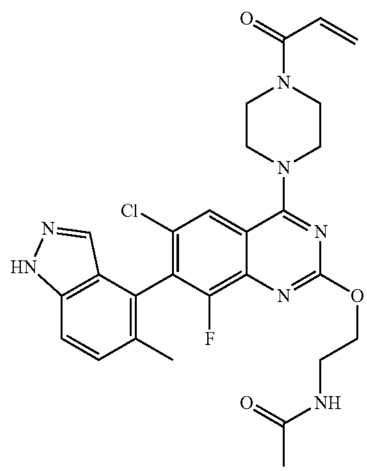 [SMILES: C=CC(=O)N1CCN(c2nc(OCCNC(C)=O)nc3c(F)c(-c4c(C)ccc5[nH]ncc45)c(Cl)cc23)CC1] | N-(2-(4-(4-acryloylpiperazin-1-yl)-6-chloro-8-fluoro-7-(5-methyl-1H-indazol-4-yl)quinazolin-2-yloxy)ethyl)acetamide | AC | 552.35 |
| 367 | 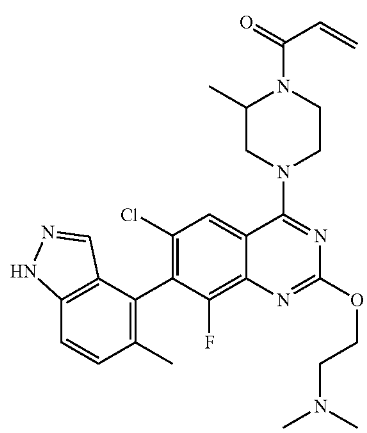 [SMILES: C=CC(=O)N1CCN(c2nc(OCCN(C)C)nc3c(F)c(-c4c(C)ccc5[nH]ncc45)c(Cl)cc23)CC1C] | 1-(4-(6-chloro-2-(2-(dimethylamino)ethoxy)-8-fluoro-7-(5-methyl-1H-indazol-4-yl)quinazolin-4-yl)-2-methylpiperazin-1-yl)prop-2-en-1-one | F | 552.30 |
| 368 | 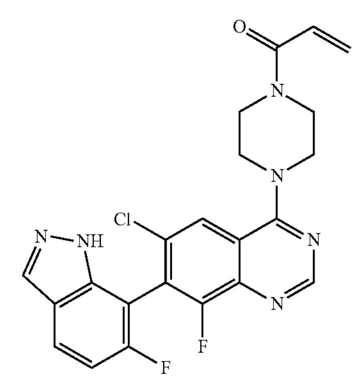 [SMILES: C=CC(=O)N1CCN(c2ncnc3c(F)c(-c4c(F)ccc5cn[nH]c45)c(Cl)cc23)CC1] | 1-(4-(6-chloro-8-fluoro-7-(6-fluoro-1H-indazol-7-yl)quinazolin-4-yl)piperazin-1-yl)prop-2-en-1-one | B | 455.1 |

TABLE 1-continued

Exemplary Compounds of Structure (I)

| No. | Structure | Name | Method | [M + H]+ |
|---|---|---|---|---|
| 369 | 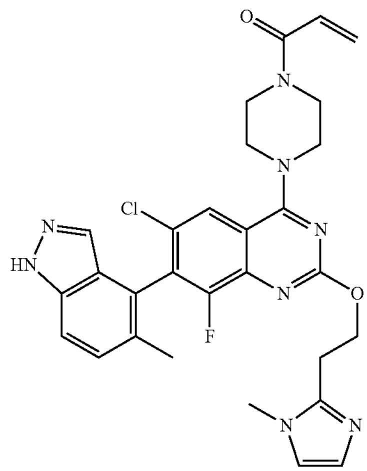 [SMILES: C=CC(=O)N1CCN(c2nc(OCCc3nccn3C)nc3c(F)c(-c4c(C)ccc5[nH]ncc45)c(Cl)cc23)CC1] | 1-(4-(6-chloro-8-fluoro-2-(2-(1-methyl-1H-imidazol-2-yl)ethoxy)-7-(5-methyl-1H-indazol-4-yl)quinazolin-4-yl)piperazin-1-yl)prop-2-en-1-one | F | 575.2 |
| 370 | 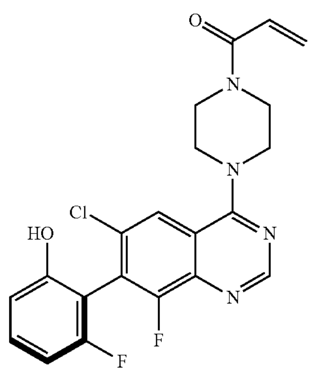 | (R)-1-(4-(6-chloro-8-fluoro-7-(2-fluoro-6-hydroxyphenyl)quinazolin-4-yl)piperazin-1-yl)prop-2-en-1-one | O | 431.2 |
| 371 | 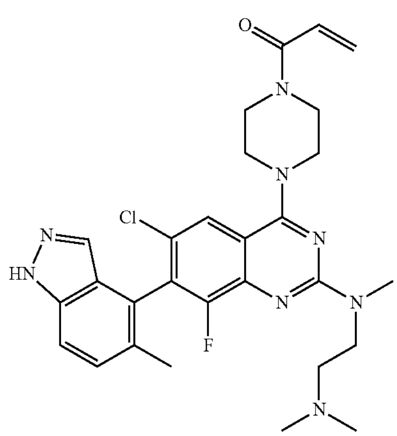 [SMILES: C=CC(=O)N1CCN(c2nc(N(C)CCN(C)C)nc3c(F)c(-c4c(C)ccc5[nH]ncc45)c(Cl)cc23)CC1] | 1-(4-(6-chloro-2-((2-(dimethylamino)ethyl)(methyl)amino)-8-fluoro-7-(5-methyl-1H-indazol-4-yl)quinazolin-4-yl)piperazin-1-yl)prop-2-en-1-one | AC | 551.35 |

TABLE 1-continued

Exemplary Compounds of Structure (I)

| No. | Structure | Name | Method | [M + H]⁺ |
|---|---|---|---|---|
| 372 | 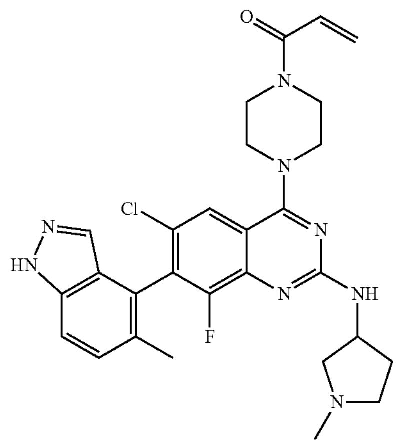 [SMILES: C=CC(=O)N1CCN(c2nc(NC3CCN(C)C3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1-methylpyrrolidin-3-ylamino)quinazolin-4-yl)piperazin-1-yl)prop-2-en-1-one | AC | 549.30 |
| 373 | 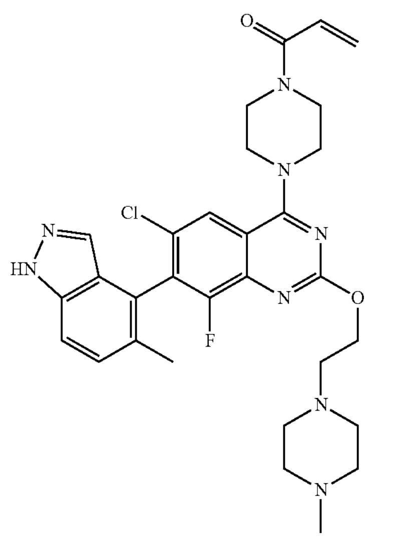 [SMILES: C=CC(=O)N1CCN(c2nc(OCCN3CCN(C)CC3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(2-(4-methylpiperazin-1-yl)ethoxy)quinazolin-4-yl)piperazin-1-yl)prop-2-en-1-one | F | 593.30 |
| 374 | 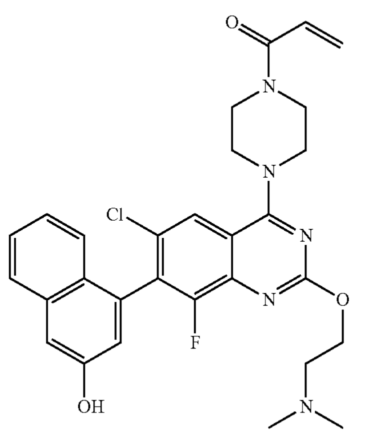 [SMILES: C=CC(=O)N1CCN(c2nc(OCCN(C)C)nc3c(F)c(-c4cc(O)cc5ccccc45)c(Cl)cc23)CC1] | 1-(4-(6-chloro-2-(2-(dimethylamino)ethoxy)-8-fluoro-7-(3-hydroxynaphthalen-1-yl)quinazolin-4-yl)piperazin-1-yl)prop-2-en-1-one | F | 550.25 |

TABLE 1-continued

Exemplary Compounds of Structure (I)

| No. | Structure | Name | Method | [M + H]+ |
|---|---|---|---|---|
| 375 | 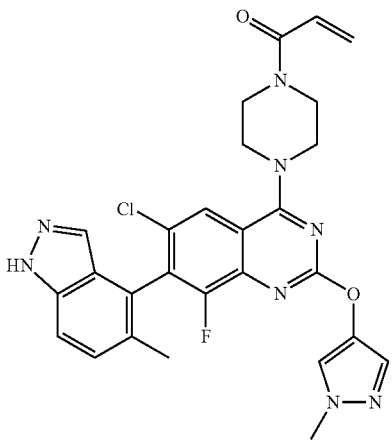 [SMILES: C=CC(=O)N1CCN(c2nc(Oc3cnn(C)c3)nc3c(F)c(-c4c(C)ccc5[nH]ncc45)c(Cl)cc23)CC1] | 1-(4-(6-chloro-8-fluoro-7-(5-methyl-1H-indazol-4-yl)-2-(1-methyl-1H-pyrazol-4-yloxy)quinazolin-4-yl)piperazin-1-yl)prop-2-en-1-one | F | 547.25 |
| 376 | 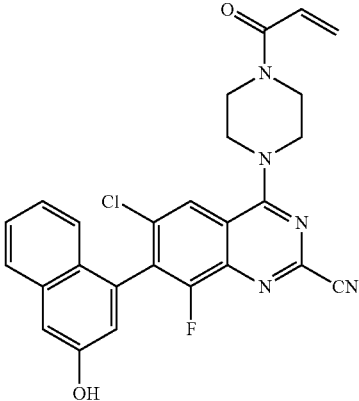 [SMILES: C=CC(=O)N1CCN(c2nc(C#N)nc3c(F)c(-c4cc(O)cc5ccccc45)c(Cl)cc23)CC1] | 4-(4-acryloylpiperazin-1-yl)-6-chloro-8-fluoro-7-(3-hydroxynaphthalen-1-yl)quinazoline-2-carbonitrile | AI | 488.15 |

*[M + Na]+
†[M − H]−
[M]
€ Prepared according to methods analogous to those illustrated herein The compounds in Table 1 were each prepared and analyzed by mass spectrometry and/or $^1$H NMR. Experimental mass spectrometry data is included in Table 1 above. Exemplary synthetic procedures are described in more detail below and in the Examples. General methods by which the compounds may be prepared are provided below and indicated in Table 1 above.

It is understood that in the present description, combinations of substituents and/or variables of the depicted formulae are permissible only if such contributions result in stable compounds.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a subject and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following General Reaction Schemes illustrate exemplary methods of making compounds of compounds of structure (I):

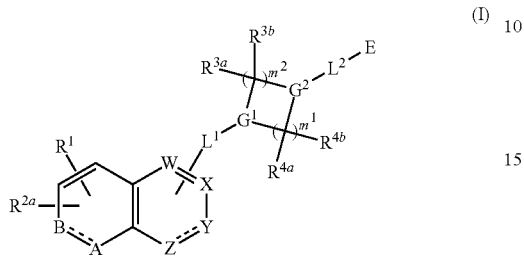

or a pharmaceutically acceptable salt, tautomer or stereoisomer thereof, wherein $R^1$, $R^{2a}$, $R^{3a}$, $R^{3b}$, $R^{4a}$, $R^{4b}$, $G^1$, $G^2$, $L^1$, $L^2$, $m^1$, $m^2$, A, B, W, X, Y, Z and E are as defined above. For ease of illustration, many of the schemes which follow illustrate an "$R^2$" moiety. The R2 moiety is meant to include any one of $R^{2a}$, $R^{2b}$ or $R^{2c}$. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

General Reaction Scheme 1

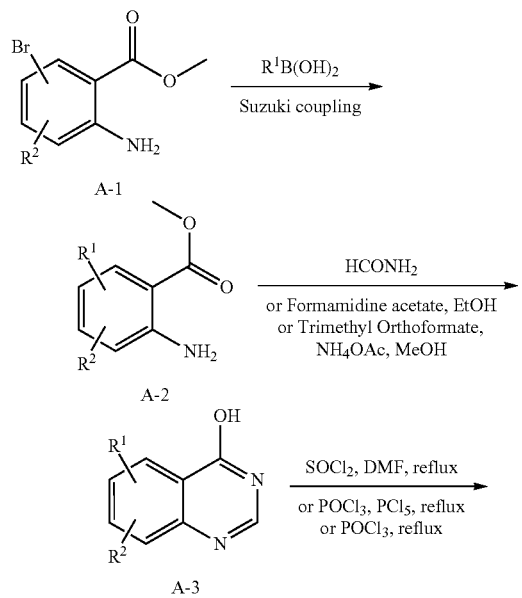

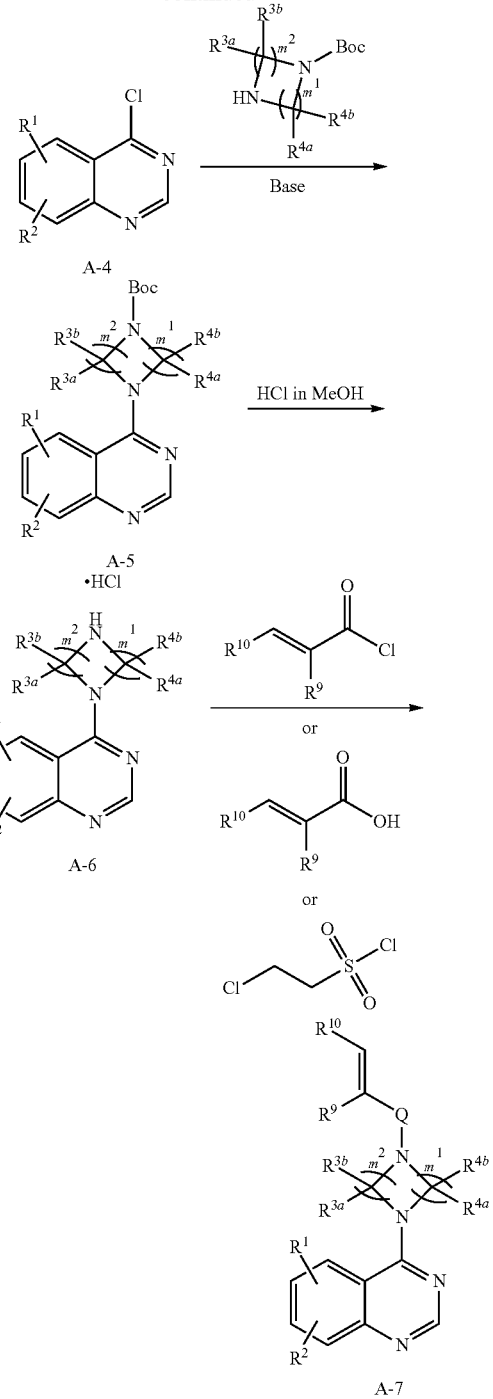

Embodiments of the compound of structure (I) (e.g., compound A-7) can be prepared according to General Reaction Scheme 1 ("Method A"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 1, compounds of structure A-1 can be purchased from commercial sources or prepared according to methods familiar to one of ordinary skill in the art. Reaction of A-1 under Suzuki conditions yields A-2. Reaction of compounds of structure A-2 with formamide or other suitable reagents, such as formamidine acetate or trimethyl orthoformate, yields quinazolines of structure A-3. A-3 is chlorinated under appropriate conditions (e.g., SOCl$_2$, POCl$_3$/PCl$_5$ or POCl$_3$) to yield chloroquinazoline A-4. Reaction of A-4 with an appropriately protected heterocycle under basic conditions yields A-5. Appropriate protecting groups include butyloxycarbonyl (BOC) as depicted in General reaction Scheme 1, as well as other protecting groups known in the art. Deprotection of A-5 followed by acylation with an acid chloride (or sulfonyl chloride) or acid and appropriate activating reagents yields A-7.

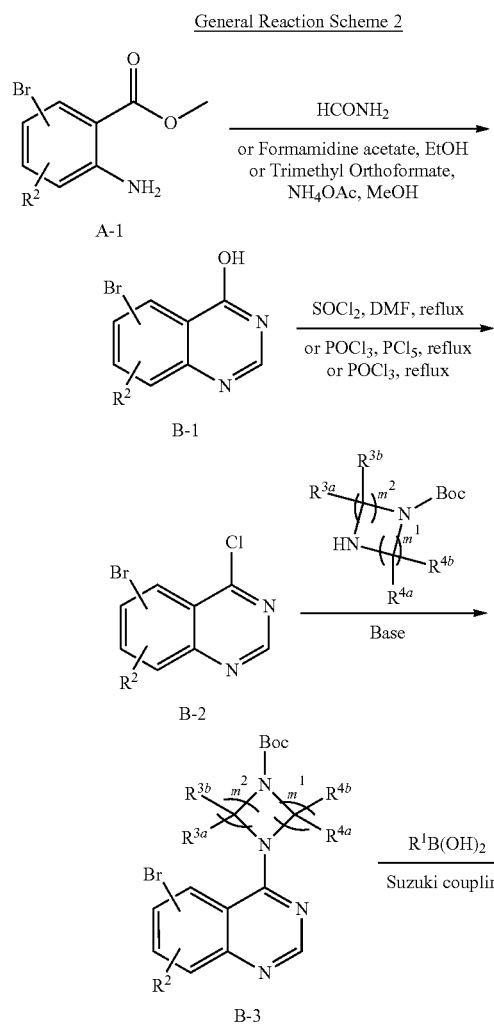

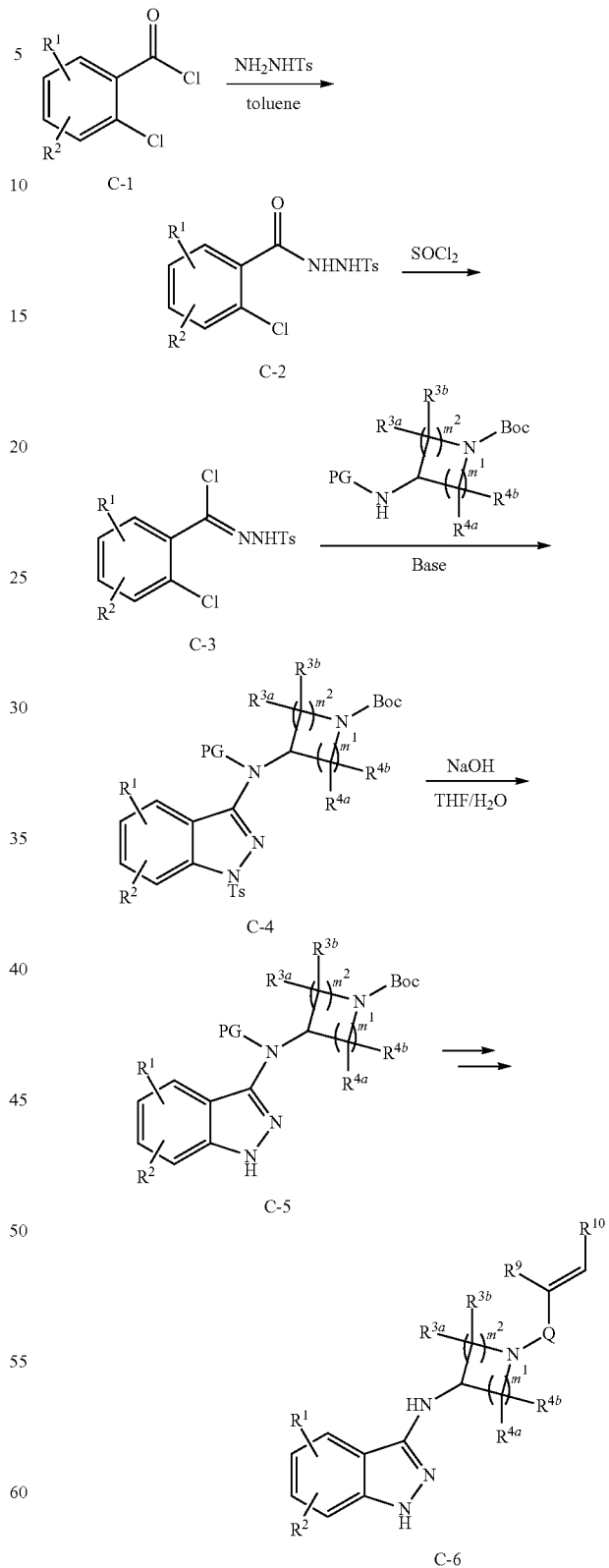

Alternatively, embodiments of the compound of structure (I) (e.g., compound A-7) can be prepared according to General Reaction Scheme 2 ("Method B"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Compounds of structure A-1 are prepared or purchased as described above. Treatment of A-1 with formamide or other suitable reagents, such as formamidine acetate or trimethyl orthoformate, yields quinazolines of structure B-1. B-1 can then be chlorinated to yield B-2 and reacted with an appropriately protected heterocycle under basic conditions to yield B-3 as described above for Method A. Suzuki coupling then yields A-5 which can be converted to A-7 as described in Method A above.

Other embodiments of the compound of structure (I) (e.g., compound C-6) can be prepared according to General Reaction Scheme 3 ("Method C"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 3, compounds of structure C-1, which can be purchased from commercial sources or prepared according to well-known procedures, are reacted with tosyl hydrazine to yield C-2. Chlorination of C-2 with an appropriate reagent(s), such as thionyl chloride, then yields C-3 which can be reacted under basic conditions with an appropriately protected heterocycle (PG=protecting group or $C_1$-$C_6$alkyl) to yield indazole C-4. The tosyl group is removed from C-4 by treatment with sodium hydroxide in THF/$H_2O$ to yield C-5. Removal of the nitrogen protecting group and acylation or thioacylation as described in Method A then yields the desired compound C-6.

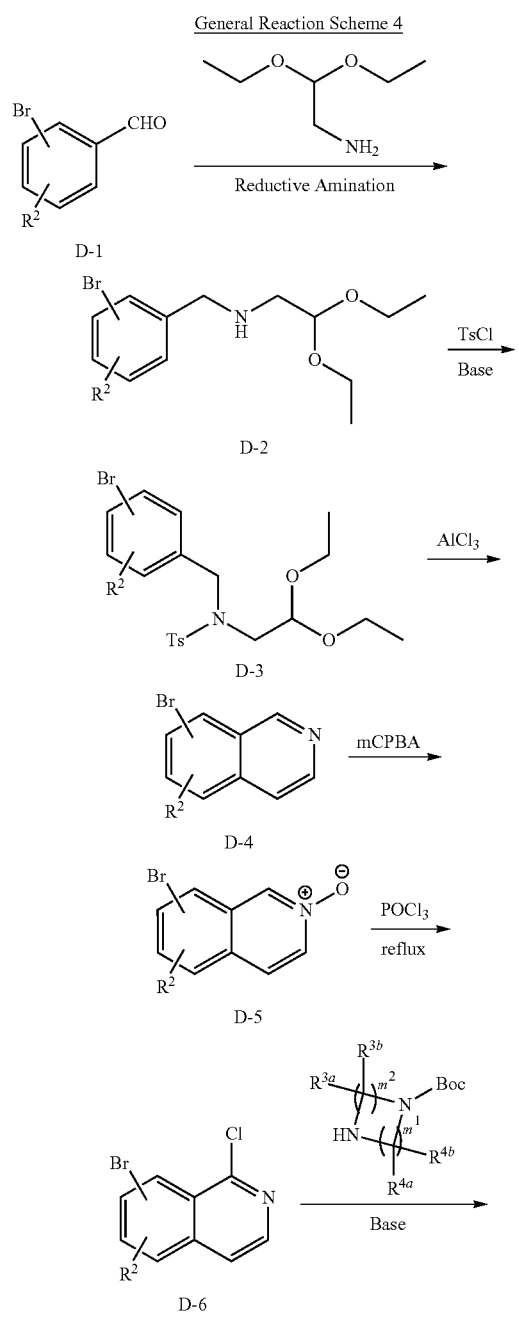

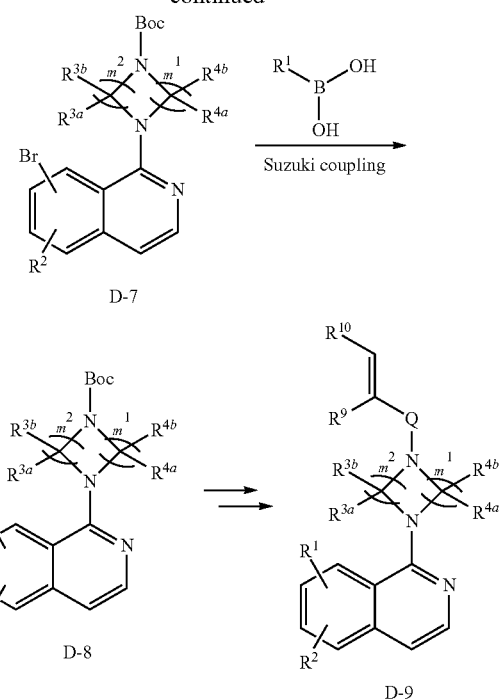

Other embodiments of the compound of structure (I) (e.g., compound D-9) can be prepared according to General Reaction Scheme 4 ("Method D"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 4, benzaldehyde D-1 is treated under reductive amination conditions to yield D-2. Formation of the tosyl-protected amine (D-3) followed by treatment with an appropriate Lewis acid (e.g., $AlCl_3$) yields isoquinoline D-4. Oxidation of D-4 with meta-chloroperbenzoic acid (mCPBA) yields D-5 which can be chlorinated by treatment with an appropriate reagent, such as $POCl_3$. Chloride D-6 is then treated in a manner analogous to that described for Method B to yield D-9.

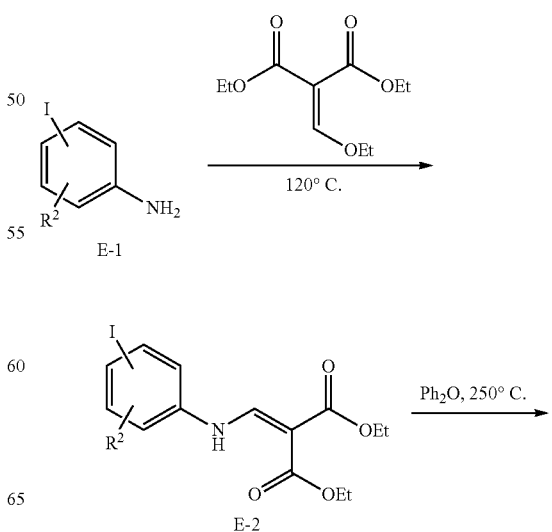

-continued

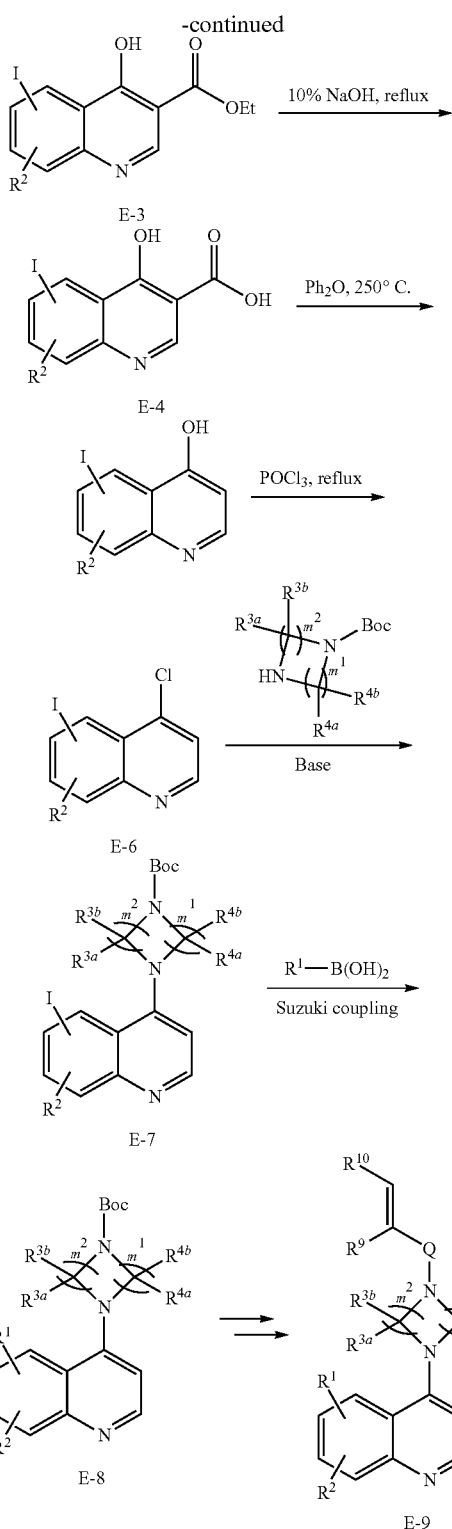

General Reaction Scheme 6

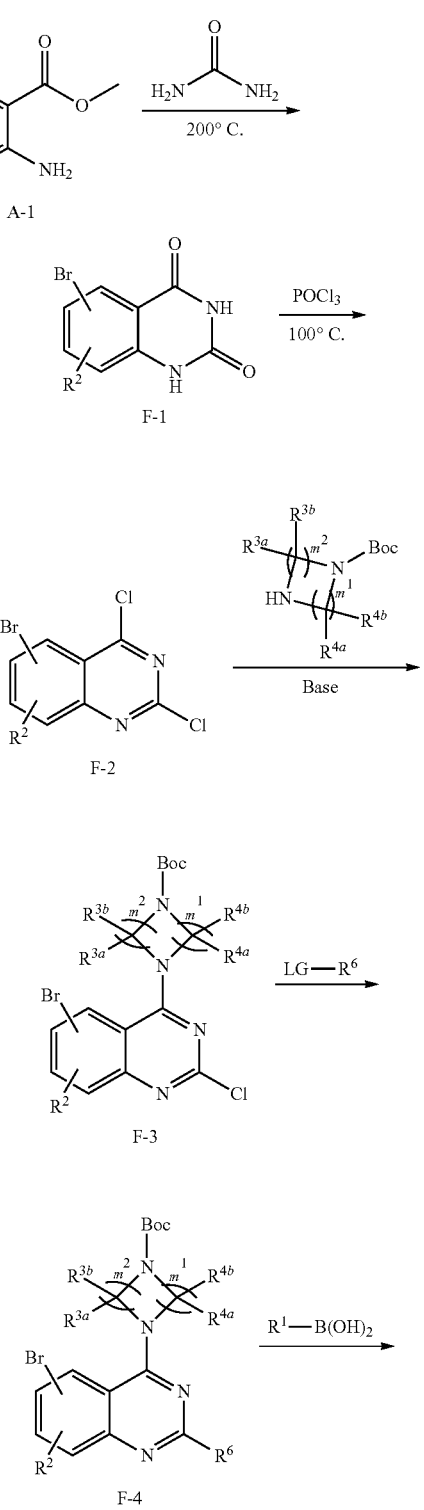

cyclized by heating in an appropriate high-boiling solvent (e.g., Ph$_2$O) to yield quinolone E-3. Saponification of E-3 followed by decarboxylation yields E-4 and E-5, respectively. E-5 is then treated in a manner analogous to that described for Method B to yield E-9.

Other embodiments of the compound of structure (I) (e.g., compound E-9) can be prepared according to General Reaction Scheme 5 ("Method E"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 5, aniline E-1, which can be purchased from commercial sources or prepared via well-known procedures, can be reacted with diethyl 2-(ethoxymethylene)malonate to yield E-2. E-2 can then be

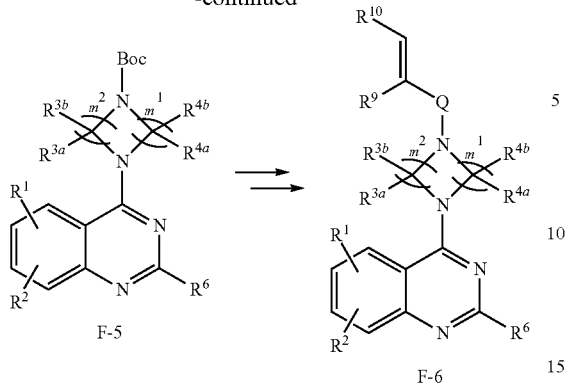

F-5

F-6

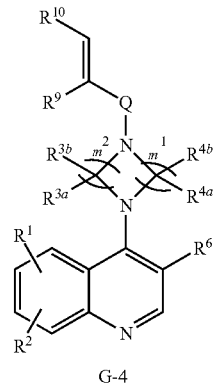

G-4

Other embodiments of the compound of structure (I) (e.g., compound F-6) can be prepared according to General Reaction Scheme 6 ("Method F"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 6, A-1 is cyclized to quinazolinedione F-1 by treatment with urea. Chlorination of F-1 by treatment with $POCl_3$ followed by reaction with a protected heterocycle yield F-2 and F-3, respectively. The $R^6$ substituent is installed by $S_NAr$ reaction of G-3 with LG-R6, wherein LG is an appropriate leaving group. For example, where $R^6$ is cyano or alkoxy, LG is sodium or another appropriate action. The general procedures described above with respect to Method B can then be employed to yield F-6.

Other embodiments of the compound of structure (I) (e.g., compound G-4) can be prepared according to General Reaction Scheme 7 ("Method G"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 7, aniline E-1 is treated under Suzuki conditions to install the R-1 substituent. G-1 is then heated in toluene with an appropriately substituted unsaturated ester to yield G-2. Cyclization of G-2 to hydroxyquinoline G-3 is accomplished by heating in a high boiling solvent (e.g., $Ph_2O$) for an appropriate amount of time. Following the general procedures outlined in Method A then yields G-4.

General Reaction Scheme 7

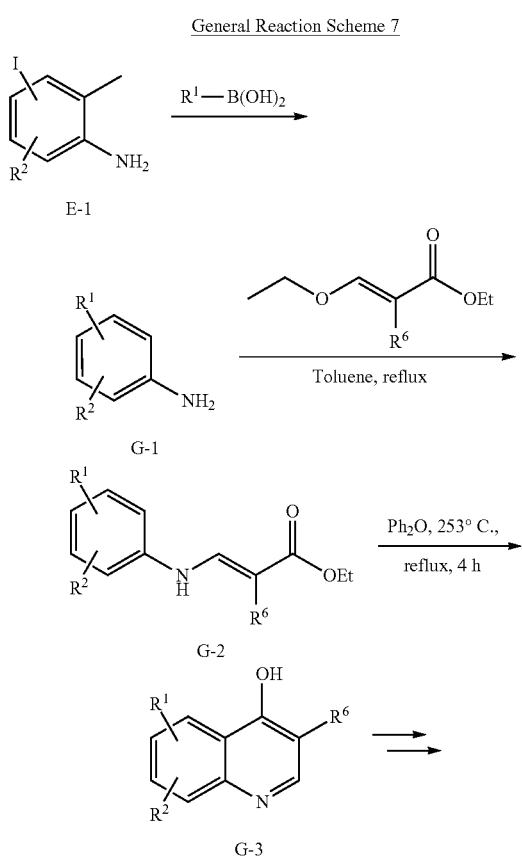

General Reaction Scheme 8

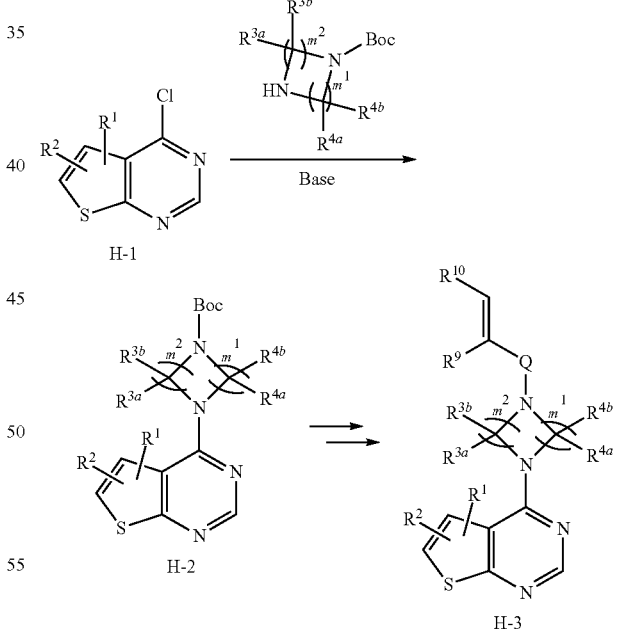

Other embodiments of the compound of structure (I) (e.g., compound H-3) can be prepared according to General Reaction Scheme 8 ("Method H"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Referring to General Reaction Scheme 8, thienopyrimidine H-1 can be prepared according to well-known procedures or purchased from commercial sources. H-1 is treated with an appropriately protected heterocycle under basic conditions to yield H-2. Deprotection followed by acylation or thioacylation according to the procedures described above then yields H-3.

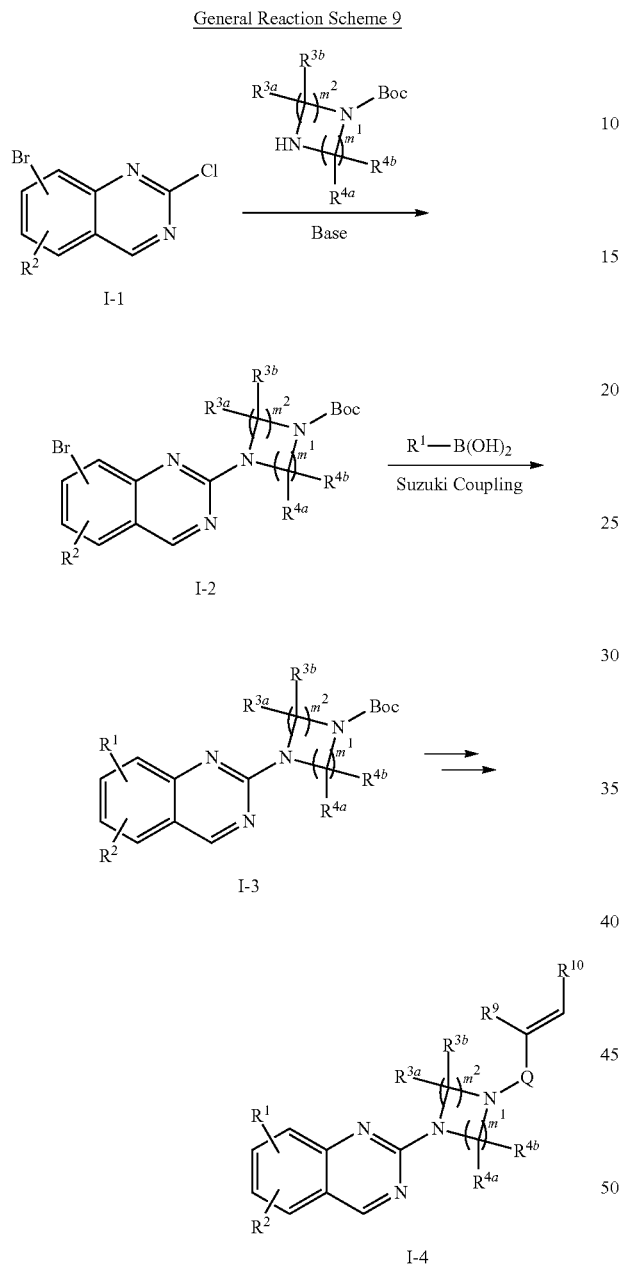

General Reaction Scheme 9

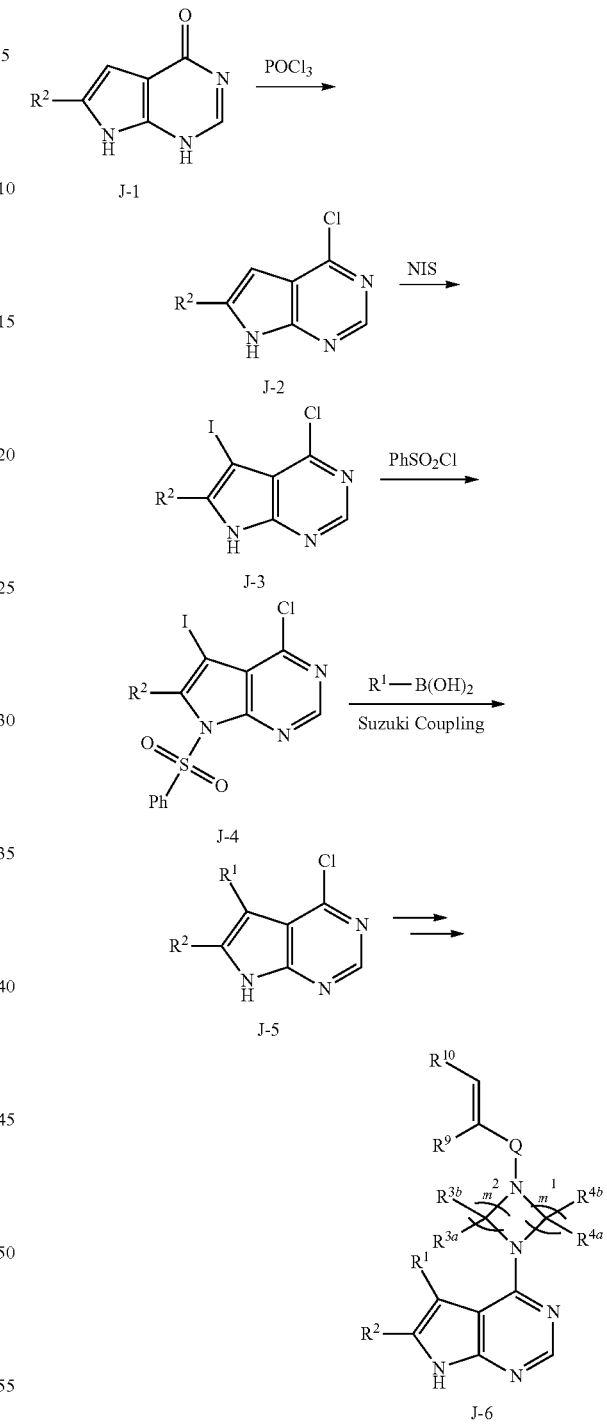

General Reaction Scheme 10

Other embodiments of the compound of structure (I) (e.g., compound I-4) can be prepared according to General Reaction Scheme 9 ("Method I"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Referring to General Reaction Scheme 9, quinazoline I-1 can be prepared according to well-known procedures or purchased from commercial sources. I-1 is treated with an appropriately protected heterocycle under basic conditions to yield I-2. Suzuki reaction of I-2 with an appropriate reagent to install the $R^1$ moiety results in I-3. I-3 is then deprotected and acylated (or thioacylated) according to the procedures described above to yield I-4.

Other embodiments of the compound of structure (I) (e.g., compound J-6) can be prepared according to General Reaction Scheme 10 ("Method J"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Referring to General Reaction Scheme 10, pyrrolopyrimidinone J-1 can be prepared according to well-known procedures or purchased from commercial sources. J-1 is chlorinated with an appropriate reagent (e.g., POCl3) to yield J-2 which is then iodinated with an appropriate reagent, such as N-iodosuccinimide (NIS) to yield J-3. Protection of J-3 followed by Suzuki reaction yields J-5. J-5 is then treated according to the procedures described above to yield J-6.

yield K-3. Suzuki reaction, deprotection and acylation or thioacylation are then carried out as described in the above schemes to yield K-5.

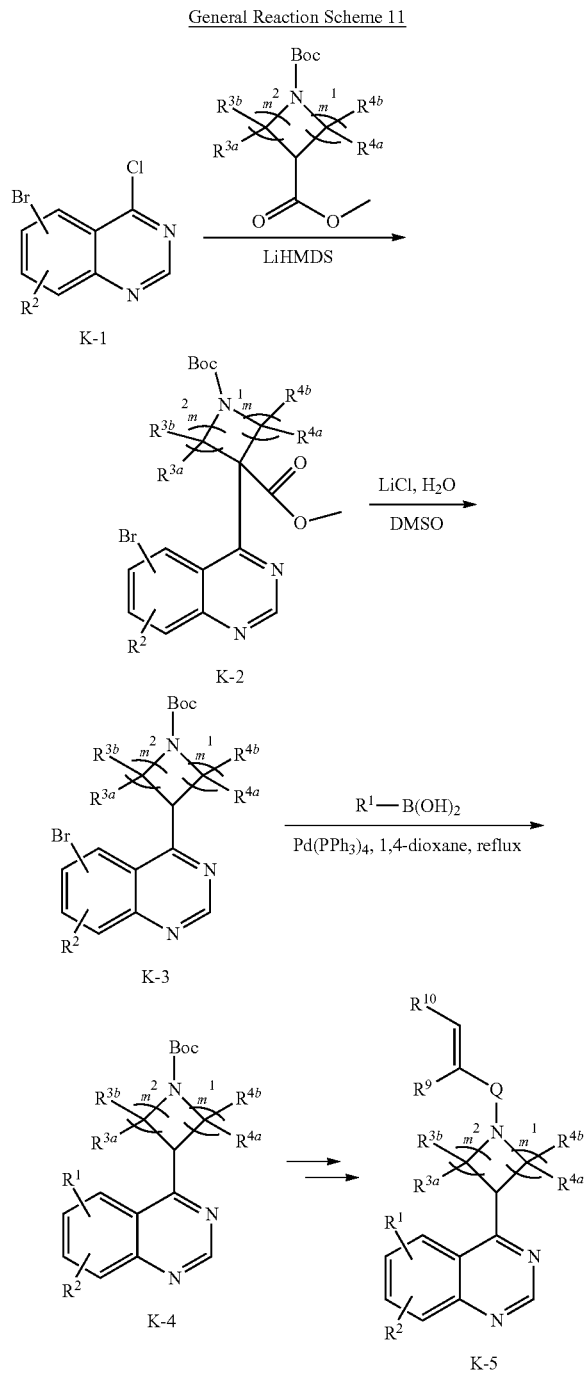

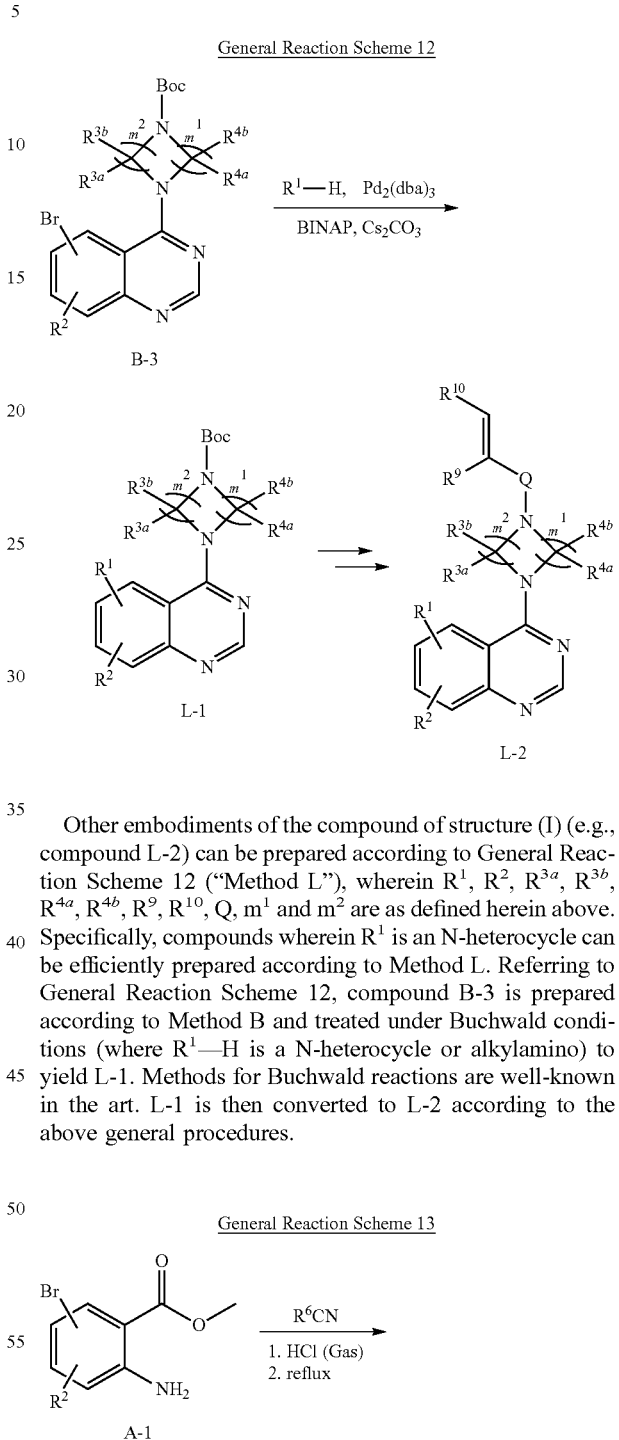

Other embodiments of the compound of structure (I) (e.g., compound L-2) can be prepared according to General Reaction Scheme 12 ("Method L"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Specifically, compounds wherein $R^1$ is an N-heterocycle can be efficiently prepared according to Method L. Referring to General Reaction Scheme 12, compound B-3 is prepared according to Method B and treated under Buchwald conditions (where $R^1$—H is a N-heterocycle or alkylamino) to yield L-1. Methods for Buchwald reactions are well-known in the art. L-1 is then converted to L-2 according to the above general procedures.

Other embodiments of the compound of structure (I) (e.g., compound K-5) can be prepared according to General Reaction Scheme 11 ("Method K"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. Referring to General Reaction Scheme 11, quinazoline K-1 can be prepared according to well-known procedures or purchased from commercial sources. K-1 is reacted with an appropriate ester under basic conditions to form the requisite carbon-carbon bond. K-2 is then decarboxylated to -continued

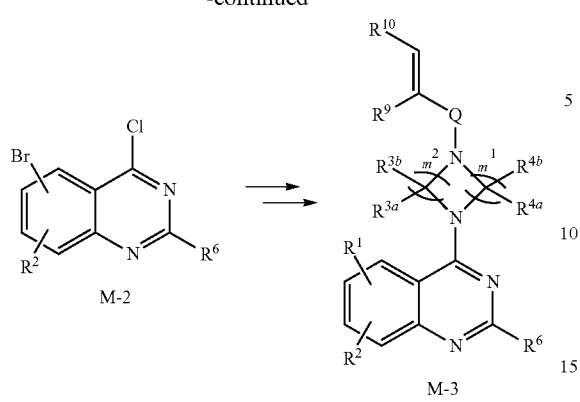

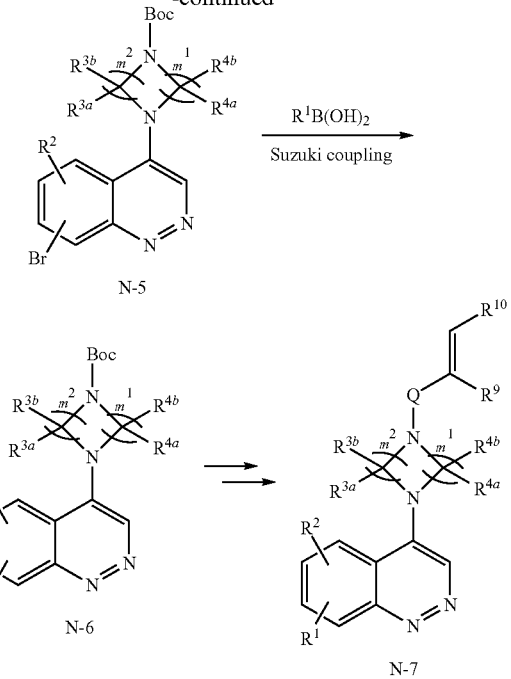

Other embodiments of the compound of structure (I) (e.g., compound M-3) can be prepared according to General Reaction Scheme 13 ("Method M"), wherein $R^1$, $R^2$, $R^{3a}$, $R^{3b}$, $R^{4a}$, $R^{4b}$, $R^6$, $R^9$, $R^{10}$, Q, $m^1$ and $m^2$ are as defined herein above. Referring to General Reaction Scheme 13, compound A-1 is reacted with an appropriate nitrile (R6CN) to form compound M-1. In this regard, $R^6$ may be any of the $R^6$ moieties described herein, for example alkyl. M-1 is chlorinated by reaction with an appropriate reagent such as thionyl chloride. Compound M-3 is then prepared according to the general procedures outlined herein, for example the procedures of General Reaction Scheme 2.

Embodiments of the compound of structure (I) (e.g., compound N-7) can be prepared according to General Reaction Scheme 14 ("Method N"), wherein $R^1$, $R^2$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 14, compounds of structure N-1 can be purchased from commercial sources or prepared according to methods familiar to one of ordinary skill in the art. Compound N-1 is reacted with methylnitrile to form compound N-2. Reaction of N-2 with sodium nitrite under acidic conditions yields cinnolines of structure N-3. N-3 is chlorinated under appropriate conditions (e.g., $SOCl_2$, $POCl_3/PCl_5$ or $POCl_3$) to yield the chlorocinnoline N-4. Reaction of N-4 with an appropriately protected heterocycle under basic conditions yields N-5. Appropriate protecting groups include butyloxycarbonyl (BOC) as depicted in General reaction Scheme 1, as well as other protecting groups known in the art. Suzuki reaction of N-5 with an appropriate reagent to install the $R^1$ moiety results in N-6. Deprotection of N-6 followed by acylation with an acid chloride (or sulfonyl chloride) or acid and appropriate activating reagents yields N-7.

General Reaction Scheme 14

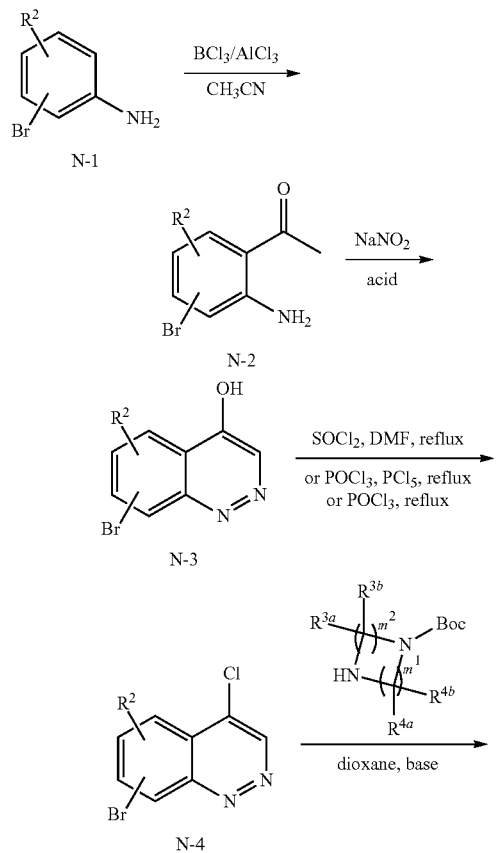

General Reaction Scheme 15

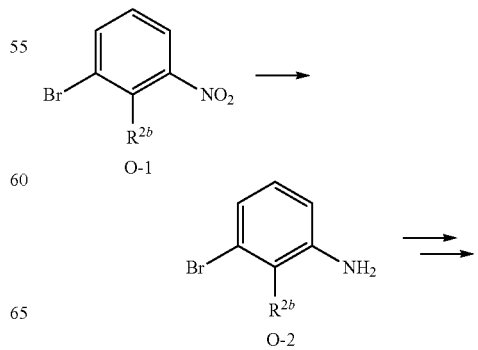

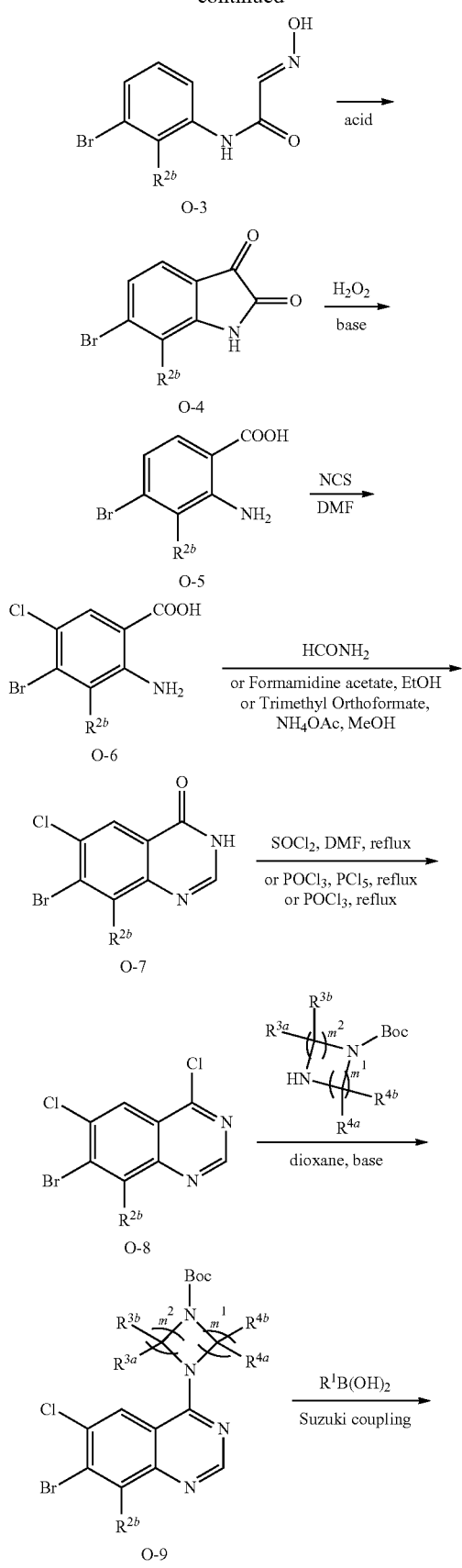

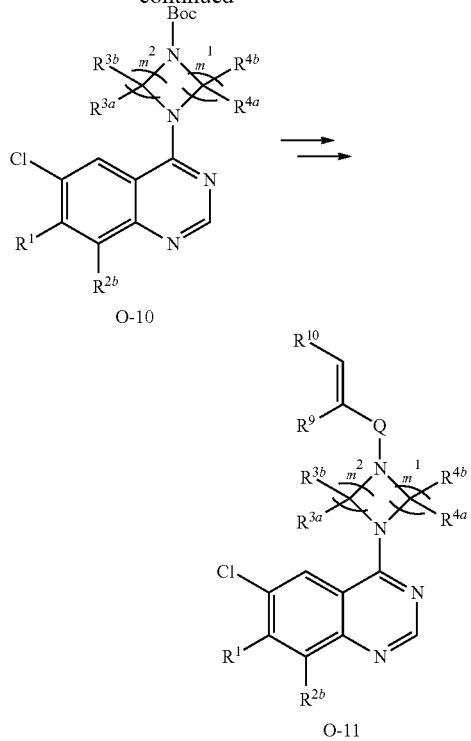

Embodiments of the compound of structure (I) (e.g., compound O-11) can be prepared according to General Reaction Scheme 15 ("Method O"), wherein $R^1$, $R^{2b}$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 15, compounds of structure O-1 can be purchased from commercial sources or prepared according to methods familiar to one of ordinary skill in the art. Compound O-1 is reduced to form compound O-2. Reaction of O-2 with 2,2,2-trichloroethane-1,1-diol under acidic conditions, then hydroxylamine hydrochloride, yields O-3. O-3 is cyclized in the presence of acid to yield O-4. O-4 is reacted in the presence $H_2O_2$ under basic conditions to yield O-5. O-5 is chlorinated using N-chlorosuccinimide to yield O-6. Reaction of O-6 with formamide or other suitable reagents such as formamidine acetate or trimethyl orthoformate yields the quinazolin-4(3H)-one, O-7. O-7 is chlorinated under appropriate conditions (e.g., $SOCl_2$, $POCl_3/PCl_5$ or $POCl_3$) to yield the chloroquinazoline, O-8. Reaction of O-8 with an appropriately protected heterocycle under basic conditions yields O-9. Appropriate protecting groups include butyloxycarbonyl (BOC) as depicted in General reaction Scheme 1, as well as other protecting groups known in the art. Suzuki reaction of O-9 with an appropriate reagent to install the $R^1$ moiety results in O-10. Deprotection of O-10 followed by acylation with an acid chloride (or sulfonyl chloride) or acid and appropriate activating reagents yields O-11.

General Reaction Scheme 16

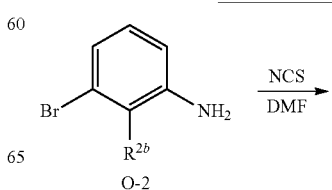

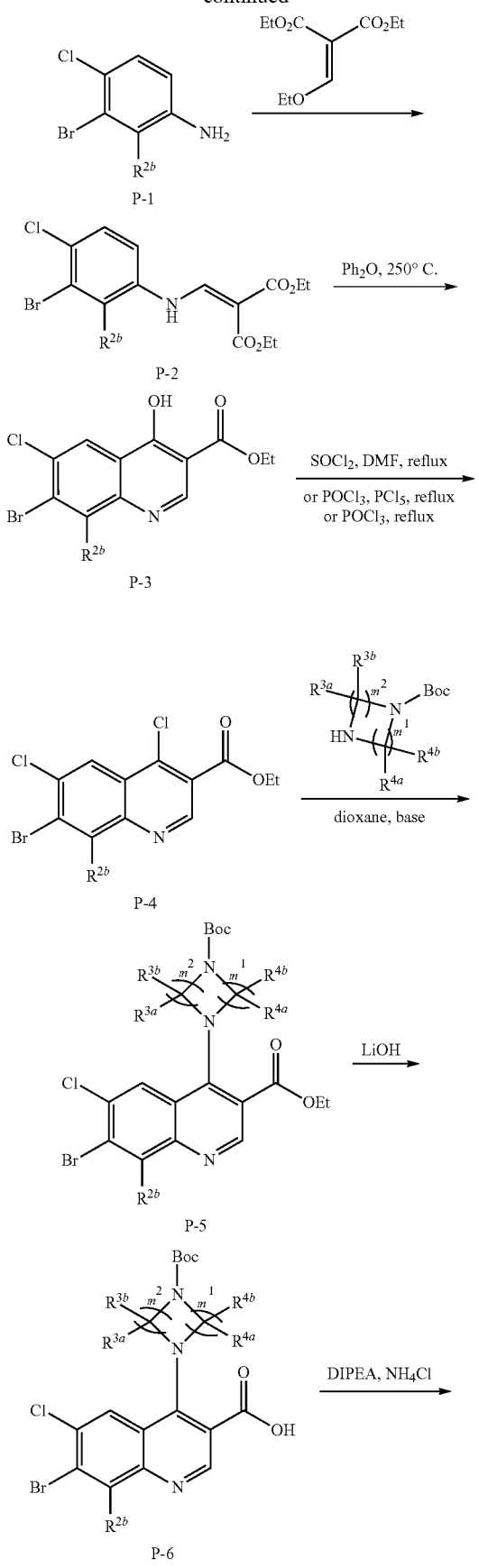
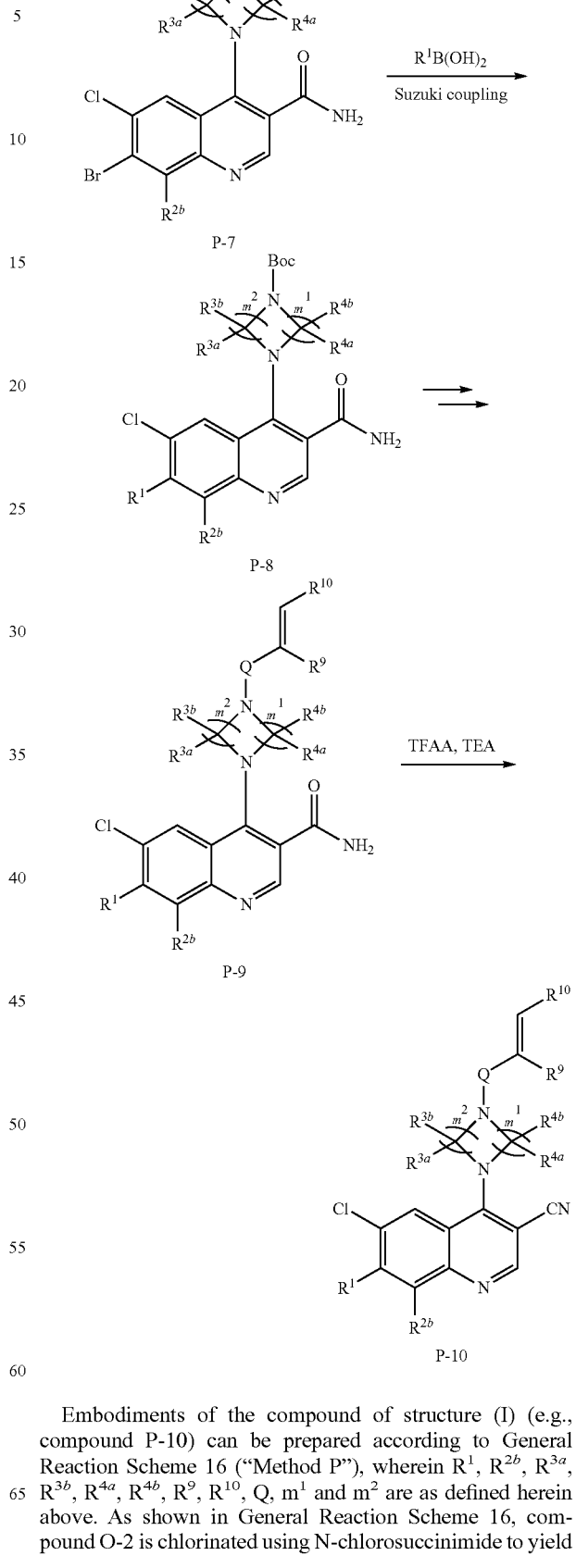
Embodiments of the compound of structure (I) (e.g., compound P-10) can be prepared according to General Reaction Scheme 16 ("Method P"), wherein $R^1$, $R^{2b}$, $R^{3a}$, $R^{3b}$, $R^{4a}$, $R^{4b}$, $R^9$, $R^{10}$, Q, $m^1$ and $m^2$ are as defined herein above. As shown in General Reaction Scheme 16, compound O-2 is chlorinated using N-chlorosuccinimide to yield P-1. Reaction of P-1 with diethyl-2-(ethoxymethylene)malonate yields P-2. P-2 is then cyclized by heating in an appropriate high-boiling solvent (e.g. Ph$_2$O) to yield the quinolone, P-3. P-3 is chlorinated under appropriate conditions (e.g., SOCl$_2$, POCl$_3$/PCl$_5$ or POCl$_3$) to yield the chloroquinoline, P-4. Reaction of P-4 with an appropriately protected heterocycle under basic conditions yields P-5. Appropriate protecting groups include butyloxycarbonyl (BOC) as depicted in General reaction Scheme 1, as well as other protecting groups known in the art. Saponification of P-5 followed by amidation yields P-6 and P-7, respectively. Suzuki reaction of P-7 with an appropriate reagent to install the R$^1$ moiety results in P-8. Deprotection of P-8 followed by acylation with an acid chloride (or sulfonyl chloride) or acid and appropriate activating reagents yields P-9. Reaction of P-9 in the presence of acid yielded P-10.

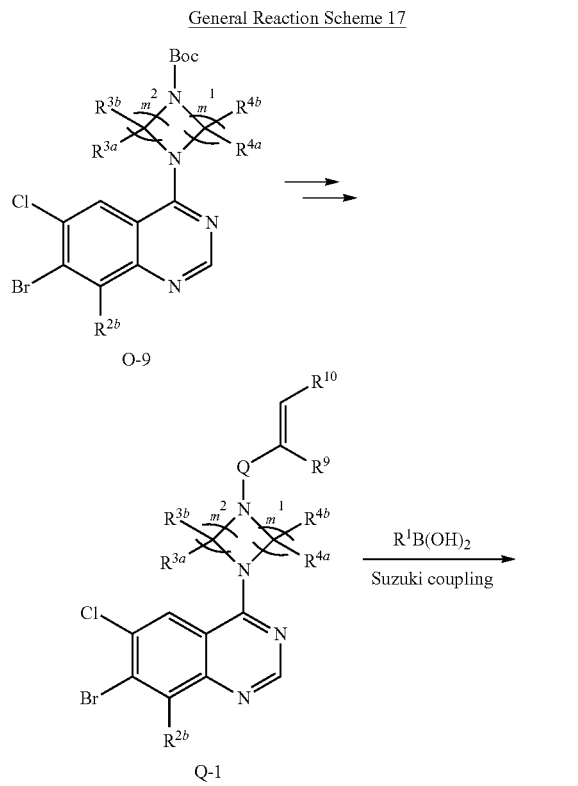

General Reaction Scheme 17

Embodiments of the compound of structure (I) (e.g., compound Q-2) can be prepared according to General Reaction Scheme 16 ("Method Q"), wherein R$^1$, R$^{2b}$, R$^{3a}$, R$^{3b}$, R$^{4a}$, R$^{4b}$, R$^9$, R$^{10}$, Q, m$^1$ and m$^2$ are as defined herein above. As shown in General Reaction Scheme 17, deprotection of compound O-9 followed by acylation with an acid chloride (or sulfonyl chloride) or acid and appropriate activating reagents yields Q-1. Suzuki reaction of Q-1 with an appropriate reagent to install the R$^1$ moiety results in Q-2.

One skilled in the art will recognize that certain modifications to the above schemes are possible to prepare different embodiments of compounds of structure (I). For example, for ease of illustration, most of the above schemes depict preparation of compounds of structure (I) wherein L$^1$ is a bond. However, one of ordinary skill in the art will readily recognize that compounds wherein L$^1$ is NR$^7$ can be prepared by substituting a heterocycle having the following structure (see e.g., Method C):

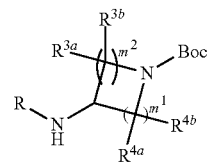

where R is H, a protecting group or C$_1$-C$_6$ alkyl.

2. Compounds of Structure (II)

In still other embodiments, the compound used in combination with one or more additional therapeutic agent has the following structure II):

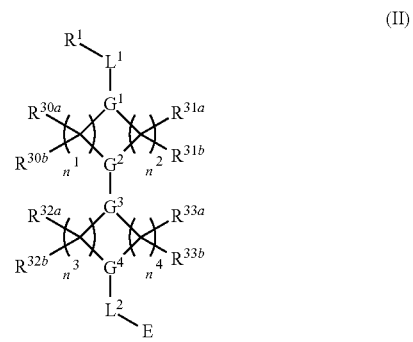

(II)

or a pharmaceutically acceptable salt, tautomer, stereoisomer or prodrug thereof, wherein:

R$^1$ is aryl or heteroaryl;

R$^{30a}$ and R$^{30b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; or R$^{30a}$ and R$^{30b}$ join to form a carbocyclic or heterocyclic ring; or R$^{30a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and R$^{30b}$ joins with R$^{31b}$ to form a carbocyclic or heterocyclic ring;

R$^{31a}$ and R$^{31b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; or R$^{31a}$ and R$^{31b}$ join to form a carbocyclic or heterocyclic ring; or R$^{31a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and R$^{31b}$ joins with R$^{30b}$ to form a carbocyclic or heterocyclic ring;

$R^{32a}$ and $R^{32b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; or $R^{32a}$ and $R^{32b}$ join to form a carbocyclic or heterocyclic ring; or $R^{32a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{32b}$ joins with $R^{33b}$ to form a carbocyclic or heterocyclic ring;

$R^{33a}$ and $R^{33b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; or $R^{33a}$ and $R^{33b}$ join to form a carbocyclic or heterocyclic ring; or $R^{33a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{33b}$ joins with $R^{32b}$ to form a carbocyclic or heterocyclic ring;

L$^1$ is carbonyl, —NHC(=O)—, alkylene, alkenylene, heteroalkylene, heterocycloalkylene, heteroarylene, alkylenecarbonyl, alkenylenecarbonyl, heteroalkylenecarbonyl, heterocycloalkylenecarbonyl or heteroarylenecarbonyl;

L$^2$ is a bond or alkylene;

G$^1$, G$^2$, G$^3$ and G$^4$ are each independently N or CR, where R is H, cyano, halo or C$_1$-C$_6$alkyl;

n$^1$, n$^2$, n$^3$ and n$^4$ are each independently 1, 2 or 3; and

E is an electrophilic moiety capable of forming a covalent bond with the cysteine residue at position 12 of a KRAS, HRAS or NRAS G12C mutant protein.

In some embodiments of the compounds of structure II, L$^1$ is carbonyl, —NHC(=O)—, alkylene, heteroalkylene, alkylenecarbonyl or heteroalkylenecarbonyl;

In some other embodiments, the compound has the following structure (IIa):

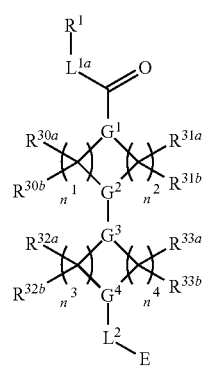

(IIa)

wherein:

L$^{1a}$ is a bond, —NH—, alkylene, alkenylene, heteroalkylene, heterocycloalkylene or heteroarylene.

In other embodiments of compound (IIa), L$^{1a}$ is a bond, —NH—, alkylene or heteroalkylene.

In some more embodiments, the compound has the following structure (IIb):

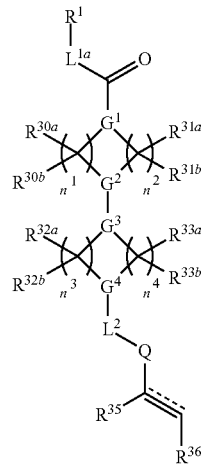

(IIb)

wherein:

Q is —C(=O)—, —NR$^{34}$C(=O)—, —S(=O)$_2$— or —NR$^{34}$S(=O)$_2$—;

R$^{34}$ is H, C$_1$-C$_6$alkyl or hydroxylalkyl;

⩵ is a carbon-carbon double bond or a carbon-carbon triple bond; and

R$^{35}$ and R$^{36}$ are each independently H, cyano, C$_1$-C$_6$alkyl, aminoalkyl, alkylaminoalkyl, or hydroxylalkyl or R$^{35}$ and R$^{36}$ join to form a carbocyclic or heterocyclic ring when ⩵ is a double bond; or R$^{35}$ is absent and R$^{36}$ is H, C$_1$-C$_6$alkyl, aminoalkyl, alkylaminoalkyl or hydroxylalkyl when ⩵ is a triple bond.

In some different embodiments, the compound has one of the following structures (IIc), (IId), (IIe) or (IIf):

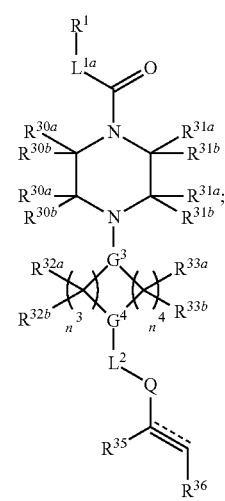

(IIc)

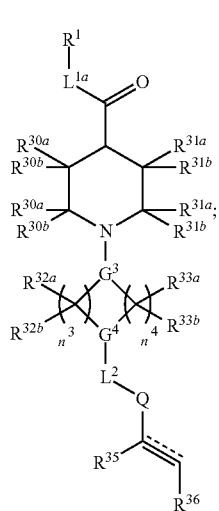
(IId)
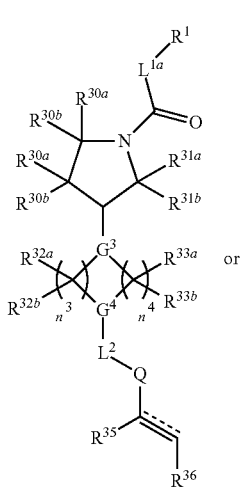
(IIe)
or
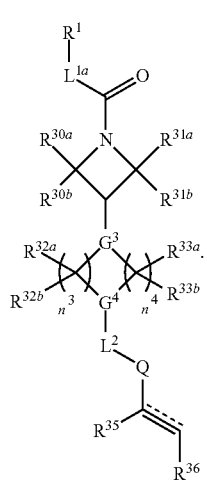
(IIf)
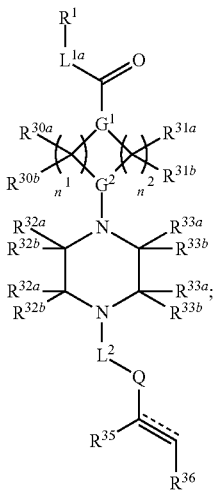
(IIg)
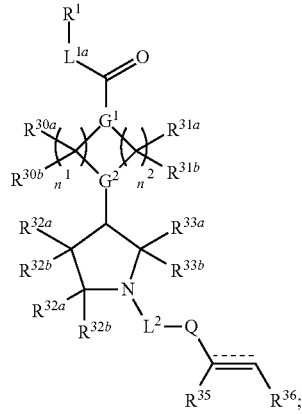
(IIh)
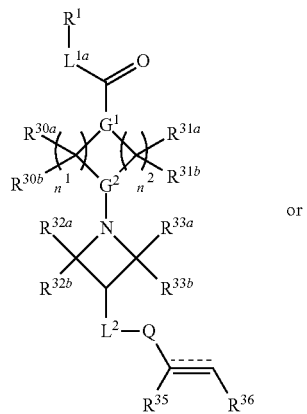
(IIi)
or
In still other embodiments, wherein the compound has one of the following structures (IIg), (IIh), (IIi) or (IIj):

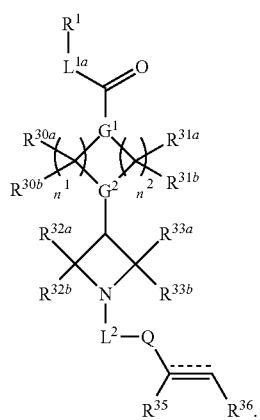
(IIj)
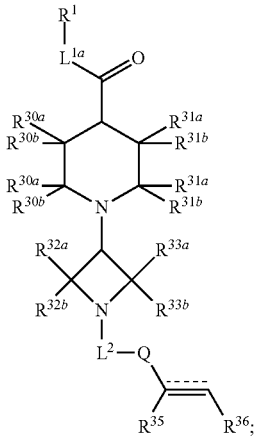
(IIm)
In some other embodiments, the compound has one of the following structures (IIk), (Il), (IIm), (IIn); (IIo) or (IIp):
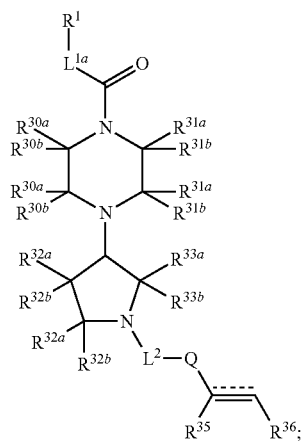
(IIk)
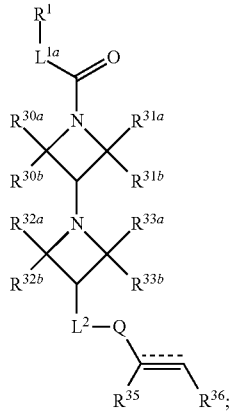
(IIn)
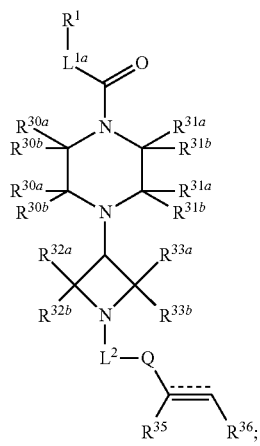
(Il)

-continued (IIp)

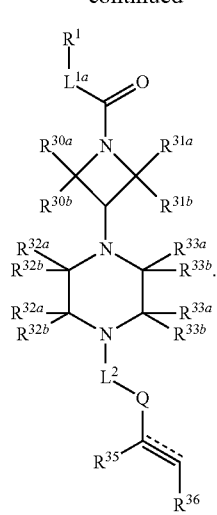

In various other embodiments, R¹ is aryl. For example, in some embodiments the aryl is bicyclic, such as a fused bicyclic aryl. In some more specific embodiments, the aryl is naphthyl.

In various other embodiments, the aryl is monocyclic. For example, in some embodiments the aryl is phenyl.

In some of the foregoing embodiments, the aryl is unsubstituted. In other of the foregoing embodiments, the aryl is substituted with one or more substituents. For example, in some embodiments the substituents are selected from halo, hydroxyl, cyano, aminocarbonyl, formyl, $C_1$-$C_6$alkyl, $C_1$-$C_6$alkylsulfonyl, $C_1$-$C_6$haloalkyl, $C_3$-$C_8$cycloalkyl, $C_1$-$C_6$alkoxy, $C_1$-$C_6$hydroxylalkyl, $C_1$-$C_6$alkoxyalkyl, $C_1$-$C_6$aminoalkyl, aliphatic heterocyclyl, heteroaryl and aryl.

In other embodiments, the aryl substituents are selected from fluoro, chloro, bromo, iodo, hydroxyl, cyano, methyl, ethyl, isopropyl, methylsulfonyl, methoxy, aminocarbonyl, trifluoromethyl, 2,2,2-trifluorethyl, cyclobutyl, cyclopropyl and phenyl, wherein the cyclopropyl and phenyl are optionally substituted with one or more substituents selected from $C_1$-$C_6$alkyl, halo, hydroxyl and cyano In some different embodiments, the substituents are selected from fluoro, chloro, bromo, iodo, hydroxyl, cyano, methyl, ethyl, methylsulfonyl, methoxy, aminocarbonyl, trifluoromethyl, cyclopropyl and phenyl, wherein the cyclopropyl and phenyl are optionally substituted with one or more substituents selected from halo, hydroxyl and cyano.

In other exemplary embodiments, the aryl substituents are selected from fluoro, chloro, bromo, iodo, hydroxyl, methyl, ethyl, cyclobutyl and cyclopropyl, wherein the cyclopropyl is optionally substituted with one or more substituents selected from $C_1$-$C_6$alkyl, halo, hydroxyl and cyano In some more embodiments, the substituents are selected from fluoro, chloro, bromo, iodo, hydroxyl, methyl, ethyl and cyclopropyl, wherein the cyclopropyl is optionally substituted with one or more substituents selected from halo, hydroxyl and cyano.

In still more embodiments, the substituents are selected from fluoro, chloro, bromo, hydroxyl and cyclopropyl, wherein the cyclopropyl is optionally substituted with one or more substituents selected from $C_1$-$C_6$alkyl, halo, hydroxyl and cyano.

In some more specific embodiments, the substituents are selected from fluoro, chloro, bromo, hydroxyl and cyclo- propyl, wherein the cyclopropyl is optionally substituted with one or more substituents selected from halo, hydroxyl and cyano. For example, in some embodiments the cyclopropyl comprises a geminal difluoro substitution.

In still other embodiments, R¹ has one of the following structures:

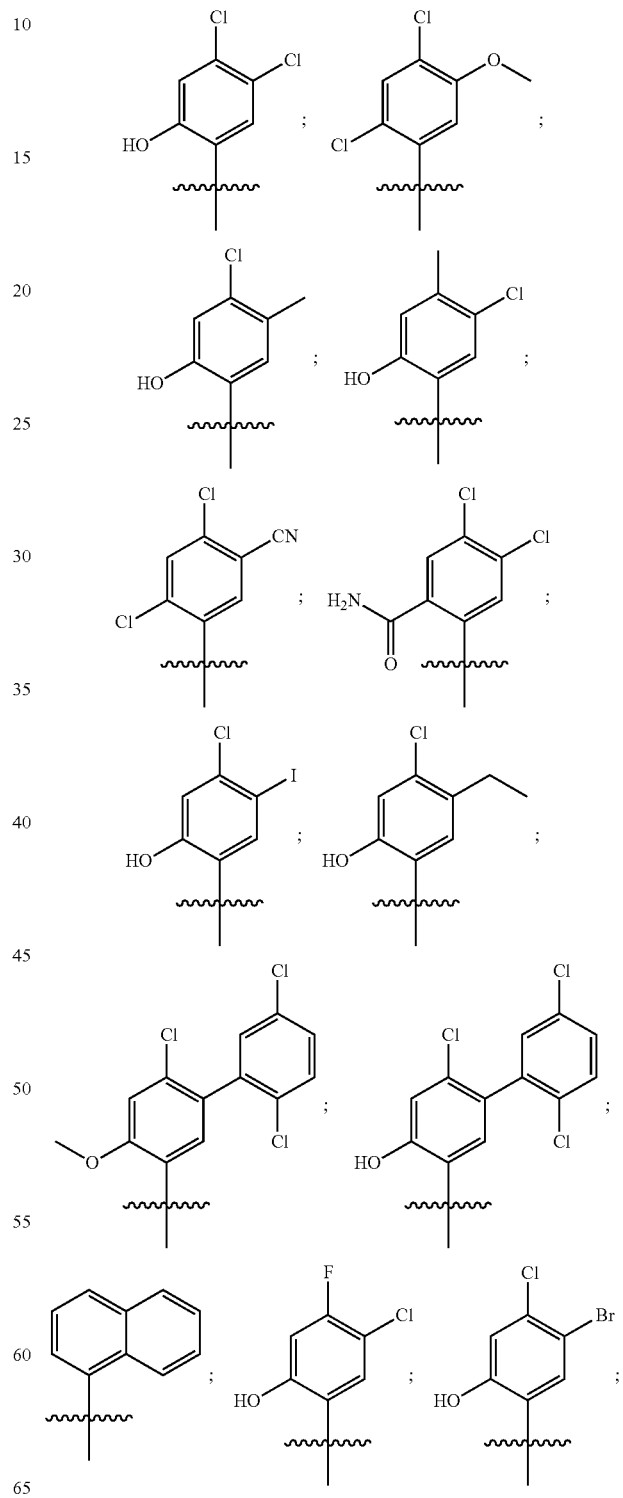

-continued
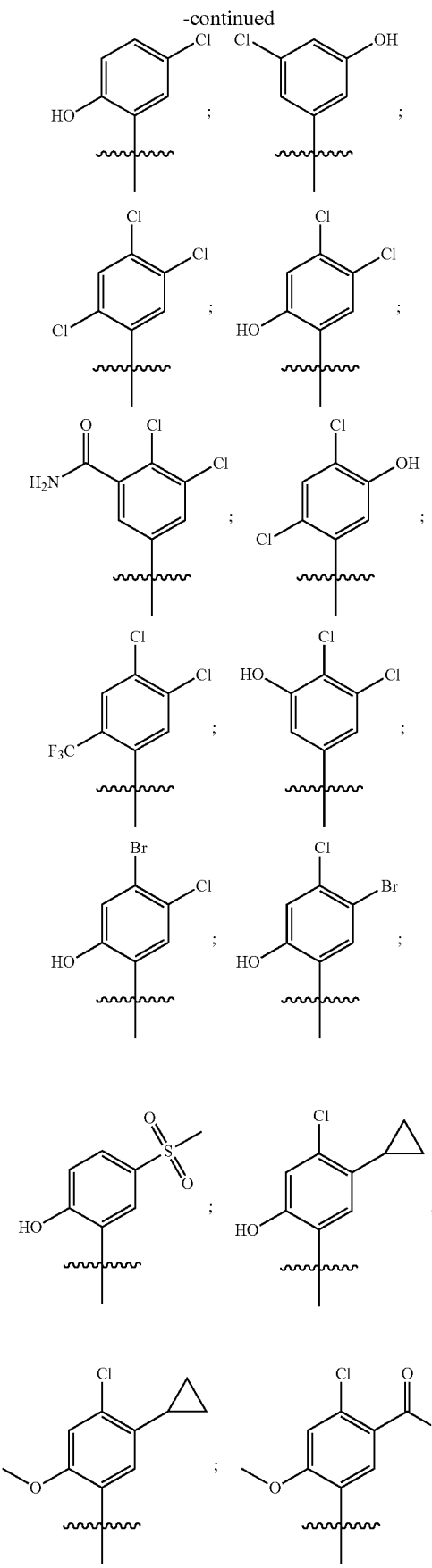
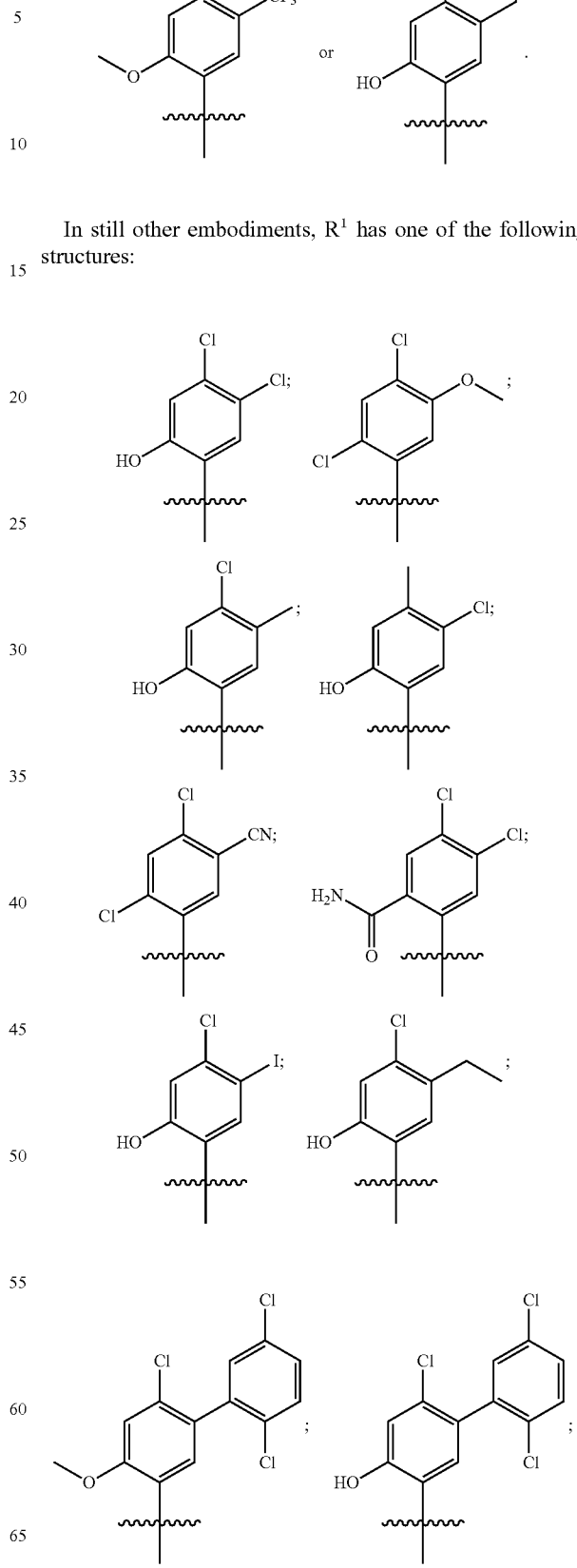
In still other embodiments, R$^1$ has one of the following structures:

-continued
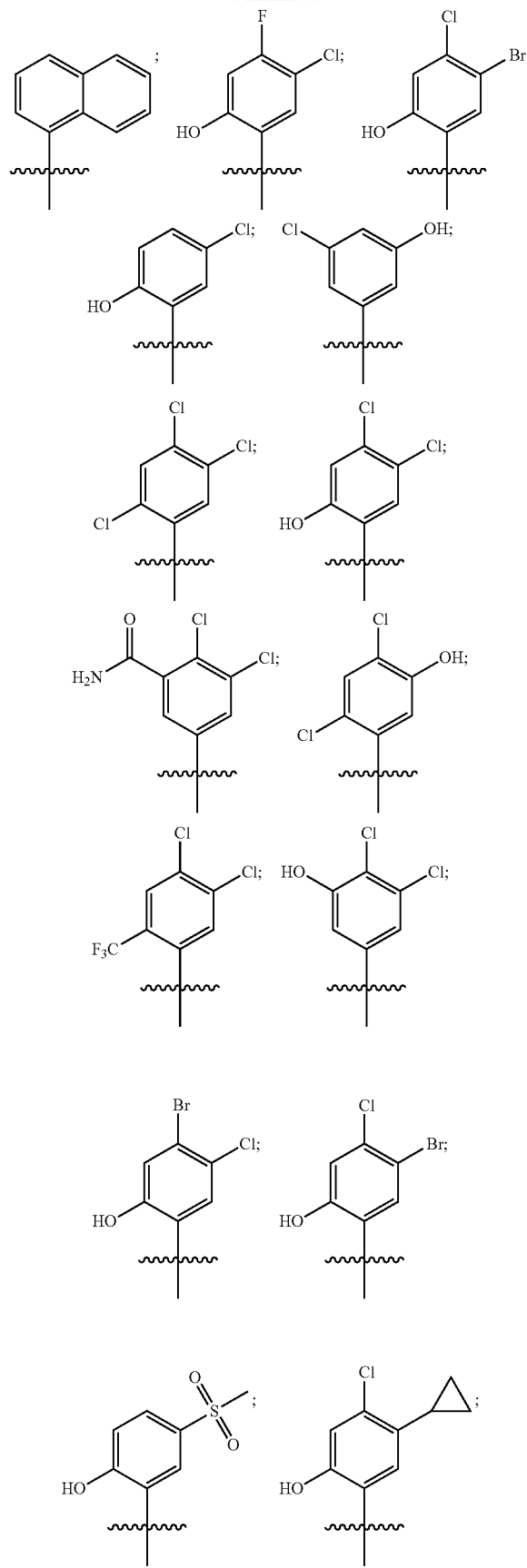
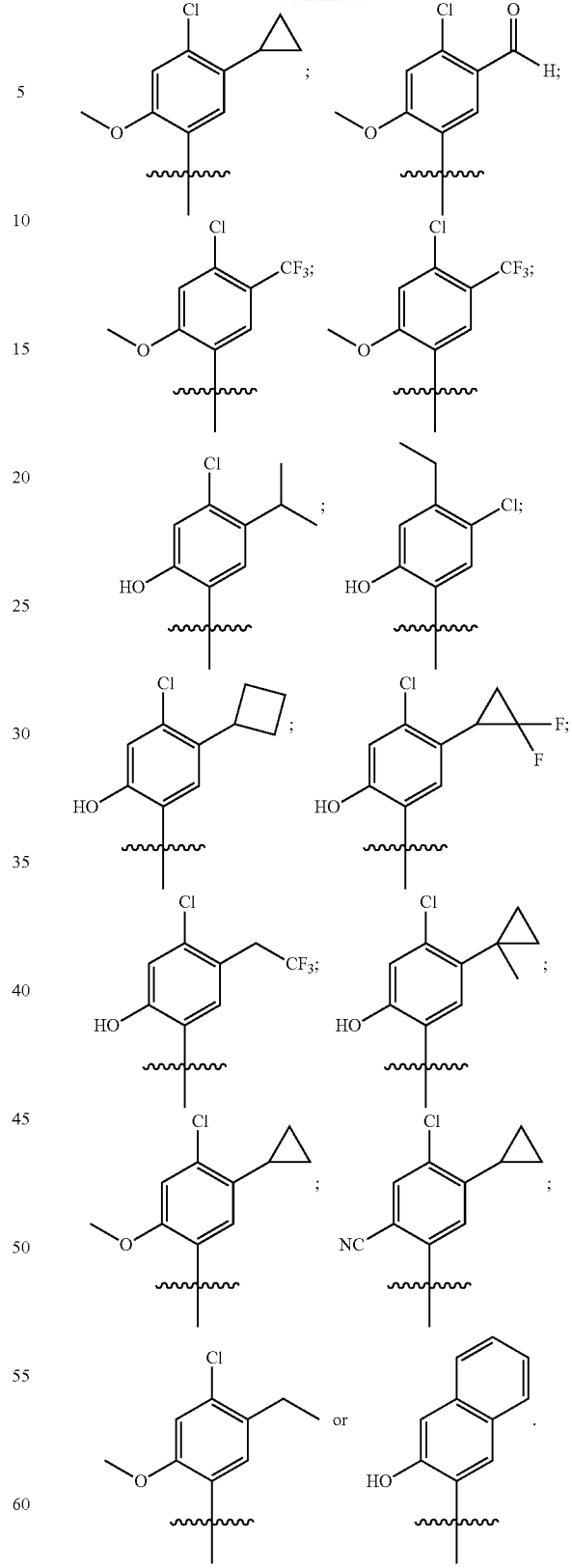
In still other embodiments, $R^1$ is heteroaryl. For example, in some embodiments the heteroaryl is bicyclic, such as a fused bicyclic heteroaryl.

In some more embodiments, the heteroaryl is monocyclic.

In some of the foregoing embodiments, the heteroaryl comprises nitrogen, sulfur or a combination thereof. For example, in some embodiments the heteroaryl is dihydroquinoxalinyl, indoleyl, benzoimidazolyl, pyridinyl or thiazolyl.

In some embodiments, the heteroaryl is unsubstituted. In some other embodiments, the heteroaryl is substituted with one or more substituents. In some embodiments, the substituents are selected from $C_1$-$C_6$alkyl, halo and oxo. For example, in some embodiments the substituents are selected from halo and oxo. In other embodiments, the substituents are selected from ethyl and chloro. In some more specific embodiments, the substituents are chloro.

In some embodiments of the forgoing compounds of structure (II), $R^1$ has one of the following structures:

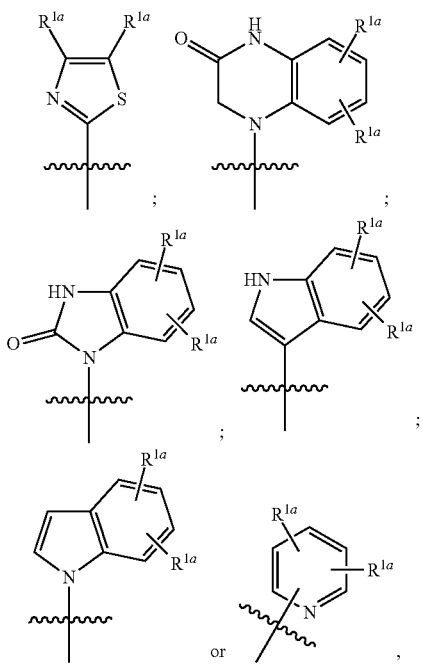

wherein $R^{1a}$ is, at each occurrence, independently H, $C_1$-$C_6$alkyl or halo.

In various other embodiments, $R^1$ has one of the following structures:

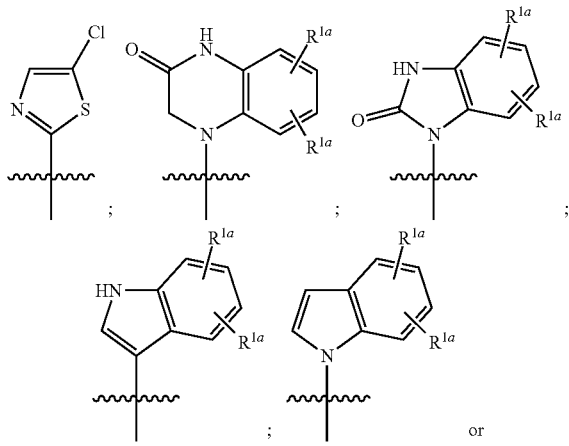

wherein $R^{1a}$ is, at each occurrence, independently H or halo.

In still other embodiments of structure (II), $R^1$ has one of the following structures:

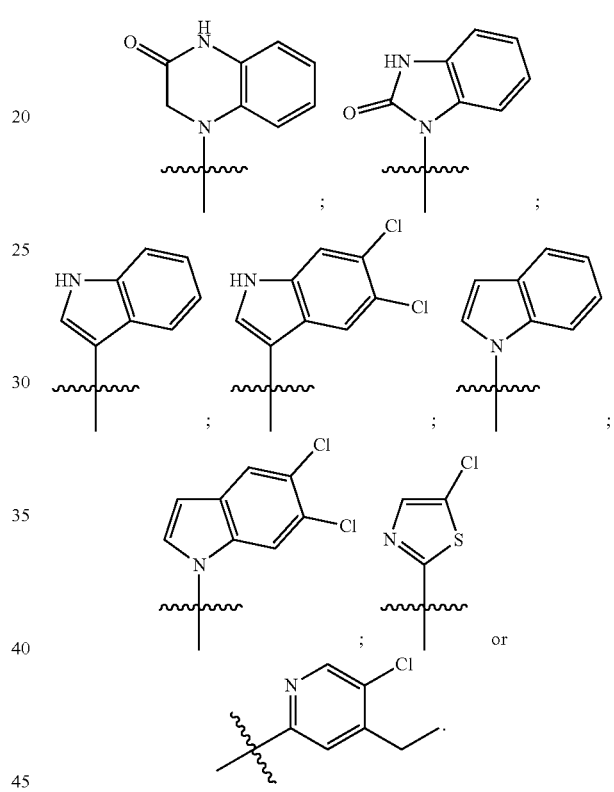

In some embodiments, Q is —C(=O)—. In some other embodiments, Q is —S(=O)$_2$—. In still other embodiments, Q is —NR$^{34}$C(=O)—. In still more other embodiments, Q is —NR$^{34}$S(=O)$_2$—.

In some more specific embodiments, $R^{34}$ is H. For example, in some embodiments $R^{34}$ is hydroxylalkyl, such as 2-hydroxylalkyl.

In other of the foregoing embodiments, at least one of $R^{35}$ or $R^{36}$ is H. For example, in some embodiment search of $R^{35}$ and $R^{36}$ are H.

In various other embodiments, $R^{36}$ is alkylaminoalkyl. For example, in some embodiments $R^{36}$ has the following structure:

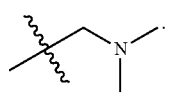

In some different embodiments, $R^{36}$ is hydroxylalkyl, for example 2-hydroxylalkyl In various other embodiments, $R^{35}$ and $R^{36}$ join to form a ring. In some of these embodiments, the ring is a cyclopentene, cyclohexene or phenyl ring.

In other of the foregoing embodiments, E has one of the following structures:

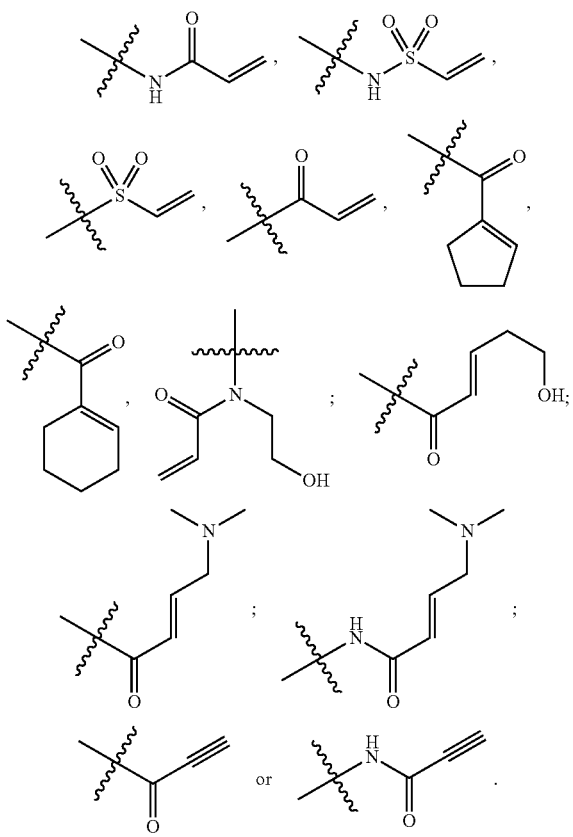

In some embodiments, E is

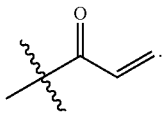 [SMILES: *C(=O)C=C]

In some more of the foregoing embodiments, L is heteroalkylene. In some more embodiments, the heteroalkylene is unsubstituted. In some different embodiments, the heteroalkylene is substituted.

In various other embodiments, $L^1$ is aminoalkylene. For example, in some embodiments $L^1$ is —CH$_2$CH$_2$NH—.

In other embodiments of the foregoing, $L^1$ is heterocycloalkylene or heteroarylene. In some embodiments, the heterocycloalkylene or heteroarylene is unsubstituted. In other embodiments, the heterocycloalkylene or heteroarylene is substituted. In some further embodiments, $L^1$ has one of the following structures:

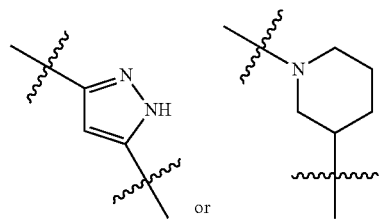

In some different embodiments, $L^{1a}$ is a bond.

In some embodiments, $L^{1a}$ is alkylene, alkenylene, heteroalkylene or heterocycloalkylene. In some other embodiments, $L^{1a}$ is alkylene or heteroalkylene. In some of these embodiments, $L^{1a}$ is substituted alkylene. In various other embodiments, $L^{1a}$ is unsubstituted alkylene. For example, in some embodiments $L^{1a}$ is

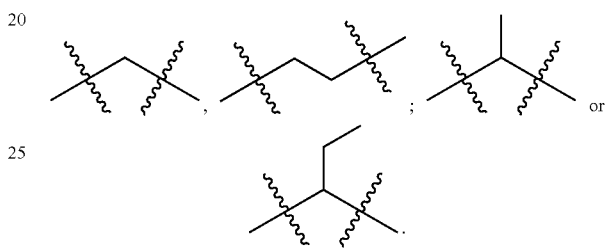

In some different embodiments, $L^{1a}$ is substituted heteroalkylene. In some other embodiments, $L^{1a}$ is unsubstituted heteroalkylene. In some of the foregoing embodiments, $L^{1a}$ is aminoalkylene or thioalkylene, for example aminoalkylene. For example, in some embodiments $L^{1a}$ has one of the following structures:

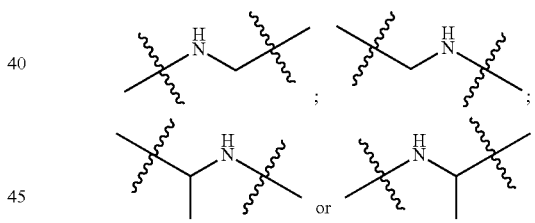

In other embodiments, $L^{1a}$ is

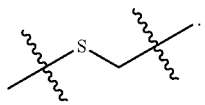

In other embodiments, $L^{1a}$ is substituted alkenylene. In different embodiments, $L^{1a}$ is unsubstituted alkenylene. In some more specific embodiments, $L^{1a}$ has the following structure:

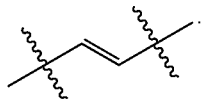 [SMILES: */C=C/*]

In yet other embodiments, $L^{1a}$ is substituted heterocycloalkylene. In some other embodiments, $L^{1a}$ is unsubstituted heterocycloalkylene. For Example, in some embodiments, $L^{1a}$ has the following structure:

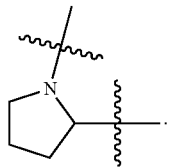 [SMILES: *C1CCCN1*]

In some of the foregoing embodiments, $L^2$ is a bond.
In various other embodiments, $L^2$ is substituted alkylene. In still other embodiments, $L^2$ is unsubstituted alkylene.
In various embodiments of any of the foregoing compounds of structure (II):
$R^{30a}$ and $R^{30b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl;
$R^{31a}$ and $R^{31b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl;
$R^{32a}$ and $R^{32b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl; and $R^{33a}$ and $R^{33b}$ are, at each occurrence, independently H, —OH, —NH$_2$, —CO$_2$H, cyano, cyanoalkyl, C$_1$-C$_6$alkyl, C$_3$-C$_8$cycloalkyl, hydroxylalkyl, aminoalkyl, carboxylalkyl or aminocarbonyl.
In other embodiments, $R^{30a}$, $R^{30b}$, $R^{31a}$, $R^{31b}$, $R^{32a}$, $R^{32b}$, $R^{33a}$ and $R^{33b}$ are selected from H, C$_1$-C$_6$alkyl, hydroxylalkyl, cyano, cyanoalkyl and aminocarbonyl, for example H, C$_1$-C$_6$alkyl, hydroxylalkyl, cyano, and aminocarbonyl or in other embodiments H, C$_1$-C$_6$alkyl and hydroxylalkyl.
In some of the foregoing embodiments, at least one of $R^{30a}$, $R^{30b}$, $R^{31a}$, $R^{31b}$, $R^{32a}$, $R^{32b}$, $R^{33a}$ or $R^{33b}$ is H. For example, in some embodiments each of $R^{30a}$, $R^{30b}$, $R^{31a}$, $R^{31b}$, $R^{32a}$, $R^{32b}$, $R^{33a}$ or $R^{33b}$ is H.
In some other of the foregoing embodiments, at least one of $R^{30a}$, $R^{30b}$, $R^{31a}$, $R^{31b}$, $R^{32a}$, $R^{32b}$, $R^{33a}$ or $R^{33b}$ is hydroxylalkyl.
In still other of the foregoing embodiments, at least one of $R^{30a}$, $R^{30b}$, $R^{31a}$, $R^{31b}$, $R^{32a}$, $R^{32b}$, $R^{33a}$ or $R^{33b}$ is cyano.
In still more of the foregoing embodiments of compound (II), at least one of $R^{30a}$, $R^{30b}$, $R^{31a}$, $R^{31b}$, $R^{32a}$, $R^{32b}$, $R^{33a}$ or $R^{33b}$ is aminocarbonyl.
In other embodiments, at least one of $R^{30a}$, $R^{30b}$, $R^{31a}$, $R^{31b}$, $R^{32a}$, $R^{32b}$, $R^{33a}$ or $R^{33b}$ is C$_1$-C$_6$alkyl.
In some embodiments, $R^{30a}$ and $R^{30b}$ join to form a carbocyclic or heterocyclic ring. In different embodiments, $R^{31a}$ and $R^{31b}$ join to form a carbocyclic or heterocyclic ring. In more embodiments, $R^{32a}$ and $R^{32b}$ join to form a carbocyclic or heterocyclic ring. In yet other embodiments, $R^{33a}$ and $R^{33b}$ join to form a carbocyclic or heterocyclic ring.
In even other embodiments, $R^{30a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{30b}$ joins with $R^{31b}$ to form a carbocyclic or heterocyclic ring.
In more embodiments, $R^{31a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{31b}$ joins with $R^{30b}$ to form a carbocyclic or heterocyclic ring.

In other embodiments, $R^{32a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{32b}$ joins with $R^{33b}$ to form a carbocyclic or heterocyclic ring.
In still more embodiments, $R^{33a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{33b}$ joins with $R^{32b}$ to form a carbocyclic or heterocyclic ring.
In some other embodiments, the compound is selected from a compound in Table 2.

TABLE 2a

Representative Compounds of Structure (II)

| No. | Structure | Name |
|---|---|---|
| II-1 | 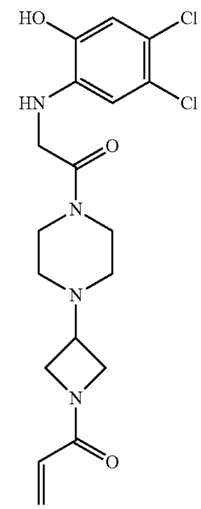 [SMILES: C=CC(=O)N1CC(N2CCN(C(=O)CNc3cc(Cl)c(Cl)cc3O)CC2)C1] | 1-(3-(4-(2-(4,5-dichloro-2-hydroxyphenylamino)acetyl)-piperazin-1-yl)azetidin-1-yl)prop-2-en-1-one |
| II-2 | 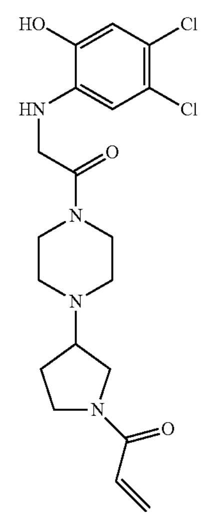 [SMILES: C=CC(=O)N1CCC(N2CCN(C(=O)CNc3cc(Cl)c(Cl)cc3O)CC2)C1] | 1-(3-(4-(2-(4,5-dichloro-2-hydroxyphenylamino)acetyl)piperazin-1-yl)pyrrolidin-1-yl)prop-2-en-1-one |

TABLE 2a-continued

Representative Compounds of Structure (II)

| No. | Structure | Name |
|---|---|---|
| II-3 | 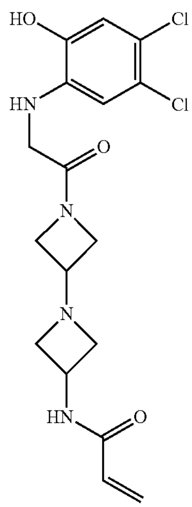 [SMILES: C=CC(=O)NC1CN(C2CN(C(=O)CNc3cc(Cl)c(Cl)cc3O)C2)C1] | N-(1'-(2-(4,5-dichloro-2-hydroxyphenyl-amino)acetyl)-1,3'-biazetidin-3-yl)acrylamide |
| II-4 | 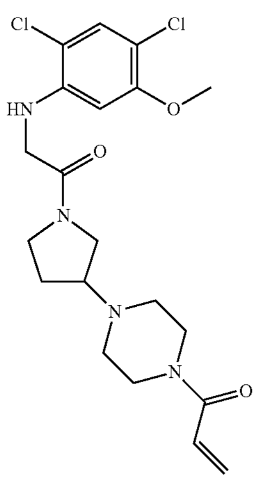 [SMILES: C=CC(=O)N1CCN(C2CCN(C(=O)CNc3cc(OC)c(Cl)cc3Cl)C2)CC1] | 1-4-(1-(2-(4,5-dichloro-2-hydroxyphenyl-amino)acetyl)pyrrolidin-3-yl)piperazin-1-yl)prop-2-en-1-one |
| II-5 | 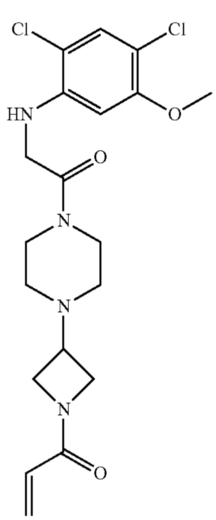 [SMILES: C=CC(=O)N1CC(N2CCN(C(=O)CNc3cc(OC)c(Cl)cc3Cl)CC2)C1] | 1-(3-(4-(2-(2,4-dichloro-5-methoxyphenyl-amino)acetyl)-piperazin-1-yl)azetidin-1-yl)prop-2-en-1-one |
| II-6 | | 1-(3-(4-(3-(4,5-dichloro-2-hydroxyphenyl)-propanoyl)piperazin-1-yl)azetidin-1-yl)prop-2-en-1-one |
| II-7 | | 1-(3-(4-(2-(4-chloro-2-hydroxy-5-methylphenylamino)-acetyl)piperazin-1-yl)pyrrolidin-1-yl)prop-2-en-1-one |
| II-8 | | 1-(3-(4-(2-(5-chloro-2-hydroxy-4-methylphenylamino)-acetyl)piperazin-1-yl)pyrrolidin-1-yl)prop-2-en-1-one |

TABLE 2a-continued

Representative Compounds of Structure (II)

| No. | Structure | Name |
|---|---|---|
| II-9 | 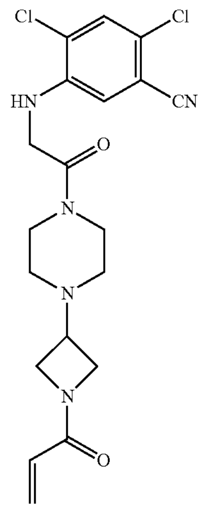 | 5-(2-(4-(1-acryloylazetidin-3-yl)piperazin-1-yl)-2-oxoethylamino)-2,4-dichlorobenzonitrile |
| II-10 | 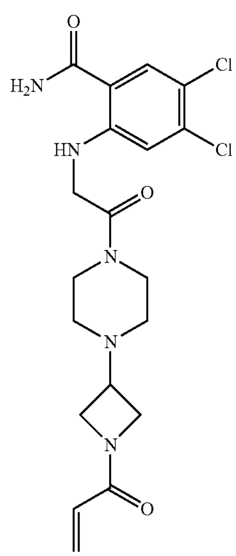 [SMILES: C=CC(=O)N1CC(N2CCN(C(=O)CNc3cc(Cl)c(Cl)cc3C(N)=O)CC2)C1] | 2-(2-(4-(1-acryloylazetidin-3-yl)piperazin-1-yl)-2-oxoethylamino)-4,5-dichlorobenzamide |
| II-11 | 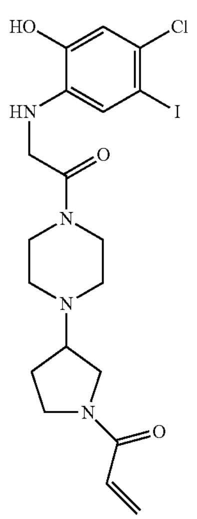 [SMILES: C=CC(=O)N1CCC(N2CCN(C(=O)CNc3cc(I)c(Cl)cc3O)CC2)C1] | 1-(3-(4-(2-(4-chloro-5-hydroxy-5-iodophenylamino)-acetyl)piperazin-1-yl)pyrrolidin-1-yl)prop-2-en-1-one |
| II-12 | | 1-(3-(4-(2-(4-chloro-5-ethyl-2-hydroxyphenylamino)-acetyl)piperazin-1-yl)pyrrolidin-1-yl)prop-2-en-1-one |
| II-13 | | 1-(3-(4-(2',5',6-trichloro-4-methoxybiphenyl-carbonyl)piperazin-1-yl)azetidin-1-yl)prop-2-en-1-one |
| II-14 | | 1-(3-(4-(2-(5-chloro-4-fluoro-2-hydroxyphenyl-amino)acetyl)piperazin-1-yl)azetidin-1-yl)prop-2-en-1-one |

TABLE 2a-continued

Representative Compounds of Structure (II)

| No. | Structure | Name |
|---|---|---|
| II-15 | 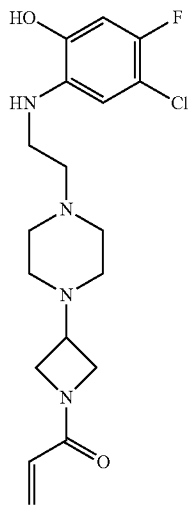 [SMILES: C=CC(=O)N1CC(N2CCN(CCNc3cc(Cl)c(F)cc3O)CC2)C1] | 1-(3-(4-(2-(4,5-dichloro-2-mino)ethyl)piperazin-1-yl)azetidin-1-yl)prop-2-en-1-one |
| II-16 | 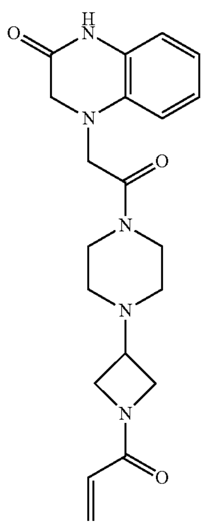 [SMILES: C=CC(=O)N1CC(N2CCN(C(=O)CN3CC(=O)Nc4ccccc43)CC2)C1] | 4-(2-(4-(1-acryloylazetidin-3-yl)piperazin-1-yl)-2-oxoethyl)-3,4-dihydroquinoxalin-2(1H)-one |
| II-17 | 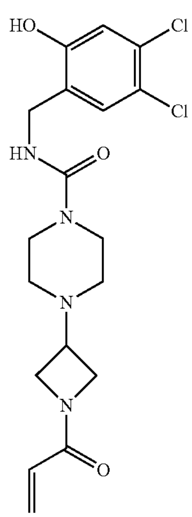 [SMILES: C=CC(=O)N1CC(N2CCN(C(=O)NCc3cc(Cl)c(Cl)cc3O)CC2)C1] | 1-(1-acryloylazetidin-3-yl)-N-(4,5-dichloro-2-hydroxybenzyl)-piperidine-4-carboxamide |
| II-18 | 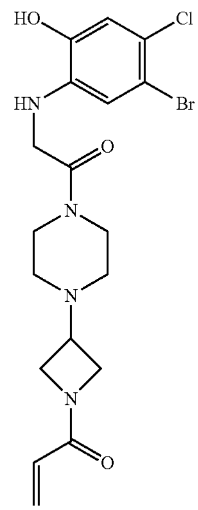 [SMILES: C=CC(=O)N1CC(N2CCN(C(=O)CNc3cc(Br)c(Cl)cc3O)CC2)C1] | 1-(3-(4-(2-(5-bromo-4-chloro-2-hydroxyphenyl-amino)acetyl)piperazin-1-yl)azetidin-1-yl)prop-2-en-1-one |
| II-19 | 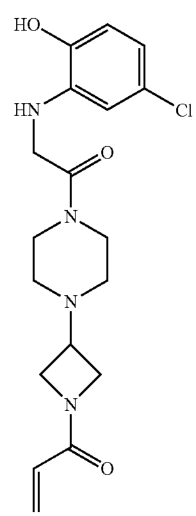 [SMILES: C=CC(=O)N1CC(N2CCN(C(=O)CNc3cc(Cl)ccc3O)CC2)C1] | 1-(3-(4-(2-(5-chloro-2-hydroxyphenyl-amino)acetyl)-piperazin-1-yl)azetidin-1-yl)prop-2-en-1-one |

TABLE 2a-continued

Representative Compounds of Structure (II)

| No. | Structure | Name |
|---|---|---|
| II-20 | 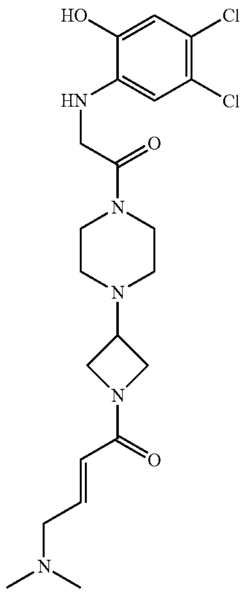 [SMILES: CN(C)C/C=C/C(=O)N1CC(N2CCN(C(=O)CNc3cc(Cl)c(Cl)cc3O)CC2)C1] | (E)-1-(3-(4-((4,5-dichloro-2-hydroxyphenyl)-glycyl)piperazin-1-yl)azetidin-1-yl)-4-(dimethylamino)but-2-en-1-one |
| II-21 | 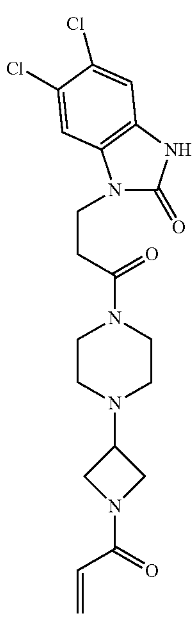 [SMILES: C=CC(=O)N1CC(N2CCN(C(=O)CCn3c(=O)[nH]c4cc(Cl)c(Cl)cc43)CC2)C1] | 1-(3-(4-(1-acryloylazetidin-3-yl)piperazin-1-yl)-3-oxopropyl)-5,6-dichloro-1H-benzo[d]imidazol-2(3H)-one |
| II-22 | 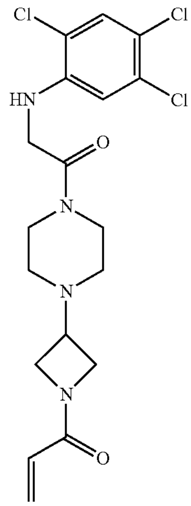 [SMILES: C=CC(=O)N1CC(N2CCN(C(=O)CNc3cc(Cl)c(Cl)cc3Cl)CC2)C1] | 1-(3-(4-(2-(2,4,5-trichlorophenyl-amino)acetyl)-piperazin-1-yl)azetidin-1-yl)prop-2-en-1-one |
| II-23 | 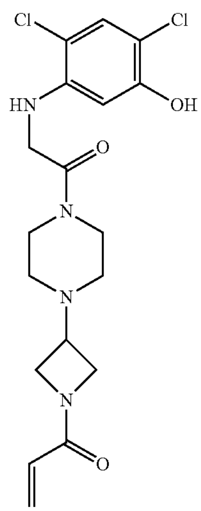 [SMILES: C=CC(=O)N1CC(N2CCN(C(=O)CNc3cc(O)c(Cl)cc3Cl)CC2)C1] | 1-(3-(4-(2-(2,4-dichloro-5-hydroxyphenyl-amino)acetyl)piperazin-1-yl)azetidin-1-yl)prop-2-en-1-one |
| II-24 | 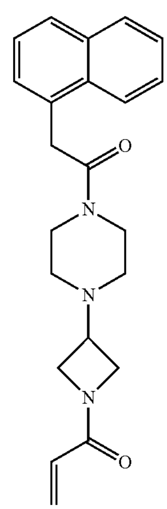 [SMILES: C=CC(=O)N1CC(N2CCN(C(=O)Cc3cccc4ccccc34)CC2)C1] | 1-(3-(4-(2-(naphthalen-1-yl)acetyl)piperazin-1-yl)azetidin-1-yl)prop-2-en-1-one |

TABLE 2a-continued

Representative Compounds of Structure (II)

| No. | Structure | Name |
|---|---|---|
| II-25 | 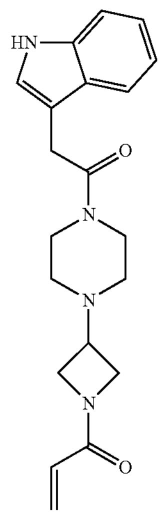 [SMILES: C=CC(=O)N1CC(N2CCN(C(=O)Cc3c[nH]c4ccccc34)CC2)C1] | 1-(3-(4-(2-(1H-indol-3-yl)acetyl)piperazin-1-yl)azetidin-1-yl)prop-2-en-1-one |
| II-26 | 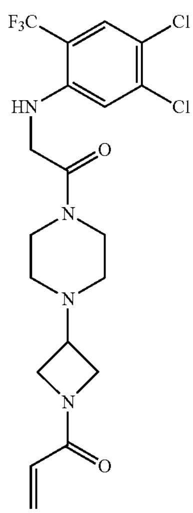 [SMILES: C=CC(=O)N1CC(N2CCN(C(=O)CNc3cc(Cl)c(Cl)cc3C(F)(F)F)CC2)C1] | 1-(3-(4-(2-(4,5-dichloro-2-(trifluoromethyl)-phenylamino)acetyl)-piperazin-1-yl)azetidin-1-yl)prop-2-en-1-one |
| II-27 | 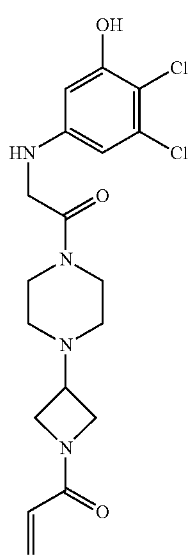 [SMILES: C=CC(=O)N1CC(N2CCN(C(=O)CNc3cc(O)c(Cl)c(Cl)c3)CC2)C1] | 1-(3-(4-(2-(3,4-dichloro-5-hydroxyphenyl-amino)acetyl)piperazin-1-yl)azetidin-1-yl)prop-2-en-1-one |
| II-28 | | 1-(3-(4-(2-(4-bromo-5-chloro-2-hydroxyphenylamino)-cetyl)piperazin-1-yl)azetidin-1-yl)prop-2-en-1-one |
| II-29 | | 1-(3-(4-(2-(1H-indol-1-yl)acetyl)piperazin-1-yl)azetidin-1-yl)prop-2-en-1-one |
| II-30 | | 1-(3-(4-(2-(5,6-dichloro-1H-indol-1-yl)acetyl)piperazin-1-yl)azetidin-1-yl)prop-2-en-1-one |

TABLE 2a-continued

Representative Compounds of Structure (II)

| No. | Structure | Name |
|---|---|---|
| II-31 | 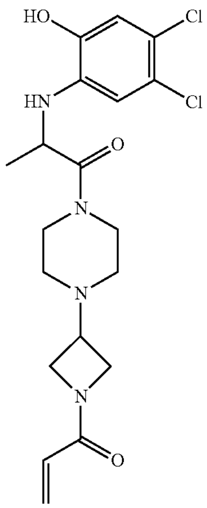 [SMILES: C=CC(=O)N1CC(N2CCN(C(=O)C(C)Nc3cc(Cl)c(Cl)cc3O)CC2)C1] | 1-(3-(4-(2-(4,5-dichloro-2-hydroxyphenylamino)propanoyl)piperazin-1-yl)azetidin-1-yl)prop-2-en-1-one |
| II-32 | 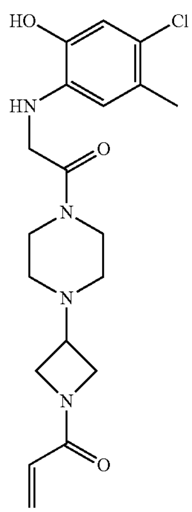 [SMILES: C=CC(=O)N1CC(N2CCN(C(=O)CNc3cc(C)c(Cl)cc3O)CC2)C1] | 1-(3-(4-(2-(4-chloro-2-hydroxy-5-methylphenylamino)acetyl)piperazin-1-yl)azetidin-1-yl)prop-2-en-1-one |
| II-33 | 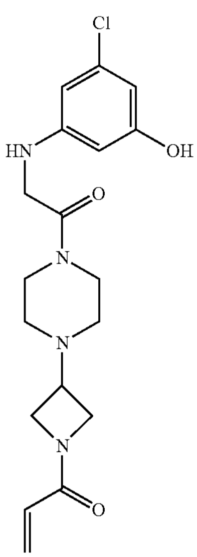 [SMILES: C=CC(=O)N1CC(N2CCN(C(=O)CNc3cc(O)cc(Cl)c3)CC2)C1] | 1-(3-(4-(2-(3-chloro-5-hydroxyphenylamino)acetyl)piperazin-1-yl)azetidin-1-yl)prop-2-en-1-one |
| II-34 | | 1-(3-(4-(2-(2-hydroxy-5-(methylsulfonyl)phenylamino)acetyl)piperazin-1-yl)azetidin-1-yl)prop-2-en-1-one |
| II-35 | | 1-(3-(4-(2-(4-chloro-5-cyclopropyl-2-hydroxyphenylamino)acetyl)piperazin-1-yl)azetidin-1-yl)prop-2-en-1-one |
| II-36 | | N-(1'-(2-(5-bromo-4-chloro-2-hydroxyphenylamino)acetyl)-1,3'-biazetidin-3-yl)acrylamide |

TABLE 2a-continued

Representative Compounds of Structure (II)

| No. | Structure | Name |
|---|---|---|
| II-37 | 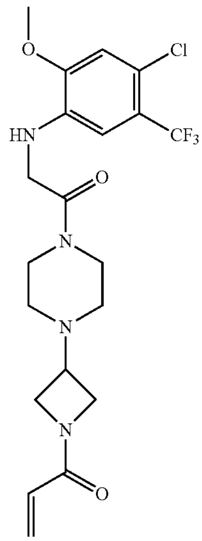 [SMILES: C=CC(=O)N1CC(N2CCN(C(=O)CNc3cc(C(F)(F)F)c(Cl)cc3OC)CC2)C1] | 1-(3-(4-(2-(4-chloro-2-methoxy-5-(trifluoromethyl)-phenylamino)acetyl)-piperazin-1-yl)azetidin-1-yl)prop-2-en-1-one |
| II-38 | 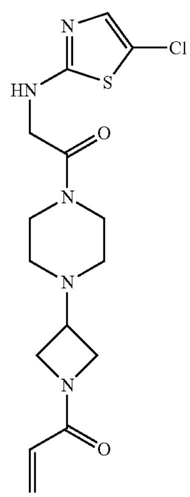 [SMILES: C=CC(=O)N1CC(N2CCN(C(=O)CNc3ncc(Cl)s3)CC2)C1] | 1-(3-(4-(2-(5-chlorothiazol-2-ylamino)acetyl)piperazin-1-yl)azetidin-1-yl)prop-2-en-1-one |
| II-39 | 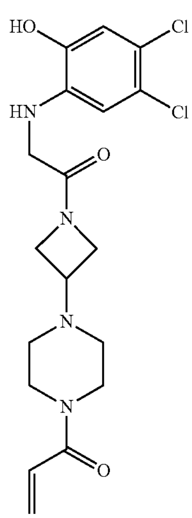 [SMILES: C=CC(=O)N1CCN(C2CN(C(=O)CNc3cc(Cl)c(Cl)cc3O)C2)CC1] | 1-(4-(1-(2-(4,5-dichloro-2-hydroxyphenyl-amino)acetyl)azetidin-3-yl)piperazin-1-yl)prop-2-en-1-one |
| II-40 | | 2-(4,5-dichloro-2-hydroxyphenylamino)-1-(3-(4-(vinylsulfonyl)-piperazin-1-yl)azetidin-1-yl)ethanone |
| II-41 | | 2-(4,5-dichloro-2-hydroxyphenylamino)-1-(4-(1-(vinylsulfonyl)-pyrrolidin-3-yl)piperazin-1-yl)ethanone |
| II-42 | | 4-(2-(4-(1-acryloylazetidin-3-yl)piperazin-1-yl)-2-oxoethyl)-3,4-dihydroquinoxalin-2(1H)-one |

TABLE 2a-continued

Representative Compounds of Structure (II)

| No. | Structure | Name |
|---|---|---|
| II-43 | 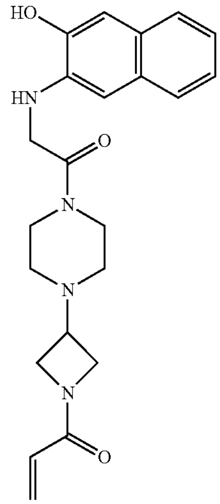 [SMILES: C=CC(=O)N1CC(N2CCN(C(=O)CNc3cc4ccccc4cc3O)CC2)C1] | 1-(3-(4-(2-(3-hydroxynaphthalen-2-ylamino)acetyl)-piperazin-1-yl)azetidin-1-yl)prop-2-en-1-one |
| II-44 | 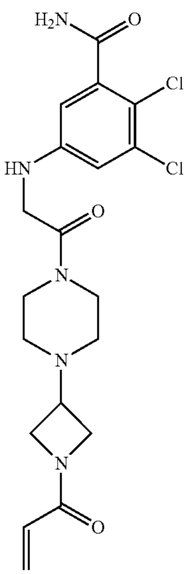 [SMILES: C=CC(=O)N1CC(N2CCN(C(=O)CNc3cc(Cl)c(Cl)c(C(N)=O)c3)CC2)C1] | 5-(2-(4-(1-acryloylazetidin-3-yl)piperazin-1-yl)-2-oxoethylamino)-2,3-dichlorobenzamide |
| II-45 | 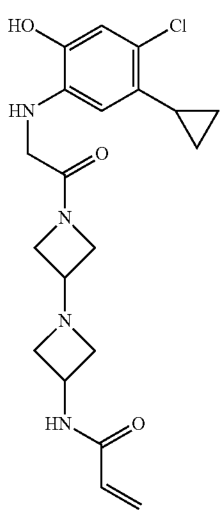 [SMILES: C=CC(=O)NC1CN(C2CN(C(=O)CNc3cc(C4CC4)c(Cl)cc3O)C2)C1] | N-(1'-(2-(4-chloro-5-cyclopropyl-2-hydroxyphenylamino)acetyl)-1,3'-biazetidin-3-yl)acrylamide |
| II-46 | 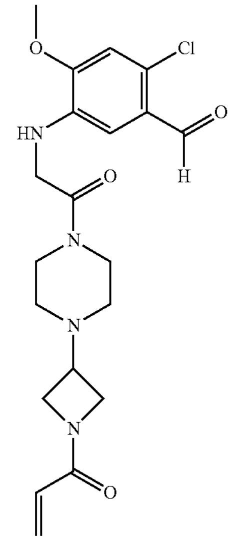 [SMILES: C=CC(=O)N1CC(N2CCN(C(=O)CNc3cc(C=O)c(Cl)cc3OC)CC2)C1] | 5-(2-(4-(1-acryloylazetidin-3-yl)piperazin-1-yl)-2-oxoethylamino)-2-chloro-4-methoxybenzaldehyde |
| II-47 | 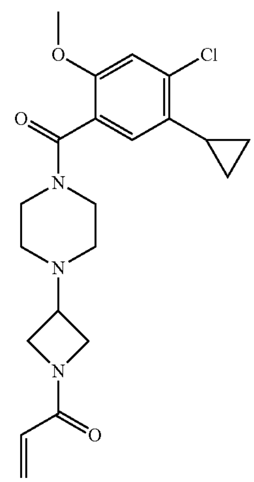 [SMILES: C=CC(=O)N1CC(N2CCN(C(=O)c3cc(C4CC4)c(Cl)cc3OC)CC2)C1] | 1-(3-(4-(4-chloro-5-cyclopropyl-2-methoxybenzoyl)-piperazin-1-yl)azetidin-1-yl)prop-2-en-1-one |
| II-48 | 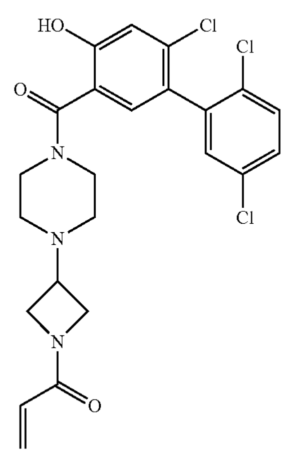 [SMILES: C=CC(=O)N1CC(N2CCN(C(=O)c3cc(-c4cc(Cl)ccc4Cl)c(Cl)cc3O)CC2)C1] | 1-(3-(4-(2',5',6-trichloro-4-hydroxybiphenyl-carbonyl)piperazin-1-yl)azetidin-1-yl)prop-2-en-1-one |

TABLE 2a-continued

Representative Compounds of Structure (II)

| No. | Structure | Name |
|---|---|---|
| II-49 | 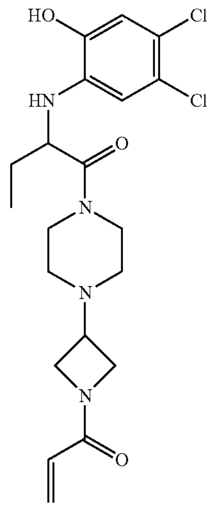 [SMILES: C=CC(=O)N1CC(N2CCN(C(=O)C(CC)Nc3cc(Cl)c(Cl)cc3O)CC2)C1] | 1-(4-(1-acryloylazetidin-3-yl)piperazin-1-yl)-2-(4,5-dichloro-2-hydroxyphenyl-amino)butan-1-one |
| II-50 | 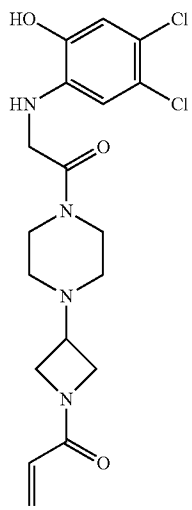 [SMILES: C=CC(=O)N1CC(N2CCN(C(=O)CNc3cc(Cl)c(Cl)cc3O)CC2)C1] | 1-(3-(4-(2-(4-chloro-2-hydroxy-5-isopropylphenyl-amino)acetyl)piper-azin-1-yl)azetidin-1-yl)prop-2-en-1-one |
| II-51 | 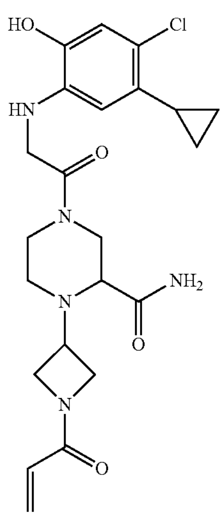 [SMILES: C=CC(=O)N1CC(N2CCN(C(=O)CNc3cc(C4CC4)c(Cl)cc3O)CC2C(N)=O)C1] | 1-(1-acryloylazetidin-3-yl)-4-(2-(4-chloro-5-cyclopropyl-2-hydroxyphenyl-amino)acetyl)-piperazine-2-carboxamide |
| II-52 | | 1-(3-(4-(2-(5-chloro-4-ethyl-2-hydroxyphenylamino)-acetyl)piperazin-1-yl)azetidin-1-yl)prop-2-en-1-one |
| II-53 | | 1-(3-(4-(2-(4-chloro-5-cyclobutyl-2-hydroxyphenyl-amino)acetyl)piper-azin-1-yl)azetidin-1-yl)prop-2-en-1-one |
| II-54 | | 1-(3-(4-(2-(4-chloro-5-cyclopropyl-2-hydroxyphenylamino)-acetyl)-2-(hydroxymethyl)-piperazin-1-yl)azetidin-1-yl)prop-2-en-1-one |

TABLE 2a-continued

Representative Compounds of Structure (II)

| No. | Structure | Name |
|---|---|---|
| II-55 | 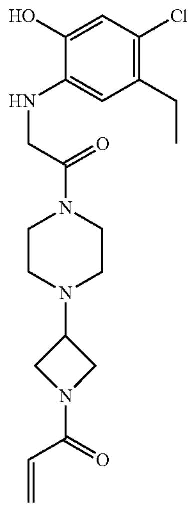 [SMILES: C=CC(=O)N1CC(N2CCN(C(=O)CNc3cc(CC)c(Cl)cc3O)CC2)C1] | 1-(3-(4-(2-(4-chloro-5-ethyl-2-hydroxyphenyl-amino)acetyl)-piperazin-1-yl)azetidin-1-yl)prop-2-en-1-one |
| II-56 | 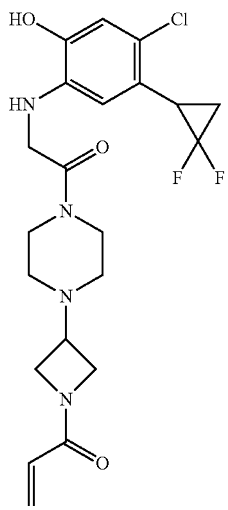 [SMILES: C=CC(=O)N1CC(N2CCN(C(=O)CNc3cc(C4CC4(F)F)c(Cl)cc3O)CC2)C1] | 1-(3-(4-(2-(4-chloro-5-(2,2-difluorocyclopropyl)-2-hydroxyphenylamino)-acetyl)piperazin-1-yl)azetidin-1-yl)prop-2-en-1-one |
| II-57 | 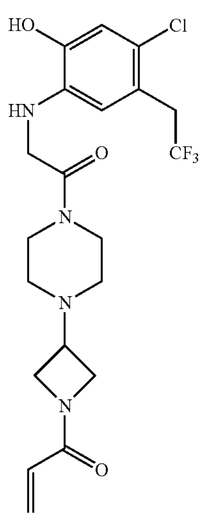 [SMILES: C=CC(=O)N1CC(N2CCN(C(=O)CNc3cc(CC(F)(F)F)c(Cl)cc3O)CC2)C1] | 1-(3-(4-(2-(4-chloro-2-hydroxy-5-(2,2,2-trifluoroethyl)-phenylamino)acetyl)-piperazin-1-yl)azetidin-1-yl)prop-2-en-1-one |
| II-58 | | 1-(3-(4-(3-(4-chloro-5-cyclopropyl-2-hydroxyphenyl)-propanoyl)piperazin-1-yl)azetidin-1-yl)prop-2-en-1-one |
| II-59 | | 1-(3-(4-(2-(4-chloro-5-cyclobutyl-2-hydroxyphenyl-amino)propanoyl)-piperazin-1-yl)azetidin-1-yl)prop-2-en-1-one |
| II-60 | | 1-(3-(4-(2-(4-chloro-5-cyclopropyl-2-hydroxyphenyl-amino)acetyl)-2-methylpiperazin-1-yl)azetidin-1-yl)prop-2-en-1-one |

TABLE 2a-continued

Representative Compounds of Structure (II)

| No. | Structure | Name |
|---|---|---|
| II-61 | | 1-(3-(4-(2-(5,6-dichloro-1H-indol-3-yl)acetyl)piperazin-1-yl)azetidin-1-yl)prop-2-en-1-one |
| II-62 | | (E)-1-(4-(1-acryloylazetidin-3-yl)piperazin-1-yl)-3-(4-chloro-5-cyclopropyl-2-hydroxyphenyl)prop-2-en-1-one |
| II-63 | 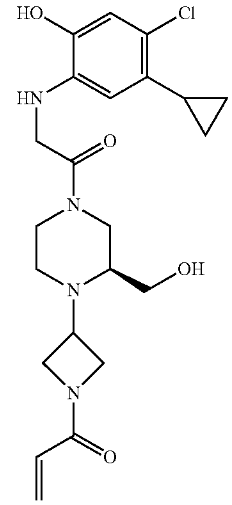 [SMILES: C=CC(=O)N1CC(N2CCN(C(=O)CNc3cc(C4CC4)c(Cl)cc3O)C[C@H]2CO)C1] | (S)-1-(3-(4-(2-(4-chloro-5-cyclopropyl-2-hydroxyphenyl-amino)acetyl)-2-(hydroxymethyl)-piperazin-1-yl)azetidin-1-yl)prop-2-en-1-one |
| II-64 | 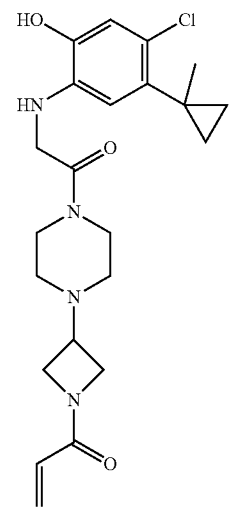 [SMILES: C=CC(=O)N1CC(N2CCN(C(=O)CNc3cc(C4(C)CC4)c(Cl)cc3O)CC2)C1] | 1-(3-(4-(2-(4-chloro-2-hydroxy-5-(1-methylcyclopropyl)-phenylamino)-acetyl)piperazin-1-yl)azetidin-1-yl)prop-2-en-1-one |
| II-65 | 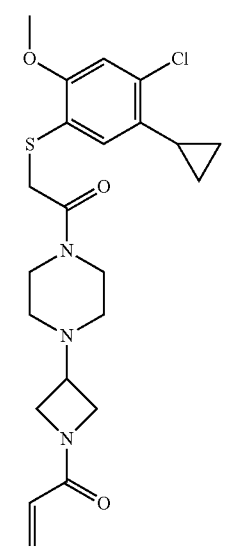 [SMILES: C=CC(=O)N1CC(N2CCN(C(=O)CSc3cc(C4CC4)c(Cl)cc3OC)CC2)C1] | 1-(3-(4-(2-(4-chloro-5-cyclopropyl-2-methoxyphenyl-thio)acetyl)piperazin-1-yl)azetidin-1-yl)prop-2-en-1-one |

TABLE 2a-continued

Representative Compounds of Structure (II)

| No. | Name |
|---|---|
| II-66 | 4-(1-acryloylazetidin-3-yl)-N-(5-bromo-4-chloro-2-hydroxybenzyl)piperazine-1-carboxamide |
| II-67 | (S)-1-(3-(4-(2-(4-chloro-5-cyclopropyl-2-hydroxyphenylamino)propanoyl)piperazin-1-yl)azetidin-1-yl)prop-2-en-1-one |
| II-68 | (R)-1-(3-(4-(2-(4-chloro-5-cyclopropyl-2-hydroxyphenylamino)propanoyl)piperazin-1-yl)azetidin-1-yl)prop-2-en-1-one |
| II-69 | (S)-1-(3-(4-(2-(4-chloro-5-ethyl-2-hydroxyphenylamino)propanoyl)piperazin-1-yl)azetidin-1-yl)prop-2-en-1-one |
| II-70 | (R)-1-(3-(4-(2-(4-chloro-5-ethyl-2-hydroxyphenylamino)propanoyl)piperazin-1-yl)azetidin-1-yl)prop-2-en-1-one |
| II-71 | 2-(2-(4-(1-acryloylazetidin-3-yl)piperazin-1-yl)-2-oxoethylamino)-5-chloro-4-cyclopropylbenzonitrile |

TABLE 2a-continued

Representative Compounds of Structure (II)

| No. | Structure | Name |
|---|---|---|
| II-72 | 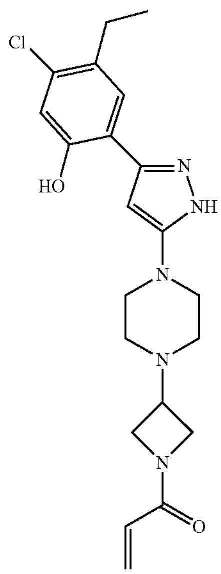 [SMILES: C=CC(=O)N1CC(N2CCN(c3cc(-c4cc(CC)c(Cl)cc4O)n[nH]3)CC2)C1] | 1-(3-(4-(3-(4-chloro-5-ethyl-2-hydroxyphenyl)-1H-pyrazol-5-yl)piperazin-1-yl)azetidin-1-yl)prop-2-en-1-one |
| II-73 | 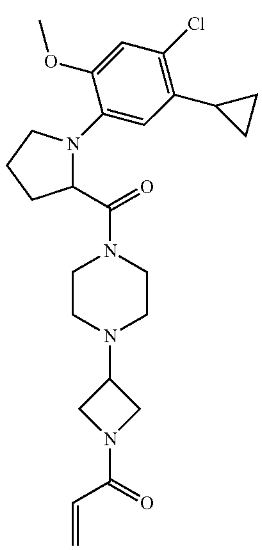 [SMILES: C=CC(=O)N1CC(N2CCN(C(=O)C3CCCN3c3cc(C4CC4)c(Cl)cc3OC)CC2)C1] | 1-(3-(4-(1-(4-chloro-5-cyclopropyl-2-methoxyphenyl)-pyrrolidine-2-carbonyl)piperazin-1-yl)azetidin-1-yl)prop-2-en-1-one |
| II-74 |  | 1-(3-(4-(2-(5-chloro-4-ethylpyridin-2-ylamino)acetyl)-piperazin-1-yl)azetidin-1-yl)prop-2-en-1-one |
| II-75 |  | 1-(3-(4-(2-(4,5-dichloro-7-methoxy-1H-indol-1-yl)acetyl)piperazin-1-yl)azetidin-1-yl)prop-2-en-1-one |

TABLE 2a-continued

Representative Compounds of Structure (II)

| No. | Structure | Name |
|---|---|---|
| II-76 | (structure shown) | 1-(3-(4-(1-(4-chloro-5-ethyl-2-methoxyphenyl)piperidin-3-yl)piperazin-1-yl)azetidin-1-yl)prop-2-en-1-one |

Compounds of structure II are prepared according to procedures well-known or derivable by one of ordinary skill in the art, for example by procedures analogous to those exemplified in the examples provided below. Each of the compounds in Table 2a was prepared in such a manner and analyzed by mass spectrometry and/or $^1$H NMR. The mass spectrum ([M+H$^+$] or [M+Na$^+$]) and/or NMR spectrum was found to be consistent with the structures in Table 2a. Mass spectrometry data for the compounds in Table 2a are provided in Table 2b.

TABLE 2b

Experimental Mass Spectral Data for Compounds in Table 2a

| No. | [M + H$^+$] | No. | [M + H$^+$] | No. | [M + H$^+$] | No. | [M + H$^+$] |
|---|---|---|---|---|---|---|---|
| II-1 | 411.30 | II-2 | 425.25 | II-3 | 399.20 | II-4 | 427.30 |
| II-5 | 449.25* | II-6 | 410.25 | II-7 | 429.35* | II-8 | 407.35 |
| II-9 | 422.25 | II-10 | 462.25* | II-11 | 519.25 | II-12 | 443.30* |
| II-13 | 532.25* | II-14 | 395.30 | II-15 | 399.25 | II-16 | 419.25 |
| II-17 | 434.25* | II-18 | 457.35 | II-19 | 379.30 | II-20 | 470.35 |
| II-21 | 450.35 | II-22 | 433.05 | II-23 | 435.25* | II-24 | 386.25* |
| II-25 | 351.35 | II-26 | 487.30* | II-27 | 413.30 | II-28 | 479.20* |
| II-29 | 353.30 | II-30 | 421.30 | II-31 | 449.25* | II-32 | 393.30 |
| II-33 | 377.30$^+$ | II-34 | 423.35 | II-35 | 441.30* | II-36 | 445.20 |
| II-37 | 461.30 | II-38 | 368.30$^+$ | II-39 | 411.20 | II-40 | 447.25$^+$ |
| II-41 | 463.20 | II-42 | 382.40$^+$ | II-43 | 417.35* | II-44 | 440.30 |
| II-45 | 405.35 | II-46 | 421.30 | II-47 | 404.35 | II-48 | 494.30 |
| II-49 | 441.30 | II-50 | 421.35 | II-51 | 462.45 | II-52 | 407.40 |
| II-53 | 433.40 | II-54 | 449.35 | II-55 | 407.30 | II-56 | 455.20 |
| II-57 | 461.40 | II-58 | 418.40 | II-59 | 447.40 | II-60 | 433.45 |
| II-61 | 421.25 | II-62 | 416.35 | II-63 | 449.40 | II-64 | 433.35 |
| II-65 | 451.30 | II-66 | 459.25 | II-67 | 433.20 | II-68 | 433.40 |
| II-69 | 421.35 | II-70 | 421.35 | II-71 | 428.35 | II-72 | 416.35 |
| II-73 | 473.90 | II-74 | 392.30 | II-75 | 451.30 | II-76 | 447.85 |

*[M + Na]$^+$
$^+$[M − H]$^−$

General Reaction Scheme 18 illustrates an exemplary procedure for preparing compounds of structure (II).

General Reaction Scheme 18

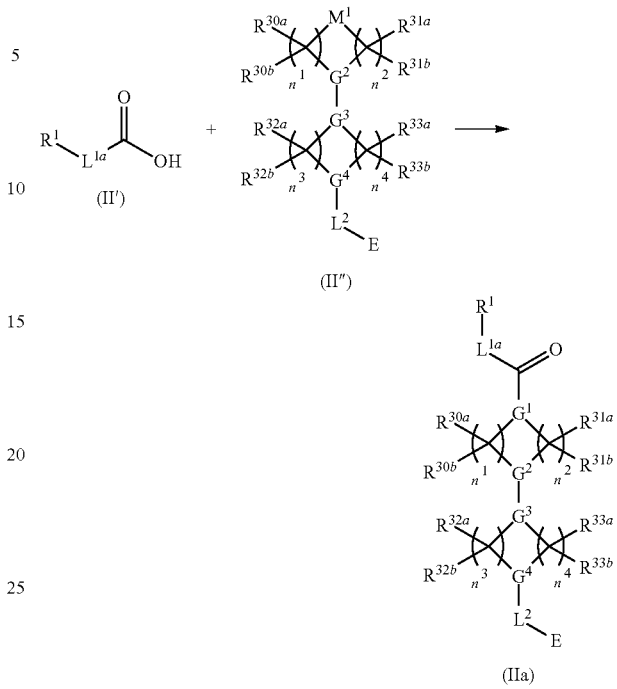

Referring to General Reaction Scheme I, (II') and (II") are available from commercial sources and/or are easily prepared according to procedures known in the art. All variables on (II') and (II"), with the exception of M$^1$, are as defined above. In some procedures, M$^1$ is NH. Briefly, an appropriately substituted acid (II') is activated and reacted with an appropriately substituted heterocycle (II") under appropriate coupling conditions. The L$^2$-E moiety may be present in (II") as illustrated or may be installed after coupling For example L$^2$-E may be installed before or after coupling via acylation (or thioacylation) using a reagent such as an acid chloride or thionyl chloride.

It should be noted that variations of the above procedure are possible, some of which are exemplified in the examples. For example, in some procedures (II") is monocyclic and the second cyclic moiety is added after the coupling step. In other procedures, the acid moiety is present on the cyclic moiety (II") and R$^1$ is appropriately substituted with a nucleophilic moiety to enable coupling to form (IIa).

Various other options are available to one of ordinary skill in the art to add various substituents and or modify or reorder the above described steps to arrive at different embodiments of compounds of structure II. It should also be noted that various substitutions on (II') and/or (II") can be present during the coupling step (in protected or unprotected form) or the substituents can be added after (II') and (II") are coupled. Methods for inclusion of these substituents are known in the art.

It is understood that although an exemplary procedure for prepare (IIa) is provided above, other compounds of structure (II) can be prepared by analogous methods. For example, the carbonyl of (IIa) may be reduced to form compounds of structure (II) wherein L$^1$ does not comprise a carbonyl. Embodiments wherein L$^1$ is heterocycloalkylene or heteroarylene can be prepared from analogous methods, for example by use of Buchwald chemistry to include the heterocycloalkylene or heteroarylene portion. Other methods for preparation of different compounds of structure (II) are known in the art.

Briefly, an appropriately substituted acid is reacted with an appropriately substituted heterocycle under amide coupling conditions. Acylation (or thioacylation) using a reagent such as an acid chloride or thionyl chloride results in compounds of structure (II). Various options are available to one of ordinary skill in the art to add various substituents and/or modify or reorder the above described steps to arrive at different embodiments of compounds of structure (II). The appropriate acid is purchased commercially or made according to well-known procedures.

3. Compounds of Structure (III)

In still other embodiments, the compound used in combination with one or more additional therapeutic agent has the following structure (III):

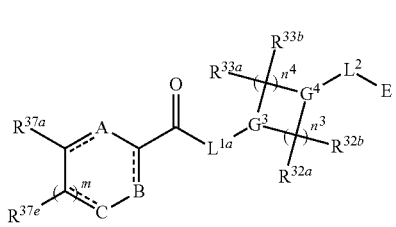

(III)

or a pharmaceutically acceptable salt, tautomer, stereoisomer or prodrug thereof, wherein:

A is $CR^{37b}$, N or $NR^{38a}$;

B is $CR^{37c}$, N, $NR^{38b}$ or S

C is $CR^{37d}$, N, $NR^{38e}$ or S $G^3$ and $G^4$ are each independently N or CR, wherein R is H, cyano, halo or $C^1$-$C^6$alkyl;

$L^{1a}$ is a bond, —NH—, alkylene or heteroalkylene $L^2$ is a bond or alkylene;

$R^{32a}$ and $R^{32b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; or $R^{32a}$ and $R^{32b}$ join to form a carbocyclic or heterocyclic ring; or $R^{32a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{32b}$ joins with $R^{33b}$ to form a carbocyclic or heterocyclic ring;

$R^{33a}$ and $R^{33b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; or $R^{33a}$ and $R^{33b}$ join to form a carbocyclic or heterocyclic ring; or $R^{33a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{33b}$ joins with $R^{32b}$ to form a carbocyclic or heterocyclic ring;

$R^{37a}$, $R^{37b}$, $R^{37c}$, $R^{37d}$ and $R^{37e}$ are each independently H, halo, oxo, hydroxyl, cyano, aminocarbonyl, formyl, $C_1$-$C_6$alkyl, $C_1$-$C_6$alkylsulfonyl, $C_1$-$C_6$haloalkyl, $C_3$-$C_8$cycloalkyl, $C_1$-$C_6$alkoxy, $C_1$-$C_6$hydroxylalkyl, $C_1$-$C_6$alkoxyalkyl, $C_1$-$C_6$aminoalkyl, heterocyclyl or aryl;

$R^{38a}$, $R^{38b}$ and $R^{38c}$ are each independently H, $C_1$-$C_6$alkyl or aryl;

$n^3$ and $n^4$ are each independently 1, 2 or 3 m is 0 or 1;

═══ is a single or double bond such that all valences are satisfied; and

E is an electrophilic moiety capable of forming a covalent bond with the cysteine residue at position 12 of a KRAS, HRAS or NRAS G12C mutant protein.

In various other embodiments, the compound has one of the following structures (IIIa), (IIIb), (IIIc), (IIId), (IIIe), (IIIf) or (IIIg):

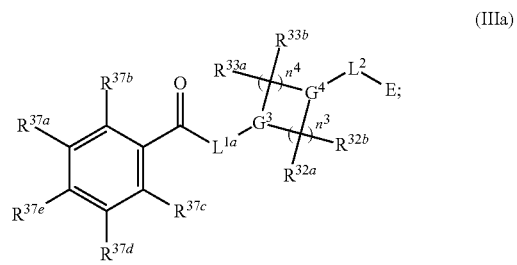

(IIIa)

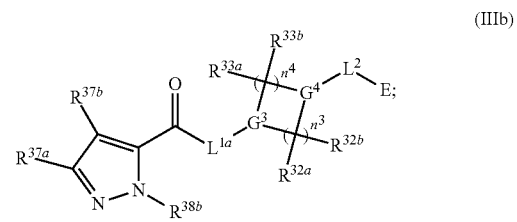

(IIIb)

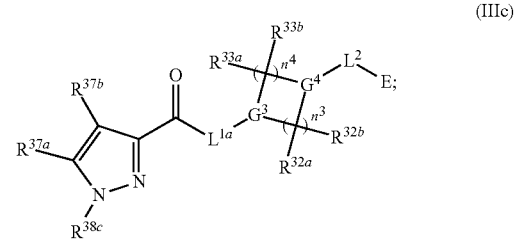

(IIIc)

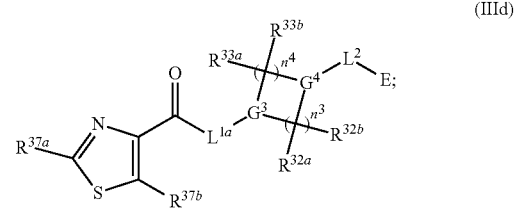

(IIId)

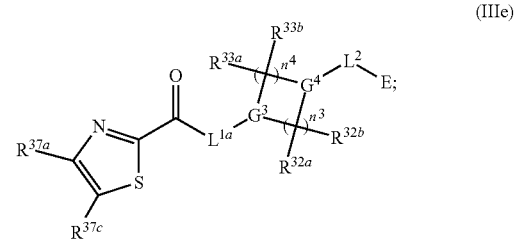

(IIIe)

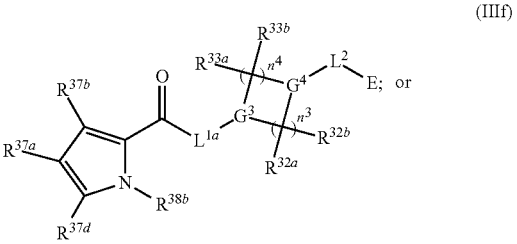

(IIIf)

-continued (IIIg)

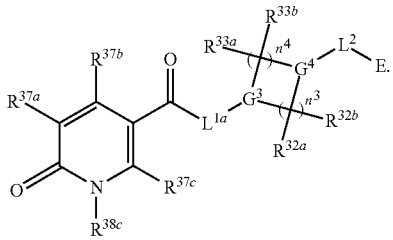

In some different embodiments, the compound has one of the following structures (IIIa'), (IIIb'), (IIIc'), (IIId'), (IIIe'), (IIIf'), or (IIIg')

(IIIa')

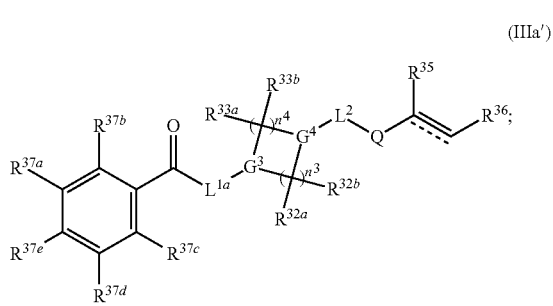

(IIIb')

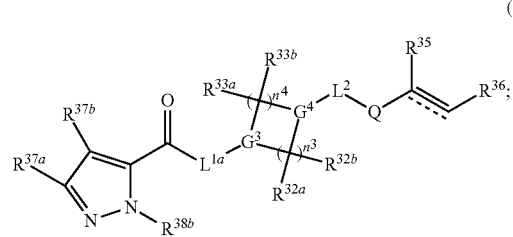

(IIIc')

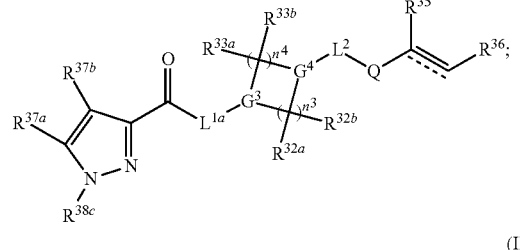

(IIId')

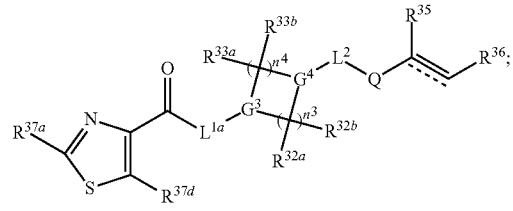

(IIIe')

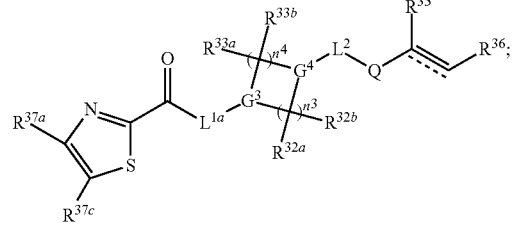

-continued (IIIf')

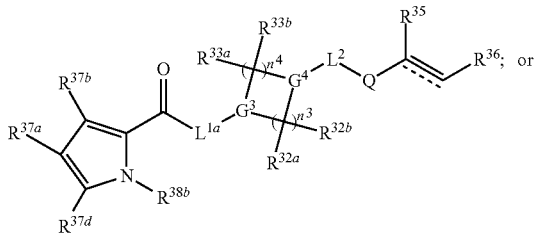

(IIIg')

wherein:

Q is —C(=O)—, —NR$^{34}$C(=O)—, —S(=O)$_2$— or —NR$^{34}$S(=O)$_2$—;

R$^{34}$ is H, C$_1$-C$_6$alkyl or hydroxylalkyl;

≡ is a carbon-carbon double bond or a carbon-carbon triple bond; and

R$^{35}$ and R$^{36}$ are each independently H, cyano, C$_1$-C$_6$alkyl, aminoalkyl, alkylaminoalkyl, or hydroxylalkyl or R$^{35}$ and R$^{36}$ join to form a carbocyclic or heterocyclic ring when ≡ is a double bond; or R$^{35}$ is absent and R$^{36}$ is H, C$_1$-C$_6$alkyl, aminoalkyl, alkylaminoalkyl or hydroxylalkyl when ≡ is a triple bond.

In some specific embodiments of the foregoing compounds of structure (III), and substructures thereof, R$^{37a}$ is halo, aryl or heteroaryl. In further such embodiments, R$^{35}$ and R$^{36}$ are each H.

In various other embodiments, G$^3$ is N and G$^4$ is CR, for example CH.

In some different embodiments, G$^3$ is CR, for example CH, and G$^4$ is N.

In still other embodiments, G$^3$ is N and G$^4$ is N.

In various other embodiments, n$^3$ is 2 and n$^4$ is 2. In still other embodiments, n$^3$ is 1 and n$^4$ is 1. In some more embodiments, n$^3$ is 2 and n$^4$ is 1.

In other of the foregoing embodiments, R$^{37a}$, R$^{37b}$, R$^{37c}$, R$^{37d}$ and R$^{37e}$ are each independently H, —OH, halo, oxo, C$_1$-C$_6$alkyl, C$_1$-C$_6$alkoxy, heterocyclyl or aryl.

In still other embodiments, R$^{37a}$, R$^{37b}$, R$^{37c}$, R$^{37d}$ and R$^{37e}$ are each independently H, —OH, fluoro, chloro, bromo, iodo, oxo, methyl, methoxy, heteroaryl or aryl.

In some embodiments, R$^{37a}$ or R$^{37e}$ is aryl. In some more specific embodiments, R$^{37a}$ is aryl, such as phenyl.

In some different embodiments, the aryl is unsubstituted. In some other embodiments, the aryl is substituted. For example, in some embodiments the aryl is substituted with one or more halo substituents. In some of these embodiments, the halo substituents are selected from fluoro and chloro.

In still other embodiments, R$^{37a}$ is heteroaryl. In some of these embodiments, the heteroaryl is unsubstituted. In various other embodiments, the heteroaryl is substituted. In some more embodiments, the heteroaryl comprises nitrogen, sulfur or a combination thereof.

In some more specific embodiments, the heteroaryl is thiophenyl.

In other of the foregoing embodiments, $R^{37a}$ is halo. For example, in some embodiments halo is chloro, bromo or iodo.

In some embodiments, $R^{37a}$ or $R^{37e}$ has one of the following structures:

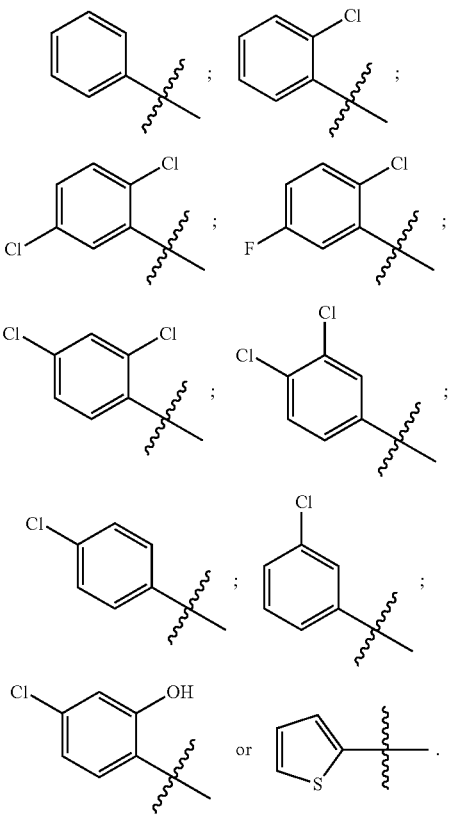

In still other embodiments, $R^{37a}$ has one of the following structures:

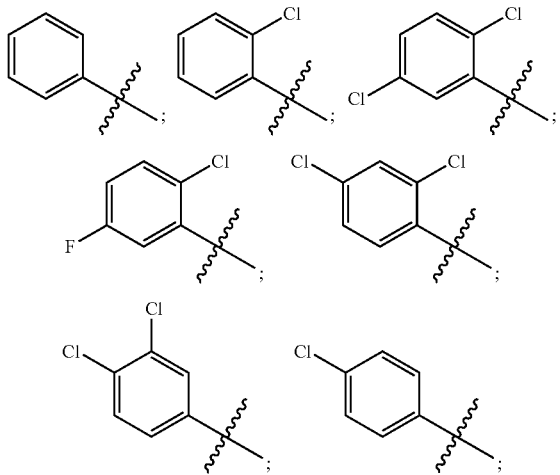

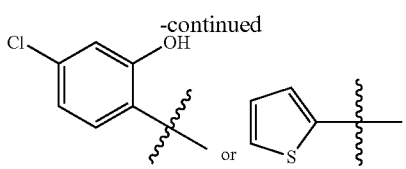

In various different embodiments, $R^{38a}$, $R^{38b}$ and $R^{38c}$ are each independently H or aryl. In still other embodiments, $R^{38a}$, $R^{38b}$ and $R^{38c}$ are each independently H.

In some other different embodiments, $R^{38c}$ is aryl. For example, in some embodiments the aryl is substituted with one or more halo substituents. In some of these embodiments, halo is chloro.

In some other embodiments of the compounds of structure (III), Q is —C(=O)—. In some other embodiments, Q is —S(=O)$_2$—. In still other embodiments, Q is —NR$^{34}$C(=O)—. In still more other embodiments, Q is —NR$^{34}$S(=O)$_2$—.

In some more specific embodiments, $R^{34}$ is H. For example, in some embodiments $R^{34}$ is hydroxylalkyl, such as 2-hydroxylalkyl.

In other of the foregoing embodiments, at least one of $R^{35}$ or $R^{36}$ is H. For example, in some embodiment search of $R^{35}$ and $R^{36}$ are H.

In various other embodiments, $R^{36}$ is alkylaminoalkyl. For example, in some embodiments $R^{36}$ has the following structure:

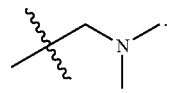

In some different embodiments, $R^{36}$ is hydroxylalkyl, for example 2-hydroxylalkyl In various other embodiments, $R^{35}$ and $R^{36}$ join to form a ring. In some of these embodiments, the ring is a cyclopentene, cyclohexene or phenyl ring.

In other of the foregoing embodiments, E has one of the following structures:

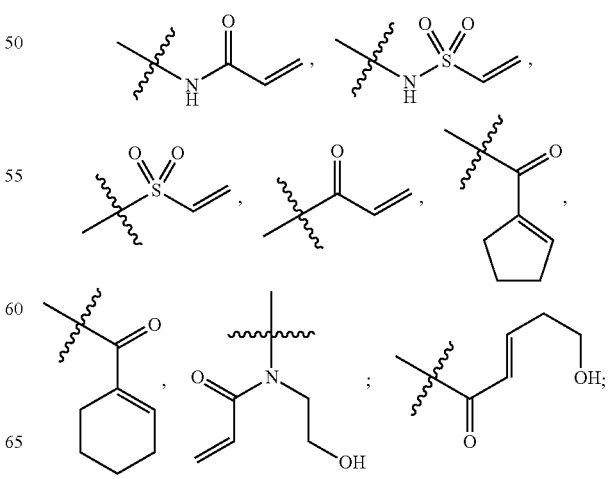

-continued

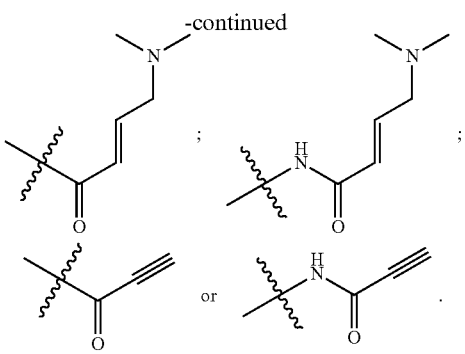

In some embodiments, E is

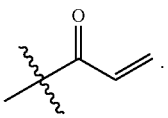 [SMILES: *C(=O)C=C]

In some more of the foregoing embodiments, $L^1$ is heteroalkylene. In some more embodiments, the heteroalkylene is unsubstituted. In some different embodiments, the heteroalkylene is substituted.

In various other embodiments, $L^1$ is aminoalkylene. For example, in some embodiments $L^1$ is —CH$_2$CH$_2$NH—.

In some different embodiments, $L^{1a}$ is a bond.

In some embodiments, $L^{1a}$ is alkylene, alkenylene, heteroalkylene or heterocycloalkylene. In some other embodiments, $L^{1a}$ is alkylene or heteroalkylene. In some of these embodiments, $L^{1a}$ is substituted alkylene. In various other embodiments, $L^{1a}$ is unsubstituted alkylene. For example, in some embodiments $L^{1a}$ is

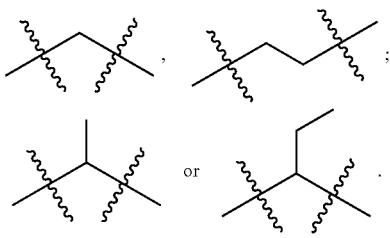

In some different embodiments, $L^{1a}$ is substituted heteroalkylene. In some other embodiments, $L^{1a}$ is unsubstituted heteroalkylene. In some of the foregoing embodiments, $L^{1a}$ is aminoalkylene or thioalkylene, for example aminoalkylene. For example, in some embodiments $L^{1a}$ has one of the following structures:

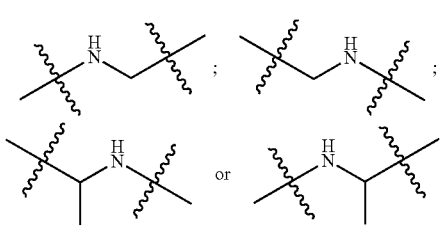

In other embodiments, $L^{1a}$ is

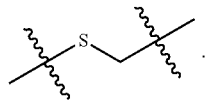 [SMILES: *CS*]

In other embodiments, $L^{1a}$ is substituted alkenylene. In different embodiments, $L^{1a}$ is unsubstituted alkenylene. In some more specific embodiments, $L^{1a}$ has the following structure:

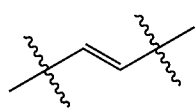

In yet other embodiments, $L^{1a}$ is substituted heterocycloalkylene. In some other embodiments, $L^{1a}$ is unsubstituted heterocycloalkylene. For Example, in some embodiments, $L^{1a}$ has the following structure:

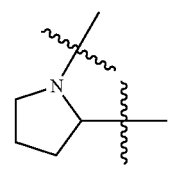

In some of the foregoing embodiments, $L^2$ is a bond.

In various other embodiments, $L^2$ is substituted alkylene. In still other embodiments, $L^2$ is unsubstituted alkylene.

In some embodiments of any of the foregoing compounds of structure (III):

$R^{32a}$ and $R^{32b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl; and $R^{33a}$ and $R^{33b}$ are, at each occurrence, independently H, —OH, —NH$_2$, —CO$_2$H, cyano, cyanoalkyl, $C_1$-$C_6$alkyl, $C_3$-$C_8$cycloalkyl, hydroxylalkyl, aminoalkyl, carboxylalkyl or aminocarbonyl.

In other embodiments, $R^{32a}$, $R^{32b}$, $R^{33a}$ or $R^{33b}$ are selected from H, $C_1$-$C_8$alkyl, hydroxylalkyl, cyano, cyanoalkyl and aminocarbonyl, for example H, hydroxyl alkyl and cyano.

In other of the foregoing embodiments, at least one of $R^{32a}$, $R^{32b}$, $R^{33a}$ or $R^{33b}$ is H. For example, in some embodiments each of $R^{32a}$, $R^{32b}$, $R^{33a}$ or $R^{33b}$ is H.

In other of the foregoing embodiments, at least one of $R^{32a}$, $R^{32b}$, $R^{33a}$ or $R^{33b}$ is hydroxylalkyl.

In still other embodiments, at least one of $R^{32a}$, $R^{32b}$, $R^{33a}$ or $R^{33b}$ is cyano.

In some other different embodiments, least one of $R^{32a}$, $R^{32b}$, $R^{33a}$ or $R^{33b}$ is aminocarbonyl.

In some embodiments, $R^{32a}$ and $R^{32b}$ join to form a carbocyclic or heterocyclic ring. In other embodiments, $R^{33a}$ and $R^{33b}$ join to form a carbocyclic or heterocyclic ring.

In different embodiments, $R^{32a}$ is H, —OH, —NH$_2$, —CO$_2$H, cyano, $C_1$-$C_6$alkyl, $C_3$-$C_8$cycloalkyl, hydroxylalkyl, aminoalkyl, carboxylalkyl or aminocarbonyl and $R^{32b}$ joins with $R^{33b}$ to form a carbocyclic or heterocyclic ring.

In still other embodiments, $R^{33a}$ is H, —OH, —NH$_2$, —CO$_2$H, cyano, C$_1$-C$_6$alkyl, C$_3$-C$_8$cycloalkyl, hydroxylalkyl, aminoalkyl, carboxylalkyl or aminocarbonyl and $R^{33b}$ joins with $R^{32b}$ to form a carbocyclic or heterocyclic ring.

In some more specific embodiments, the compound of structure (III) is selected from a compound in Table 3.

TABLE 3

Representative Compounds of Structure (III)

| No. | Structure | Name | [M + H]⁺ |
|---|---|---|---|
| VI-1 | 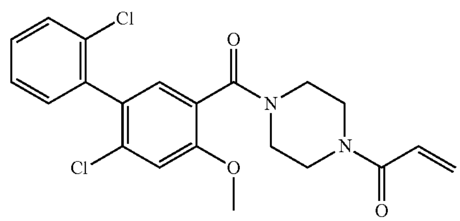 [SMILES: C=CC(=O)N1CCN(C(=O)c2cc(-c3ccccc3Cl)c(Cl)cc2OC)CC1] | 1-(4-(2',6-dichloro-4-methoxybiphenyl-carbonyl)piperazin-1-yl)prop-2-en-1-one | 441.20* |
| VI-2 | 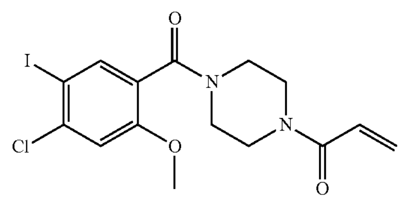 [SMILES: C=CC(=O)N1CCN(C(=O)c2cc(I)c(Cl)cc2OC)CC1] | 1-(4-(4-chloro-5-iodo-2-methoxybenzoyl)piper-azin-1-yl)prop-2-en-1-one | 457.05* |
| VI-3 | 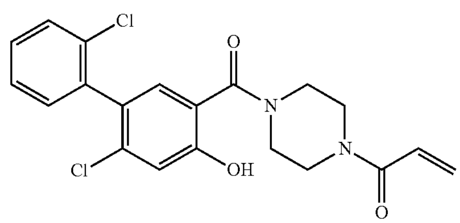 [SMILES: C=CC(=O)N1CCN(C(=O)c2cc(-c3ccccc3Cl)c(Cl)cc2O)CC1] | 1-(4-(2',6-dichloro-4-hydroxybiphenylcarbonyl)-piperazin-1-yl)prop-2-en-1-one | 427.15 |
| VI-4 | 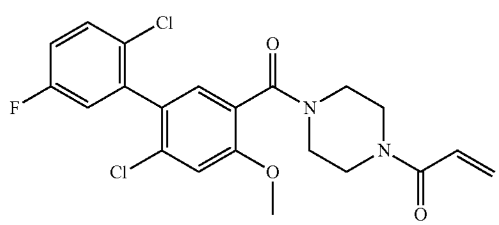 [SMILES: C=CC(=O)N1CCN(C(=O)c2cc(-c3cc(F)ccc3Cl)c(Cl)cc2OC)CC1] | 1-(4-(2',6-dichloro-5'-fluoro-4-methoxybiphenylcarbonyl)-piperazin-1-yl)prop-2-en-1-one | 459.15 |
| VI-5 | 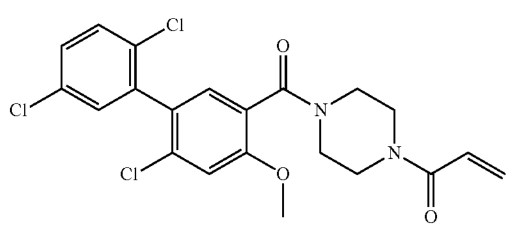 [SMILES: C=CC(=O)N1CCN(C(=O)c2cc(-c3cc(Cl)ccc3Cl)c(Cl)cc2OC)CC1] | 1-(4-(2',5',6-trichloro-4-methoxybiphenyl-carbonyl)piperazin-1-yl)prop-2-en-1-one | 453.15 |
| VI-6 | 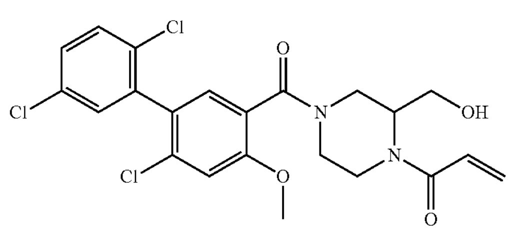 [SMILES: C=CC(=O)N1CCN(C(=O)c2cc(-c3cc(Cl)ccc3Cl)c(Cl)cc2OC)CC1CO] | 1-(2-(hydroxymethyl)-4-(2',5',6-trichloro-4-methoxybiphenyl-carbonyl)piperazin-1-yl)prop-2-en-1-one | 483.20# |

TABLE 3-continued

| No. | Structure | Name | [M + H]⁺ |
|---|---|---|---|
| VI-7 | 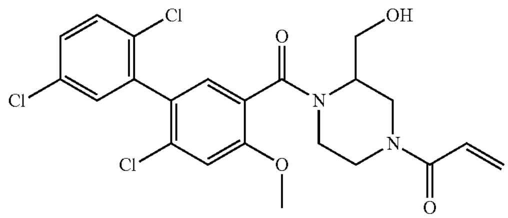 [SMILES: C=CC(=O)N1CCN(C(=O)c2cc(-c3cc(Cl)ccc3Cl)c(Cl)cc2OC)C(CO)C1] | 1-(3-(hydroxymethyl)-4-(2',5',6-trichloro-4-methoxy-biphenylcarbonyl)-piperazin-1-yl)prop-2-en-1-one | 485.20 |
| VI-8 | 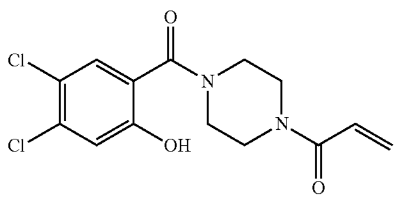 [SMILES: C=CC(=O)N1CCN(C(=O)c2cc(Cl)c(Cl)cc2O)CC1] | 1-(4-(4,5-dichloro-2-hydroxybenzoyl)piperazin-1-yl)prop-2-en-1-one | 327.15 |
| VI-9 | 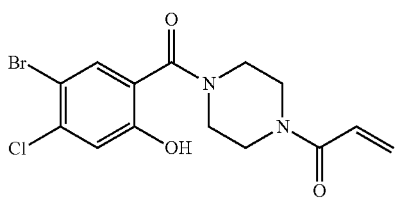 | 1-(4-(5-bromo-4-chloro-2-hydroxybenzoyl)piperazin-1-yl)prop-2-en-1-one | 388* |
| VI-10 | 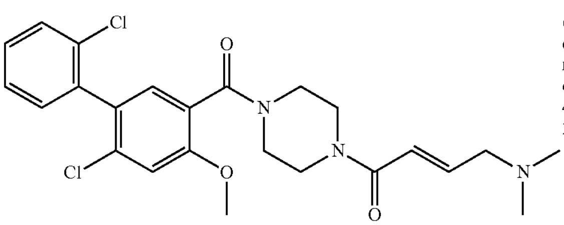 [SMILES: COc1cc(Cl)c(-c2ccccc2Cl)cc1C(=O)N1CCN(C(=O)/C=C/CN(C)C)CC1] | (E)-1-(4-(2',6-dichloro-4-methoxybiphenyl-carbonyl)piperazin-1-yl)-4-(dimethylamino)but-2-en-1-one | 476.23 |
| VI-11 | 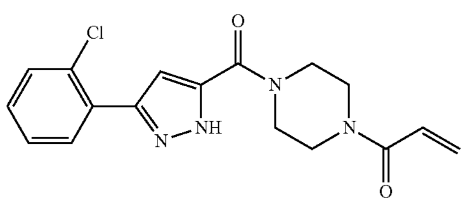 [SMILES: C=CC(=O)N1CCN(C(=O)c2cc(-c3ccccc3Cl)n[nH]2)CC1] | 1-(4-(3-(2-chlorophenyl)-1H-pyrazole-5-carbonyl)piperazin-1-yl)prop-2-en-1-one | 467.20* |
| VI-12 | 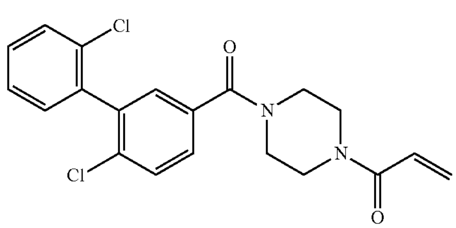 [SMILES: C=CC(=O)N1CCN(C(=O)c2ccc(Cl)c(-c3ccccc3Cl)c2)CC1] | 1-(4-(2',6-dichlorobiphenylcarbonyl)-piperazin-1-yl)prop-2-en-1-one | 389.20 |
| VI-13 | 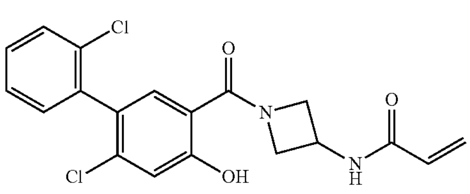 [SMILES: C=CC(=O)NC1CN(C(=O)c2cc(-c3ccccc3Cl)c(Cl)cc2O)C1] | N-(1-(2',6-dichloro-4-hydroxybiphenylcarbonyl)-azetidin-3-yl)acrylamide | 389.30 |

TABLE 3-continued

Representative Compounds of Structure (III)

| No. | Structure | Name | [M + H]+ |
|---|---|---|---|
| VI-14 | 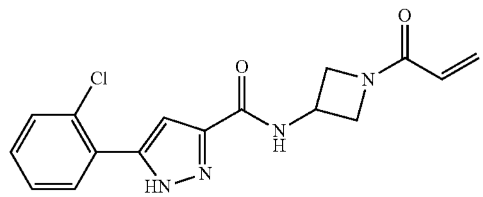 [SMILES: C=CC(=O)N1CC(NC(=O)c2cc(-c3ccccc3Cl)[nH]n2)C1] | N-(1-acryloylazetidin-3-yl)-3-(2-chlorophenyl)-1H-pyrazole-5-carboxamide | 331.15 |
| VI-15 | 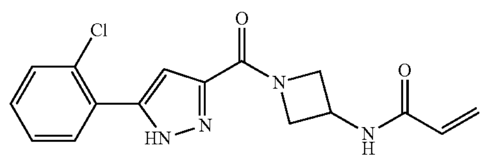 [SMILES: C=CC(=O)NC1CN(C(=O)c2cc(-c3ccccc3Cl)[nH]n2)C1] | N-(1-(3-(2-chlorophenyl)-1H-pyrazole-5-carbonyl)azetidin-3-yl)acrylamide | 331.15 |
| VI-16 | 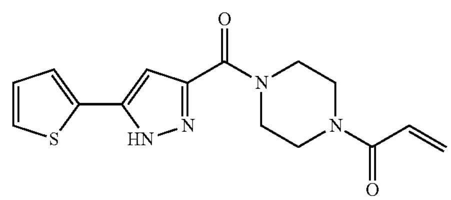 [SMILES: C=CC(=O)N1CCN(C(=O)c2cc(-c3cccs3)[nH]n2)CC1] | 1-(4-(5-(thiophen-2-yl)-1H-pyrazole-3-carbonyl)piperazin-1-yl)prop-2-en-1-one | 339.15 |
| VI-17 | 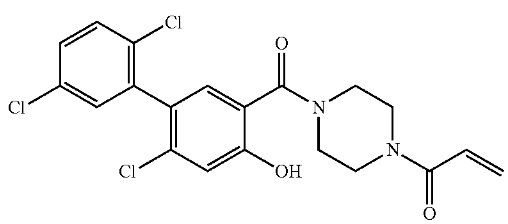 [SMILES: C=CC(=O)N1CCN(C(=O)c2cc(-c3cc(Cl)ccc3Cl)c(Cl)cc2O)CC1] | 1-(4-(2',5',6-trichloro-4-hydroxybiphenylcarbonyl)-piperazin-1-yl)prop-2-en-1-one | 438.30+ |
| VI-18 | 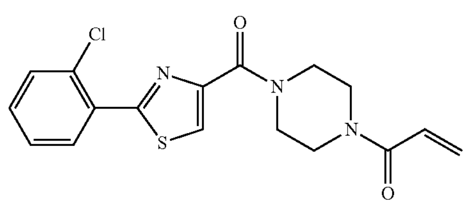 [SMILES: C=CC(=O)N1CCN(C(=O)c2csc(-c3ccccc3Cl)n2)CC1] | 1-(4-(2-(2-chlorophenyl)thiazole-4-carbonyl)piperazin-1-yl)prop-2-en-1-one | 384.15+ |
| VI-19 | 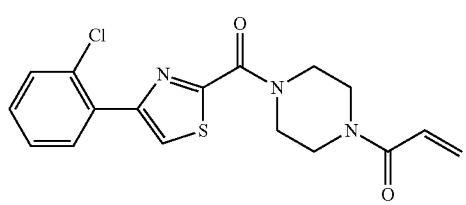 [SMILES: C=CC(=O)N1CCN(C(=O)c2nc(-c3ccccc3Cl)cs2)CC1] | 1-(4-(4-(2-chlorophenyl)thiazole-2-carbonyl)piperazin-1-yl)prop-2-en-1-one | 384.15+ |
| VI-20 | 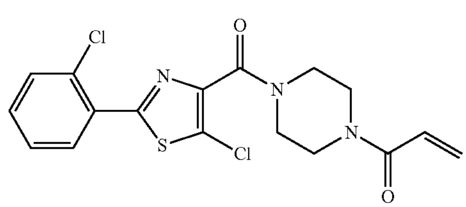 [SMILES: C=CC(=O)N1CCN(C(=O)c2nc(-c3ccccc3Cl)sc2Cl)CC1] | 1-(4-(5-chloro-2-(2-chlorophenyl)thiazole-4-carbonyl)piperazin-1-yl)prop-2-en-1-one | 418.10* |

TABLE 3-continued

Representative Compounds of Structure (III)

| No. | Structure | Name | [M + H]+ |
|---|---|---|---|
| VI-21 | 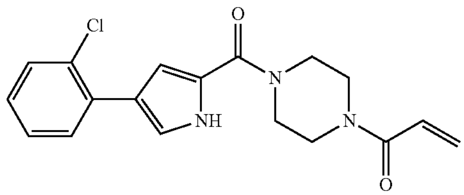 [SMILES: C=CC(=O)N1CCN(C(=O)c2cc(-c3ccccc3Cl)c[nH]2)CC1] | 1-(4-(4-(2-chlorophenyl)-1H-pyrrole-2-carbonyl)piperazin-1-yl)prop-2-en-1-one | 344.20 |
| VI-22 | 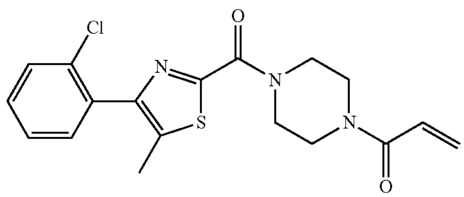 [SMILES: C=CC(=O)N1CCN(C(=O)c2nc(-c3ccccc3Cl)c(C)s2)CC1] | 1-(4-(4-(2-chlorophenyl)-5-methylthiazole-2-carbonyl)piperazin-1-yl)prop-2-en-1-one | 376.25 |
| VI-23 | 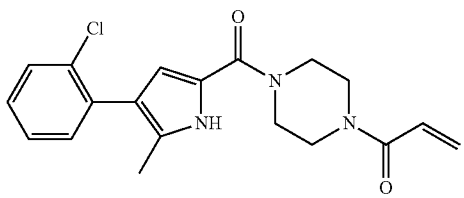 [SMILES: C=CC(=O)N1CCN(C(=O)c2cc(-c3ccccc3Cl)c(C)[nH]2)CC1] | 1-(4-(4-(2-chlorophenyl)-5-methyl-1H-pyrrole-2-carbonyl)piperazin-1-yl)prop-2-en-1-one | 356.35+ |
| VI-24 | 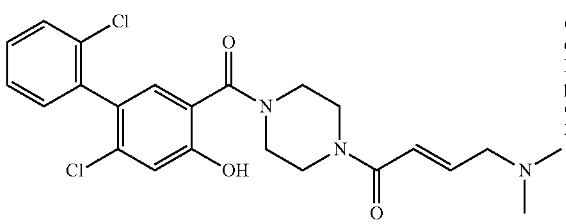 [SMILES: CN(C)C/C=C/C(=O)N1CCN(C(=O)c2cc(-c3ccccc3Cl)c(Cl)cc2O)CC1] | (E)-1-(4-(2',6-dichloro-4-hydroxybiphenylcarbonyl)-piperazin-1-yl)-4-(dimethylamino)but-2-en-1-one | 462.35 |
| VI-25 | 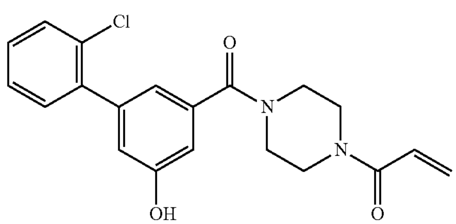 [SMILES: C=CC(=O)N1CCN(C(=O)c2cc(O)cc(-c3ccccc3Cl)c2)CC1] | 1-(4-(2'-chloro-5-hydroxybiphenylcarbonyl)-piperazin-1-yl)prop-2-en-1-one | 371.25 |
| VI-26 | 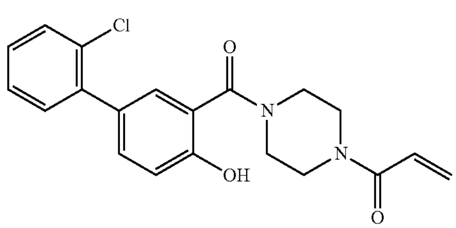 [SMILES: C=CC(=O)N1CCN(C(=O)c2cc(-c3ccccc3Cl)ccc2O)CC1] | 1-(4-(2'-chloro-4-hydroxybiphenylcarbonyl)-piperazin-1-yl)prop-2-en-1-one | 371.25 |
| VI-27 | 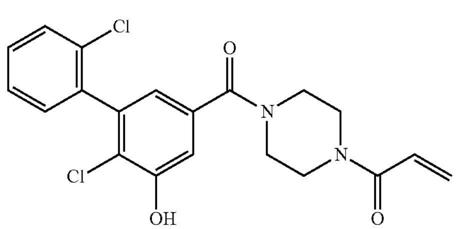 [SMILES: C=CC(=O)N1CCN(C(=O)c2cc(O)c(Cl)c(-c3ccccc3Cl)c2)CC1] | 1-(4-(2',6-dichloro-5-hydroxybiphenylcarbonyl)-piperazin-1-yl)prop-2-en-1-one | 403.35+ |

TABLE 3-continued

Representative Compounds of Structure (III)

| No. | Structure | Name | [M + H]⁺ |
|---|---|---|---|
| VI-28 | 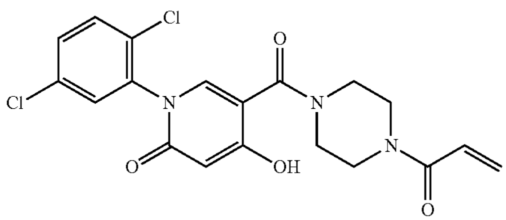 [SMILES: C=CC(=O)N1CCN(C(=O)c2cn(-c3cc(Cl)ccc3Cl)c(=O)cc2O)CC1] | 5-(4-acryloylpiperazine-1-carbonyl)-1-(2,5-dichlorophenyl)-4-hydroxypyridin-2(1H)-one | 422.06 |
| VI-29 | 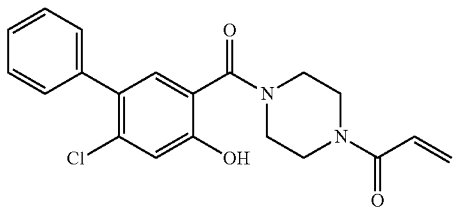 [SMILES: C=CC(=O)N1CCN(C(=O)c2cc(-c3ccccc3)c(Cl)cc2O)CC1] | 1-(4-(6-chloro-4-hydroxybiphenylcarbonyl)-piperazin-1-yl)prop-2-en-1-one | 371.25 |
| VI-30 | 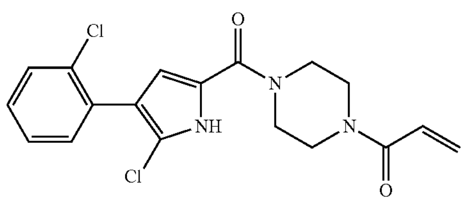 [SMILES: C=CC(=O)N1CCN(C(=O)c2cc(-c3ccccc3Cl)c(Cl)[nH]2)CC1] | 1-(4-(5-chloro-4-(2-chlorophenyl)-1H-pyrrole-2-carbonyl)piperazin-1-yl)prop-2-en-1-one | 378.25⁺ |
| VI-31 | 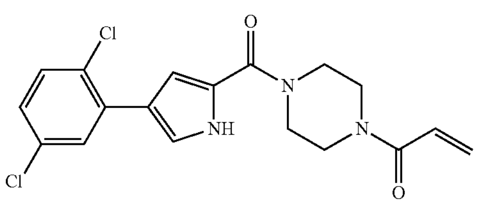 [SMILES: C=CC(=O)N1CCN(C(=O)c2cc(-c3cc(Cl)ccc3Cl)c[nH]2)CC1] | 1-(4-(4-(2,5-dichlorophenyl)-1H-pyrrole-2-carbonyl)piperazin-1-yl)prop-2-en-1-one | 378.20 |
| VI-32 | 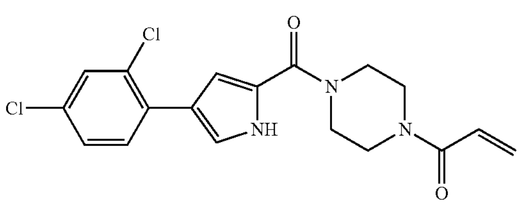 [SMILES: C=CC(=O)N1CCN(C(=O)c2cc(-c3ccc(Cl)cc3Cl)c[nH]2)CC1] | 1-(4-(4-(2,4-dichlorophenyl)-1H-pyrrole-2-carbonyl)piperazin-1-yl)prop-2-en-1-one | 377.90 |
| VI-33 | 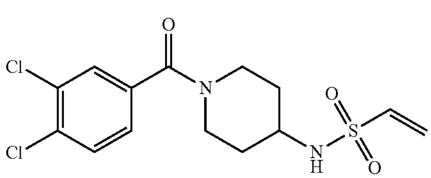 [SMILES: C=CS(=O)(=O)NC1CCN(C(=O)c2ccc(Cl)c(Cl)c2)CC1] | N-(1-(3,4-dichlorobenzoyl)-piperidin-4-yl)ethenesulfonamide | 363.02 |
| VI-34 | 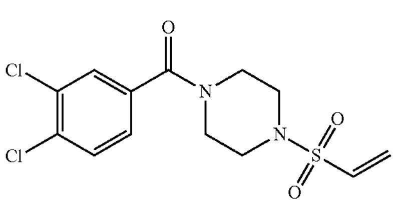 [SMILES: C=CS(=O)(=O)N1CCN(C(=O)c2ccc(Cl)c(Cl)c2)CC1] | (3,4-dichlorophenyl)(4-(vinylsulfonyl)piperazin-1-yl)methanone | 349.04 |

TABLE 3-continued

Representative Compounds of Structure (III)

| No. | Structure | Name | [M + H]+ |
|---|---|---|---|
| VI-35 | 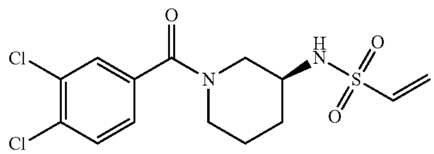 [SMILES: C=CS(=O)(=O)N[C@H]1CCCN(C(=O)c2ccc(Cl)c(Cl)c2)C1] | (S)-N-(1-(3,4-dichlorobenzoyl)piperidin-3-yl)ethenesulfonamide | 363.06 |
| VI-36 | 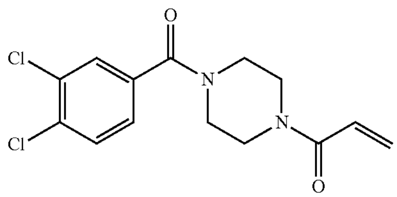 [SMILES: C=CC(=O)N1CCN(C(=O)c2ccc(Cl)c(Cl)c2)CC1] | 1-(4-(3,4-dichlorobenzoyl)piperazin-1-yl)prop-2-en-1-one | 312.99 |
| VI-37 | 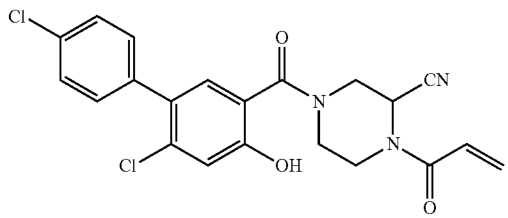 [SMILES: C=CC(=O)N1CCN(C(=O)c2cc(-c3ccc(Cl)cc3)c(Cl)cc2O)CC1C#N] | 1-acryloyl-4-(4',6-dichloro-4-hydroxybiphenylcarbonyl)-piperazine-2-carbonitrile | 430.30 |
| VI-38 | 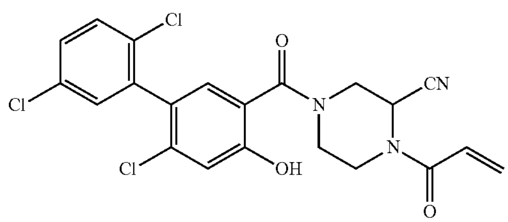 [SMILES: C=CC(=O)N1CCN(C(=O)c2cc(-c3cc(Cl)ccc3Cl)c(Cl)cc2O)CC1C#N] | 1-acryloyl-4-(2',5',6-trichloro-4-hydroxybiphenylcarbonyl)-piperazine-2-carbonitrile | 464.30 |
| VI-39 | 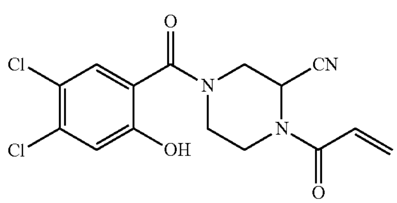 [SMILES: C=CC(=O)N1CCN(C(=O)c2cc(Cl)c(Cl)cc2O)CC1C#N] | 1-acryloyl-4-(4,5-dichloro-2-hydroxybenzoyl)piperazine-2-carbonitrile | 354.15 |
| VI-40 | 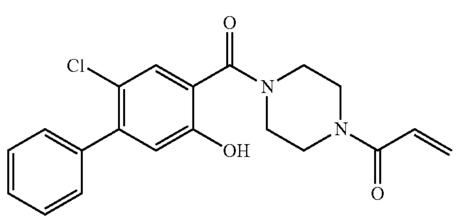 [SMILES: C=CC(=O)N1CCN(C(=O)c2cc(Cl)c(-c3ccccc3)cc2O)CC1] | 1-(4-(2-chloro-5-hydroxybiphenylcarbonyl)-piperazin-1-yl)prop-2-en-1-one | 371.25 |
| VI-41 | 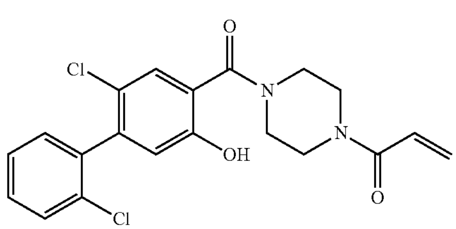 [SMILES: C=CC(=O)N1CCN(C(=O)c2cc(Cl)c(-c3ccccc3Cl)cc2O)CC1] | 1-(4-(2,2'-dichloro-5-hydroxybiphenylcarbonyl)-piperazin-1-yl)prop-2-en-1-one | 405.25 |

TABLE 3-continued

Representative Compounds of Structure (III)

| No. | Structure | Name | [M + H]+ |
|---|---|---|---|
| VI-42 | 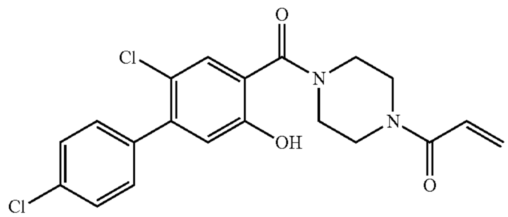 [SMILES: C=CC(=O)N1CCN(C(=O)c2cc(Cl)c(-c3ccc(Cl)cc3)cc2O)CC1] | 1-(4-(2,4'-dichloro-5-hydroxybiphenylcarbonyl)-piperazin-1-yl)prop-2-en-1-one | 405.20 |
| VI-43 | 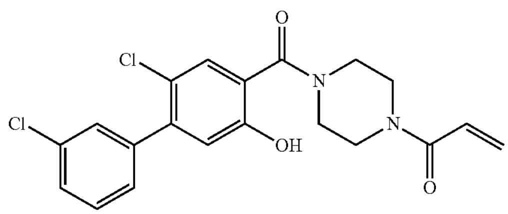 [SMILES: C=CC(=O)N1CCN(C(=O)c2cc(Cl)c(-c3cccc(Cl)c3)cc2O)CC1] | 1-(4-(2,3'-dichloro-5-hydroxybiphenylcarbonyl)-piperazin-1-yl)prop-2-en-1-one | 405.25 |

*[M + Na]+
†[M − H]−
[M]

Compounds of structure III are prepared according to procedures well-known or derivable by one of ordinary skill in the art, for example by procedures analogous to those exemplified in the examples provided below. Each of the compounds in Table 3 was prepared in such a manner and analyzed by mass spectrometry and/or $^1$H NMR. The mass spectrum ([M+H$^+$] or [M+Na$^+$]) and/or NMR spectrum was found to be consistent with the structures in Table 3.

General Reaction Scheme 19 illustrates an exemplary procedure for preparing compounds of structure (III).

General Reaction Scheme 19

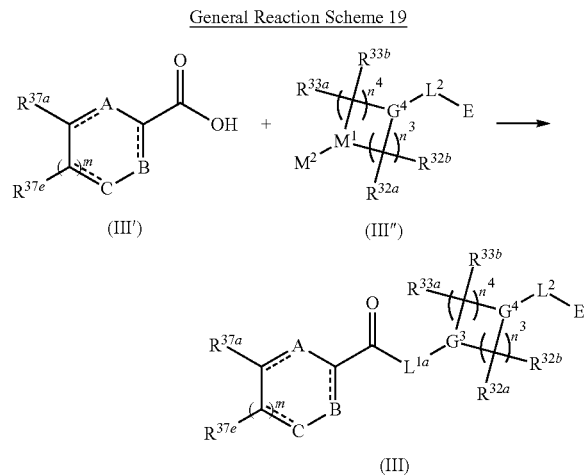

(III)

Referring to General Reaction Scheme 19, (III') and (III") are available from commercial sources and/or are easily prepared according to procedures known in the art. All variables on (III') and (III"), with the exception of M$^1$ and M$^2$, are as defined above for compounds of structure (III). In some procedures, M$^1$ is NH and M$^2$ is absent. In other procedures M$^1$ is N or CH and M$^2$ is a precursor to L$^{1a}$ which reacts with an activated acid. For example, in various procedures M$^2$ is NH$_2$, aminoalkyl or other heterosubstituted alkyl. Embodiments where M$^2$ comprises a carbanion (or M$^1$ is a carbanion) are also contemplated such that L$^1$ is alkylene. Briefly, an appropriately substituted acid (III') is activated and reacted with an appropriately substituted heterocycle (III") under appropriate coupling conditions. The L$^2$-E moiety may be present in (III") as illustrated or may be installed after coupling For example L2-E may be installed before or after coupling via acylation (or thioacylation) using a reagent such as an acid chloride or thionyl chloride.

It should be noted that variations of the above procedure are possible, some of which are exemplified in the examples. For example, in some procedures, the acid moiety is present on the cyclic moiety (III') and (III') is appropriately substituted with a nucleophilic moiety to enable coupling to form (III). Other methods of bond formation, which do not require reaction of an activated acid, are also available for preparation of the compounds. It should also be noted that various substitutions on (III') and/or (III") can be present during the coupling step (in protected or unprotected form) or the substituents can be added after (III') and (III") are coupled. Methods for inclusion of these substituents are known in the art.

Various options are available to one of ordinary skill in the art to add various substituents and or modify or reorder the above described steps to arrive at different embodiments of compounds of structure III. The appropriate acid is purchased commercially or made according to well-known procedures.

It will also be appreciated by those skilled in the art that in the processes described herein (e.g., General Reaction Scheme I and II and the below examples) the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a subject and thereafter metabolized in the body to form compounds of the invention which are pharmacologically active. Such derivatives may therefore be described as "prodrugs". All prodrugs of compounds of this invention are included within the scope of the invention.

It is also understood that one skilled in the art may be able to make these compounds by similar methods or by combining other methods known to one skilled in the art. It is further understood that one skilled in the art would be able to make, in a similar manner as described below, other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, *Advanced Organic Chemistry: Reactions, Mechanisms, and Structure*, 5th edition (Wiley, December 2000)) or prepared as described in this invention.

In some other embodiments, the compound has one of the following structures:

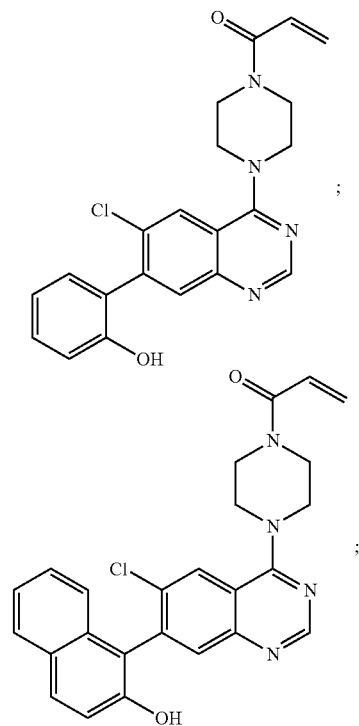

C. Pharmaceutical Compositions

Other embodiments are directed to pharmaceutical compositions. The pharmaceutical composition comprises any one (or more) of the foregoing compounds, any one of the foregoing addition therapeutic agents and a pharmaceutically acceptable carrier. In some embodiments, the pharmaceutical composition is formulated for oral administration. In other embodiments, the pharmaceutical composition is formulated for injection.

Suitable routes of administration include, but are not limited to, oral, intravenous, rectal, aerosol, parenteral, ophthalmic, pulmonary, transmucosal, transdermal, vaginal, optical, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, the compound and/or additional therapeutic agent as described herein are administered in a local rather than systemic manner, for example, via injection of the compound and/or additional therapeutic agent directly into an organ, often in a depot preparation or sustained release formulation. In specific embodiments, long acting formulations are administered by implantation (for example subcutaneously or intramuscularly) or by intramuscular injection. Furthermore, in other embodiments, the compound and additional therapeutic agent are delivered in a targeted drug delivery system, for example, in a liposome coated with organ-specific antibody. In such embodiments, the liposomes are targeted to and taken up selectively by the organ. In yet other embodiments, the compound and/or additional therapeutic agent is provided in the form of a rapid release formulation, in the form of an extended release formulation, or in the form of an intermediate release formulation. In yet other embodiments, the compound and/or additional therapeutic agent described herein is administered topically.

The compound and additional therapeutic agent according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound and additional therapeutic agent are administered, the subject to be treated, the body weight of the subject to be treated, and the preference and experience of the attending physician.

In some embodiments, the compound and/or additional therapeutic agent is administered in a single dose. Typically, such administration will be by injection, e.g., intravenous injection, in order to introduce the agent quickly. However, other routes are used as appropriate. A single dose of the compound and/or additional therapeutic agent of the invention may also be used for treatment of an acute condition.

In some embodiments, the compound and/or additional therapeutic agent of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment the compound and additional therapeutic agent are administered together about once per day to about 6 times per day. In another embodiment the administration of the compound and additional therapeutic agent continues for less than about 7 days. In yet another embodiment the administration continues for more than about 6, 10, 14, 28 days, two months, six months, or one year. In some cases, continuous dosing is achieved and maintained as long as necessary.

Administration of the compound and additional therapeutic agent may continue as long as necessary. In some embodiments, the compound and/or additional therapeutic agent are administered for more than 1, 2, 3, 4, 5, 6, 7, 14, or 28 days. In some embodiments, the compound and additional therapeutic agent are administered for less than 28, 14, 7, 6, 5, 4, 3, 2, or 1 day. In some embodiments, the compound and additional therapeutic agent is administered chronically on an ongoing basis, e.g., for the treatment of chronic effects.

In some embodiments, the compound and/or additional therapeutic agent are administered in dosages. It is known in the art that due to intersubjective variability in compound pharmacokinetics, individualization of dosing regimen is necessary for optimal therapy. Dosing for a compound of the invention may be found by routine experimentation in light of the instant disclosure.

In some embodiments, the compound and/or additional therapeutic agent described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A pharmaceutical composition, as used herein, refers to a mixture of compound and/or additional therapeutic agent with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of the compound and/or additional therapeutic agent provided herein are administered in a pharmaceutical composition to a subject having a disease, disorder or medical condition to be treated. In specific embodiments, the subject is a human. In certain embodiments, therapeutically effective amounts vary depending on the severity of the disease, the age and relative health of the subject, the potency of the compound used and other factors.

In one embodiment, the compound and/or additional therapeutic agent is formulated in an aqueous solution. In specific embodiments, the aqueous solution is selected from, by way of example only, a physiologically compatible buffer, such as Hank's solution, Ringer's solution, or physiological saline buffer. In other embodiments, compound and/or additional therapeutic agent are formulated for transmucosal administration. In specific embodiments, transmucosal formulations include penetrants that are appropriate to the barrier to be permeated. In still other embodiments wherein the compound and/or additional therapeutic agent described herein are formulated for other parenteral injections, appropriate formulations include aqueous or non-aqueous solutions. In specific embodiments, such solutions include physiologically compatible buffers and/or excipients.

In another embodiment, the compound and/or additional therapeutic agent described herein are formulated for oral administration. The compound and/or additional therapeutic agent described herein are formulated by combining the components with, e.g., pharmaceutically acceptable carriers or excipients. In various embodiments, the compound and/or additional therapeutic agent described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with the compound and/or additional therapeutic agent described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of the compound and/or additional therapeutic agent described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of the compound and/or additional therapeutic agent described herein are formulated for buccal or sublingual administration. Formulations suitable for buccal or sublingual administration include, by way of example only, tablets, lozenges, or gels. In still other embodiments, the compound and/or additional therapeutic agent described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the compound and/or additional therapeutic agent in water-soluble form. In additional embodiments, suspensions of the compound and/ or additional therapeutic agent are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compound and/or additional therapeutic agent to allow for the preparation of highly concentrated solutions. Alternatively, in other embodiments, the active ingredient is in powder form for constitution with a suitable vehicle, e.g., sterile pyrogen-free water, before use.

In still other embodiments, the compound and/or additional therapeutic agent are administered topically. The compound and/or additional therapeutic agent described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compound and/or additional therapeutic agent are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compound and/or additional therapeutic agent is accomplished by means of iontophoretic patches and the like. In certain embodiments, transdermal patches provide controlled delivery of the compound and/or additional therapeutic agent. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compound and/or additional therapeutic agent are formulated for administration by inhalation. Various forms suitable for administration by inhalation include, but are not limited to, aerosols, mists or powders. Pharmaceutical compositions of compound and/or additional therapeutic agent are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, the compound and/or additional therapeutic agent are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising the compound and/or additional therapeutic agent are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least the compound and/or additional therapeutic agent, described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compound and/or additional therapeutic agent described herein are included within the scope of the compounds presented herein. Additionally, the compound and/or additional therapeutic agent described herein encompass unsolvated as well as solvated forms with pharmaceutically acceptable solvents such as water, ethanol, and the like. The solvated forms of the compound and/or additional therapeutic agent presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compound and/or additional therapeutic agent described herein include formulating the compound and/or additional therapeutic agent with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising the compound and/or additional therapeutic agent illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of the compound and/or additional therapeutic agent. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-re-closeable containers. Alternatively, multiple-dose re-closable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of the compound and/or additional therapeutic agent provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound and/or additional therapeutic agent is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the compound and/or additional therapeutic agent is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound and/or additional therapeutic agent is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of the compound and/or additional therapeutic agent is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound and/or additional therapeutic agent is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound and/or additional therapeutic agent is in the range of 0.0001-10 g, 0.0005-9 g, 0.001-8 g, 0.005-7 g, 0.01-6 g, 0.05-5 g, 0.1-4 g, 0.5-4 g, or 1-3 g.

D. Kits/Articles of Manufacture

For use in the therapeutic applications described herein, kits and articles of manufacture are also provided. In some embodiments, a kit comprising a KRAS, HRAS or NRAS G12C mutant modulating compound, an additional therapeutic agent and directions for use of the compound and the additional therapeutic agent for treatment of cancer is provided. The compound and the additional therapeutic agent can be selected from any of those described herein.

In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes the compound and/or additional therapeutic agent described herein, optionally in a separate composition or in a combined composition. The container(s) optionally have a sterile access port (for example the container is an intravenous solution bag or a vial having a stopper pierceable by a hypodermic injection needle). Such kits optionally comprising the compound and/or additional therapeutic agent with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing the compound and/or additional therapeutic agent. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

EXAMPLES

Example 1

Strategy for Identifying Signaling Pathways Maintained or Hyper-Activated Following KRAS G12C Inhibition Pathways suggesting the need for KRAS G12C targeting compounds in combination with other cancer therapeutics were assessed as follows. Western blots were used to analyze downstream KRAS signaling nodes (AKT, ERK, S6, EGFR/HER2, SRC, MET) and a transcription factor (STAT3). An assessment following treatment of mutant cells (H358, Calu-1, MiaPaca2, NCI-H23, SW1463, H1792) with an exemplary KRAS G12C inhibitor (compound I-272) for 48 hours showed sustained or induced pathways suggesting targeting with RTK, PI3K, mTOR, SRC, and JAK/STAT inhibitors (FIG. 1). Sustained or induced pathways were assessed by comparing untreated cell lines with those treated by compound I-272.

Specifically, H358 cell lines showed EGFR and HER2 induction, suggesting additional targeting with RTK inhibitors. Calu-1 and MiaPaca2 cell lines showed refractory PI3K and STAT3, both with induction, high SRC levels and c-MET induction suggesting additional targeting with RTK, PI3K, SRC or JAK/STAT inhibitors. NCI-H23, SW1463, and H1792 cell lines showed refractory PI3K with induction, refractory ERK, S6 and STAT3, high SRC levels, c-MET induction, EGFR induction and other sustained RTKs suggesting additional targeting with RTK, PI3K, SRC, mTOR, or JAK/STAT.

Example 2

Exemplary KRAS G12C Inhibitor in Combination with One of RTK, PI3K, mTOR, SRC or JAK/STAT Inhibitors Cancer therapeutics to target specific pathways induced or sustained by treatment of KRAS G12C cells with an exemplary KRAS G12C inhibitor (compound I-272) were assessed and demonstrated as follows. Therapeutics that are RTK, PI3K, mTOR, SRC or JAK/STAT inhibitors were selected based on data obtained from testing described in EXAMPLE 1. Cancer therapeutics were selected based on their potential to have a synergistic effect on targeted cell lines. Their synergistic effect was assessed and demonstrated as follows. Comprehensive growth inhibition combination tests were performed on mutant cell lines (H358, H1792, Calu-1, SW1463, SW1573, MiaPaca2, NCI-H23) or control cell line (A549) were tested with an exemplary G12C inhibitor (compound I-272, dosing range of 0.063 µM-2.0 µM) alone or with compound I-272 (dosing range of 0.063 µM-2.0 µM) in combination with one of erlotinib (EGFR inhibitor, dose range of 0.16 µM-5.0 µM), GDC0941 (PI3K inhibitor, dose range of 0.16 µM-5.0 µM), Dasatinib (SRC inhibitor, dose range 9.3 nM-300 nM), momelotinib (JAK inhibitor, dose range of 0.16 µM-5.0 µM), or trametinib (MEK inhibitor, dose range of 1.5 nM-50 nM). Data generated from 3 day proliferation assays were assessed by luminescence (n=3) and percentage of growth inhibition was plotted to create an index of growth inhibition. The growth inhibition index was then color coded to show areas where combinations tended to produce increased percentage growth inhibition. That data set was then converted using the BLISS synergy index to show synergistic combination treatments.

Caspase activity in multiple KRAS G12C mutant cells lines (H358, H2122, H1792, Calu-1, SW1453, SW1573, MiaPaca2, NCI-H23) or control cell line (A549) was tested with an exemplary G12C inhibitor (compound I-272, dose range of 0.063 µM-2.0 µM) alone or compound I-272 (dose range of 0.063 µM-2.0 µM) in combination with one of erlotinib (EGFR inhibitor, dose range of 0.16 µM-5.0 µM), GDC0941 (PI3K inhibitor, dose range of 0.16 µM-5.0 µM), Dasatinib (SRC inhibitor, dose range 9.3 nM-300 nM), momelotinib (JAK inhibitor, dose range of 0.16 µM-5.0 µM), or trametinib (MEK inhibitor, dose range of 1.5 nM-50 nM). Caspase activity was measured using a standard caspase activity luminescence assay (Capase-Glo, Promega) at 6, 24, and 48 hours (n>7).

The maximal caspase activity achieved between 6-48 hours was reported for each cell line and plotted. The plot was then color coded to show the combinations that had a synergistic effect. The color coding produced an apoptosis induction index that was used to assess the combination of therapies. In the H358 cell line, combinations that induced superior apoptosis compared to treatment with a single compound or agent include compound I-272 in combination with one of an EGFR inhibitor, a PI3K inhibitor, a JAK/TBK1 inhibitor, or an IGF1R inhibitor. In the H2122 cell line, combinations that induced superior apoptosis compared to treatment with a single compound or agent include compound I-272 in combination with one of an EGFR inhibitor, a MEK inhibitor, a PI3K inhibitor, or an IGF1R inhibitor. In the H1792 cell line, combinations that induced superior apoptosis compared to treatment with a single compound or agent include compound I-272 in combination with one of a JAK/TBK1 inhibitor, a SRC inhibitor, an EGFR inhibitor, or an IGF1R inhibitor. In the Calu-1 cell line, combinations that induced superior apoptosis compared to treatment with a single compound or agent include compound I-272 in combination with an SRC inhibitor. In the SW1453 cell line, combinations that induced superior apoptosis compared to treatment with a single compound or agent include compound I-272 in combination with one of an EGFR inhibitor or a MEK inhibitor. In the SW1573 cell line, combinations that induced superior apoptosis compared to treatment with a single compound or agent include compound I-272 in combination with an SRC inhibitor. In the MiaPaca2 cell line, combinations that induced superior apoptosis compared to treatment with a single compound or agent include compound I-272 in combination with one of a PI3K inhibitor, a JAK/TBK1 inhibitor, or an SRC inhibitor.

No levels of apoptotic induction were observed for any combination of a KRAS G12C inhibitor with any one chemotherapeutic agent tested in A549. While not wishing to be bound by theory, it is believed that this data indicates that the synergistic effects in H358, H2122, H1792, Calu-1, SW1453, SW1573, MiaPaca2, and NCI-H23 cell lines are mediated by KRAS G12C specific inhibition.

Using the BLISS synergy index data and the apoptosis induction index data in concert, the best combinations of an exemplary G12C inhibitor (compound I-272) and one other chemotherapeutic agent was selected for each cell line. In the H358 cell line, the combination of I-272 with one of erlotinib (EGFR inhibitor) or GDC0941 (PI3K inhibitor) was selected. In the H1792 cell line, the combination of I-272 with one of dasatinib (SRC inhibitor) or momelotinib (JAK inhibitor) was selected. In cell line Calu-1, the combination of I-272 with dasatinib (SRC inhibitor) was selected. In cell line SW1463, the combination of I-272 and one of erlotinib (EGFR inhibitor) or GDC0941 (PI3K inhibitor) was selected. In the cell line SW1573, the combination of I-272 and one of GDC0941 (PI3K inhibitor) or dasatinib (SRC inhibitor) was selected. In the cell line MiaPaca2, the combination of I-272 and one of GDC0941 (PI3K inhibitor) or momelotinib (JAK inhibitor) was selected. In the cell line NCI-H23, the combination of I-272 and one of dasatinib (SRC inhibitor) or momelotinib (JAK inhibitor) was selected. The most frequently synergistic pairs observed across the cell lines showed combinations of I-272 and one of a PI3K inhibitor, a SRC inhibitor, or an EGFR inhibitor.

Example 3

Figure 2:
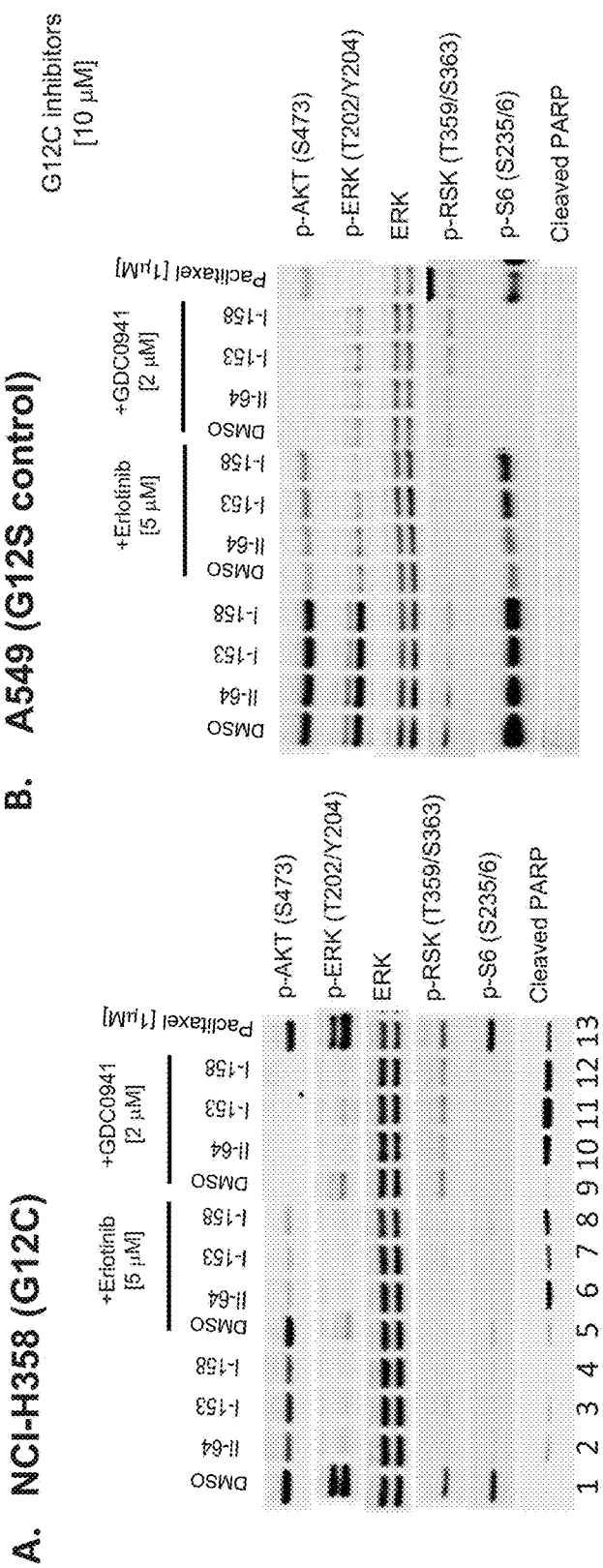
FIG. 2 depicts western blot analysis of downstream targets of K-Ras signaling. A) NCI-H358 cells expressing the K-Ras G12C isoform were treated with a DMSO control or K-Ras G12C inhibitors II-64, I-153, or I-158 at a concentration of 10 μM (lanes 1-4). Cells were then treated with DMSO, II-64, I-153, or I-158 in combination with either the EGFR inhibitor erlotinib at 5 μM (lanes 5-7) or the PI3K inhibitor GDC0941 at 2 μM (lanes 8-12). Paclitaxel was used as a positive control. The western blots were probed with antibodies for p-AKT, p-ERK, total ERK, p-RSK, p-S6 and cleaved PARP. Cleaved PARP is indicative of apoptosis. B) A549 cells that express the G12S isoform of K-Ras were used a control for K-Ras G12C inhibitor specificity. A549 cells were treated as in A). Little to no PARP cleavage was detected.

Exemplary KRAS G12C Inhibitor Used in Combination with One of an EGFR Inhibitor or PI3K Inhibitor for Synergistic Induction of Apoptosis The effectiveness of KRAS G12C targeting compounds in combination with other cancer therapeutics was assessed and demonstrated as follows. Western blots were used to analyze downstream KRAS signaling nodes (AKT, ERK, RSK, S6) and a marker of apoptosis (cleaved PARP). Treatment of H358 cells (KRAS G12C) with exemplary KRAS G12C inhibitors (compounds II-64, I-153 and I-158) alone for 24 hours causes clear and nearly complete inhibition of p-ERK, p-RSK, and p-S6, with partial inhibition of p-AKT (FIG. 2A). However, minimal cleaved PARP is seen, suggesting low levels of apoptosis (FIG. 2A, lanes 2-4 compared to lane 1). Likewise, treatment with erlotinib (EGFR inhibitor, lane 5) or GDC0941 (class I PI3K inhibitor, FIG. 2A, lane 9) alone does not induce robust apoptosis based on cleaved PARP levels (FIG. 2A, lanes 5 and 9 compared to lane 1). Combination treatment with a KRAS G12C inhibitor and either erlotinib (FIG. 2A, lanes 6-8) or GDC0941 (FIG. 2A, lanes 9-11) leads to greatly enhanced apoptosis based on cleaved PARP levels.

As a control, a non-G12C cell line (i.e., A549) was subjected to the same single agent and combination treatments (FIG. 2B). The KRAS G12C inhibitors show no single agent or additive/synergistic effects in this line. While not wishing to be bound by theory, it is believed that this data indicates that the synergistic effects in H358 cells are mediated by KRAS G12C specific inhibition.

The ability of KRAS G12C targeting compounds in combination with other cancer therapeutics in inducing apoptosis was assessed and demonstrated as follows. Caspase activity in multiple KRAS G12C mutant cells lines (H358, H2122, H2030, H1792, Calu-1, MiaPaca2, and NCI-H23) or control cell lines (A549 G12S, A375 KRAS WT, NCI-H411 KRAS G12V, and the HCT115 G13D) was tested with compound II-64 alone or compound II-64 in combination with one of erlotinib, afatinib, PI3K (GDC0941), docetaxel, SN38 (active metabolite of irinotecan), Taxol, IGFIRi (NVP-AEW541), or MEKi (trametinib). Caspase activity was measured using a standard caspase activity luminescence assay (Capase-Glo, Promega). Taxol (paclitaxel) was used as a positive control.

Figure 3:
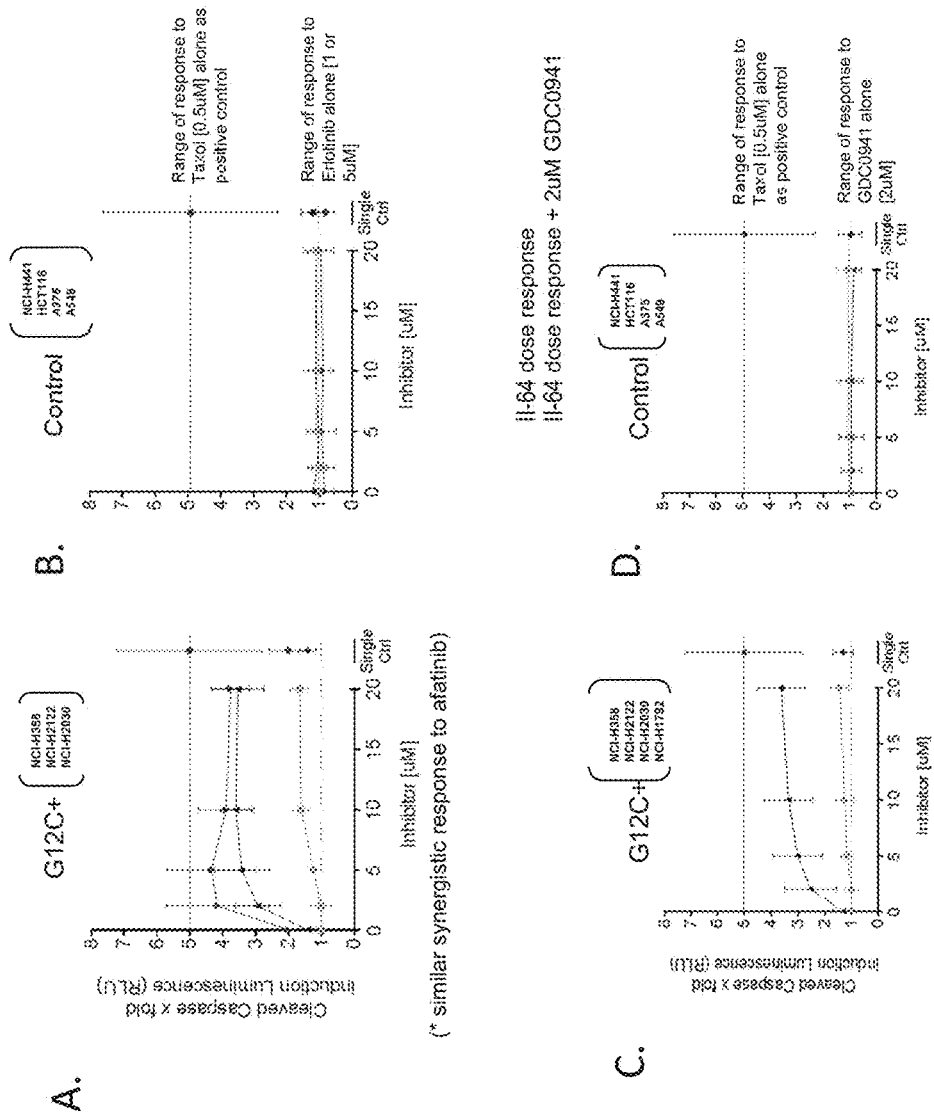
FIG. 3 depicts caspase activity in K-Ras G12C cell lines and control cells lines treated with a K-Ras G12C inhibitor alone, erlotinib alone, or a combination treatment. Taxol (0.5 μM) was used as a positive control. Caspase activity was evaluated by measuring luminescence from cleavable substrate in a caspase assay. A) K-Ras G12C expressing cell lines NCI-H358, NCI-H2122, and NCI-H2030 were treated with increasing doses of II-64 (■), II-64+1 μM erlotinib (▲), or II-64+5 μM erlotinib (▼). B) Control cell lines NCI-H441, HCT116, A375, and A549 were treated as in A). C) K-Ras G12C expressing cell lines NCI-H358, NCI-H2122, NCI-H2030, and NCI-H1792 were treated with increasing doses of II-64 (■) or II-64+2 μM GDC0941 (▲). D) Control cell lines NCI-H441, HCT116, A375, and A549 were treated as in C).

Three out of seven tested KRAS G12C mutant cell lines exhibited synergistic induction of apoptosis when a KRAS G12C inhibitor was combined with an EGFR inhibitor (erlotinib, FIG. 3A). Four out of seven tested KRAS G12C mutant cell lines exhibit synergistic induction of apoptosis when a KRAS G12C inhibitor is combined with a PI3K inhibitor (GDC0941, FIG. 3C). No effect of KRAS G12C inhibitor is observed in cell line without the KRAS G12C mutation (FIGS. 3B, 3D). Compound II-64, erlotinib, or GDC0941 alone did not induce significant caspase activity.

Figure 4:
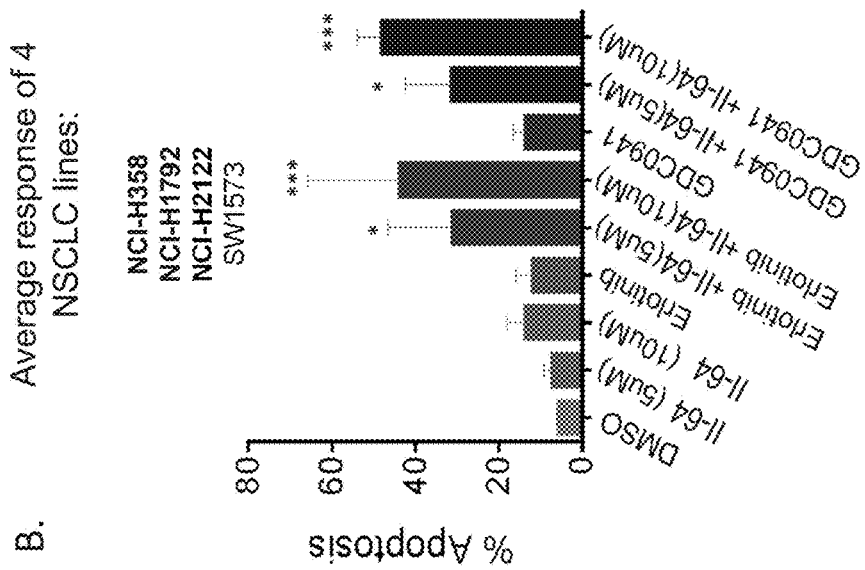
FIG. 4 depicts the ability of the compounds disclosed herein in inhibiting Ras-mediated cell cycle progression and induction of apoptosis. A) Flow cytometry data demonstrating cell cycle progression in NCI-H358 cells treated with II-64 alone at 5 μM or 10 μM, II-64+erlotinib (5 μM), or II-64+GDC0941 (2 μM). B) The average apoptosis response of NCI-H358, NCI-H1792, NCI-H2122, and SW1573 cell lines generated by flow cytometry as described in A).
Figure 4:
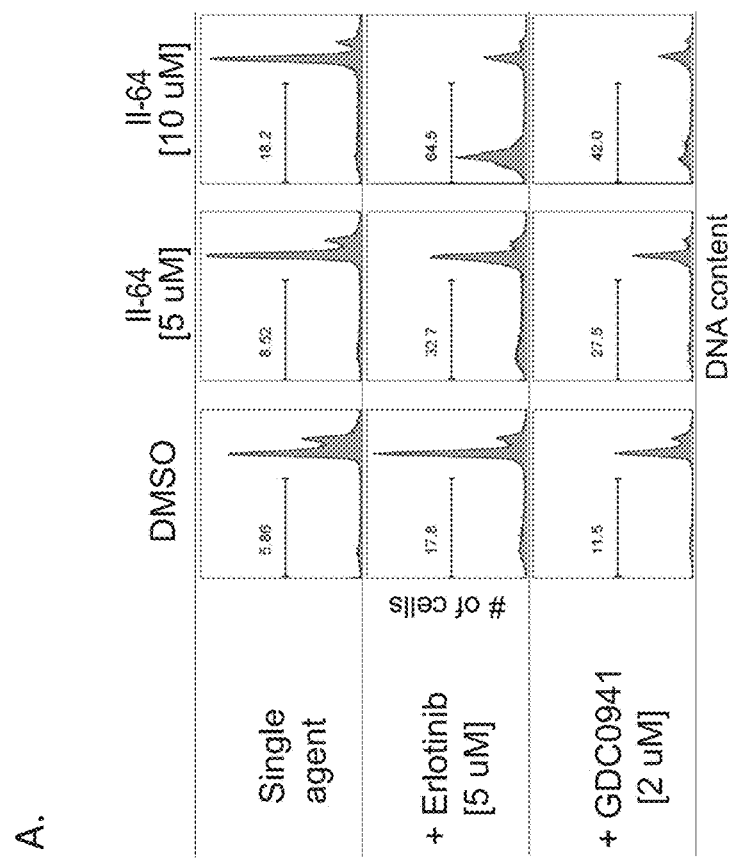

The ability of KRAS G12C targeting compounds in combination with other cancer therapeutics in inhibiting Ras-mediated cell cycle progression and induced apoptosis was assessed and demonstrated as follows. Flow cytometry was used to evaluate KRAS G12C inhibitor combination treatments. Treatment of H358 cells with compound II-64, erlotinib, or GDC0941 as single agents leads to G1 arrest with low to modest induction of apoptosis (FIG. 4A, sub-diploid cell population 8.5-17.8%). Combination treatments dramatically increase the fraction of apoptotic cells (sub diploid cell population 40-65%). Similar results are observed for additional KRAS G12C cell lines (H1792, H2122, SW1573; FIG. 4B).

Figure 5:
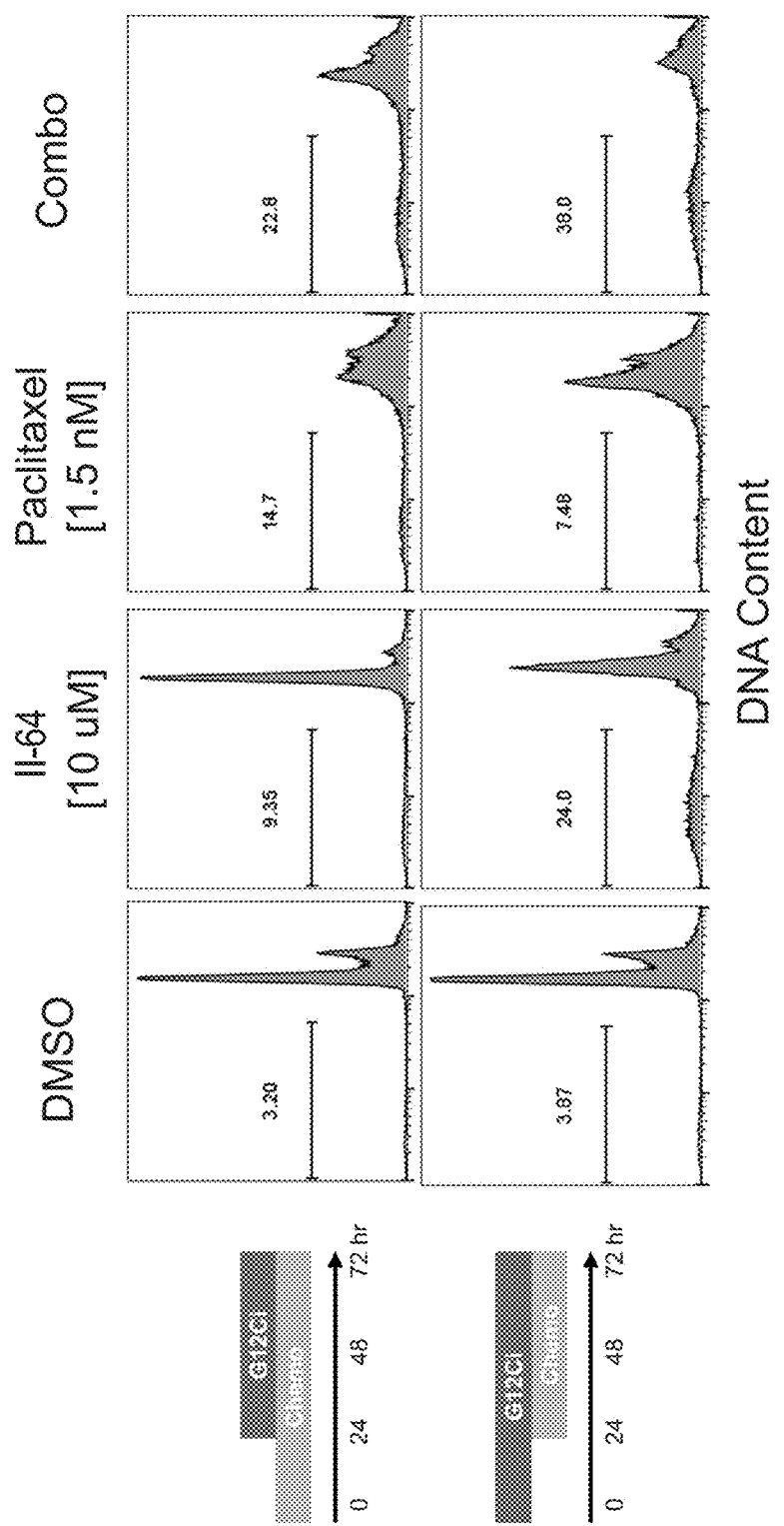
FIG. 5 depicts apoptosis in NCI-H358 cells treated with II-64 (10 μM), paclitaxel (1.5 nM), or a combination treatment (II-64+paclitaxel). The top row shows results from cells that were pretreated with paclitaxel for 24 hours and then treated with II-64 for an additional 48 hours (72 hours total). The bottom row shows results from cells that were pretreated with II-64 for 24 hours and then treated with paclitaxel for an additional 48 hours (72 hours total). Apoptosis was measured via flow cytometry. Gated populations=% of subdiploid apoptotic cells.
Figure 6:
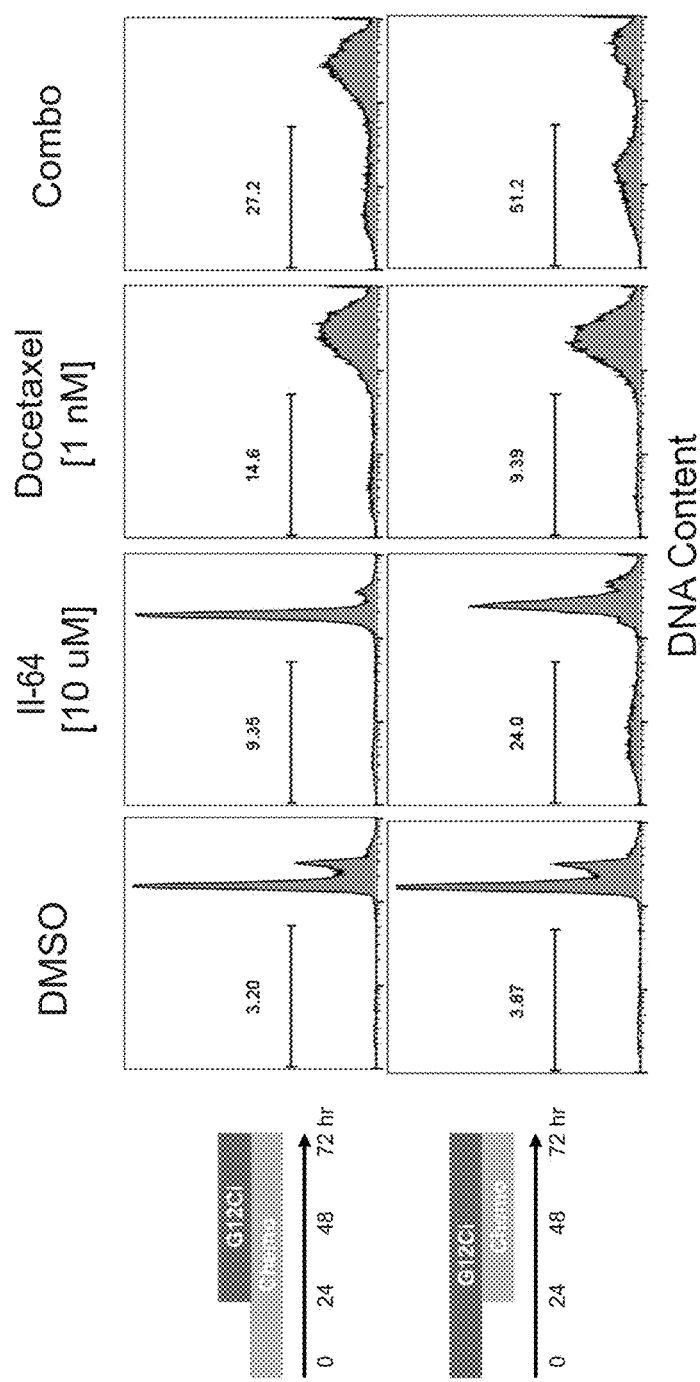
FIG. 6 depicts apoptosis in NCI-H358 cells treated with II-64 (10 μM), docetaxel (1 nM), or a combination treatment (II-64+docetaxel). The top row shows results from cells that were pretreated with docetaxel for 24 hours and then treated with II-64 for an additional 48 hours (72 hours total). The bottom row shows results from cells that were pretreated with II-64 for 24 hours and then treated with docetaxel for an additional 48 hours (72 hours total). Apoptosis was measured via flow cytometry. Gated populations=% of subdiploid apoptotic cells.
Figure 7:
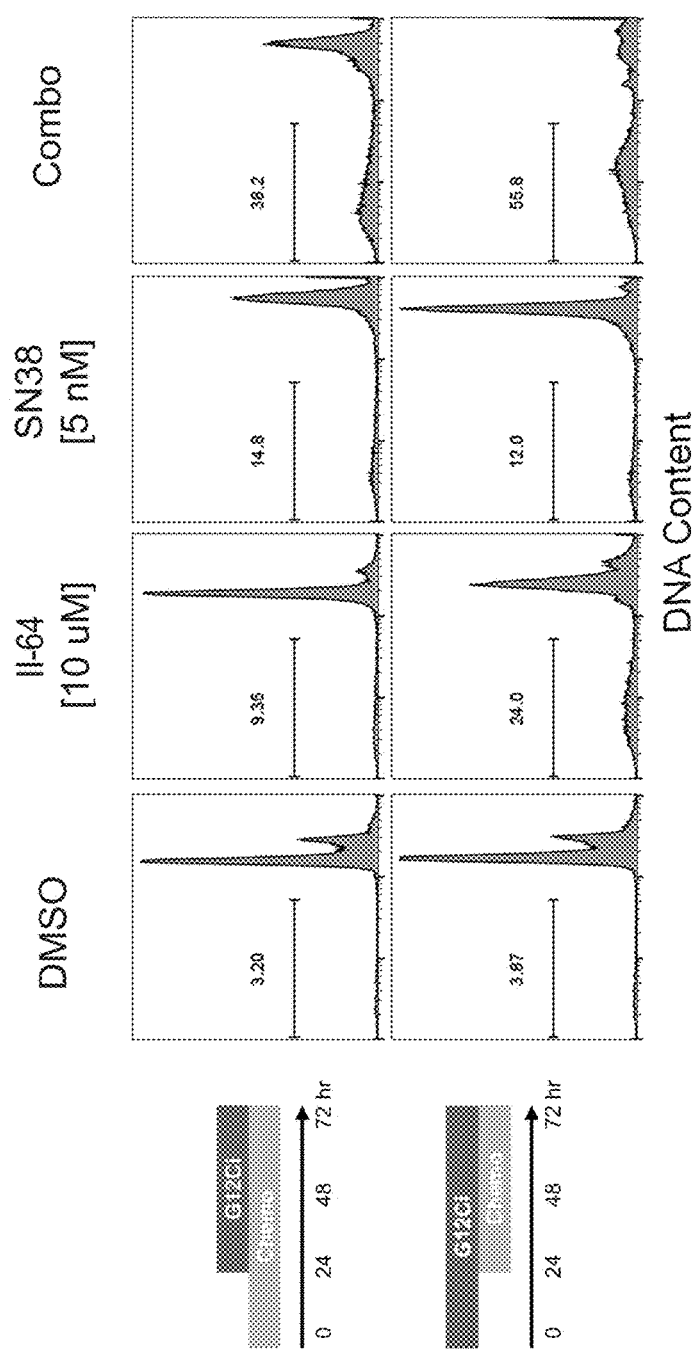
FIG. 7 depicts apoptosis in NCI-H358 cells treated with II-64 (10 μM), SN38 (5 nM), or a combination treatment (II-64+SN38). The top row shows results from cells that were pretreated with SN38 for 24 hours and then treated with II-64 for an additional 48 hours (72 hours total). The bottom row shows results from cells that were pretreated with II-64 for 24 hours and then treated with SN38 for an additional 48 hours (72 hours total). Apoptosis was measured via flow cytometry. Gated populations=% of subdiploid apoptotic cells.

Next, flow cytometry was used to evaluate a KRAS G12C inhibitor in combination with the chemotherapeutic agents paclitaxel or docetaxel. Synergistic increases in apoptotic (sub-diploid) H358 cells were observed when compound II-64 was combined with paclitaxel (FIG. 5), docetaxel (FIG. 6), and SN38 (active form of irinotecan, FIG. 7).

Figure 8:
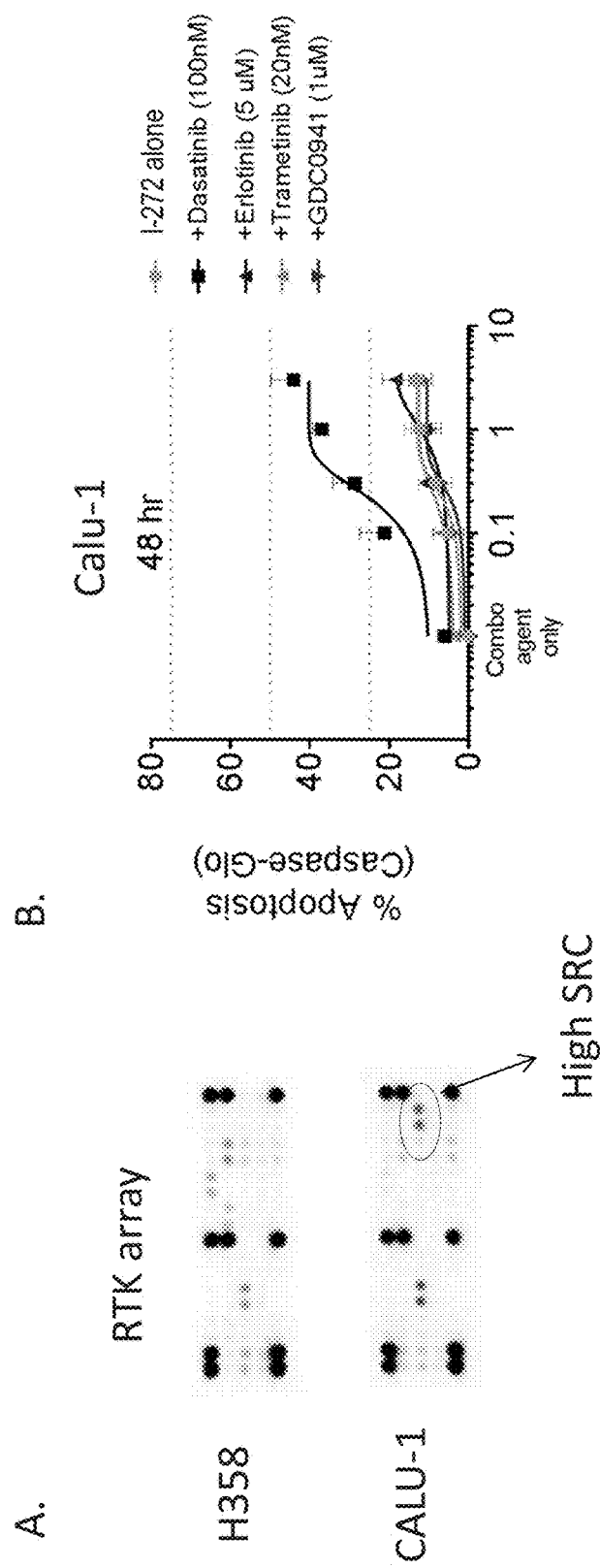
FIG. 8 depicts a tyrosine kinase activity array and caspase activity in Calu-1 cells. A) An RTK array was used to measure tyrosine kinase activity in NCI-H358 cells and Calu-1 cells. High SRC activity was detected in Calu-1 cells. B) Caspase activity was measured in Calu-1 cells using a Caspase-Glo assay. Cells were treated for 48 hours with increasing concentrations of I-272 alone, or I-272+dasatinib (SRC inhibitor; 100 nM), I-272+erlotinib (5 μM), I-272+ trametinib (20 nM), or I-272+GDC0941 (1 μM). I-272+ dasatinib induced significantly increased apoptosis.

The ability KRAS G12C targeting compounds in combination with other cancer therapeutics was assessed and demonstrated as follows. Calu-1 cells are generally resistant to single agent KRAS G12C inhibitor as well as combinations with the targeted agents tested in previous studies disclosed herein (EGFRi, MEKi, PI3Ki, IGF1Ri; FIG. 7B). Evaluation of phospho-tyrosine levels on a panel of tyrosine kinases revealed relatively high levels of SRC phosphorylation in Calu-1 cells (FIG. 8A). Treatment of Calu-1 cells with a KRAS G12C inhibitor (compound I-272) and a SRC inhibitor (Dasatinib) lead to high levels of apoptosis induction (FIG. 8B).

Example 4

Exemplary KRAS G12C Inhibitor in Combination with an EGFR, MEK or Class I PI3K Inhibitor for Synergistic Induction of Apoptosis The effectiveness of KRAS G12C targeting compounds in combination with other cancer therapeutics was assessed and demonstrated as follows. Western blots were used to analyze downstream KRAS signaling nodes (AKT, ERK, RSK, S6) and a marker of apoptosis (cleaved PARP). Treatment of H358 cells (KRAS G12C) with an exemplary KRAS G12C inhibitor (compound I-74) alone at a concentration of 15 µM for 24 hours causes clear and nearly complete inhibition of p-ERK, p-RSK, and p-S6 (FIG. 9, left panel). However, minimal cleaved PARP is seen, suggesting low levels of apoptosis (FIG. 9, left panel, lane 2 compared to lane 9). Likewise, treatment with erlotinib (EGFR inhibitor, 5 µM, FIG. 9, left panel, lane 3), PD0325901 (MEK inhibitor, 100 nM, FIG. 9, left panel, lane 5), GDC0941 (class I PI3K inhibitor, 1 µM, FIG. 9, left panel, lane 7) alone does not induce robust apoptosis based on cleaved PARP levels (FIG. 9, left panel, lanes 3, 5, and 7 compared to lane 9). Combination treatment of H358 cells with compound I-74, at a concentration of 15 µM, and erlotinib (EGFR inhibitor, 5 µM, FIG. 9, left panel, lane 4) leads to greatly enhanced apoptosis based on cleaved PARP levels. An increase in apoptosis based on cleaved PARP levels is also observed when compound I-74 (15 µM) is used in combination with PD0325901 (MEK inhibitor, 100 nM, FIG. 9, left panel, lane 6) or GDC0941 (PI3K inhibitor, 1 µM, FIG. 9, left panel, lane 8) to treat H358 cells. Taxol (paclitaxel) was used as a positive control.

As a control, a non-G12C cell line (A549) was subjected to the same single agent and combination treatments (FIG. 9, right panel). The KRAS G12C inhibitors show no single agent or additive/synergistic effects in this line. While not wishing to be bound by theory, it is believed that this data indicates that the synergistic effects in H358 cells are mediated by KRAS G12C specific inhibition.

Treatment of H358 cells with compound II-74, erlotinib, PD0325901, or GDC0941 as single agents leads to G1 arrest with low to modest induction of apoptosis (FIG. 9, left panel), while combination treatments dramatically increase the fraction of apoptotic cells.

Example 5

Figure 10:
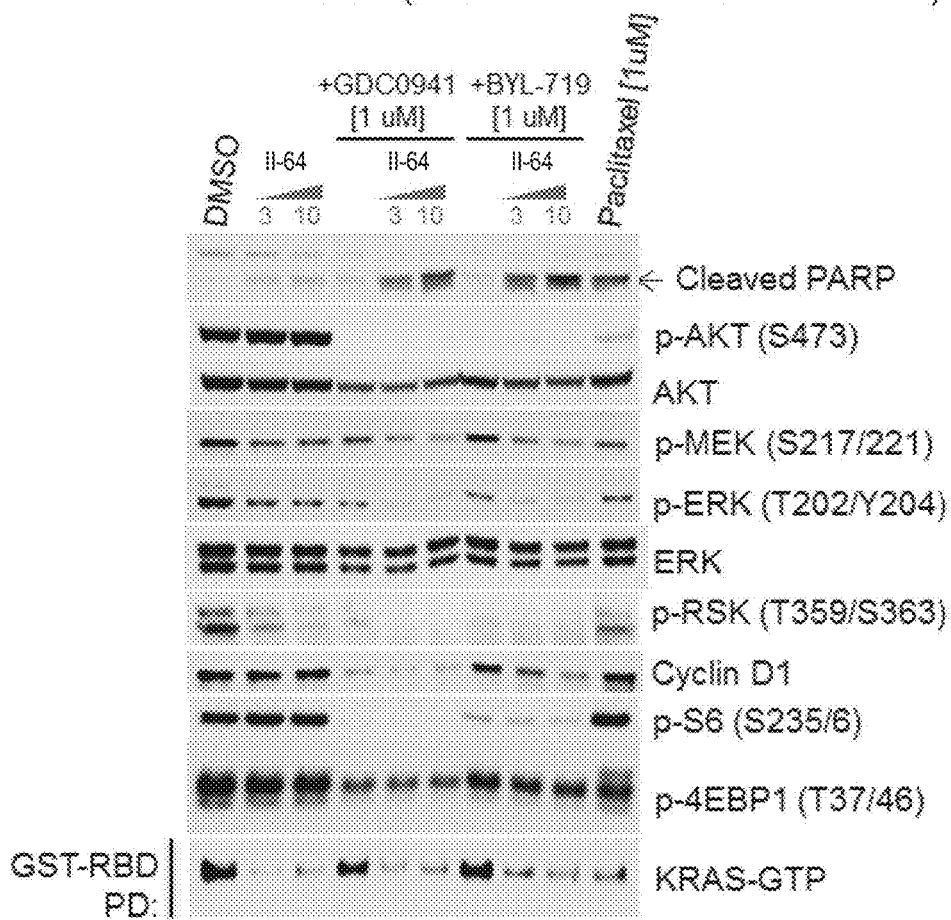
FIG. 10 is another western blot showing data from combinations of an exemplary G12C inhibitor with PI3KPI3K inhibition.

Exemplary KRAS G12C Inhibitor Used in Combination with Pan-PI3K and Selective PI3Kα for Synergistic Induction of Apoptosis Western blots were used to analyze downstream KRAS signaling nodes (AKT, ERK, RSK, S6) and a marker of apoptosis (cleaved PARP). Treatment of SW1573 cells with an exemplary KRAS G12C inhibitor (compound II-64) alone for 24 hours causes inhibition of p-ERK, p-RSK, and KRAS-GTP (FIG. 10). However, minimal cleaved PARP is seen, suggesting low levels of apoptosis (FIG. 10, lanes 2-3 compared to lane 1). Likewise, treatment with GDC0941 (class I PI3K inhibitor, FIG. 10, lane 4) and BYL-719 (selective PI3Kα inhibitor, FIG. 10, lane 7) alone does not induce robust apoptosis based on cleaved PARP levels (FIG. 10, lanes 7 compared to lane 1). Combination treatment with a KRAS G12C inhibitor and either GDC0941 (class I PI3K inhibitor, lanes 5-6) or BYL-719 (selective PI3Kα inhibitor, FIG. 10, lanes 8-9) leads to greatly enhanced apoptosis based on cleaved PARP levels. Taxol (paclitaxel) was used as a positive control. Pan PI3K and selective PI3Kα inhibitors induce equivalent synergistic apoptosis, measured by cleavage of PARP, when one is used in combination with a selective KRAS-G12C inhibitor.

Example 6

Figure 11:
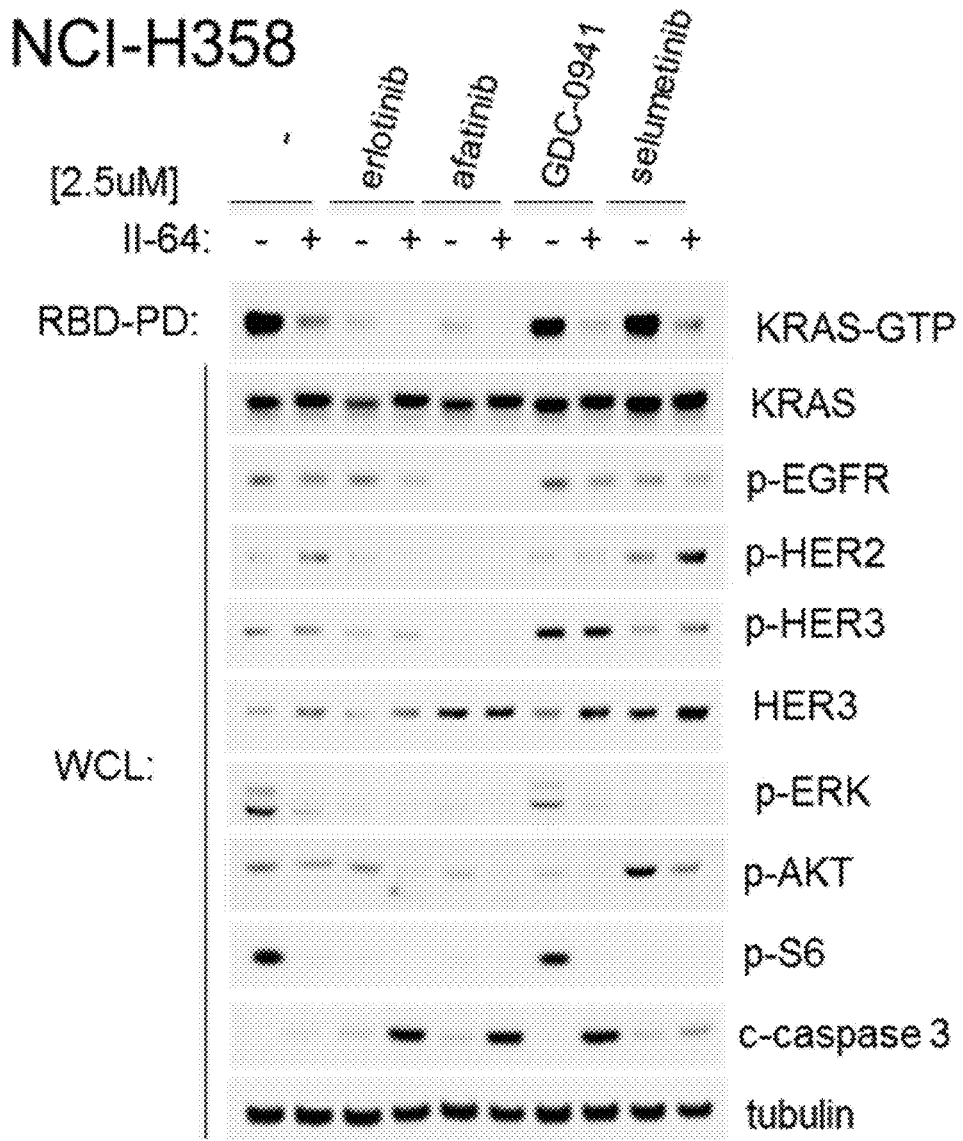
FIG. 11 provides data for combinations of a G12C inhibitor with an EGFR, EGFR/HER2 or PI3K inhibitor in NCI-H358 cells.

Exemplary KRAS G12C Inhibitor in Combination of One of an EGFR, EGFR/HER2, or PI3K Inhibitor for Synergistic Apoptosis and Pathway Inhibition Western blots were used to analyze downstream KRAS signaling nodes (AKT, ERK, RSK, S6) and a marker of apoptosis (cleaved PARP). Treatment of H358 cells (KRAS G12C) with an exemplary G12C inhibitor (compound II-64) alone at 2.5 µM for 24 hours causes clear and nearly complete inhibition of p-ERK and p-S6, with partial inhibition of p-AKT (FIG. 11). However, minimal c-caspase 3 is seen, suggesting low levels of apoptosis (FIG. 11, lanes 2 compared to lane 1). Likewise, treatment with erlotinib (EGFR inhibitor, lane 3), afatinib (MEK inhibitor, FIG. 11, lane 5) GDC0941 (class I PI3K inhibitor, FIG. 11, lane 7), and selumetinib (MEK inhibitor, FIG. 11, lane 9) alone does not induce robust apoptosis based on c-caspase 3 levels (FIG. 11, lanes 3, 5, 7, and 9 compared to lane 1). However, combination treatment with compound I-64 and either erlotinib (EGFR inhibitor, FIG. 11, lane 4), afatinib (MEK inhibitor, FIG. 11, lane 6), GDC0941 (class I PI3K inhibitor, FIG. 11, lane 8), or selumetinib (MEK inhibitor, FIG. 11, lane 10) leads to greatly enhanced apoptosis based on c-caspase 3 levels. Caspase activity was measured using a standard caspase activity luminescence assay (Capase-Glo, Promega).

Example 7

Figure 12:
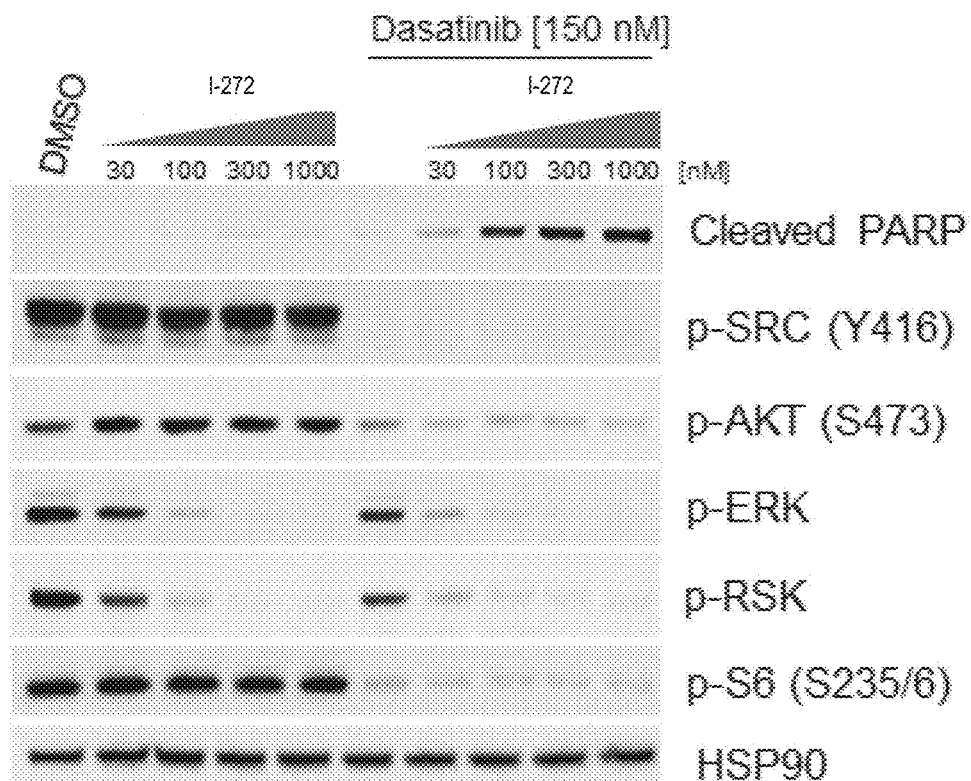
FIG. 12 is Western blot data from experiments treating CALU-1 cells with an exemplary G12C inhibitor or Dasunatinib, or both.

Exemplary KRAS G12C Inhibitor Used in Combination with an SRC Inhibitor for Synergistic Induction of Apoptosis of Calu-1 Cells Western blots were used to analyze downstream KRAS signaling nodes (AKT, ERK, RSK, S6) and a marker of apoptosis (cleaved PARP). Treatment of Calu-1 cells with an exemplary KRAS G12C inhibitor (compound I-272) alone for 24 hours at concentrations of 30, 100, 300, and 1000 nM causes clear and, at higher concentrations, nearly complete inhibition of p-ERK and p-RSK (FIG. 12). However, minimal cleaved PARP is seen, suggesting low levels of apoptosis (FIG. 12, lanes 2-5 compared to lane 1). Likewise, treatment with dasatinib (SRC inhibitor, FIG. 12, lane 6) alone does not induce robust apoptosis based on cleaved PARP levels (FIG. 12, lane 6 compared to lane 1).

In contrast, combination treatment with compound I-272 (dosed at 30, 100, 300, and 1000 nM, FIG. 12, lanes 7-10 respectively) and Dasatinib (SRC inhibitor, dosed at 150 nM, FIG. 12, lanes 7-10) leads to greatly enhanced apoptosis based on cleaved PARP levels. In addition, the combination treatment shows clear and nearly complete inhibition of p-SRC, p-AKT, p-ERK, p-RSK, and p-S6.

Example 8

Exemplary KRAS G12C Inhibitor Used in Combination with an SRC Inhibitor for Synergistic Induction of Apoptosis Western blots were used to analyze downstream KRAS signaling nodes (AKT, ERK, RSK, S6) and a marker of apoptosis (cleaved PARP). Treatment of mutant cell lines (H358, NCI-H23, SW1463, H1792, Calu-1, SW1573) or a control cell line (A549) was tested with an exemplary KRAS G12C inhibitor (compound I-272, 1 µM) alone or in combination with one of dasatinib ("Das," SRC inhibitor, 100 nM) or Saracatinib ("Sarc," SRC inhibitor, 2 µM). Treatment of mutant cell lines with KRAS G12C inhibitor, compound I-272, alone for 24 hours causes clear and, in some cases (H358, SW1463, Calu-1), nearly complete inhibition of p-ERK. The same treatment also shows inhibition of p-S6 in H358, SW1463, H1792, and Calu-1 cell lines (FIG. 13).

However, minimal cleaved PARP is seen, suggesting low levels of apoptosis. Likewise, treatment with Dasatinib or Sarcatinib alone does not induce robust apoptosis based on cleaved PARP levels. In contrast, combination treatment with a KRAS G12C inhibitor (compound I-272) and either dasatinib or Sarcatinib leads to greatly enhanced apoptosis based on cleaved PARP levels. Additionally, the combination of compound I-272 (1 µM) with dasatinib fully reduces p-S6 in the Calu-1 and SW1573 cell lines. As a control, a non-G12C cell line (A549) was subjected to the same single agent and combination treatments. The KRAS G12C inhibitors show no single agent or additive/synergistic effects in this line. While not wishing to be bound by theory, it is believed that this data indicates that the synergistic effects in mutant cell lines (i.e., H358, NCI-H23, SW1463, H1792, Calu-1, SW1573) are mediated by KRAS G12C specific inhibition.

Figure 13:
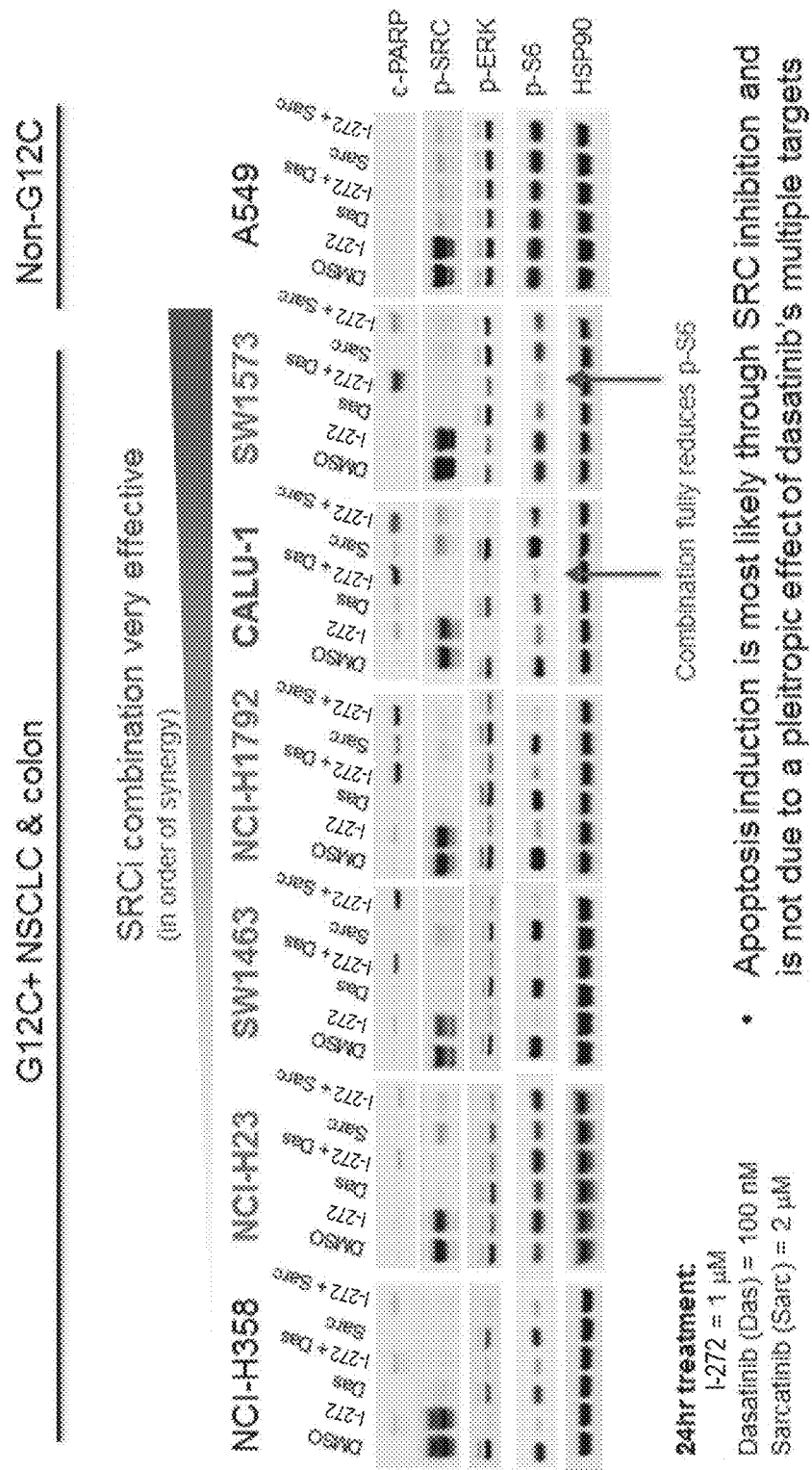
FIG. 13 presents data for combinations of Dasatinib (Das) or Sarcatinib (Sarc) with an exemplary G12C inhibitor in various cell lines.
Figure 14:
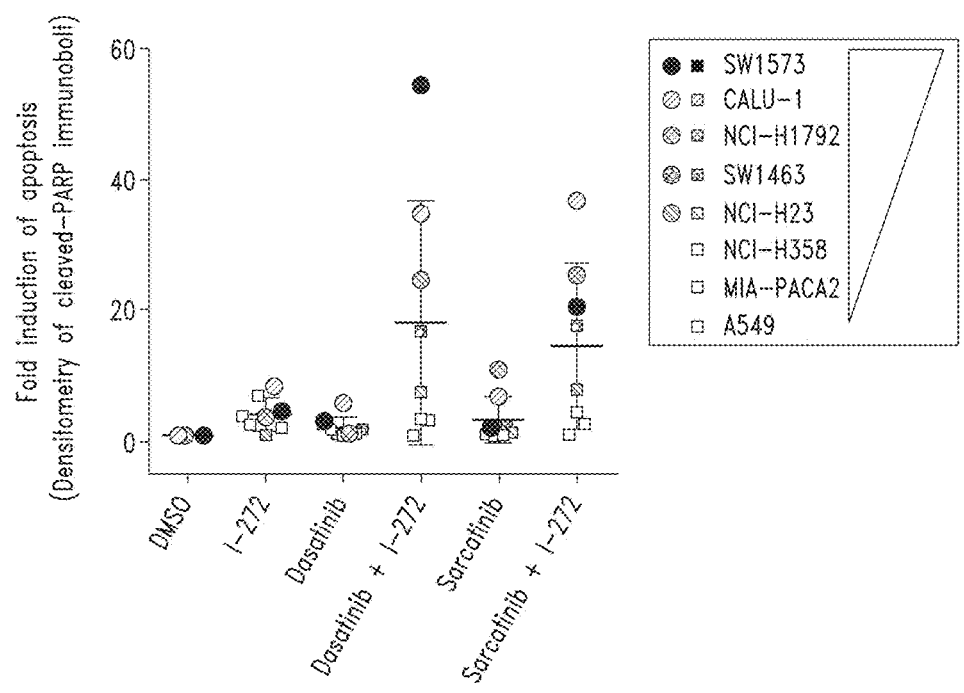
FIG. 14 is densitometry data for the gel of FIG. 14.

FIG. 14 provides densitometry data for the gels of FIG. 13.

Example 9

Figure 15:
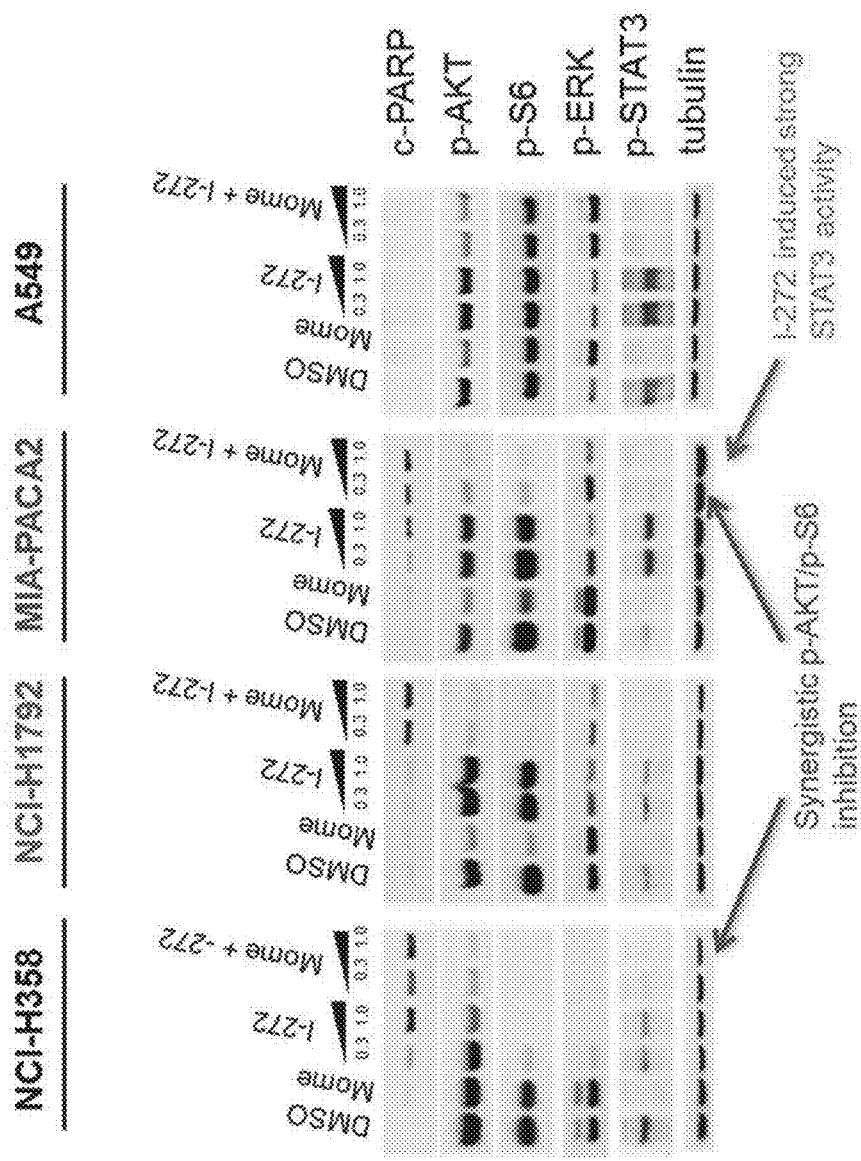
FIG. 15 is data for combinations of an exemplary G12C inhibitor and momelotinib in various cell lines.

Assessing and Demonstrating the Mechanism of Action for Synergistic Induction of Apoptosis of an Exemplary KRAS G12C Inhibitor Used in Combination with a JAK Inhibitor in Multiple Mutant Cell Lines Western blots were used to analyze downstream KRAS signaling nodes (AKT, ERK, S6), a transcription factor (STAT3), and a marker of apoptosis (cleaved PARP). Gel data is provided in FIG. 15. Treatment of mutant cell lines (H358, H1792, MiaPaca2) or a control cell line (A549) was tested with an exemplary KRAS G12C inhibitor (compound I-272, 0.3 and 1 µM) alone or in combination with momelotinib (JAK inhibitor, 5 µM). Treatment of mutant cell lines with KRAS G12C inhibitor, compound I-272, alone for 24 hours causes some and nearly complete inhibition of p-ERK (in H1792 and H358 respectfully), some inhibition of p-ANK (in H358), some to nearly complete inhibition of S6 (in H358) as well as some induction of apoptosis as observed by the presence of cleaved PARP (in H358 and MiaPaca2). Treatment with I-272 alone also induces STAT3 in certain cell lines (slight in H358 and H1792, strong in MiaPaca2 and A549). The combination of compound I-272 (0.3 and 1 µM) and momelotinib (JAK inhibitor, 5 µM) induces apoptosis in a broad range of G12C positive cell lines and potentiates inhibition of p-AKT and p-S6. Specifically, when compound I-272 is used in combination with momelotinib (JAK inhibitor) PARP is detected in H358, H1792, and MiaPaca2.

As a control, a non-G12C cell line (A549) was subjected to the same single agent and combination treatments. The KRAS G12C inhibitors show no single agent or additive/synergistic effects in this line. While not wishing to be bound by theory, it is believed that this data indicates that the synergistic effects in the H358, H1792, and MiaPaca2 cell lines are mediated by KRAS G12C specific inhibition.

Example 10

Figure 16:
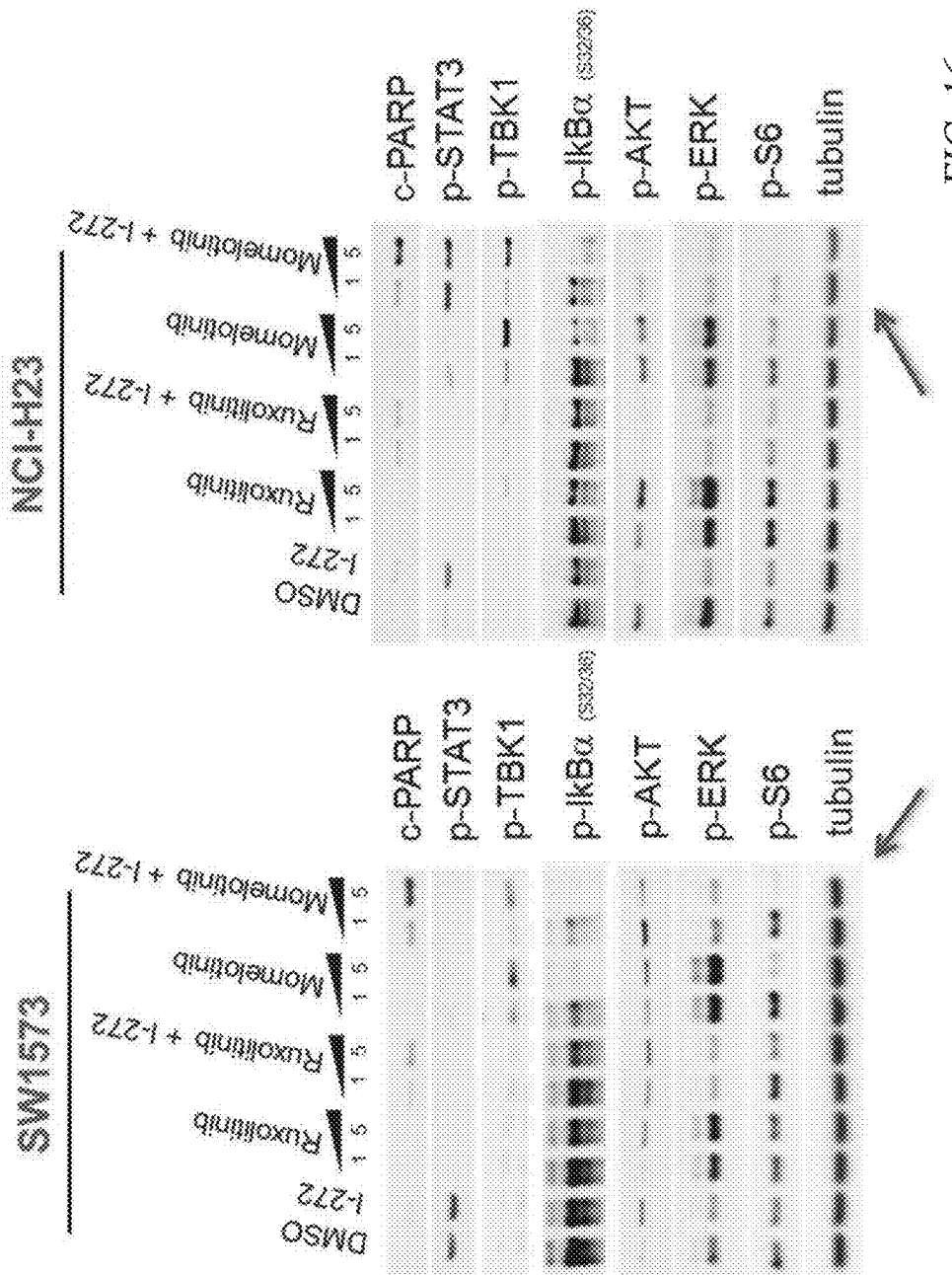
FIG. 16 provides Western blot data for combinations of an exemplary G12C inhibitor and momelotinib or ruxolitinib in various cell lines.

Assessing and Demonstrating the Mechanism of Action for Synergistic Induction of Apoptosis of an Exemplary KRAS G12C Inhibitor Used in Combination with a JAK Inhibitor in Mutant Cell Lines Western blots were used to analyze downstream KRAS signaling nodes (AKT, ERK, S6), transcription factors (STAT3, IκBα), protein marker (TBK1) and a marker of apoptosis (cleaved PARP). Treatment of mutant cell lines (NCI-H23, SW1573) were tested with an exemplary KRAS G12C inhibitor (compound I-272, 1 µM) alone or in combination with one of ruxolitinib (JAK 1/2 inhibitor, 1 and 5 µM) or momelotinib (JAK1/2, TBK1, IKKe inhibitor, 1 and 5 µM). Treatment of mutant cell lines with KRAS G12C inhibitor, compound I-272, alone for 24 hours causes clear and nearly complete inhibition of p-ERK. The same treatment also shows inhibition of p-S6 and p-AKT in NCI-H23. However, minimal cleaved PARP is seen, suggesting low levels apoptosis (FIG. 16). Likewise, treatment with ruxolitinib (JAK1/2 inhibitor, FIG. 16, lane 2-3) or momelotinib (JAK1/2, TBK1, IKKe inhibitor, FIG. 16, lane 7-8) alone does not induce robust apoptosis based on cleaved PARP levels (FIG. 16, lanes 2-3 and 7-8 compared to lane 1). Combination treatment with either ruxolitinib (JAK1/2, TBK1, IKKe inhibitor, FIG. 16, lane 5-6) or momelotinib (JAK1/2, TBK1, IKKe inhibitor, FIG. 16, lane 9-10) leads to greatly enhanced apoptosis based on PARP levels. Further, there is synergistic p-S6 inhibition in each of the combinations. Synergistic apoptosis strongly occurred when TBK1 and non-canonical NFκB signaling is inhibited. This effect suggests the mechanism of action of apoptosis in these combination treatments is independent from JAK/STAT.

The following synthetic examples are provided for exemplary purposes. Other compounds of structures (I), (II) and (III) were prepared according to analogous procedures.

Example 11

Synthesis of 1-(4-(7-chloro-6-(2-chlorophenyl)quinazolin-4-yl)piperazin-1-yl)prop-2-en-1-one (I-1)

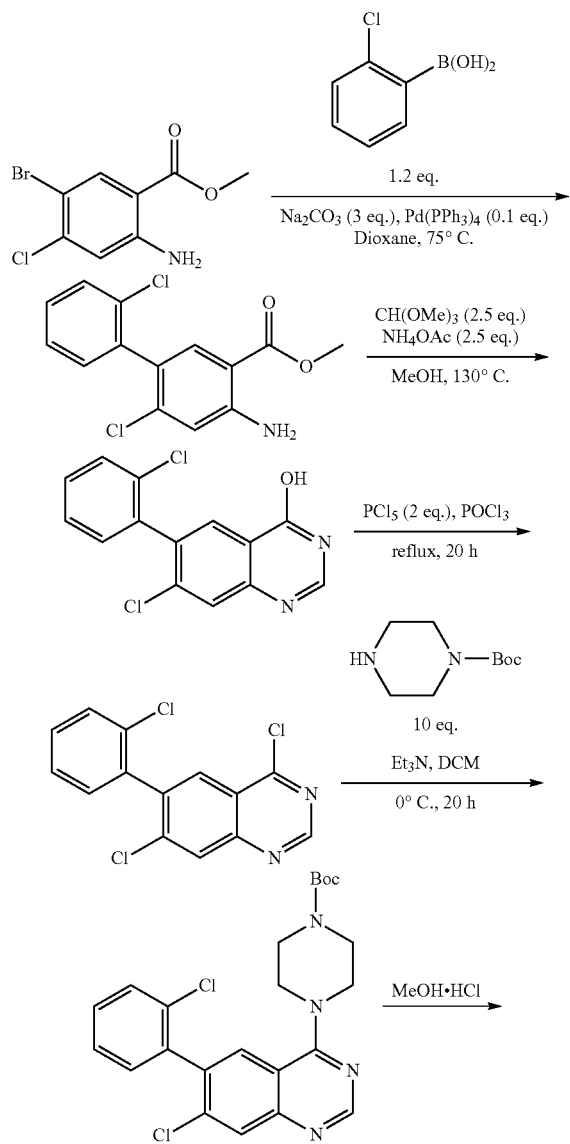

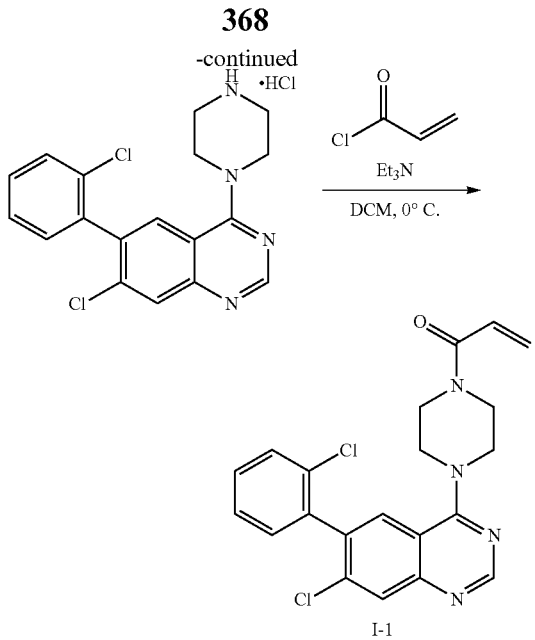

Compound I-1 was prepared according to Method A as described below:

Methyl 2-amino-5-(2-chlorophenyl)-4-chlorobenzoate

A mixture of methyl 2-amino-5-bromo-4-chlorobenzoate (1.2 g, 4.54 mmol), 2-chlorophenylboronic acid (0.85 g, 5.44 mmol), $Na_2CO_3$ (1.44 g, 13.61 mmol), and $Pd(PPh_3)_4$ (0.52 g, 0.45 mmol) in 1,4-dioxane (30 mL) and water (6 mL) was stirred at 75° C. under argon for 16 h. The mixture was allowed to cool to room temperature (RT), and concentrated in vacuo. The residue was purified by flash column chromatography on silica gel (ethyl acetate/petroleum=8:1) to afford the desired product (1.22 g, 91% yield) as a yellow solid.

7-Chloro-6-(2-chlorophenyl)quinazolin-4-ol

A mixture of methyl 2-amino-5-(2-chlorophenyl)-4-chlorobenzoate (342 mg, 1.16 mmol), $CH(OMe)_3$ (306 mg, 2.89 mmol), and $NH_4OAc$ (223 mg, 2.89 mmol) in MeOH (1 mL) in a sealed tube was stirred at 130° C. for 4.5 h. The mixture was allowed to cool to RT, and concentrated in vacuo. The residue was purified by flash column chromatography on silica gel eluting with DCM and MeOH (40:1) to yield the desired product (277 mg, 82% yield) as a white solid. ESI-MS m/z: 289.2 [M–H]⁻.

4,7-Dichloro-6-(2-chlorophenyl)quinazoline

A mixture of 7-chloro-6-(2-chlorophenyl)quinazolin-4-ol (277 mg, 0.95 mmol), $PCl_5$ (397 mg, 1.90 mmol) and $POCl_3$ (16 mL) was stirred at reflux for 20 h. The mixture was allowed to cool to RT, and then concentrated in vacuo to yield the crude product (1.19 g) as dark oil which was used directly in next step without further purification.

tert-Butyl-4-(7-chloro-6-(2-chlorophenyl)quinazolin-4-yl)piperazine-1-carboxylate The above obtained crude 4,7-dichloro-6-(2-chlorophenyl)quinazoline (1.19 g) was added to the mixture of tert-butyl piperazine-1-carboxylate (5 g, 26.9 mmol) and Et₃N (7.76 g, 76.8 mmol) in DCM (200 mL) at 0° C. and the resulting mixture was stirred at the same temperature for 1 h. The mixture was poured into water (500 mL) and brine (100 mL), and then dichloromethane (DCM) (200 mL) was added. The mixture was filtered through filter paper. The organic layer was separated, dried over Na₂SO₄ and concentrated in vacuo. The residue was purified by flash column chromatography on silica gel eluting with DCM and MeOH (30:1) to yield the desired product (184 mg, 42% yield, 2 steps) as a light yellow oil. ESI-MS m/z: 459.3 [M+H]⁺.

1-(4-(7-Chloro-6-(2-chlorophenyl)quinazolin-4-yl)piperazin-1-yl)prop-2-en-1-one

A mixture of tertbutyl-4-(7-chloro-6-(2-chlorophenyl)quinazolin-4-yl)piperazine-1-carboxylate (184 mg, 0.40 mmol) and HCl in MeOH (20 mL) was stirred at RT for 1 h. The mixture was concentrated in vacuo to yield the crude product (176 mg) as a yellow solid which was used directly in next step without further purification.

1-(4-(7-Chloro-6-(2-chlorophenyl)quinazolin-4-yl)piperazin-1-yl)prop-2-en-1-one (1)

The above obtained crude 1-(4-(7-chloro-6-(2-chlorophenyl)quinazolin-4-yl)piperazin-1-yl)prop-2-en-1-one (17 6 mg) was dissolved in Et₃N (450 mg, 4.45 mmol) and DCM (30 mL) and cooled to 0° C., acryloyl chloride (44 mg, 0.49 mmol) in DCM (50 mL) was added to the mixture. The resulting mixture was allowed to warm to RT and stirred at RT for 1.5 h. The reaction mixture was quenched with saturated NaHCO₃ aqueous solution, and then extracted with ethyl acetate. The organic layer was washed with saturated NaHCO₃ solution and brine, dried over Na₂SO₄ and concentrated in vacuo. The residue was purified by flash column chromatography on silica gel eluting with DCM and MeOH (30:1) to yield the desired product (82 mg, 50% yield, 2 steps) as a yellow solid. ¹H NMR (400 MHz, DMSO-d6) δ: 8.75 (s, 1H), 8.03 (s, 1H), 7.96 (s, 1H), 7.62-7.49 (m, 4H), 6.81 (dd, J=10.4, 16.4 Hz, 1H), 6.15 (dd, J=16.4, 2.4 Hz, 1H), 5.71 (dd, J=10.4, 2.0 Hz, 1H), 3.87-3.72 (m, 8H). ESI-MS m/z: 413.2 [M+H]⁺.

Example 12

Synthesis of 1-(4-(7-chloro-6-phenylquinazolin-4-yl)piperazin-1-yl)prop-2-en-1-one (I-18)

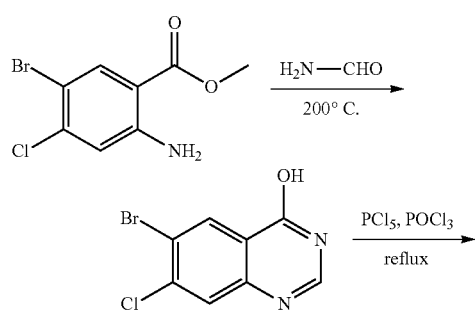

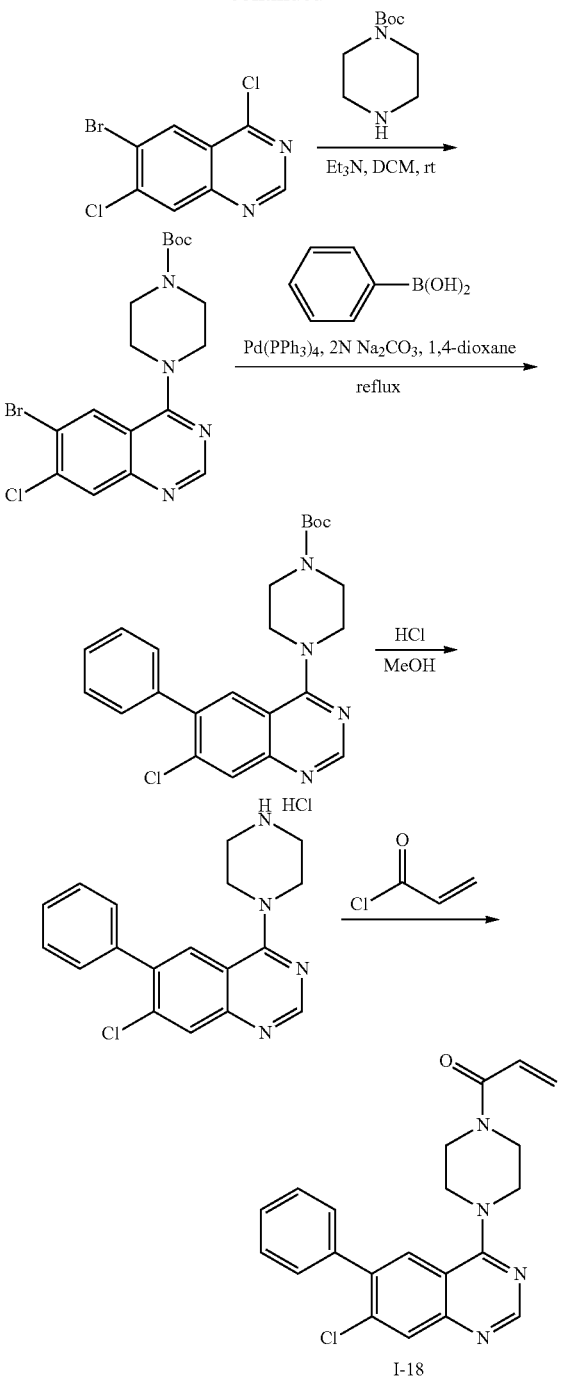

Compound I-18 was prepared according to Method B as described below:

6-Bromo-7-chloroquinazolin-4-ol

A mixture of methyl 2-amino-5-bromo-4-chlorobenzoate (1 g, 3.95 mmol) and NH₂CHO (20 mL) was stirred at 200° C. for 3 h. The mixture was allowed to cool to RT and quenched with water. The solid precipitate was collected by filtration and dried in vacuo to yield the desired product (669 mg, 66% yield) as a brown solid.

6-Bromo-4,7-dichloroquinazoline

A mixture of 6-bromo-7-chloroquinazolin-4-ol (669 mg, 2.59 mmol), PCl$_5$ (1.6 g, 7.78 mmol) and POCl$_3$ (15 mL) was stirred at reflux for 16 h. The mixture was allowed to cool to RT and then concentrated in vacuo to yield the desired product as dark oil which was used directly in next step without further purification.

tert-Butyl 4-(6-bromo-7-chloroquinazolin-4-yl)piperazine-1-carboxylate

The above obtained crude 6-bromo-4,7-dichloroquinazoline was added to the mixture of tert-butyl piperazine-1-carboxylate (4.82 g, 25.9 mmol) and Et$_3$N (2.62 g, 25.9 mmol) in DCM (70 mL). The resulting mixture was stirred at RT for 2 h and then was quenched with saturated NaHCO$_3$ aqueous solution. The mixture was extracted with DCM, washed with saturated NaHCO$_3$ aqueous solution and brine, dried over Na$_2$SO$_4$ and concentrated in vacuo. The residue was purified by flash column chromatography on silica gel eluting with ethyl acetate and petroleum ether (4:1) to yield the desired product (631 mg, 57% yield, 2 steps) as a yellow solid. ESI-MS m/z: 429.3 [M+H]$^+$.

tert-Butyl 4-(7-chloro-6-phenylquinazolin-4-yl)piperazine-1-carboxylate

A mixture of tert-butyl 4-(6-bromo-7-chloroquinazolin-4-yl)piperazine-1-carboxylate (200 mg, 0.47 mmol), phenylboronic acid (115 mg, 0.94 mmol), Na$_2$CO$_3$ solution (2.0 M, 0.71 mL, 1.41 mmol), Pd(PPh$_3$)$_4$ (109 g, 0.094 mmol) in 1,4-dioxane (10 mL) was stirred at reflux under argon for 16 h. The mixture was allowed to cool to RT, diluted with ethyl acetate, and then washed with H$_2$O and brine. The organic layer was dried over Na$_2$SO$_4$ and concentrated in vacuo. The residue was purified by flash column chromatography on silica gel eluting with ethyl acetate and petroleum ether (1:4) to yield the desired product (120 mg, 60% yield) as a yellow oil. ESI-MS m/z: 425.4 [M+H]$^+$.

1-(4-(7-Chloro-6-phenylquinazolin-4-yl)piperazin-1-yl)prop-2-en-1-one

The title compound was prepared from tert-butyl 4-(7-chloro-6-phenylquinazolin-4-yl)piperazine-1-carboxylate in two steps following the procedure described in Example 2. $^1$H NMR (400 MHz, CDCl$_3$) δ: 8.74 (s, 1H), 8.15 (s, 1H), 7.83 (s, 1H), 7.50-7.45 (m, 5H), 6.58 (dd, J=16.8, 10.4 Hz, 1H), 6.36 (dd, J=16.4, 1.6 Hz, 1H), 5.77 (dd, J=10.4, 2.0 Hz, 1H), 3.92-3.81 (m, 8H). ESI-MS m/z: 379.3 [M+H]$^+$.

Example 13

Synthesis of 1-(4-(6-chloro-5-(2-chlorophenyl)-1H-indazol-3-ylamino)piperidin-1-yl)prop-2-en-1-one (I-31)

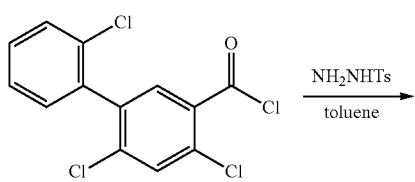
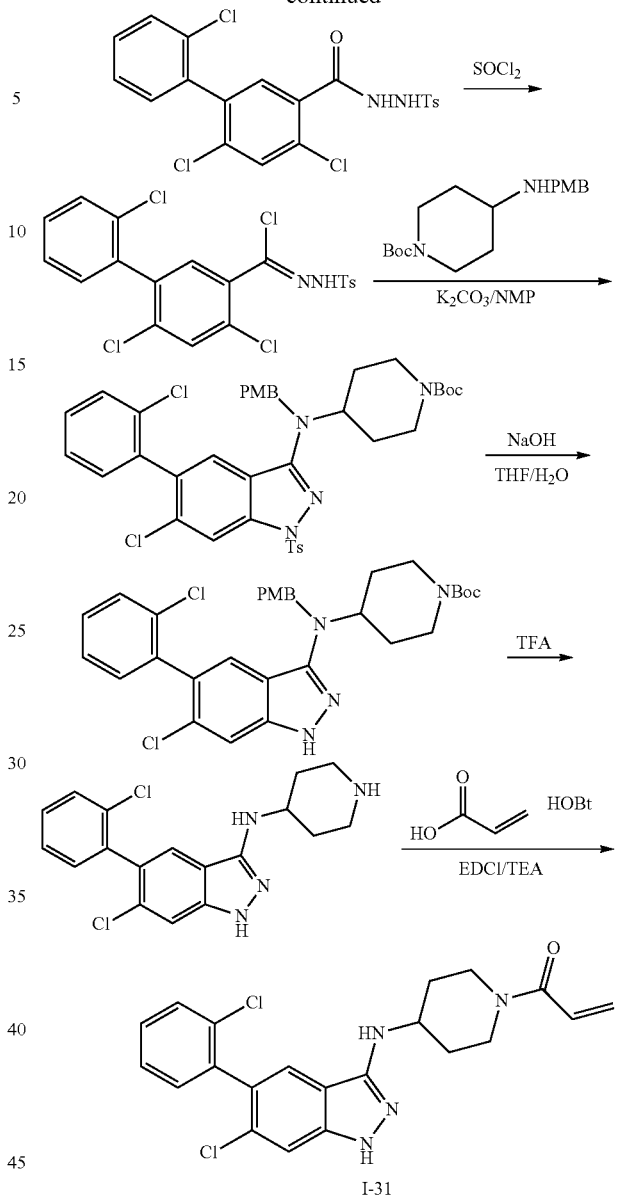

Compound I-31 was prepared according to Method C as described below:

4-Methyl-N'-(2',4,6-trichlorobiphenylcarbonyl)benzenesulfonohydrazide

To a stirred solution of 2',4,6-trichlorobiphenyl-3-carbonyl chloride (5.5 g) in toluene at RT, NH$_2$NHTs (3.8 g, 20.3 mmol) was added and the resulting mixture was stirred at 75° C. overnight. The mixture was allowed to cool to RT. The solid was collected by filtration and dried in vacuo to afford the desired product (6 g, 75% yield) as a white solid.

2',4,6-Trichloro-N'-tosylbiphenyl-3-carbohydrazonoyl chloride

A solution of 4-methyl-N'-(2',4,6-trichlorobiphenylcarbonyl)benzenesulfonohydrazide (2.3 g, 4.5 mmol) in SOCl$_2$ (5.8 g, 45 mmol) was stirred at 75° C. for 4 h. The mixture was allowed to cool to RT, and then petroleum ether was added. The resulting mixture was stirred at 0° C. for 1 h. The precipitate was collected by filtration and dried in vacuo to afford the desired product (1.6 g, 67% yield) as a white solid.

tert-Butyl 4-((6-chloro-5-(2-chlorophenyl)-1-tosyl-1H-indazol-3-yl)(4-methoxybenzyl)amino) piperidine-1-carboxylate To a stirred solution of 2',4,6-trichloro-N'-tosylbiphenyl-3-carbohydrazonoyl chloride (1.6 g, 3.4 mmol) in 100 mL of NMP at RT, tert-butyl 4-(4-methoxybenzylamino)piperidine-1-carboxylate (1.1 g, 3.4 mmol) was added followed by $K_2CO_3$ (1.4 g, 10.2 mmol). The reaction mixture was stirred at 40° C. overnight. The mixture was allowed to cool to RT, and partitioned between water and ethyl acetate. The organic layer was dried over anhydrous $Na_2SO_4$, filtered and concentrated in vacuo. The residue was purified by flash column chromatography on silica gel (1-20% ethyl acetate/petroleum ether) to afford the desired product (550 mg, 23% yield) as a white solid.

tert-Butyl 4-((6-chloro-5-(2-chlorophenyl)-1H-indazol-3-yl)(4-methoxybenzyl)amino) piperidine-1-carboxylate To a stirred solution of tert-butyl 4-((6-chloro-5-(2-chlorophenyl)-1-tosyl-1H-indazol-3-yl)(4-methoxybenzyl)amino) piperidine-1-carboxylate (550 mg, 0.75 mmol) in THF (20 mL) and water (5 mL) at RT, NaOH (75 mg, 1.87 mmol) was added, and the resulting mixture was stirred at reflux overnight. The reaction mixture was cooled to RT and partitioned between water and ethyl acetate. The organic layer was dried over anhydrous $Na_2SO_4$, filtered and concentrated in vacuo. The residue was purified by flash column chromatography on silica gel (1-10% ethyl acetate/petroleum ether) to afford the desired product (100 mg, 23% yield) as a white solid. ESI-MS m/z: 581.5 [M+H]$^+$.

6-Chloro-5-(2-chlorophenyl)-N-(piperidin-4-yl)-1H-indazol-3-amine

A solution of tert-butyl 4-((6-chloro-5-(2-chlorophenyl)-1H-indazol-3-yl)(4-methoxybenzyl)amino) piperidine-1-carboxylate (100 mg, 0.17 mmol) in 5 mL of TFA was stirred at reflux for 2 h. The reaction mixture was allowed to cool to RT and then partitioned between saturated $NaHCO_3$ aqueous solution and ethyl acetate. The organic layer was dried over anhydrous $Na_2SO_4$, filtered and concentrated in vacuo to afford the desired product (62 mg) as a yellow solid. The crude product was used directly in the next step without further purification.

1-(4-(6-Chloro-5-(2-chlorophenyl)-1H-indazol-3-ylamino)piperidin-1-yl)prop-2-en-1-one To a stirred solution of acrylic acid (12.4 mg, 0.17 mmol) in 5 mL of DMF at RT, 6-chloro-5-(2-chlorophenyl)-N-(piperidin-4-yl)-1H-indazol-3-amine (62 mg, 0.17 mmol), HOBT (30 mg, 0.22 mmol), EDCI (42 mg, 0.22 mmol), and TEA (52 mg, 0.51 mmol) were added sequentially. The reaction mixture was stirred at RT overnight. The mixture was partitioned between brine and ethyl acetate. The organic layer was dried over anhydrous $Na_2SO_4$, filtered and concentrated in vacuo. The residue was purified by prep-HPLC to give the desired product (2 mg, 3% yield) as a white solid. $^1$H NMR (300 MHz, DMSO-d6) δ: 11.67 (s, 1H), 7.73 (s, 1H), 7.56-7.58 (m, 1H), 7.41-7.47 (m, 2H), 7.42 (s, 1H), 7.36-7.39 (m, 1H), 6.80-6.87 (m, 1H), 6.07 (dd, J=2.5, 16.7 Hz, 1H), 6.04 (d, J=7.3 Hz, 1H), 5.65 (dd, J=2.4, 10.4 Hz, 1H), 4.23 (d, J=12.3 Hz, 1H), 3.98 (d, J=13.6 Hz, 1H), 3.76-3.80 (m, 1H), 3.26 (t, J=13.0 Hz, 1H), 2.97 (t, J=10.2 Hz, 1H), 2.06 (m, 2H), 1.38 (m, 2H). ESI-MS m/z: 415.1 [M+H]$^+$.

Example 14

Synthesis of 1-(4-(6-chloro-7-(2-chlorophenyl)isoquinolin-1-yl)piperazin-1-yl)prop-2-en-1-one (I-24)

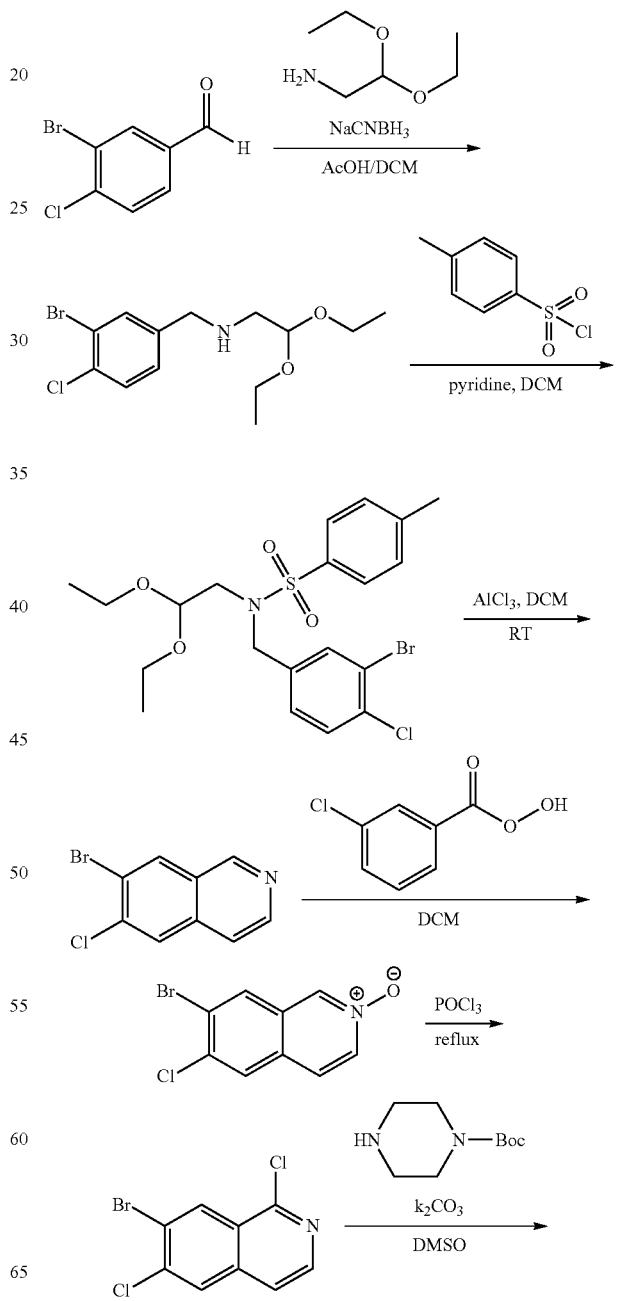

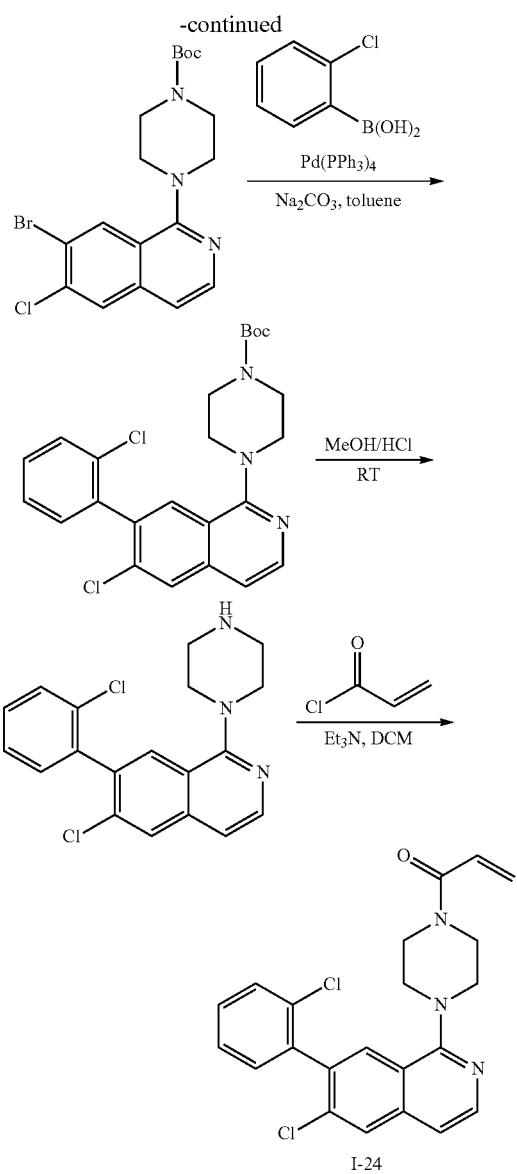

Compound I-24 was prepared according to Method D as described below:

N-(3-Bromo-4-chlorobenzyl)-2,2-diethoxyethanamine

To a solution of 3-bromo-4-chlorobenzaldehyde (10.0 g, 45 mmol) and 2,2-diethoxyethanamine (6.68 g, 50 mmol) in 200 mL of DCM at RT, 0.5 mL of AcOH was added and the resulting mixture was stirred at RT for 30 min. To this mixture, NaCNBH$_3$ (8.1 g, 135 mmol) was added in portions and then stirred at RT overnight. The reaction mixture was portioned between water and DCM. The organic layer was washed with water (80 mL×2) and brine, dried over anhydrous Na$_2$SO$_4$, filtered and concentrated in vacuo to afford the desired product (11 g, 72% yield) as an oil. The crude product obtained was used directly in the next step without further purification.

N-(3-Bromo-4-chlorobenzyl)-2,2-diethoxy-N-tosyle-thanamine

To a solution of N-(3-bromo-4-chlorobenzyl)-2,2-diethoxyethanamine (11 g, 33 mmol) in 100 mL of DCM, pyridine (10 mL) was added and the resulting mixture was cooled to 0° C. To this mixture, a solution of 4-methylbenzene-1-sulfonyl chloride (6.8 g, 36 mmol) in 50 mL of DCM was added dropwise. The reaction mixture was allowed to warm to RT and stirring was continued until conversion was completed. The reaction mixture was washed twice with HCl aqueous solution (2 M), sodium bicarbonate solution and brine. The organic layer was dried over anhydrous Na$_2$SO$_4$, filtered and concentrated in vacuo. The residue was purified by flash column chromatography on silica gel (5-20% ethyl acetate/petroleum ether) to afford the desired product (12.5 g, 78% yield). ESI-MS m/z: 490.2 [M+H]$^+$.

7-Bromo-6-chloroisoquinoline

AlCl$_3$ (14.9 g) was suspended in DCM at RT, a solution of N-(3-bromo-4-chlorobenzyl)-2,2-diethoxy-N-tosylethan-amine (11.0 g, 22.5 mmol) in 75 mL of DCM was added and the resulting mixture was stirred overnight. The mixture was poured into ice water, and extracted with DCM. The combined organic layer was dried over anhydrous Na$_2$SO$_4$, filtered and concentrated in vacuo. The residue was purified by flash column chromatography on silica gel (10-40% ethyl acetate/petroleum ether) to afford the desired product (5 g, 92.5% yield) as a white solid. ESI-MSm/z: 242 [M+H]$^+$.

7-Bromo-6-chloroisoquinoline2-oxide

To a solution of 7-bromo-6-chloroisoquinoline (5.5 g, 22.8 mmol) in 100 mL of DCM at RT, was added m-chloroperbenzoic acid (70%, 5.88 g, 34.2 mmol) and the resulting mixture was stirred at RT overnight. The precipitate was filtered off and rinsed with DCM. The filtrate was washed with sodium bicarbonate solution. The layers were separated and the aqueous layer was extracted with DCM. The combined organic layer was dried with anhydrous Na$_2$SO$_4$ and concentrated in vacuo to afford the desired product (4.6 g, 79% yield). The crude product was used directly in the next step without further purification. ESI-MS m/z: 258.2 [M+H]$^+$.

1-(4-(6-chloro-7-(2-chlorophenyl)isoquinolin-1-yl)piperazin-1-yl)prop-2-en-1-one The title compound was prepared from 7-Bromo-6-chloroisoquinoline2-oxide in five steps following the procedure described in Example 2. $^1$H NMR (400 MHz, DMSO-d6) δ: 8.22-8.21 (m, 2H), 8.00 (s, 1H), 7.65-7.47 (m, 5H), 6.87 (dd, J=16.9, 10.5 Hz, 1H), 6.16 (dd, J=16.7, 1.7 Hz, 1H), 5.72 (dd, J=10.3, 2.1 Hz, 1H), 3.83 (m, 4H), 3.37 (m, 4H). ESI-MS m/z: 412.2 [M+H]$^+$.

Example 15

Synthesis of 1-(4-(7-chloro-6-(2-chlorophenyl)quinolin-4-yl)piperazin-1-yl)prop-2-en-1-one (I-27)

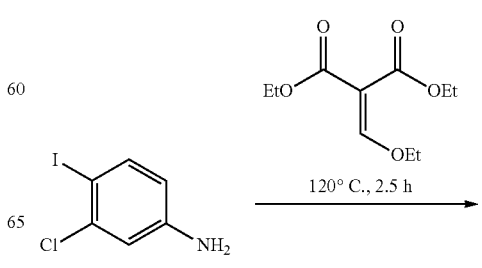

-continued

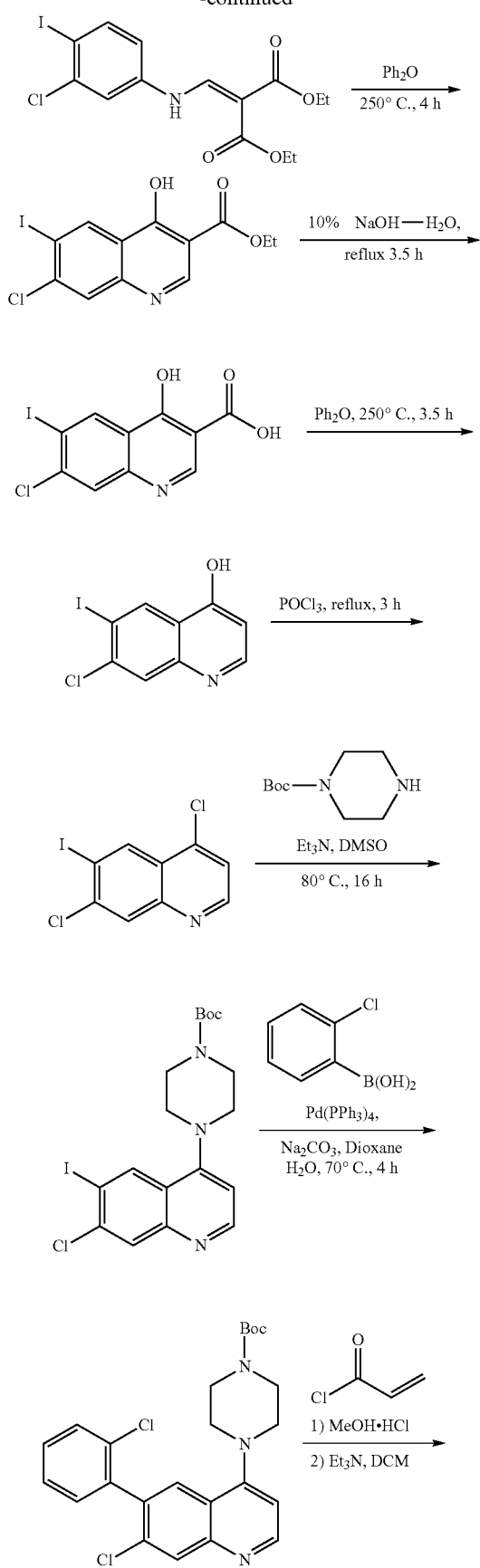

-continued

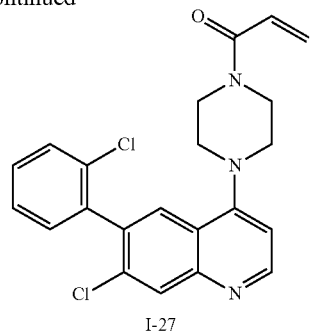

I-27

Compound I-27 was prepared according to Method E as described below:

Diethyl 2-((3-chloro-4-iodophenylamino)methylene)malonate

3-Chloro-4-iodoaniline (3.0 g, 11.8 mmol) and diethyl 2-(ethoxymethylene)malonate (12.78 g, 59.2 mmol) were mixed in a 100 mL single neck flask, and the resulting mixture was heated to 120° C. and stirred for 2.5 h. The mixture was allowed to cool to RT and purified by flash column chromatography on silica gel (10-20% ethyl acetate/petroleum ether) to afford the desired product (3.93 g) as a white solid. ESI-MS m/z: 422.1 [M−H]⁻.

Ethyl 7-chloro-4-hydroxy-6-iodoquinoline-3-carboxylate (E)-diethyl 2-(((3-chloro-4-iodophenyl)imino)methyl)malonate (2.0 g, 4.73 mmol) was suspended in 30 mL of Ph₂O. The mixture was stirred at 250° C. for 4 h. The mixture was allowed to cool to RT and then 100 mL of petroleum ether was added. The white solid was collected by filtration and rinsed with petroleum ether (100 mL) to afford the desired product (1.20 g) as a white solid.

7-Chloro-4-hydroxy-6-iodoquinoline-3-carboxylic acid

Ethyl 7-chloro-4-hydroxy-6-iodoquinoline-3-carboxylate (1.2 g, 3.18 mmol) was suspended in 10% NaOH aqueous solution (50 mL). The mixture was stirred at reflux for 3.5 h. The white solid was slowly dissolved in NaOH solution. After the mixture turned to a colorless phase, it was kept heating for additional 1 h. The mixture was allowed to cool to RT, and the white solid was separated out. The mixture was acidified with con. HCl to adjust the pH to 2. The white precipitate was collected by filtration and rinsed with petroleum ether to afford the desired product (1.13 g) as a white solid.

7-Chloro-6-iodoquinolin-4-ol

7-Chloro-4-hydroxy-6-iodoquinoline-3-carboxylic acid (1.134 g, 3.25 mmol) was suspended in 40 mL of Ph₂O. The mixture was stirred at 250° C. for 3.5 h. The mixture was allowed to cool to RT and 100 mL of petroleum ether was added. The solid was collected by filtration, and rinsed with petroleum ether to afford the desired product (0.92 g) as a white solid.

4,7-Dichloro-6-iodoquinoline

7-Chloro-6-iodoquinolin-4-ol (591 mg, 1.94 mmol) was dissolved in 40 mL of POCl₃ and the mixture was stirred at reflux for 3 h. The mixture was allowed to cool to RT and concentrated in vacuo. The residue was poured into a solution of Et$_3$N (2.93 g, 29.03 mmol, 15 eq.) in 40 mL of DCM at 0° C. The mixture was partitioned between ethyl acetate and brine. The organic layer was dried and concentrated in vacuo. The residue was purified by flash column chromatography on silica gel (40% ethyl acetate/petroleum ether) to afford the desired product (895 mg) as a solid. ESI-MS m/z: 323.9 [M+H]$^+$.

tert-Butyl 4-(7-chloro-6-iodoquinolin-4-yl)piperazine-1-carboxylate 4,7-Dichloro-6-iodoquinoline (200 mg, 0.62 mmol) was mixed with tert-butyl piperazine-1-carboxylate (172 mg, 0.93 mmol) and Et$_3$N (250 mg, 2.47 mmol) in 15 mL DMSO. The resulting mixture was stirred at 80° C. under argon for 16 h. The mixture was poured into 250 mL of water and 50 mL of brine, and then extracted with ethyl acetate. The combined organic layer was washed with brine, dried over Na$_2$SO$_4$, and concentrated in vacuo. The residue was purified by flash column chromatography on silica gel (20-30% ethyl acetate/petroleum ether) to afford the desired product (132 mg). ESI-MS m/z: 374.2 [M+H]$^+$.

tert-Butyl 4-(7-chloro-6-(2-chlorophenyl)quinolin-4-yl)piperazine-1-carboxylate tert-Butyl 4-(7-chloro-6-iodoquinolin-4-yl)piperazine-1-carboxylate (130 mg, 0.28 mmol) was mixed with (2-chlorophenyl)boronic acid (109 mg, 0.33 mmol), Pd(PPh$_3$)$_4$ (32 mg, 0.028 mmol) and Na$_2$CO$_3$ (88 mg, 0.83 mmol) in 1,4-dioxane (20 mL) and water (4 mL). The mixture was stirred at 70° C. under argon for 4 h. The mixture was allowed to cool to RT and concentrated in vacuo. The residue was purified by flash column chromatography on silica gel (30-40% ethyl acetate/petroleum ether) to afford the desired product (100 mg). ESI-MS m/z: 458.3 [M+H]$^+$.

1-(4-(7-Chloro-6-(2-chlorophenyl)quinolin-4-yl)piperazin-1-yl)prop-2-en-1-one tert-butyl 4-(7-chloro-6-(2-chlorophenyl)quinolin-4-yl) piperazine-1-carboxylate (100 mg, 0.22 mmol) was dissolved in 20% MeOH—HCl solution (20 mL). The mixture was stirred at RT for 1 h. The mixture was concentrated in vacuo to yield a yellow solid salt (124 mg). The yellow salt (124 mg, 0.32 mmol) was dissolved in 30 mL of DCM in the presence of Et$_3$N (191 mg, 1.89 mmol). The mixture was cooled to 0° C. and then a solution of acryloyl chloride (32 mg, 0.35 mmol) in DCM (2 mL) was added dropwise. The mixture was stirred at 0° C. for 30 min. The mixture was concentrated in vacuo and the residue was purified by flash column chromatography on silica gel (50-100% ethyl acetate/petroleum ether) to afford the desired product (35 mg). $^1$H NMR (300 MHz, DMSO-d6) δ: 8.78-8-79 (m, 1H), 8.17 (s, 1H), 7.96 (s, 1H), 7.65-7.51 (m, 4H), 7.10-7.09 (m, 1H), 6.87 (dd, J=16.4, 10.4 Hz, 1H), 6.15 (d, J=16.4 Hz, 1H), 5.71 (d, J=10.4 Hz, 1H), 3.81 (br s, 4H), 3.22 (br s, 4H). ESI-MS m/z: 412.2 [M+H]$^+$.

Example 16

Synthesis of 4-(4-acryloylpiperazin-1-yl)-7-chloro-6-(4-chlorophenyl)quinoline-3-carbonitrile (I-42)

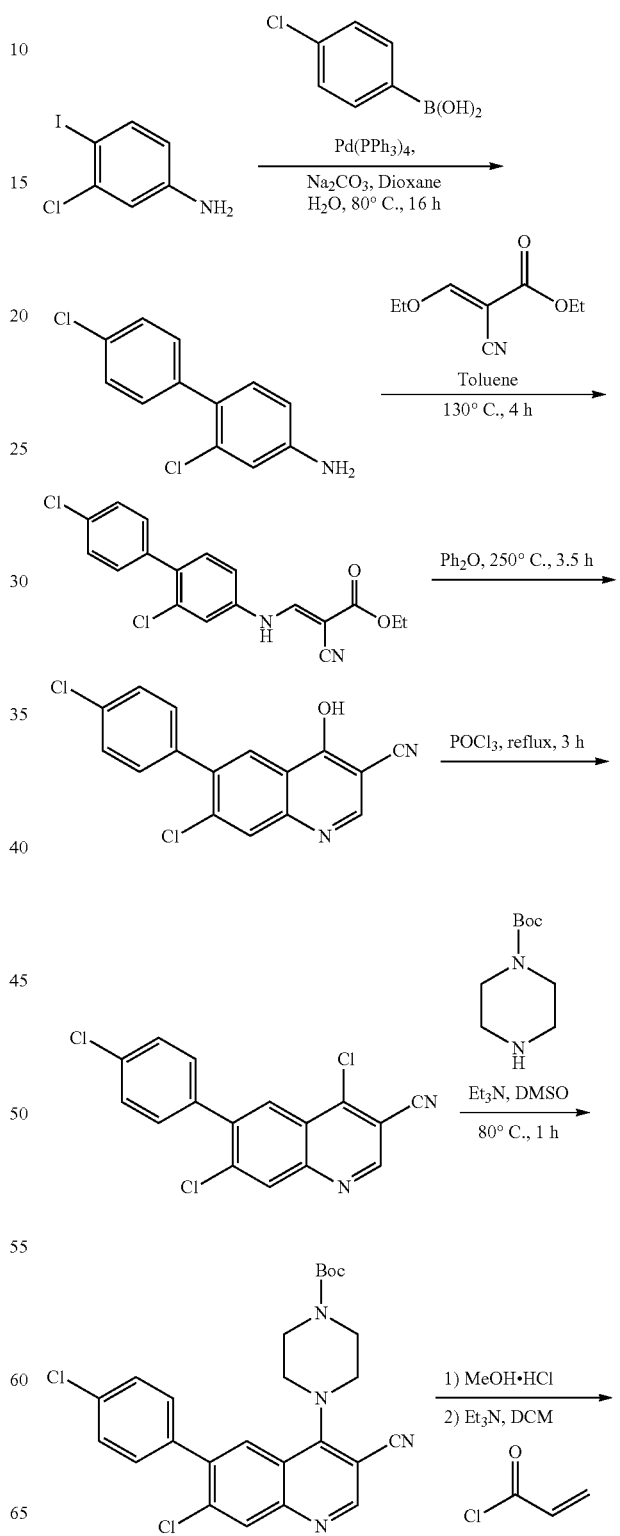

381
-continued

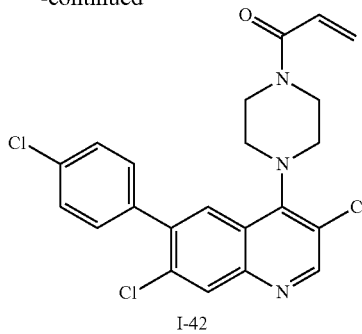

I-42

Compound I-42 was prepared according to Method G as described below:

3-Chloro-4-(4-chlorophenyl)benzenamine

A mixture of 3-chloro-4-iodobenzenamine (500 mg, 1.97 mmol), 4-chlorophenylboronic acid (324 mg, 2.07 mmol), $Na_2CO_3$ (627 mg, 5.92 mmol) and $Pd(PPh_3)_4$ (228 mg, 0.20 mmol) in 1,4-dioxane (21 mL) and $H_2O$ (4 mL) was stirred at 80° C. under argon for 16 h. The mixture was allowed to cool to RT and concentrated in vacuo. The residue was purified by flash column chromatography on silica gel (ethyl acetate/petroleum ether=5/1) to afford the desired product (424 mg, 91% yield) as a yellow solid.

(E)-Ethyl 3-(3-chloro-4-(4-chlorophenyl)-phenylamino)-2-cyanoacrylate

A mixture of 3-chloro-4-(4-chlorophenyl)benzenamine (250 mg, 1.05 mmol) and (E)-ethyl 2-cyano-3-ethoxyacrylate (186 mg, 1.10 mmol) was stirred at 100° C. for 2 h and then at 130° C. for 4 h. The mixture was allowed to cool to RT and concentrated in vacuo. The residue was triturated with ethyl acetate to afford the desired product (219 mg, 55% yield) as a white solid. ESI-MS m/z: 359.1 [M−H]⁻.

7-chloro-6-(4-chlorophenyl)-4-hydroxyquinoline-3-carbonitrile

A mixture of (E)-Ethyl-3-(3-chloro-4-(4-chlorophenyl)-phenylamino)-2-cyanoacrylate (219 mg, 0.608 mmol) in $Ph_2O$ (8 mL) was stirred at 253° C. for 4 h. The mixture was cooled to RT and poured into petroleum ether (20 mL). The precipitate was collected by filtration and washed with petroleum ether (50 mL×2) to yield the desired product (65 mg, 34% yield) as a brown solid.

4-(4-acryloylpiperazin-1-yl)-7-chloro-6-(4-chlorophenyl)quinoline-3-carbonitrile The title compound was prepared from 7-chloro-6-(4-chlorophenyl)quinolin-4-ol in four steps according to the procedure described in Example 2. ¹H NMR (400 MHz, DMSO-d6) δ: 8.84 (s, 1H), 8.21 (s, 1H), 8.05 (s, 1H), 7.66-7.59 (m, 4H), 6.88 (dd, J=16.8, 10.4 Hz, 1H), 6.17 (dd, J=16.8, 2.0 Hz, 1H), 5.74 (dd, J=10.4, 2.0 Hz, 1H), 3.83-3.74 (m, 8H). ESI-MS m/z: 437.2 [M+H]⁺.

382

Example 17

Synthesis of 1-(4-(5-(4-chlorophenyl)thieno[2,3-d]pyrimidin-4-yl)piperazin-1-yl)prop-2-en-1-one (I-22)

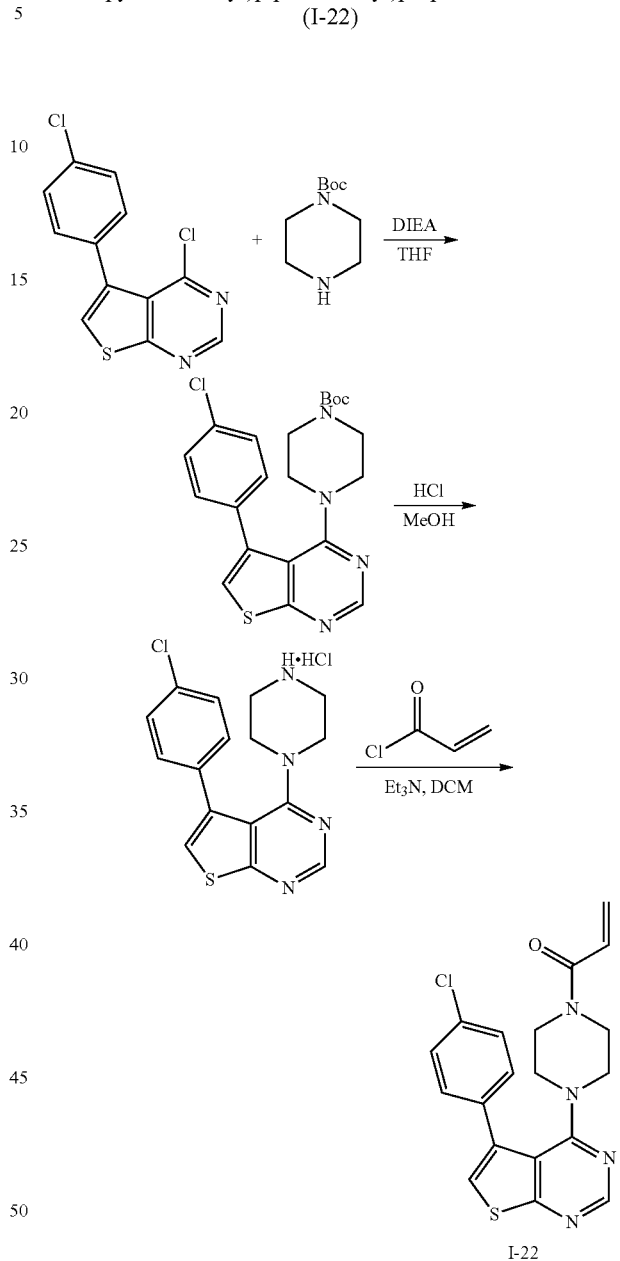

Compound I-22 was prepared according to Method H as described below:

tert-Butyl 4-(5-(4-chlorophenyl)thieno[2,3-d]pyrimidin-4-yl)piperazine-1-carboxylate A solution of 4-chloro-5-(4-chlorophenyl)thieno[2,3-d]pyrimidine (180 mg, 0.64 mmol), tert-butyl piperazine-1-carboxylate (119 mg, 0.64 mmol) and diisopropyl amine in THF (6 mL) was stirred at RT overnight. The mixture was partitioned between DCM and water. The organic layer was dried over $Na_2SO_4$, filtered and concentrated in vacuo to afford the desired product which was used directly in the next step without further purification.

5-(4-Chlorophenyl)-4-(piperazin-1-yl)thieno[2,3-d]pyrimidine hydrochloride

To a suspension of tert-butyl 4-(5-(4-chlorophenyl)thieno[2,3-d]pyrimidin-4-yl)piperazine-1-carboxylate obtained from the previous step in 1,4-dioxane (10 mL) and MeOH (5 mL), was added a solution of HCl in 1,4-dioxane (4 M, 1.0 mL). The mixture was stirred at RT overnight. The mixture was concentrated in vacuo and the residue was used directly in the next step without further purification.

1-(4-(5-(4-Chlorophenyl)thieno[2,3-d]pyrimidin-4-yl)piperazin-1-yl)prop-2-en-1-one To a solution of 5-(4-Chlorophenyl)-4-(piperazin-1-yl)thieno[2,3-d]pyrimidine hydrochloride obtained above in DCM (10 mL) at 0° C., Et$_3$N (0.2 mL) was added followed by acryloyl chloride. The resulting mixture was allowed to warm to RT and stirred for 1 h. The mixture was partitioned between DCM and water. The organic layer was dried over Na$_2$SO$_4$, filtered and concentrated in vacuo. The residue was purified via Isolera One (silica cartridge, 0-60% ethyl acetate/hexanes) to afford the desired product (27.5 mg). $^1$H NMR (300 MHz, CDCl$_3$), δ: 8.64 (s, 1H), 7.35-7.48 (m, 4H), 7.30 (s, 1H), 6.42-6.60 (m, 1H), 6.26 (d, J=24 Hz, 1H), 5.69 (d, J=10.5 Hz, 1H), 3.10-3.35 (m, 8H). ESI-MS m/z: 385.0 [M+H]$^+$

Example 18

Synthesis of 1-(4-(8-(2-chlorophenyl)quinazolin-2-yl)piperazin-1-yl)prop-2-en-1-one (I-35)

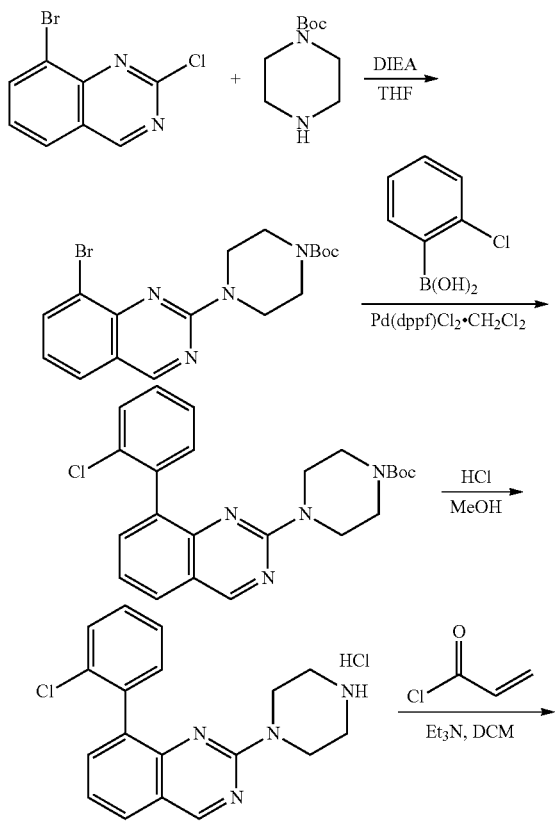

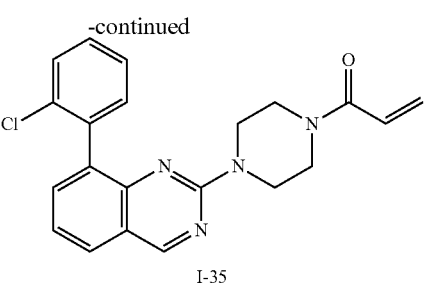

I-35

Compound I-35 was prepared according to Method I as described below:

tert-Butyl 4-(8-bromoquinazolin-2-yl)piperazine-1-carboxylate

The title compound was prepared from 8-bromo-2-chloroquinazoline according to the procedure described in step 1 in Example 8.

tert-Butyl 4-(8-(2-chlorophenyl)quinazolin-2-yl)piperazine-1-carboxylate

A mixture of tert-Butyl 4-(8-bromoquinazolin-2-yl)piperazine-1-carboxylate (250 mg, 0.64 mmol), 2-chlorophenylbronic acid (110 mg, 1.1 mmol) and Pd(dppf)Cl$_2$.CH$_2$Cl$_2$ (50 mg) in a mixture of 1,4-dioxane (6 mL) and sat. NaHCO$_3$ solution (3 mL) was stirred at 100° C. for 1 h. The mixture was allowed to cool to RT, and partitioned between water and ethyl acetate. The organic layer was dried over Na$_2$SO$_4$, filtered and concentrated in vacuo. The residue was purified via Isolera One (silica cartridge, 0-60% ethyl acetate/hexanes) to afford the desired product.

1-(4-(8-(2-Chlorophenyl)quinazolin-2-yl)piperazin-1-yl)prop-2-en-1-one

The title compound was prepared from tert-Butyl 4-(8-(2-chlorophenyl)quinazolin-2-yl)piperazine-1-carboxylate according to the procedure described in steps 2 and 3 in Example 8. $^1$H NMR (300 MHz, CDCl$_3$) δ: 9.07 (s, 1H), 7.74 (dd, J=8.0, 1.6 Hz, 1H), 7.67 (dd, J=6.8, 1.2 Hz, 1H), 7.46-7.56 (m, 1H), 7.39-7.42 (m, 4H), 6.58 (dd, J=16.8, 10.8 Hz, 1H), 6.32 (dd, J=16.8, 2.0 Hz, 1H), 5.71 (dd, J=10.6, 1.9 Hz, 1H), 3.8-3.9 (br., 4H), 3.68-3.78 (br., 2H), 3.55-3.62 (br., 2H). ESI-MS m/z: 379.1 [M+H]$^+$.

Example 19

Synthesis of 1-(4-(5-(2-chlorophenyl)-7H-pyrrolo[2,3-d]pyrimidin-4-yl)piperazin-1-yl)prop-2-en-1-one (I-28)

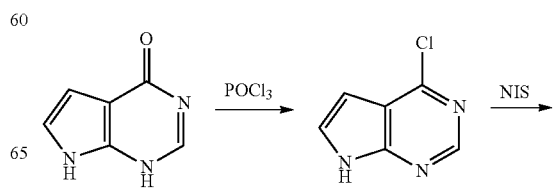

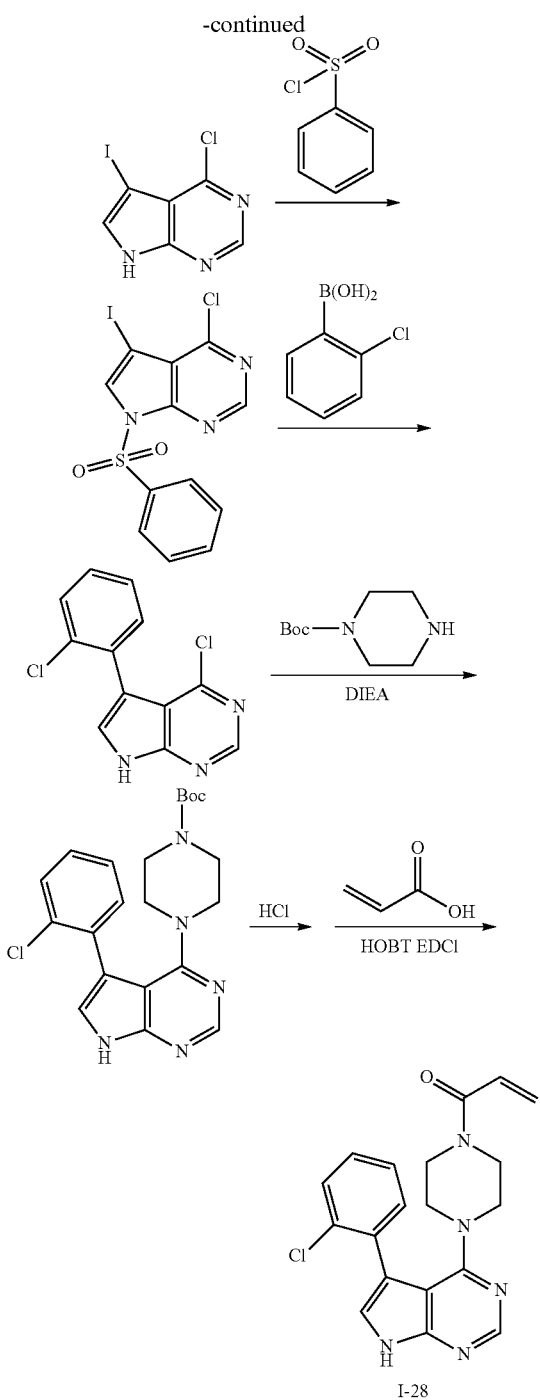

Compound I-28 was prepared according to Method J as described below:

4-Chloro-7H-pyrrolo[2,3]pyrimidine

A mixture of 1H-pyrrolo[2,3-d]pyrimidin-4(7H)-one (2.5 g. 18.6 mmol) in 46 mL of POCl$_3$ was stirred at reflux for 5 h. The mixture was allowed to cool to RT and then concentrated in vacuo to remove the excess amount of POCl$_3$. Ice was added to the residue and the mixture was stirred at RT for 10 min. The aqueous layer was extracted with diethyl ether. The organic layer was dried over MgSO$_4$, filtered, and concentrated in vacuo to afford the desired product (1.5 g, 54% yield) as an off-white solid.

4-Chloro-5-iodo-7H-pyrrolo[2,3]pyrimidine

4-Chloro-7H-pyrrolo[2,3-d]pyrimidine (1.8 g 11.9 mmol) and N-iodosuccinamide (3 g, 13.1 mmol) were mixed in a round bottomed flask. The flask was dried under high vacuum for 5 h and then back-filled with argon. To this mixture, dry DMF (100 mL) was added and the resulting mixture was stirred in the dark for 20 h. The reaction was quenched with methanol and concentrated in vacuo. The residue was diluted with 150 mL of DCM and washed with water (200 mL), saturated aqueous sodium sulfite (200 mL), and brine (100 mL). The organic layer was dried over MgSO$_4$, filtered, and concentrated in vacuo. The residue was purified by flash column chromatography on silica gel (50% ethyl acetate/hexanes) to afford the desired product (3.1 g, 95% yield) as a white solid. ESI-MS m/z: 279.5 [M+H]$^+$.

4-Chloro-5-iodo-7benzenesulfonyl-pyrrolo[2,3-d]pyrimidine

To a solution of 4-chloro-5-iodo-7H-pyrrolo[2,3]pyrimidine (280 mg, 1 mmol) in DMF (5 mL) at 0° C., NaH (60%, 52 mg, 1.3 mmol) was added and the resulting mixture was stirred at 0° C. for 30 min. To this mixture, benzenesulfonyl chloride (194 mg, 1.1 mmol) was added. The mixture was then stirred at RT for 2 h. The mixture was partitioned between ethyl acetate and water. The organic layer was dried over MgSO$_4$, filtered, and concentrated in vacuo. The residue was purified by flash column chromatography on silica gel to afford the desired product (300 mg, 71.6% yield).

4-Chloro-5-(2-chlorophenyl)-7H-pyrrolo[2,3-d]pyrimidine

To a solution of 4-chloro-5-iodo-7benzenesulfonyl-pyrrolo[2,3-d]pyrimidine (300 mg, 0.71 mmol) and 2-chlorophenylboronic acid (167 mg, 1.07 mmol) in 1,4-dioxane (15 mL) and water (3 mL), Pd(PPh$_3$)$_4$ (60 mg) and Na$_2$CO$_3$ (227 mg, 2.14 mmol) were added. The mixture was stirred at 80° C. overnight. The mixture was allowed to cool to RT and concentrated in vacuo. The residue was purified by flash column chromatography on silica gel to afford the desired product (120 mg, 63% yield). ESI-MS m/z: 262.2 [M−H]$^−$.

tert-butyl-4-(5-(2-chlorophenyl)-7H-pyrrolo[2,3-d]pyrimidin-4-yl)piperazine-1-carboxylate To a solution of 4-chloro-5-(2-chlorophenyl)-7H-pyrrolo[2,3-d]pyrimidine (120 mg, 0.45 mmol) and tert-butyl piperazine-1-carboxylate (254 mg, 1.36 mmol) in 1,4-dioxane (15 mL), DIEA (293 mg, 2.27 mmol) was added. The mixture was stirred at 100° C. overnight. The mixture was concentrated in vacuo and the residue was purified by flash column chromatography on silica gel to afford the desired product (120 mg, 64% yield).

1-(4-(5-(2-Chlorophenyl)-7H-pyrrolo[2,3-d]pyrimidin-4-yl)piperazin-1-yl)prop-2-en-1-one The title compound was prepared from tert-butyl-4-(5-(2-chlorophenyl)-7H-pyrrolo[2,3-d]pyrimidin-4-yl)piperazine-1-carboxylate in two steps according to the procedure described in Example 2. $^1$H NMR (400 MHz, DMSO-d6) δ: 8.5 (s, 1H), 7.5 (m, 1H), 7.4 (m, 3H), 7.3 (s, 2H), 6.5 (m, 1H), 6.3 (m, 1H), 5.7 (m, 1H), 3.4 (m, 8H). ESI-MS m/z: 368.3 [M+H]$^+$.

Example 20
Synthesis of 1-(4-(2-AMINO-7-chloro-6-(4-chloro-phenyl)quinazolin-4-yl)piperazin-1-yl)prop-2-en-1-one (I-39) and 1-(4-(7-chloro-6-(4-chlorophenyl)-2-methoxyquinazolin-4-yl)piperazin-1-yl)prop-2-en-1-one (I-43)
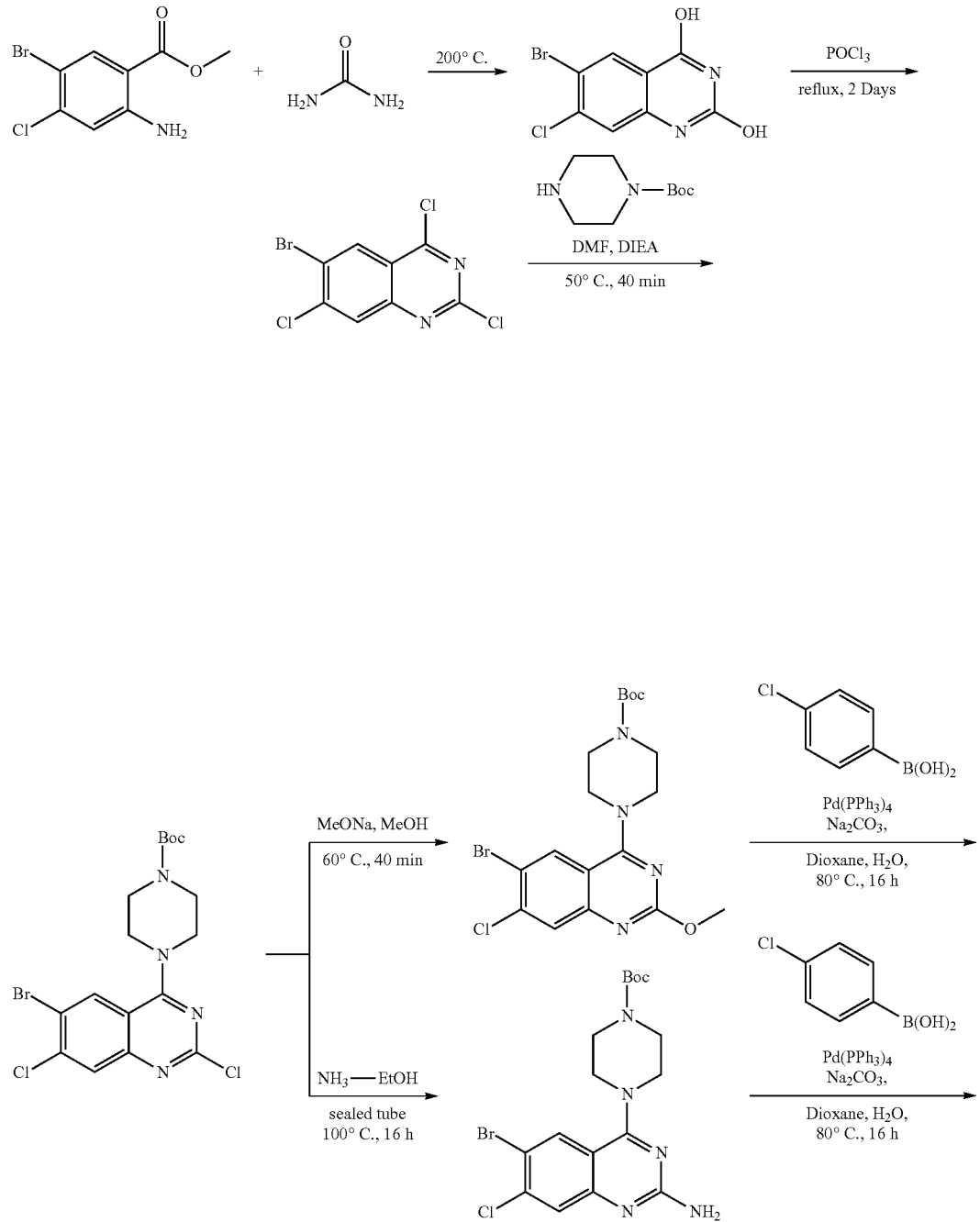

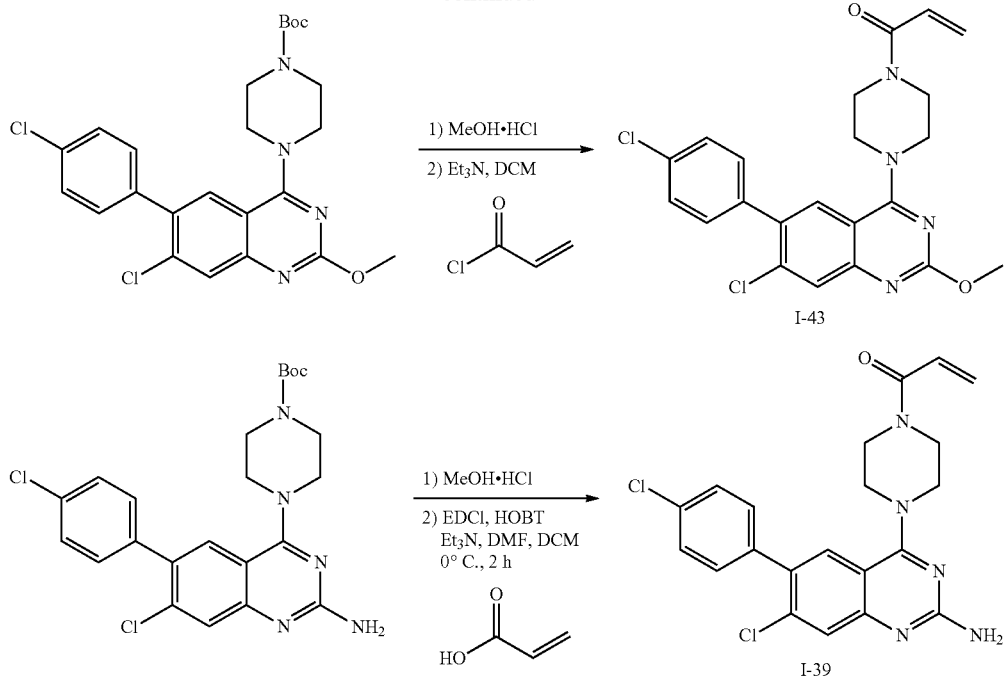

Compounds I-39 and I-43 were prepared according to Method F as described below:

6-Bromo-7-chloroquinazoline-2,4-diol

A mixture of methyl 2-amino-5-bromo-4-chlorobenzoate (3.0 g, 11.34 mmol) and urea (1.36 g, 22.68 mmol, 2 eq.) was stirred at 200° C. for 3 h. The mixture was allowed to cool to RT, triturated with ethyl acetate and dried to afford the desired product (2.39 g) as a brown solid.

6-Bromo-2,4,7-trichloroquinazoline

The mixture of 6-bromo-7-chloroquinazoline-2,4-diol (1.1 g, 6.79 mmol) in 30 mL of POCl$_3$ was stirred at reflux for 2 days. The mixture was allowed to cool to RT and concentrated in vacuo to remove POCl$_3$. The residue was poured into a solution of Et$_3$N (13.7 g, 20 eq.) in 30 mL of DCM at 0° C. The mixture was partitioned between ethyl acetate and brine. The organic layer was dried over Na$_2$SO$_4$, filtered and concentrated in vacuo. The residue was purified by flash chromatography on silica gel (5-10% ethyl acetate/ petroleum ether) to afford the desired product (474 mg) as a yellow solid.

tert-Butyl-4-(6-bromo-2,7-dichloroquinazolin-4-yl) piperazine-1-carboxylate

To a solution of tert-butyl piperazine-1-carboxylate (123 mg, 0.66 mmol) in DMF (10 mL) at RT, DIEA (94 mg, 0.72 mmol) was added followed by 6-bromo-2,4,7-trichloroquinazoline (206 mg, 0.66 mmol). The resulting mixture was stirred at 50° C. for 40 min. The mixture was allowed to cool to RT and partitioned between water and ethyl acetate. The organic layer was washed with brine, dried over Na$_2$SO$_4$ and concentrated. The residue was purified by flash column chromatography on silica gel (5% ethyl acetate/petroleum ether) to afford the desired product (222 mg) as a yellow solid. ESI-MS m/z: 463.2 [M+H]$^+$.

tert-Butyl 4-(6-bromo-7-chloro-2-methoxyquinazo-lin-4-yl)piperazine-1-carboxylate To a solution of NaOMe (26 mg, 0.476 mmol) in MeOH (20 mL), tert-butyl-4-(6-bromo-2,7-dichloroquinazolin-4-yl)piperazine-1-carboxylate (110 mg, 0.238 mmol) was added. The mixture was stirred at 60° C. under argon for 40 min. The mixture was quenched by water (1.0 mL) and then concentrated in vacuo. The residue was purified by flash column chromatography on silica gel (10-20% ethyl acetate/ petroleum ether) to afford the desired product (55 mg) as a yellow solid. ESI-MS m/z: 459.2 [M+H]$^+$.

tert-Butyl-4-(7-chloro-6-(4-chlorophenyl)-2-methoxyquinazolin-4-yl)piperazine-1-carboxylate The mixture of tert-butyl 4-(6-bromo-7-chloro-2-methoxyquinazolin-4-yl)piperazine-1-carboxylate (85 mg, 0.19 mmol), (4-chlorophenyl)boronic acid (35 mg, 0.22 mmol), Pd(PPh$_3$)$_4$ (22 mg, 0.019 mmol), Na$_2$CO$_3$ (60 mg, 0.56 mmol) in dioxane (20 mL) and water (2 mL) was stirred at 80° C. under argon for 16 h. The mixture was allowed to cool to RT and concentrated in vacuo. The residue was purified by flash column chromatography on silica gel (10-20% ethyl acetate/petroleum ether) followed by Prep-TLC to afford the desired product (100 mg) as a white solid. ESI-MS m/z: 489.4 [M+H]$^+$.

1-(4-(7-Chloro-6-(4-chlorophenyl)-2-methoxyquinazolin-4-yl)piperazin-1-yl)prop-2-en-1-one tert-Butyl-4-(7-chloro-6-(4-chlorophenyl)-2-methoxyquinazolin-4-yl)piperazine-1-carboxylate (100 mg, 0.20 mmol) was dissolved in 20 mL of 20% HCl methanol solution. The mixture was stirred at RT for 1 h and then concentrated in vacuo to yield a yellow solid salt (90 mg).

The above yellow solid (90 mg, 0.21 mmol) was dissolved in 30 mL of DCM with Et$_3$N (129 mg, 1.27 mmol). The mixture was cooled to 0° C. and then added dropwise to a solution of acryloyl chloride (23 mg, 0.25 mmol) in DCM (2 mL). The resulting mixture was stirred at 0° C. for 30 min. The mixture was poured into H$_2$O (100 mL), sat. NaHCO$_3$ (50 mL) and brine (50 mL), and then extracted with ethyl acetate. The organic layer was washed with brine, dried over Na$_2$SO$_4$ and concentrated. The residue was purified by Prep-TLC followed by Prep-HPLC to afford the desired product (8 mg) as a white solid. ESI-MS m/z: 443.2 [M+H]$^+$.

tert-Butyl-4-(2-amino-6-bromo-7-chloroquinazolin-4-yl)piperazine-1-carboxylate

The mixture of tert-butyl 4-(6-bromo-2,7-dichloroquinazolin-4-yl)piperazine-1-carboxylate in sat. NH$_3$-EtOH (4 mL) in a sealed tube was stirred at 100° C. for 16 h. The mixture was allowed to cool to RT and concentrated in vacuo. The residue was purified by flash column chromatography on silica gel (20-30% ethyl acetate/petroleum ether) to afford the desired product (70 mg) as a white solid.

tert-Butyl-4-(2-amino-7-chloro-6-(4-chlorophenyl)quinazolin-4-yl)piperazine-1-carboxylate The mixture of tert-butyl-4-(2-amino-6-bromo-7-chloroquinazolin-4-yl)piperazine-1-carboxylate (70 mg, 0.16 mmol), (4-chlorophenyl)boronic acid (29 mg, 0.19 mmol), Pd(PPh$_3$)$_4$ (18 mg, 0.019 mmol), and Na$_2$CO$_3$ (50 mg, 0.48 mmol) in dioxane (20 mL) and water (2 mL) was stirred at 80° C. under argon for 16 h. The mixture was allowed to cool to RT and then concentrated in vacuo. The residue was purified by flash column chromatography on silica gel (10-20% ethyl acetate/petroleum ether) followed by Prep-TLC to afford the desired product (70 mg) as a red solid. ESI-MS m/z: 474.5[M+H]$^+$.

1-(4-(2-Amino-7-chloro-6-(4-chlorophenyl)quinazolin-4-yl)piperazin-1-yl)prop-2-en-1-one tert-Butyl-4-(2-amino-7-chloro-6-(4-chlorophenyl)quinazolin-4-yl)piperazine-1-carboxylate (70 mg, 0.15 mmol) was dissolved in 20% HCl methanol solution (20 mL) and the resulting mixture was stirred at RT for 1 h. The mixture was concentrated to afford the desired product (70 mg) as a yellow solid salt.

The mixture of above obtained yellow solid (70 mg, 0.21 mmol), acrylic acid (18 mg, 0.25 mmol), EDCI (73 mg, 0.381 mmol) and HOBT (52 mg, 0.381 mmol) in 10 mL of DMF at 0° C., a solution of Et$_3$N (120 mg, 1.2 mmol) in DCM (2 mL) was added dropwise. The resulting mixture was stirred at 0° C. for 30 min and at RT for 1.5 h. The mixture was poured into water (100 mL), sat. NaHCO$_3$ (50 mL) and brine (50 mL), and then extracted with ethyl acetate. The organic layer was washed with brine, dried over Na$_2$SO$_4$ and concentrated in vacuo. The residue was purified by flash column chromatography on silica gel to yield the desired product (5 mg) as a gray solid. ESI-MS m/z: 428.3 [M+H]$^+$.

Example 21

Synthesis of 1-(4-(7-chloro-6-(2-chlorophenyl)quinazolin-4-yl)piperidin-1-yl)prop-2-en-1-one (I-36)

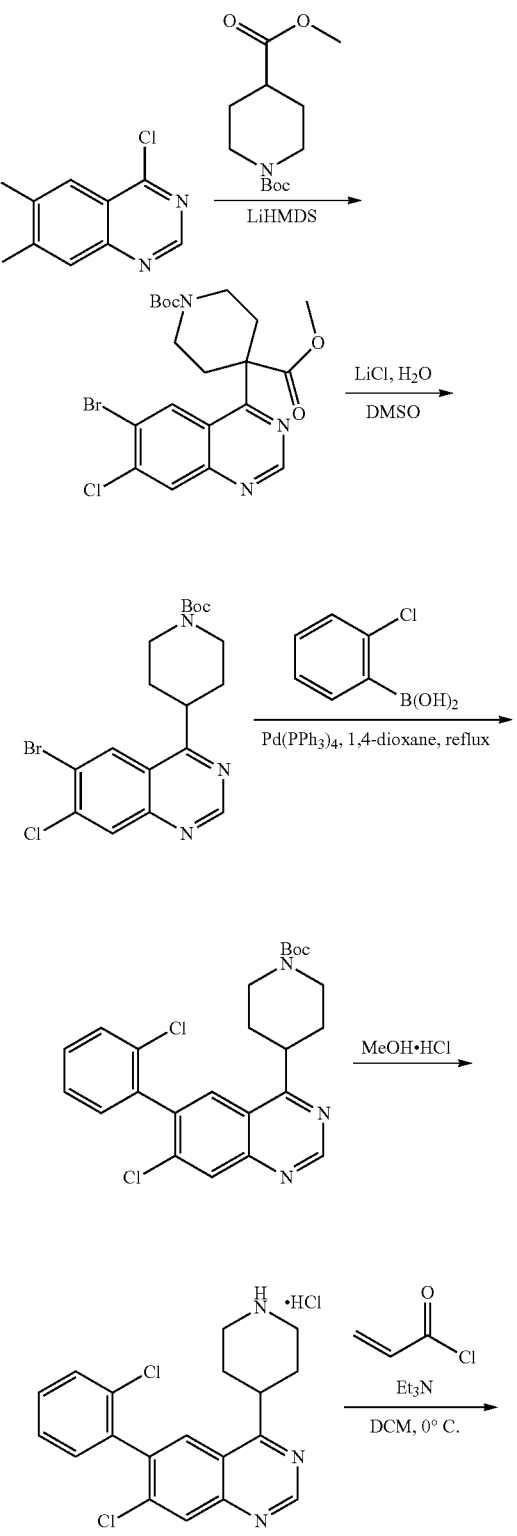

393
-continued

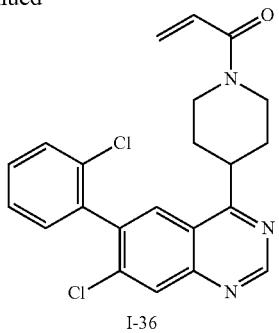

I-36

Compound I-36 was prepared according to Method K as described below:

1-tert-Butyl 4-methyl 4-(6-bromo-7-chloroquinazolin-4-yl)piperidine-1,4-dicarboxylate To a stirred solution of tert-butyl methyl piperidine-1,4-dicarboxylate (3.3 g, 13.5 mmol) in anhydrous THF (30 mL) at 0° C. under nitrogen, LiHMDS (15 mL, 15 mmol) was added and the resulting mixture was stirred at 0° C. for 1 h. To this mixture, a solution of 6-bromo-4,7-dichloroquinazoline (748 mg, 2.7 mmol) in THF (5 mL) was added and the resulting mixture was stirred at room temperature for 4 h. The mixture was quenched with ice-water and partitioned between water and ethyl acetate. The organic layer was dried over anhydrous $Na_2SO_4$, filtered and concentrated in vacuo. The residue was purified by flash column chromatography on silica gel (1-10% ethyl acetate/petroleum ether) to afford the desired product (580 mg, 37% yield) as a white solid.

tert-Butyl 4-(6-bromo-7-chloroquinazolin-4-yl)piperidine-1-carboxylate

To a solution of 1-tert-butyl 4-methyl 4-(6-bromo-7-chloroquinazolin-4-yl)piperidine-1,4-dicarboxylate (483 mg, 1.2 mmol) in DMSO (10 mL), LiCl (103 mg, 2.4 mmol) and water (65 mg, 3.6 mmol) were added, and the rusting mixture was stirred at 110° C. for 16 h. The mixture was allowed to cool to room temperature and partitioned between water and ethyl acetate. The organic layer was dried over anhydrous $Na_2SO_4$, filtered and concentrated in vacuo. The residue was purified by flash column chromatography on silica gel (1-20% ethyl acetate/petroleum ether) to afford the desired product (170 mg, 33% yield) as a white solid.

tert-Butyl 4-(7-chloro-6-(2-chlorophenyl)quinazolin-4-yl)piperidine-1-carboxylate A mixture of tert-butyl 4-(6-bromo-7-chloroquinazolin-4-yl)piperidine-1-carboxylate (230 mg, 0.59 mmol), 2-chlorophenylboronic acid (138 mg, 0.88 mmol), $Pd(PPh_3)_4$ (69 mg, 0.06 mmol) and $Na_2CO_3$ (188 mg, 106 mmol) in 1,4-dioxane (10 mL) under argon was stirred at 100° C. for 16 h. The mixture was allowed to cool to room temperature, and partitioned between water and ethyl acetate. The organic layer was dried over anhydrous $Na_2SO_4$, filtered and concentrated in vacuo. The residue was purified by flash column chromatography on silica gel (1-20% ethyl acetate/petroleum ether) to afford the desired product (160 mg, 65% yield) as a white solid.

394

1-(4-(7-Chloro-6-(2-chlorophenyl)quinazolin-4-yl) piperidin-1-yl)prop-2-en-1-one (I-36)

The title compound was prepared from tert-butyl 4-(7-chloro-6-(2-chlorophenyl) quinazolin-4-yl)piperidine-1-carboxylate according to the procedure described in steps 5 and 6 in Example 2. $^1H$ NMR (400 MHz, DMSO-d6) δ: 9.28 (s, 1H), 8.55 (s, 1H), 8.27 (s, 1H), 7.70 (m, 2H), 7.53-7.68 (m, 2H), 6.82-6.88 (m, 1H), 6.10 (dd, J=2.5, 16.8 Hz, 1H), 5.68 (dd, J=2.3, 10.3 Hz, 1H), 4.55 (d, J=12.2 Hz, 1H), 4.09-4.16 (m, 2H), 3.32 (t, J=12.2 Hz, 1H), 2.89 (t, J=12.1 Hz, 1H), 1.72-1.93 (m, 4H). ESI-MS m/z: 410.35 $[M-H]^-$.

Example 22

Synthesis of 7-chloro-6-(4-chlorophenyl)-4-(4-(vinylsulfonyl)piperazin-1-yl)quinazoline (I-45)

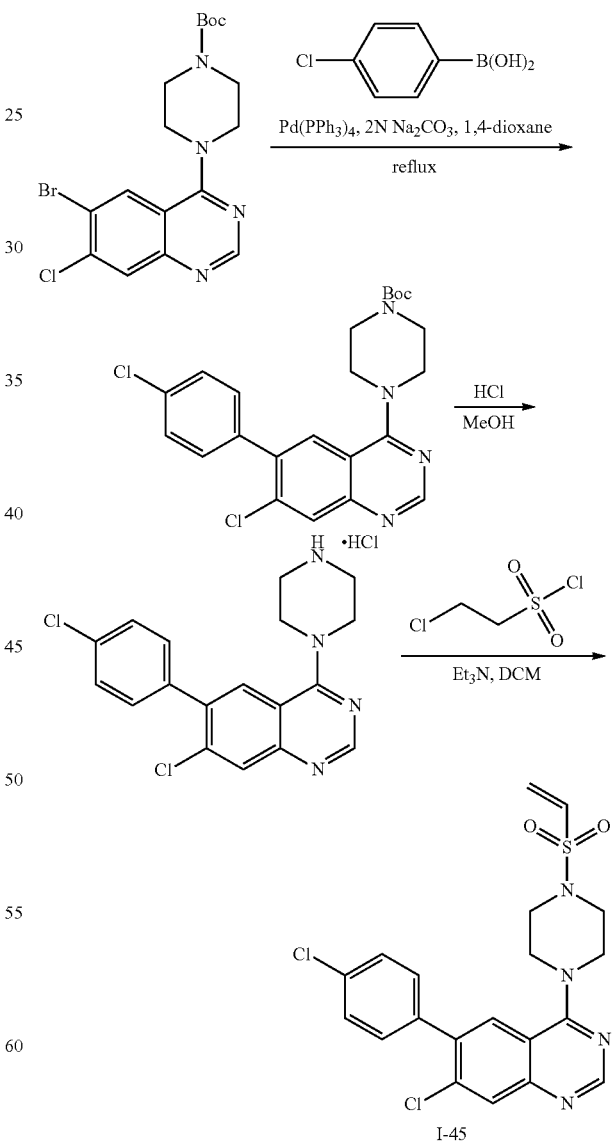

Compound I-45 was prepared according to the general procedures of Method A as described below:

tert-Butyl 4-(7-chloro-6-(4-chlorophenyl)quinazolin-4-yl)piperazine-1-carboxylate The title compound was prepared from tert-butyl 4-(6-bromo-7-chloroquinazolin-4-yl)piperazine-1-carboxylate and 4-chlorophenylboronic acid according to the procedure described in step 4 in Example 3.

tert-Butyl4-(7-chloro-6-(4-chlorophenyl)quinazolin-4-yl)piperazine-1-carboxylate A solution of tert-butyl4-(7-chloro-6-(4-chlorophenyl)quinazolin-4-yl)piperazine-1-carboxylate (500 mg, 1.09 mmol) in HCl/MeOH (10 mL, 28.6 mmol) was stirred at room temperature for 30 min. The mixture was concentrated in vacuo to afford the crude product.

7-Chloro-6-(4-chlorophenyl)-4-(4-(vinylsulfonyl)piperazin-1-yl)quinazoline

The above obtained crude product was dissolved with DCM (15 mL) and cooled to 0° C. To this mixture, 2-chloroethanesulfonyl chloride (213.2 mg, 1.31 mmol) and Et$_3$N (1.5 mL, 10.9 mmol) were added and the resulting mixture was stirred at 0° C. for 10 min. The mixture was quenched with ice-water and partitioned between water and ethyl acetate. The organic layer was dried over anhydrous Na$_2$SO$_4$, filtered and concentrated in vacuo. The residue was purified by prep-HPLC to afford the desired product (3 mg, 0.6% yield). $^1$H-NMR (400 M Hz, CDCl$_3$) δ: 8.78 (s, 1H), 8.08 (s, 1H), 7.75 (s, 1H), 7.49 (d, J=8.4 Hz, 2H), 7.42 (d, J=8.4 Hz, 2H), 6.46 (dd, J=10, 16.8 Hz, 1H), 6.31 (d, J=16.8 Hz, 1H), 6.11 (d, J=9.6 Hz, 1H), 3.91 (t, J=4.8 Hz, 4H), 3.35 (t, J=4.8 Hz, 4H). ESI-MS m/z: 449.25 [M+H]$^+$.

Example 23

Synthesis of 1-(4-(7-chloro-6-(4-chlorophenyl)quinazolin-4-yl)-2-(hydroxymethyl)piperazin-1-yl)prop-2-en-1-one (I-46)

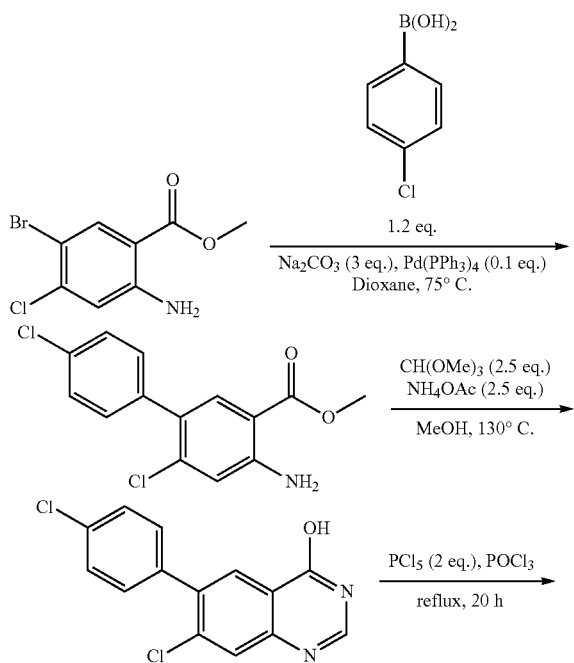

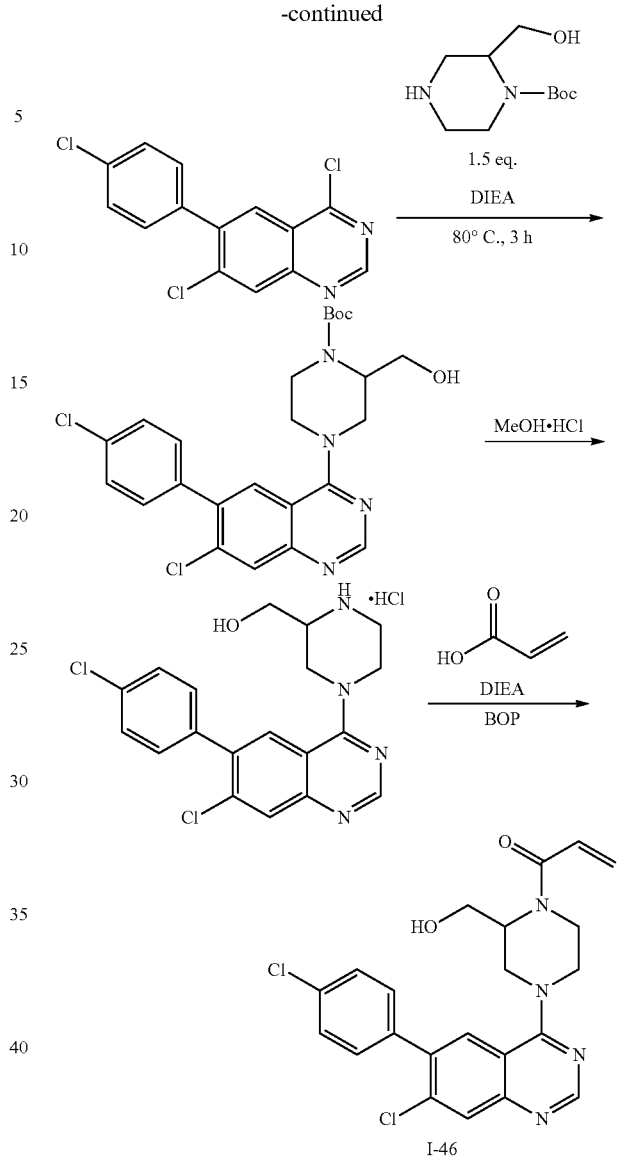

Compound I-46 was prepared according to the general procedures of Method A as described below:

4,7-Dichloro-6-(4-chlorophenyl)quinazoline

The title compound was prepared from 2-amino-5-bromo-4-chlorobenzoate according to the procedure described in steps 1, 2 and 3 in Example 2.

tert-Butyl 4-(7-chloro-6-(4-chlorophenyl)quinazolin-4-yl)-2-(hydroxymethyl)piperazine-1-carboxylate The above obtained crude 4,7-dichloro-6-(4-chlorophenyl)quinazoline (200 mg, 0.464 mmol) was added to the mixture of tert-butyl 2-(hydroxymethyl)piperazine-1-carboxylate (210 mg, 0.968 mmol) and DIEA (418 mg, 3.24 mmol) in 1,4-dioxane (20 mL) at room temperature and the resulting mixture was stirred at 80° C. for 3 h. The mixture was allowed to cool to room temperature and then concentrated in vacuo. The residue was purified by flash column chromatography on silica gel (DCM/MeOH=30:1) to afford the desired product (110 mg, 35% yield) as a light yellow oil. ESI-MS m/z: 498.9 [M+H]+.

(4-(7-Chloro-6-(4-chlorophenyl)quinazolin-4-yl)piperazin-2-yl)methanol hydrochloride A mixture of 4-(7-chloro-6-(4-chlorophenyl)quinazolin-4-yl)-2-(hydroxymethyl)piperazine-1-carboxylate (110 mg, 0.225 mmol) and HCl in MeOH (10 mL, 28.6 mmol) was stirred at room temperature for 1 h. The mixture was concentrated in vacuo to afford the crude product (106 mg) as a yellow solid which was used directly in next step without further purification.

1-(4-(7-Chloro-6-(4-chlorophenyl)quinazolin-4-yl)-2-(hydroxymethyl)piperazin-1-yl)prop-2-en-1-one To a stirred solution of above obtained yellow solid (106 mg, 0.225 mmol) in DMF (5 mL) at room temperature, acrylic acid (19 mg, 0.27 mmol), BOP (149 mg, 0.338 mmol) and DIEA (203 mg, 1.58 mmol) were added and the resulting mixture was stirred at room temperature for 30 min. The mixture was poured into saturated aqueous NaHCO3 solution (50 mL), and then extracted with ethyl acetate. The organic layer was washed with brine, dried over Na2SO4 and concentrated in vacuo. The residue was purified by flash column chromatography on silica gel (DCM/MeOH=20:1) to afford the desired product (20 mg, 20% yield, 2 steps) as a solid. $^1$H NMR (400 MHz, DMSO-d6) δ: 8.7 (s, 1H), 8.2 (d, J=2.8 Hz, 1H), 8.0 (s, 1H), 7.5 (m, 4H), 6.8 (dd, J=10.4, 16.4 Hz, 1H), 6.1 (d, J=17 Hz, 1H), 5.7 (dd, J=2.4, 10.4 Hz, 1H), 5.0 (m, 1H), 4.3 (m, 2H), 4.2 (m, 2H), 3.6 (m, 3H), 2.5 (s, 2H). ESI-MS m/z: 443.30 [M+H]+.

Example 24

Synthesis of 1-acryloyl-4-(7-chloro-6-(4-chlorophenyl)quinazolin-4-yl)piperazine-2-carbonitrile (I-47)

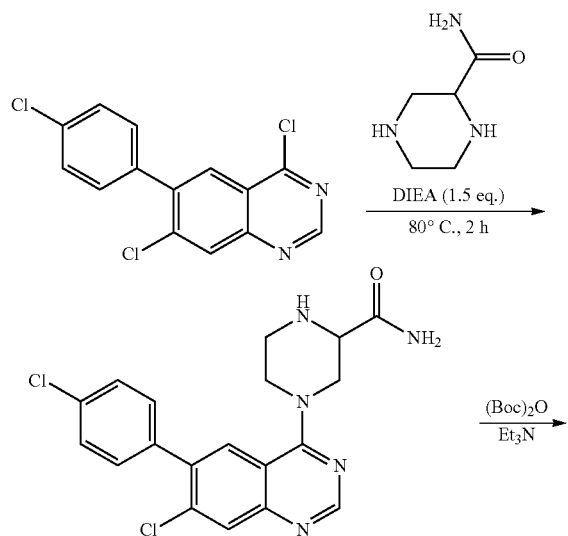

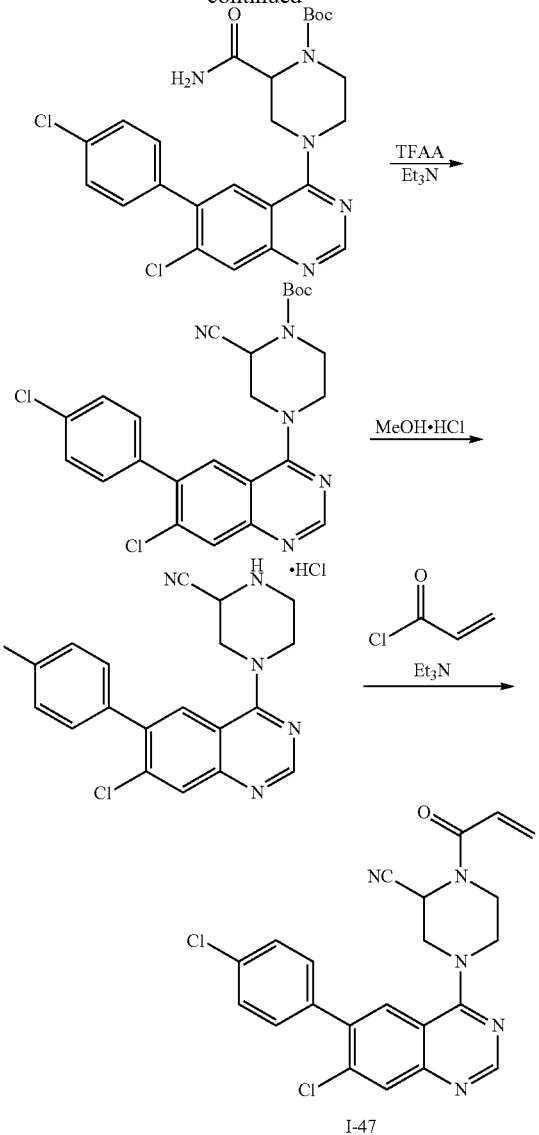

Compound I-47 was prepared according to the general procedures of Method A as described below:

4-(7-Chloro-6-(4-chlorophenyl)quinazolin-4-yl)piperazine-2-carboxamide

The crude 4,7-dichloro-6-(4-chlorophenyl)quinazoline (310 mg, 1 mmol) was added to the mixture of piperazine-2-carboxamide (249 mg, 1.5 mmol) and DIEA (645 mg, 5 mmol) in 1,4-dioxane (20 mL) at room temperature and the resulting mixture was stirred at 80° C. for 2 h. The mixture was allowed to cool to room temperature and then concentrated in vacuo. The residue was used in the next step without further purification. ESI-MS m/z: 402.3 [M+H]+.

tert-Butyl 2-carbamoyl-4-(7-chloro-6-(4-chlorophenyl)quinazolin-4-yl)piperazine-1-carboxylate To a solution of the above obtained crude product 4-(7-chloro-6-(4-chlorophenyl)quinazolin-4-yl)piperazine-2-carboxamide in DCM (20 mL) at room temperature, Et3N (152 mg, 1.5 mmol) and di-tert-butyl dicarbonate (262 mg, 1.2 mmol) were added. The mixture was stirred at room temperature for 3 h. The mixture was concentrated in vacuo and the residue was purified by flash column chromatography on silica gel (DCM/MeOH=30:1) to afford the desired product (60 mg, 12% yield) as a solid. ESI-MS m/z: 502.4 [M+H]+.

tert-Butyl 4-(7-chloro-6-(4-chlorophenyl)quinazolin-4-yl)-2-cyanopiperazine-1-carboxylate To a solution of tert-butyl 2-carbamoyl-4-(7-chloro-6-(4-chlorophenyl)quinazolin-4-yl)piperazine-1-carboxylate (60 mg, 0.12 mmol) and Et$_3$N (48 mg, 0.48 mmol) in DCM (20 mL) at 0° C., TFAA (50 mg, 0.24 mmol) and the resulting mixture was stirred at room temperature for 1 h. The reaction mixture was quenched with saturated NaHCO$_3$ solution, and then extracted with DCM. The organic layer was washed with saturated NaHCO$_3$ solution and brine, dried over Na$_2$SO$_4$ and concentrated in vacuo. The residue was purified by flash column chromatography on silica gel (DCM/MeOH=50:1) to afford the desired product (50 mg, 86% yield) as a solid. ESI-MS m/z: 484.4 [M+H]+.

1-Acryloyl-4-(7-chloro-6-(4-chlorophenyl)quinazolin-4-yl)piperazine-2-carbonitrile The title compound was prepared from tert-butyl 4-(7-chloro-6-(4-chlorophenyl)quinazolin-4-yl)-2-cyanopiperazine-1-carboxylate according to the procedure described in steps 5 and 6 in Example 2. $^1$H NMR (400 MHz, DMSO-d6) δ: 8.7 (s. 1H), 8.1 (s, 1H), 8.0 (d, J=2.0 Hz, 1H), 7.5 (m, 4H), 6.8 (dd, J=10.4, 16.8 Hz, 1H), 6.3 (dd, J=1.6, 16.8 Hz, 1H), 5.8 (dd, J=1.6, 10.4 Hz, 1H), 4.6 (m, 1H), 4.3 (m, 3H), 3.6 (m, 2H), 3.4 (s, 1H). ESI-MS m/z: 438.25 [M+H]+.

Example 25

Synthesis of 1-(4-(7-chloro-6-(4-chlorophenyl)-2-methylquinazolin-4-yl)piperazin-1-yl)prop-2-en-1-one (I-50)

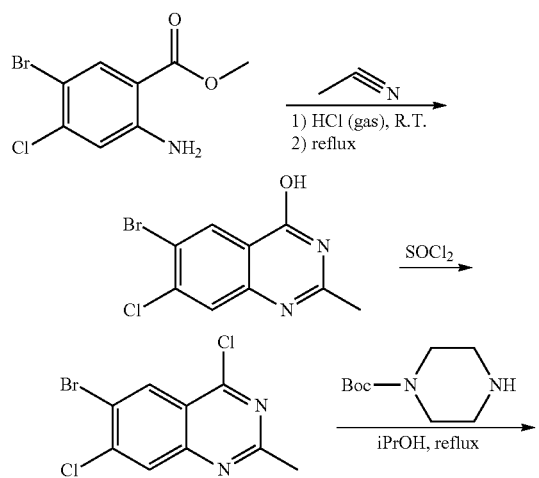

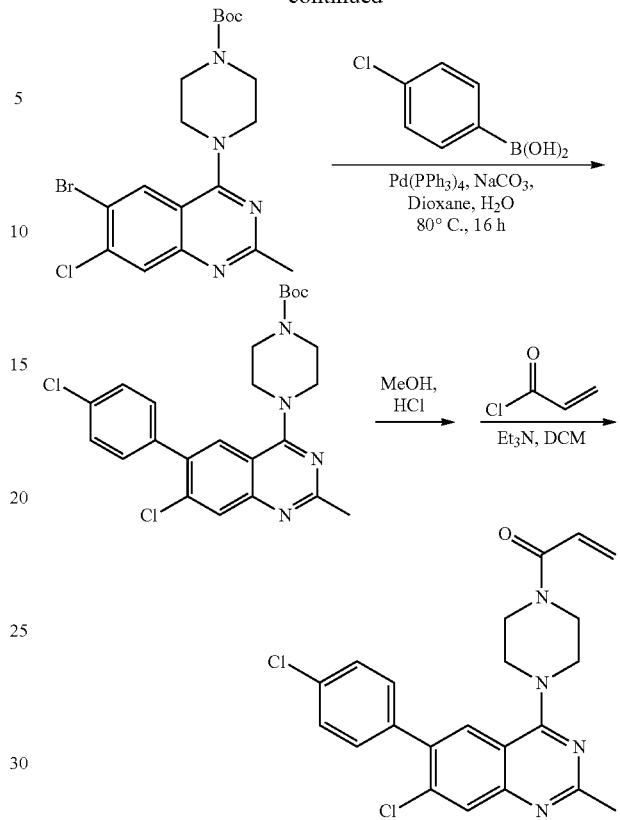

Compound I-50 was prepared according to the general procedures of Method M as described below:

6-Bromo-7-chloro-2-methylquinazolin-4-ol

To a solution of methyl 2-amino-5-bromo-4-chlorobenzoate (1.0 g, 3.781 mmol) in MeCN (35 mL) at RT, dry hydrogen chloride was added continuously for 20 min. The resulting mixture was stirred at reflux for 2 h. The mixture was allowed to cool to RT and poured into saturated NaHCO$_3$ solution. The white solid was filtered, and the filtrate was extracted with ethyl acetate. The filtrate cake and organic layer was combined and dried over Na$_2$SO$_4$, concentrated in vacuo to afford the crude product (1.62 g) as a white solid. ESI-MS m/z: 273.3 [M+H]+.

6-Bromo-4,7-dichloro-2-methylquinazoline

The mixture of 6-bromo-7-chloro-2-methylquinazolin-4-ol (500 mg, 1.828 mmol) in 30 mL of SOCl$_2$ was stirred at reflux for 16 h. The mixture was allowed to cool to RT and concentrated in vacuo. The residue was purified through silica chromatography (5-10% ethyl acetate/petroleum ether) to afford the desired product (180 mg, 34% yield) as a yellow solid.

tert-Butyl 4-(6-bromo-7-chloro-2-methylquinazolin-4-yl)piperazine-1-carboxylate

To a solution of tert-butyl piperazine-1-carboxylate (76 mg, 0.410 mmol) in i-PrOH (10 mL) at RT, 6-bromo-4,7-dichloro-2-methylquinazoline (60 mg, 0.205 mmol) was added. The resulting mixture was stirred at reflux for 40 min. The mixture was allowed to cool to RT and partitioned between water and ethyl acetate. The organic layer was washed with saturated NaHCO₃ and brine, dried over Na₂SO₄ and concentrated. The residue was purified by flash column chromatography on silica gel (5% ethyl acetate/petroleum ether) to afford the desired product (53 mg, 59% yield) as a yellow solid.

1-(4-(7-Chloro-6-(4-chlorophenyl)-2-methylquinazolin-4-yl)piperazin-1-yl)prop-2-en-1-one The title compound was prepared from tert-butyl 4-(6-bromo-7-chloro-2-methylquinazolin-4-yl)piperazine-1-carboxylate in three steps according to the procedure described in Example 3. ¹H NMR (400 MHz, DMSO-d6) δ: 7.92 (s, 2H), 7.59 (m, 4H), 6.84-6.77 (dd, J=10.4, 16.8 Hz, 1H), 6.17-6.36 (m, 1H), 5.74-5.71 (m, 1H), 3.85-3.72 (m, 8H), 2.54 (s, 3H). ESI-MS m/z: 428.3 [M+H]⁺.

Example 26

Synthesis of 1-acryloyl-4-(7-chloro-6-(4-chlorophenyl)-2-methylquinazolin-4-yl)piperazine-2-carbonitrile (I-56)

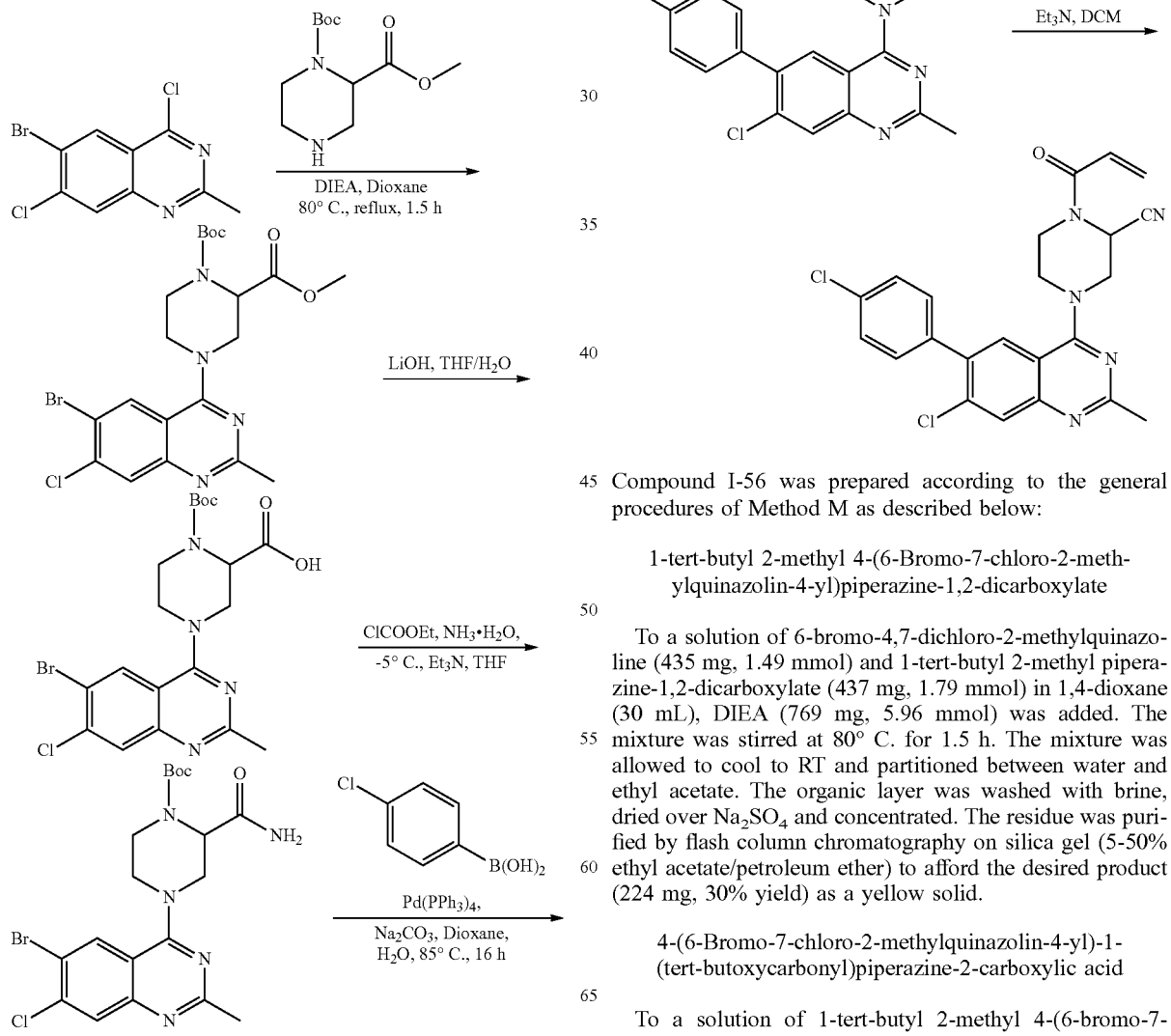

Compound I-56 was prepared according to the general procedures of Method M as described below:

1-tert-butyl 2-methyl 4-(6-Bromo-7-chloro-2-methylquinazolin-4-yl)piperazine-1,2-dicarboxylate To a solution of 6-bromo-4,7-dichloro-2-methylquinazoline (435 mg, 1.49 mmol) and 1-tert-butyl 2-methyl piperazine-1,2-dicarboxylate (437 mg, 1.79 mmol) in 1,4-dioxane (30 mL), DIEA (769 mg, 5.96 mmol) was added. The mixture was stirred at 80° C. for 1.5 h. The mixture was allowed to cool to RT and partitioned between water and ethyl acetate. The organic layer was washed with brine, dried over Na₂SO₄ and concentrated. The residue was purified by flash column chromatography on silica gel (5-50% ethyl acetate/petroleum ether) to afford the desired product (224 mg, 30% yield) as a yellow solid.

4-(6-Bromo-7-chloro-2-methylquinazolin-4-yl)-1-(tert-butoxycarbonyl)piperazine-2-carboxylic acid To a solution of 1-tert-butyl 2-methyl 4-(6-bromo-7-chloro-2-methylquinazolin-4-yl)piperazine-1,2-dicarboxylate (224 mg, 0.448 mmol) in THF (15 mL) and H$_2$O (5 mL), LiOH.H$_2$O (114 mg, 2.690 mmol) was added and the resulting mixture was stirred at RT for 1 h. The mixture was diluted with H$_2$O, acidified with HCl to adjust pH to 4 and then extracted with ethyl acetate. The organic layer was washed with brine, dried over Na$_2$SO$_4$ and concentrated in vacuo to afford the desired product (211 mg, 97% yield) as a yellow solid.

tert-Butyl 4-(6-bromo-7-chloro-2-methylquinazolin-4-yl)-2-carbamoylpiperazine-1-carboxylate To a solution of 4-(6-bromo-7-chloro-2-methylquinazolin-4-yl)-1-(tert-butoxycarbonyl)piperazine-2-carboxylic acid (221 mg, 0.435 mmol) and Et$_3$N (176 mg, 1.738 mmol) in THF (35 mL) at −5° C., ethyl chloroformate (51 mg, 0.465 mmol) was added. The mixture was stirred at −5° C. for 40 min and NH$_3$.H$_2$O (30%, 507 mg, 4.346 mmol) was added. The resulting mixture was kept stirring for 5 min at 0° C. The mixture was partitioned between water and ethyl acetate. The organic layer was washed with brine, dried over Na$_2$SO$_4$ and concentrated. The residue was purified by flash column chromatography on silica gel (3% methanol/dichloromethane) to afford the desired product (179 mg, 85% yield) as a yellow solid. ESI-MS m/z: 484.3 [M+H]$^+$.

tert-Butyl 2-carbamoyl-4-(7-chloro-6-(4-chlorophenyl)-2-methylquinazolin-4-yl)piperazine-1-carboxylate A mixture of tert-butyl 4-(6-bromo-7-chloro-2-methylquinazolin-4-yl)-2-carbamoylpiperazine-1-carboxylate (179 mg, 0.371 mmol), (4-chlorophenyl)boronic acid (67 mg, 0.426 mmol), Pd(PPh$_3$)$_4$ (51 mg, 0.0445 mmol) and Na$_2$CO$_3$ (118 mg, 1.113 mmol) in 1,4-dioxane (25 mL) was stirred at 85° C. for 16 h under argon. The mixture was allowed to cool to RT and concentrated in vacuo. The residue was purified by flash column chromatography on silica gel (3% methanol/dichloromethane) to afford the desired product (181 mg, 95% yield) as a brown solid. ESI-MS m/z: 517.4 [M+H]$^+$.

tert-Butyl 4-(7-chloro-6-(4-chlorophenyl)-2-methylquinazolin-4-yl)-2-cyanopiperazine-1-carboxylate To a solution of tert-butyl 2-carbamoyl-4-(7-chloro-6-(4-chlorophenyl)-2-methylquinazolin-4-yl)piperazine-1-carboxylate (100 mg, 0.194 mmol) and Et$_3$N (78 mg, 0.775 mmol) in DCM (30 mL) at 0° C., TFAA (162 mg, 0.776 mmol) was added and the resulting mixture was stirred at RT for 1 h. The reaction mixture was quenched with saturated NaHCO$_3$ solution, and then extracted with dichloromethane. The organic layer was washed with saturated NaHCO$_3$ solution and brine, dried over Na$_2$SO$_4$ and concentrated in vacuo. The residue was purified by flash column chromatography on silica gel (petroleum ether/ethyl acetate=2:1) to afford the desired product (58 mg, 60% yield) as a yellow solid. ESI-MS m/z: 499.4[M+H]$^+$.

1-Acryloyl-4-(7-chloro-6-(4-chlorophenyl)-2-methylquinazolin-4-yl)piperazine-2-carbonitrile tert-Butyl 4-(7-chloro-6-(4-chlorophenyl)-2-methylquinazolin-4-yl)-2-cyanopiperazine-1-carboxylate (100 mg, 0.194 mmol) was dissolved in 20 mL of 20% HCl/Et$_2$O solution. The mixture was stirred at RT for 30 min and then concentrated in vacuo to yield a solid salt (44 mg, 87% yield). The above solid (44 mg, 0.101 mmol) was dissolved in 25 mL of DCM with Et$_3$N (51 mg, 0.505 mmol). The mixture was cooled to 0° C. and then a solution of acryloyl chloride (10 mg, 0.111 mmol) in dichloromethane (2 mL) was added. The resulting mixture was stirred at 0° C. for 40 min. The mixture was extracted with ethyl acetate. The organic layer was washed with saturated NaHCO$_3$ and brine, dried over Na$_2$SO$_4$ and concentrated. The residue was purified with silica chromatography (petroleum ether/ethyl acetate=2:1) to afford the desired product (24 mg, 52% yield) as a white solid. $^1$H NMR (400 MHz, DMSO-d6) δ: 8.01 (d, J=6.4 Hz, 2H), 7.63 (q, J=8.4, 20.4 Hz, 4H), 6.90 (dd, J=10.4, 16.4 Hz, 1H), 6.30 (m, 1H), 5.68 (s, 1H), 4.60 (m, 1H), 4.32 (m, 2H), 3.57 (m, 2H), 2.59 (s, 3H), 3.36 (m, 1H). ESI-MS m/z: 453.3 [M+H]$^+$.

Example 27

Synthesis of 1-(4-(7-chloro-6-(4-chlorophenyl)quinazolin-4-yl)-2-(2-hydroxyethyl)piperazin-1-yl)prop-2-en-1-one (T-62)

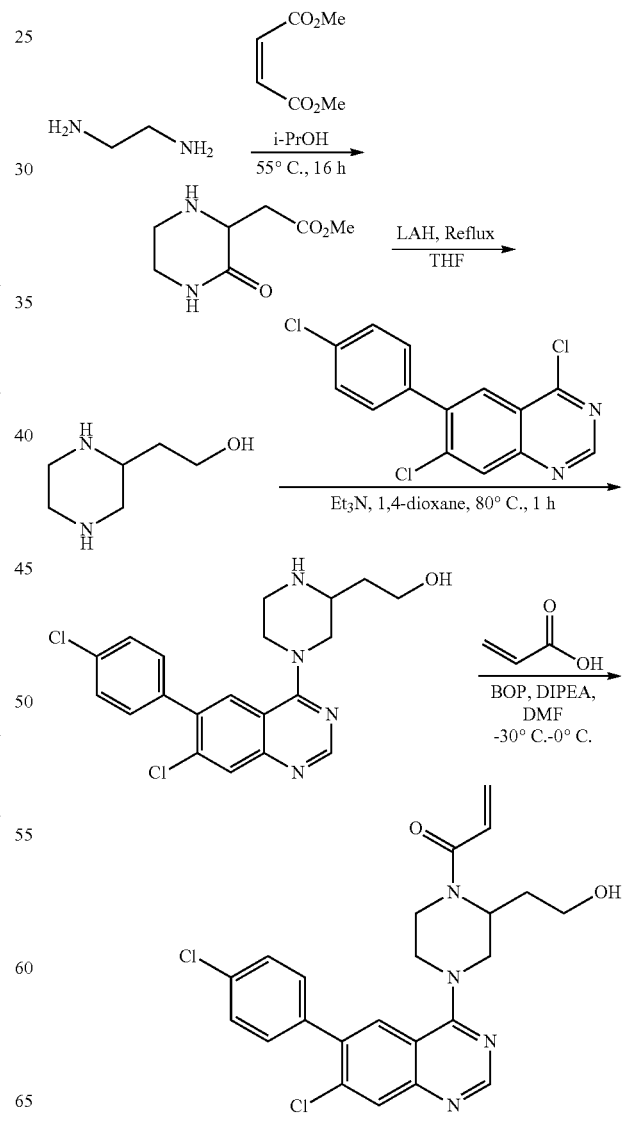

405

Compound I-62 was prepared according to the general procedures of Method A as described below:

Methyl 2-(3-oxopiperazin-2-yl)acetate

To a solution of dimethyl maleate (4.0 g, 27.78 mmol) in propan-2-ol (40 mL) at RT, ethane-1,2-diamine (1.167 g, 27.78 mmol) was added. The resulting mixture was stirred at 55° C. for 16 h and concentrated in vacuo. The residue was washed by a mixture of ethyl acetate/petroleum ether=1:1 to afford the desired product (2.8 g, 59% yield) as a white solid.

2-(Piperazin-2-yl)ethanol

To a solution of methyl 2-(3-oxopiperazin-2-yl)acetate (1.82 g, 10.58 mmol) in THF (150 mL) at 0° C., LiAlH$_4$ (2.01 g, 52.9 mmol) was added. The resulting mixture was stirred at reflux for 16 h. Then the mixture was cooled to RT. It was quenched with 10H$_2$O.Na$_2$SO$_4$ and filtered, washed with ethyl acetate. The filtrated was dried over Na$_2$SO$_4$ and concentrated in vacuo to afford the desired product (674 mg, 49% yield) as a yellow oil.

2-(4-(7-Chloro-6-(4-chlorophenyl)quinazolin-4-yl)piperazin-2-yl)ethanol

A mixture of 4,7-dichloro-6-(4-chlorophenyl)quinazoline (150 mg, 0.48 mmol), 2-(piperazin-2-yl)ethanol (187 mg, 1.44 mmol), Et$_3$N (0.33 mL, 2.4 mmol), in 1,4-dioxane (5 mL) was stirred at 80° C. for 30 min. The mixture was allowed to cool to RT, quenched with saturated NaHCO$_3$ solution and then extracted with ethyl acetate. The organic layer was washed with brine, dried over Na$_2$SO$_4$, filtered and concentrated in vacuo. The residue was purified by flash column chromatography on silica gel (methanol/dichloroethane=1:30) to afford the desired product (121 mg, 63% yield) as a colorless oil. ESI-MS m/z: 403.3 [M+H]$^+$.

1-(4-(7-Chloro-6-(4-chlorophenyl)quinazolin-4-yl)-2-(2-hydroxyethyl)piperazin-1-yl)prop-2-en-1-one To a solution of 2-(4-(7-chloro-6-(4-chlorophenyl)quinazolin-4-yl)piperazin-2-yl)ethanol (123 mg, 0.305 mmol), acrylic acid (24 mg, 0.336 mmol), BOP (270 mg, 0.61 mmol) in DMF (5 mL) at −30° C., DIEA (157 mg, 1.22 mmol) was added. The resulting mixture was warmed to 0° C. over 1 h, quenched with saturated NaHCO$_3$ solution, and then extracted with ethyl acetate. The organic layer was washed with saturated NaHCO$_3$ solution and brine, dried over Na$_2$SO$_4$ and concentrated in vacuo. The residue was purified by Pre-HPLC to afford the desired product (16 mg, 12% yield) as a light-yellow oil. $^1$H NMR (400 MHz, DMSO-d6) δ: 8.64 (s, 1H), 8.01 (s, 1H), 7.99 (s, 1H), 7.64-7.57 (m, 4H), 6.89-6.78 (m, 1H), 6.17-6.13 (m, 1H), 5.72 (dd, J=2.4, 10.4 Hz, 1H), 4.72-4.58 (m, 2H), 4.38-4.29 (m, 4H), 4.06-3.99 (m, 1H), 3.67-3.60 (m, 2H), 1.79-1.68 (m, 2H). ESI-MS m/z: 457.4 [M+H]$^+$.

Example 28

Synthesis of 2-(1-acryloyl-4-(7-chloro-6-(4-chlorophenyl)quinazolin-4-yl)piperazin-2-yl)acetonitrile (I-70)

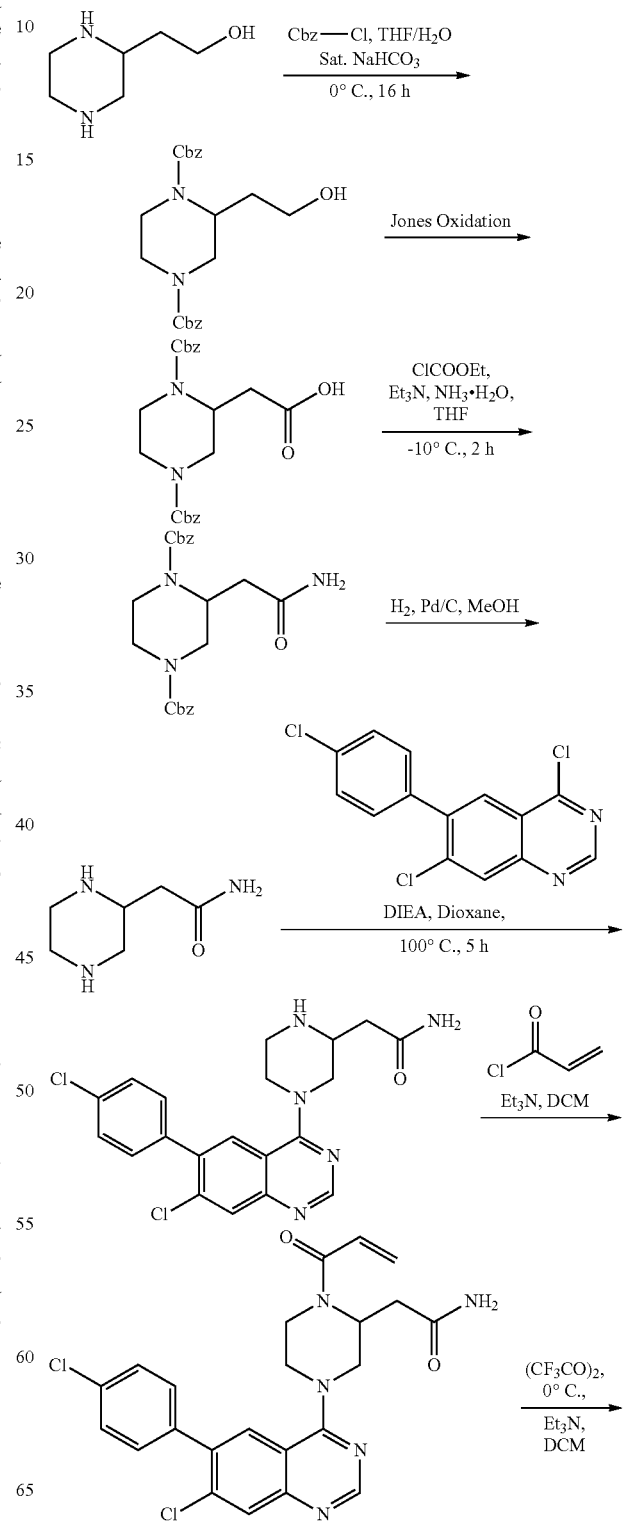

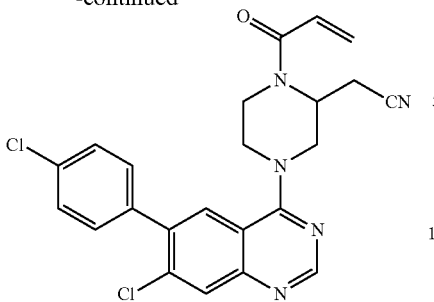

Compound I-70 was prepared according to the general procedures of Method A as described below:

Dibenzyl 2-(2-hydroxyethyl)piperazine-1,4-dicarboxylate

To a solution of 2-(piperazin-2-yl)ethanol (2.0 g, 15.4 mmol) in THF (48 mL), H$_2$O (32 mL) and saturated NaHCO$_3$ (32 mL) at 0° C., Cbz-Cl (5.5 g, 32.3 mmol) was added dropwise. The mixture was stirred at 0° C. for 2 h and at RT for 16 h. The mixture was diluted with brine, extracted with dichloromethane. The organic layer was washed with brine, dried over Na$_2$SO$_4$ and concentrated. The residue was purified by flash column chromatography on silica gel (25%-50% ethyl acetate/petroleum ether) to afford the desired product (1.454 g, 23% yield) as a colorless oil. ESI-MS m/z: 399.4 [M+H]$^+$.

2-(1,4-Bis((benzyloxy)carbonyl)piperazin-2-yl)acetic acid

To a solution of dibenzyl 2-(2-hydroxyethyl)piperazine-1,4-dicarboxylate (515 mg, 1.294 mmol) in acetone (30 mL), Jones reagent (1.48 mL, 3.88 mmol, 2.6 M) was added dropwise at 0° C., which was stirred at RT for 1 h. The mixture was quenched with i-PrOH (2 mL) and filtered through celite. The filtrate was extracted with ethyl acetate. The organic layer was washed with brine, dried over Na$_2$SO$_4$ and concentrated to afford the crude product (545 mg) as a colorless oil. ESI-MS m/z: 413.2 [M+H]$^+$.

Dibenzyl 2-(2-amino-2-oxoethyl)piperazine-1,4-dicarboxylate

To a solution of 2-(1,4-bis((benzyloxy)carbonyl)piperazin-2-yl)acetic acid (545 mg, 1.323 mmol) and Et$_3$N (535 mg, 5.292 mmol) in THF (20 mL), ethyl chloroformate (154 mg, 1.415 mmol) was added at −10° C. and stirred at this temperature for 40 min. Then the mixture was added NH$_3$.H$_2$O (1.984 g, 15.87 mmol) at −10° C. and stirred for 20 min at −10° C. The mixture was partitioned between water and ethyl acetate. The organic layer was washed with brine, dried over Na$_2$SO$_4$ and concentrated. The residue was purified by flash column chromatography on silica gel (2% methanol/dichloromethane) to afford the desired product (393 mg, 72% yield) as a colorless oil. ESI-MS m/z: 412.3[M+H]$^+$.

2-(Piperazin-2-yl)acetamide

A mixture of dibenzyl 2-(2-amino-2-oxoethyl)piperazine-1,4-dicarboxylate (385 mg, 0.937 mmol), Pd/C (10%, 40 mg) and MeOH (30 mL) was stirred at 40° C. for 2.5 h under H$_2$ (1 atm). The mixture was filtered through celite and concentrated to afford the crude product (188 mg) as a colorless oil.

2-(4-(7-Chloro-6-(4-chlorophenyl)quinazolin-4-yl)piperazin-2-yl)acetamide

A mixture of 4,7-dichloro-6-(4-chlorophenyl)quinazoline (313 mg, 1.315 mmol), 2-(piperazin-2-yl)acetamide (188 mg, 1.315 mmol), DIEA (848 mg, 6.575 mmol) and 1,4-dioxane (30 mL) at 100° C. for 5 h. The mixture was allowed to cool to RT and concentrated in vacuo. The residue was purified by flash column chromatography on silica gel (5-20% methanol/dichloromethane) to afford the desired product (78 mg, 14% yield) as a brown solid. ESI-MS m/z: 417.3 [M+H]$^+$.

2-(1-Acryloyl-4-(7-chloro-6-(4-chlorophenyl)quinazolin-4-yl)piperazin-2-yl)acetamide A mixture of 2-(4-(7-chloro-6-(4-chlorophenyl)quinazolin-4-yl)piperazin-2-yl)acetamide (78 mg, 0.1875 mmol), Et$_3$N (76 mg, 0.750 mmol) and dichloromethane (30 mL) at 0° C., a solution of acryloyl chloride (21 mg, 0.225 mmol) in dichloromethane (2 mL) was added dropwise. The resulting mixture was stirred at 0° C. for 40 min. The mixture was quenched with saturated NaHCO$_3$ and extracted with ethyl acetate. The organic layer was washed with brine, dried over Na$_2$SO$_4$ and concentrated. The residue was purified with column chromatography on silica gel (2.5-4% methanol in dichloromethane) to afford the desired product (32 mg, 36% yield) as a white solid. $^1$H NMR (400 MHz, DMSO-d6) δ: 8.74 (s, 1H), 8.07 (s, 1H), 7.80 (s, 1H), 7.50-7.42 (dd, J=8.8, 14.4 Hz, 1H), 6.79-6.24 (m, 3H), 5.83 (m, 1H), 5.36-5.14 (m, 2H), 4.72-4.49 (m, 2H, 4.32 (m, 1H), 3.99-3.49 (m, 3H), 3.07-2.44 (m, 3H). ESI-MS m/z: 470.2 [M+H]$^+$.

2-(1-Acryloyl-4-(7-chloro-6-(4-chlorophenyl)quinazolin-4-yl)piperazin-2-yl)acetonitrile To a solution of 2-(1-acryloyl-4-(7-chloro-6-(4-chlorophenyl)quinazolin-4-yl)piperazin-2-yl)acetamide (25 mg, 0.0533 mmol) and Et$_3$N (27 mg, 0.267 mmol) in DCM (10 mL) at 0° C., TFAA (46 mg, 0.214 mmol) and the resulting mixture was stirred at RT for 20 min. The reaction mixture was quenched with saturated NaHCO$_3$ solution, and then extracted with dichloromethane. The organic layer was washed with saturated NaHCO$_3$ solution and brine, dried over Na$_2$SO$_4$ and concentrated in vacuo. The residue was purified by flash column chromatography on silica gel (2.5% methanol in dichloromethane) to afford the desired product (21 mg, 87% yield) as a white solid. $^1$H NMR (400 MHz, DMSO-d6) δ: 8.67 (s, 1H), 8.06 (m, 2H), 7.70 (s, 4H), 6.88 (m, 1H), 6.20 (d, J=10.0 Hz, 1H), 5.76 (s, 1H), 4.97 (m, 1H), 4.30 (m, 4H), 3.75 (m, 2H), 2.99 (m, 2H). ESI-MS m/z: 453.3 [M+H]$^+$.

Example 29

Synthesis of 4-(4-acryloyl-3-cyanopiperazin-1-yl)-7-chloroquinazoline-6-carbonitrile (53)

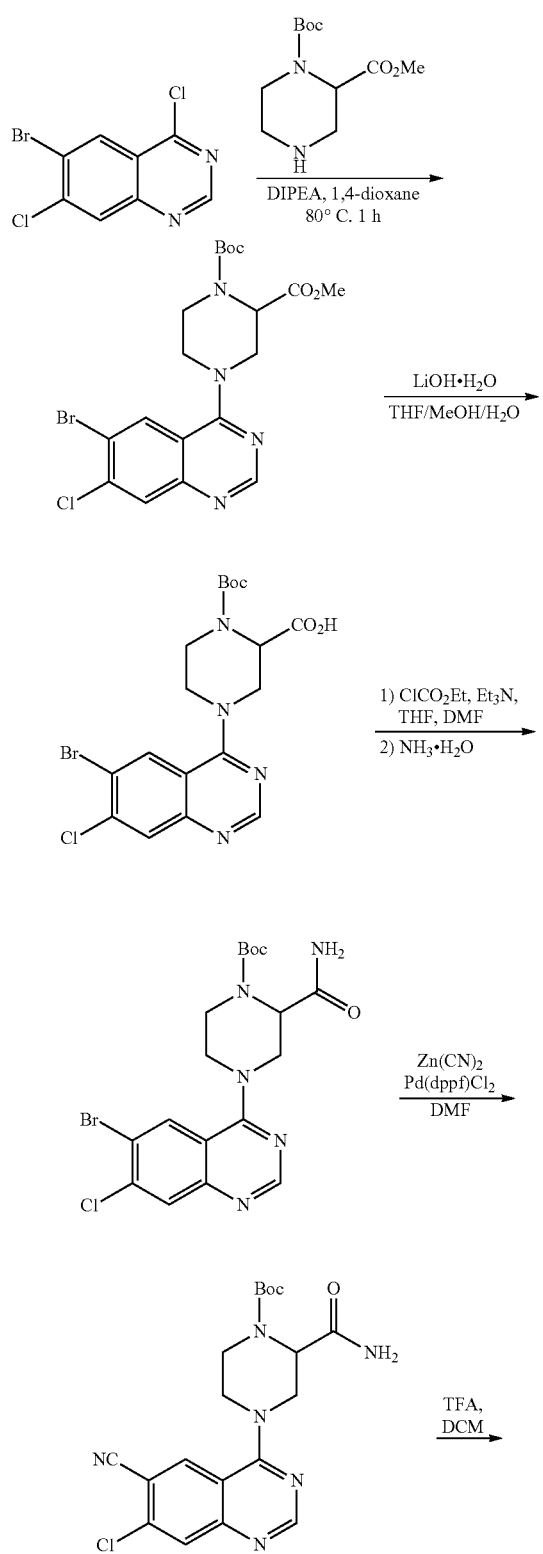

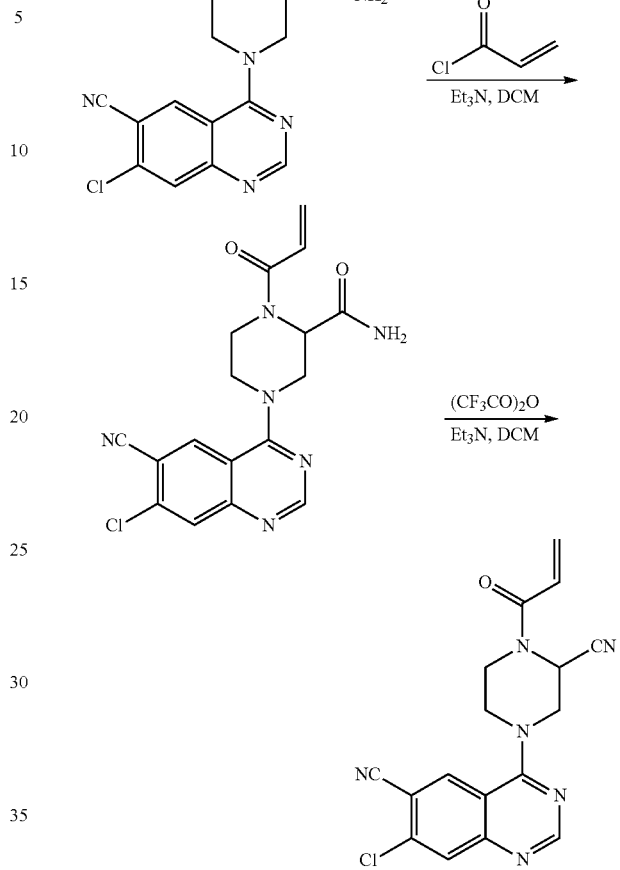

Compound I-53 was prepared according to the general procedures of Method B as described below:

1-tert-Butyl 2-methyl 4-(6-bromo-7-chloroquinazolin-4-yl)piperazine-1,2-dicarboxylate A mixture of 6-bromo-4,7-dichloroquinazoline (300 mg, 1.08 mmol), tert-butyl methyl piperazine-1,2-dicarboxylate (395 mg, 1.62 mmol), DIEA (836 mg, 6.48 mmol) in 1,4-dioxane (8 mL) was stirred at 80° C. for 1 h. The mixture was allowed to cool to RT, quenched with saturated NaHCO$_3$ solution and then extracted with ethyl acetate. The organic layer was washed with brine, dried over Na$_2$SO$_4$, filtered and concentrated in vacuo. The residue was purified by flash column chromatography on silica gel (ethyl acetate/petroleum ether=1:5) to afford the desired product (367 mg, 70% yield) as a white solid.

1-(tert-Butoxycarbonyl)-4-(6-bromo-7-chloroquinazolin-4-yl)piperazine-2-carboxylic acid To a solution of 1-tert-butyl 2-methyl 4-(6-bromo-7-chloroquinazolin-4-yl)piperazine-1,2-dicarboxylate (100 mg, 0.206 mmol) in THF (2 mL), MeOH (2 mL) and water (2 mL), LiOH.H$_2$O (165 mg, 4.12 mmol) was added and the resulting mixture was stirred at RT for 1 h. The mixture was washed with 20% ethyl acetate/petroleum ether. The aqueous layer was acidified with aqueous HCl (1 N) to adjust pH to 5 and extracted with ethyl acetate. The organic layer was dried over MgSO4, filtered, and concentrated in vacuo to afford the desired product (65 mg, 67% yield).

tert-Butyl 4-(6-bromo-7-chloroquinazolin-4-yl)-2-carbamoylpiperazine-1-carboxylate To a mixture of 1-(tert-butoxycarbonyl)-4-(6-bromo-7-chloroquinazolin-4-yl)piperazine-2-carboxylic acid (65 mg, 0.14 mmol), Et$_3$N (0.11 mL, 0.77 mmol) in THF (4 mL) and DMF (2 mL) at 0° C., ethyl chloroformate (83 mg, 0.77 mmol) was added. The resulting mixture was stirred at 0° C. for 1 h and NH$_3$.H$_2$O (1 mL, 15 N) was added. Then the mixture was warmed to RT and stirred for another 1 h. It was quenched with saturated NaHCO$_3$ solution and then extracted with ethyl acetate. The organic layer was washed with brine, dried over Na$_2$SO$_4$, filtered and concentrated in vacuo to afford the crude product (77 mg) as a yellow solid. ESI-MS m/z: 471.4 [M+H]$^+$.

tert-Butyl2-carbamoyl-4-(7-chloro-6-cyanoquinazolin-4-yl)piperazine-1-carboxylate A mixture of tert-butyl 4-(6-bromo-7-chloroquinazolin-4-yl)-2-carbamoylpiperazine-1-carboxylate (200 mg, 0.43 mmol), PdCl$_2$(dppf) (31 mg, 0.043 mmol), Zn(CN)$_2$ (80 mg, 0.68 mmol) and DMF (20 mL) was stirred at reflux for 5 h. The mixture was allowed to cool to room temperature, and partitioned between ethyl acetate and water. The organic layer was washed with brine, dried over Na$_2$SO$_4$ and concentrated. The residue was purified by flash column chromatography on silica gel (1-2% methanol/dichloromethane) to afford the desired product (140 mg, 79% yield) as a solid. ESI-MS m/z: 417.3 [M+H]$^+$.

4-(7-Chloro-6-cyanoquinazolin-4-yl)piperazine-2-carboxamide

A solution of tert-butyl2-carbamoyl-4-(7-chloro-6-cyanoquinazolin-4-yl)piperazine-1-carboxylate (140 mg, 0.34 mmol) in dichloromethane (20 mL) at RT, TFA (2 mL) was added. The resulting mixture was stirred at RT for 2 h. The mixture was concentrated in vacuo to afford the crude product (100 mg) which was used directly in the next step without further purification.

1-Acryloyl-4-(7-chloro-6-cyanoquinazolin-4-yl)piperazine-2-carboxamide

A mixture of 4-(7-chloro-6-cyanoquinazolin-4-yl)piperazine-2-carboxamide (100 mg, 0.32 mmol), Et$_3$N (96 mg, 0.96 mmol) in dichloromethane (10 mL) at 0° C., acryloyl chloride (35 mg, 0.384 mmol) was added. The resulting mixture was stirred at RT for 0.5 h, poured into water and then extracted with dichloromethane. The organic layer was washed with brine, dried over Na$_2$SO$_4$ and concentrated. The residue was purified by flash column chromatography on silica gel (1-2% methanol/dichloromethane) to afford the desired product (50 mg, 43% yield) as a solid. ESI-MS m/z: 371.3 [M+H]$^+$.

4-(4-Acryloyl-3-cyanopiperazin-1-yl)-7-chloroquinazoline-6-carbonitrile

A mixture of 1-acryloyl-4-(7-chloro-6-cyanoquinazolin-4-yl)piperazine-2-carboxamide (50 mg, 0.14 mmol) and Et$_3$N (82 mg, 0.81 mmol) in DCM (10 mL) at RT, trifluoroacetic anhydride (117.6 mg, 0.56 mmol) was added. The resulting mixture was stirred at RT for 0.5 h and poured into water and then extracted with dichloromethane. The organic layer was washed with brine, dried over Na$_2$SO$_4$ and concentrated. The residue was purified by flash column chromatography on silica gel (1-3% methanol/dichloromethane) to afford the desired product (15 mg, 32% yield). $^1$H NMR (400 MHz, DMSO-d6) δ: 8.79 (s, 1H), 8.77 (s, 1H), 8.16 (s, 1H), 6.92-6.85 (m, 1H), 6.32-6.28 (m, 1H), 5.91-5.88 (m, 1H), 5.68 (s, 1H), 4.73-4.70 (d, J=14 Hz, 1H), 4.46-4.43 (d, J=13.2 Hz, 1H), 4.25-4.22 (d, J=12.8 Hz, 1H), 3.82-3.74 (m, 2H), 3.59-3.56 (m, 1H). ESI-MS m/z: 353.2 [M+H]$^+$.

Example 30

Synthesis of 1-acryloyl-4-(7-chloro-6-cyclopropylquinazolin-4-yl)piperazine-2-carbonitrile (55)

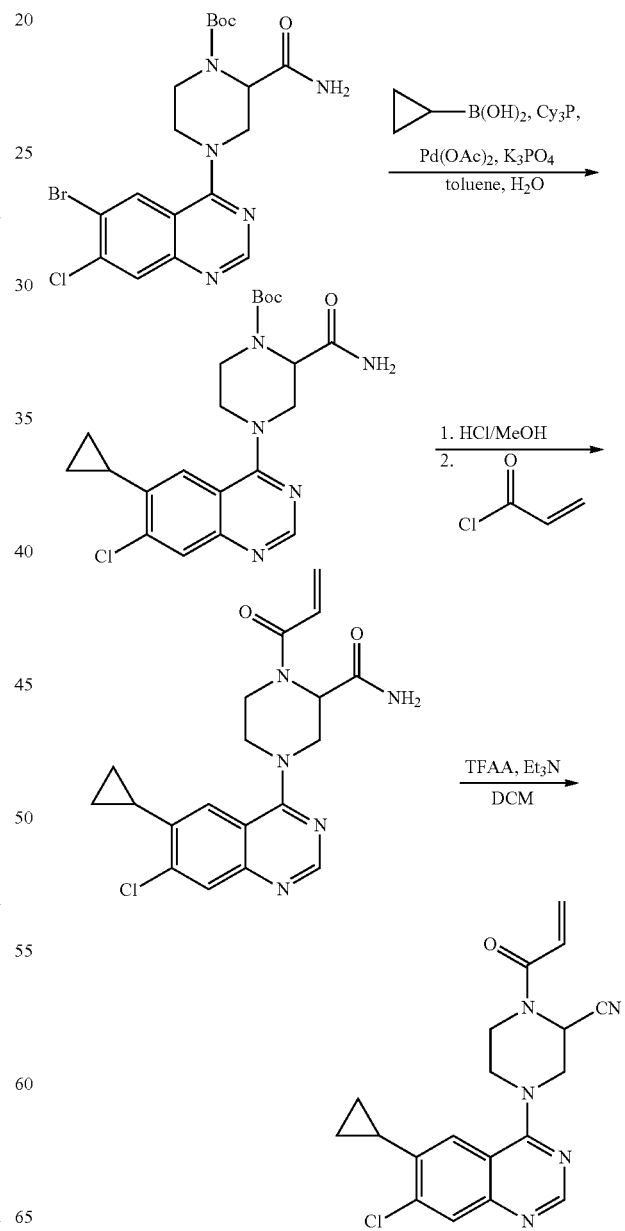

Compound I-55 was prepared according to the general procedures of Method B as described below:

tert-Butyl 2-carbamoyl-4-(7-chloro-6-cyclopropylquinazolin-4-yl)piperazine-1-carboxylate A mixture of tert-butyl 4-(6-bromo-7-chloroquinazolin-4-yl)-2-carbamoylpiperazine-1-carboxylate (200 mg, 0.414 mmol), cyclopropylboronic acid (44 mg, 0.51 mmol), K$_3$PO$_4$·3H$_2$O (270 mg, 1.272 mmol), Pd(OAc)$_2$ (18 mg, 0.08 mmol) and tricyclohexyl phosphine (22 mg, 0.08 mmol) in toluene (10 mL) and water (1 mL) was stirred at reflux under argon for 16 h. The solvent was removed, and the residue was purified by flash column chromatography on silica gel (dichloromethane/methanol=50:1) to afford the desired product (100 mg, 56% yield) as a solid. ESI-MS m/z: 432.4 [M+H]$^+$.

Acryloyl-4-(7-chloro-6-cyclopropylquinazolin-4-yl) piperazine-2-carboxamide

The title compound was prepared from tert-butyl 2-carbamoyl-4-(7-chloro-6-cyclopropylquinazolin-4-yl)piperazine-1-carboxylate in two steps following the procedure described in Example 1.

Acryloyl-4-(7-chloro-6-cyclopropylquinazolin-4-yl) piperazine-2-carboxamide

To a solution of 1-acryloyl-4-(7-chloro-6-cyclopropylquinazolin-4-yl)piperazine-2-carboxamide (17 mg, 0.044 mmol) and Et$_3$N (18 mg, 0.176 mmol) in DCM (5 mL) at 0° C., TFAA (18 mg, 0.088 mmol) was added and the resulting mixture was stirred at RT for 1 h. The reaction mixture was quenched with saturated NaHCO$_3$ solution, and then extracted with dichloromethane. The organic layer was washed with saturated NaHCO$_3$ solution and brine, dried over Na$_2$SO$_4$ and concentrated in vacuo. The residue was purified by flash column chromatography on silica gel (dichloromethane/methanol=50:1) to afford the desired product (10 mg, 62% yield) as a solid. $^1$H NMR (400 MHz, CDCl3) δ: 8.8 (s, 1H), 8.0 (s, 1H), 7.7 (s, 1H), 6.6 (dd, J=10.0, 16.4 Hz, 1H), 6.5 (d, J=16.4 Hz, 1H), 6.0 (dd, J=2.0, 10.4 Hz, 1H), 6.0-5.9 (m, 1H), 4.4 (dd, J=2, 13.2 Hz, 1H), 4.3-4.1 (m, 2H), 3.9-3.8 (m, 1H), 3.3-3.1 (m, 2H), 2.4-2.3 (m, 1H), 1.2-1.1 (m, 2H), 1.0-0.9 (m, 2H). ESI-MS m/z: 368.3 [M+H]$^+$.

Example 31

Synthesis of (S)-1-acryloyl-4-(7-chloro-6-(4-chlorophenyl)quinazolin-4-yl)piperazine-2-carboxamide (I-54)

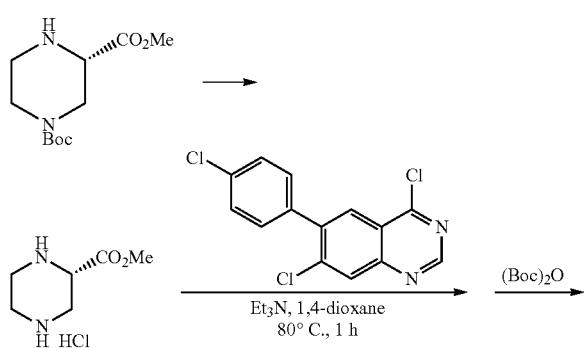

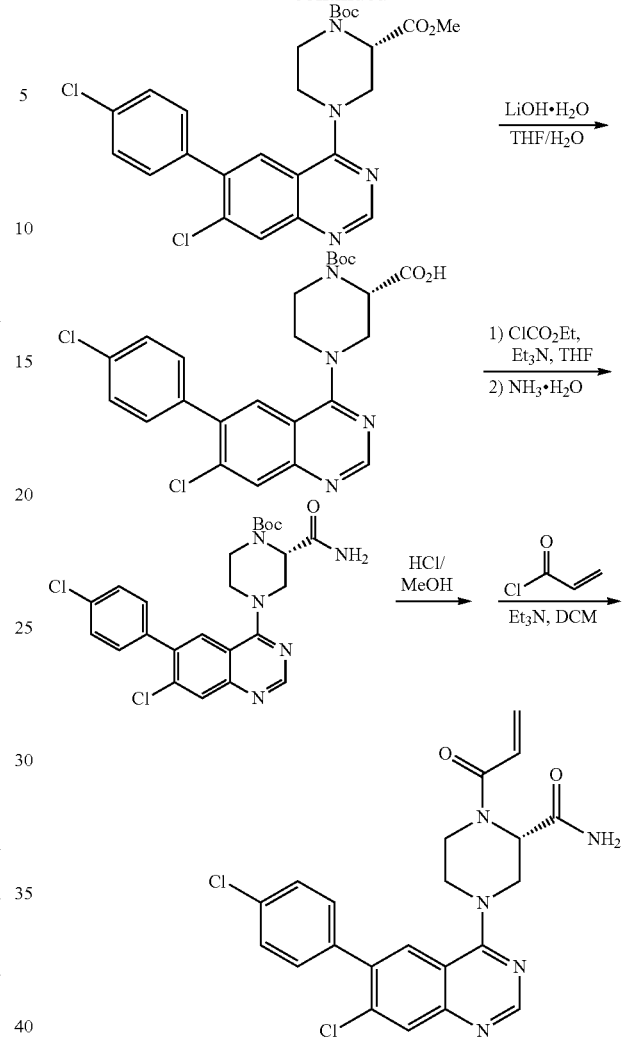

Compound I-54 was prepared according to the general procedures of Method A as described below:

(S)-Methyl piperazine-2-carboxylate hydrochloride

A mixture of (S)-tert-butyl methyl piperazine-1,3-dicarboxylate (366 mg, 1.5 mmol) and HCl in MeOH (20 mL, 2.9 M) was stirred at RT for 1 h. The mixture was concentrated in vacuo to yield the crude product (270 mg) as a yellow solid which was used directly in next step without further purification.

(S)-1-tert-Butyl 2-methyl 4-(7-chloro-6-(4-chlorophenyl)quinazolin-4-yl)piperazine-1,2-dicarboxylate To the mixture of above obtained crude (S)-methyl piperazine-2-carboxylate hydrochloride, 4,7-dichloro-6-(4-chlorophenyl)quinazoline (310 mg, 1 mmol), DIEA (1.29 g, 10 mmol) and 1,4-dioxane (20 mL) was stirred for 1 h at 80° C. Then mixture was cooled to RT and di-tert butyl dicarbonate (327 mg, 1.5 mmol) was added. The mixture was stirred for 16 h and quenched with saturated NaHCO$_3$ solution and then extracted with ethyl acetate. The organic layer was washed with brine, dried over Na$_2$SO$_4$, filtered and concentrated in vacuo. The residue was purified by flash column chromatography on silica gel (methanol/dichloroethane=1:50) to afford the desired product (300 mg, 58% yield, 2 steps) as a solid oil. ESI-MS m/z: 517.5 [M+H]+.

(S)-1-(tert-Butoxycarbonyl)-4-(7-chloro-6-(4-chlorophenyl)quinazolin-4-yl)piperazine-2-carboxylic acid To a solution of (S)-1-tert-butyl 2-methyl 4-(7-chloro-6-(4-chlorophenyl)quinazolin-4-yl)piperazine-1,2-dicarboxylate (300 mg, 0.58 mmol) in mixture of 1:1 tetrahydrofuran and water (20 mL) at RT, LiOH.H2O (49 mg, 1.16 mmol) were added and the resulting mixture was stirred for 1 h and then acidified with aqueous HCl (1 N) to adjust the pH to 3-5. The mixture was extracted with ethyl acetate. The combined organic layer was washed with brine, dried over anhydrous Na2SO4, filtered and concentrated in vacuo to afford the crude product (230 mg) which was used directly in the next step without further purification.

(S)-tert-Butyl 2-carbamoyl-4-(7-chloro-6-(4-chlorophenyl)quinazolin-4-yl)piperazine-1-carboxylate To a mixture of (S)-1-(tert-butoxycarbonyl)-4-(7-chloro-6-(4-chlorophenyl)quinazolin-4-yl)piperazine-2-carboxylic acid (230 mg, 0.46 mmol), Et3N (139 mg, 1.37 mmol) in THF (5 mL) at 0° C., ethyl chloroformate (148 mg, 1.37 mmol) was added. The resulting mixture was stirred at 0° C. for 1 h, then Ammonium hydroxide (1 mL, 15 N) was added and kept stirring for another 1 h at RT. The mixture was extracted with ethyl acetate dried over anhydrous Na2SO4, filtered and concentrated in vacuo. The residue was purified by flash column chromatography on silica gel (dichloromethane/methanol=50:1) to afford the desired product (150 mg, 65% yield) as a solid. ESI-MS m/z: 502.4 [M+H]+.

(S)-1-Acryloyl-4-(7-chloro-6-(4-chlorophenyl)quinazolin-4-yl)piperazine-2-carboxamide The title compound was prepared from (S)-tert-butyl 2-carbamoyl-4-(7-chloro-6-(4-chlorophenyl)quinazolin-4-yl)piperazine-1-carboxylatein 2 steps according to the procedure described in Example 2. $^1$H NMR (400 MHz, DMSO-d6) δ: 8.7 (s, 1H), 8.3 (d, J=8.0 Hz, 1H), 8.0 (s, 1H), 7.8-7.5 (m, 5H), 7.4-7.2 (m, 1H), 6.9-6.6 (m, 1H), 6.2 (d, J=2.4, 17.6 Hz, 1H), 5.8-5.7 (m, 1H), 5.0-4.8 (m, 1H), 4.7 (d, J=13.2 Hz, 1H), 4.2-4.0 (m, 2H), 3.9-3.8 (m, 1H), 3.7-3.5 (m, 1H), 3.5-3.4 (m, 1H). ESI-MS m/z: 456.3 [M+H]+.

Example 32

Synthesis of (S)-1-acryloyl-4-(7-chloro-6-(4-chlorophenyl)quinazolin-4-yl)piperazine-2-carbonitrile (I-59)

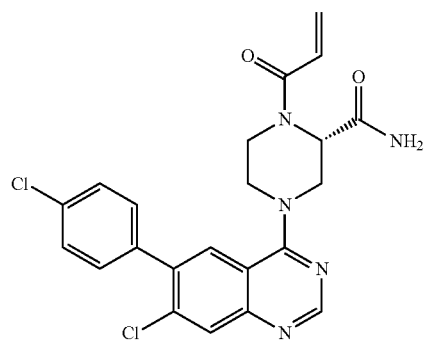

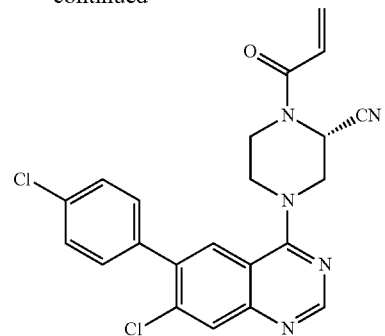

Compound I-59 was prepared according to the general procedures of Method A as described below:

(S)-1-Acryloyl-4-(7-chloro-6-(4-chlorophenyl)quinazolin-4-yl)piperazine-2-carbonitrile To a solution of (S)-1-acryloyl-4-(7-chloro-6-(4-chlorophenyl)quinazolin-4-yl)piperazine-2-carboxamide (23 mg, 0.05 mmol) and Et3N (20 mg, 0.2 mmol) in DCM (5 mL) at 0° C., trifluoroacetic anhydride (21 mg, 0.1 mmol) and the resulting mixture was stirred at RT for 1 h. The reaction mixture was quenched with saturated NaHCO3 solution, and then extracted with dichloromethane. The organic layer was washed with saturated NaHCO3 solution and brine, dried over Na2SO4 and concentrated in vacuo. The residue was purified by flash column chromatography on silica gel (dichloromethane/methanol=50:1) to afford the desired product (15 mg, 68% yield) as a solid. $^1$H NMR (400 MHz, DMSO-d6) δ: 8.7 (s, 1H), 8.1 (s, 1H), 8.0 (s, 1H), 7.5 (m, 4H), 6.8 (dd, J=10.4, 16.4 Hz, 1H), 6.3 (dd, J=2.0, 17.2 Hz, 1H), 5.8 (dd, J=2.0, 10.8 Hz, 1H), 5.7 (m, 1H), 4.6 (d, J=14.0 Hz, 3H), 4.3 (m, 2H), 3.6 (m, 2H). ESI-MS m/z: 438.3 [M+H]+.

Example 33

Synthesis of (S)-1-(4-(7-chloro-6-(4-chlorophenyl)quinazolin-4-yl)-2-(hydroxymethyl)piperazin-1-yl)prop-2-en-1-one (I-63)

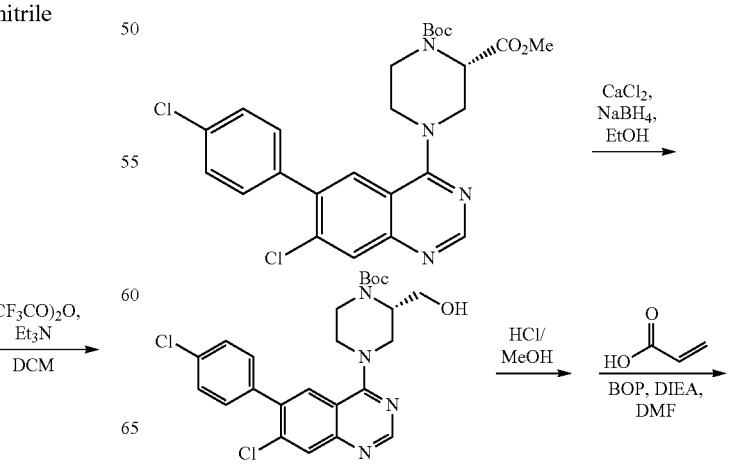

417
-continued

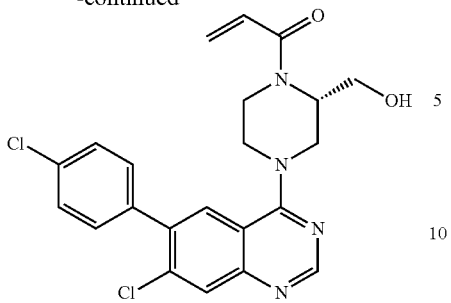

Compound I-63 was prepared according to the general procedures of Method A as described below:

(S)-tert-Butyl 4-(7-chloro-6-(4-chlorophenyl)quinazolin-4-yl)-2-(hydroxymethyl)piperazine-1-carboxylate To a solution of (S)-1-tert-butyl 2-methyl 4-(7-chloro-6-(4-chlorophenyl)quinazolin-4-yl)piperazine-1,2-dicarboxylate (200 mg, 0.387 mmol) in EtOH (10 mL) was added $CaCl_2$ (215 mg, 1.933 mmol) and $NaBH_4$ (74 mg, 1.933 mmol) at 0° C. The mixture was stirred at RT for 16 h. The mixture was filtered, and washed by ethanol. The mixture was concentrated in vacuo, and the residue was purified by flash column chromatography on silica gel (dichloromethane/methanol=50:1) to afford the desired product (80 mg, 42% yield) as a solid. ESI-MS m/z: 489.4 $[M+H]^+$.

1-((S)-4-(7-Chloro-6-(4-chlorophenyl)quinazolin-4-yl)-2-(hydroxymethyl)piperazin-1-yl)prop-2-en-1-one The title compound was prepared from (S)-tert-butyl 4-(7-chloro-6-(4-chlorophenyl)quinazolin-4-yl)-2-(hydroxymethyl)piperazine-1-carboxylate in two steps according to the procedure described in Example 14. $^1$H NMR (400 MHz, DMSO-d6) δ: 8.7 (s, 1H), 8.3-8.1 (m, 1H), 8.0 (s, 1H), 7.7-7.5 (m, 4H), 6.8 (dd, J=10.4, 16.4 Hz, 1H), 6.1 (d, J=16 Hz, 1H), 5.8 (dd, J=2, 10.4 Hz, 1H), 5.1-4.9 (m, 1H), 4.3-4.1 (m, 4H), 4.2 (m, 2H), 3.7-3.5 (m, 4H). ESI-MS m/z: 443.3 $[M+H]^+$.

Example 34

Synthesis of 1-(4-(6-chloro-7-phenylquinazolin-4-yl)piperazin-1-yl)prop-2-en-1-one (I-67)

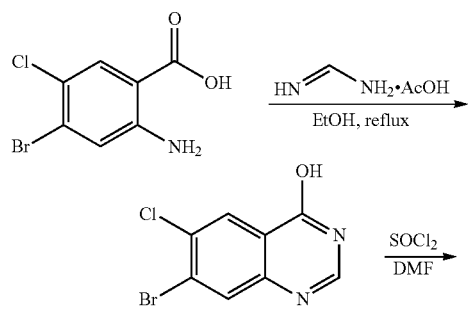

418
-continued

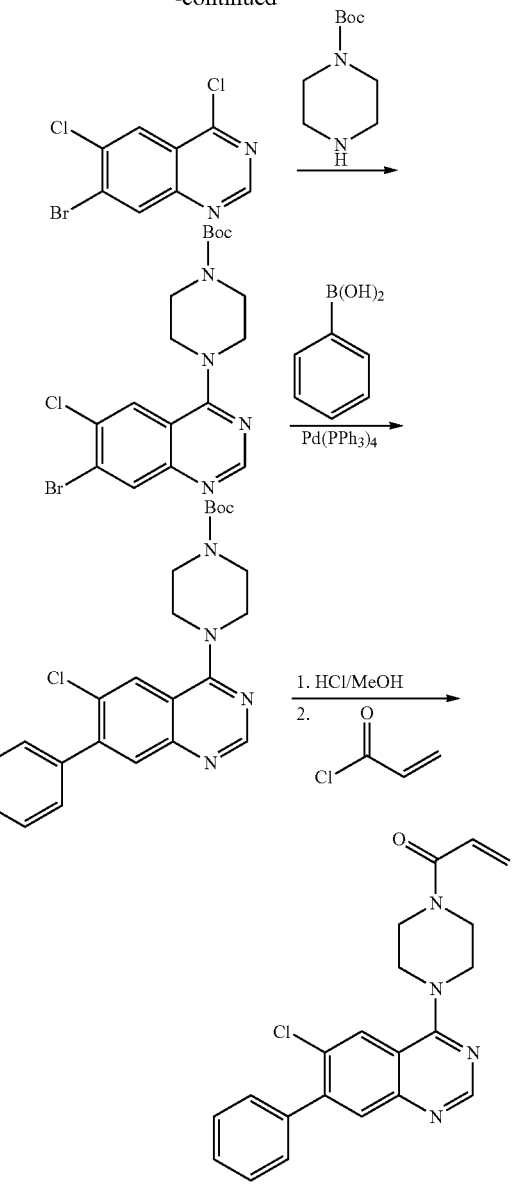

Compound I-67 was prepared according to the general procedures of Method B as described below:

7-Bromo-6-chloroquinazolin-4-ol

To a solution of 2-amino-4-bromo-5-chlorobenzoic acid (500 mg, 2 mmol) in EtOH (20 mL) at RT, formamidine acetate (620 mg, 6 mmol) was added. The mixture was reflux for 16 hour. The mixture was concentrated in vacuo, and the residue was washed by saturated $NaHCO_3$ aqueous solution, and a mixture of ethyl acetate/petroleum ether=1:2. The solid was dried in vacuo to get the product (520 mg, 100% yield) which was used directly in next step without further purification. ESI-MS m/z: 259.0 $[M+H]^+$.

7-Bromo-4,6-dichloroquinazoline

To a solution of 7-bromo-6-chloroquinazolin-4-ol (520 mg, 2 mmol) in thionyl chloride (15 mL) was added one drop of DMF. The mixture was reflux for 16 h. The mixture was concentrated in vacuo, the residue was used directly in next step without further purification.

1-(4-(6-Chloro-7-phenylquinazolin-4-yl)piperazin-1-yl)prop-2-en-1-one

The title compound was prepared from 7-bromo-4,6-dichloroquinazoline in four steps according to the procedure described in Example 3. $^1$H NMR (400 MHz, DMSO) δ: 8.7 (s, 1H), 8.2 (s, 1H), 7.8 (s, 1H), 7.6-7.4 (m, 5H), 6.85 (dd, J=10.8, 16.8 Hz, 1H), 6.2 (d, J=16.8 Hz, 1H), 5.75 (d, J=10 Hz, 1H), 3.9-3.7 (m, 8H). ESI-MS m/z: 379.3 [M+H]$^+$.

Example 35

Synthesis of 1-(4-(7-chloro-6-(4-chlorophenyl)quinazolin-4-yl)-2-((dimethylamino)methyl)piperazin-1-yl)prop-2-en-1-one (I-60)

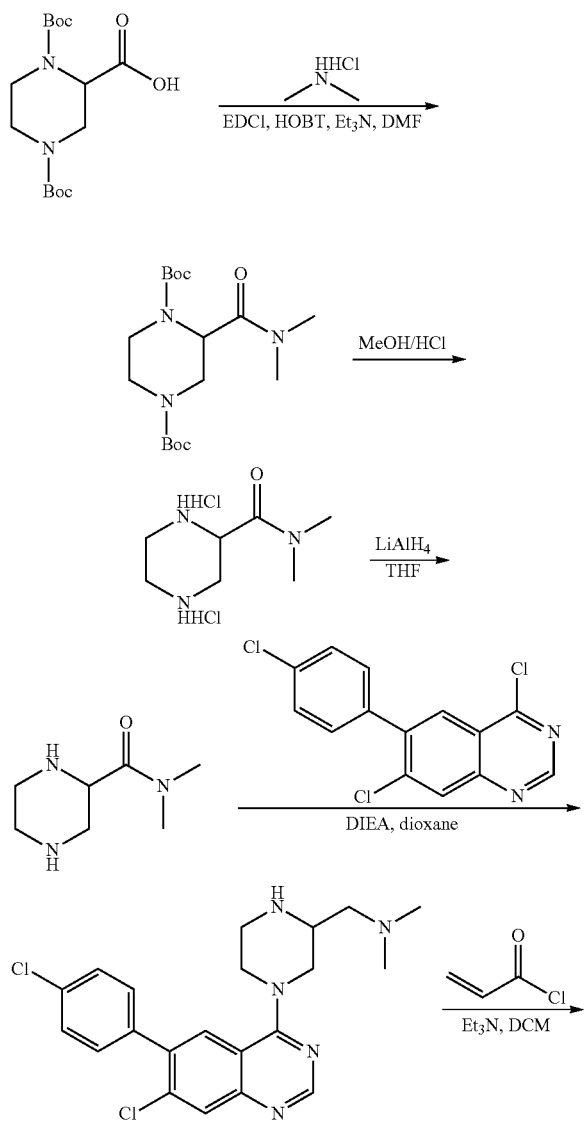

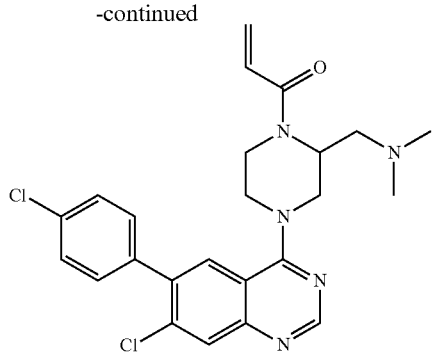

Compound I-60 was prepared according to the general procedures of Method A as described below:

di-tert-Butyl 2-(dimethylcarbamoyl)piperazine-1,4-dicarboxylate

A mixture of 1,4-bis(tert-butoxycarbonyl)piperazine-2-carboxylic acid (5 g, 15.13 mmol), dimethylamine hydrochloride (1.3 g, 15.13 mmol), EDCI (4.3 g, 22.7 mmol), HOBt (3.1 g, 22.7 mmol) and DMF (100 mL) at 0° C., Et$_3$N (4.6 g, 45.39 mmol) was added. The mixture was then warmed to RT and kept stirring for 2 h. The reaction mixture was poured into water, extracted with ethyl acetate, the combined organic layer was washed with NaHCO$_3$ solution, brine and dried over Na$_2$SO$_4$ and concentrated. The residue was washed with petroleum ether to afford the desired product (3.64 g, 67% yield).

N,N-Dimethylpiperazine-2-carboxamide dihydrochloride

A mixture of the above obtained crude of di-tert-butyl 2-(dimethylcarbamoyl)piperazine-1,4-dicarboxylate, HCl in MeOH (50 mL, 2.9 M) was stirred at RT for 1 h, evaporated the solvent to afford the crude product (2.4 g).

N,N-Dimethyl-1-(piperazin-2-yl)methanamine

A mixture of the above obtained crude of N,N-dimethylpiperazine-2-carboxamide dihydrochloride (2.4 g, 10.43 mmol) and THF (50 mL) at −40° C., LiAlH$_4$ (1.6 g, 41.73 mmol) was added slowly. The mixture was heated to reflux for 3 h and cooled to RT. It was quenched with 10H$_2$O.Na$_2$SO$_4$ and filtered, washed with ethyl acetate. The filtrated was dried over Na$_2$SO$_4$ and concentrated in vacuo to afford the desired product (693 mg, 47% yield).

1-(4-(7-Chloro-6-(4-chlorophenyl)quinazolin-4-yl) piperazin-2-yl)-N,N-dimethylmethanamine A mixture of N,N-dimethyl-1-(piperazin-2-yl)methanamine (200 mg, 0.68 mmol), 4,7-dichloro-6-(4-chlorophenyl)quinazoline (111 mg, 0.77 mmol), DIEA (397 mg, 3.08 mmol) and dioxane (10 mL) was stirred at 80° C. for 30 min. The mixture was allowed to cool to RT, quenched with saturated NaHCO$_3$ solution and then extracted with ethyl acetate. The organic layer was washed with brine, dried over Na$_2$SO$_4$, filtered and concentrated in vacuo. The residue was purified by flash column chromatography on silica gel (methanol/dichloroethane=1:20) to afford the desired product (78 mg, 30% yield). ESI-MS m/z: 416.3 [M+H]$^+$.

421

1-(4-(7-Chloro-6-(4-chlorophenyl)quinazolin-4-yl)-2-((dimethylamino)methyl)piperazin-1-yl)prop-2-en-1-one A mixture of 1-(4-(7-chloro-6-(4-chlorophenyl)quinazolin-4-yl)piperazin-2-yl)-N,N-dimethylmethanamine (78 mg, 0.19 mmol), Et₃N (58 mg, 0.57 mmol) and dichloromethane (15 mL) at 0° C., acryloyl chloride (20 mg, 0.22 mmol) was added. The reaction was stirred at RT for 30 min and quenched with water, extracted with dichloromethane. The organic layer was washed with water and brine, anhydrous sodium sulfate, filtered and concentrated in vacuo. The residue was purified by flash column chromatography on silica gel (dichloromethane/methanol=30:1) to afford the desired product (32 mg, 36% yield). $^1$H NMR (400 MHz, DMSO-d6) δ: 8.70 (s, 1H), 8.57-8.56 (bs, 1H), 8.03 (s, 1H), 7.61-7.53 (m, 4H), 6.83-6.80 (m, 1H), 6.17-6.13 (m, 1H), 5.75-5.72 (m, 1H), 4.76-4.74 (m, 0.5H), 4.70-4.57 (m, 1H), 4.36-3.29 (m, 2H), 4.11-4.08 (m, 0.5H), 3.46 (m, 1H), 3.27-3.11 (m, 2H), 2.93-2.84 (m, 1H), 1.99-1.94 (m, 1H), 1.87 (s, 6H). ESI-MS m/z: 470.4 [M+H]⁺.

Example 36

Synthesis of 1-acryloyl-4-(6-chloroisoquinolin-1-yl)piperazine-2-carbonitrile (I-61)

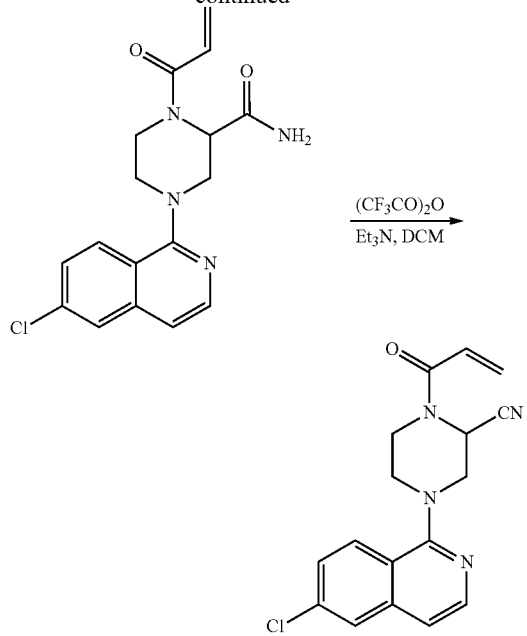

Compound I-61 was prepared according to the general procedures of Method D as described below:

6-Chloroisoquinoline 2-oxide

To a stirred solution 6-chloroisoquinoline (1.0 g, 6.1 mmol) in dichloromethane (20 mL) at RT, 3-chlorobenzoperoxoic acid (1.57 g, 9.2 mmol) was added. The reaction mixture was stirred at RT for 2 h. The precipitate was filtered off and washed with dichloromethane, the filtrate was washed twice with NaHCO₃ solution. The organic layer was dried with Na₂SO₄ and concentrated in vacuo to afford the desired product (1.05 g, 96% yield) as a white solid. ESI-MS m/z: 180.2 [M+H]⁺.

1,6-Dichloroisoquinoline

A mixture of 6-chloroisoquinoline 2-oxide (1.0 g, 5.58 mmol) and POCl₃ (10 mL) was heated to reflux for 4 h. After cooled down to RT, the reaction mixture was poured into ice-water, and extracted with dichloromethane. The organic layer was dried over anhydrous Na₂SO₄, filtered and concentrated in vacuo to afford the desired crude product which was used in the next step without further purification.

4-(6-Chloroisoquinolin-1-yl)piperazine-2-carboxamide

To a stirred solution of 1,6-dichloroisoquinoline (500 mg, 2.56 mmol) in DMSO (5 mL) at RT, piperazine-2-carboxamide (425.6 mg, 2.56 mmol) and K₂CO₃ (1.05 g, 7.68 mmol). The reaction mixture was heated at 80° C. for 5 h. The reaction mixture was diluted with ethyl acetate and washed with brine. The organic layer was dried over anhydrous Na₂SO₄, filtered and concentrated in vacuo. The residue was purified by flash column chromatography on silica gel (ethyl acetate/petroleum ether=1:5) to afford the desired product (80 mg, 12% yield). ESI-MS m/z: 291[M+H]⁺.

423

Acryloyl-4-(6-chloroisoquinolin-1-yl)piperazine-2-carboxamide

To a mixture of 4-(6-chloroisoquinolin-1-yl)piperazine-2-carboxamide (50 mg, 0.172 mmol), triethylamine (52.1 mg, 0.51 mmol) in dichloromethane (20 mL), acryloyl chloride (15.6 mg, 0.172 mmol) in dichloromethane (1 mL) was added dropwise. The reaction mixture was stirred at RT for 30 min, poured into water, and extracted with dichloromethane. The organic layer was washed with water and brine, dried over $Na_2SO_4$ and concentrated in vacuo. The residue was purified by flash column chromatography on silica gel (dichloromethane/methanol=100:1) to afford the desired product (45 mg, 76.3% yield). ESI-MS m/z: 345 $[M+H]^+$.

Acryloyl-4-(6-chloroisoquinolin-1-yl)piperazine-2-carbonitrile

To a mixture of 1-acryloyl-4-(6-chloroisoquinolin-1-yl)piperazine-2-carboxamide (40 mg, 0.116 mmol), triethylamine (46.8 mg, 0.46 mmol) in DCM (5 mL) at 0° C., trifluoroacetic anhydride (50 mg, 0.233 mmol) was added. The reaction mixture was warmed to RT over 1 h, poured into water and extracted with dichloromethane. The organic layer was washed with water and brine, dried over $Na_2SO_4$ and concentrated in vacuo. The residue was purified by flash column chromatography on silica gel (dichloromethane/methanol=100:1) to afford the desired product (20 mg, 53% yield). $^1$H NMR (400 MHz, DMSO-d6) δ: 8.25 (m, 1H), 8.22 (m, 1H), 8.11 (s, 1H), 7.71 (m, 1H), 7.52 (m, 1H), 6.96 (dd, J=10.5, 16.9 Hz, 1H), 6.32 (dd, J=1.7, 16.7 Hz, 1H), 5.90 (dd, J=1.7, 16.7 Hz, 1H), 5.79 (m, 1H), 4.34 (m, 1H), 3.99 (m, 1H), 3.79 (m, 1H), 3.66 (m, 1H), 3.16 (m, 1H), 2.97 (m, 1H). ESI-MS m/z: 327 $[M+H]^+$.

Example 37

Synthesis of (E)-4-(7-chloro-6-(4-chlorophenyl)quinazolin-4-yl)-1-(4 (dimethylamino)but-2-enoyl)piperazine-2-carbonitrile (I-66)

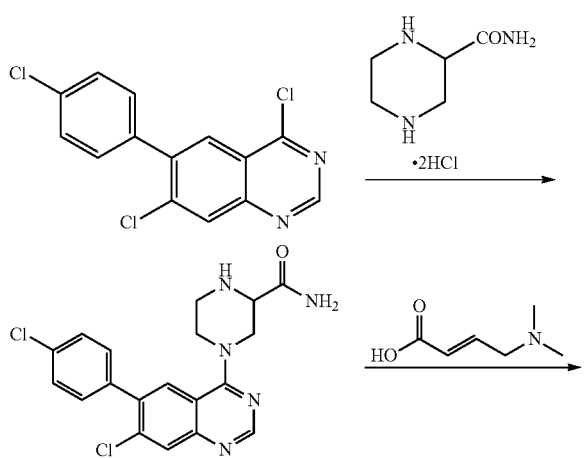

424

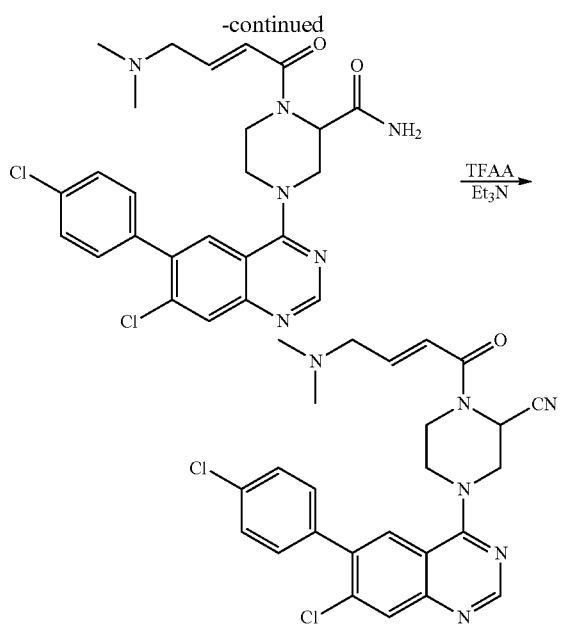

Compound I-66 was prepared according to the general procedures of Method A as described below:

4-(7-Chloro-6-(4-chlorophenyl)quinazolin-4-yl)piperazine-2-carboxamide

A mixture of 4,7-dichloro-6-(4-chlorophenyl)quinazoline (769 mg, 2.48 mmol), piperazine-2-carboxamide dihydrochloride (498 mg, 2.48 mmol), DIPEA (3.2 g, 24.8 mmol) and 1,4-dioxane (20 mL) was stirred at 80° C. for 16 h. The mixture was allowed to cool to RT, quenched with saturated $NaHCO_3$ solution and then extracted with ethyl acetate. The organic layer was washed with brine, dried over $Na_2SO_4$, filtered and concentrated in vacuo. The residue was purified by flash column chromatography on silica gel (methanol/dichloroethane=1:20) to afford the desired product (486 mg, 48.7% yield).

(E)-4-(7-Chloro-6-(4-chlorophenyl)quinazolin-4-yl)-1-(4-(dimethylamino)but-2-enoyl)piperazine-2-carboxamide To a mixture of 4-(7-chloro-6-(4-chlorophenyl)quinazolin-4-yl)piperazine-2-carboxamide (100 mg, 0.26 mmol), BOP (256.6 mg, 0.58 mmol), (E)-4-(dimethylamino)but-2-enoic acid (48 mg, 0.58 mmol) in dichloromethane (10 ml) at RT, DIEA (108.6 mg, 0.78 mmol) was added. The mixture was stirred for 30 min, extracted with ethyl acetate. The organic layer was washed with brine, dried over $Na_2SO_4$, filtered and concentrated in vacuo. The residue was purified by flash column chromatography on silica gel (methanol/dichloroethane=1:10) to afford the desired product (50 mg, 39% yield). ESI-MS m/z: 513.3 $[M+H]^+$ (E)-4-(7-Chloro-6-(4-chlorophenyl)quinazolin-4-yl)-1-(4-(dimethylamino)but-2-enoyl)piperazine-2-carbonitrile To a solution of (E)-4-(7-chloro-6-(4-chlorophenyl)quinazolin-4-yl)-1-(4-(dimethylamino)but-2-enoyl)piperazine-2-carboxamide (50 mg, 0.10 mmol) and $Et_3N$ (0.05 mL, 0.40 mmol) in DCM (10 mL) at 0° C., TFAA (51 mg, 0.20 mmol)

and the resulting mixture was stirred at RT for 1 h. The reaction mixture was quenched with saturated NaHCO₃ solution, and then extracted with dichloromethane. The organic layer was washed with saturated NaHCO₃ solution and brine, dried over Na₂SO₄ and concentrated in vacuo. The residue was purified by flash column chromatography on silica gel (dichloromethane/methanol=20:1) to afford the desired product (14 mg, 29% yield) as a solid. $^1$H NMR (400 MHz, DMSO-d6) δ: 8.76 (s, 1H), 8.08 (d, J=16 Hz, 2H), 7.61 (dd, J=8, 24 Hz, 4H), 6.78-6.72 (m, 2H), 5.67 (s, 1H), 4.62 (d, J=14.4 Hz, 1H), 4.36-4.26 (m, 2H), 3.63 (d, J=12.4 Hz, 1H), 3.21 (s, 2H), 3.03 (d, J=6.4 Hz, 2H), 2.26 (s, 1H). ESI-MS m/z: 495.4 [M+H]⁺.

Example 38

Synthesis of 1-(3-(4-(2-(4,5-dichloro-2-hydroxyphenylamino)acetyl)piperazin-1-yl)azetidin-1-yl)prop-2-en-1-one

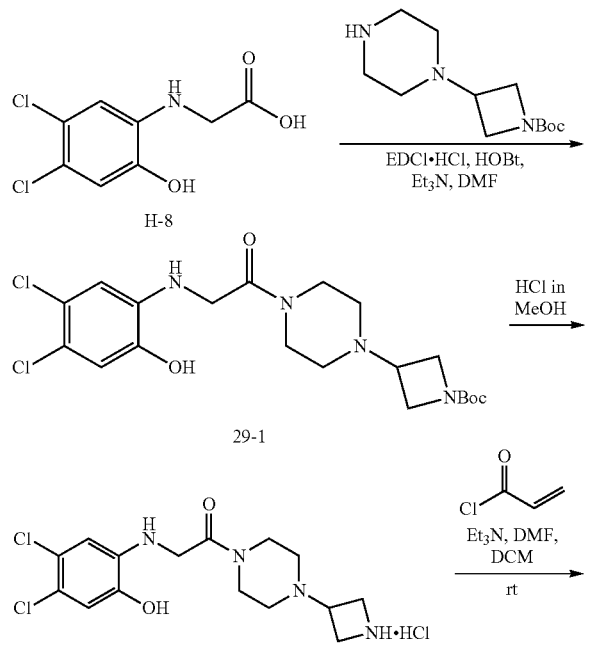

tert-Butyl 3-(4-(2-(4,5-dichloro-2-hydroxyphenylamino)acetyl)piperazin-1-yl)azetidine-1-carboxylate A mixture of 2-(4,5-dichloro-2-hydroxyphenylamino) acetic acid (500 mg, 2.12 mmol), tert-butyl 3-(piperazin-1-yl)azetidine-1-carboxylate (565 mg, 2.34 mmol), EDCI.HCl (488 mg, 2.54 mmol), HOBt (343 mg, 2.54 mmol), Et₃N (428 mg, 4.24 mmol) in DMF (20 mL) was stirred at room temperature for 15 h. The mixture was poured into water and extracted with ethyl acetate. The organic layer was washed with saturated aqueous NaHCO₃ solution and brine, dried over Na₂SO₄ and concentrated in vacuo. The residue was purified by flash column chromatography on silica gel (DCM/MeOH=30:1) to afford the desired product (300 mg, 31% yield). ESI-MS m/z: 457.4 [M−H]⁻.

2-(4,5-Dichloro-2-hydroxyphenylamino)-1-(4-(azetidin-3-yl)piperazin-1-yl)ethanone hydrochloride A mixture of tert-butyl 3-(4-(2-(4,5-dichloro-2-hydroxyphenylamino)acetyl)piperazin-1-yl)azetidine-1-carboxylate (150 mg, 0.33 mmol) in HCl-MeOH (20 mL, 57 mmol) was stirred at room temperature for 1 h. The mixture was concentrated in vacuo to afford the crude product (130 mg) which was used directly in the next step without further purification.

1-(3-(4-(2-(4,5-Dichloro-2-hydroxyphenylamino) acetyl)piperazin-1-yl)azetidin-1-yl)prop-2-en-1-one 2-(4,5-dichloro-2-hydroxyphenylamino)-1-(4-(azetidin-3-yl)piperazin-1-yl)ethanone hydrochloride (120 mg, 0.30 mmol) was added to the mixture of Et₃N (0.2 mL, 1.44 mmol) in DCM (10 mL) followed by addition of DMF (1 drop). The mixture was stirred for 5 min and then acryloyl chloride (27 mg, 0.30 mmol) was added. The resulting mixture was stirred at room temperature for 1 h, poured into water and then extracted with MeOH/DCM. The organic layer was washed with brine, dried over Na₂SO₄ and concentrated. The residue was purified by flash column chromatography on silica gel (DCM/MeOH/NH₃.H₂O=50:1:0.1 to 20:1:0.2) to afford the desired product (30 mg, 24% yield). $^1$H NMR (400 MHz, DMSO-$d_6$) δ: 10.17 (s, 1H), 6.78 (s, 1H), 6.71 (s, 1H), 6.30 (dd, J=10.4, 17.2 Hz, 1H), 6.09 (dd, J=2.0, 17.2 Hz, 1H), 5.67 (dd, J=2.4, 10.4 Hz, 1H), 5.32 (t, J=4.4 Hz, 1H), 4.26-4.22 (m, 1H), 4.11-4.04 (m, 1H), 3.93-3.91 (m, 3H), 3.79-3.75 (m, 3H), 3.52-3.51 (m, 4H), 3.19-3.16 (m, 1H), 2.36-2.30 (m, 4H). ESI-MS m/z: 411.2 [M−H]⁻.

Example 39

Synthesis of N-(1'-(2-(4,5-dichloro-2-hydroxyphenylamino)acetyl)-1,3'-biazetidin-3-yl)acrylamide

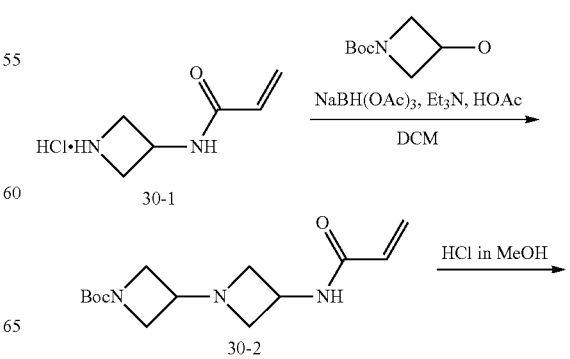

-continued

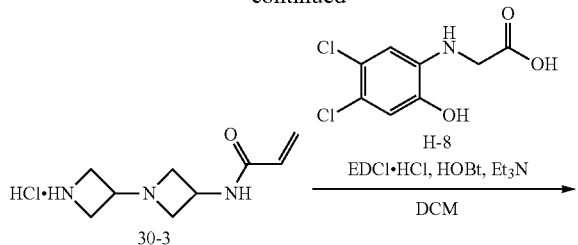

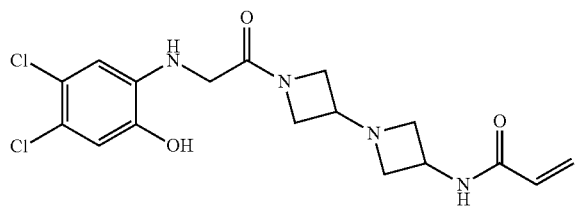

tert-Butyl 3-(3-(acrylamido)azetidin-1-yl)azetidine-1-carboxylate

To a mixture of N-(azetidin-3-yl)acrylamide hydrochloride (500 mg, 3.40 mmol), tert-butyl 3-oxoazetidine-1-carboxylate (684 mg, 4.0 mmol), Et$_3$N (343 mg, 3.40 mmol) and AcOH (100 mg, 0.167 mmol) in DCM (20 mL), NaBH(OAc)$_3$ (2.16 g, 10.2 mmol) was added, and the resulting mixture was stirred at room temperature for 16 h. The mixture was poured into water and extracted with ethyl acetate. The organic layer was washed with saturated NaHCO$_3$ solution and brine, dried over Na$_2$SO$_4$ and concentrated in vacuo. The residue was purified by flash column chromatography on silica gel (DCM/MeOH=100:1 to 20:1) to afford the desired product (300 mg, 31% yield).

N-(1-(Azetidin-3-yl)azetidin-3-yl)acrylamide hydrochloride

A mixture of tert-butyl 3-(3-(acrylamido)azetidin-1-yl)azetidine-1-carboxylate (300 mg, 1.07 mmol) in HCl-MeOH (30 mL, 86 mmol) was stirred at room temperature for 1 h. The mixture was concentrated in vacuo to afford the crude product (250 mg) which was used directly in the next step without further purification.

N-(1-(1-(2-(4,5-Dichloro-2-hydroxyphenylamino)acetyl)azetidin-3-yl)azetidin-3-yl)acrylamide A mixture of 2-(4,5-dichloro-2-hydroxyphenylamino)acetic acid (120 mg, 0.51 mmol), EDCI.HCl (147 mg, 0.77 mmol), HOBt (83 mg, 0.61 mmol), Et$_3$N (154 mg, 1.53 mmol) in DMF (20 mL) was stirred at room temperature for 5 min and then N-(1-(azetidin-3-yl)azetidin-3-yl)acrylamide hydrochloride (150 mg, 0.69 mmol) was added. The resulting mixture was stirred at room temperature for 15 h. The mixture was poured into water and extracted with ethyl acetate. The organic layer was washed with saturated NaHCO$_3$ solution and brine, dried over Na$_2$SO$_4$ and concentrated in vacuo. The residue was purified by flash column chromatography on silica gel (DCM/MeOH/NH$_3$.H$_2$O=100:10:1.5) to afford the desired product (6 mg, 3% yield). $^1$H NMR (400 MHz, DMSO-d6) δ: 10.19 (s, 1H), 8.59 (d, J=8.0 Hz, 1H), 6.79 (s, 1H), 6.55 (s, 1H), 6.20 (dd, J=10.0, 16.8 Hz, 1H), 6.09 (dd, J=2.0, 16.8 Hz, 1H), 5.62 (dd, J=2.0, 9.6 Hz, 1H), 5.20 (t, J=4.0 Hz, 1H), 4.40-4.35 (m, 1H), 4.19- 4.15 (m, 1H), 3.96-3.88 (m, 2H), 3.73-3.69 (m, 3H), 3.53-3.45 (m, 3H), 3.00-2.96 (m, 2H). ESI-MS m/z: 399.2 [M+H]$^+$.

Example 40

Synthesis of 1-(2-(2-(4,5-dichloro-2-hydroxyphenylamino)acetyl)-2,6-diazaspiro[3.4]octan-6-yl)prop-2-en-1-one

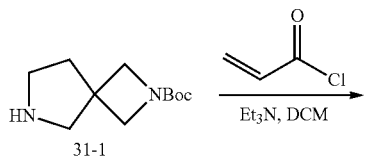

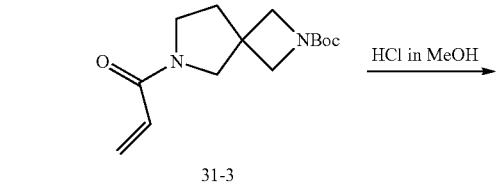

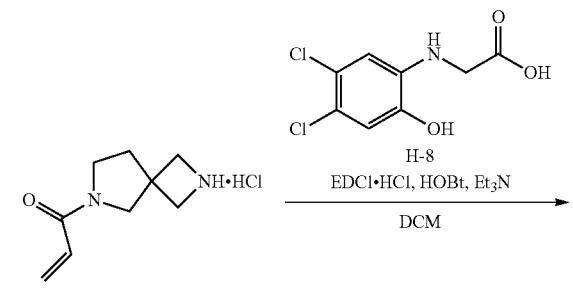

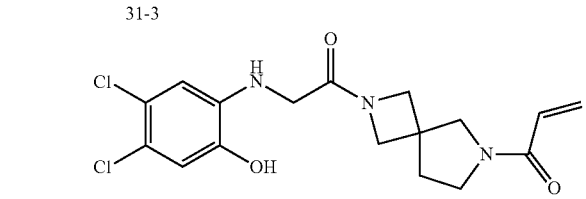

2,6-Diaza-spiro[3.4]octane-6-acryloyl-2-carboxylic acid tert-butyl ester

To a mixture of 2,6-diaza-spiro[3.4]octane-2-carboxylic acid tert-butyl ester (80 mg, 0.38 mmol), Et$_3$N (0.2 mL, 1.44 mmol) in DCM (20 mL), acryloyl chloride (34 mg, 0.38 mmol) was added and the resulting mixture was stirred at room temperature for 1 h. The mixture was poured into water and extracted with ethyl acetate. The organic layer was washed with saturated NaHCO$_3$ solution and brine, dried over Na$_2$SO$_4$ and concentrated in vacuo. The residue was purified by flash column chromatography on silica gel (DCM/MeOH=40:1) to afford the desired product (50 mg, 50% yield). ESI-MS m/z: 289.2 [M+Na]$^+$.

1-(2,6-Diazaspiro[3.4]octan-6-yl)prop-2-en-1-one

A mixture of 2,6-diaza-spiro[3.4]octane-6-acryloyl-2-carboxylic acid tert-butyl ester (50 mg, 0.19 mmol) in HCl/MeOH (10 mL, 29 mmol) was stirred at room temperature for 1 h. The mixture was concentrated in vacuo to afford the crude product (40 mg) which was used directly in the next step without further purification.

1-(2-((4,5-Dichloro-2-hydroxyphenyl)glycyl)-2,6-diazaspiro[3.4]octan-6-yl)prop-2-en-1-one The mixture of 2-(4,5-dichloro-2-hydroxyphenylamino)acetic acid (47 mg, 0.2 mmol), 1-(2,6-diazaspiro[3.4]octan-6-yl)prop-2-en-1-one (40 mg, 0.2 mmol), EDCI.HCl (46 mg, 0.24 mmol), HOBt (32 mg, 0.24 mmol) and Et$_3$N (0.61 mg, 0.6 mmol) in DMF (10 mL) was stirred at room temperature for 2 h. The mixture was poured into water and extracted with ethyl acetate. The organic layer was washed with saturated NaHCO$_3$ solution and brine, dried over Na$_2$SO$_4$ and concentrated in vacuo. The residue was purified by flash column chromatography on silica gel (DCM/MeOH=30:1) to afford the desired product (13 mg, 17% yield). $^1$H NMR (400 MHz, DMSO-d6) δ: 10.17 (s, 1H), 6.78 (s, 1H), 6.60-6.50 (m, 2H), 6.13 (dt, J=2.4, 16.4 Hz, 1H), 5.67 (dd, J=2.4, 10.4 Hz, 1H), 5.19 (dd, J=5.2, 10.0 Hz, 1H), 4.16-4.07 (m, 2H), 3.90-3.83 (m, 2H), 3.75-3.72 (m, 3H), 3.61-3.52 (m, 2H), 3.42-3.39 (m, 1H), 2.16-2.13 (m, 1H), 2.06-2.03 (m, 1H). ESI-MS m/z: 382.3 [M−H]$^−$.

Example 41

Synthesis of 1-(4-(2'-chloro-5-hydroxybiphenylcarbonyl)piperazin-1-yl)prop-2-en-1-one (III-25)

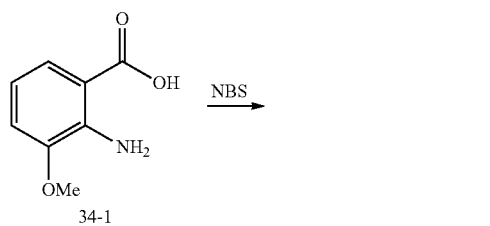

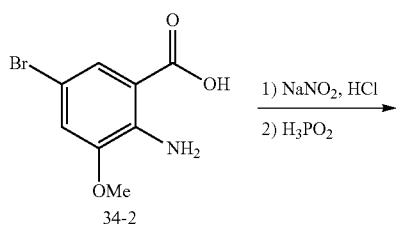

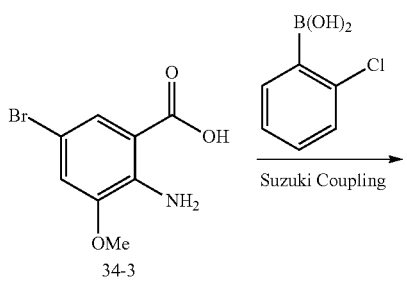

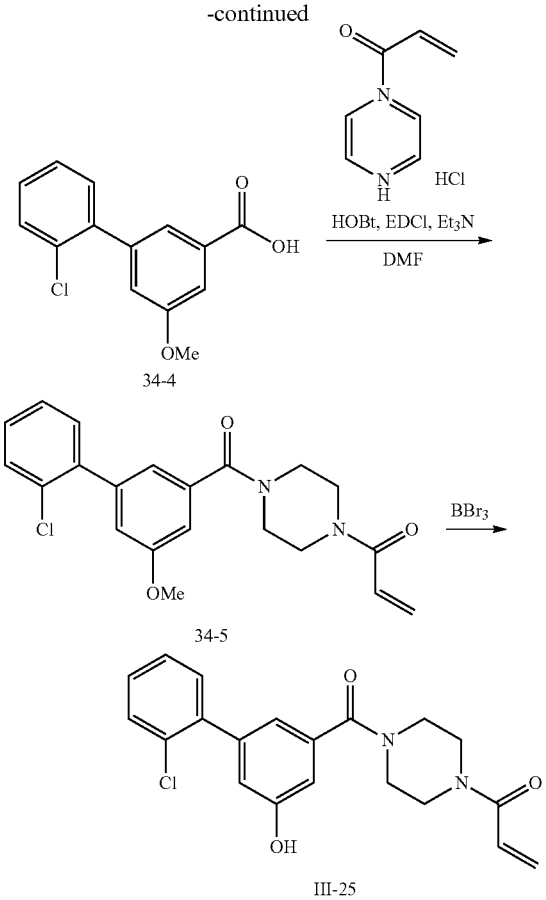

2-Amino-5-bromo-3-methoxybenzoic acid

To a solution of 2-amino-3-methoxybenzoic acid (5 g, 29.9 mmol) in MeOH (35 mL) at −5° C., NBS (5.59 g, 31.4 mmol) was added and the resulting mixture was stirred at 0° C. for 16 h. The mixture was partitioned between ethyl acetate and water. The organic layer was washed with brine, dried over MgSO$_4$, filtered and concentrated in vacuo to afford the crude product (4 g, 54% yield). ESI-MS m/z: 244.2 [M−H]$^−$.

3-Bromo-5-methoxybenzoic acid

To a solution of 2-amino-5-bromo-3-methoxybenzoic acid (4 g, 16.3 mmol) in water (20 mL) at 0° C., conc. HCl (7.5 mL, 90 mmol) and THF (20 mL) were added. The mixture was stirred for 30 min, and then NaNO$_2$ (3.16 g, 45.8 mmol) was added. The resulting mixture was stirred for 2 h and then hypophosphorous acid (5.1 g, 76 mmol, 50% in H$_2$O) was added to the reaction. The mixture was stirred at room temperature for 16 h. The precipitate was collected by filtration, washed with water and dried in vacuo to afford the desired product (3.2 g, 85% yield). ESI-MS m/z: 229.2 [M−H]$^−$.

3-(2-Chlorophenyl)-5-methoxybenzoic acid

To a solution of 3-bromo-5-methoxybenzoic acid (1 g, 4.06 mmol) and 2-chlorophenylboronic acid (1.27 g, 8.13 mmol) in 1,4-dioxane (10 mL) and water (2 mL), Pd(PPh$_3$)$_4$ (468 mg, 0.40 mmol) and Na$_2$CO$_3$ (2.15 g, 20.3 mmol) were added and the resulting mixture was stirred at 80° C. for 16 h. The mixture was allowed to cool to room temperature and acidified with aqueous HCl (1.0 M) to adjust the pH to 3-4. The mixture was extracted with ethyl acetate. The organic layer was dried over MgSO$_4$, filtered and concentrated in vacuo to afford the desired product (800 mg, 75% yield) without further purification. ESI-MS m/z: 361.2 [M−H]$^-$.

1-(4-(2'-Chloro-5-methoxy-[1,1'-biphenyl]-3-carbonyl)piperazin-1-yl)prop-2-en-1-one To a solution of tert-butyl 4-acryloylpiperazine-1-carboxylate (260 mg, 1.07 mmol) in DCM (2 mL), a solution of HCl in MeOH (10 mL, 28.6 mmol) was added and the resulting mixture was stirred at room temperature for 1 h. The mixture was concentrated in vacuo. The residue was added to the solution of 3-(2-chlorophenyl)-5-methoxybenzoic acid (280 mg, 1.07 mmol), HOBt (290 mg, 2.17 mmol), EDCI.HCl (410 mg, 2.17 mmol) and Et$_3$N (324 mg, 3.21 mmol) in DMF (10 mL). The resulting mixture was stirred at room temperature for 16 h and partitioned between DCM and saturated NaHCO$_3$ solution. The organic layer was dried over MgSO$_4$, filtered and concentrated in vacuo. The residue was purified by flash column chromatography on silica gel (dichloromethane/methanol=50:1) to afford the desired product (200 mg, 52% yield). ESI-MS m/z: 385.2[M+H]$^+$.

1-(4-(2'-Chloro-5-hydroxy-[1,1'-biphenyl]-3-carbonyl)piperazin-1-yl)prop-2-en-1-one (VI-25)

To a solution of 1-(4-(2'-chloro-5-methoxy-[1,1'-biphenyl]-3-carbonyl)piperazin-1-yl)prop-2-en-1-one (100 mg, 0.26 mmol) in DCM (15 mL) at −78° C., BBr$_3$ (650 mg, 2.6 mmol) was added and the resulting mixture was stirred at room temperature for 1 h. The mixture was poured into ice-water, basified with sat NaHCO$_3$ aqueous solution to adjust the pH to 7-8 and extracted with ethyl acetate. The organic layer was dried over MgSO$_4$, filtered and concentrated in vacuo. The residue was purified by flash column chromatography on silica gel (dichloromethane/methanol=50:1) to afford the desired product (25 mg, 26% yield). $^1$H NMR (400 MHz, DMSO-d6) δ: 9.96 (s, 1H), 7.58-7.56 (m, 1H), 7.42-7.40 (m, 3H), 6.89-6.75 (m, 4H), 6.14 (dd, J=2.0, 16.8 Hz, 1H), 5.71 (dd, J=2.0, 10.0 Hz, 1H), 3.68-3.44 (m, 8H). ESI-MS m/z: 371.2 [M+H]$^+$.

Example 42

Synthesis of 1-(4-(2',6-dichloro-4-hydroxybiphenylcarbonyl)piperazin-1-yl)prop-2-en-1-one (III-3)

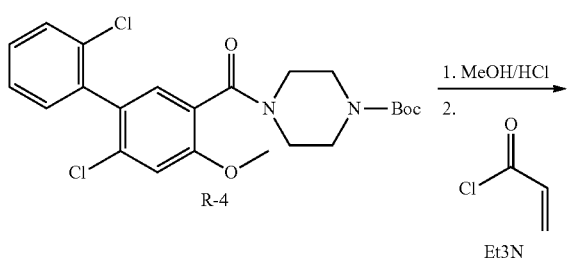

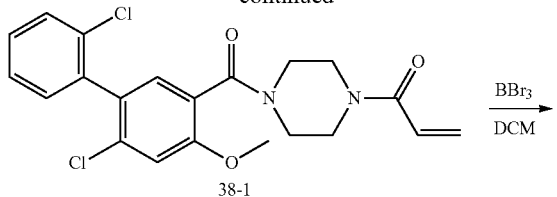

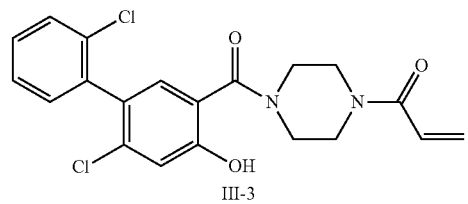

1-(4-(2',6-dichloro-4-methoxy-[1,1'-biphenyl]-3-carbonyl)piperazin-1-yl)prop-2-en-1-one tert-Butyl 4-(2',6-dichloro-4-methoxy-[1,1'-biphenyl]-3-carbonyl)piperazine-1-carboxylate (200 mg, 0.43 mmol) was stirred in HCl in MeOH (2.86 M, 10 mL) for 1 h. The mixture was concentrated in vacuo to yield the crude product. The residue was dissolved in DCM (15 mL), triethylamine (0.5 mL), acryloyl chloride (40 mg, 0.43 mmol) was added to the mixture. The reaction mixture was stirred at room temperature for 30 min, poured into water, and extracted with DCM. The organic layer was washed with water and brine, dried over Na$_2$SO$_4$ and concentrated in vacuo. The residue was purified by flash column chromatography on silica gel (dichloromethane/methanol=50:1) to afford the desired product (16 mg, 10% yield) as white solid. ESI-MS m/z: 419.2 [M+H]$^+$.

1-(4-(2',6-Dichloro-4-hydroxy-[1,1'-biphenyl]-3-carbonyl)piperazin-1-yl)prop-2-en-1-one (VI-3)

To a solution of 1-(4-(2',6-Dichloro-4-methoxy-[1,1'-biphenyl]-3-carbonyl)piperazin-1-yl)prop-2-en-1-one (200 mg, 0.48 mmol) in DCM (15 mL) at −60° C., BBr$_3$ (0.6 g, 2.4 mmol) was added dropwise and the resulting mixture was stirred at room temperature for 1 h. The mixture was poured into ice-water, basified with saturated NaHCO$_3$ solution to adjust the pH to 8-9, and extracted with DCM. The organic layer was dried over anhydrous sodium sulfate, filtered and concentrated in vacuo. The residue was purified by flash column chromatography on silica gel (dichloromethane/methanol=20:1) to afford the desired product (10 mg, 5% yield). $^1$H NMR (400 MHz, DMSO-d6) δ: 10.6 (s, 1H), 7.57-7.33 (m, 5H), 7.12 (s, 1H), 7.05 (s, 1H), 6.80 (m, 1H), 6.15-6.11 (dd, J=2, 16.8 Hz, 1H), 5.72-5.70 (m, 1H), 3.6 (m, 8H). ESI-MS m/z: 405.3 [M+H]$^+$.

Example 43

Synthesis of 1-(1-acryloylazetidin-3-yl)-N-(4,5-dichloro-2-hydroxybenzyl)piperidine-4-carboxamide (II-17)

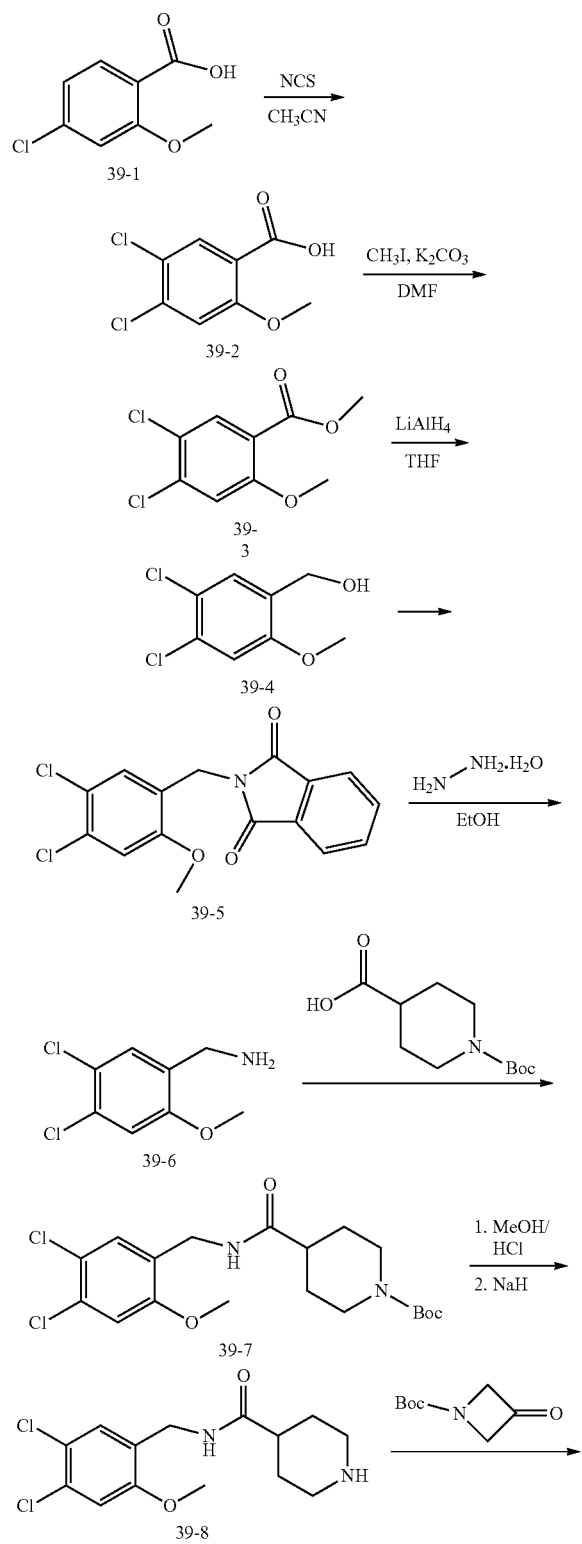

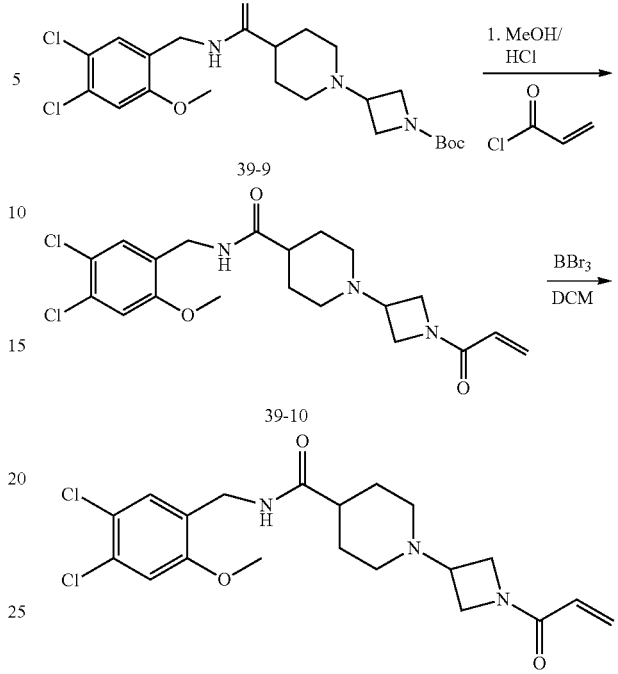

4,5-Dichloro-2-methoxybenzoic acid

A mixture of 4-chloro-2-methoxybenzoic acid (10 g, 53.6 mmol) and NCS (35 g, 19.2 mmol) in acetonitrile (200 mL) was stirred at room temperature for 48 h. The mixture was poured into water and extracted with ethyl acetate. The organic layer was washed with water and brine, dried over $Na_2SO_4$ and concentrated in vacuo to get the crude product (23.3 g).

Methyl 4,5-dichloro-2-methoxybenzoate

A mixture of 4,5-dichloro-2-methoxybenzoic acid (8.2 g, 37 mmol) and $K_2CO_3$ (11.8 g, 111 mmol) in DMF (100 mL), $CH_3I$ (6.3 g, 44 mmol) was added dropwise and the resulting mixture was stirred at room temperature for 16 h. The mixture was partitioned between ethyl acetate and water. The organic layer was washed with water and brine, dried over $Na_2SO_4$, and concentrated in vacuo. The residue was purified by flash column chromatography on silica gel (petroleum ether/ethyl acetate=10:1) to afford the desired product.

(4,5-Dichloro-2-methoxyphenyl)methanol

To a mixture of $LiAlH_4$ (2.42 g, 64 mmol) in THF (40 mL) at −40° C. under argon, a solution of methyl 4,5-dichloro-2-methoxybenzoate (6 g, 26 mmol) in THF (50 mL) was added dropwise. The reaction mixture was stirred at −5° C. to 5° C. for 1 h. The mixture was cooled to −20° C. and then water (2 mL) and NaOH (15%) aqueous were added. The resulting mixture was stirred for 15 min. The solid was filtered, and the cake rinsed with ethyl acetate. The combined filtrate was dried over $Na_2SO_4$ and concentrated in vacuo to afford the crude product (4.6 g).

2-(4,5-Dichloro-2-methoxybenzyl)isoindoline-1,3-dione

To a mixture of 4,5-dichloro-2-methoxyphenyl)methanol (4.5 g, 22 mmol), isoindoline-1,3-dione (9.6 g, 65 mmol)

and PPh$_3$ (17 g, 65 mmol) in THF (100 mL) at room temperature, DIAD (13 g, 65 mmol) was added and the resulting mixture was stirred at room temperature for 16 h. The mixture was partitioned between ethyl acetate and water. The organic layer was washed brine, dried over Na$_2$SO$_4$, concentrated in vacuo. The residue was purified by flash column chromatography on silica gel (petroleum ether/ethyl acetate=10:1) to afford the desired product.

(4,5-Dichloro-2-methoxyphenyl)methanamine

To a solution of 2-(4,5-dichloro-2-methoxybenzyl)isoindoline-1,3-dione (1.8 g, 5 mmol) in EtOH (5 mL), hydrazine hydrate (1.34 g, 27 mmol) was added and the resulting mixture was stirred at reflux for 1 h. The mixture was concentrated in vacuo and the residue was purified by flash column chromatography on silica gel (dichloromethane/methanol=20:1) to afford the desired product (0.8 g, 78% yield).

tert-Butyl 4-((4,5-dichloro-2-methoxybenzyl)carbamoyl)piperidine-1-carboxylate

The mixture of (4,5-dichloro-2-methoxyphenyl)methanamine (0.8 g, 3.90 mmol), 1-(tert-butoxycarbonyl)piperidine-4-carboxylic acid (0.88 g, 3.84 mmol), BOP (2 g, 1.16 mmol) and DIEA (1.6 g, 2.91 mmol) in DMF (20 mL) was stirred at room temperature for 1 h. The mixture was poured into water and extracted with ethyl acetate. The organic layer was washed with water and brine, dried over Na$_2$SO$_4$ and concentrated in vacuo. The residue was purified by flash column chromatography on silica gel (dichloromethane/methanol=100:1) to afford the desired product (0.987 g, 62% yield). ESI-MS m/z: 415.4 [M–H]$^-$.

N-(4,5-Dichloro-2-methoxybenzyl)piperidine-4-carboxamide

The mixture of 4-((4,5-dichloro-2-methoxybenzyl)carbamoyl)piperidine-1-carboxylate (987 mg, 2.37 mmol) in HCl/MeOH (20 mL, 57.2 mmol) was stirred at room temperature for 1 h. Then the solvent was evaporated in vacuo and the residue was dissolved with dichloromethane (5 mL). To this mixture, NaH (85 mg, 3.55 mmol) was added. Then the resulting mixture was stirred at room temperature for 30 min. The solvent was removed under reduced pressure to yield the crude product (800 mg).

tert-butyl 3-(4-(4,5-Dichloro-2-methoxybenzylcarbamoyl)piperidin-1-yl)azetidine-1-carboxylate A mixture of N-(4,5-dichloro-2-methoxybenzyl)piperidine-4-carboxamide (750 mg, 2.37 mmol), tert-butyl 3-oxoazetidine-1-carboxylate (607 mg, 3.55 mmol), AcOH (1 mL) and MeOH (5 mL) was stirred at reflux for 2 h. To this mixture, NaBH$_3$(CN) (0.74 g, 11.85 mmol) was added and the resulting mixture was stirred at 60° C. for 16 h. The mixture was allowed to cool to room temperature and partitioned between NH$_4$Cl aqueous solution and ethyl acetate. The organic layer was washed with water and brine, dried over Na$_2$SO$_4$ and concentrated in vacuo. The residue was purified by flash column chromatography on silica gel (dichloromethane/methanol=50:1) to afford the desired product (220 mg, 18% yield). ESI-MS m/z: 472.3 [M+H]$^+$.

1-(1-Acryloylazetidin-3-yl)-N-(4,5-dichloro-2-methoxybenzyl)piperidine-4-carboxamide A mixture of tert-butyl 3-(4-(4,5-dichloro-2-methoxybenzylcarbamoyl)piperidin-1-yl)azetidine-1-carboxylate (210 mg, 0.44 mmol) in HCl/MeOH (10 mL, 2.86 M) was stirred at room temperature for 1 h. The mixture was concentrated in vacuo to yield the crude residue. The residue was dissolved in DCM (5 mL), triethylamine (0.5 mL) and acryloyl chloride (40 mg, 0.43 mmol) were added. The reaction mixture was stirred at room temperature for 30 min and then partitioned between DCM and water. The organic layer was washed with water and brine, dried over Na$_2$SO$_4$ and concentrated in vacuo. The residue was purified by flash column chromatography on silica gel (dichloromethane/methanol=50:1) to afford the desired product (150 mg, 82% yield).

N-(4,5-Dichloro-2-hydroxybenzyl)-1-(1-acryloylazetidin-3-yl)piperidine-4-carboxamide To a solution of 1-(1-acryloylazetidin-3-yl)-N-(4,5-dichloro-2-methoxybenzyl)piperidine-4-carboxamide (150 mg, 0.35 mmol) in DCM (15 mL) at –60° C., BBr$_3$ (0.6 g, 2.4 mmol) was added dropwise. The resulting mixture was allowed to warm to room temperature and stirred for 1 h. The mixture was poured into ice-water, basified with saturated NaHCO$_3$ solution to adjust the pH to 8-9, and then extracted with DCM. The organic layer was dried over anhydrous sodium sulfate and concentrated in vacuo. The residue was purified by flash column chromatography on silica gel (dichloromethane/methanol=20:1) to afford the desired product (34 mg, 24% yield). $^1$H NMR (400 MHz, DMSO-d6) δ: 10.34 (s, 1H), 8.2-8.25 (m, 1H), 7.2 (s, 1H), 7.0 (s, 1H), 6.91 (s, 1H), 6.33-6.27 (m, 1H), 6.12-6.07 (dd, J=2.4, 12.4 Hz, 1H), 5.68-5.65 (dd, J=2.4, 10.4 Hz, 1H), 4.24-4.20 (m, 1H), 4.17-4.14 (m, 2H), 4.14-3.99 (m, 1H), 3.94-3.90 (m, 1H), 3.73-3.70 (m, 1H), 3.10 (s, 1H), 2.84-2.80 (m, 2H), 2.22 (m, 1H), 1.80 (s, 2H), 1.73-1.71 (m, 2H), 1.63-1.57 (m, 2H). ESI-MS m/z: 412.2 [M+H]$^+$.

Example 44

Synthesis of 1-(3-(hydroxymethyl)-4-(2',5',6-trichloro-4-methoxybiphenylcarbonyl)piperazin-1-yl)prop-2-en-1-one (III-7)

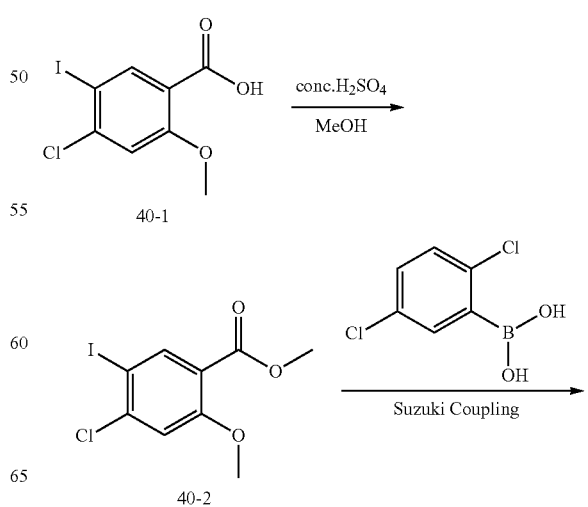

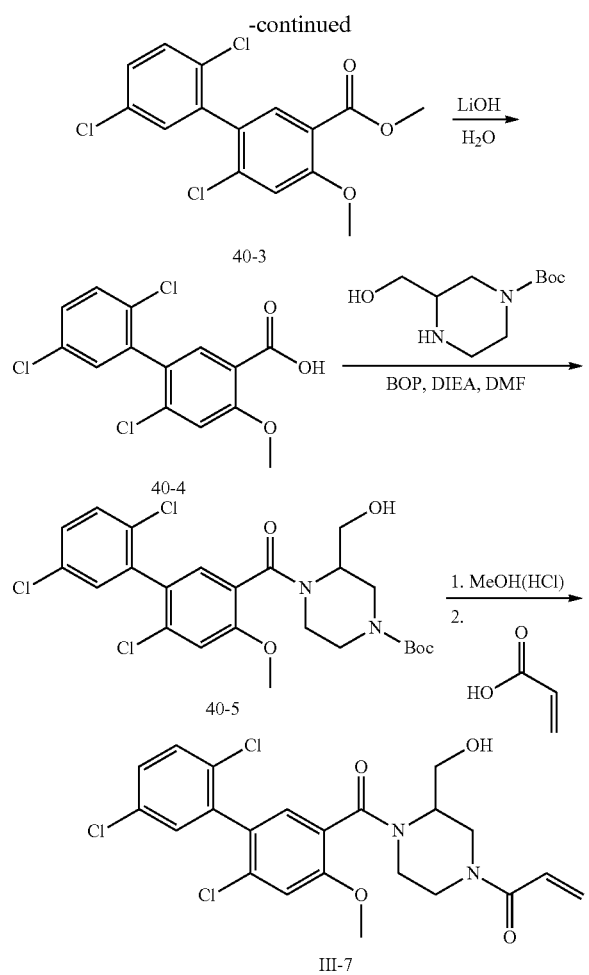

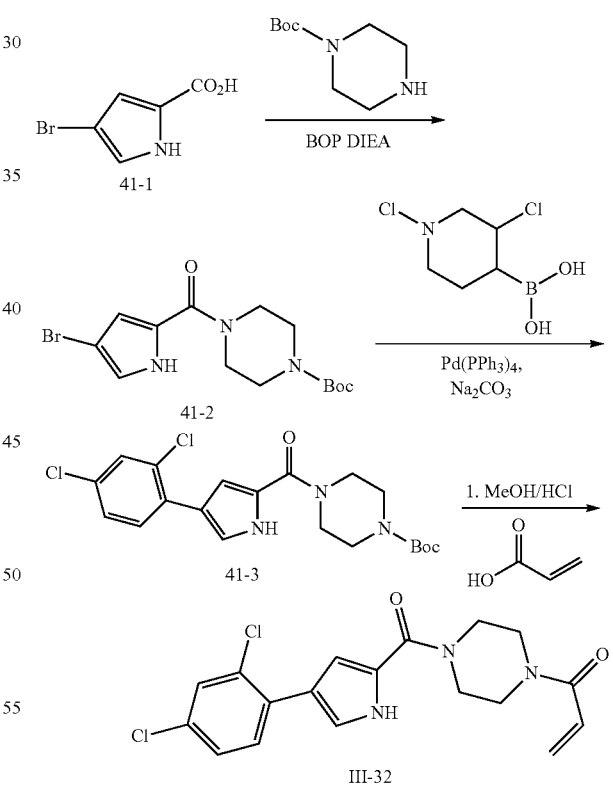

Methyl 4-chloro-5-iodo-2-methoxybenzoate

A mixture of 4-chloro-5-iodo-2-methoxybenzoic acid (2 g, 6.41 mmol) concentrated sulfuric acid (1.5 mL) in MeOH (50 mL) was stirred at reflux for 16 h. The mixture was allowed to cool to room temperature and partitioned between water and ethyl acetate. The organic layer was washed with water and brine, dried over $Na_2SO_4$ and concentrated in vacuo to afford the desired product (1.85 g, 85% yield) as a yellow oil.

Methyl 2',5',6-trichloro-4-methoxy-[1,1'-biphenyl]-3-carboxylate

A mixture of Methyl 4-chloro-5-iodo-2-methoxybenzoate (1.8 g, 5.51 mmol), (2,5-dichlorophenyl)boronic acid (2.1 g, 11.03 mmol), $Pd(PPh_3)_4$ (403 mg, 0.55 mmol), $Na_2CO_3$ (1.75 g, 16.54 mmol) in 1,4-dioxane (50 mL) and water (5 mL) was stirred at reflux under argon for 16 h. The mixture was filtered and filtrate was concentrated in vacuo. The residue was purified by flash column chromatography on silica gel (petroleum ether/ethyl acetate=20:1) to afford the desired product (1.6 g, 85% yield).

1-(3-(Hydroxymethyl)-4-(2',5',6-trichloro-4-methoxy-[1,1'-biphenyl]-3-carbonyl)piperazin-1-yl)prop-2-en-1-one (III-7)

The title compound was prepared from methyl 2',5',6-trichloro-4-methoxy-[1,1'-biphenyl]-3-carboxylate in three steps followed the procedure described in Example 36. tert-butyl3-(hydroxymethyl)-4-(2',5',6-trichloro-4-methoxy-[1,1'-biphenyl]-3-carbonyl)piperazine-1-carboxylate (420 mg, 0.79 mmol) was stirred in HCl in MeOH (2.85 N). The solvent was removed under reduced pressure to yield the crude reside which was dissolved in DMF (20 mL), acrylic acid (57 mg, 0.79 mmol), BOP (421 mg, 0.95 mmol) and DIEA (409 mg, 3.17 mmol) were added. The reaction was stirred at room temperature for 1 h. The resulting mixture was poured into water, extracted with ethyl acetate and washed with water and brine. The combined organic layer was dried over $Na_2SO_4$, filtered and concentrated. The residue was purified by column chromatography on silica gel (dichloromethane/methanol=60:1) to afford the desired product (92 mg, 24% yield). $^1$H NMR (400 MHz, DMSO-d6) δ: 7.64-7.20 (m, 5H), 6.83-6.70 (m, 1H), 6.16-6.11 (d, 1H), 5.74-5.71 (d, 1H), 6.91 (s, 1H), 5.08-4.01 (m, 3H), 3.90-3.86 (d, 3H), 3.49-3.22 (m, 2H), 2.93-2.74 (m, 2H), 2.89-2.67 (m, 2H). ESI-MS m/z: 451.2 [M−H]$^-$.

Example 45

Synthesis of 1-(4-(4-(2,4-dichlorophenyl)-1H-PYR-ROLE-2-carbonyl)piperazin-1-yl)prop-2-en-1-one (III-32)

tert-Butyl 4-(4-bromo-1H-pyrrole-2-carbonyl)piperazine-1-carboxylate

To a mixture of 4-bromo-1H-pyrrole-2-carboxylic acid (800 mg, 4.21 mmol), tert-butylpiperazine-1-carboxylate (822 mg, 4.42 mmol), BOP (2.2 g, 5.05 mmol) in DMF (5 mL), DIEA (1.63 g, 12.63 mmol) was added and the resulting mixture was stirred at room temperature for 1 h. The mixture was poured into water and extracted with ethyl acetate. The organic layer was washed with water and brine, dried over Na$_2$SO$_4$ and concentrated in vacuo to afford the crude product (920 mg, 61% yield) which was used directly in the next step without purification.

tert-Butyl 4-(4-(2,4-dichlorophenyl)-1H-pyrrole-2-carbonyl)piperazine-1-carboxylate A mixture of tert-butyl 4-(4-bromo-1H-pyrrole-2-carbonyl)piperazine-1-carboxylate (350 mg, 0.98 mmol), (2,4-dichlorophenyl) boronic acid (280 mg, 1.47 mmol), Pd(PPh$_3$)$_4$ (116 mg, 0.1 mmol), Na$_2$CO$_3$ (312 mg, 2.94 mmol) in 1,4-dioxane (10 mL) and water (2 mL) was stirred at reflux under argon for 16 h. The mixture was allowed to cool to room temperature and concentrated in vacuo. The residue was purified by flash column chromatography on silica gel (petroleum ether/ethyl acetate=30:1) to afford the desired product (273 mg, 59% yield).

1-(4-(4-(2,4-Dichlorophenyl)-1H-pyrrole-2-carbonyl)piperazin-1-yl)prop-2-en-1-one (VI-32)

The mixture of tert-butyl 4-(4-(2,4-dichlorophenyl)-1H-pyrrole-2-carbonyl)piperazine-1-carboxylate (270 mg, 0.64 mmol) in HCl/MeOH (20 mL, 57.2 mmol) was stirred for 1 h. The mixture was concentrated in vacuo and the residue was dissolved in DMF (5 mL). To this mixture, acrylic acid (50 mg, 0.7 mmol), BOP (437 mg, 0.72 mmol) and DIEA (248 mg, 1.92 mmol) were added. The reaction mixture was stirred at room temperature for 1 h. The mixture was partitioned between ethyl acetate and water. The organic layer was washed with brine, dried over Na$_2$SO$_4$ and concentrated in vacuo. The residue was purified by flash column chromatography on silica gel (dichloromethane/methanol=60:1) to afford the desired product (40 mg, 27% yield) as a white solid. $^1$H NMR (400 MHz, DMSO-d6) δ: 11.88 (s, 1H), 7.66-7.63 (m, 2H), 7.43 (m, 1H), 7.38 (s, 1H), 6.91 (s, 1H), 6.85-6.78 (m, 1H), 6.18-6.13 (dd, J=2.4, 12.4 Hz, 1H), 5.74-5.71 (dd, J=2.4, 10.4 Hz, 1H), 3.76 (s, 4H), 3.68-3.63 (m, 4H). ESI-MS m/z: 377.3 [M−H]$^−$.

Example 46

Synthesis of (E)-1-(4-(2',6-dichloro-4-hydroxybiphenylcarbonyl)piperazin-1-yl)-4-(dimethylamino)but-2-en-1-one (III-24)

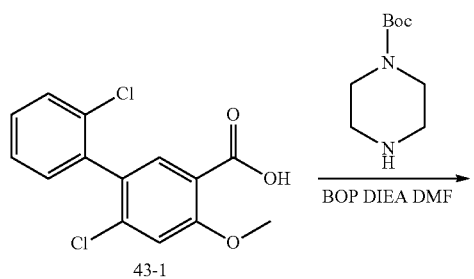

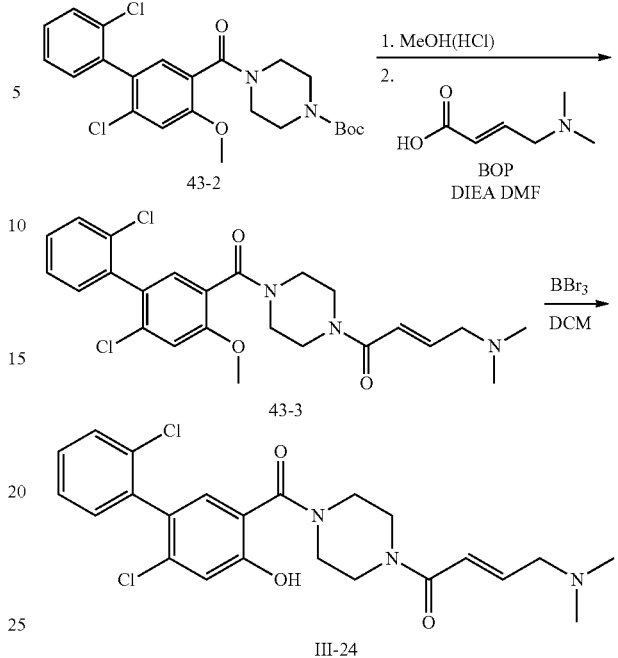

tert-Butyl 4-(2',6-dichloro-4-methoxy-[1,1'-biphenyl]-3-carbonyl)piperazine-1-carboxylate To a stirred solution of 2',6-dichloro-4-methoxy-[1,1'-biphenyl]-3-carboxylic acid (500 mg, 1.68 mmol) in DMF (10 mL) at room temperature, tert-butyl piperazine-1-carboxylate (345 mg, 1.85 mmol), BOP (892 mg, 2.02 mmol) and DIEA (542 mg, 4.2 mmol) were added and the resulting mixture was stirred at room temperature for 2 h. The reaction mixture was diluted with ethyl acetate and washed with brine. The organic layer was dried over anhydrous Na$_2$SO$_4$, filtered and concentrated in vacuo. The residue was purified by flash column chromatography on silica gel (dichloromethane/methanol=50:1) to afford the desired product (550 mg, 70% yield). ESI-MS m/z: 465.4 [M+H]$^+$.

(E)-1-(4-(2',6-dichloro-4-methoxy-[1,1'-biphenyl]-3-carbonyl)piperazin-1-yl)-4-(dimethylamino)but-2-en-1-one A mixture of tert-Butyl 4-(2',6-dichloro-4-methoxy-[1,1'-biphenyl]-3-carbonyl)piperazine-1-carboxylate (550 mg, 1.18 mmol) in HCl/MeOH (20 mL, 57.2 mmol) was stirred at room temperature for 1 h. The solvent was removed under reduced pressure to yield the crude product. The crude residue was dissolved with DMF (10 mL), 4-(dimethylamino)but-2-enoic acid (215 mg, 0.47 mmol), BOP (627 mg, 1.42 mmol) and DIEA (610 mg, 4.73 mmol) was added. The resulting mixture was stirred at room temperature for 2 h. The reaction mixture was diluted with ethyl acetate and washed with brine. The organic layer was dried over anhydrous Na$_2$SO$_4$, filtered and concentrated in vacuo. The residue was purified by flash column chromatography on silica gel (dichloromethane/methanol=50:1) to afford the desired product (450 mg, 80% yield, 2 steps). ESI-MS m/z: 476.4 [M+H]$^+$.

(E)-1-(4-(2',6-dichloro-4-hydroxy-[1,1'-biphenyl]-3-carbonyl)piperazin-1-yl)-4-(dimethylamino)but-2-en-1-one (VI-24)

A solution of (E)-1-(4-(2',6-dichloro-4-methoxy-[1,1'-biphenyl]-3-carbonyl)piperazin-1-yl)-4-(dimethylamino)but-2-en-1-one (270 mg, 0.57 mmol) in DCM (5 mL) at −78° C., BBr₃ (1.43 g, 5.7 mmol) was added dropwise. The resulting mixture was stirred at room temperature for 2 h. The mixture was poured into ice-water, basified with the aqueous NaHCO₃ to adjust the pH to 7 and then extracted with DCM (3×20 mL). The organic layer was dried over Na₂SO₄ and concentrated in vacuo. The residue was purified by column chromatography on silica gel (dichloromethane/methanol=50:1) to afford the desired product (150 mg, 57% yield). ¹H NMR (400 MHz, DMSO-d6) δ: 13.12 (s, 1H), 8.02 (s, 1H), 7.81 (s, 1H), 6.81 (m, 1H), 6.13 (dd, J=2.8, 16.8 Hz, 1H), 5.71 (dd, J=2.0, 10.4 Hz, 1H), 4.10 (s, 2H), 3.50-3.60 (m, 8H). ESI-MS m/z: 462.4 [M+H]⁺.

Example 47

Synthesis of 1-(4-(2',6-dichloro-4-methoxybiphenylcarbonyl)piperazin-1-yl)prop-2-en-1-one (III-1)

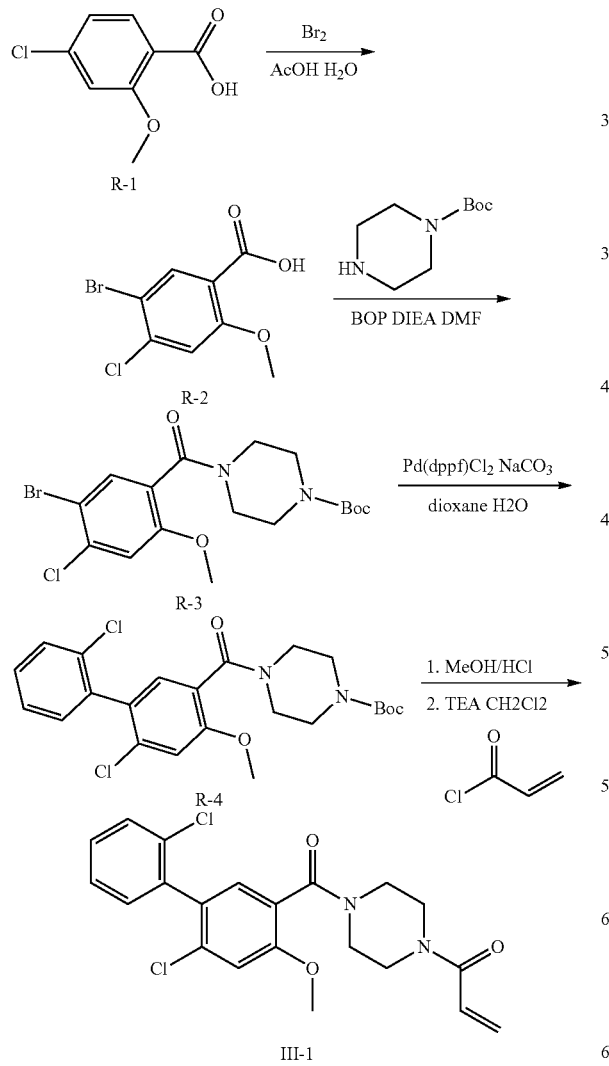

Example 48

Synthesis of 1-(3-(4-(2-(4-chloro-5-cyclobutyl-2-hydroxyphenylamino)acetyl)piperazin-1-yl)azetidin-1-yl)prop-2-en-1-one (II-53)

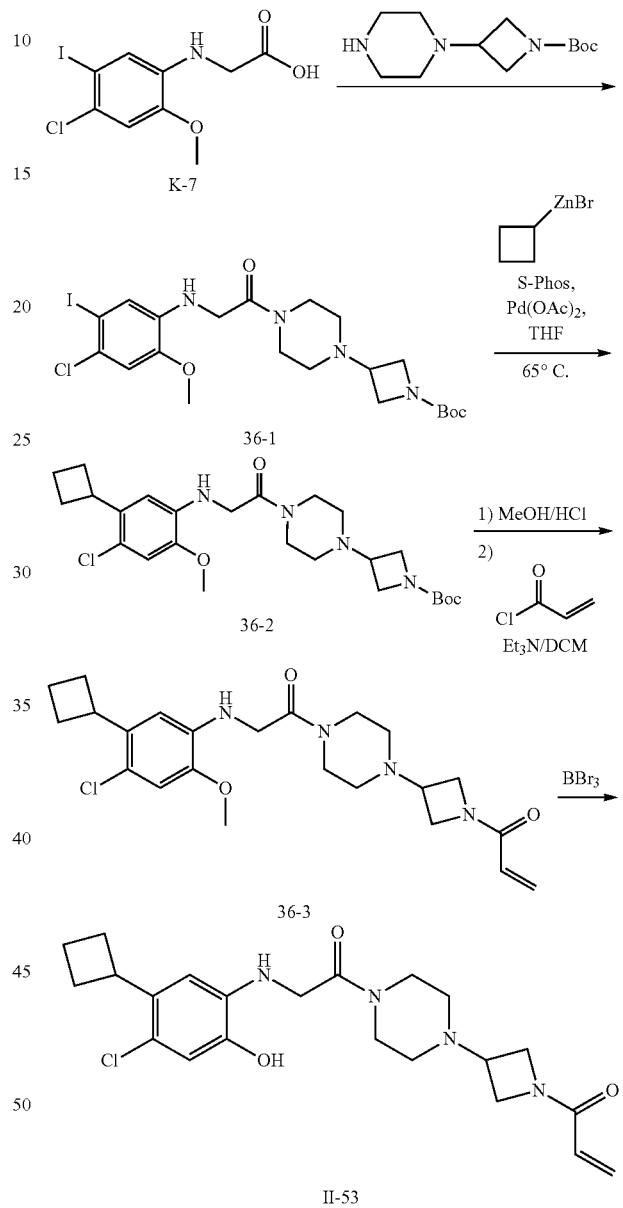

tert-Butyl 3-(4-(2-(4-Chloro-5-iodo-2-methoxyphenylamino)acetyl)piperazin-1-yl)azetidine-1-carboxylate To a solution of 2-(4-chloro-5-iodo-2-methoxyphenylamino)acetic acid (2.0 g, 5.88 mmol), tert-butyl 3-(piperazin-1-yl)azetidine-1-carboxylate (1.84 g, 7.64 mmol), EDCI.HCl (2.26 g, 11.76 mmol), and HOBt (1.59 g, 11.76 mmol) in DMF (3 mL) at 0° C., Et₃N (3.28 mL, 23.52 mmol) was added. The resulting mixture was stirred at RT for 16 h and then partitioned between ethyl acetate and water. The organic layer was washed with brine, dried over Na₂SO₄ and concentrated in vacuo. The residue was washed by a mixture of ethyl acetate/petroleum ether=1:5 to afford the desired product (2.24 g, 67% yield) as a white solid. ESI-MS m/z: 565.4 [M+H]⁺.

tert-Butyl 3-(4-(2-(4-chloro-5-cyclobutyl-2-methoxyphenylamino)acetyl)piperazin-1-yl)azetidine-1-carboxylate A mixture of tert-butyl 3-(4-(2-(4-chloro-5-iodo-2-methoxyphenylamino)acetyl)piperazin-1-yl)azetidine-1-carboxylate (697 mg, 1.24 mmol), cyclobutylzinc bromide (4.46 mL, 2.23 mmol, 0.5 M in THF), Pd(OAc)₂ (56 mg, 0.248 mmol), and S-Phos (102 mg, 0.248 mmol) in THF (15 mL) was stirred at 65° C. under argon for 16 h. The mixture was allowed to cool to RT, quenched with aqueous NH₄Cl solution and then extracted with ethyl acetate. The organic layer was washed with brine, dried over Na₂SO₄, filtered and concentrated in vacuo. The residue was purified by flash column chromatography on silica gel (methanol/dichloromethane=1:30) to afford the desired product (596 mg, 98% yield) as a brown oil. ESI-MS m/z: 493.5 [M+H]⁺.

1-(3-(4-(2-(4-Chloro-5-cyclobutyl-2-hydroxyphenylamino)acetyl)piperazin-1-yl)azetidin-1-yl)prop-2-en-1-one (V-53)

The title compound was prepared from tert-butyl 3-(4-(2-(4-chloro-5-cyclobutyl-2-methoxyphenylamino)acetyl)piperazin-1-yl)azetidine-1-carboxylate in three steps according to the procedure described in Example 33. ¹H NMR (400 MHz, DMSO-d6) δ: 9.66 (s, 1H), 6.63 (s, 1H), 6.52 (s, 1H), 6.31 (dd, J=10.2, 16.9 Hz, 1H), 6.10 (dd, J=2.1, 16.8 Hz, 1H), 5.68 (dd, J=2.1, 10.2 Hz, 1H), 5.16 (t, J=4.4 Hz, 1H), 4.27-4.23 (m, 1H), 4.08-4.04 (m, 1H), 3.97-3.93 (m, 3H), 3.80-3.76 (m, 1H), 3.65-3.59 (m, 1H), 3.56-3.54 (m, 4H), 3.20-3.14 (m, 1H), 2.40-2.25 (m, 4H), 2.20-2.15 (m, 2H), 2.09-2.05 (m, 2H), 1.97-1.90 (m, 1H), 1.80-1.74 (m, 1H). ESI-MS m/z: 433.4 [M+H]⁺.

Example 49

Synthesis of 1-(3-(4-(2-(4-chloro-5-cyclobutyl-2-hydroxyphenylamino)propanoyl)piperazin-1-yl)azetidin-1-yl)prop-2-en-1-one (II-59)

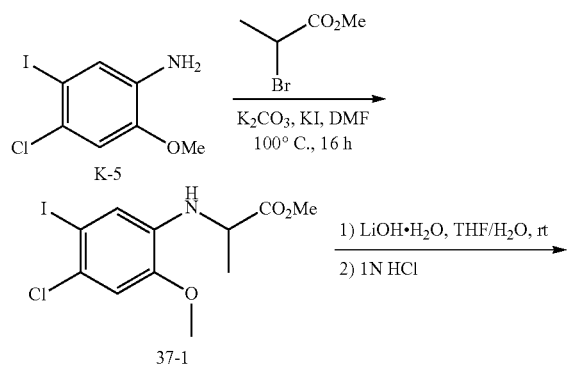

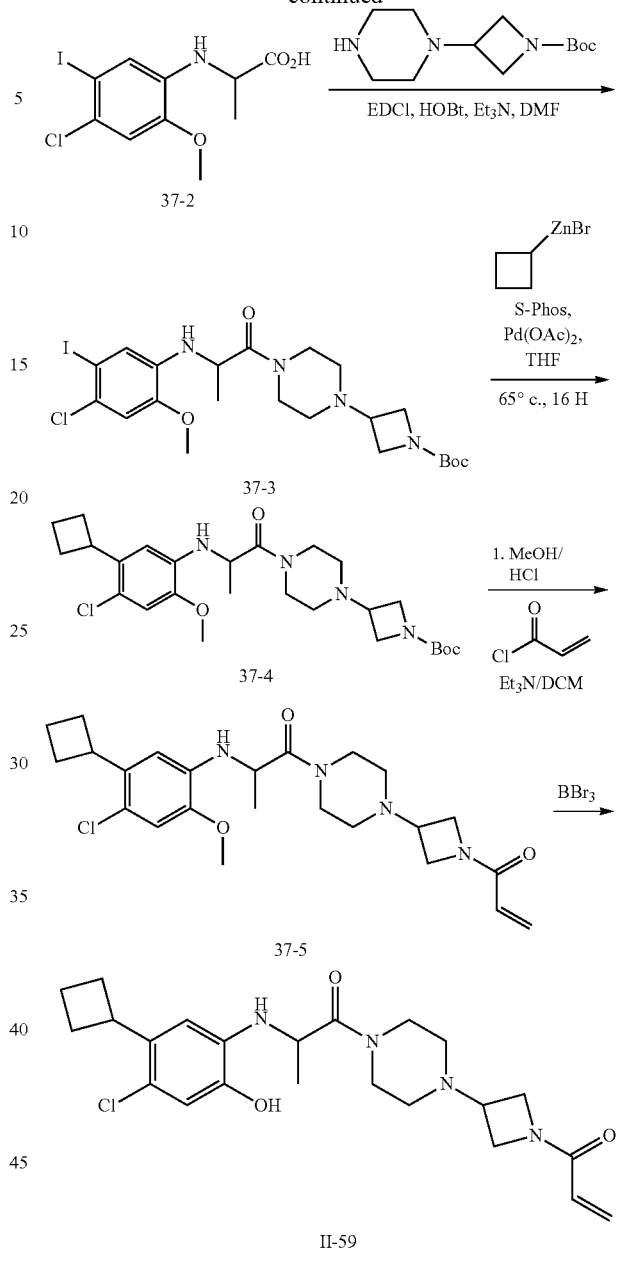

Methyl 2-(4-chloro-5-iodo-2-methoxyphenylamino)propanoate

A mixture of tert-butyl 4-chloro-5-iodo-2-methoxybenzenamine (2 g, 7.07 mmol), methyl 2-bromopropanoate (1.17 g, 7.07 mmol), K₂CO₃ (1.94 g, 14.14 mmol) and KI (0.235 g, 1.414 mmol) in DMF (25 mL) was stirred at 100° C. for 16 h. The mixture was allowed to cool to RT, quenched with aqueous NaHCO₃ solution and then extracted with ethyl acetate. The organic layer was washed with brine, dried over Na₂SO₄, filtered and concentrated in vacuo. The residue was purified by flash column chromatography on silica gel (ethyl acetate/petroleum ether=1:20) to afford the desired product (1.12 g, 43% yield) as a yellow solid. ESI-MS m/z: 370.1 [M+H]⁺.

2-(4-Chloro-5-iodo-2-methoxyphenylamino)propanoic acid

To a solution of methyl 2-(4-chloro-5-iodo-2-methoxyphenylamino)propanoate (1.12 g, 3.04 mmol) in mixture of tetrahydrofuran (20 mL) and water (10 mL) at RT, LiOH.H$_2$O (0.51 g, 12.16 mmol) was added and the resulting mixture was stirred for 1 h. The aqueous phase was washed with TBME and then acidified with aqueous HCl (1 N) to adjust the pH to 5. The mixture was extracted with ethyl acetate. The organic layer was washed with brine, dried over anhydrous Na$_2$SO$_4$, filtered and concentrated in vacuo to afford the crude product (760 mg) which was used directly in the next step without further purification. ESI-MS m/z: 356.1 [M+H]$^+$.

Tert-Butyl 3-(4-(2-((4-Chloro-5-iodo-2-methoxyphenyl)amino)propanoyl)piperazin-1-yl)azetidine-1-carboxylate To a solution of 2-(4-chloro-5-iodo-2-methoxyphenylamino)propanoic acid (760 mg, 2.13 mmol), tert-butyl 3-(piperazin-1-yl)azetidine-1-carboxylate (669 mg, 2.78 mmol), EDCI.HCl (818 mg, 4.26 mmol), HOBt (575 mg, 4.26 mmol) in DMF (8 mL) at 0° C., Et$_3$N (861 mg, 8.52 mmol) was added. The resulting mixture was stirred at RT for 16 h and then partitioned between ethyl acetate and water. The organic layer was washed with saturated NaHCO$_3$ solution and brine, dried over Na$_2$SO$_4$ and concentrated in vacuo. The residue was purified by flash column chromatography on silica gel (ethyl acetate/petroleum ether=1:1) to afford the desired product (673 mg, 55% yield) as a white solid. ESI-MS m/z: 579.4 [M+H]$^+$.

Tert-Butyl 3-(4-(2-((4-Chloro-5-cyclobutyl-2-methoxyphenyl)amino)propanoyl)piperazin-1-yl)azetidine-1-carboxylate A mixture of tert-butyl 3-(4-(2-((4-chloro-5-iodo-2-methoxyphenyl)amino)propanoyl)piperazin-1-yl)azetidine-1-carboxylate (673 mg, 1.162 mmol), cyclobutylzinc bromide (5.11 mL, 2.556 mmol, 0.5 M in THF), Pd(Oac)$_2$ (52 mg, 0.23 mmol), S-Phos (95 mg, 0.23 mmol) in THF (10 mL) was stirred at 65° C. under argon for 16 h. The mixture was allowed to cool to RT, quenched with aqueous NH$_4$Cl solution and then extracted with ethyl acetate. The organic layer was washed with brine, dried over Na$_2$SO$_4$, filtered and concentrated in vacuo. The residue was purified by flash column chromatography on silica gel (ethyl acetate/petroleum ether=1:1) to afford the desired product (565 mg, 96% yield) as a light yellow solid. ESI-MS m/z: 507.6 [M+H]$^+$.

1-(3-(4-(2-((4-Chloro-5-cyclobutyl-2-hydroxyphenyl)amino)propanoyl)piperazin-1-yl)azetidin-1-yl)prop-2-en-1-one (V-59)

The title compound was prepared from tert-butyl 3-(4-(2-((4-chloro-5-cyclobutyl-2-methoxyphenyl)amino)propanoyl)piperazin-1-yl)azetidine-1-carboxylate in three steps according to the procedure described in Example 33. $^1$H NMR (400 MHz, DMSO-d6) δ: 9.63 (s, 1H), 6.62 (s, 1H), 6.49 (s, 1H), 6.30 (dd, J=10.1, 16.8 Hz, 1H), 6.10 (d, J=18.7 Hz, 1H), 5.68 (d, J=10.4 Hz, 1H), 4.86 (d, J=9.2 Hz, 1H), 4.69-4.63 (m, 1H), 4.27-4.23 (m, 1H), 4.07-4.03 (m, 1H), 3.97-3.62 (m, 1H), 3.82-3.76 (m, 2H), 3.64-3.55 (m, 3H), 3.77-3.11 (m, 1H), 2.44-2.15 (m, 6H), 2.08-1.90 (m, 4H), 1.80-1.72 (m, 2H), 1.97-1.90 (m, 1H), 1.24 (d, J=6.4 Hz, 3H). ESI-MS m/z: 447.4 [M+H]$^+$.

Example 50

Synthesis of tert-butyl 4-(1-acryloylazetidin-3-yl)piperazine-1-carboxylate

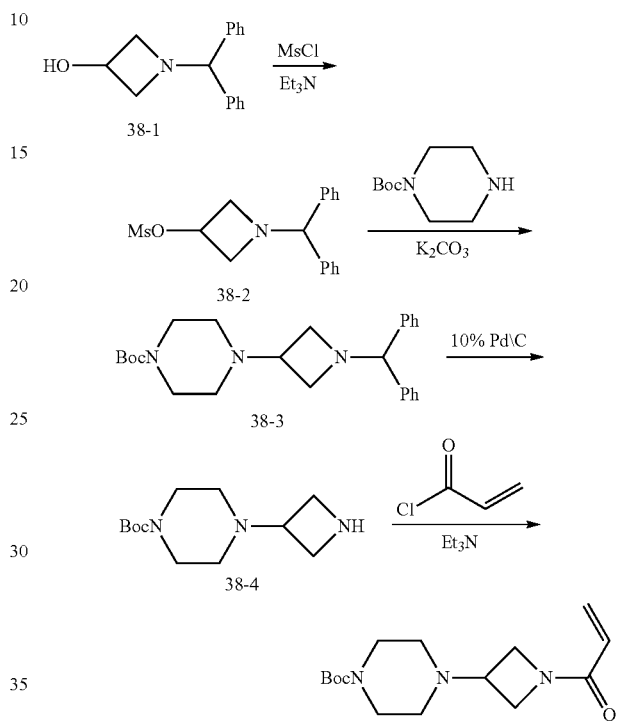

1-Benzhydrylazetidin-3-yl methanesulfonate

A mixture of 1-benzhydrylazetidin-3-ol (20.0 g, 83.68 mmol) and Et$_3$N (12.68 g, 125.52 mmol) in DCM (200 mL) at 0° C., MsCl (11.447 mg, 100.41 mmol) was added in portions and the resulting solution was stirred at RT for 1 h. The reaction mixture was diluted with ethyl acetate and washed with brine. The organic layer was dried over anhydrous Na$_2$SO$_4$, filtered and concentrated in vacuo to afford the desired product (26.526 g, 100% yield).

tert-Butyl 4-(1-benzhydrylazetidin-3-yl)piperazine-1-carboxylate

A mixture of 1-benzhydrylazetidin-3-yl methanesulfonate (26.53 g, 83.68 mmol), tert-butyl piperazine-1-carboxylate (18.68 g, 100.41 mmol) and K$_2$CO$_3$ (23.09 g, 163.36 mmol) in CH$_3$CN (200 mL) was stirred at 80° C. for 16 h. The reaction mixture was cooled to RT and diluted with ethyl acetate and washed with brine. The organic layer was dried over anhydrous Na$_2$SO$_4$, filtered and concentrated in vacuo. The residue was purified by flash column chromatography on silica gel (dichloromethane/methanol=50:1) to afford the desired product (25.5 g, 80% yield).

tert-Butyl 4-(azetidi-3-yl)piperazine-1-carboxylate

A mixture of tert-butyl 4-(1-benzhydrylazetidin-3-yl)piperazine-1-carboxylate (10.0 g, 24.57 mmol) and 10% Pd\C (2.5 g) in MeOH (100 mL) was stirred under H₂ atmosphere at 50° C. for 48 h. The reaction mixture was cooled to RT and filtered. The filtrate was diluted concentrated in vacuo to afford a crude desire product (6.7 g) as a colorless oil.

tert-Butyl 4-(1-acryloylazetidin-3-yl)piperazine-1-carboxylate

A mixture of tert-butyl 4-(azetidi-3-yl)piperazine-1-carboxylate (6.7 g, 27.80 mmol) and Et₃N (8.43 g, 83.40 mmol) in DCM (100 mL) at 0° C., acryloyl chloride (3.77 g, 41.7 mmol) was added in portions and the resulting solution was stirred at RT for 1 h. The reaction mixture was diluted with DCM and washed with brine. The organic layer was dried over anhydrous Na₂SO₄, filtered and concentrated in vacuo. The residue was purified by column chromatography on silica gel (dichloromethane/methanol=50:1) to afford the desired product (3.6 g, 49.66% yield, 2 steps). ¹H NMR (400 MHz, DMSO-d6) δ: 6.30 (dd, J=10.4, 16.8 Hz, 1H), 6.09 (dd, J=2.4, 17.2 Hz, 1H), 5.67 (dd, J=2.4, 10.4 Hz, 1H), 4.22 (t, J=8, 1H), 4.03-4.00 (m, 1H), 3.94-3.90 (m, 1H), 3.75-3.70 (m, 1H), 3.32 (t, J=8.8 Hz, 4H), 3.10-3.18 (m, 1H), 2.22-2.30 (m, 1H), 1.40 (s, 9H).

Example 51

Synthesis of 1-acryloyl-4-(4',6-dichloro-4-hydroxy-biphenylcarbonyl)piperazine-2-carbonitrile (III-37)

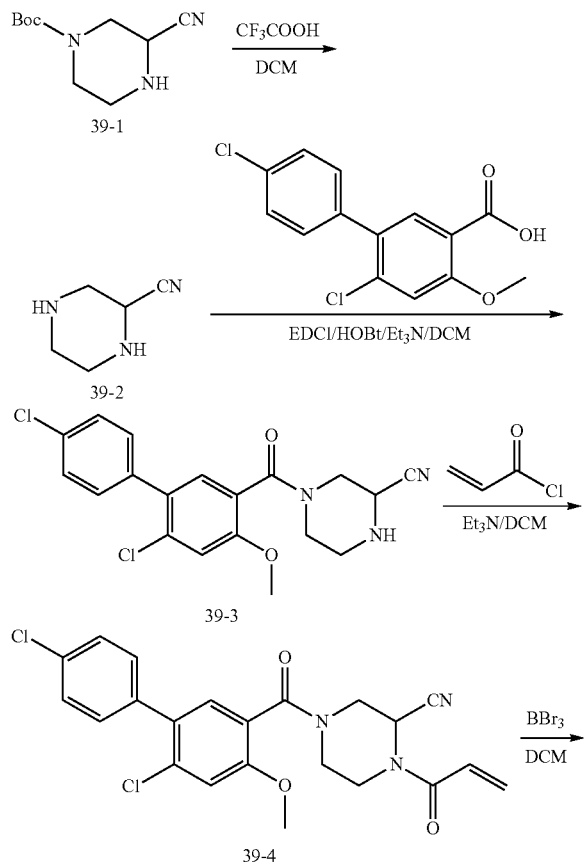

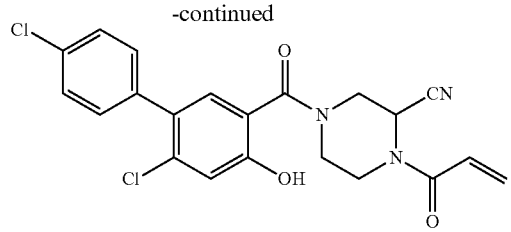

III-37

Piperazine-2-carbonitrile

To a mixture of tert-butyl 3-cyanopiperazine-1-carboxylate (200 mg, 0.95 mmol) in dichloromethane (10 mL), CF₃COOH (2 mL) was added and the resulting was stirred at RT for 1 h. The mixture was concentrated in vacuo to afford the crude product.

4-(4',6-Dichloro-4-methoxy-[1,1'-biphenyl]-3-carbonyl)piperazine-2-carbonitrile

To a mixture of 4',6-dichloro-4-methoxy-[1,1'-biphenyl]-3-carboxylic acid (309 mg, 1.04 mmol), EDCI (272 mg, 1.43 mmol), HOBt (195 mg, 1.43 mmol), Et₃N (288 mg, 2.85 mmol) in dichloromethane (10 mL) at 0° C., piperazine-2-carbonitrile was added at 0° C. and the resulting mixture was stirred at RT for 8 h. The mixture was partitioned between dichloromethane and water. The organic layer was washed brine, dried over MgSO₄, filtered and concentrated in vacuo. The residue was purified by flash column chromatography on silica gel (dichloromethane/methanol=50:1) to afford the desired product (225 mg, 61% yield). ESI-MS m/z: 444.3 [M+H]⁺.

1-Acryloyl-4-(4',6-dichloro-4-hydroxy-[1,1'-biphenyl]-3-carbonyl)piperazine-2-carbonitrile (III-37)

The title compound was prepared from 4-(4',6-dichloro-4-methoxy-[1,1'-biphenyl]-3-carbonyl)piperazine-2-carbonitrile in two steps according to the procedure described in Example 33. ¹H NMR (400 MHz, CDCl₃) δ: 9.24 (s, 1H), 7.44-7.33 (m, 5H), 7.20 (s, 1H), 6.57-6.45 (m, 2H), 6.79 (s, 1H), 5.94-5.91 (m, 1H), 5.75 (s, 1H), 4.62-4.61 (m, 1H), 4.50-4.46 (m, 1H), 4.06 (s, 1H), 3.61 (s, 1H), 3.36-3.33 (m, 1H), 3.16-3.10 (m, 1H). ESI-MS m/z: 428.4 [M+H]⁺.

Example 52

Synthesis of 1-(3-(4-(3-(4-chloro-5-cyclopropyl-2-hydroxyphenyl)propanoyl)piperazin-1-yl)azetidin-1-yl)prop-2-en-1-one (II-58)

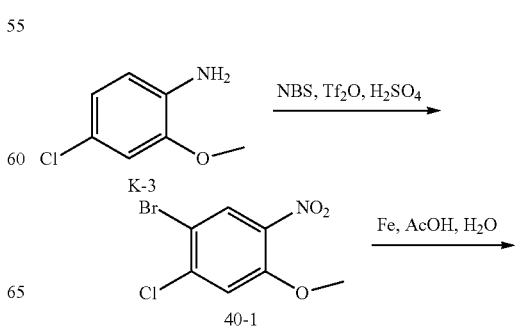

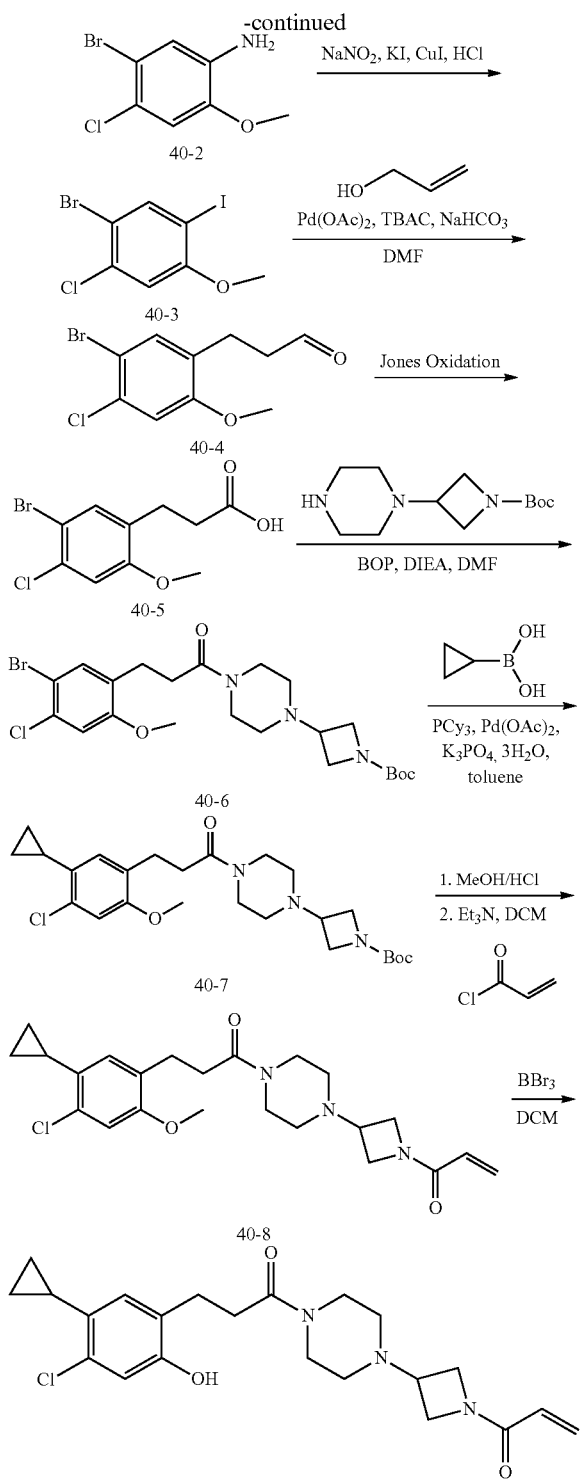

pH to 3-4. The mixture was extracted with ethyl acetate. The combined organic layer was washed with brine, dried over $Na_2SO_4$, filtered and concentrated in vacuo. The residue was used directly in the next step (80 g, 88% yield).

To a solution of 5-chloro-2-nitrophenol (40 g, 0.23 mol) in DMF (200 mL), $K_2CO_3$ (47.6 g, 0.345 mol) and iodomethane (49 g, 0.345 mol) were added and the resulting mixture was stirred at room temperature for 16 h. The mixture was partitioned between ethyl acetate and water. The organic layer was washed with brine, dried over $MgSO_4$, filtered and concentrated in vacuo. The residue was purified by flash column chromatography on silica gel (petroleum ether) to afford the desired product (30 g, 70% yield).

To a solution of $H_2SO_4$ (600 mL, 90%), trifluoromethanesulfonic anhydride (11.3 g, 0.04 mol) and NIS (49.68 g, 0.22 mol) were added and resulting mixture was stirred at room temperature for 1 h. To this mixture, 4-chloro-2-methoxy-1-nitrobenzene (69 g, 0.368 mol) was added quickly. The mixture was stirred for 1 h, and then NIS (33.12 g, 0.148 mol) was slowly added to the mixture. The mixture was stirred at room temperature for 1 h and then was poured into ice-water. The precipitate collected by filtration, rinsed with water, aqueous $NaSO_3$ and $NaHCO_3$ solutions, and then dried in vacuo to afford the desired product (113 g, 98% yield).

To a solution of 1-chloro-2-iodo-5-methoxy-4-nitrobenzene (113 g, 0.361 mol) in acetic acid (1 L) and water (50 mL) at 50° C., Fe (50.5 g, 0.903 mol) was added and the resulting mixture was stirred at 50° C. for 2 h. The mixture was allowed to cool to room temperature and then poured into ice-water. The precipitate was collected by filtration and rinsed with water. This crude product was dissolved with ethyl acetate (1 L) and filtered. The filtrate was washed with saturated $NaHCO_3$ solution and brine. The organic layer was dried over $MgSO_4$, filtered, and concentrated in vacuo to afford the desired product (87 g, 85% yield).

1-Bromo-2-chloro-5-iodo-4-methoxybenzene

To a mixture of 5-bromo-4-chloro-2-methoxyaniline (3 g, 12.7 mmol) in 6N HCl (60 mL, 360 mmol) at 0° C., a solution of $NaNO_2$ (963 mg, 13.9 mmol) in water (20 mL) was added dropwise while keeping the internal temperature around 0° C. KI (10.5 g, 63.4 mmol) and CuI (4.8 g, 25.4 mmol) were dissolved in water (20 mL) and added to the stirred reaction mixture. The reaction was kept at 5° C. for 2 h. The reaction mixture was extracted with ethyl acetate. The combined organic layer was washed with water, $Na_2SO_3$ (aq, 10%) and brine, dried over anhydrous $Na_2SO_4$, an concentrated. The residue was purified by flash column chromatography on silica gel (ethyl acetate/petroleum ether=1:100) to afford the desired product (3.2 g, 73% yield).

3-(5-Bromo-4-chloro-2-methoxyphenyl)propanal

A mixture of 1-bromo-2-chloro-5-iodo-4-methoxybenzene (3.2 g, 9.2 mmol), prop-2-en-1-ol (1.3 g, 23.0 mmol), $Pd(OAc)_2$ (206 mg, 0.9 mmol), TBAC (2.56 g, 9.2 mmol), $NaHCO_3$ (2.3 g, 27.6 mmol) in DMF (50 mL) was stirred under Argon at 60° C. for 16 h. The mixture was allowed to cool to RT, and then partitioned between ethyl acetate and water. The combined organic layer was washed with brine, dried over anhydrous $Na_2SO_4$ and concentrated. The residue was purified by flash column chromatography on silica gel 5-Bromo-4-chloro-2-methoxybenzenamine To a solution of 2,4-dichloro-1-nitrobenzene (100 g, 0.52 mol) in DMSO (200 mL), aqueous solution of NaOH (41.6 g, 1.04 mol) in water (42 mL) was added and the resulting mixture was stirred 60° C. for 16 h. The mixture was allowed to cool to room temperature, poured to ice water, and then acidified with aqueous HCl (1 M) to adjusted the (ethyl acetate/petroleum ether=1:20) to afford the desired product (860 mg, 34% yield).

3-(5-Bromo-4-chloro-2-methoxyphenyl)propanoic acid

To a stirred solution of Jones reagent (3 mL, 5.4 mmol, 2.8 M) in acetone (20 mL), 3-(5-bromo-4-chloro-2-methoxyphenyl)propanal (860 mg, 3.1 mmol) was added. The reaction was stirred at RT for 12 h, quenched with iso-propylalcohol and then stirred for 10 min. The resulting mixture was diluted with water, extracted with ethyl acetate. The combined organic layer was washed with water and brine, dried over $Na_2SO_4$ and concentrated. The residue was purified by flash column chromatography on silica gel (ethyl acetate/petroleum ether=1:1) to afford the desired product (358 mg, 38% yield). ESI-MS m/z: 291.1 [M+H]$^-$.

tert-Butyl-3-(4-(3-(5-bromo-4-chloro-2-methoxyphenyl)propanoyl)piperazin-1-yl)azetidine-1-carboxylate To a stirred solution of 3-(5-bromo-4-chloro-2-methoxyphenyl)propanoic acid (350 mg, 1.2 mmol) in DMF (30 mL) at RT, tert-butyl 3-(piperazin-1-yl)azetidine-1-carboxylate (317 mg, 1.3 mmol), BOP (731 mg, 1.4 mmol) and DIEA (461 mg, 3.6 mmol) were added and the mixture was stirred at RT for 1 h. The reaction mixture was partitioned between ethyl acetate and water. The organic layer was washed with brine and dried over anhydrous $Na_2SO_4$, filtered and concentrated in vacuo. The residue was purified by flash column chromatography on silica gel (dichloromethane/methanol=50:1) to afford the desired product (285 mg, 46% yield).

tert-Butyl 3-(4-(3-(4-chloro-5-cyclopropyl-2-hydroxyphenyl)propanoyl)piperazin-1-yl)azetidine-1-carboxylate A mixture of tert-butyl 3-(4-(3-(5-bromo-4-chloro-2-methoxyphenyl)propanoyl)piperazin-1-yl)azetidine-1-carboxylate (280 mg, 0.54 mmol), cyclopropylboronic acid (185 mg, 2.2 mmol), $K_3PO_4 \cdot 3H_2O$ (444 mg, 1.9 mmol), tricyclohexylphosphine (30 mg, 0.1 mmol), $Pd(OAc)_2$ (24 mg, 0.11 mmol) in toluene (10 mL) and water (1 mL) was stirred at reflux under argon for 16 h. The mixture was allowed to cool to RT and concentrated in vacuo. The residue was purified by flash column chromatography on silica gel (dichloromethane/methanol=60:1) to afford the desired product (194 mg, 75% yield). ESI-MS m/z: 477.3 [M+H]$^+$.

1-(3-(4-(3-(4-Chloro-5-cyclopropyl-2-hydroxyphenyl)propanoyl)piperazin-1-yl)azetidin-1-yl)prop-2-en-1-one (II-58)

The title compound was prepared from tert-butyl 3-(4-(3-(4-chloro-5-cyclopropyl-2-hydroxyphenyl)propanoyl)piperazin-1-yl)azetidine-1-carboxylate in three steps according to the procedure described in Example 33. $^1$H NMR (400 MHz, DMSO-d6) δ: 9.68 (s, 1H), 6.79 (s, 1H), 6.74 (s, 1H), 6.33-6.26 (m, 1H), 6.12-6.07 (dd, J=1.9, 17.2 Hz, 1H), 5.68-5.65 (dd, J=2.0, 10.2 Hz, 1H), 4.24-4.20 (m, 1H), 4.05-4.01 (m, 1H), 3.94-3.90 (m, 1H), 3.76-3.72 (m, 1H), 3.45-3.42 (m, 4H), 3.13-3.11 (m, 1H), 2.69-2.65 (m, 2H), 2.53-2.51 (m, 2H), 2.25-2.23 (bs, 4H), 1.97-1.93 (m, 1H), 0.90-0.86 (m, 1H), 0.60-0.55 (m, 1H). ESI-MS m/z: 418.4 [M+H]$^+$.

Example 53

Synthesis of 1-(3-(4-(2-(4-chloro-2-hydroxy-5-(1-Methylcyclopropyl)phenylamino)acetyl)piperazin-1-yl)azetidin-1-yl)prop-2-en-1-one (II-64)

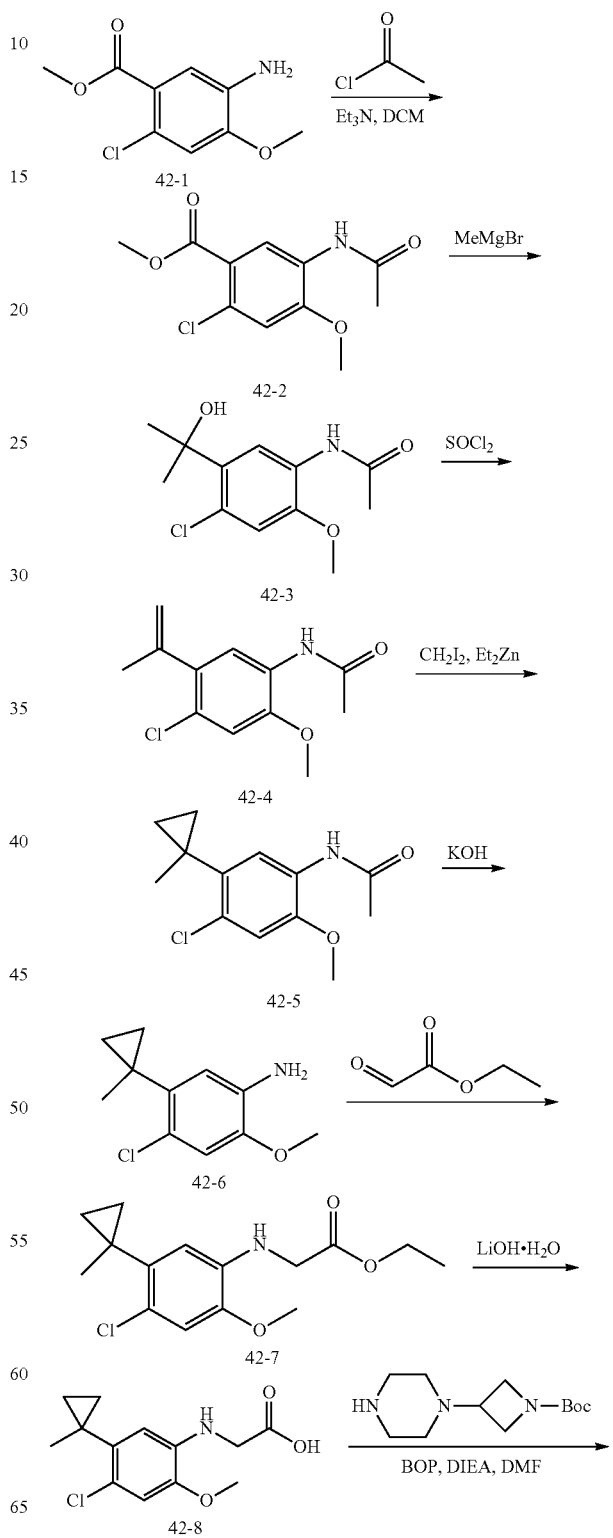

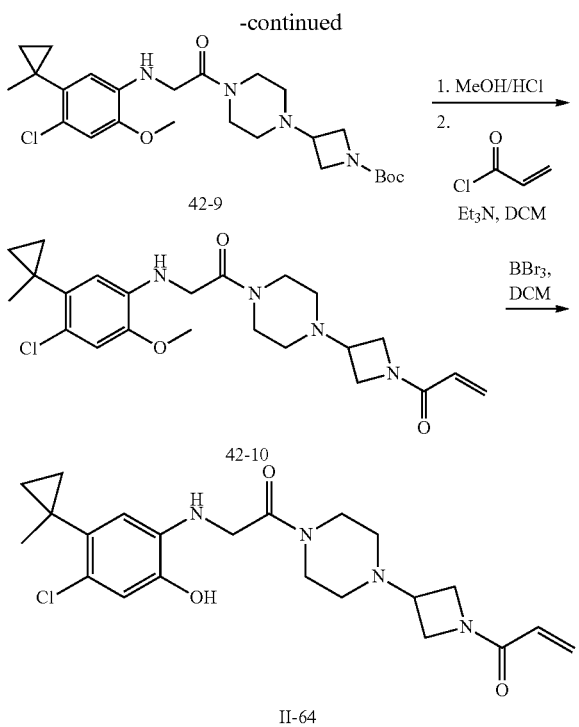

Methyl 5-acetamido-2-chloro-4-methoxybenzoate

To a mixture of methyl 5-amino-2-chloro-4-methoxybenzoate (3.6 g, 16.7 mmol), Et₃N (6.7 g, 66.8 mmol) and DCM (100 mL) at RT, acetyl chloride (1.57 g, 20.1 mmol) was added dropwise and the resulting mixture was stirred for 12 h. The reaction mixture was partitioned between dichloromethane and water. The organic layer was washed with saturated NaHCO₃ solution and brine, dried over anhydrous Na₂SO₄ and concentrated in vacuo. The residue was purified by flash column chromatography on silica gel (ethyl acetate/petroleum ether=1:1) to afford the desired product (2.7 g, 63% yield).

N-(4-Chloro-5-(2-hydroxypropan-2-yl)-2-methoxyphenyl)acetamide

To a solution of methyl 5-acetamido-2-chloro-4-methoxybenzoate (2.7 g, 11.1 mmol), in THF (40 mL) at −40° C. under Argon, methylmagnesium bromide (21 mL, 21 mmol, 1M in ether) was added dropwise while keeping the internal temperature at −40° C. Then the mixture was allowed to warm to RT, and stirred for 2 h. The reaction mixture was poured into ice-cooled NH₄Cl (10%) solution, and extracted with ethyl acetate. The combined organic layer was washed with water and brine, dried over anhydrous Na₂SO₄ and concentrated in vacuo to afford the desire product (2.3 g, 80% yield).

N-(4-Chloro-2-methoxy-5-(prop-1-en-2-yl)phenyl)acetamide

To a solution of N-(4-chloro-5-(2-hydroxypropan-2-yl)-2-methoxyphenyl)acetamide (3.2 g, 12.4 mmol) in DCM (20 mL) at −5° C., SOCl₂ (3.7 g, 37.25 mmol) was added dropwise. The mixture was warmed to RT, and then stirred at reflux for 2 h. The reaction mixture was concentrated and the residue was purified by flash column chromatography on silica gel (ethyl acetate/petroleum ether=3:1) to afford the desired product (1.9 g, 64% yield).

N-(4-Chloro-2-methoxy-5-(1-methylcyclopropyl)phenyl)acetamide

To a solution of N-(4-chloro-2-methoxy-5-(prop-1-en-2-yl)phenyl)acetamide (1.0 g, 4.17 mmol) in toluene (20 mL) at 0° C., CH₂I₂ (5.6 g, 20.86 mmol) and Et₂Zn (41.7 mL, 41.7 mmol, 1.0 M in hexane) was added. The mixture was kept at 0° C. for 30 min, and then stirred at RT for 16 h. The reaction mixture was quenched with saturated NH₄Cl solution and stirred for 15 min. The mixture was concentrated in vacuo to remove toluene and the resulting mixture was extracted with dichloromethane. The combined organic layer was washed with water and brine, dried over anhydrous Na₂SO₄, concentrated to afford the desired product (820 mg, 77% yield).

4-Chloro-2-methoxy-5-(1-methylcyclopropyl)aniline

A mixture of N-(4-chloro-2-methoxy-5-(1-methylcyclopropyl)phenyl)acetamide (820 mg, 3.23 mmol), KOH (1.8 g, 32.3 mmol), ethanol (40 mL) and water (20 mL) was stirred at reflux for 12 h. The reaction mixture was extracted with ethyl acetate. The combined organic layer was washed with water and brine, dried over anhydrous Na₂SO₄ and filtered. The filtrate was concentrated in vacuo and the residue was purified by flash column chromatography on silica gel (ethyl acetate/petroleum ether=20:1) to afford the desired product (460 mg, 67% yield). ESI-MS m/z: 212.4 [M+H]⁺.

Ethyl 2-((4-chloro-2-methoxy-5-(1-methylcyclopropyl)phenyl)amino)acetate

To a solution of 4-chloro-2-methoxy-5-(1-methylcyclopropyl)aniline (450 mg, 2.13 mmol) in MeOH (20 mL) at RT, AcOH (3 drops) and ethyl glyoxalate (326 mg, 3.19 mmol, 50% in toluene) were added. The mixture was stirred at RT for 2 h and then sodium cyanoborohydride (403 mg, 6.39 mmol) was added to the mixture. The resulting mixture was stirred at 50° C. for 16 h. The mixture was allowed to cool to RT, and partitioned between ethyl acetate and water. The organic layer was dried over MgSO₄, filtered, and concentrated in vacuo to afford the crude product (636 mg). ESI-MS m/z: 298.2 [M+H]⁺.

2-((4-Chloro-2-methoxy-5-(1-methylcyclopropyl)phenyl)amino)acetic acid

To a solution of ethyl 2-((4-chloro-2-methoxy-5-(1-methylcyclopropyl)phenyl)amino)acetate (630 mg, 2.12 mmol) in THF (15 mL) and water (5 mL), LiOH.H2O (889 mg, 21.2 mmol) was added and the resulting mixture was stirred at RT for 2 h. The mixture was washed with 20% ethyl acetate/petroleum ether. The aqueous layer was acidified with aqueous HCl (1 N) to adjust pH to 3-4 and extracted with ethyl acetate. The organic layer was dried over MgSO₄, filtered and concentrated in vacuo to afford the desired product (200 mg, 33% yield).

tert-Butyl 3-(4-(2-((4-chloro-2-methoxy-5-(1-methylcyclopropyl)phenyl)amino)acetyl)piperazin-1-yl)azetidine-1-carboxylate To a solution of 2-((4-chloro-2-methoxy-5-(1-methylcyclopropyl)phenyl)amino)acetic acid (110 mg, 0.41 mmol)

and tert-butyl 3-(piperazin-1-yl)azetidine-1-carboxylate (118 mg, 0.49 mmol) in DMF (15 mL) at RT, BOP (217 mg, 0.49 mmol) and DIEA (159 mg, 1.23 mmol) were added and the resulting mixture was stirred at RT for 1 h. The mixture was partitioned between ethyl acetate and water. The organic layer was washed with brine, dried over MgSO₄, filtered and concentrated in vacuo to afford the desired product (192 mg, 95% yield).

1-(3-(4-(2-((4-Chloro-2-hydroxy-5-(1-methylcyclopropyl)phenyl)amino)acetyl)piperazin-1-yl)azetidin-1-yl)prop-2-en-1-one (II-64)

The title compound was prepared from tert-butyl 3-(4-(2-((4-chloro-2-methoxy-5-(1-methylcyclopropyl)phenyl) amino)acetyl)piperazin-1-yl)azetidine-1-carboxylate in three steps according to the procedure described in Example 33. $^1$H NMR (400 MHz, DMSO-d6) δ: 9.70 (s, 1H), 6.64 (s, 1H), 6.51 (s, 1H), 6.35-6.28 (m, 1H), 6.13-6.08 (dd, J=1.9, 17.9 Hz, 1H), 5.69-5.66 (dd, J=2.1, 10.1 Hz, 1H), 5.13-5.11 (m, 1H), 4.25-4.23 (m, 1H), 4.08-4.05 (m, 1H), 3.95-3.91 (m, 3H), 3.80-3.76 (m, 1H), 3.53 (bs, 4H), 3.18-3.16 (m, 1H), 2.38-2.31 (m, 4H), 1.26 (s, 3H), 0.72-0.64 (m, 4H). ESI-MS m/z: 434.4 [M+H]⁺.

Example 54

Synthesis of 1-(4-(2-chloro-5-hydroxybiphenylcarbonyl)piperazin-1-yl)prop-2-en-1-one (III-42)

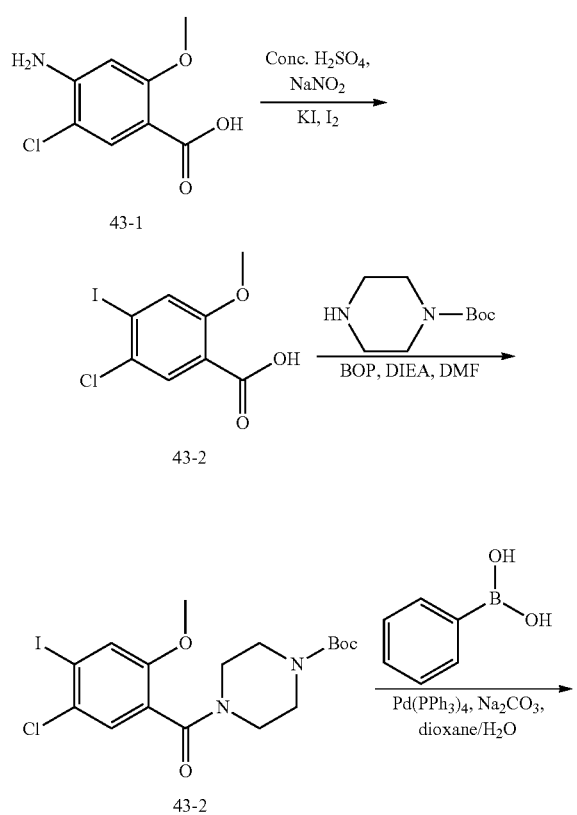

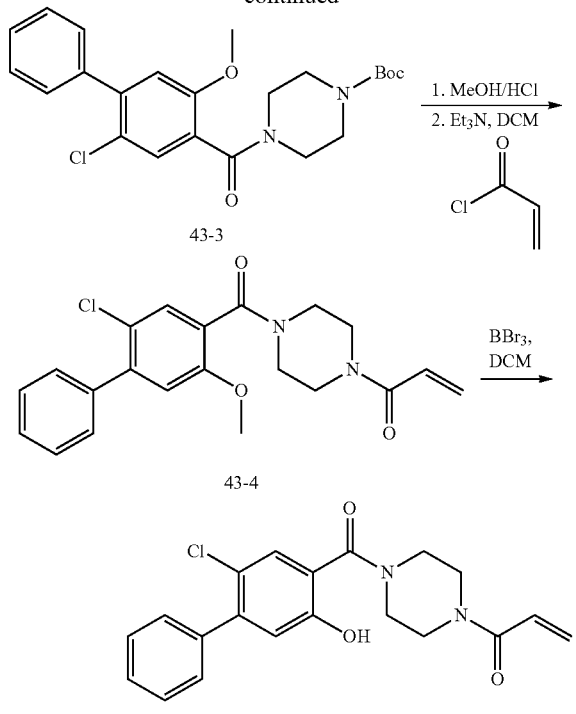

5-Chloro-4-iodo-2-methoxybenzoic acid

To a stirred solution of 4-amino-5-chloro-2-methoxybenzoic acid (5 g, 24.8 mmol) in water (10 mL) at 0° C., concentrated sulfuric acid (50 mL) was added. Then a solution of NaNO₂ (1.9 g, 27.3 mmol) in water (10 mL) was added dropwise while keeping the internal temperature around 0° C. KI (4.5 g, 27.3 mmol) and I₂ (3.5 g, 13.64 mmol) were dissolved in water and added dropwise to the stirred reaction mixture. The reaction was stirred at 5° C. for 2 h and then extracted with ethyl acetate. The organic layer was washed with water, Na₂SO₃ (aq, 10%) and brine, dried over anhydrous Na₂SO₄ and concentrated in vacuo to afford desired product (1.55 g, 19% yield). ESI-MS m/z: 311.1 [M+H]⁺.

tert-Butyl 4-(5-chloro-4-iodo-2-methoxybenzoyl) piperazine-1-carboxylate

To a stirred solution of 5-chloro-4-iodo-2-methoxybenzoic acid (1.55 g, 4.9 mmol) in DMF (30 mL) at RT, tert-butyl piperazine-1-carboxylate (1.02 g, 5.5 mmol), BOP (2.63 g, 25.9 mmol) and DIEA (1.92 g, 14.9 mmol) were added and the resulting mixture was stirred at RT for 1 h. The reaction mixture was extracted with ethyl acetate and washed with brine. The organic layer was dried over anhydrous Na₂SO₄, filtered and concentrated in vacuo. The residue was purified by flash column chromatography on silica gel (dichloromethane/methanol=50:1) to afford the desired product (1.96 g, 76% yield).

tert-Butyl-4-(2-chloro-5-methoxy-[1,1'-biphenyl]-4-carbonyl)piperazine-1-carboxylate A mixture of tert-butyl 4-(5-chloro-4-iodo-2-methoxybenzoyl)piperazine-1-carboxylate (300 mg, 0.56 mmol), phenylboronic acid (82 mg, 0.67 mmol), Pd(PPh₃)₄ (129 mg, 0.1 mmol), Na₂CO₃(180 mg, 1.68 mmol) in 1,4-dioxane (10 mL) and water (2 mL) was stirred at reflux under argon for 16 h. The mixture was allowed to cool to room temperature and concentrated in vacuo. The residue was purified by flash column chromatography on silica gel (petroleum ether/ethyl acetate=30:1) to afford the desired product (219 mg, 80% yield).

1-(4-(2-Chloro-5-hydroxy-[1,1'-biphenyl]-4-carbonyl)piperazin-1-yl)prop-2-en-1-one (III-42)

The title compound was prepared from tert-butyl-4-(2-chloro-5-methoxy-[1,1'-biphenyl]-4-carbonyl)piperazine-1-carboxylatein three steps according to the procedure described in Example 33. ¹H NMR (400 MHz, DMSO-d6) δ: 10.40 (s, 1H), 7.50-7.41 (m, 5H), 7.35 (s, 1H), 6.89 (s, 1H), 6.84 (m, 1H), 6.17-6.13 (d, 1H), 5.73-5.71 (m, 1H), 3.63 (s, 6H), 3.30 (s, 2H). ESI-MS m/z: 371.2 [M+H]⁺.

Example 55

Synthesis of 1-(3-(4-(2-(4-chloro-2-hydroxy-5-isopropylphenylamino)acetyl)piperazin-1-yl)azetidin-1-yl)prop-2-en-1-one (II-50)

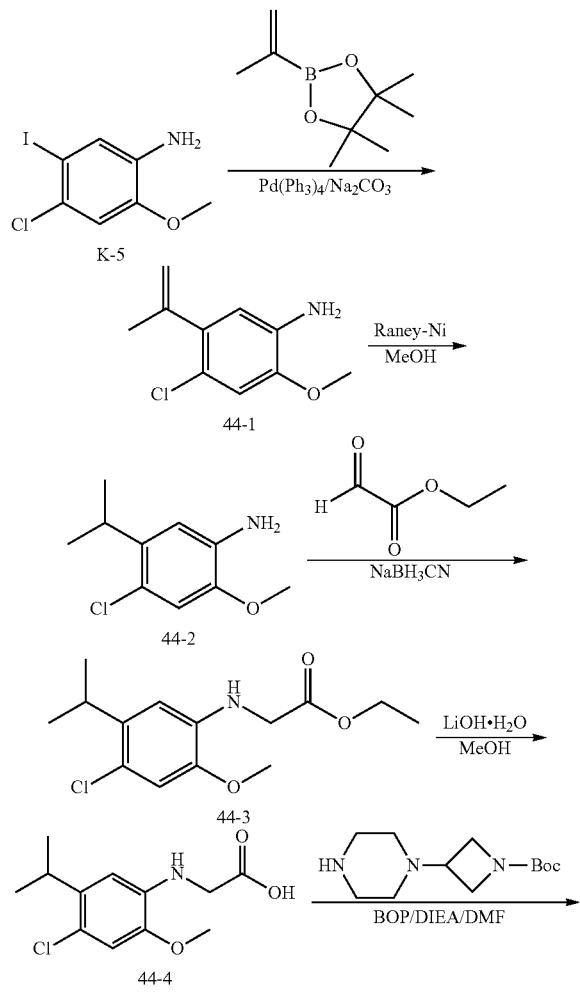

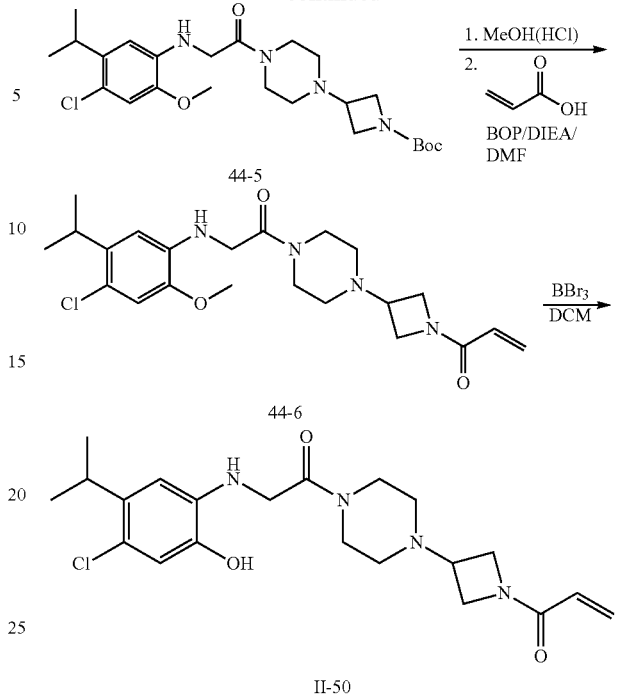

4-Chloro-2-methoxy-5-(prop-1-en-2-yl)benzenamine

A mixture of 4-chloro-5-iodo-2-methoxybenzenamine (1.0 g, 3.53 mmol), 4,4,5,5-tetramethyl-2-(prop-1-en-2-yl)-1,3,2-dioxaborolane (889 mg, 5.29 mmol), Pd(PPh₃)₄ (363 mg, 0.353 mmol), Na₂CO₃ (1.12 g, 10.6 mmol) in DME (10 mL) and water (3 mL) was stirred at reflux under argon for 6 h. The reaction mixture was allowed to cool to RT and extracted with ethyl acetate. The organic layer was washed with brine, dried over Na₂SO₄ and concentrated in vacuo. The residue was purified by flash column chromatography on silica gel (5% petroleum ether/ethyl acetate) to afford the desired product (173 mg, 25% yield) as an off-white solid. ESI-MS m/z: 198.5[M+H]⁺.

4-Chloro-5-isopropyl-2-methoxybenzenamine

A mixture of 4-chloro-2-methoxy-5-(prop-1-en-2-yl)benzenamine (160 mg, 0.81 mmol), Raney-Ni (20 mg) in MeOH (5 mL) was stirred at RT under H₂ (1 atm) atmosphere for 8 h. The mixture was filtered and the filtrate was concentrated in vacuo to afford the desired product (150 mg, 93% yield).

tert-Butyl3-(4-(2-(4-chloro-5-isopropyl-2-methoxyphenylamino)acetyl)piperazin-1-yl)azetidine-1-carboxylate The title compound was prepared from 4-chloro-5-isopropyl-2-methoxybenzenamine in three steps according to the procedure described in Example 45.

1-(3-(4-(2-(4-Chloro-5-isopropyl-2-methoxyphenylamino)acetyl)piperazin-1-yl)azetidin-1-yl)prop-2-en-1-one A mixture of tert-butyl 3-(4-(2-(4-chloro-5-isopropyl-2-methoxyphenylamino)acetyl)piperazin-1-yl)azetidine-1- carboxylate (102 mg, 0.212 mmol) in HCl/MeOH (2.86 M, 5 mL) was stirred at RT for 1 h. The mixture was concentrated in vacuo to afford the crude product, the crude was dissolved in DMF (5 mL) at RT, acrylic acid (17 mg, 0.233 mmol), BOP (113 mg, 0.254 mmol) and DIEA (82 mg, 0.636 mmol) were added and the resulting mixture was stirred at RT for 1 h. The mixture was partitioned between ethyl acetate and water. The organic layer was washed brine, dried over MgSO$_4$, filtered and concentrated in vacuo. The residue was purified by flash column chromatography on silica gel (dichloromethane/methanol=50:1) to afford the desired product (77 mg, 85% yield, 2 steps). ESI-MS m/z: 435.4 [M+H]$^+$.

1-(3-(4-(2-(4-Chloro-2-hydroxy-5-isopropylphenylamino)acetyl)piperazin-1-yl)azetidin-1-yl)prop-2-en-1-one (II-50)

To a solution of 1-(3-(4-(2-(4-chloro-5-isopropyl-2-methoxyphenylamino)acetyl)piperazin-1-yl)azetidin-1-yl)prop-2-en-1-one (77 mg, 0.18 mmol) in DCM (15 mL) at −60° C., BBr$_3$ (443 mg, 1.8 mmol) was added dropwise and the resulting mixture was stirred at RT for 1 h. The mixture was cooled to −60° C., MeOH was added dropwise and then basified with Et$_3$N to adjust the pH to 8-9. The mixture was poured into water and extracted with dichloromethane. The organic layer was dried over anhydrous Na$_2$SO$_4$, filtered and concentrated in vacuo. The residue was purified by flash column chromatography on silica gel (dichloromethane/methanol=50:1) to afford the desired product (25 mg, 33% yield). $^1$H NMR (400 MHz, DMSO-d6) δ: 9.50 (bs, 1H), 6.62 (s, 1H), 6.470 (s, 1H), 6.30 (m, 1H), 6.10 (dd, J=2.4, 17.2 Hz, 1H), 5.68 (dd, J=2.0, 10.4 Hz, 1H), 5.14 (m, 1H), 4.25 (m, 1H), 4.06 (m, 1H), 3.96 (m, 1H), 3.91 (m, 2H), 3.78 (m, 1H), 3.54 (m, 4H), 3.17 (m, 2H), 2.35 (m, 4H), 1.21 (m, 6H). ESI-MS m/z: 421.4 [M+H]$^+$.

Example 56

Synthesis of 1-(1-acryloylazetidin-3-yl)-4-(2-(4-chloro-5-cyclopropyl-2-hydroxyphenylamino)acetyl)piperazine-2-carboxamide (II-51)

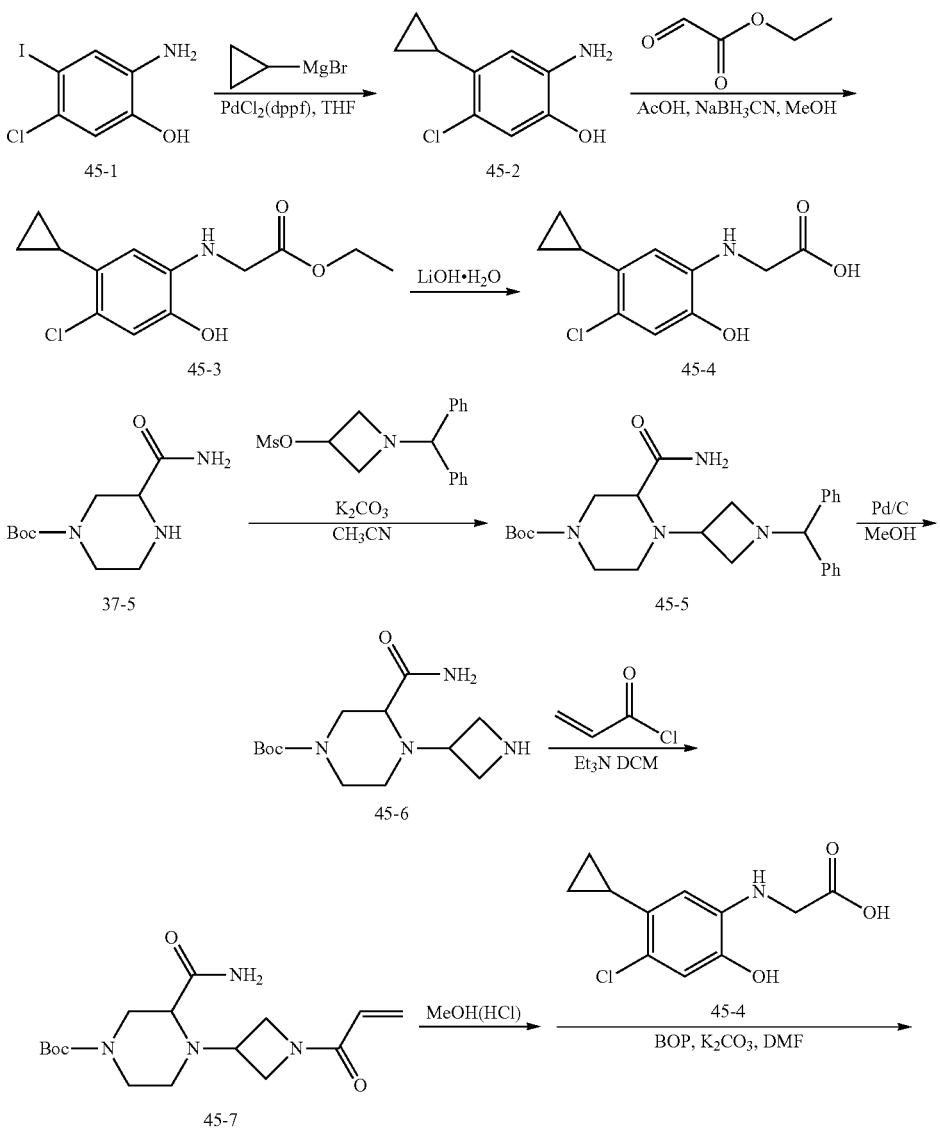

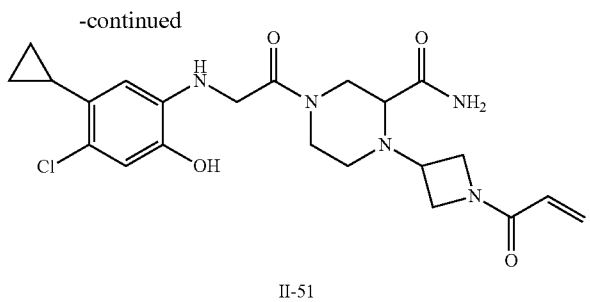

II-51

2-Amino-5-chloro-4-cyclopropylphenol

To a mixture of 2-amino-5-chloro-4-iodophenol (500 mg, 1.9 mmol), PdCl$_2$(dppf) (136 mg, 0.19 mmol) in THF (10 mL) under argon at RT, cyclopropylmagnesium bromide (16 mL, 11.4 mmol, 0.7 M in THF) was added and the mixture was stirred at reflux for 15 h. The mixture was allowed to cool to RT, and partitioned between ethyl acetate and water. The organic layer was washed with brine, dried over Na$_2$SO$_4$ and concentrated. The residue was purified by flash column chromatography on silica gel (10-20% ethyl acetate/hexanes) to afford the desired product (220 mg, 63% yield) as a brown solid. $^1$H NMR (400 MHz, DMSO-d6) δ: 9.27 (s, 1H), 6.62 (s, 1H), 6.22 (s, 1H), 4.53 (s, 2H), 1.89-1.93 (m, 1H), 0.83-0.87 (m, 2H), 0.46-0.49 (m, 2H).

Ethyl 2-(4-chloro-5-cyclopropyl-2-hydroxyphenylamino)acetate

To a solution of 2-amino-5-chloro-4-cyclopropylphenol (200 mg, 1.01 mmol) in MeOH (20 mL) at RT, AcOH (3 drops) and ethyl glyoxalate (416 mg, 2.02 mmol, 50% in toluene) were added. The mixture was stirred at RT for 2 h and then sodium cyanoborohydride (190 mg, 3.03 mmol) was added to the mixture. The resulting mixture was stirred at 40° C. for 15 h. The mixture was allowed to cool to RT and partitioned between ethyl acetate and water. The organic layer was washed with brine, dried over Na$_2$SO$_4$ and concentrated. The residue was purified by flash column chromatography on silica gel (10-20% methanol/dichloromethane) to afford the desired product (290 mg, 100% yield) as a solid. $^1$H NMR (400 MHz, DMSO-d6) δ: 9.63 (s, 1H), 6.66 (s, 1H), 5.93 (s, 1H), 5.07 (t, J=6.4 Hz, 1H), 4.12 (q, J=7.2 Hz, 2H), 3.91 (d, J=6.4 Hz, 2H), 1.92-1.97 (m, 1H), 1.20 (t, J=6.8 Hz, 2H), 0.84-0.87 (m, 2H), 0.51-0.55 (m, 2H).

2-(4-Chloro-5-cyclopropyl-2-hydroxyphenylamino)acetic acid

To a solution of ethyl 2-(4-chloro-5-cyclopropyl-2-hydroxyphenylamino)acetate (290 mg, 0.89 mmol) in of 4:1 mixture of tetrahydrofuran and water (30 mL) at RT, LiOH.H$_2$O (226 mg, 5.34 mmol) was added and the resulting mixture was stirred for 2 h at 60° C. The mixture was acidified with aqueous HCl (1 N) to adjust the pH to 3-5 and then extracted with ethyl acetate. The organic layer was washed with brine, dried over anhydrous Na$_2$SO$_4$, filtered and concentrated in vacuo to afford the product (100 mg, 47% yield). $^1$H NMR (400 MHz, DMSO-d6) δ: 9.64 (s, 1H), 6.66 (s, 1H), 5.96 (s, 1H), 3.81 (s, 2H), 1.89-1.96 (m, 1H), 0.84-0.87 (m, 2H), 0.54-0.56 (m, 2H).

tert-Butyl 4-(1-benzhydrylazetidin-3-yl)-3-carbamoylpiperazine-1-carboxylate A mixture of 1-benzhydrylazetidin-3-yl methanesulfonate (2.69 g, 8.5 mmol), K$_2$CO$_3$ (1.76 g, 12.8 mmol), tert-butyl 3-carbamoylpiperazine-1-carboxylate (1.95 g, 8.5 mmol) in CH$_3$CN (40 mL) was stirred at reflux for 16 h. The mixture was partitioned between ethyl acetate and water. The organic layer was washed with water and brine, dried over Na$_2$SO$_4$, and concentrated in vacuo. The residue was purified by flash column chromatography on silica gel (dichloromethane/methanol=50:1) to afford the desired product. (2.08 g, 54% yield).

tert-Butyl 4-(azetidin-3-yl)-3-carbamoylpiperazine-1-carboxylate

A mixture of 4-chloro-2-methoxy-5-(prop-1-en-2-yl)benzenamine (1 g, 2.22 mmol), Pd/C (300 mg) in MeOH (25 mL) was stirred at 50° C. under H$_2$ (1 atm) atmosphere for 12 h. The mixture was cooled and filtered. The filtrate was concentrated in vacuo to afford the desired product (640 mg, 100% yield).

tert-Butyl 4-(1-acryloylazetidin-3-yl)-3-carbamoylpiperazine-1-carboxylate

To a solution of tert-butyl 4-(azetidin-3-yl)-3-carbamoylpiperazine-1-carboxylate (640 mg, 2.22 mmol) and Et$_3$N (463 mg, 4.58 mmol) in DCM (10 mL) at 0° C., acryloyl chloride (248 mg, 2.74 mmol) was added dropwise and the resulting mixture was stirred at RT for 1.5 h. The mixture was partitioned between dichloromethane and saturated NaHCO$_3$ solution. The organic layer was washed with saturated brine, dried over Na$_2$SO$_4$ and concentrated in vacuo. The residue was purified by flash column chromatography on silica gel (dichloromethane/methanol=50:1) to afford the desired product (350 mg, 47% yield).

1-(1-acryloylazetidin-3-yl)-4-(2-(4-chloro-5-cyclopropyl-2-hydroxyphenylamino)acetyl)piperazine-2-carboxamide (II-51)

A mixture of tert-butyl 4-(1-acryloylazetidin-3-yl)-3-carbamoylpiperazine-1-carboxylate (120 mg, 0.35 mmol) in HCl/MeOH (2.86 M, 10 mL) was stirred at RT for 1 h. The mixture was concentrated in vacuo to afford the crude residue. It was dissolved in DMF (5 mL) at 0° C., 2-(4-chloro-5-cyclopropyl-2-hydroxyphenylamino)acetic acid (31 mg, 0.427 mmol), BOP (206 mg, 0.466 mmol) and K$_2$CO$_3$ (150 mg, 1.164 mmol) were added and the resulting mixture was stirred at RT for 1 h. The mixture was partitioned between ethyl acetate and water. The organic layer was washed brine, dried over MgSO$_4$, filtered and concentrated in vacuo. The residue was purified by flash column chromatography on silica gel (dichloromethane/methanol=20:1) to afford the desired product (126 mg, 75% yield, 2 steps). $^1$H NMR (400 MHz, DMSO-d6) δ: 9.63 (bs, 1H), 7.53 (d, 1H), 7.26-6.94 (m, 2H), 6.67 (s, 1H), 6.34-6.27 (m, 1H), 6.10 (m, 2H), 5.68 (d, J=10.4, 1H), 5.08 (m, 1H), 4.30 (m, 2H), 3.93 (m, 6H), 3.52 (m, 2H), 3.29 (m, 1H), 3.15 (m, 1H), 3.06 (m, 1H), 2.47 (m, 1H), 1.98 (m, 1H), 0.87 (m, 2H), 0.64 (m, 2H). ESI-MS m/z: 462.5 [M+H]$^+$.

Example 57

Synthesis of 1-(3-(4-(2-(4-chloro-5-cyclopropyl-2-hydroxyphenylamino)acetyl)-2-(hydroxymethyl)piperazin-1-yl)azetidin-1-yl)prop-2-en-1-one (II-54)

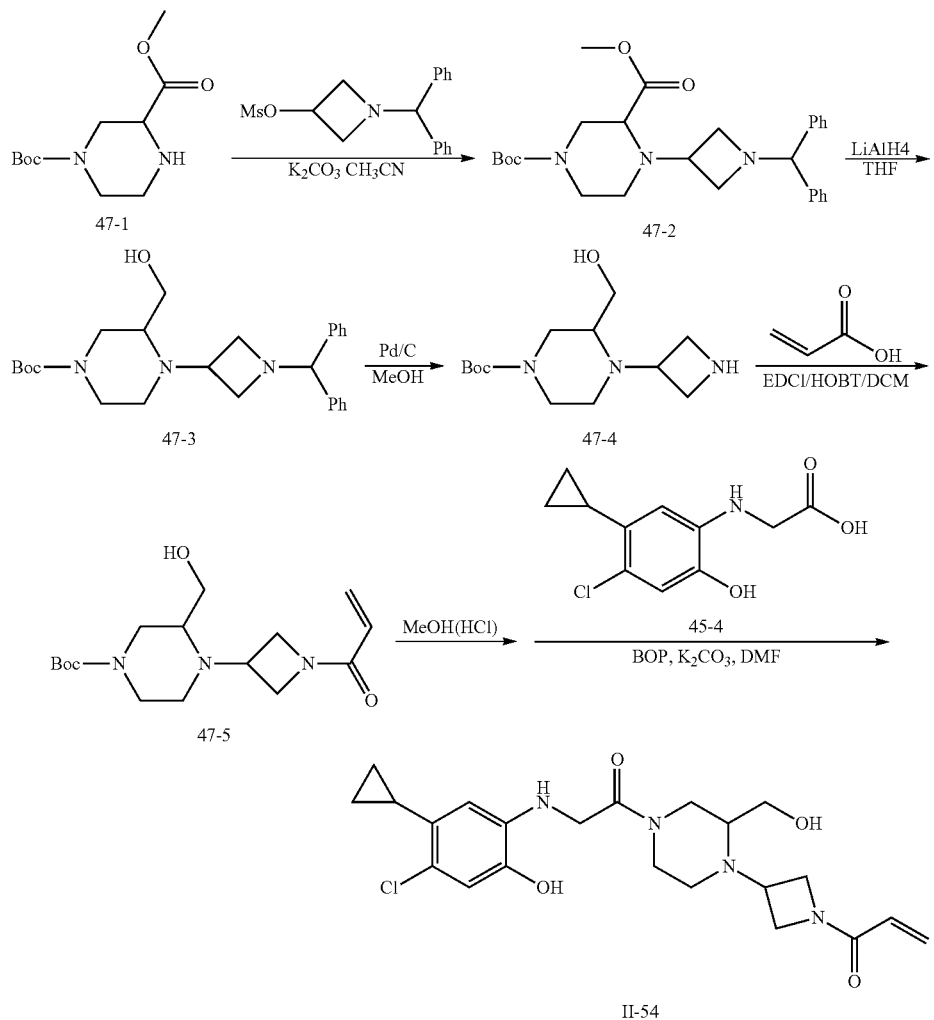

1-tert-Butyl 3-methyl 4-(1-benzhydrylazetidin-3-yl)piperazine-1,3-dicarboxylate

A mixture of 1-benzhydrylazetidin-3-yl methanesulfonate (2.4 g, 7.56 mmol), tert-butyl methyl piperazine-1,3-dicarboxylate (1.85 g, 7.56 mmol), K$_2$CO$_3$ (1.6 g, 11.34 mmol) in CH$_3$CN (40 mL) was stirred at reflux for 16 h. The mixture was partitioned between ethyl acetate and water. The organic layer was washed with water and brine, dried over Na$_2$SO$_4$, and concentrated in vacuo. The residue was purified by flash column chromatography on silica gel (10% petroleum ether/ethyl acetate) to afford the desired product (1.85 g, 51% yield).

tert-Butyl 4-(1-benzhydrylazetidin-3-yl)-3-(hydroxymethyl)piperazine-1-carboxylate To a mixture of LiAlH$_4$ (500 mg, 13.5 mmol) in THF (40 mL) at −40° C. under argon, a solution of 1-tert-butyl 3-methyl 4-(1-benzhydrylazetidin-3-yl) piperazine-1,3-dicarboxylate (1.8 g, 3.87 mmol) in THF (10 mL) was added dropwise. The reaction mixture was stirred at −5° C. to 5° C. for 1 h and cooled to −20° C. Then water (2 mL) and NaOH (15%) aqueous were added. The resulting mixture was stirred for 15 min. The solid was filtered, and the cake rinsed with ethyl acetate. The combined filtrate was dried over Na$_2$SO$_4$ and concentrated in vacuo to afford the product (1.6 g, 94% yield).

1-(3-(4-(2-(4-Chloro-5-cyclopropyl-2-hydroxyphenylamino)acetyl)-2-(hydroxymethyl)piperazin-1-yl)azetidin-1-yl)prop-2-en-1-one (II-54)

The title compound was prepared from 4-(2-(4,5-dichloro-2-methoxyphenylamino)acetyl)piperazine-2-carbonitrile in four steps according to the procedure described in Example 47. $^1$H NMR (400 MHz, DMSO-d6) δ: 9.68 (bs, 1H), 6.67 (s, 1H), 6.35-6.27 (m, 1H), 6.12-6.05 (m, 2H), 5.67 (dd, J=1.6, 10.4 Hz, 1H), 5.11 (m, 1H), 4.82-4.63 (m, 1H), 4.24 (m, 1H), 4.13 (m, 1H), 3.95 (m, 1H), 3.88 (m, 2H), 3.85 (m, 1H), 3.77-3.67 (m, 2H), 3.20 (m, 1H), 3.15 (m, 1H), 2.76-2.60 (m, 2H), 2.40 (m, 1H), 1.95 (m, 1H), 0.87 (m, 2H), 0.62 (m, 2H). ESI-MS m/z: 449.4 [M+H]$^+$.

Example 58

Synthesis of 1-(3-(4-(2-(5,6-dichloro-1H-indol-3-yl)acetyl)piperazin-1-yl)azetidin-1-yl)prop-2-en-1-one (II-61)

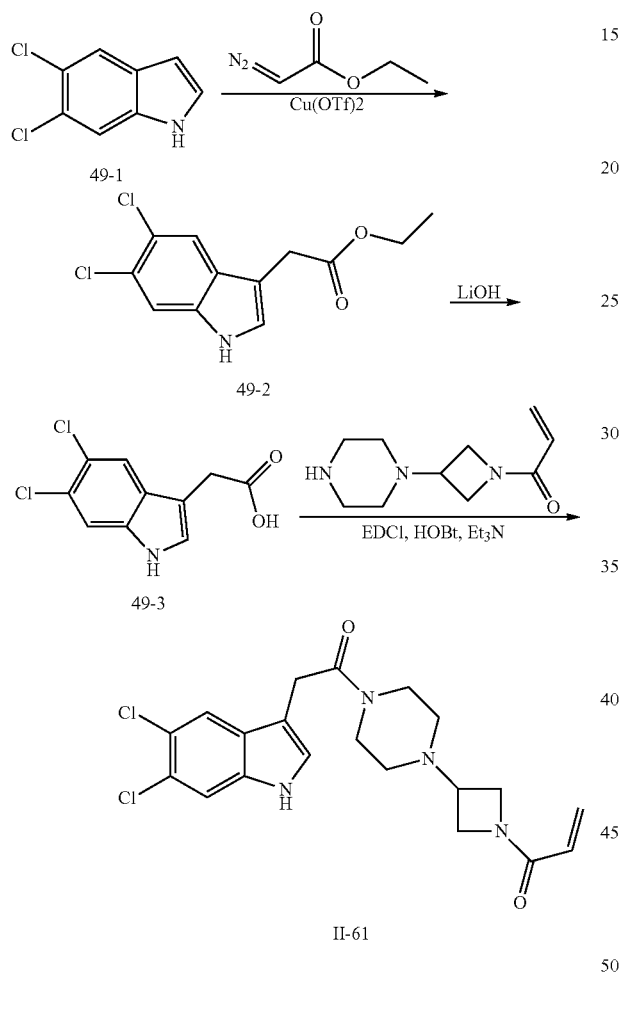

Ethyl 2-(5,6-dichloro-1H-indol-3-yl)acetate

To a mixture of 5,6-dichloro-1H-indole (1.0 g, 5.37 mmol), Cu(OTf)$_2$ (194 mg, 0.537 mmol) in DCM (15 mL) at RT, ethyl 2-diazoacetate (918 mg, 8.05 mmol) was added dropwise. The resulting mixture was stirred at RT for 16 h, quenched with water, and then extracted dichloromethane. The organic layer was dried over Na$_2$SO$_4$, filtered and concentrated in vacuo. The residue was purified by Prep-HPLC to afford the desired product (120 mg, 8.2% yield) as light yellow solid. ESI-MS m/z: 272.1 [M+H]$^+$.

2-(5,6-Dichloro-1H-indol-3-yl)acetic acid

A mixture of ethyl 2-(5,6-dichloro-1H-indol-3-yl)acetate (120 mg, 0.44 mmol), LiOH (90 mg, 2.20 mmol) in THF (3 mL) and H$_2$O (1 mL) was stirred at RT for 16 h. The solution was poured into water, adjusted pH to 3-4 with IN HCl and extracted with ethyl acetate. The organic layer was dried over Na$_2$SO$_4$ and concentrated in vacuo to afford the desired product (90 mg, 84.5% yield) as a yellow solid.

1-(3-(4-(2-(5,6-Dichloro-1H-indol-3-yl)acetyl)piperazin-1-yl)azetidin-1-yl)prop-2-en-1-one (II-61)

A mixture of 2-(5,6-dichloro-1H-indol-3-yl)acetic acid (90 mg, 0.372 mmol), 1-(3-(piperazin-1-yl)azetidin-1-yl)prop-2-en-1-one (87 mg, 0.446 mmol), EDCI.HCl (107 mg, 0.558 mmol), HOBt (75 mg, 0.558 mmol) in DMF (3 mL) at 0° C., Et$_3$N (112 mg, 1.11 mmol) was added. The resulting mixture was stirred at RT for 16 h. The mixture was partitioned between ethyl acetate and water. The organic layer was washed with brine, dried over Na$_2$SO$_4$ and concentrated in vacuo. The residue was purified by flash column chromatography on silica gel (dichloromethane/methanol=30:1) to afford the desired product (12 mg, 7.66% yield) as an off-white solid. $^1$H NMR (400 MHz, DMSO-d6) δ: 11.19 (bs, 1H), 7.79 (s, 1H), 7.59 (s, 1H), 7.35 (d, 1H), 6.28 (dd, J=9.6, 16.8 Hz, 1H), 6.09 (dd, J=2.4, 17.2 Hz, 1H), 5.66 (dd, J=2.4, 10.4 Hz, 1H), 4.21-4.18 (m, 1H), 4.02-3.98 (m, 1H), 3.93-3.88 (m, 1H), 3.78 (s, 2H), 3.74-3.70 (m, 1H), 3.53-3.47 (m, 4H), 3.10-3.07 (m, 1H), 2.25-2.19 (m, 4H). ESI-MS m/z: 423.3 [M+1]$^+$.

Example 59

Synthesis of 1-(3-(4-(2-(5-chloro-4-ethyl-2-hydroxyphenylamino)acetyl)piperazin-1-yl)azetidin-1-yl)prop-2-en-1-one (II-52)

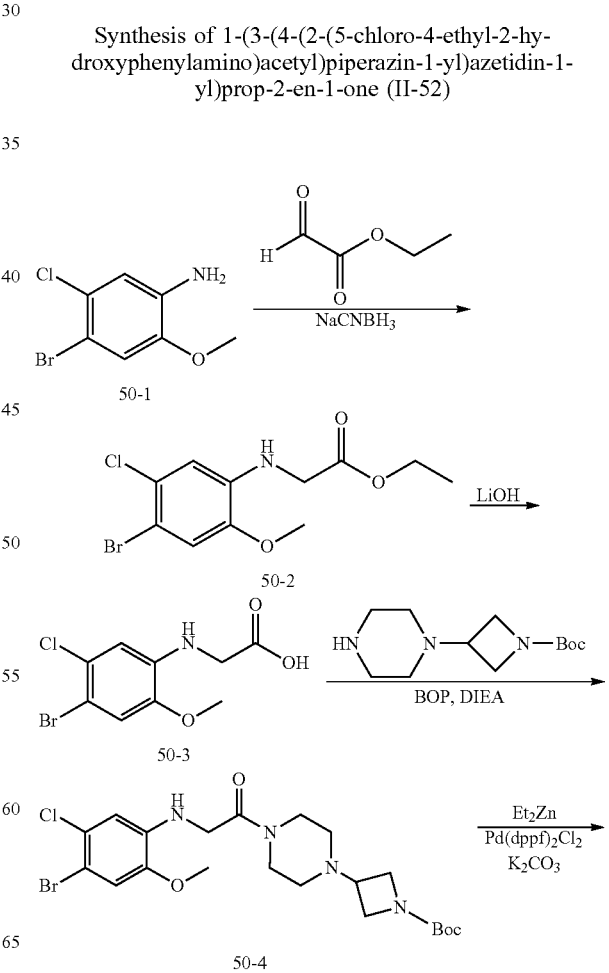

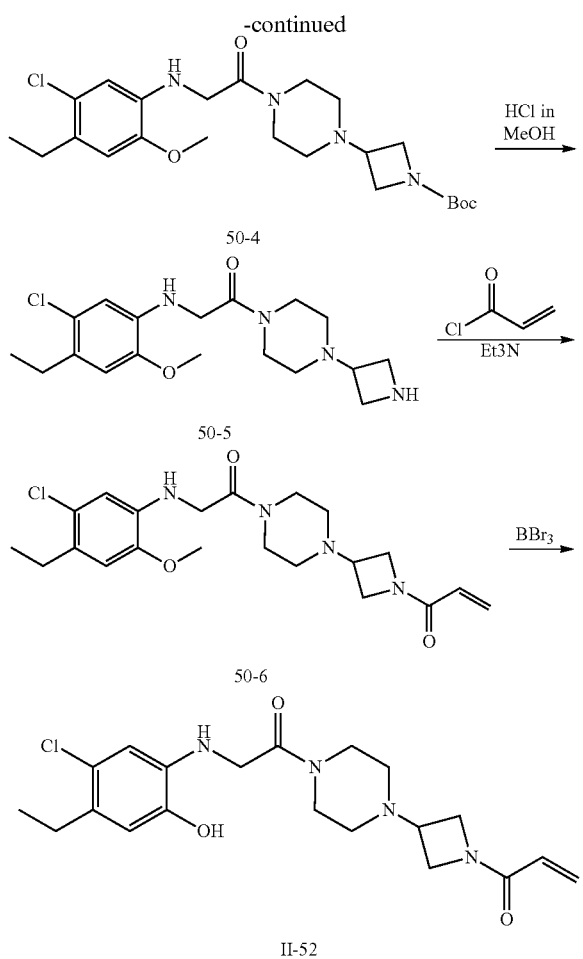

tert-Butyl 3-(4-(2-(4-bromo-5-chloro-2-methoxyphenylamino)acetyl)piperazin-1-yl)azetidine-1-carboxylate The title compound was prepared from 4-bromo-5-chloro-2-methoxybenzenamine in three steps according to the procedure described in Example 43.

tert-Butyl 3-(4-(2-(5-chloro-4-ethyl-2-methoxyphenylamino)acetyl)piperazin-1-yl)azetidine-1-carboxylate To a mixture of tert-butyl 3-(4-(2-(4-bromo-5-chloro-2-methoxyphenylamino)acetyl)piperazin-1-yl)azetidine-1-carboxylate (100 mg, 0.193 mmol), Pd(dppf)$_2$Cl$_2$ (29 mg, 0.04 mmol) and K$_2$CO$_3$ (55 mg, 0.386 mmol) in DMF (10 mL) at RT, Et$_2$Zn (0.8 mL, 0.8 mmol, 1.0 M in hexane) was added. The resulting mixture was stirred at 80° C. for 16 h. The mixture was partitioned between ethyl acetate and water. The organic layer was washed with brine, dried over Na$_2$SO$_4$ and concentrated in vacuo. The residue was purified by flash column chromatography on silica gel (dichloromethane/methanol=50:1) to afford the crude product (100 mg). ESI-MS m/z: 467.5 [M+1]$^+$.

1-(3-(4-(2-(5-Chloro-4-ethyl-2-hydroxyphenylamino)acetyl)piperazin-1-yl)azetidin-1-yl)prop-2-en-1-one (V-52)

The title compound was prepared from tert-butyl 3-(4-(2-(5-chloro-4-ethyl-2-methoxyphenylamino)acetyl)piperazin-1-yl)azetidine-1-carboxylate in 3 steps according to the procedure described in Example 33. $^1$H NMR (400 MHz, DMSO-d6) δ: 9.6 (s, 1H), 6.6 (s, 1H), 6.5 (s, 1H), 6.3 (dd, J=10.4, 17.2 Hz, 1H), 6.1 (dd, J=2.4, 17.2 Hz, 1H), 5.7 (dd, J=2.4, 10.4 Hz, 1H), 5.1 (t, J=4.4 Hz, 1H), 4.2 (t, J=8 Hz, 1H), 4.1 (dd, J=4.8, 8.8 Hz, 1H), 3.95 (dd, J=7.2, 10.0 Hz, 1H), 3.9 (d, J=4.4 Hz, 2H), 3.8 (dd, J=4.8, 10.4 Hz, 1H), 3.6-3.5 (m, 4H), 3.2-3.1 (m, 1H), 3.1-3.0 (m, 1H), 2.5-2.3 (m, 4H), 1.1 (t, J=7.2 Hz, 3H); ESI-MS m/z: 407.4 [M+H]$^+$.

Example 60

Synthesis of 1-(3-(4-(2-(4-chloro-5-ethyl-2-hydroxyphenylamino)acetyl)piperazin-1-yl)azetidin-1-yl)prop-2-en-1-one (II-55)

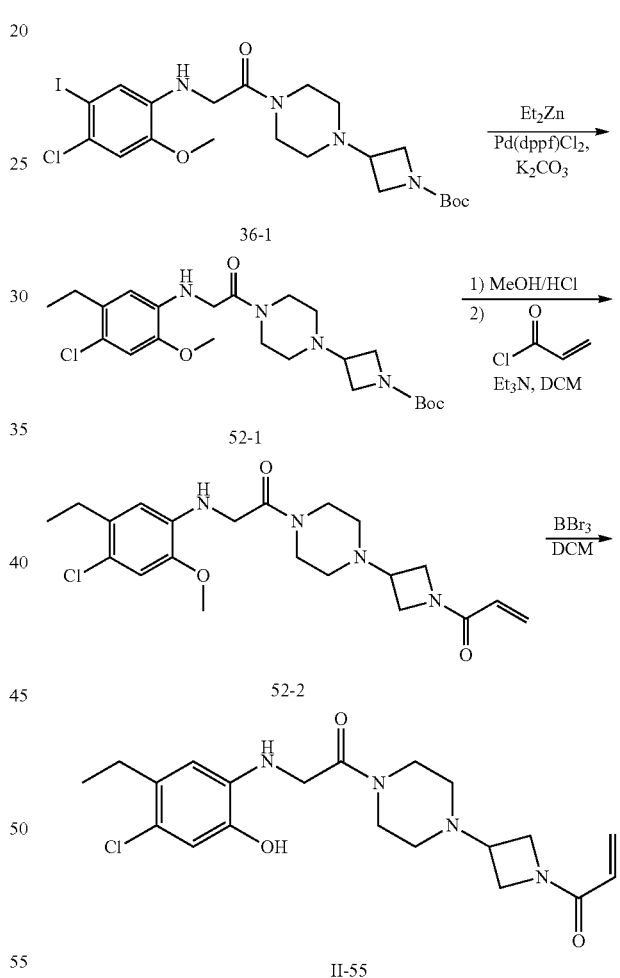

tert-Butyl 3-(4-(2-((4-chloro-5-ethyl-2-methoxyphenyl)amino)acetyl)piperazin-1-yl) azetidine-1-carboxylate The title compound was prepared from tert-butyl 3-(4-(2-(4-chloro-5-iodo-2-methoxyphenylamino)acetyl)piperazin-1-yl)azetidine-1-carboxylate in one step according to the procedure described in Example 52.

1-(3-(4-(2-(4-chloro-5-ethyl-2-hydroxyphenylamino)
acetyl)piperazin-1-yl)azetidin-1-yl)prop-2-en-1-one
(II-55)

The title compound was prepared from tert-butyl3-(4-(2-((4-chloro-5-ethyl-2-methoxyphenyl)amino)acetyl)piperazin-1-yl) azetidine-1-carboxylate in three steps according to the procedure described in Example 33. $^1$H NMR (400 MHz, DMSO-d6) δ:9.67 (s, 1H), 6.66 (s, 1H), 6.47 (s, 1H), 6.30 (dd, J=10.5, 16.9 Hz, 1H), 6.12 (dd, J=1.7, 16.7 Hz, 1H), 5.69 (dd, J=1.7, 16.7 Hz, 1H), 5.1 (m, 1H), 4.26 (m, 1H), 4.07 (m, 1H), 3.96 (m, 1H), 3.88 (d, J=4.4, 2H), 3.78 (m, 1H), 3.53 (m, 4H), 3.17 (m, 1H), 2.54 (m, 2H), 2.37 (m, 4H), 1.14 (m, 3H). ESI-MS m/z: 407.3[M+H]$^+$.

Example 61

Synthesis of 1-(3-(4-(2-(4-chloro-2-hydroxy-5-(2,2,2-trifluoroethyl)phenylamino)acetyl)piperazin-1-yl)azetidin-1-yl)prop-2-en-1-one (II-57)

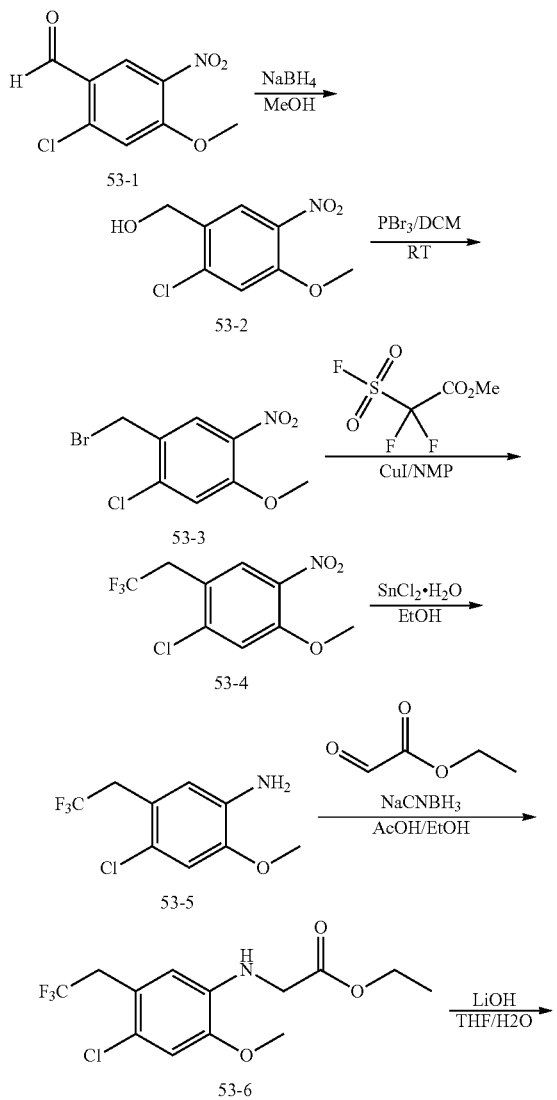

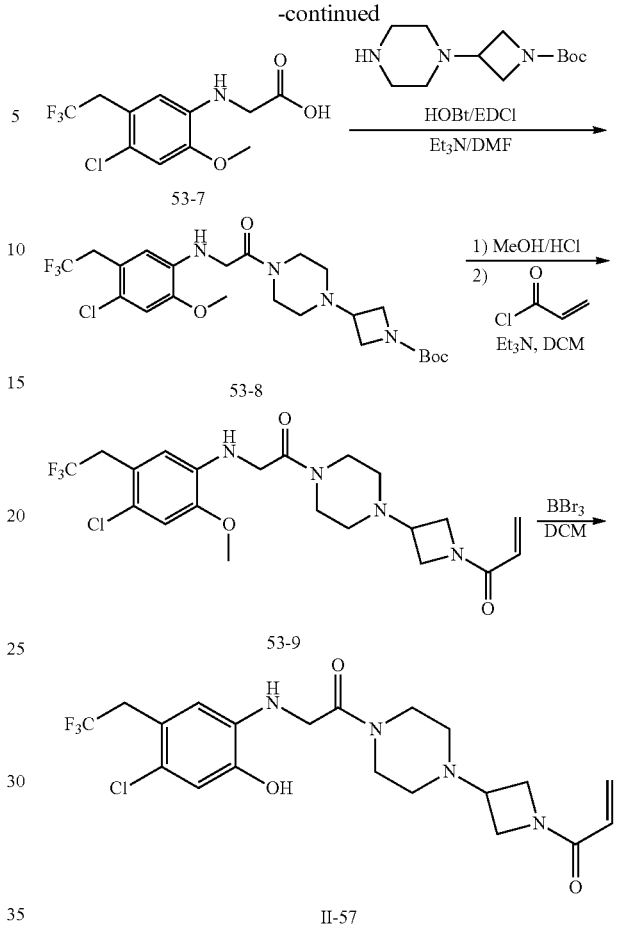

(2-Chloro-4-methoxy-5-nitrophenyl)methanol

To a solution of 2-chloro-4-methoxy-5-nitrobenzaldehyde (6.0 g, 29 mmol) in MeOH at 0° C. (50 mL), sodium borohydride (4.45 g, 117 mmol) was added in portions and the resulting mixture was stirred at RT for 30 min. The mixture was concentrated in vacuo. The residue was dissolved in ethyl acetate, washed with brine, dried over Na$_2$SO$_4$ and concentrated in vacuo. The residue was purified by flash column chromatography on silica gel (petroleum ether/ethyl acetate=10:1) to afford the desired product (5.0 g, 78.4% yield).

1-(Bromomethyl)-2-chloro-4-methoxy-5-nitrobenzene

To a solution of (2-chloro-4-methoxy-5-nitrophenyl)methanol (5.0 g, 23 mmol) in dichloromethane (50 mL) at 0° C., tribromophosphine (3.08 g, 11.5 mmol) was added in portions and the resulting mixture was stirred at RT for 2 h. The mixture was poured into ice-water and extracted with dichloromethane. The organic layer was washed with brine, dried over Na$_2$SO$_4$ and concentrated in vacuo. The residue was purified by flash column chromatography on silica gel (petroleum ether/ethyl acetate=10:1) to afford the desired product (3.5 g, 54.2% yield).

1-Chloro-5-methoxy-4-nitro-2-(2,2,2-trifluoroethyl)benzene

A mixture of (2-chloro-4-methoxy-5-nitrophenyl)methanol (3.5 g, 12.5 mmol), methyl 2,2-difluoro-2-(fluorosulfonyl)acetate (4.8 g, 25 mmol), copper iodide (617 mg, 3.25 mmol) in NMP (20 mL) was stirred at 80° C. for 24 h under Argon. After cooled to RT, the reaction mixture was dissolved in ethyl acetate, washed with brine, dried over $Na_2SO_4$ and concentrated in vacuo. The residue was purified by flash column chromatography on silica gel (petroleum ether/ethyl acetate=100:1) to afford the desired product (1.2 g, 36.4% yield). $^1$H NMR (400 MHz, DMSO-d6) δ: 8.15 (s, 1H), 7.60 (s, 1H), 3.98 (s, 3H), 3.89 (dd, J=1.7, 11.2 Hz, 2H).

4-Chloro-2-methoxy-5-(2,2,2-trifluoroethyl)aniline

A mixture of 1-chloro-5-methoxy-4-nitro-2-(2,2,2-trifluoroethyl)benzene (1.2 g, 4.51 mmol), tin(II) chloride dehydrate (5.0 g, 22.5 mmol) in EtOH (20 mL) was stirred at reflux for 2 h. After cooled to RT, the reaction mixture was added saturated $NaHCO_3$ solution to adjusted pH to 7-8 and then extracted with ethyl acetate. The organic layer washed with brine, dried over $Na_2SO_4$ and concentrated in vacuo to afford the desired product (900 mg, 85% yield). $^1$H NMR (400 MHz, DMSO-d6) δ: 7.29 (s, 1H), 7.11 (s, 1H), 5.41 (s, 2H), 4.21 (s, 3H), 3.99 (dd, J=1.7, 11.2 Hz, 2H).

1-(3-(4-(2-((4-Chloro-2-hydroxy-5-(2,2,2-trifluoroethyl)phenyl)amino)acetyl)piperazin-1-yl)azetidin-1-yl)prop-2-en-1-one (II-57)

The title compound was prepared from 4-chloro-2-methoxy-5-(2,2,2-trifluoroethyl)aniline in six steps according to the procedure described in Example 48. $^1$H NMR (400 MHz, DMSO-d6) δ: 10.08 (s, 1H), 6.74 (s, 1H), 6.59 (s, 1H), 6.34 (dd, J=10.5, 16.9 Hz, 1H), 6.12 (dd, J=1.7, 16.7 Hz, 1H), 5.69 (dd, J=1.7, 16.7 Hz, 1H), 5.22 (m, 1H), 4.24 (m, 1H), 4.04 (m, 1H), 3.94 (m, 1H), 3.88 (d, J=4.4 Hz, 2H), 3.78 (m, 1H), 3.57 (m, 2H), 3.54 (m, 4H), 3.18 (m, 1H), 2.37 (m, 4H). ESI-MS m/z: 461.2[M+H]$^+$.

Example 62

Synthesis of (E)-1-(4-(1-acryloylazetidin-3-yl)piperazin-1-yl)-3-(4-chloro-5-cyclopropyl-2-hydroxyphenyl)prop-2-en-1-one (II-62)

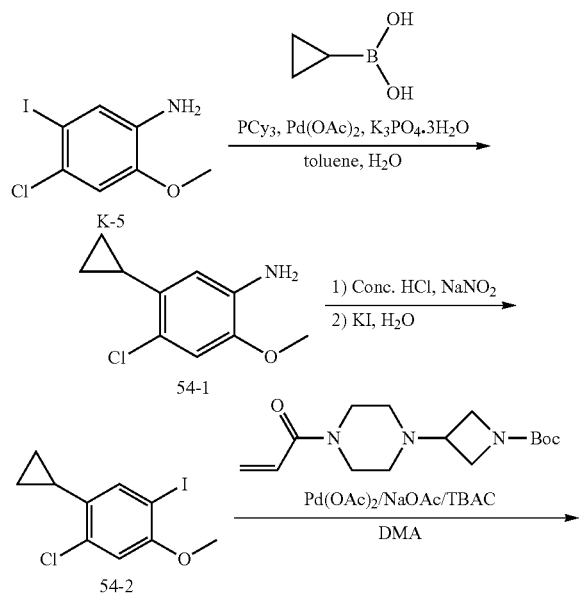

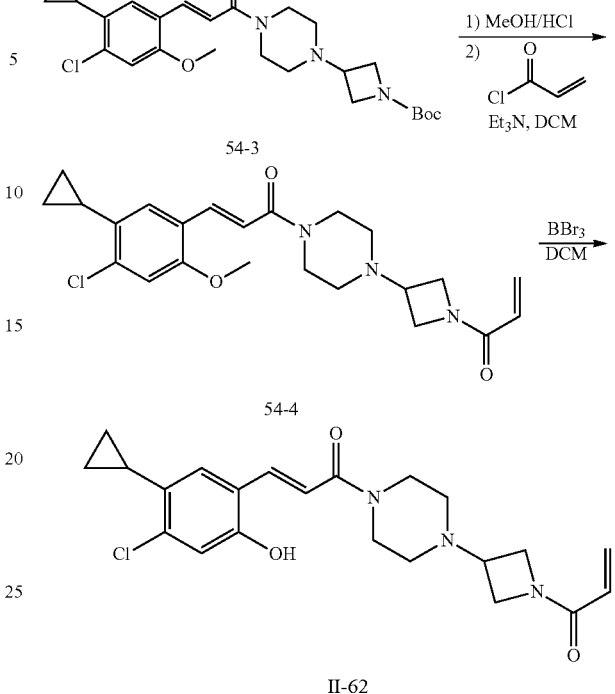

4-Chloro-5-cyclopropyl-2-methoxybenzenamine

A mixture of 4-chloro-5-iodo-2-methoxyaniline (5.0 g, 17.6 mmol), cyclopropylboronic acid (1.8 g, 21.1 mmol), $Pd(OAc)_2$ (314 mg, 1.4 mmol), tricyclohexylphosphine (500 mg, 17.6 mmol), $K_3PO_4 \cdot 3H_2O$ (16.4 g, 61.6 mmol) in toluene (62.5 mL) and $H_2O$ (3 mL) was stirred at 80° C. under argon for 16 h. The mixture was allowed to cool to RT, and then partitioned between ethyl acetate and water. The organic layer was washed with brine, dried over $Na_2SO_4$ and concentrated in vacuo. The residue was purified by flash column chromatography on silica gel (petroleum ether/ethyl acetate=10:1) to afford the desired product (3.1 g, 88.5% yield). ESI-MS m/z: 198.2[M+H]$^+$.

1-Chloro-2-cyclopropyl-4-iodo-5-methoxybenzene

To a mixture of 4-chloro-5-cyclopropyl-2-methoxyaniline (2.2 g, 11.05 mmol), conc. HCl (12 mL) and water (12 mL) at 0° C., the solution of sodium nitrate (762.8 mg, 11.05 mmol) in water (2.5 mL) was added dropwise. After stirring at 0° C. for 15 min, a solution of KI (1.83 g, 11.05 mmol) in water (5 mL) was added dropwise. The resulting mixture was stirred at RT for 4 h, poured into water (20 mL) and then extracted with dichloromethane. The organic layer was washed with brine, dried over anhydrous $Na_2SO_4$, filtered and concentrated in vacuo. The residue was purified by flash column chromatography on silica gel (0-10% ethyl acetate/ petroleum ether) to afford the desired product (680 mg, 20% yield) as a solid. $^1$H NMR (400 MHz, DMSO-d6) δ: 7.37 (s, 1H), 7.08 (s, 1H), 3.84 (s, 3H), 2.00 (m, 1H), 0.89 (m, 2H), 0.65 (m, 1H).

(E)-1-(4-(1-Acryloylazetidin-3-yl)piperazin-1-yl)-3-(4-chloro-5-cyclopropyl-2-methoxyphenyl)prop-2-en-1-one A mixture of 1-chloro-2-cyclopropyl-4-iodo-5-methoxybenzene (300 mg, 0.974 mmol), tert-butyl 3-(4-acryloylpiperazin-1-yl)azetidine-1-carboxylate (431 mg, 1.46 mmol), Pd(OAc)$_2$ (54.6 mg, 0.243 mmol), sodium acetate (239 mg, 2.92 mmol), tetrabutylammonium chloride (539 mg, 1.95 mmol) in DMF (7 mL) was stirred at 100° C. for 24 h. The mixture was partitioned between ethyl acetate and water. The organic layer was washed with brine, dried over Na$_2$SO$_4$, filtered and concentrated in vacuo to purified by silica gel (dichloromethane/methanol=40:1) to afford the desired product (350 mg, 84% yield). ESI-MS m/z: 476.2 [M+H]$^+$.

(E)-1-(4-(1-Acryloylazetidin-3-yl)piperazin-1-yl)-3-(4-chloro-5-cyclopropyl-2-hydroxyphenyl)prop-2-en-1-one (II-62)

The title compound was prepared from (E)-1-(4-(1-acryloylazetidin-3-yl)piperazin-1-yl)-3-(4-chloro-5-cyclopropyl-2-methoxyphenyl)prop-2-en-1-one in three steps according to the procedure described in Example 33. $^1$H NMR (400 MHz, DMSO-d6) δ: 10.3 (s, 1H), 7.71 (m, 1H), 7.30 (s, 1H), 7.22 (m, 1H), 6.93 (s, 1H), 6.34 (dd, J=10.5, 16.9 Hz, 1H), 6.12 (dd, J=1.7, 16.7 Hz, 1H), 5.66 (dd, J=1.7, 16.7 Hz, 1H), 4.26 (m, 1H), 4.08 (m, 1H), 3.94 (m, 1H), 3.79 (m, 1H), 3.69 (m, 2H), 3.58 (m, 2H), 3.18 (m, 1H), 2.33 (m, 4H), 1.99 (m, 1H), 0.92 (m, 2H), 0.73 (m, 2H). ESI-MS m/z: 416 [M+H]$^+$.

Example 63

Synthesis of 1-(3-(4-(2-(4-chloro-5-cyclopropyl-2-methoxyphenylthio)acetyl)piperazin-1-yl)azetidin-1-yl)prop-2-en-1-one (II-65)

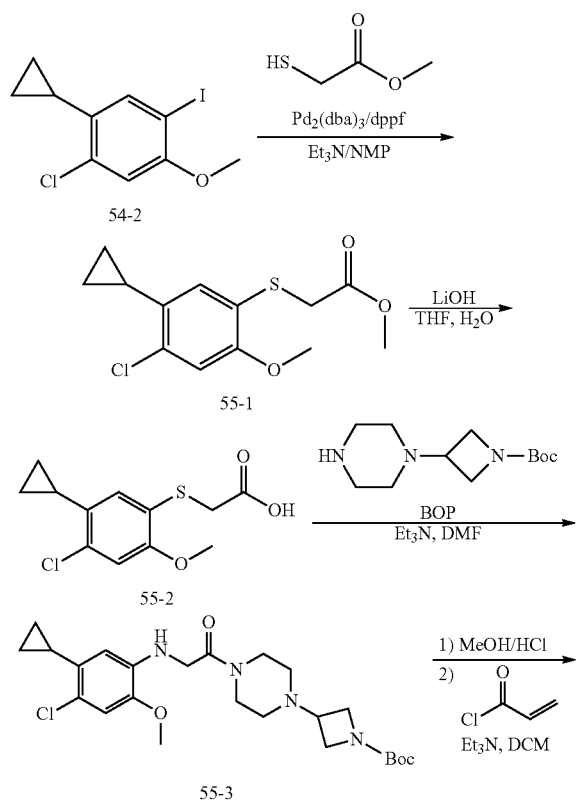

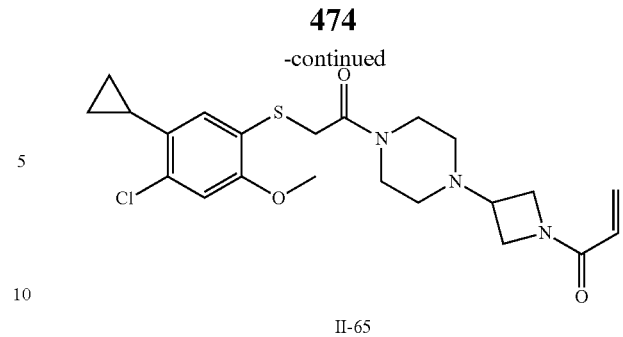

Methyl 2-((4-chloro-5-cyclopropyl-2-methoxyphenyl)thio)acetate

A mixture of 1-chloro-2-cyclopropyl-4-iodo-5-methoxybenzene (380 mg, 1.23 mmol), Pd$_2$(dba)$_3$ (56 mg, 0.061 mmol), methyl 2-mercaptoacetate (196 mg, 1.85 mmol), 1,1'-Bis(diphenylphosphino)ferrocene (136 mg, 0.246 mmol), Et$_3$N (372 mg, 3.69 mmol) in NMP (8 mL) was stirred under argon at 80° C. for 24 h. After cooled to RT, the reaction mixture was extracted with ethyl acetate. The organic layer was washed with brine, dried over Na$_2$SO$_4$ and concentrated in vacuo. The residue was purified by flash column chromatography on silica gel (petroleum ether/ethyl acetate=20:1) to afford the desired product (340 mg, 92% yield). $^1$H NMR (400 MHz, DMSO-d6) δ: 7.05 (s, 1H), 6.81 (s, 1H), 3.84 (s, 2H), 3.82 (s, 3H), 3.62 (s, 3H), 2.00 (m, 1H), 0.94 (m, 2H), 0.64 (m, 2H).

1-(3-(4-(2-(4-Chloro-5-cyclopropyl-2-methoxyphenylthio)acetyl)piperazin-1-yl)azetidin-1-yl)prop-2-en-1-one (II-65)

The title compound was prepared from methyl 2-((4-chloro-5-cyclopropyl-2-methoxyphenyl)thio)acetate in four steps according to the procedure described in Example 43. $^1$H NMR (400 MHz, DMSO-d6) δ: 7.03 (s, 1H), 6.93 (s, 1H), 6.31 (dd, J=10.5, 16.9 Hz, 1H), 6.11 (dd, J=1.7, 16.7 Hz, 1H), 5.68 (dd, J=1.7, 16.7 Hz, 1H), 4.25 (m, 1H), 4.04 (m, 1H), 3.88 (s, 2H) 3.81 (s, 3H), 3.75 (m, 1H), 3.52 (m, 4H), 3.16 (m, 1H), 2.36-2.25 (m, 4H), 2.02 (m, 1H), 0.93 (m, 2H), 0.66 (m, 2H). ESI-MS m/z: 450 [M+H]$^+$.

Example 64

Synthesis of (S)-1-(3-(4-(2-(4-chloro-5-cyclopropyl-2-hydroxyphenylamino)propanoyl)piperazin-1-yl)azetidin-1-yl)prop-2-en-1-one (II-67)

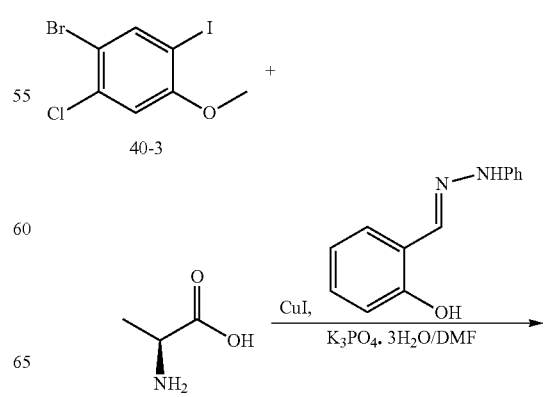

-continued

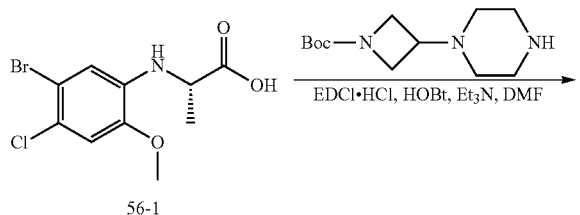

56-1

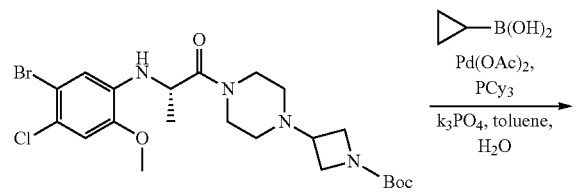

56-2

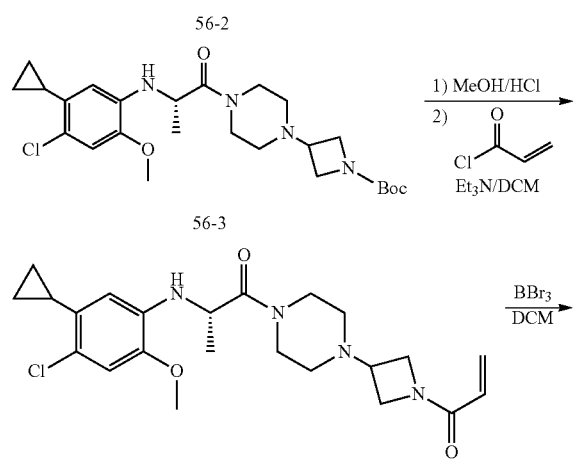

56-3

56-4

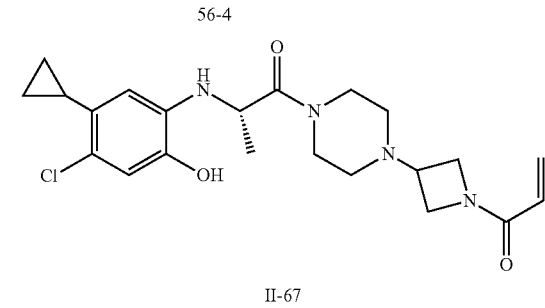

II-67

(S)-2-(5-Bromo-4-chloro-2-methoxyphenylamino) propanoic acid

A mixture of 1-bromo-2-chloro-5-iodo-4-methoxybenzene (3 g, 8.64 mmol), (S)-2-aminopropanoic acid (769 mg, 8.64 mmol), CuI (164 mg, 0.864 mmol), 2-hydroxybenzaldehyde phenylhydrazone (366 mg, 1.73 mmol), $K_3PO_4 \cdot 3H_2O$ (4.6 g, 17.28 mmol) in DMF (10 mL) was stirred under argon at 80° C. for 16 h. The mixture was allowed to cool to RT, $H_2O$ and $Et_2O$ were added to the solution. The resulting solution was partitioned into two phases, the aqueous phase was separated, and the organic layer was extracted with 5% NaOH. The combined aqueous phase was acidified to pH 4 with 20% HCl, and then extracted with $Et_2O$. The resulting organic layer was dried over $MgSO_4$ and concentrated in vacuo to afford the desired product (1.7 g, 64% yield). ESI-MS m/z: 306.1 [M+H]$^-$ (S)-tert-Butyl 3-(4-(2-((5-bromo-4-chloro-2-methoxyphenyl)amino)propanoyl)piperazin-1-yl) azetidine-1-carboxylate To a solution of (S)-2-(5-bromo-4-chloro-2-methoxyphenylamino)propanoic acid (1.6 g, 5.21 mmol), tert-butyl 3-(piperazin-1-yl)azetidine-1-carboxylate (1.88 g, 7.82 mmol), EDCI.HCl (2.0 g, 10.42 mmol), HOBt (1.41 g, 10.42 mmol) in DMF (20 mL) at 0° C., $Et_3N$ (1.58 g, 15.63 mmol) was added. The resulting mixture was stirred at RT for 16 h and then partitioned between ethyl acetate and water. The organic layer was washed with brine, dried over $Na_2SO_4$ and concentrated in vacuo. The residue was purified by flash column chromatography on silica gel (methanol/dichloroethane=1:50) to afford the desired product (2.1 g, 76% yield). ESI-MS m/z: 531.3 [M+H]$^+$.

((S)-tert-Butyl 3-(4-(2-((4-chloro-5-cyclopropyl-2-methoxyphenyl)amino)propanoyl)piperazin-1-yl) azetidine-1-carboxylate A mixture of (S)-tert-butyl 3-(4-(2-((5-bromo-4-chloro-2-methoxyphenyl)amino)propanoyl)piperazin-1-yl)azetidine-1-carboxylate (700 mg, 1.32 mmol), cyclopropylboronic acid (114 mg, 1.32 mmol), Pd(OAc)$_2$ (15 mg, 0.066 mmol), tricyclohexylphosphine (37 mg, 0.132 mmol), $K_3PO_4 \cdot 3H_2O$ (974 mg, 4.62 mmol) in DMF (10 mL) and $H_2O$ (0.5 mL) was stirred under argon at 80° C. for 16 h. The mixture was allowed to cool to RT, and then partitioned between ethyl acetate and water. The organic layer was washed with brine, dried over $Na_2SO_4$ and concentrated in vacuo. The residue was purified by flash column chromatography on silica gel (methanol/dichloroethane=1:100) to afford the desired product (400 mg, 62%). ESI-MS m/z: 493.2[M+H]$^+$.

(S)-1-(3-(4-(2-((4-Chloro-5-cyclopropyl-2-hydroxyphenyl)amino)propanoyl)piperazin-1-yl)azetidin-1-yl)prop-2-en-1-one (II-67)

The title compound was prepared from (S)-tert-butyl 3-(4-(2-((4-chloro-5-cyclopropyl-2-methoxyphenyl)amino) propanoyl)piperazin-1-yl)azetidine-1-carboxylate in three steps according to the procedure described in Example 33. $^1$H NMR (400 MHz, DMSO-d6) δ: 9.69 (s, 1H), 6.66 (s, 1H), 6.29 (dd, J=10.5, 16.9 Hz, 1H), 6.12 (dd, J=1.7, 16.7 Hz, 1H), 6.05 (s, 1H), 5.68 (dd, J=1.7, 16.7 Hz, 1H), 4.84 (m, 1H), 4.61 (m, 1H), 4.24 (m, 1H), 4.06 (m, 1H), 3.94 (m, 1H), 3.78 (m, 4H), 3.55 (m, 1H), 2.43-2.17 (m, 4H), 1.97 (m, 1H), 0.88 (m, 2H), 0.63 (m, 2H). ESI-MS m/z: 433.3 [M+H]$^+$.

Example 65

Synthesis of (S)-1-(3-(4-(2-(4-chloro-5-ethyl-2-hydroxyphenylamino)propanoyl)piperazin-1-yl)azetidin-1-yl)prop-2-en-1-one (II-69)

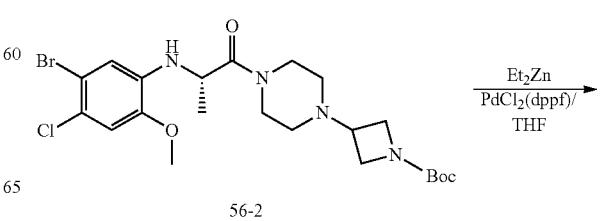

56-2

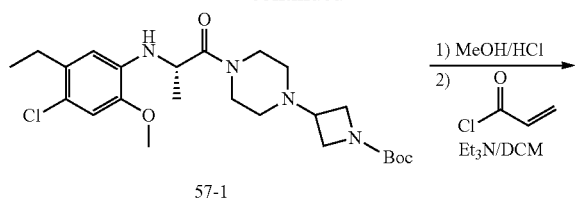

57-1

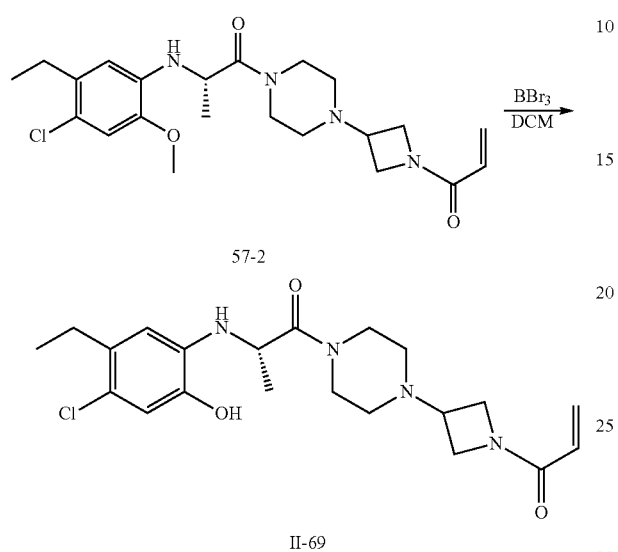

(S)-tert-Butyl 3-(4-(2-((4-chloro-5-ethyl-2-methoxy-phenyl)amino)propanoyl)piperazin-1-yl)azetidine-1-carboxylate To a solution of (S)-tert-butyl 3-(4-(2-((5-bromo-4-chloro-2-methoxyphenyl)amino)propanoyl)piperazin-1-yl)azetidine-1-carboxylate (400 mg, 0.75 mmol), PdCl$_2$(dppf) (95 mg, 0.13 mmol) in THF (20 mL) at RT, Et$_2$Zn (2.86 mL, 2.86 mmol, 1.0 M in hexane) was added. The resulting mixture was stirred under argon at 80° C. for 4 h and then partitioned between ethyl acetate and water. The organic layer was washed with brine, dried over Na$_2$SO$_4$ and concentrated in vacuo. The residue was purified by flash column chromatography on silica gel (methanol/dichloroethane=1:80) to afford the desired product (250 mg, 69% yield). ESI-MS m/z: 481.2 [M+H]$^+$.

(S)-1-(3-(4-(2-((4-Chloro-5-ethyl-2-hydroxyphenyl)amino)propanoyl)piperazin-1-yl)azetidin-1-yl)prop-2-en-1-one (II-69)

The title compound was prepared from (S)-tert-butyl 3-(4-(2-((4-chloro-5-ethyl-2-methoxyphenyl)amino)propanoyl)piperazin-1-yl)azetidine-1-carboxylate in three steps according to the procedure described in Example 33. $^1$H NMR (400 MHz, DMSO-d6) δ: 9.61 (s, 1H), 6.64 (s, 1H), 6.48 (s, 1H), 6.29 (dd, J=10.5, 16.9 Hz, 1H), 6.12 (dd, J=1.7, 16.7 Hz, 1H), 5.68 (dd, J=1.7, 16.7 Hz, 1H), 4.89 (m, 1H), 4.61 (m, 1H), 4.25 (m, 1H), 4.06 (m, 1H), 3.94 (m, 1H), 3.72-3.53 (m, 4H), 3.16 (m, 1H), 2.5 (m, 2H), 2.43-2.17 (m, 4H), 1.21 (dd, 3H), 1.15 (m, 3H). ESI-MS m/z: 406.2 [M+H]$^+$.

Example 66

Synthesis of 1-(3-(4-(2-(4-chloro-5-cyclopropyl-2-hydroxyphenylamino)acetyl)-2-methylpiperazin-1-yl)azetidin-1-yl)prop-2-en-1-one (II-60)

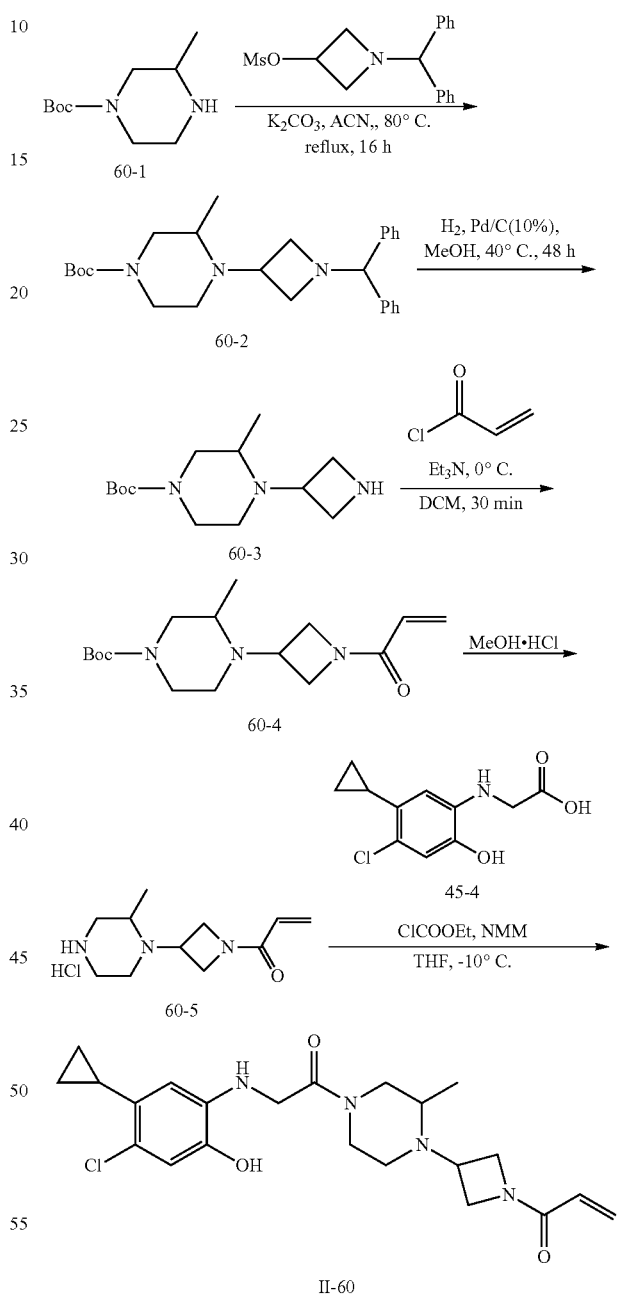

tert-Butyl 4-(1-acryloylazetidin-3-yl)-3-methylpiperazine-1-carboxylate

The title compound was prepared from tert-butyl 3-methylpiperazine-1-carboxylate in three steps according to the procedure described in Example 41.

1-(3-(2-Methylpiperazin-1-yl)azetidin-1-yl)prop-2-en-1-one hydrochloride

The mixture of tert-butyl 4-(1-acryloylazetidin-3-yl)-3-methylpiperazine-1-carboxylate (62 mg, 0.199 mmol) in MeOH/HCl (20 mL, 2.9 M) was stirred at RT for 1 h. The mixture was concentrated in vacuo to afford the crude product (59 mg). The crude product was used directly in the next step without further purification.

1-(3-(4-(2-((4-Chloro-5-cyclopropyl-2-hydroxyphenyl)amino)acetyl)-2-methylpiperazin-1-yl)azetidin-1-yl)prop-2-en-1-one (II-60)

To the mixture of 2-((4-chloro-5-cyclopropyl-2-hydroxyphenyl)amino)acetic acid (30 mg, 0.124 mmol) and NMM (50 mg, 0.496 mmol) in dry THF (30 mL) at −10° C., ethyl chloroformate (15 mg, 0.136 mmol) was added and the resulting mixture was stirred at −10° C. for 45 min. Then it was added a mixture of 1-(3-(2-methylpiperazin-1-yl)azetidin-1-yl)prop-2-en-1-one hydrochloride (37 mg, 0.149 mmol), Et₃N (50 mg, 0.496 mmol) and dichloromethane (3 mL). The resulting mixture was stirred at RT for 30 min. The mixture was partitioned between ethyl acetate and water. The organic layer was washed with saturated NaHCO₃ solution and brine, dried over Na₂SO₄, filtered and concentrated in vacuo. The residue was purified with column chromatography on silica gel (dichloromethane/methanol=40:1) to afford the desired product (10 mg, 18.6% yield) as a white solid. ¹H NMR (400 MHz, DMSO-d6) δ: 9.65 (s, 1H), 6.66 (s, 1H), 6.34-6.27 (m, 1H), 6.10-6.07 (m, 2H), 5.68-5.65 (d, J=10.4 Hz, 1H), 5.12 (m, 1H), 4.29-4.19 (m, 1H), 4.12-4.10 (m, 1H), 4.08-3.81 (m, 4H), 3.78 (s, 4H), 2.63 (m, 2H), 2.25 (m, 1H), 1.96 (m, 1H), 1.24 (s, 1H), 0.96-0.87 (m, 5H), 0.63 (m, 2H). ESI-MS m/z: 433.5 [M+H]⁺.

Example 67

Synthesis of 2-(2-(4-(1-acryloylazetidin-3-yl)piperazin-1-yl)-2-oxoethylamino)-5-chloro-4-cyclopropylbenzonitrile (II-71)

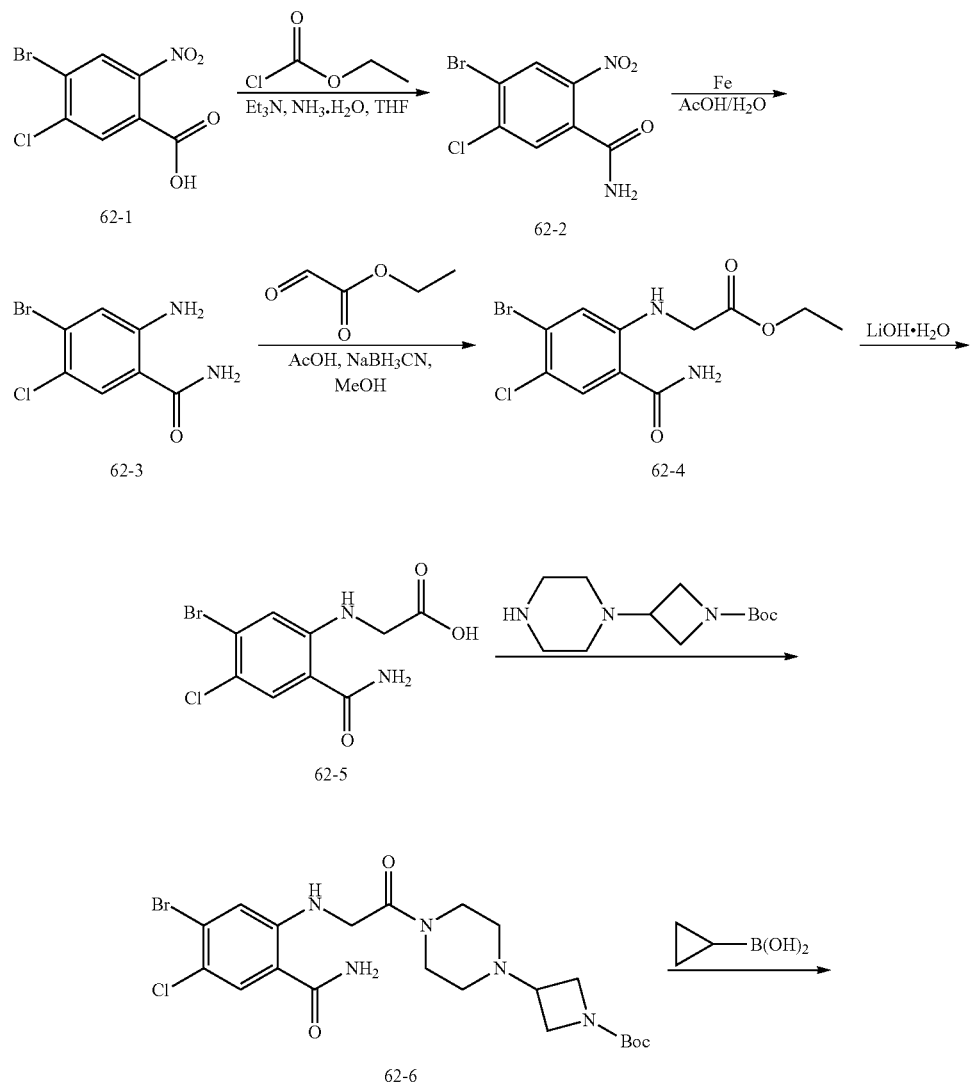

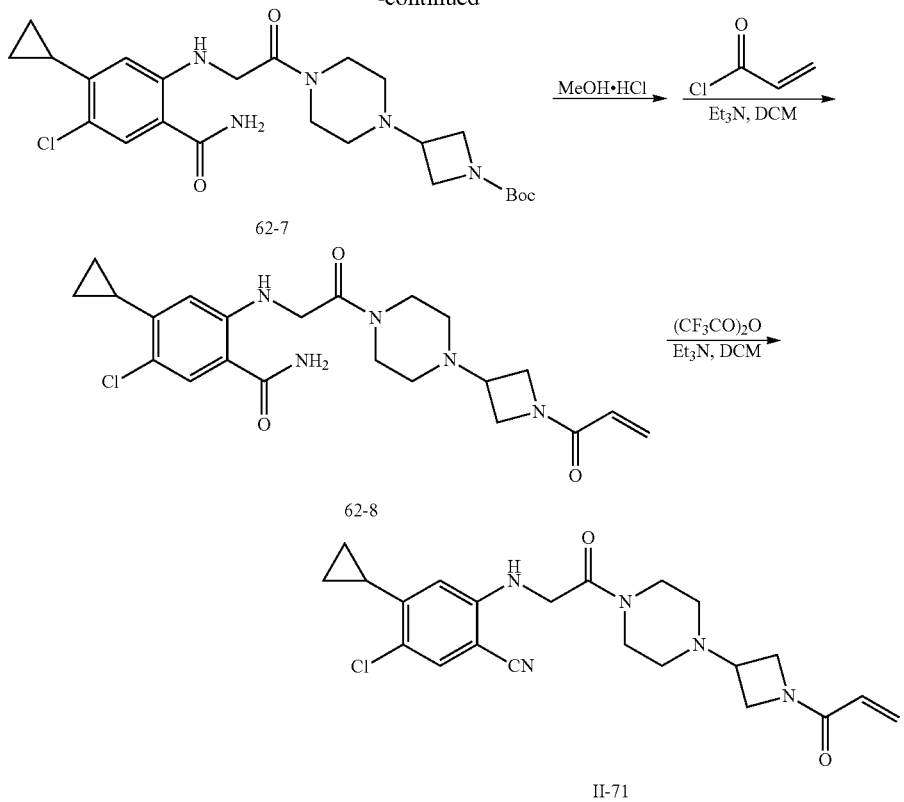

4-Bromo-5-chloro-2-nitrobenzamide

A mixture of 4-bromo-5-chloro-2-nitrobenzoic acid (1.3 g, 4.63 mmol), Et$_3$N (1.4 g, 13.9 mmol) in THF (20 mL) at 0° C., ethyl chloroformate (1.5 g, 13.9 mmol) was added. The resulting mixture was stirred at 0° C. for 1 h. Then NH$_3$.H$_2$O (4 mL) was added and stirred for 0.5 h. The mixture was extracted with ethyl acetate. The organic layer was washed with brine, dried over anhydrous Na$_2$SO$_4$, filtered and concentrated in vacuo to afford the crude product (900 mg).

2-Amino-4-bromo-5-chlorobenzamide

To a solution of 4-bromo-5-chloro-2-nitrobenzamide (900 mg, 3.2 mmol) in AcOH (20 mL) and water (5 mL) at 70° C., Fe powder (900 mg, 16.1 mmol) was added and the resulting mixture was stirred at 70° C. for 1 h. The mixture was allowed to cool to RT and poured into ice-water. The precipitate was collected by filtration and rinsed with water. This crude product was dissolved with ethyl acetate and filtered. The filtrate was washed with saturated NaHCO$_3$ solution and brine. The organic layer was dried over MgSO$_4$, filtered, and concentrated in vacuo to afford the desired product (770 mg, 97% yield). ESI-MS m/z: 250.1 [M+H]$^+$.

tert-Butyl 3-(4-(2-((5-bromo-2-carbamoyl-4-chlorophenyl)amino)acetyl)piperazin-1-yl)azetidine-1-carboxylate The title compound was prepared from 2-amino-4-bromo-5-chlorobenzamide in three steps according to the procedure described in Example 44. ESI-MS m/z: 532.5 [M+H]$^+$.

tert-Butyl 3-(4-(2-((2-carbamoyl-4-chloro-5-cyclopropylphenyl)amino)acetyl)piperazin-1-yl)azetidine-1-carboxylate To a solution of tert-butyl 3-(4-(2-((5-bromo-2-carbamoyl-4-chlorophenyl)amino)acetyl)piperazin-1-yl)azetidine-1-carboxylate (350 mg, 0.66 mmol) and cyclopropylboronic acid (226 mg, 2.64 mmol) in toluene (10 mL) and water (2 mL), Pd(OAc)$_2$ (15 mg, 0.07 mmol), PCy$_3$ (37 mg, 0.132 mmol) and K$_3$PO$_4$ (487 mg, 2.31 mmol) were added. The mixture was stirred at 80° C. for 16 h. The mixture was allowed to cool to RT and concentrated in vacuo. The residue was purified by flash column chromatography on silica gel (1-5% methanol/dichloroethane) to afford the desired product (150 mg, 46% yield) as a solid.

2-((2-(4-(1-Acryloylazetidin-3-yl)piperazin-1-yl)-2-oxoethyl)amino)-5-chloro-4-cyclopropylbenzamide The title compound was prepared from tert-butyl 3-(4-(2-((2-carbamoyl-4-chloro-5-cyclopropylphenyl)amino)acetyl) piperazin-1-yl)azetidine-1-carboxylate in two steps according to the procedure described in Example 33. ESI-MS m/z: 446.4 [M+H]$^+$.

2-((2-(4-(1-Acryloylazetidin-3-yl)piperazin-1-yl)-2-oxoethyl)amino)-5-chloro-4-cyclopropylbenzonitrile (II-71)

A mixture of 2-((2-(4-(1-acryloylazetidin-3-yl)piperazin-1-yl)-2-oxoethyl)amino)-5-chloro-4-cyclopropylbenzamide (3 0 mg, 0.067 mmol) and Et$_3$N (41 mg, 0.404 mmol) in DCM (10 mL) at RT, trifluoroacetic anhydride (56 mg, 0.268 mmol) was added. The resulting mixture was stirred at RT for 0.5 h, poured into water and then extracted with dichloromethane. The organic layer was washed with brine, dried over Na₂SO₄ and concentrated. The residue was purified by flash column chromatography on silica gel (1-4% methanol/dichloroethane) to afford the desired product (20 mg, 72% yield). ¹H NMR (400 MHz, DMSO-d6) δ: 7.60 (s, 1H), 6.34-6.30 (m, 1H), 6.27 (s, 1H), 6.12-6.07 (m, 1H), 6.01-5.99 (t, J=4 Hz, 1H), 5.69-5.65 (m, 1H), 4.26-4.22 (m, 1H), 4.07-4.04 (m, 3H), 3.96-3.92 (m, 1H), 3.80-3.76 (m, 1H), 3.53-3.51 (m, 4H), 3.19-3.13 (m, 1H), 2.45-2.30 (m, 4H), 2.16-2.09 (m, 1H), 1.08-1.03 (m, 2H), 0.87-0.80 (m, 2H). ESI-MS m/z: 428.4 [M+H]⁺.

Example 68

Synthesis of 1-(3-(4-(2-(4-chloro-5-(2,2-difluorocyclopropyl)-2-hydroxyphenylamino)acetyl)piperazin-1-yl)azetidin-1-yl)prop-2-en-1-one (II-56)

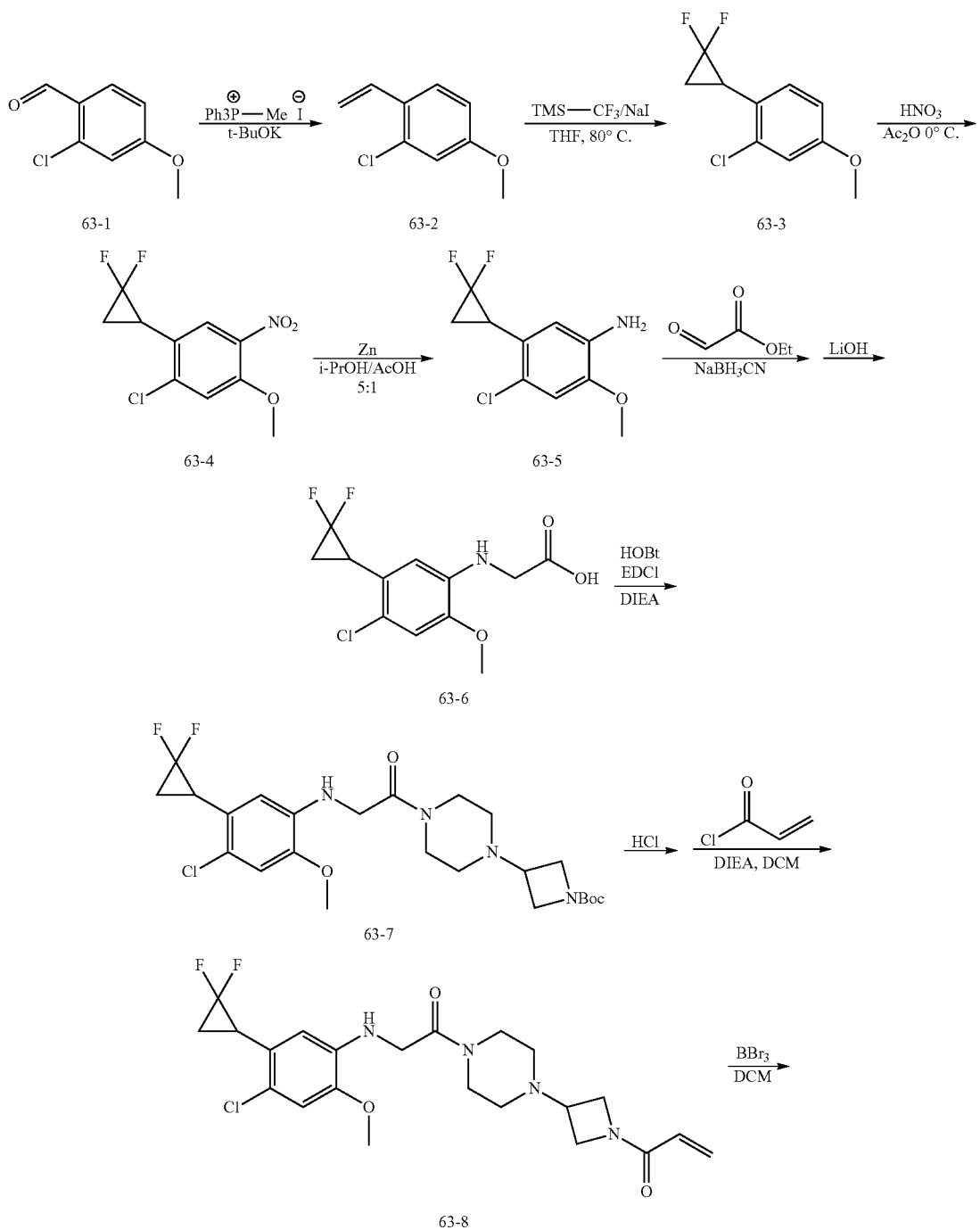

-continued

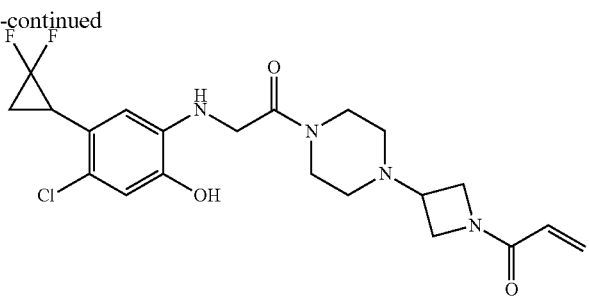

II-56

2-Chloro-4-methoxy-1-vinylbenzene

To a suspension of phosphonium salt (2.05 g, 5 mmol) in THF (50 mL), was added t-BuOK (0.84 g, 7.5 mmol). The mixture turned to yellow and was kept stirring at RT for 1 h. 2-Chloro-4-methoxybenzaldehyde (0.85 g, 5 mmol) was added to the mixture. The mixture was stirred for 24 h, diluted with sat. NaHCO3 and then extracted with hexane. Organic layer was dried over $Na_2SO_4$, filtered and concentrated in vacuo. The residue was purified by Isolera One (100% hexanes to afford the desired product (0.45 g, 53% yield). $^1$H NMR (CDCl$_3$, δ): 7.49 (d, J=6.8 Hz, 1H), 7.03 (dd, J=8.8, 14.0 Hz, 1H), 6.90 (d, J=2.0, 1H), 6.79 (dd, J=2.0, 6.8 Hz, 1H), 5.62 (d, J=14.0 Hz, 1H), 5.26 (d, J=8.8 Hz, 1H), 3.80 (s, 3H).

2-Chloro-1-(2,2-difluorocyclopropyl)-4-methoxybenzene

The solution of 2-chloro-4-methoxy-1-vinylbenzene (290 mg, 1.72 mmol) in dry THF (4 mL) was degassed, and then TMS-CF$_3$ and NaI were added. The mixture was stirred at 80° C. overnight. TLC (100% Hexane) showed the reaction as complete. The mixture was diluted with hexane (20 mL). The inorganic salt was removed by filtration. The filtrate was concentrate in vacuo. The residue was purified via Isolera One (Hexane=100%).

1-Chloro-2-(2,2-difluorocyclopropyl)-5-methoxy-4-nitrobenzene

To a solution of 2-chloro-1-(2,2-difluorocyclopropyl)-4-methoxybenzene (328 mg, 1.5 mmol) in Ac$_2$O (2 mL), was added HNO$_3$ (10 drops) at 0° C. The mixture was stirred from 0° C. to rt. Ac$_2$O was removed in vacuo. The residue was diluted with DCM and washed with water. The organic layer was dried over $Na_2SO_4$. The solvent was removed in vacuo. The residue was purified via Isolera One (EtOAc/Hexane=0-15%) to afford the desired product. $^1$H NMR (CDCl$_3$, δ): 7.77 (s, 1H), 7.16 (s, 1H), 3.98 (s, 3H), 2.78-2.90 (m, 1H), 1.90-1.98 (m, 1H), 1.60-1.68 (m, 1H). ESI-MS m/z: 264.1 [M+H]$^+$.

4-Chloro-5-(2,2-difluorocyclopropyl)-2-methoxyaniline

The above obtained 1-chloro-2-(2,2-difluorocyclopropyl)-5-methoxy-4-nitrobenzene was dissolved in 10 mL of co-solvent of AcOH/i-PrOH (1:5). Zn dust was added to the mixture. The mixture was stirred at 60° C. for 30 min. The solvent was removed in vacuo. The residue was diluted was DCM and the inorganic salt was removed by filtration. The filtrate was concentrated to give crude product which was used in next step without further purification.

1-(3-(4-((4-chloro-5-(2,2-difluorocyclopropyl)-2-hydroxyphenyl)glycyl)piperazin-1-yl)azetidin-1-yl)prop-2-en-1-one (II-56)

The title compound was prepared from 4-chloro-5-(2,2-difluorocyclopropyl)-2-methoxyaniline in 6 steps according to the procedure described in Example 44. $^1$H NMR (CDCl$_3$, δ): 9.90 (s, 1H), 6.73 (s, 1H), 6.40 (s, 1H), 6.30 (dd, J=8.4, 13.6 Hz, 1H), 6.10 (dd, J=1.6, 12.0 Hz, 1H), 5.66 (dd, J=1.6, 8.4 Hz, 1H), 5.18 (t, J=3.2, 3.6 Hz, 1H), 4.24 (t, J=6.0, 6.8 Hz, 1H), 4.03-4.08 (m, 1H), 3.86-3.97 (m, 3H), 3.74-3.80 (m, 1H), 3.52 (br. s, 4H), 3.13-3.20 (m, 1H), 2.77-2.87 (m, 1H), 2.25-2.43 (m, 4H), 1.87-1.97 (m, 2H). ESI-MS m/z: 455.2 [M+H]$^+$.

Example 69

Biochemical Assay of Compounds of Structure (I), (II) and (III)

Test compounds were prepared as 10 mM stock solutions in DMSO (Fisher cat#BP-231-100). KRAS G12C 1-169, his-tagged protein, GDP-loaded was diluted to 2 μm in buffer (20 mM Hepes, 150 mM NaCl, 1 mM MgCl$_2$). Compounds were tested for activity as follows:

Compounds were diluted to 50× final test concentration in DMSO in 96-well storage plates. Compound stock solutions were vortexed before use and observed carefully for any sign of precipitation. Dilutions were as follow:

For 100 μM final compound concentration, compounds were diluted to 5000 μM (5 μl 10 mM compound stock+5 μl DMSO and mixed well by pipetting.

For 30 μM final compound concentration, compounds were diluted to 1500 μM (3 μl 10 mM compound stock+17 μl DMSO) and mixed well by pipetting.

For 10 μM final compound concentration, compounds were diluted to 500 μM (2 μl 10 mM compound stock+38 μl DMSO) and mixed well by pipetting.

49 μl of the stock protein solution was added to each well of a 96-well PCR plate (Fisher cat#1423027). 1 μl of the diluted 50× compounds were added to appropriate wells in the PCR plate using 12-channel pipettor. Reactions were mixed carefully and thoroughly by pipetting up/down with a 200 μl multi-channel pipettor. The plate was sealed well with aluminum plate seal, and stored in drawer at room temperature for 24 hrs. 5 μl of 2% formic acid (Fisher cat#A117) in DI H$_2$O was then added to each well followed by mixing with a pipette. The plate was then resealed with aluminum seal and stored on dry ice until analyzed as described below.

The above described assays were analyzed by mass spectrometry according to the following procedure:

The MS instrument is set to positive polarity, 2 GHz resolution, and low mass (1700) mode and allowed to equilibrate for 30 minutes. The instrument is then calibrated, switched to acquisition mode and the appropriate method loaded.

After another 30 minute equilibration time, a blank batch (i.e., buffer) is run to ensure equipment is operating properly. The samples are thawed at 37° C. for 10 minutes, briefly centrifuged, and transfer to the bench top. Wells A1 and H12 are spiked with 1 μL 500 μM internal standard peptide, and the plates centrifuged at 2000×g for 5 minutes. The method is then run and masses of each individual well recorded.

The masses (for which integration data is desired) for each well are pasted into the platemap and exported from the analysis. Masses for the internal standards are exported as well. The data at 50 ppm is extracted for the +19 charge state, and identity of well A1 is assigned using the internal standard spike and integrated. Peak data is exported as a TOF list and the above steps are repeated individually, for the +20, 21, 22, 23, 24, and 25 charge states.

Other in vitro analyses are as follows:
Inhibition of Cell Growth:

The ability of the subject compounds to inhibit Ras-mediated cell growth is assessed and demonstrated as follows. Cells expressing a wildtype or a mutant Ras are plated in white, clear bottom 96 well plates at a density of 5,000 cells per well. Cells are allowed to attach for about 2 hours after plating before a compound disclosed herein is added. After certain hours (e.g., 24 hours, 48 hours, or 72 hours of cell growth), cell proliferation is determined by measuring total ATP content using the Cell Titer Glo reagent (Promega) according to manufacturer's instructions. Proliferation EC50s is determined by analyzing 8 point compound dose responses at half-log intervals decreasing from 100 μM.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by a decrease in the steady-state level of phosphorylated MEK, and/or Raf binding in cells treated with the one or more of the subject compounds as compared to the control cells.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by percentage binding of compound to the G12C mutated Ras protein in cells treated with the one or more of the subject compounds as compared to the control cells.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12V, or G12A) are treated with or without (control cells) a subject compound. Inhibition of Ras signaling by one or more subject compounds is demonstrated by a decrease in binding of Ras complex to downstream signaling molecules (for example Raf) in cells treated with the one or more of the subject compounds as compared to the control cells.

Each of the compounds in Tables 1, 2a and 3 were tested according to the above methods and found to covalently bind to KRAS G12C to the extent of at least about 5% (i.e., at least about 5% of the protein present in the well was found to be covalently bound to test compound).

TABLE 4

Activity of Representative Compounds of Structure (I)*

| No. | Binding % | No. | Binding % | No. | Binding % | No. | Binding % |
|---|---|---|---|---|---|---|---|
| 1 | +++ | 2 | + | 3 | + | 4 | ++++ |
| 5 | +++ | 6 | +++ | 7 | ++++ | 8 | ++ |
| 9 | +++ | 10 | ++ | 11 | ++++ | 12 | + |
| 13 | ++ | 14 | ++ | 15 | +++ | 16 | ++ |
| 17 | + | 18 | ++ | 19 | ++ | 20 | + |
| 21 | +++ | 22 | + | 23 | ++ | 24 | + |
| 25 | ++ | 26 | ++ | 27 | ++ | 28 | + |
| 29 | + | 30 | + | 31 | + | 32 | + |
| 33 | ++ | 34 | +++ | 35 | + | 36 | + |
| 37 | ++ | 38 | ++ | 39 | + | 40 | +++ |
| 41 | + | 42 | +++ | 43 | +++ | 44 | +++ |
| 45 | + | 46 | ++++ | 47 | ++++ | 48 | ++++ |
| 49 | ++++ | 50 | + | 51 | ++++ | 52 | ++++ |
| 53 | ++++ | 54 | ++ | 55 | ++++ | 56 | ++++ |
| 57 | + | 58 | +++ | 59 | ++++ | 60 | + |
| 61 | + | 62 | + | 63 | + | 64 | ++ |
| 65 | + | 66 | ++++ | 67 | +++ | 68 | + |
| 69 | + | 70 | +++ | 71 | + | 72 | ++ |
| 73 | ++ | 74 | +++ | 75 | + | 76 | + |
| 77 | +++ | 78 | + | 79 | + | 80 | + |
| 81 | +++ | 82 | + | 83 | ++ | 84 | ++ |
| 85 | +++ | 86 | + | 87 | + | 88 | + |
| 89 | + | 90 | + | 91 | ++ | 92 | + |
| 93 | + | 94 | ++ | 95 | ++ | 96 | + |
| 97 | ++ | 98 | + | 99 | +++ | 100 | +++ |
| 101 | +++ | 102 | +++ | 103 | ++ | 104 | +++ |
| 105 | + | 106 | ++++ | 107 | ++++ | 108 | ++ |
| 109 | ++++ | 110 | +++ | 111 | +++ | 112 | +++ |
| 113 | +++ | 114 | +++ | 115 | +++ | 116 | ++ |
| 117 | +++ | 118 | +++ | 119 | +++ | 120 | +++ |
| 121 | ++++ | 122 | ++ | 123 | ++++ | 124 | +++ |
| 125 | ++++ | 126 | ++++ | 127 | ++++ | 128 | +++ |
| 129 | + | 130 | + | 131 | + | 132 | +++ |
| 133 | ++ | 134 | ++ | 135 | + | 136 | ++ |
| 137 | + | 138 | ++++ | 139 | ++++ | 140 | +++ |
| 141 | + | 142 | + | 143 | +++ | 144 | + |
| 145 | ++++ | 146 | ++++ | 147 | ++ | 148 | +++ |
| 149 | + | 150 | ++++ | 151 | + | 152 | +++ |
| 153 | ++++ | 154 | ++ | 155 | ++ | 156 | ++ |
| 157 | + | 158 | ++++ | 159 | +++ | 160 | + |
| 161 | ++ | 162 | + | 163 | + | 164 | + |
| 165 | N/A | 166 | + | 167 | + | 168 | ++ |
| 169 | +++ | 170 | + | 171 | +++ | 172 | +++ |
| 173 | ++++ | 174 | ++ | 175 | +++ | 176 | +++ |
| 177 | + | 178 | + | 179 | + | 180 | + |
| 181 | + | 182 | +++ | 183 | +++ | 184 | ++++ |
| 185 | ++ | 186 | +++ | 187 | +++ | 188 | +++ |
| 189 | ++ | 190 | + | 191 | +++ | 192 | ++ |
| 193 | ++ | 194 | ++++ | 195 | ++++ | 196 | ++++ |
| 197 | ++ | 198 | ++++ | 199 | N/A | 200 | ++ |
| 201 | +++ | 202 | +++ | 203 | ++++ | 204 | +++ |
| 205 | + | 206 | ++++ | 207 | ++++ | 208 | ++++ |
| 209 | ++++ | 210 | ++++ | 211 | + | 212 | ++++ |
| 213 | ++ | 214 | + | 215 | ++ | 216 | + |
| 217 | +++ | 218 | +++ | 219 | + | 220 | +++ |
| 221 | ++ | 222 | +++ | 223 | + | 224 | +++ |
| 225 | ++ | 226 | + | 227 | ++++ | 228 | + |
| 229 | ++ | 230 | + | 231 | +++ | 232 | + |
| 233 | +++ | 234 | ++++ | 235 | +++ | 236 | +++ |
| 237 | ++++ | 238 | +++ | 239 | +++ | 240 | +++ |
| 241 | + | 242 | ++++ | 243 | ++++ | 244 | + |
| 245 | + | 246 | ++++ | 247 | +++ | 248 | N/A |
| 249 | + | 250 | ++ | 251 | ++++ | 252 | ++++ |

TABLE 4-continued

Activity of Representative Compounds of Structure (I)*

| No. | Binding % | No. | Binding % | No. | Binding % | No. | Binding % |
|---|---|---|---|---|---|---|---|
| 253 | ++++ | 254 | +++ | 255 | +++ | 256 | +++ |
| 257 | ++++ | 258 | ++ | 259 | +++ | 260 | ++ |
| 261 | + | 262 | + | 263 | + | 264 | ++ |
| 265 | + | 266 | +++ | 267 | + | 268 | +++ |
| 269 | +++ | 270 | +++ | 271 | +++ | 272 | ++++ |
| 273 | ++++ | 274 | ++++ | 275 | ++ | 276 | + |
| 277 | + | 278 | ++ | 279 | +++ | 280 | +++ |
| 281 | ++ | 282 | +++ | 283 | ++ | 284 | ++++ |
| 285 | +++ | 286 | + | 287 | ++ | 288 | ++ |
| 289 | +++ | 290 | +++ | 291 | ++++ | 292 | + |
| 293 | ++++ | 294 | ++++ | 295 | + | 296 | + |
| 297 | + | 298 | ++ | 299 | + | 300 | ++ |
| 301 | ++ | 302 | +++ | 303 | ++ | 304 | ++ |
| 305 | ++ | 306 | ++ | 307 | ++ | 308 | +++ |
| 309 | +++ | 310 | ++++ | 311 | +++ | 312 | ++++ |
| 313 | +++ | 314 | ++++ | 315 | + | 316 | ++ |
| 317 | N/A | 318 | + | 319 | ++ | 320 | ++ |
| 321 | + | 322 | +++ | 323 | +++ | 324 | + |
| 325 | ++ | 326 | + | 327 | ++ | 328 | + |
| 329 | ++ | 330 | ++ | 331 | ++ | 332 | ++ |
| 333 | + | 334 | ++++ | 335 | ++++ | 336 | +++ |
| 337 | + | 338 | ++ | 339 | ++++ | 340 | ++++ |
| 341 | ++++ | 342 | ++++ | N/A | N/A | N/A | N/A |

*Binding for compounds 1-47 was measured at 24 h; binding for compounds 48-246 was measured at 2 h; binding for compounds 247-342 was measured at 30 min.
+indicates binding activity from 5% to 25%
++indicates binding activity greater than 25% and up to 50%
+++indicates binding activity greater than 50% and up to 75%
++++indicates binding activity greater than 75%

TABLE 5

Activity of Representative Compounds of Structure (II)*

| No. | Binding % | No. | Binding % | No. | Binding % | No. | Binding % |
|---|---|---|---|---|---|---|---|
| II-1 | ++++ | II-2 | +++ | II-3 | ++++ | II-4 | +++ |
| II-5 | + | II-6 | + | II-7 | ++ | II-8 | ++ |
| II-9 | + | II-10 | + | II-11 | ++++ | II-12 | +++ |
| II-13 | ++ | II-14 | +++ | II-15 | + | II-16 | + |
| II-17 | ++ | II-18 | ++++ | II-19 | +++ | II-20 | ++ |
| II-21 | + | II-22 | + | II-23 | + | II-24 | + |
| II-25 | + | II-26 | + | II-27 | ++ | II-28 | +++ |
| II-29 | + | II-30 | + | II-31 | ++++ | II-32 | ++++ |
| II-33 | + | II-34 | + | II-35 | ++++ | II-36 | ++++ |
| II-37 | ++ | II-38 | + | II-39 | +++ | II-40 | ++++ |
| II-41 | ++++ | II-42 | + | II-43 | ++++ | II-44 | + |
| II-45 | ++++ | II-46 | + | II-47 | + | II-48 | ++ |
| II-49 | ++++ | N/A | N/A | N/A | N/A | N/A | N/A |

*Binding activity determined at 24 hrs.
+indicates binding activity from 5% to 15%
++indicates binding activity greater than 15% and up to 25%
+++indicates binding activity greater than 25% and up to 50%
++++indicates binding activity greater than 50%

TABLE 6

Activity of Representative Compounds of Structure (II)*

| No. | Binding % | No. | Binding % | No. | Binding % | No. | Binding % |
|---|---|---|---|---|---|---|---|
| II-50 | ++ | II-51 | ++ | II-52 | + | II-53 | ++ |
| II-54 | ++ | II-55 | ++ | II-56 | ++ | II-57 | ++ |
| II-58 | + | II-59 | ++ | II-60 | ++ | II-61 | + |
| II-62 | + | II-63 | ++ | II-64 | ++ | II-65 | + |
| II-66 | + | II-67 | ++ | II-68 | ++ | II-69 | ++ |

TABLE 6-continued

Activity of Representative Compounds of Structure (II)*

| No. | Binding % | No. | Binding % | No. | Binding % | No. | Binding % |
|---|---|---|---|---|---|---|---|
| II-70 | ++ | II-71 | + | II-72 | + | II-73 | + |
| II-74 | + | II-75 | + | II-76 | N/A | N/A | N/A |

*Binding activity determined at 2 hrs.
+indicates binding activity from 5% to 20%
++indicates binding activity greater than 20%

TABLE 7

Activity of Representative Compounds of Structure (III)*

| No. | Binding % | No. | Binding % | No. | Binding % | No. | Binding % |
|---|---|---|---|---|---|---|---|
| III-1 | + | III-2 | ++ | III-3 | ++++ | III-4 | ++ |
| III-5 | ++++ | III-6 | ++ | III-7 | +++ | III-8 | + |
| III-9 | + | III-10 | + | III-11 | + | III-12 | +++ |
| III-13 | + | III-14 | + | III-15 | + | III-16 | + |
| III-17 | ++++ | III-18 | + | III-19 | + | III-20 | + |
| III-21 | ++ | III-22 | + | III-23 | +++ | III-24 | ++++ |
| III-25 | +++ | III-26 | ++ | III-27 | +++ | III-28 | ++ |
| III-29 | +++ | III-30 | ++ | III-31 | + | III-32 | ++++ |
| III-33 | + | III-34 | +++ | III-35 | ++ | III-36 | + |

*Binding activity determined at 24 hrs.
+indicates binding activity from 5% to 10%
++indicates binding activity greater than 10% and up to 20%
+++indicates binding activity greater than 20% and up to 30%
++++indicates binding activity greater than 30%

TABLE 8

Activity of Representative Compounds of Structure (III)*

| No. | Binding % | No. | Binding % | No. | Binding % | No. | Binding % |
|---|---|---|---|---|---|---|---|
| III-37 | ++ | III-38 | ++ | III-39 | ++ | III-40 | + |
| III-41 | + | III-42 | + | III-43 | + | N/A | N/A |

*Binding activity determined at 2 hrs.
+indicates binding activity from 5% to 20%
++indicates binding activity greater than 20%

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for treating a KRAS G12C mutant cancer, the method comprising administering an effective amount of a KRAS G12C mutant modulating compound and an additional therapeutic agent to a subject in need thereof, wherein the KRAS G12C mutant modulating compound has the following structure (I'b):

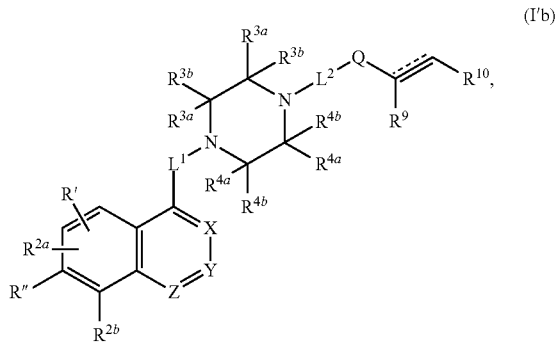

(I'b)

or a pharmaceutically acceptable salt, tautomer or stereoisomer thereof, wherein:

X and Y are each independently N or $CR^6$;
$Z$ is N or $CR^{6a}$;
$L^1$ is a bond;
$L^2$ is a bond or alkylene;
R' is $R^1$ and R" is $R^{2c}$; or R' is H and R" is $R^1$;
$R^1$ is substituted or unsubstituted aryl or heteroaryl;
$R^{2a}$, $R^{1b}$ and $R^{2C}$ are each independently H, halo, hydroxyl, $C_1$-$C_6$ alkyl, $C_1$-$C_6$ haloalkyl, $C_1$-$C_6$ alkoxy, $C_3$-$C_8$ cycloalkyl or aryl;
$R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminocarbonylalkyl or aminocarbonyl;
$R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminocarbonylalkyl or aminocarbonyl;
$R^6$ is, at each occurrence, independently H, cyano, cyanoalkyl, amino, aminylalkyl, aminylalkylaminyl, aminocarbonyl, alkylaminyl, haloalkylamino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino or arylalkyloxy;
$R^{6a}$ is H or $C_1$-$C_6$ alkyl;
=== represents a double or triple bond;
Q is —C(=O)-, —C(=$NR^{8'}$)—, —$NR^8$C(=O)-, —S(=O)$_2$- or —$NR^8$S(=O)$_2$-;
$R^8$ is H, $C_1$-$C_6$ alkyl or hydroxylalkyl;
$R^{8'}$ is H, —OH, —CN or $C_1$-$C_6$ alkyl; and
when === is a double bond then $R^9$ and $R^{10}$ are each independently H, cyano, carboxyl, $C_1$-$C_6$alkyl, alkoxycarbonyl, aminylalkyl, alkylaminylalkyl, or hydroxylalkyl or $R^9$ and $R^{10}$ join to form a carbocyclic or heterocyclic ring, provided at least one of X, Y and Z is N,
wherein the KRAS mutant cancer is a pancreatic cancer, a colorectal cancer or a lung cancer.

2. The method of claim 1, wherein the additional therapeutic agent is a phosphatidylinositol-3 kinase (PI3K) inhibitor.

3. The method of claim 2, wherein the phosphatidylinositol kinase (PI3K) inhibitor is GDC0941, MLN1117, BYL719 (Alpelisib) or BKM120 (Buparlisib).

4. The method of claim 1, wherein the additional therapeutic agent is a protein kinase inhibitor.

5. The method of claim 4, wherein the protein kinase inhibitor is Afatinib, Axitinib, Bevacizumab, Bostutinib, Cetuximab, Crizotinib, Dasatinib, Erlotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib or Vemurafenib.

6. A method for inducing apoptosis in a cell population comprising a KRAS G12C mutant protein, the method comprising administering an effective amount of a KRAS G12C mutant modulating compound and an additional therapeutic agent to the cell population, wherein the KRAS G12C mutant modulating compound has the following structure (I'b):

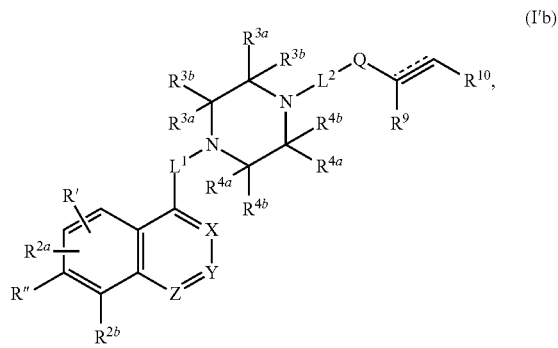

(I'b)

or a pharmaceutically acceptable salt, tautomer or stereoisomer thereof, wherein:

X and Y are each independently N or $CR^6$;
Z is N or $CR^{6a}$;
$L^1$ is a bond;
$L^2$ is a bond or alkylene;
R' is $R^1$ and R" is $R^{2c}$; or R' is H and R" is $R^1$;
$R^1$ is substituted or unsubstituted aryl or heteroaryl;
$R^{2a}$, $R^{2b}$ and $R^{2C}$ are each independently H, halo, hydroxyl, $C_1$-$C_6$ alkyl, $C_1$-$C_6$ haloalkyl, $C_1$-$C_6$ alkoxy, $C_3$-$C_8$ cycloalkyl or aryl;
$R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminocarbonylalkyl or aminocarbonyl;
$R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminocarbonylalkyl or aminocarbonyl;
$R^6$ is, at each occurrence, independently H, cyano, cyanoalkyl, amino, aminylalkyl, aminylalkylaminyl, aminocarbonyl, alkylaminyl, haloalkylamino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino or arylalkyloxy;

$R^{6a}$ is H or $C_1$-$C_6$ alkyl;

≡ represents a double or triple bond;

Q is —C(=O)—, —C(=NR$^{8'}$)-, —NR$^8$C(=O)-, —S(=O)$_2$- or —NR$^8$S(=O)$_2$-;

$R^8$ is H, $C_1$-$C_6$ alkyl or hydroxylalkyl;

$R^{8'}$ is H, —OH, —CN or $C_1$-$C_6$ alkyl; and when ≡ is a double bond then $R^9$ and $R^{10}$ are each independently H, cyano, carboxyl, $C_1$-$C_6$alkyl, alkoxycarbonyl, aminylalkyl, alkylaminylalkyl, or hydroxylalkyl or $R^9$ and $R^{10}$ join to form a carbocyclic or heterocyclic ring, provided at least one of X, Y and Z is N.

7. A method for inhibiting G12C mutant protein in a subject, the method comprising administering an effective amount of a KRAS G12C mutant modulating compound and an additional therapeutic agent to the subject, wherein the KRAS G12C mutant modulating compound has the following structure (I'b):

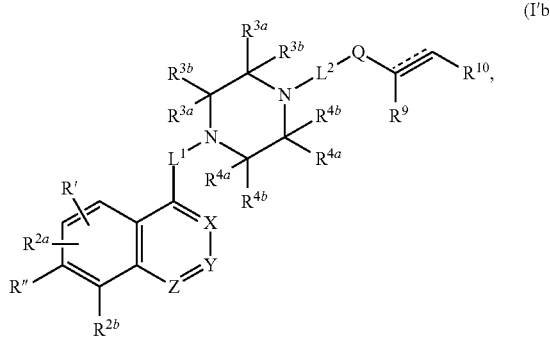

(I'b)

or a pharmaceutically acceptable salt, tautomer or stereoisomer thereof, wherein:

X and Y are each independently N or CR$^6$;

Z is N or CR$^{6a}$;

$L^1$ is a bond;

$L^2$ is a bond or alkylene;

R' is $R^1$ and R" is $R^{2c}$; or R' is H and R" is $R^1$;

$R^1$ is substituted or unsubstituted aryl or heteroaryl;

$R^{2a}$, $R^{2b}$ and $R^{2C}$ are each independently H, halo, hydroxyl, $C_1$-$C_6$ alkyl, $C_1$-$C_6$ haloalkyl, $C_1$-$C_6$ alkoxy, $C_3$-$C_8$ cycloalkyl or aryl;

$R^{3a}$ and $R^{3b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminocarbonylalkyl or aminocarbonyl;

$R^{4a}$ and $R^{4b}$ are, at each occurrence, independently H, —OH, —NH$_2$, —CO$_2$H, halo, cyano, $C_1$-$C_6$ alkyl, $C_1$-$C_6$ alkynyl, hydroxylalkly, aminylalkyl, alkylaminylalkyl, cyanoalkyl, carboxyalkyl, aminocarbonylalkyl or aminocarbonyl;

$R^6$ is, at each occurrence, independently H, cyano, cyanoalkyl, amino, aminylalkyl, aminylalkylaminyl, aminocarbonyl, alkylaminyl, haloalkylamino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino or arylalkyloxy;

$R^{6a}$ is H or $C_1$-$C_6$ alkyl;

≡ represents a double or triple bond;

Q is —C(=O)—, —C(=NR$^{8'}$)-, —NR$^8$C(=O)-, —S(=O)$_2$- or —NR$^8$S(=O)$_2$-;

$R^8$ is H, $C_1$-$C_6$ alkyl or hydroxylalkyl;

$R^{8'}$ is H, —OH, —CN or $C_1$-$C_6$ alkyl; and when ≡ is a double bond then $R^9$ and $R^{10}$ are each independently H, cyano, carboxyl, $C_1$-$C_6$alkyl, alkoxycarbonyl, aminylalkyl, alkylaminylalkyl, or hydroxylalkyl or $R^9$ and $R^{10}$ join to form a carbocyclic or heterocyclic ring, provided at least one of X, Y and Z is N.

8. The method of claim 1, 6 or 7, wherein:

≡ represents a double bond;

Q is —C(=O)—, —C(=NR$^{8'}$)-, —NR$^8$C(=O)-, —S(=O)$_2$- or —NR$^8$S(=O)$_2$-;

$R^8$ is H, $C_1$-$C_6$ alkyl or hydroxylalkyl;

$R^{8'}$ is H, —OH, —CN or $C_1$-$C_6$alkyl; and $R^9$ and $R^{10}$ are each independently H, cyano, $C_1$-$C_6$alkyl, aminylalkyl, alkylaminylalkyl, or hydroxylalkyl or $R^9$ and $R^{10}$ join to form a carbocyclic or heterocyclic ring.

9. The method of claim 8, wherein Q is —C(=O)—, and $R^9$ and $R^{10}$ are each H.

10. The method of claim 1, 6 or 7, wherein the G12C mutant modulating compound has the following structure:

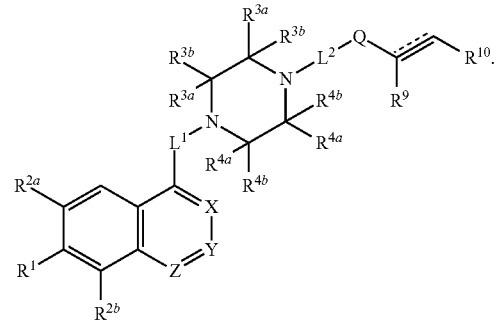

11. The method of claim 1, 6 or 7, wherein X and Z are N, and Y is CR$^6$.

12. The method of claim 1, 6 or 7, wherein $R^1$ is substituted or unsubstituted phenyl or substituted or unsubstituted naphthyl.

13. The method of claim 1, 6 or 7, wherein $R^1$ has one of the following structures:

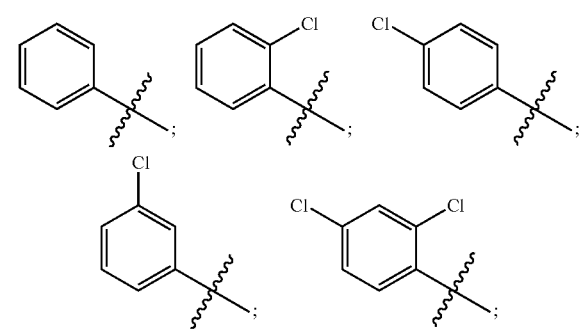

495
-continued
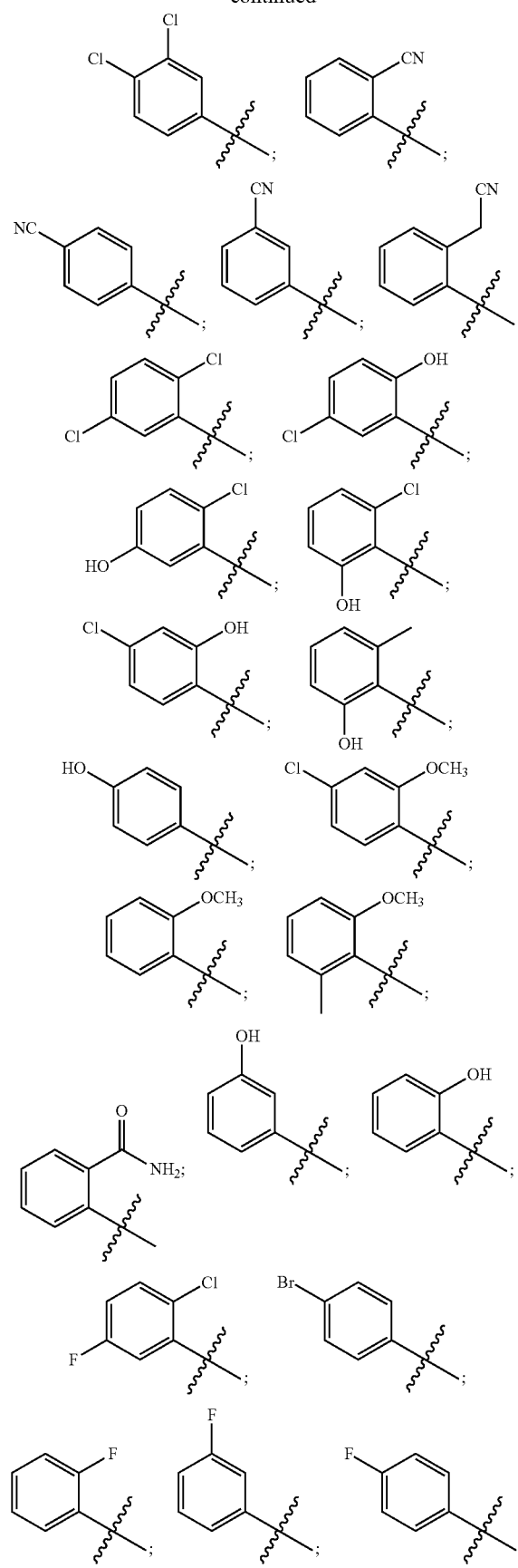
496
-continued
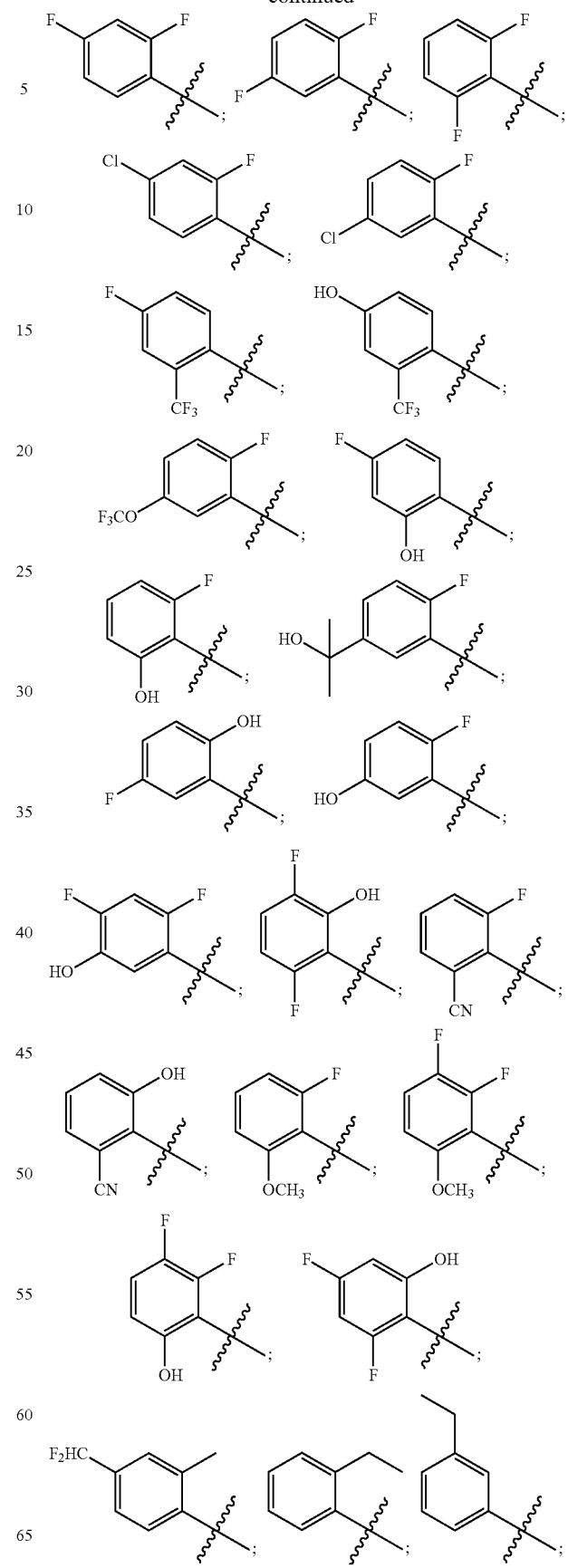

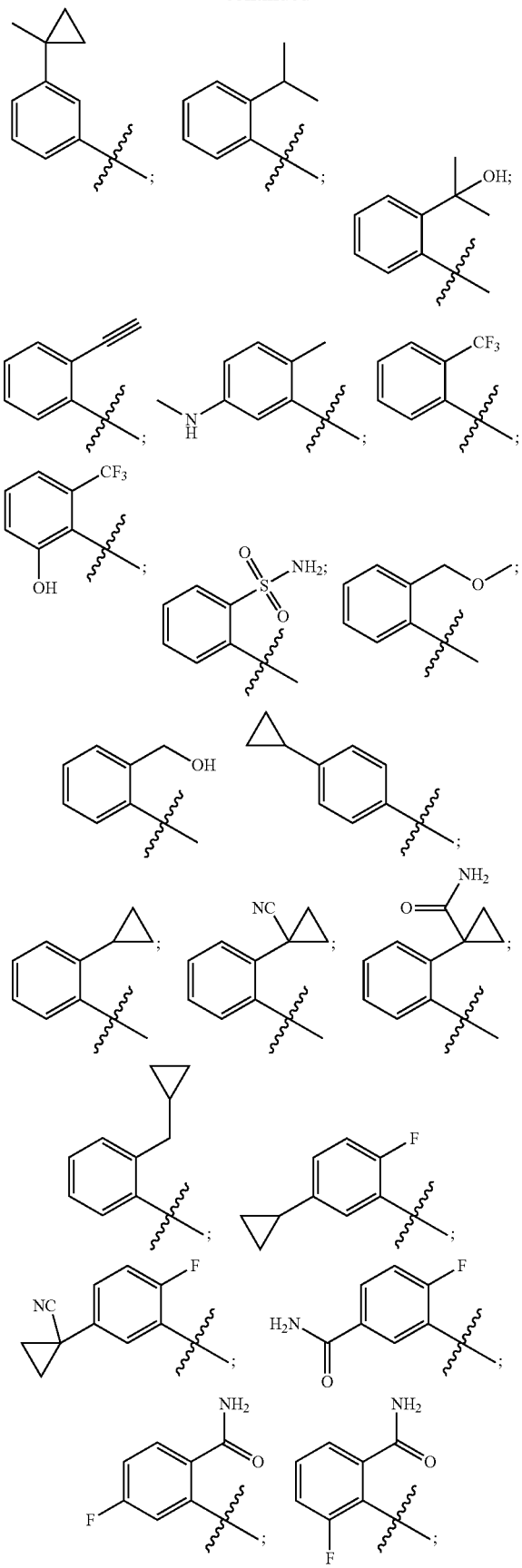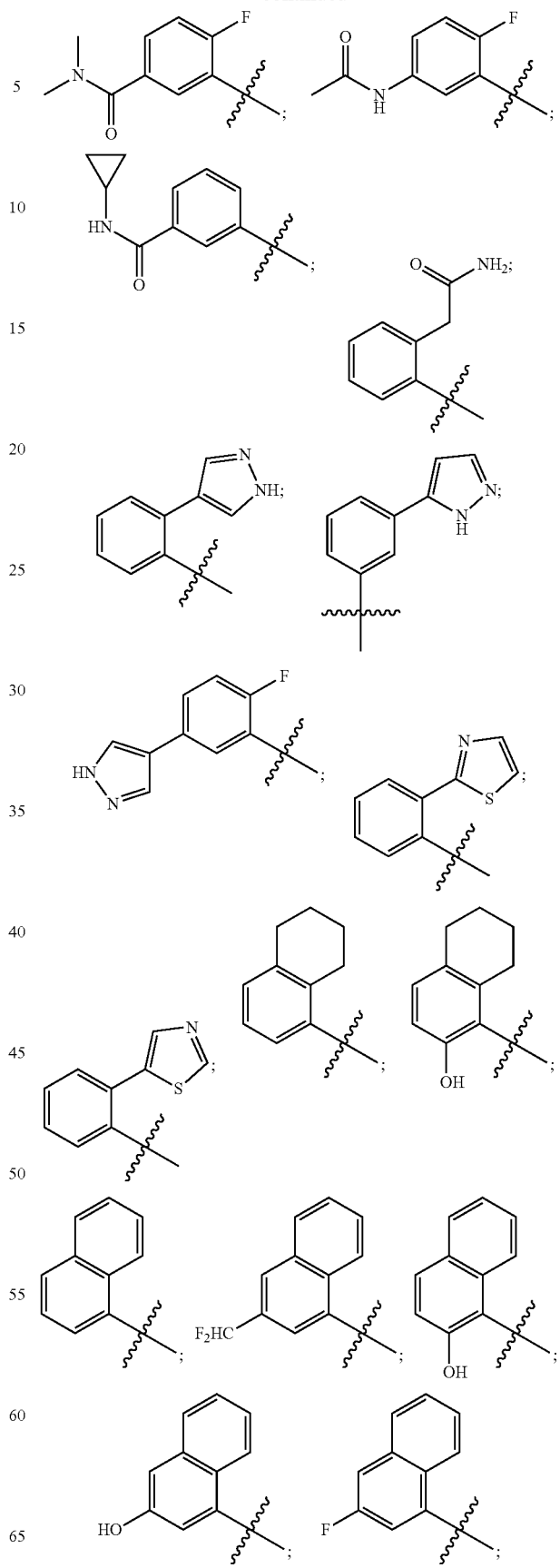

-continued

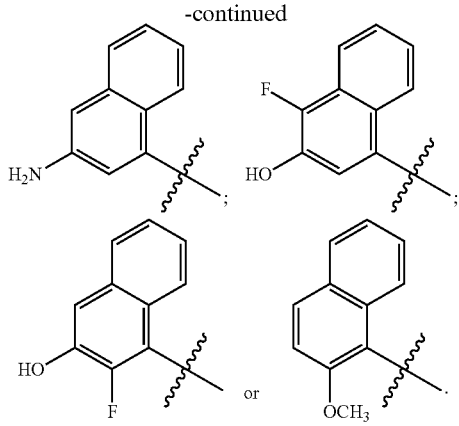

14. The method of claim 1, 6 or 7, wherein $R^{2a}$ and $R^{2b}$ are each independently H or halo.

15. The method of claim 1, 6 or 7, wherein the KRAS G12C mutant modulating compound has one of the following structures:

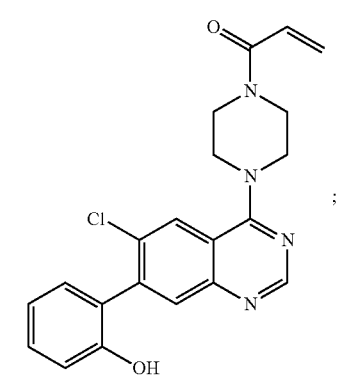

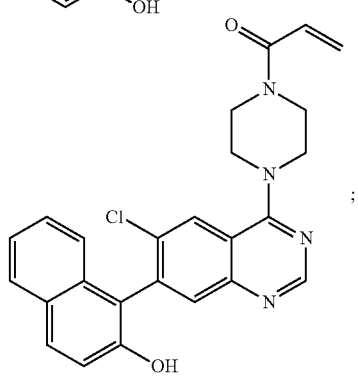

-continued

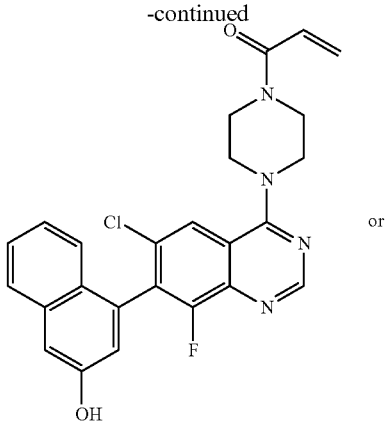

16. The method of claim 1, 6 or 7, wherein the additional therapeutic agent is an epidermal growth factor receptor (EGFR) inhibitor, phosphatidylinositol kinase (PI3K) inhibitor, insulin-like growth factor receptor (IGF1R) inhibitor, Janus kinase (JAK) inhibitor, a Met kinase (MET) inhibitor, a SRC family kinase (SFK) inhibitor, a mitogen-activated protein kinase (MEK) inhibitor, an extracellular-signal-regulated kinase (ERK) inhibitor, mechanistic target of rapamycin (mTOR) inhibitor, a topoisomerase inhibitor, a taxane, an anti-metabolite agent, an alkylating agent or a taxane.

17. The method of claim 16, wherein the additional therapeutic agent is an epidermal growth factor receptor (EGFR) inhibitor.

18. The method of claim 17, wherein the epidermal growth factor receptor (EGFR) inhibitor is Erlotinib, Afatinib or Iressa.

19. The method of claim 1, 6 or 7 wherein the compound and the additional therapeutic agent are co-administered.

20. The method of claim 1, 6 or 7 wherein the compound and the additional therapeutic agent are separately administered.

* * * * *